(12) United States Patent
Chen et al.

(10) Patent No.: US 12,364,702 B2
(45) Date of Patent: Jul. 22, 2025

(54) HIGHLY ACTIVE STING PROTEIN AGONIST COMPOUND

(71) Applicant: ADLAI NORTYE BIOPHARMA CO., LTD., Zhejiang (CN)

(72) Inventors: Yufeng Chen, Zhejiang (CN); Kaixuan Chen, Zhejiang (CN); Pan Li, Zhejiang (CN); Canfeng Liu, Zhejiang (CN); Ji Wang, Zhejiang (CN); Qingchong Qiu, Zhejiang (CN); Yang Lu, Zhejiang (CN)

(73) Assignee: ADLAI NORTYE BIOPHARMA CO., LTD., Zhejiang (CN)

( * ) Notice: Subject to any disclaimer, the term of this patent is extended or adjusted under 35 U.S.C. 154(b) by 351 days.

(21) Appl. No.: 17/270,480

(22) PCT Filed: Aug. 22, 2019

(86) PCT No.: PCT/CN2019/101925
§ 371 (c)(1),
(2) Date: Feb. 23, 2021

(87) PCT Pub. No.: WO2020/042995
PCT Pub. Date: Mar. 5, 2020

(65) Prior Publication Data
US 2024/0189320 A1  Jun. 13, 2024

(30) Foreign Application Priority Data

Aug. 29, 2018 (CN) .......................... 201810996231.0
Nov. 23, 2018 (CN) .......................... 201811407028.1

(51) Int. Cl.
*A61K 31/5386* (2006.01)
*A61K 31/437* (2006.01)
(Continued)

(52) U.S. Cl.
CPC ........ *A61K 31/5386* (2013.01); *A61K 31/437* (2013.01); *A61K 31/4985* (2013.01);
(Continued)

(58) Field of Classification Search
CPC ..... A61P 35/00; C07D 519/00; C07D 471/06; C07D 487/06; C07D 498/06;
(Continued)

(56) References Cited

U.S. PATENT DOCUMENTS 11,535,633 B2 * 12/2022 Liu .......................... A61P 29/00
2011/0003801 A1   1/2011 Jetter et al.
2021/0300944 A1   9/2021 Liu et al.

FOREIGN PATENT DOCUMENTS

CN         102802731 A    11/2012
WO         2006069155 A2   6/2006
(Continued)

OTHER PUBLICATIONS

International Search Report for PCT/CN2019/101925 mailed Oct. 10, 2019, ISA/CN.
(Continued)

*Primary Examiner* — Erich A Leeser
(74) *Attorney, Agent, or Firm* — Yue (Robert) Xu; Apex Attorneys at Law, LLP

(57) ABSTRACT

The present invention provides compounds of Formula (I) or (II), pharmaceutical compositions thereof, and methods of using compounds of Formula (I) or (II) to prevent and/or treat immune-related disorders.

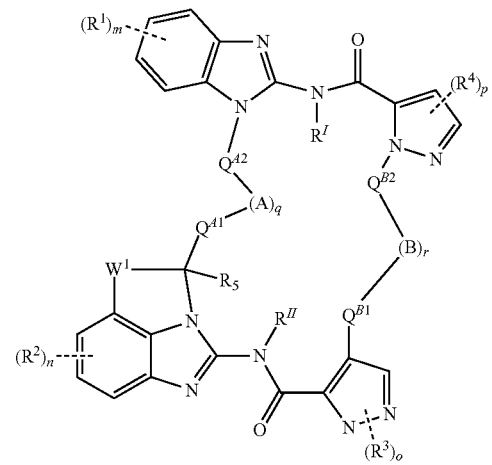

Formula (I)

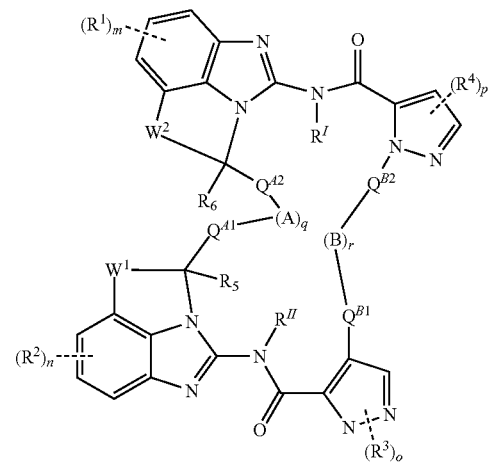

Formula (II)

13 Claims, 1 Drawing Sheet

Figure 1:
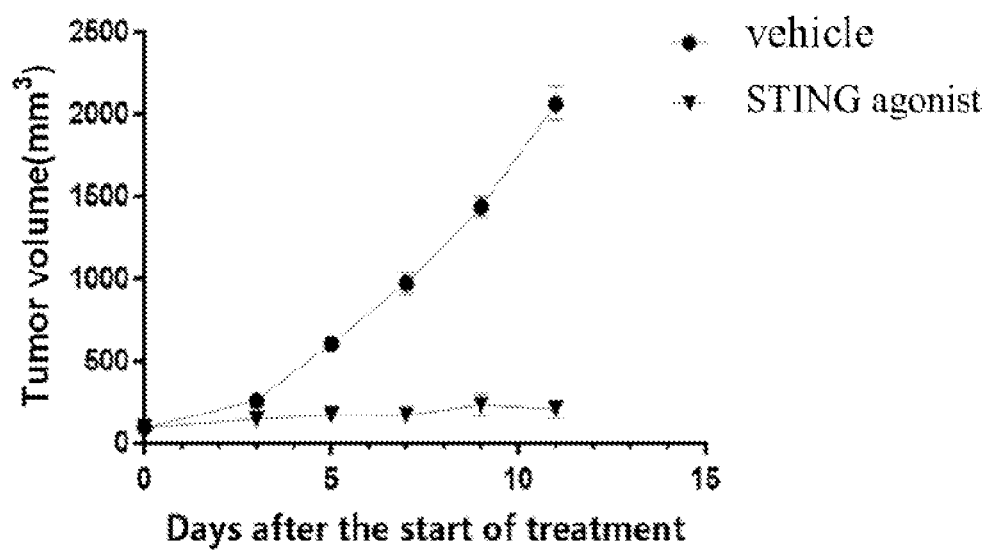

(51) Int. Cl.
- *A61K 31/4985* (2006.01)
- *A61K 31/5383* (2006.01)
- *A61K 31/551* (2006.01)
- *A61K 31/553* (2006.01)
- *A61P 35/00* (2006.01)
- *C07D 471/06* (2006.01)
- *C07D 487/06* (2006.01)
- *C07D 498/06* (2006.01)
- *C07D 498/22* (2006.01)
- *C07D 519/00* (2006.01)

(52) U.S. Cl.
CPC ........ *A61K 31/5383* (2013.01); *A61K 31/551* (2013.01); *A61K 31/553* (2013.01); *A61P 35/00* (2018.01); *C07D 471/06* (2013.01); *C07D 487/06* (2013.01); *C07D 498/06* (2013.01); *C07D 498/22* (2013.01); *C07D 519/00* (2013.01)

(58) Field of Classification Search
CPC .......................... C07D 498/22; A61K 31/5386; A61K 31/437; A61K 31/4985; A61K 31/5383; A61K 31/551; A61K 31/553
See application file for complete search history.

(56) References Cited

FOREIGN PATENT DOCUMENTS

| | | |
|---|---|---|
| WO | 2017049401 A1 | 3/2017 |
| WO | 2017175147 A1 | 10/2017 |
| WO | 2017175156 A1 | 10/2017 |
| WO | 2018032104 A1 | 2/2018 |
| WO | 2019069269 A1 | 4/2019 |
| WO | 2019069270 A1 | 4/2019 |
| WO | 2019069275 A1 | 4/2019 |
| WO | 2019134705 A1 | 7/2019 |
| WO | 2019134707 A1 | 7/2019 |
| WO | 2020006432 A1 | 1/2020 |
| WO | 2020038387 A1 | 2/2020 |

OTHER PUBLICATIONS

Joshi M. Ramanjulu et al., Design of Amidobenzimidazole STING Receptor Agonists with Systemic Activity. Nature, vol. 564, Dec. 27, 2018 (Dec. 27, 2018) pp. 439-443.
The Chinese 1st Office Action issued on Aug. 23, 2021 for CN202011595914.9.
The Australian 2nd Office Action issued on Jan. 18, 2022 for AU2019331993.
The European search report issued on Feb. 16, 2022 for EP19853404.2.

* cited by examiner

HIGHLY ACTIVE STING PROTEIN AGONIST COMPOUND

CROSS REFERENCE TO RELATED APPLICATIONS

This application is the national phase of International Application No. PCT/CN2019/101925, titled "HIGHLY ACTIVE STING PROTEIN AGONIST COMPOUND", filed on Aug. 22, 2019, which claims the priority to Chinese Patent Application No. 201810996231.0 filed with the China National Intellectual Property Administration on Aug. 29, 2018 and titled "HIGHLY ACTIVE STING PROTEIN AGONIST COMPOUND", and to Chinese Patent Application No. 201811407028.1 filed with the China National Intellectual Property Administration on Nov. 23, 2018 and titled "HIGHLY ACTIVE STING PROTEIN AGONIST COMPOUND", the content of which are incorporated herein by reference in their entirety.

TECHNICAL FIELD

The present invention relates to a heterocyclic compound, in particular to a high active STING protein agonist and use thereof.

BACKGROUND

The positive response to immunotherapy generally depends on the interaction of tumor cells with immunoregulation within the tumor microenvironment (TME). Under these interactions, the tumor microenvironment plays an important role in suppressing or enhancing the immune response. Understanding the interaction between immunotherapy and TME is not only the key to analyze the mechanism of action, but also provides a new method to improve the efficacy of current immunotherapy. Cytokines are a broad class of proteins that can modulate immune responses and can directly activate immune effector cells or stimulate tumor stromal cells to produce chemokines and adhesion molecules for lymphocyte recruitment. These functions suggest that targeting cytokines may also be an effective approach for tumor immunotherapy, depending on different tumor microenvironments.

STING (interferon gene-stimulating protein) is currently the latest and hottest immunotherapy target in drug development in the field of tumor immunotherapy. Interferon gene-stimulating protein is a transmembrane protein, which is usually dimerized and self-inhibited in the region 152-173. Upon stimulation by a partial ligand, the molecular conformation changes and is activated, recruiting TANK-binding kinase 1 in the cytoplasm, mediating phosphorylation of IRF3 by TBK1, resulting in the formation of interferon-β and a variety of other cytokines. The production of IFNβ is a sign of STING activation. The signal transduction of innate immunity in the tumor microenvironment is a key step in the activation of tumor-specific T cells and infiltration of tumor-infiltrating lymphocytes. Where type I IFN plays a key role in tumor-activated T cell activation. Thus, STING not only induces the expression of type I interferon gene, but also plays an important role in innate immune signaling pathway; STING agonists may activate immunostimulatory cells including dendritic cells, alter the tumor microenvironment and induce the production of tumor-specific T cells. In murine experiments, DMXAA, a flavonoid vascular disrupting agent, induced the production of IFN-β and other natural cytokines by activating murine STING proteins, and effectively inhibited the growth of a variety of solid tumors. However, no significant effect was observed in a human non-small cell clinical trial in combination with standard chemotherapy. Later experiments demonstrated that although the similarity between human and murine STING proteins reached 81%, the former encoded 379 amino acids and the latter encoded 378 amino acids, DMXAA failed to activate human STING proteins. Cyclic dinucleotide is the only type of STING agonists discovered to date that activates both murine and human STING proteins directly. Direct injection of CDN into B16 melanoma, CT26 rectal cancer, and 4T1 breast cancer tumors not only resulted in significant inhibition until the tumor disappeared, but also induced systemic persistent antigen-specific T cell immunity, resulting in inhibition of tumor growth in other parts of the animal without drug injection. MLRR-S2CDA causes changes in the microenvironment of a variety of solid tumors, activates effective tumor-induced CD8+T cells and has a long-lasting therapeutic effect. In recent years, a large number of study reports have demonstrated that STING pathway can effectively initiate the body's natural immune system, which is one of a few signaling pathways that have been proven to induce cytokine interferon production, and is very important in innate immunity. Sufficient infiltration of lymphocytes into tumor tissue is the key to successful immunotherapy. The activation of the target pathway also promotes the infiltration and response to effector T cells in the tumor microenvironment. Therefore, this target has gradually become an important target for anti-tumor therapy, especially immunotherapy. In a plurality of mouse inoculation models, the composition is effective for a plurality of refractory and metastatic solid tumors, not only is the tumor injected directly disappeared, but also the growth of tumor at other parts is obviously inhibited, and even the occurrence of the tumor can be prevented.

SUMMARY

The present invention provides a compound having STING protein agonist activity.

One of objects of the present invention is to provide a compound having a structure of Formula (I), Formula (I)

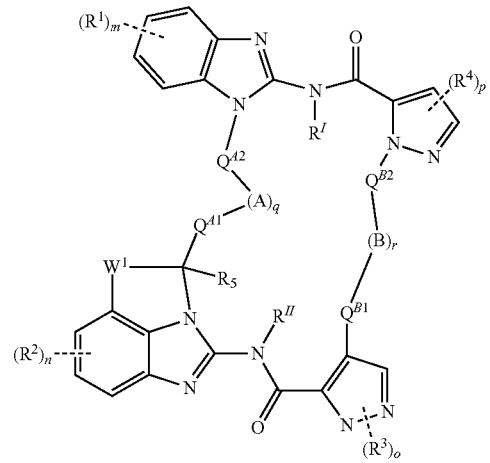

where $W^1$ represents $(CR^aR^{a'})s$, where any one $CR^aR^{a'}$ is optionally substituted by 0, 1 or 2O, S or $NR^b$, or any one $CR^aR^{a'}$ is optionally taken together to form —C=O;

s is selected from integers of 1, 2 and 3;

q is selected from 0 and 1;

r is selected from 0 and 1; and q and r are not 0 at the same time;

where $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R^c$, —$CON(R^c)(R^{c'})$, —$C(=NH)N(R^c)(R^{c'})$, —$NR^cC(O)R^c$, —$SO_2R^c$, —$SO_2NR^cR^{c'}$, —$N(R^c)$—$SO_2$—($C_1$-$C_6$ alkyl)-$NR^cR^{c'}$, —$N(R^c)$—$C(O)$—($C_1$-$C_6$ alkyl)-$NR^cR^{c'}$, —$NR^cS(O)R^{c'}$, —$NR^cSO_2R^{c'}$, —O—P(O)($OR^c$)($OR^{c'}$), 6- to 12-membered aryl or 5- to 12-membered heteroaryl;

$R^5$ is selected from hydrogen or $C_1$-$C_6$ alkyl;

where when q=0, $Q^{A1}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $Q^{A1}$ and $R^5$ together with atoms adjacent thereto, form a 3- to 6-membered ring optionally containing 0, 1, or 2 heteroatoms selected from O, N, and S; Q is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); when q=1, -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

where when r=0, $Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

when q=1, -$Q^{B1}$-B-$Q^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$R^I$ and $R^{II}$ each independently represent hydrogen or $C_1$-$C_6$ alkyl;

where $R^a$ and $R^{a'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^dR^{d'}$, —$NR^dCOR^{d'}$, —$NR^dS(O)R^{d'}$, —$NR^dSO_2R^{d'}$, —$OR^d$, or —$OCOR^d$;

$R^b$ each independently represents hydrogen, $C_1$-$C_6$ alkyl, $C_3$-$C_6$ cycloalkyl, —($C_0$-$C_6$ alkylene)-(6- to 12-membered aryl), —$C(O)R^e$, —$SOR^e$, —$SO_2R^e$, —C(O)$OR^e$, or —$C(O)NR^eR^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

where m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from 0, N and S;

or when n=2, the two adjacent $R^2$ and the atom bound thereto are optionally cyclized to each other into a 5- to 8-membered ring optionally containing 0, 1 or 2 heteroatoms selected from 0, N and S;

or when p=2, the two adjacent $R^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —$OC(O)R^f$, —$S(O)R^f$, —$S(O)_2R^f$, —$S(O)_2NR^fR^{f'}$, —$OCONR^fR^{f'}$, —$NR^fCOR^{f'}$, —$NR^fS(O)R^{f'}$, —$NR^fS(O)_2R^{f'}$, —$NR^fC(O)OR^{f'}$, —$CONR^fR^{f'}$, —$NR^fR^{f'}$, —NHC=$NHNR^fR^{f'}$, $C_1$-$C_6$ haloalkyl, $C_1$-$C_6$ haloalkoxy, and —O—P(O)($OR^f$)($OR^{f'}$);

where $R^d$, $R^{d'}$, $R^e$, $R^{e'}$, $R^f$, and $R^{f'}$ each independently represent hydrogen or $C_1$-$C_6$ alkyl, where the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —C(O)—$OR^g$, —$OC(O)R^g$, —$S(O)R^g$, —$S(O)_2R^g$, —$S(O)_2NR^gR^{g'}$, —$OCONR^gR^{g'}$, —$NR^gCOR^{g'}$, —$NR^gS(O)R^{g'}$, —$NR^gS(O)_2R^{g'}$, —$NR^gC(O)$ $OR^{g'}$, —$CONR^gR^{g'}$, —$NR^gR^{g'}$, $C_1$-$C_6$ haloalkyl, $C_1$-$C_6$ haloalkoxy, or —O—P(O)($OR^g$)($OR^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

where $R^g$ and $R^{g'}$ are each independently selected from hydrogen or $C_1$-$C_6$ alkyl.

One of objects of the present invention is to provide a compound having a structure of Formula (II),

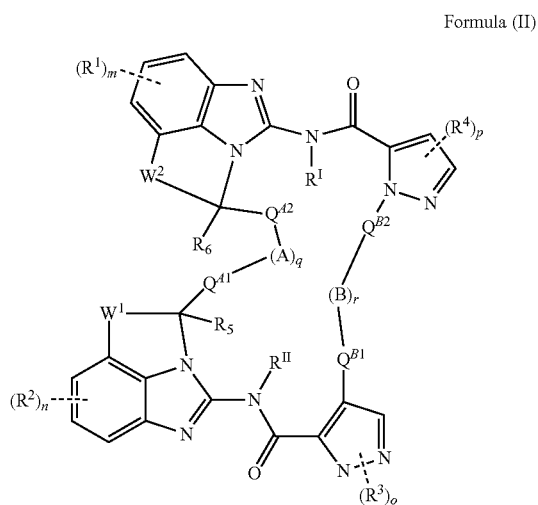

Formula (II)

where $W^1$ represents $(CR^aR^{a'})s$, where any one $CR^aR^{a'}$ is optionally substituted by 0, 1 or 2 O, S or $NR^b$, or any one $CR^aR^{a'}$ is optionally taken together to form —C=O;

$W^2$ represents $(CR^hR^{h'})_t$, where any one $CR^hR^{h'}$ is optionally substituted by 0, 1 or 2 O, S or $NR^j$, or any one $CR^hR^{h'}$ is optionally taken together to form —C=O;

s and t each independently consist of an integer selected from 1, 2, and 3;

q is selected from 0 and 1;

r is selected from 0 and 1; and q and r are not 0 at the same time;

where $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R^c$, —$CON(R^c)(R^{c'})$, —$C(=NH)N(R^c)(R^{c'})$, —$NR^cC(O)R^{c'}$, —$SO_2R^c$, —$SO_2NR^cR^{c'}$, —$N(R^c)$—$SO_2$—($C_1$-$C_6$ alkyl)-$NR^cR^{c'}$, —$N(R^c)$—$C(O)$—($C_1$-$C_6$ alkyl)-$NR^cR^{c'}$, —$NR^cS(O)R^{c'}$, —$NR^cSO_2R^{x'}$, —O—P(O)($OR^c$)($OR^{c'}$), 6- to 12-membered aryl, or 5- to 12-membered heteroaryl;

$R^5$ and $R^6$ are each independently selected from hydrogen or $C_1$-$C_6$ alkyl;

where when q=0, $Q^{A1}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $Q^{A1}$ and $R^5$ together with atoms adjacent thereto, form a 3- to 6-membered ring optionally containing 0, 1, or 2 heteroatoms selected from O, N, and S; $Q^2$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $QA^2$ and $R^6$ together with atoms adjacent thereto, form a 3- to 6-membered ring optionally containing 0, 1, or 2 heteroatoms selected from O, N, and S;

when q=1, -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

where when r=0, $Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

when q=1, -$Q^{B1}$-B-$Q^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$R^I$ and $R^{II}$ each independently represent hydrogen or $C_1$-$C_6$ alkyl;

where $R^a$, $R^{a'}$, $R^h$, and $R^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^dR^{d'}$, —$NR^dCOR^{d'}$, —$NR^dS(O)R^{d'}$, —$NR^dSO_2R^{d'}$, —$OR^d$, or —$OCOR^d$;

$R^b$ and $R^j$ each independently represent hydrogen, $C_1$-$C_6$ alkyl, $C_3$-$C_6$ cycloalkyl, —($C_0$-$C_6$ alkylene)-(6- to 12-membered aryl), —$C(O)R^e$, —$SOR^e$, —$SO_2R^e$, —$C(O)OR^e$, or —$C(O)NR^eR^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

or $R^h$ and $R^{h'}$ together with the atom bound thereto are optionally cyclized to each other into a 3- to 6-membered ring optionally containing 0, 1, or 2 heteroatoms selected from O, N and S;

where m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from O, N and S;

or when n=2, the two adjacent $R^2$ and the atom bound thereto are optionally cyclized to each other into a 5- to 8-membered ring optionally containing 0, 1 or 2 heteroatoms selected from O, N and S;

or when p=2, the two adjacent $R^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —OC(O)$R^f$, —S(O)R, —S(O)$_2$R, —S(O)$_2$N$R^fR''$, —OCON$R^fR''$, —N$R^f$CO$R''$, —N$R^f$S(O) $R''$, —N$R^f$S(O)$_2R''$, —N$R^f$C(O)O$R^f$, —CON$R^fR''$, —N$R^fR''$, $C_1$-$C_8$ haloalkyl, $C_1$-$C_8$ haloalkoxy, and —O—P(O)(O$R^f$)(O$R^{f'}$);

where $R^d$, $R^{d'}$, $R^e$, $R^{e'}$, $R^f$, and $R^{f'}$ each independently represent hydrogen or $C_1$-$C_6$ alkyl, where the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —C(O)—$OR^g$, —OC(O)$R^g$, —S(O)$R^g$, —S(O)$_2R^g$, —S(O)$_2NR^gR^{g'}$, —OCON$R^gR^{g'}$, —N$R^g$CO$R^{g'}$, —N$R^g$S(O) $R^{g'}$, —N$R^g$S(O)$_2R^{g'}$, —N$R^g$C(O)O$R^{g'}$, —CON$R^gR^{g'}$, —N$R^gR^{g'}$, $C_1$-$C_6$ haloalkyl, $C_1$-$C_6$ haloalkoxy, or —O—P(O)(O$R^g$)(O$R^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

where $R^g$ and $R^{g'}$ are each independently selected from hydrogen or $C_1$-$C_6$ alkyl.

One of objects of the present invention is to provide a compound having a structure of Formula (III),

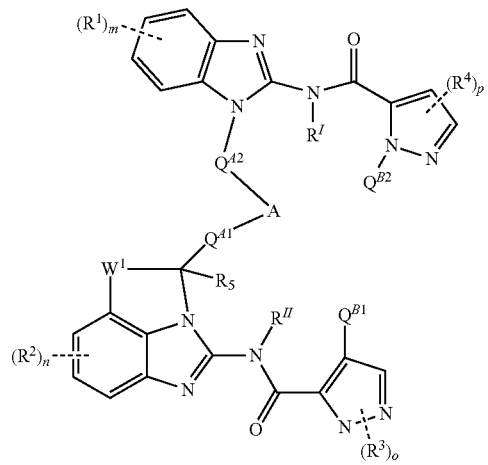

Formula (III)

where $W^1$ represents $(CR^aR^{a'})s$, where any one $CR^aR^{a'}$ is optionally substituted by 0, 1 or 2O, S or $NR^b$, or any one $CR^aR^{a'}$ is optionally taken together to form —C=O;

s is selected from integers of 1, 2 and 3;

where $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —OC(O)$R^c$, —C(O)$R^c$, —CO$_2R^c$, —CON($R^c$)($R^{c'}$), —C(=NH)N($R^c$)($R^{c'}$), —WC(O)$R^c$, —SO$_2R^c$, —SO$_2NR^cR^{c'}$, —N($R^c$)—SO$_2$—($C_1$-$C_6$ alkyl)-$NR^cR^{c'}$, —N($R^c$)—C(O)—($C_1$-$C_6$ alkyl)-$NR^cR^{c'}$, —$NR^cS(O)R^{c'}$, —$NR^cSO_2R^{c'}$, —O—P(O)(O$R^c$)(O$R^{c'}$), 6- to 12-membered aryl or 5- to 12-membered heteroaryl;

$R^5$ is selected from hydrogen or $C_1$-$C_6$ alkyl;

where -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

$R^I$ and $R^{II}$ each independently represent hydrogen or $C_1$-$C_6$ alkyl;

where $R^a$ and $R^{a'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —NR$^d$R$^{d'}$, —NR$^d$COR$^{d'}$, —NR$^d$S(O)R$^{d'}$, —NR$^d$SO$_2$R$^{d'}$, —OR$^d$, or —OCOR$^d$;

R$^b$ each independently represents hydrogen, C$_1$-C$_6$ alkyl, C$_3$-C$_6$ cycloalkyl, —(C$_0$-C$_6$ alkylene)-(6- to 12-membered aryl), —C(O)R$^e$, —SOR$^e$, —SO$_2$R$^e$, —C(O)OR$^e$, or —C(O)NR$^e$R$^{e'}$;

R$^c$ and R$^{c'}$ each independently represent hydrogen, C$_1$-C$_6$ alkyl, —(C$_0$-C$_6$ alkylene)-(C$_3$-C$_6$ cycloalkyl), or —(C$_0$-C$_6$ alkylene)-(4- to 6-membered heterocyclyl);

or R$^a$ and R$^{a'}$ together with the atom bound thereto are optionally cyclized to each other into a 3- to 6-membered ring optionally containing 0, 1, or 2 heteroatoms selected from O, N and S;

or R$^c$ and R$^{c'}$ together with the atom bound thereto are optionally cyclized to each other into a 3- to 6-membered ring optionally containing 0, 1, or 2 heteroatoms selected from O, N and S;

where m=1, 2, 3 or 4;
n=1, 2 or 3;
o=1 or 2; and
p=1 or 2;

or when m=2, the two adjacent R$^1$ and the atom bound thereto are optionally cyclized to each other into a 5- to 8-membered ring optionally containing 0, 1 or 2 heteroatoms selected from 0, N and S;

or when n=2, the two adjacent R$^2$ and the atom bound thereto are optionally cyclized to each other into a 5- to 8-membered ring optionally containing 0, 1 or 2 heteroatoms selected from 0, N and S;

or when p=2, the two adjacent R$^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

C$_1$-C$_6$ alkyl, C$_2$-C$_6$ alkenyl, C$_2$-C$_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, C$_1$-C$_6$ mercapto, C$_1$-C$_6$ alkoxy, —OR$^f$, —C(O)—OR, —OC(O)R$^f$, —S(O)R, —S(O)$_2$R, —S(O)$_2$NR$^f$R$^{f'}$, —OCONR$^f$R$^{f'}$, —NR$^f$COR$^{f'}$, —NR$^f$S(O), R$^{f'}$, —NR$^f$S(O)$_2$R$^{f'}$, —NR$^f$C(O)OR$^{f'}$, —CONR$^f$R$^{f'}$, —NR$^f$R$^{f'}$, —NHC=NHNR$^f$R$^{f'}$, C$_1$-C$_6$ haloalkyl, C$_1$-C$_6$ haloalkoxy, and —O—P(O)(OR$^f$)(OR$^{f'}$);

where R$^d$, R$^{d'}$, R$^e$, R$^{e'}$, R$^f$, and R$^{f'}$ each independently represent hydrogen or C$_1$-C$_6$ alkyl, where the C$_1$-C$_6$ alkyl is also optionally substituted by C$_1$-C$_6$ alkyl, C$_2$-C$_6$ alkenyl, C$_2$-C$_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, C$_1$-C$_6$ mercapto, C$_1$-C$_6$ alkoxy, —OR$^g$, —C(O)—OR$^g$, —OC(O)R$^g$, —S(O)R$^g$, —S(O)$_2$R$^g$, —S(O)$_2$NR$^g$R$^{g'}$, —OCONR$^g$R$^{g'}$, —NR$^g$COR$^{g'}$, —NR$^g$S(O) R$^{g'}$, —NR$^g$S(O)$_2$R$^{g'}$, —NR$^g$C(O)OR$^{g'}$, —CONR$^g$R$^{g'}$, —NR$^g$R$^{g'}$, C$_1$-C$_6$ haloalkyl, C$_1$-C$_6$ haloalkoxy, or —O—P(O)(OR$^g$)(OR$^{g'}$);

or R$^d$, R$^{d'}$, R$^e$, R$^{e'}$, R$^f$, and R$^{f'}$ together with the nitrogen atom bound thereto form a 5- to 8-membered carbocycle or a 5- to 8-membered heterocycle;

where R$^g$ and R$^{g'}$ are each independently selected from hydrogen or C$_1$-C$_6$ alkyl.

One of objects of the present invention is to provide a compound having a structure of Formula (IV),

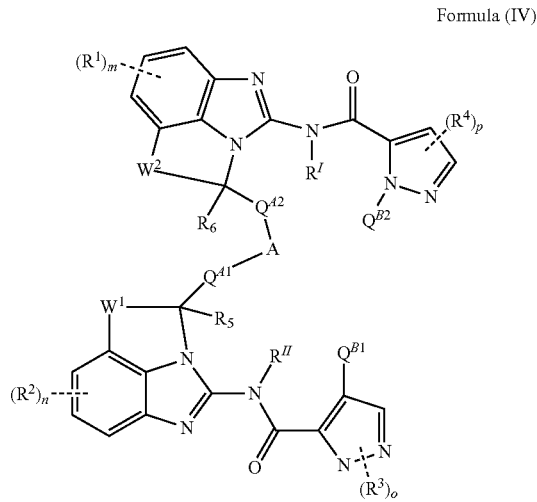

Formula (IV)

where W$^1$ represents (CR$^a$R$^{a'}$)s, where any one CR$^a$R$^{a'}$ is optionally substituted by 0, 1 or 2 O, S or NR$^b$, or any one CR$^a$R$^{a'}$ is optionally taken together to form —C=O;

W$^2$ represents (CR$^h$R$^{h'}$)$_t$, where any one CR$^h$R$^{h'}$ is optionally substituted by 0, 1 or 2O, S or NR$^j$, or any one CR$^h$R$^{h'}$ is optionally taken together to form —C=O;

s and t each independently consist of an integer selected from 1, 2, and 3;

where R$^1$, R$^2$, R$^3$, and R$^4$ each independently represent hydrogen, halogen, cyano, C$_1$-C$_6$ alkyl, C$_2$-C$_6$ alkenyl, C$_2$-C$_6$ alkynyl, —OR$^c$, —O—(C$_1$-C$_6$ alkylene)-NR$^c$R$^{c'}$, —NR$^c$R$^{c'}$, —OC(O)R$^c$, —C(O)R$^c$, —CO$_2$R$^c$, —CON(R$^c$)(R$^{c'}$), —C(=NH)N(R$^c$)(R$^{c'}$), —NR$^c$C.(0)R$^{c'}$, —SO$_2$R$^c$, —SO$_2$NR$^c$R$^{c'}$, —N(R$^c$)—SO$_2$—(C$_1$-C$_6$ alkyl)-NR$^c$R$^{c'}$, —N(R$^c$)—C(O)—(C$_1$-C$_6$ alkyl)-NR$^c$R$^{c'}$, —NR$^c$S(O)R$^{c'}$, —NR$^c$SO$_2$R$^{c'}$, —O—P(O)(OR$^c$)(OR$^{c'}$), 6- to 12-membered aryl, or 5- to 12-membered heteroaryl;

R$^5$ and R$^6$ are each independently selected from hydrogen or C$_1$-C$_6$ alkyl;

where -Q$^{41}$-A-Q$^{42}$- is taken together to form a linking group selected from: —C$_1$-C$_6$ alkylene-, —C$_2$-C$_6$ alkenylene-, —C$_2$-C$_6$ alkynylene-, —(C$_0$-C$_6$ alkylene)-O—(C$_0$-C$_6$ alkylene)-, —(C$_0$-C$_6$ alkylene)-C(O)—(C$_0$-C$_6$ alkylene)-, —C(O)—(C$_0$-C$_6$ alkylene)-O—(C$_0$-C$_6$ alkylene)-, —(C$_0$-C$_6$ alkylene)-OC(O)—(C$_0$-C$_6$ alkylene)-, —(C$_0$-C$_6$ alkylene)-NR$^c$—C(O)—(C$_0$-C$_6$ alkylene)-, —(C$_0$-C$_6$ alkylene)-C(O)—NR$^c$—(C$_0$-C$_6$ alkylene)-, —(C$_0$-C$_6$ alkylene)-NR$^c$—(C$_0$-C$_6$ alkylene)-, —(C$_0$-C$_6$ alkylene)-C(O)O—(C$_0$-C$_6$ alkylene)-, —(C$_0$-C$_6$ alkylene)-(C$_3$-C$_6$ carbocyclyl)-(C$_0$-C$_6$ alkylene)-, —(C$_0$-C$_6$ alkylene)-(4- to 6-membered heterocyclyl)-(C$_0$-C$_6$ alkylene)-, —(C$_0$-C$_6$ alkylene)-(6- to 12-membered aryl)-(C$_0$-C$_6$ alkylene)-, and —(C$_0$-C$_6$ alkylene)-(5- to 12-membered heteroaryl)-(C$_0$-C$_6$ alkylene)-;

Q$^{B1}$ and Q$^{B2}$ are each independently selected from the group consisting of hydrogen, C$_1$-C$_6$ alkyl, C$_2$-C$_6$ alkenyl, C$_2$-C$_6$ alkynyl, —(C$_0$-C$_6$ alkyl)-(C$_3$-C$_6$ cycloalkyl), —(C$_0$-C$_6$ alkyl)-(4- to 6-membered heterocyclyl), —(C$_0$-C$_6$ alkyl)-(6- to 12-membered aryl), and —(C$_0$-C$_6$ alkyl)-(5- to 12-membered heteroaryl);

R$^I$ and R$^{II}$ each independently represent hydrogen or C$_1$-C$_6$ alkyl;

where $R^a$, $R^{a'}$, $R^h$, and $R^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^dR^{d'}$, —$NR^dCOR^{d'}$, —$NR^dS(O)R^{d'}$, —$NR^dSO_2R^{d'}$, —$OR^d$, or —$OCOR^d$;

$R^b$ and $R^j$ each independently represent hydrogen, $C_1$-$C_6$ alkyl, $C_3$-$C_6$ cycloalkyl, —($C_0$-$C_6$ alkylene)-(6- to 12-membered aryl), —$C(O)R^e$, —$SOR^e$, —$SO_2R^e$, —$C(O)OR^e$, or —$C(O)NR^eR^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

or $R^h$ and $R^{h'}$ together with the atom bound thereto are optionally cyclized to each other into a 3- to 6-membered ring optionally containing 0, 1, or 2 heteroatoms selected from O, N and S;

where m=1, 2, 3 or 4;
n=1, 2 or 3;
o=1 or 2; and
p=1 or 2;

or when m=2, the two adjacent $R^1$ and the atom bound thereto are optionally cyclized to each other into a 5- to 8-membered ring optionally containing 0, 1 or 2 heteroatoms selected from 0, N and S;

or when n=2, the two adjacent $R^2$ and the atom bound thereto are optionally cyclized to each other into a 5- to 8-membered ring optionally containing 0, 1 or 2 heteroatoms selected from 0, N and S;

or when p=2, the two adjacent $R^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^e$, —$C(O)$—OR, —$OC(O)R^f$, —$S(O)R$, —$S(O)_2R$, —$S(O)_2NR^fR^{f'}$, —$OCONR^fR^{f'}$, —$NR^fCOR^{f'}$, —$NR^fS(O) R^{f'}$, —$NR^fS(O)_2R^{f'}$, —$NR^fC(O)OR^{f'}$, —$CONR^fR^{f'}$, —$NR^fR^{f'}$, $C_1$-$C_8$ haloalkyl, $C_1$-$C_8$ haloalkoxy, and —O—P(O)($OR^f$)($OR^{f'}$);

where $R^d$, $R^{d'}$, $R^e$, $R^{e'}$, $R^f$, and $R^{f'}$ each independently represent hydrogen or $C_1$-$C_6$ alkyl, where the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —$C(O)$—$OR^g$, —$OC(O)R^g$, —$S(O)R^g$, —$S(O)_2R^g$, —$S(O)_2NR^gR^{g'}$, —$OCONR^gR^{g'}$, —$NR^g$-$COR^{g'}$, —$NR^gS(O) R^{g'}$, —$NR^gS(O)_2R^{g'}$, —$NR^gC(O)$ $OR^{g'}$, —$CONR^gR^{g'}$, —$NR^gR^{g'}$, $C_1$-$C_6$ haloalkyl, $C_1$-$C_6$ haloalkoxy, or —O—P(O)($OR^g$)($OR^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

where $R^g$ and $R^{g'}$ are each independently selected from hydrogen or $C_1$-$C_6$ alkyl.

One of objects of the present invention is to provide a compound having a structure of Formula (V),

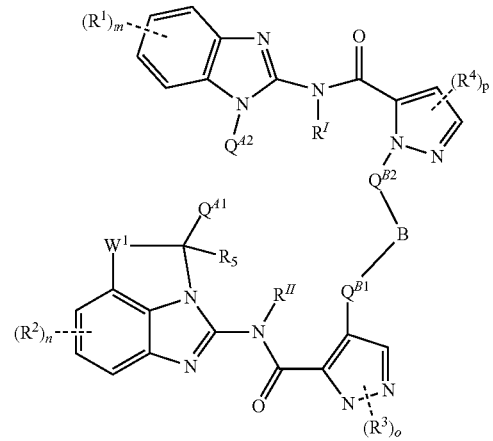

Formula (V)

where $W^1$ represents ($CR^aR^{a'}$)s, where any one $CR^aR^{a'}$ is optionally substituted by 0, 1 or 2 O, S or $NR^b$, or any one $CR^aR^{a'}$ is optionally taken together to form —C=O;

s is selected from integers of 1, 2 and 3;

where $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R^c$, —$CON(R^c)(R^{c'})$, —$C(=NH)N(R^c)(R^{c'})$, —$NR^c(O)$ $R^{c'}$, —$SO_2R^c$, —$SO_2NR^cR^{c'}$, —$N(R^c)$—$SO_2$—($C_1$-$C_6$ alkyl)-$NR^cR^{c'}$, —$N(R^c)$—$C(O)$—($C_1$-$C_6$ alkyl)-$NR^cR^{c'}$, —$NR^cS(O)R^{c'}$, —$NR^cSO_2R^{c'}$, —O—P(O) ($OR^c$)($OR^{c'}$), 6- to 12-membered aryl or 5- to 12-membered heteroaryl;

$R^5$ is selected from hydrogen or $C_1$-$C_6$ alkyl;

where $Q^{A1}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $Q^{A1}$ and $R^5$ together with the atoms adjacent thereto, form a 3- to 6-membered ring optionally containing 0, 1, or 2 heteroatoms selected from O, N, and S; $Q^2$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

where -$Q^{B1}$-B-$Q^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —(C₀-C₆ alkylene)-OC(O)—(C₀-C₆ alkylene)-, —(C₀-C₆ alkylene)-NR^c—C(O)—(C₀-C₆ alkylene)-, —(C₀-C₆ alkylene)-C(O)—NR^c—(C₀-C₆ alkylene)-, —(C₀-C₆ alkylene)-NR^c—(C₀-C₆ alkylene)-, —(C₀-C₆ alkylene)-C(O)O—(C₀-C₆ alkylene)-, —(C₀-C₆ alkylene)-(C₃-C₆ carbocyclyl)-(C₀-C₆ alkylene)-, —(C₀-C₆ alkylene)-(4- to 6-membered heterocyclyl)-(C₀-C₆ alkylene)-, —(C₀-C₆ alkylene)-(6- to 12-membered aryl)-(C₀-C₆ alkylene)-, and —(C₀-C₆ alkylene)-(5- to 12-membered heteroaryl)-(C₀-C₆ alkylene)-;

$R^I$ and $R^{II}$ each independently represent hydrogen or $C_1$-$C_6$ alkyl;

where $R^a$ and $R^{a'}$ each independently represent hydrogen, halogen, hydroxy, $C_1$-$C_6$ alkyl, $C_1$-$C_6$ alkylthio, —(C₀-C₆ alkylene)-(C₃-C₆ cycloalkyl), —(C₀-C₆ alkylene)-(4- to 6-membered heterocyclyl), —(C₀-C₆ alkylene)-(6- to 12-membered aryl), —(C₀-C₆ alkylene)-(5- to 12-membered heteroaryl), —NR^dR^d NR^dCOR^{d'}, —NR^dS(O)R^d NR^dSO₂R^d, —OR^d, or —OCOR^d;

$R^b$ each independently represents hydrogen, $C_1$-$C_6$ alkyl, $C_3$-$C_6$ cycloalkyl, —(C₀-C₆ alkylene)-(6- to 12-membered aryl), —C(O)R^e, —SOR^B, —SO₂R^e, —C(O)OR^e, or —C(O)NR^eR^{e'};

$R^c$ and $R^{c'}$ each independently represent hydrogen, $C_1$-$C_6$ alkyl, —(C₀-C₆ alkylene)-(C₃-C₆ cycloalkyl), or —(C₀-C₆ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

where m=1, 2, 3 or 4;
n=1, 2 or 3;
o=1 or 2; and
p=1 or 2;

or when m=2, the two adjacent $R^1$ and the atom bound thereto are optionally cyclized to each other into a 5- to 8-membered ring optionally containing 0, 1 or 2 heteroatoms selected from 0, N and S;

or when n=2, the two adjacent $R^2$ and the atom bound thereto are optionally cyclized to each other into a 5- to 8-membered ring optionally containing 0, 1 or 2 heteroatoms selected from 0, N and S;

or when p=2, the two adjacent $R^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR^f, —C(O)—OR^f, —OC(O)R^f, —S(O)R, —S(O)₂R, —S(O)₂NR^fR^{f'}, —OCONR^fR^{f'}, —NR^fCOR^{f'}, —NR^fS(O) R^{f'}, —NR^fS(O)₂R^{f'}, —NR^fC(O)OR^{f'}, —CONR^fR^{f'}, —NR^fR^{f'}, —NHC=NHNR^fR^{f'}, $C_1$-$C_6$ haloalkyl, $C_1$-$C_6$ haloalkoxy, and —O—P(O)(OR^f)(OR^{f'});

where $R^d$, $R^{d'}$, $R^e$, $R^{e'}$, $R^f$, and $R^{f'}$ each independently represent hydrogen or $C_1$-$C_6$ alkyl, where the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR^g, —C(O)—OR^g, —OC(O)R^g, —S(O)R^g, —S(O)₂R^g, —S(O)₂NR^gR^{g'}, —OCONR^gR^{g'}, —NR^gCOR^{g'}, —NR^gS(O) R^{g'}, —NR^gS(O)₂R^{g'}, —NR^gC(O)OR^{g'}, —CONR^gR^{g'}, —NR^gR^{g'}, $C_1$-$C_6$ haloalkyl, $C_1$-$C_6$ haloalkoxy, or —O—P(O)(OR^g)(OR^{g'});

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

where $R^g$ and $R^{g'}$ are each independently selected from hydrogen or $C_1$-$C_6$ alkyl.

One of objects of the present invention is to provide a compound having a structure of Formula (VI),

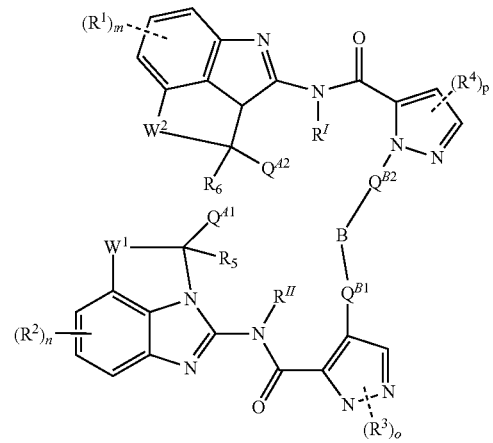

Formula (VI)

where $W^1$ represents $(CR^aR^{a'})_s$, where any one $CR^aR^{a'}$ is optionally substituted by 0, 1 or 2 O, S or NR^b, or any one $CR^aR^{a'}$ is optionally taken together to form —C=O;

$W^2$ represents $(CR^hR^{h'})_t$, where any one $CR^hR^{h'}$ is optionally substituted by 0, 1 or 2 O, S or NR^j, or any one $CR^hR^{h'}$ is optionally taken together to form —C=O;

s and t each independently consist of an integer selected from 1, 2, and 3;

where $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —OR^c, —O—(C₁-C₆ alkylene)-NR^cR^{c'}, —NR^cR^{c'}, —OC(O)R^c, —C(O)R^c, —CO₂R^c, —CON(R^c)(R^{c'}), —C(=NH)N(R^c)(R^{c'}), —NR^cC(O)R^{c'}, —SO₂R^c, —SO₂NR^cR^{c'}, —N(R^c)—SO₂—(C₁-C₆ alkyl)-NR^cR^{c'}, —N(R^c)—C(O)—(C₁-C₆ alkyl)-NR^cR^{c'}, —NR^cS(O)R^{c'}, —NR^cSO₂R^{c'}, —O—P(O)(OR^c)(OR^{c'}), 6- to 12-membered aryl, or 5- to 12-membered heteroaryl;

$R^5$ and $R^6$ are each independently selected from hydrogen or $C_1$-$C_6$ alkyl;

where $Q^{A1}$ is each independently selected from the group consisting of hydrogen, $C_1$-$C_6$ alkyl, $C_2$-$C_6$ alkenyl, $C_2$-$C_6$ alkynyl, —(C₀-C₆ alkyl)-(C₃-C₆ cycloalkyl), —(C₀-C₆ alkyl)-(4- to 6-membered heterocyclyl), —(C₀-C₆ alkyl)-(6- to 12-membered aryl), and —(C₀-C₆ alkyl)-(5- to 12-membered heteroaryl); or $Q^{A1}$ and $R^5$ together with the atoms adjacent thereto, form a 3- to 6-membered ring optionally containing 0, 1, or 2 heteroatoms selected from O, N, and S; Q is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $QA^2$ and $R^6$ together with the atoms adjacent thereto, form a 3- to 6-membered ring optionally containing 0, 1, or 2 heteroatoms selected from O, N, and S;

where -$Q^{B1}$-B-$Q^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-NR$^c$—C(O)—($C_0$-$C_6$ alkylene)-, —($C_0$-$C_6$ alkylene)-C(O)—NR$^c$—($C_0$-$C_6$ alkylene)-, —($C_0$-$C_6$ alkylene)-NR$^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$R^I$ and $R^{II}$ each independently represent hydrogen or $C_1$-$C_6$ alkyl;

where $R^a$, $R^{a'}$, $R^h$, and $R^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —NR$^d$R$^{d'}$, —NR$^d$COR$^{d'}$, —NR$^d$S(O)R$^{d'}$, —NR$^d$SO$_2$R$^{d'}$, —OR$^d$, or —OCOR$^d$;

$R^b$ and $R^j$ each independently represent hydrogen, $C_1$-$C_6$ alkyl, $C_3$-$C_6$ cycloalkyl, —($C_0$-$C_6$ alkylene)-(6- to 12-membered aryl), —C(O)R$^e$, —SOR$^e$, —SO$_2$R$^e$, —C(O)OR$^e$, or —C(O)NR$^e$R$^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

or $R^h$ and $R^{h'}$ together with the atom bound thereto are optionally cyclized to each other into a 3- to 6-membered ring optionally containing 0, 1, or 2 heteroatoms selected from O, N and S;

where m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from 0, N and S;

or when n=2, the two adjacent $R^2$ and the atom bound thereto are optionally cyclized to each other into a 5- to 8-membered ring optionally containing 0, 1 or 2 heteroatoms selected from 0, N and S;

or when p=2, the two adjacent $R^4$ and the atom bound thereto are optionally cyclized to each other into a 5- to 8-membered ring optionally containing 0, 1 or 2 heteroatoms selected from 0, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR$^f$, —C(O)—OR, —OC(O)R$^f$, —S(O)R, —S(O)$_2$R, —S(O)$_2$NR$^f$R$^{f'}$, —OCONR$^f$R$^{f'}$, —NR$^f$COR$^{f'}$, —NR$^f$S(O) R$^{f'}$, —NR$^f$S(O)$_2$R$^{f'}$, —R$^f$C(O)OR$^{f'}$, —CONR$^f$R$^{f'}$, —NR$^f$R$^{f'}$, $C_1$-$C_8$ haloalkyl, $C_1$-$C_8$ haloalkoxy, and —O—P(O)(OR$^f$)(OR$^{f'}$);

where $R^d$, $R^{d'}$, $R^e$, $R^{e'}$, $R^f$, and $R^{f'}$ each independently represent hydrogen or $C_1$-$C_6$ alkyl, where the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR$^g$, —C(O)—OR$^g$, —OC(O)R$^g$, —S(O)R$^g$, —S(O)$_2$R$^g$, —S(O)$_2$NR$^g$R$^{g'}$, —OCONR$^g$R$^{g'}$, —NR$^g$COR$^{g'}$, —NR$^g$S(O) R$^{g'}$, —NR$^g$S(O)$_2$R$^{g'}$, —NR$^g$C(O)OR$^{g'}$, —CONR$^g$R$^{g'}$, —NR$^g$R$^{g'}$, $C_1$-$C_6$ haloalkyl, $C_1$-$C_6$ haloalkoxy, or —O—P(O)(OR$^g$)(OR$^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

where $R^g$ and $R^{g'}$ are each independently selected from hydrogen or $C_1$-$C_6$ alkyl.

In some preferred embodiments of the present invention, $R^1$ and $R^2$ are each independently selected from hydrogen, halogen, cyano, $C_1$-$C_6$ alkyl, —OR$^c$, —O—($C_1$-$C_6$ alkylene)-NR$^c$R$^{c'}$, —NR$^c$R$^{c'}$, —CON(R$^c$)(R$^{c'}$), —C(=NH)N(R$^c$)(R$^{c'}$), and —NR$^c$C(O)R$^{c'}$.

In some preferred embodiments of the present invention, $R^1$ is each independently selected from: $C_1$-$C_6$ alkyl, $C_1$-$C_6$ alkoxy, —CON(R$^c$)(R$^{c'}$), —NR$^c$R$^{c'}$, and —O—($C_1$-$C_6$ alkylene)-NR$^c$R$^{c'}$.

In some preferred embodiments of the present invention, $R^1$ is each independently selected from: —O—($C_1$-$C_6$ alkylene)-NR$^c$R$^{c'}$.

In some preferred embodiments of the present invention, $R^2$ is each independently selected from: —CON(R$^c$)(R$^{c'}$).

In some preferred embodiments of the present invention, $R^c$ and $R^{c'}$ consist of hydrogen or $C_1$-$C_6$ alkyl, and are also optionally substituted by 0, 1, 2, 3 or 4 substituents selected from the group consisting of —OR$^d$, —C(O)—OR$^d$, —OC(O)R$^d$, —CONR$^d$R$^{d'}$, —NR$^d$R$^{d'}$, and —O—P(O)(OR$^d$)(OR$^{d'}$), where $R^d$ and $R^{d'}$ consist of hydrogen or $C_1$-$C_6$ alkyl, or $R^d$ and $R^{d'}$ together with the nitrogen atom adjacent thereto form a 5- to 8-membered carbocycle or a 5- to 8-membered heterocycle.

In some preferred embodiments of the present invention, $R^3$ and $R^4$ are each independently selected from the group consisting of hydrogen, $C_1$-$C_6$ alkyl, $C_3$-$C_6$ cycloalkyl, and $C_1$-$C_6$ haloalkyl.

In some preferred embodiments of the present invention, $R^5$ consists of hydrogen or $C_1$-$C_6$ alkyl.

In some preferred embodiments of the present invention, $R^6$ consists of hydrogen or $C_1$-$C_6$ alkyl.

In some preferred embodiments of the present invention, $W^1$ consists of —$(CR^aR^{a'})$—O—, —O—$(CR^aR^{a'})$—, —C(O)—$NR^b$—, or —$NR^b$—C(O)—, where $R^a$, $R^{a'}$, and $R^b$ independently represent hydrogen, $C_1$-$C_6$ alkyl, or $C_3$-$C_6$ cycloalkyl.

In some preferred embodiments of the present invention, $W^2$ consists of —$(CR^hR^{h'})$—O—, —O—$(CR^hR^{h'})$—, —C(O)—$NR^j$—, or —$NR^j$—C(O)—, where $R^h$, $R^{h'}$, and $R^j$ each independently represent hydrogen, $C_1$-$C_6$ alkyl, or $C_3$-$C_6$ cycloalkyl.

In some preferred embodiments of the present invention, when q=1, -$Q^{A1}$-A-$Q^{A2}$- is taken together to form —$CH_2CH_2CH_2CH_2$—, —$CH_2CH=CHCH_2$—, —CH(OH)CH(OH)CH_2—, —$CH_2CH_2CH_2$—, —$CH_2CH=CH$—, —CH(OH)CH_2CH_2—, —CH=CHCH_2—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —CH=CH—, —$CH_2CH_2$—, —CH(OH)CH_2, —$CH_2CH(OH)$—, or —$CH_2OCH_2CH_2$—.

In some preferred embodiments of the present invention, -$Q^{A1}$-A-$Q^{A2}$- is taken together to form —$CH_2CH_2CH_2CH_2$—, —$CH_2CH=CHCH_2$—, —CH(OH)CH(OH)CH_2—, —$CH_2CH_2CH_2$—, —$CH_2CH=CH$—, —CH(OH)CH_2CH_2—, —CH=CHCH_2—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —CH=CH—, —$CH_2CH_2$—, —CH(OH)CH_2, —$CH_2CH(OH)$—, or —$CH_2OCH_2CH_2$—.

In some preferred embodiments of the present invention, when q=0, $Q^{A1}$ and $Q^2$ are each independently selected from the group consisting of hydrogen, $C_1$-$C_6$ alkyl, $C_1$-$C_6$ haloalkyl, $C_2$-$C_6$ alkenyl, and $C_3$-$C_6$ cycloalkyl.

In some preferred embodiments of the present invention, when r=0, $Q^{B1}$ and $Q^{B2}$ are each independently selected from the group consisting of hydrogen, $C_1$-$C_6$ alkyl, $C_1$-$C_6$ haloalkyl, $C_2$-$C_6$ alkenyl, and $C_3$-$C_6$ cycloalkyl.

In some preferred embodiments of the present invention, when r=1, -$Q^{B1}$-A-$Q^{B2}$- is taken together to form —$CH_2CH_2CH_2CH_2$—, —$CH_2CH=CHCH_2$—, —CH(OH)CH(OH)CH_2—, —$CH_2CH_2CH_2$—, —$CH_2CH=CH$—, —CH(OH)CH_2CH_2—, —CH=CHCH_2—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —CH=CH—, —$CH_2CH_2$—, —CH(OH)CH_2, —$CH_2CH(OH)$—, or —$CH_2OCH_2CH_2$—.

In some preferred embodiments of the present invention, -$Q^{B1}$-A-$Q^{B2}$- is taken together to form —$CH_2CH_2CH_2CH_2$—, —$CH_2CH=CHCH_2$—, —CH(OH)CH(OH)CH_2—, —$CH_2CH_2CH_2$—, —$CH_2CH=CH$—, —CH(OH)CH_2CH_2—, —CH=CHCH_2—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —CH=CH—, —$CH_2CH_2$—, —CH(OH)CH_2, —$CH_2CH(OH)$—, or —$CH_2OCH_2CH_2$—.

When reference is made herein to a "compound" having a specific structural formula, stereoisomers, diastereomers, enantiomers, racemic mixtures, and isotopic derivatives thereof are also generally contemplated.

It is well known to those skilled in the art that a salt, solvate, and hydrate of a compound is an alternative form of the compound that can be converted to the compound under conditions; therefore, reference to a compound generally includes pharmaceutically acceptable salts thereof, and further includes solvates and hydrates thereof.

Similarly, when a compound is referred to herein, prodrugs, metabolites, and nitrogen oxides thereof are also generally included.

The pharmaceutically acceptable salts described herein may be formed using, for example, the following inorganic or organic acids: "pharmaceutically acceptable salt" means a salt that is, within the scope of sound medical judgment, suitable for use in contact with the tissues of humans and lower animals without undue toxicity, irritation, and allergic response, commensurate with a reasonable benefit/risk ratio. As outlined below, the salts may be prepared in situ during the final isolation and purification of the compounds of the present invention, or prepared by reacting the free base or free acid with a suitable reagent separately. For example, the free base function may be reacted with a suitable acid. In addition, when the compounds of the present invention carry an acidic moiety, suitable pharmaceutically acceptable salts thereof may include metal salts, such as alkali metal salts (e.g., sodium or potassium salts); and alkaline earth metal salts (e.g., calcium or magnesium salts). Examples of pharmaceutically acceptable non-toxic acid addition salts are salts formed by amino groups with inorganic acids (e.g., hydrochloric acid, hydrobromic acid, phosphoric acid, sulfuric acid, and perchloric acid) or organic acids (e.g., acetic acid, oxalic acid, maleic acid, tartaric acid, citric acid, succinic acid, or malonic acid), or formed by using other methods known in the prior art such as ion exchange. Other pharmaceutically acceptable salts include adipate, sodium alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfonate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectate, persulfate, 3-phenylpropionate, phosphate, picrate, pivalate, propionate, stearate, succinate, sulfate, tartrate, thiocyanate, p-toluenesulfonate, undecanoate, and valerate. Representative alkali metal or alkaline earth metal salts include salts of sodium, lithium, potassium, calcium, and magnesium. Other pharmaceutically acceptable salts include, nontoxic ammonium salts (where appropriate), quaternary ammonium salts, and amine cations formed with counterions, for example, halides, hydroxides, carboxylates, sulfates, phosphates, nitrates, lower alkyl sulfonates, and aryl sulfonates.

The pharmaceutically acceptable salts of the present invention can be prepared by a conventional method, for example, by dissolving the compound of the present invention in a water-miscible organic solvent (e.g., acetone, methanol, ethanol, and acetonitrile), adding an excess of an aqueous organic or inorganic acid thereto to precipitate the salt from the resulting mixture, removing the solvent and remaining free acid therefrom, and then isolating the precipitated salt.

The precursors or metabolites of the present invention may be those known in the art as long as the precursors or metabolites are converted into compounds by metabolism in vivo. For example, "prodrugs" refer to those of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use. The term "prodrugs" refer to compounds which yield the parent compounds of the above formulae rapidly through transformation in vivo, for example, through metabolism in vivo, or N-demethylation of a compound of the present invention.

"Solvate" as used herein means a physical association of a compound of the present invention with one or more solvent molecules (whether organic or inorganic). The physical association includes hydrogen bonding. In some cases, for example when one or more solvent molecules are incorporated in the crystal lattice of the crystalline solid, the solvate will be capable of being isolated. The solvent molecules in the solvate may be present in a regular and/or disordered arrangement. Solvates may include stoichiometric or non-stoichiometric solvent molecules. "Solvate" encompasses both solution-phase and isolatable solvates. Exemplary solvates include, but are not limited to, hydrates, ethanolates, methanolates, and isopropanolates. Methods of solvation are well known in the art.

The "stereoisomerism" disclosed by the persent invention is intended to include conformational isomerism and configurational isomerism, where the configurational isomerism may also be intended to include cis-trans isomerism and rotational isomerism (i.e. optical isomerism); and the conformational isomerism refers to a stereoisomerism phenomenon in which the rotation or distortion of the carbon-carbon single bond of an organic molecule with a certain configuration makes the atoms or atomic groups of the molecule produce different arrangements in space, and common examples include the structures of alkanes and cycloalkanes, such as chair and boat conformations as found in the cyclohexane structure. "Stereoisomers" means when the compounds of the present invention contain one or more asymmetric centers, thus they can be served as racemates and racemic mixtures, single enantiomers, diastereomeric mixtures, and single diastereomers. The compounds of the present invention have asymmetric centers, each of which produces two optical isomers, and the scope of the present invention includes all possible optical isomers and diastereomeric mixtures and pure or partially pure compounds. The compounds of the present invention may exist in the form of tautomers, which have different linking points of hydrogen through the displacement of one or more double bonds. For example, ketone and its enol form are keto-enol tautomers. Each tautomer and mixtures thereof are included in the compounds of the present invention. All enantiomers, diastereomers, racemates, mesomers, cis-trans-isomers, tautomers, geometric isomers, epimers, and mixtures thereof of the compounds of Formula (I) are included within the scope of the present invention.

An "isotopic derivative" of the present invention refers to a molecule in which a compound is labeled with an isotope in this patent. Isotopes commonly used as isotopic labels are: hydrogen isotopes, $^2H$ and $^3H$; carbon isotope: $^{11}C$ $^{13}C$ and $^{14}C$; chlorine isotope: $^{35}Cl$ and $^{37}Cl$; fluorine isotope: $^{18}F$; iodine isotope: $^{123}I$ and $^{125}I$; nitrogen isotopes: $^{13}N$ and $^{15}N$; oxygen isotopes: $^{15}O$, $^{17}O$ and $^{18}O$ and sulfur isotope $^{35}S$. These isotopically labeled compounds can be used to study the distribution of pharmaceutical molecules in tissues. Deuterium $^3H$ and carbon $^{13}C$, in particular, are more widely used due to their ease of labeling and ease of detection. Substitution of certain heavy isotopes, such as heavy hydrogen ($^2H$), may enhance metabolic stability, prolong the half-life, and provide therapeutic advantages resulting from reduced dosage. Generally, starting from the labeled starting materials, isotopically-labeled compounds are synthesized by using known synthesis techniques in the same way as the synthesis of non-isotopically labeled compounds.

The present invention also provides use of the compound of the present invention in the preparation of a medicament for the prevention and/or treatment of cancer, tumors, inflammatory diseases, autoimmune diseases or immune-mediated diseases.

In addition, the present invention provides a pharmaceutical composition for the prevention and/or treatment of cancer, tumors, inflammatory diseases, autoimmune diseases, neurodegenerative diseases, attention-related diseases or immune-mediated diseases, including the compound of the present invention as an active ingredient.

The present invention also provides a method of agonizing a STING protein, including exposing a compound or pharmaceutical composition or pharmaceutical formulation of the present invention to the STING protein.

The present invention also provides a method for the prevention and/or treatment of diseases which can be prevented and/or treated by agonizing STING proteins, including administering to a subject in need thereof a compound or a pharmaceutical composition of the present invention.

Furthermore, the present invention provides a method for the prevention and/or treatment of cancer, tumors, inflammatory diseases, autoimmune diseases, neurodegenerative diseases, attention-related diseases or immune-mediated diseases, including administering to a subject in need thereof a compound or pharmaceutical composition of the present invention.

Representative examples of inflammatory diseases, autoimmune diseases, and immune-mediated diseases may include, but are not limited to, arthritis, rheumatoid arthritis, spondyloarthritis, gouty arthritis, osteoarthritis, juvenile arthritis, other arthritic conditions, lupus, systemic lupus erythematosus (SLE), skin-related diseases, psoriasis, eczema, dermatitis, allergic dermatitis, pain, lung disease, lung Inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia-reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenotransplantation, idiopathic thrombocytopenic purpura (ITP), Parkinson's disease, Alzheimer's disease, diabetes-related diseases, inflammation, pelvic inflammatory diseases, allergic rhinitis, allergic bronchitis, allergic sinusitis, leukemia, lymphoma, B-cell lymphoma, T-cell lymphoma, myeloma, acute lymphocytic leukemia (ALL), chronic lymphocytic leukemia (CLL), acute myelogenous leukemia (ANVIL), chronic myelogenous leukemia (CML), hairy cell leukemia, Hodgkin's disease, non-Hodgkin's lymphoma, multiple myeloma, myelodysplastic syndrome (KIDS), myeloproliferative tumor (NWN), diffuse large B-cell lymphoma, and follicular lymphoma.

Representative examples of cancers or tumors may include, but are not limited to, skin cancer, bladder cancer, ovarian cancer, breast cancer, gastric cancer, pancreatic cancer, prostate cancer, colon cancer, lung cancer, bone cancer, brain cancer, neurocytoma, rectal cancer, colon cancer, familial adenomatous polyposis cancer, hereditary nonpolyposis colorectal cancer, esophageal cancer, lip cancer, laryngeal cancer, hypopharyngeal cancer, tongue cancer, salivary gland cancer, gastric cancer, adenocarcinoma, medullary thyroid cancer, papillary thyroid cancer, renal cancer, carcinoma of renal parenchyma, ovarian cancer, cervical cancer, corpus carcinoma, endometrial cancer, choriocarcinoma, pancreatic cancer, prostate cancer, testicular cancer, carcinoma of urinary system, melanoma, brain tumors such as glioblastoma, astrocytoma, meningioma, medulloblastoma and peripheral neuroectodermal tumors, Hodgkin's lymphoma, non-Hodgkin's lymphoma, Burkitt's lymphoma, acute lymphoblastic leukemia (ALL), chronic lymphocytic leukemia (CLL), acute myelogenous leukemia (AML,), chronic myelogenous leukemia (CIVIL), adult T-cell leukemia lymphoma, diffuse large B-cell lymphoma (DLBCL), hepatocellular carcinoma, gallbladder carcinoma, bronchial carcinoma, small cell lung carcinoma, non-small cell lung carcinoma, multiple myeloma, basal cell tumor, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, or plasmacytoma.

When a compound of the present invention or a pharmaceutically acceptable salt thereof is administered in combination with another anticancer agent or immune checkpoint inhibitor for the treatment of cancer or tumors, the compound of the present invention or a pharmaceutically acceptable salt thereof may provide an enhanced anticancer effect.

Representative examples of anti-cancer agents for treating a cancer or tumor may include, but are not limited to, cell signal transduction inhibitors, Chlorambucil, Melphalan, Cyclophosphamide, Ifosfamide, Busulfan, Carmustine, Lomustine, Streptozotocin, Cisplatin, Carboplatin, Oxaliplatin, Dacarbazine, Temozolomide, Procarbazine, Methotrexate, Fluorouracil, Cytarabine, Gemcitabine, Mercaptopurine, Fludarabine, Vinblastine, Vincristine, Vinorelbine, Paclitaxel, Docetaxel, Topotecan, Irinotecan, Etoposide, Trabectedin, Dactinomycin, Doxorubicin, Epirubicin, Daunorubicin, Mitoxantrone, Bleomycin, Mitomycin C, Ixabepilone, Tamoxifen, Flutamide, Gonadorelin Analogs, Megestrol, Prednisone, Dexamethasone, Methylprednisolone, Thalidomide, Interferon A, Calcium Folinate, Sirolimus, Sirolimus Lipide, Everolimus, Afatinib, Alisertib, Amuvatinib, Apatinib, Axitinib, Bortezomib, Bosutinib, Brivanib, Cabozantinib, Cediranib, Crenolanib, Crizotinib, Dabrafenib, Dacomitinib, Danusertib, Dasatinib, Dovitinib, Erlotinib, Foretinib, Ganetespib, Gefitinib, Ibrutinib, Icotinib, Imatinib, Iniparib, Lapatinib, Lenvatinib, Linifanib, Linsitinib, Masitinib, Momelotinib, Motesanib, Neratinib Nilotinib, Niraparib, Oprozomib, Olaparib, Pazopanib, Pictiliisib, Ponatinib, Quizartinib, Regorafenib, Rigosertib, Rucaparib, Ruxolitinib, Saracatinib, Saridegib, Sorafenib, Sunitinib, Telatinib, Tivantinib, Tivozanib, Tofacitinib, Trametinib, Vandetanib, Veliparib, Vemurafenib, Erivedge, Volasertib, Alemtuzumab, Bevacizumab, Brentuximab Vedotin, Catumaxomab, Cetuximab, Denosumab, Gemtuzumab, Ipilimumab, Nimotuzumab, Ofatumumab, Panitumumab, Rituximab, Tositumomab, Trastuzumab, PI3K inhibitors, CSF1R inhibitors, A2A and/or A2B receptor antagonists, IDO inhibitors, anti-PD-1 antibodies, anti-PD-L1 antibodies, LAG3 antibodies, TIM-3 antibodies, and anti-CTLA-4 antibodies, or any combination thereof.

When a compound of the present invention or a pharmaceutically acceptable salt thereof is administered in combination with another therapeutic agent for the treatment of inflammatory diseases, autoimmune diseases and immune-mediated diseases, the compound of the present invention or a pharmaceutically acceptable salt thereof may provide an enhanced therapeutic effect.

Representative examples of therapeutic agents for the treatment of inflammatory diseases, autoimmune diseases, and immune-mediated diseases may include, but are not limited to, steroidal drugs (e.g., prednisone, prednisolone, methylprednisolone, cortisone, hydroxycortisone, betamethasone, dexamethasone, etc.), methotrexate, leflunomide, anti-TNF a agents (e.g., etanercept, infliximab, adalimumab, etc.), calcineurin inhibitors (e.g., tacrolimus, pimecrolimus, etc.), and antihistamines (e.g., diphenhydramine, hydroxyzine, loratadine, ebastine, ketotifen, cetirizine, levocetirizine, fexofenadine, etc.), and at least one therapeutic agent selected therefrom may be included in the pharmaceutical compositions of the present invention.

The compound of the present invention or a pharmaceutically acceptable salt thereof can be administered orally or parenterally as an active ingredient in an effective amount ranging from 0.1 mg/kg body weight/day to 2,000 mg/kg body weight/day, preferably 1 mg/kg body weight/day to 1,000 mg/kg body weight/day in the case of mammals including humans (body weight about 70 kg), and administered in a single or four divided doses per day, or following/not following a predetermined time. The dosage of the active ingredient may be adjusted according to a number of relevant factors, such as the condition of the subject to be treated, the type and severity of the disease, the rate of administration and the opinion of the physician). In some cases, amounts less than the above doses may be suitable. If it does not cause harmful side effects, an amount larger than the above dose can be used and the amount can be administered in divided doses per day.

The pharmaceutical compositions of the present invention may be formulated into dosage forms, such as tablets, granules, powders, capsules, syrups, emulsions, microemulsions, solutions or suspensions, for oral or parenteral administration (including intramuscular, intravenous and subcutaneous routes) according to any of the conventional methods.

The pharmaceutical compositions of the present invention for oral administration may be prepared by mixing the active ingredient with carriers such as: cellulose, calcium silicate, corn starch, lactose, sucrose, dextrose, calcium phosphate, stearic acid, magnesium stearate, calcium stearate, gelatin, talc, surfactants, suspending agents, emulsifying agents, and diluents. Examples of carriers employed in the injectable compositions of the present invention consist of water, saline solutions, dextrose solutions, glucose-like solutions, alcohols, glycols, ethers (e.g., polyethylene glycol 400), oils, fatty acids, fatty acid esters, glycerides, surfactants, suspending agents, and emulsifying agents.

Additional features of the present invention will become apparent from the description of exemplary embodiments of the present invention which are presented for purposes of illustration and are not intended to be limiting thereof, and the following examples are prepared, isolated and characterized using the methods disclosed herein.

The compounds of the present invention may be prepared in a variety of ways known to those skilled in the art of organic synthesis, and may be synthesized using the methods described below, as well as synthetic methods known in the art of organic synthetic chemistry, or by variations thereof known to those skilled in the art. Preferred methods include, but are not limited to, those described below. The reaction is carried out in a solvent or solvent mixture suitable for the kit materials used and for the transformations achieved. Those skilled in the art of organic synthesis will appreciate that the functionality present on the molecule is consistent with the proposed transformations. This sometimes requires judgment to modify the order of the synthetic steps or starting materials in order to obtain the desired compounds of the present invention.

DETAILED DESCRIPTION

Terms

Terms used in the present application, including the specification and claims, are defined as follows, unless otherwise indicated. It must be noted that, in the description and the appended claims, the singular forms "a", "an", and "the" include plural referents unless the context clearly dictates otherwise. If not stated otherwise, conventional methods of mass spectrometry, nuclear magnetic, HPLC, protein chemistry, biochemistry, recombinant DNA techniques and pharmacology are used. In this application, the use of "or" or "and" means "and/or" if not stated otherwise.

Throughout the specification and claims, a given chemical formula or name shall encompass all stereo and optical isomers and racemates in which such isomers exist. Unless otherwise indicated, all chiral (enantiome and diastereoisomer) and racemic forms are within the scope of the present invention. Many geometric isomers of C=C double bonds, C=N double bonds, and ring systems may also be present in the compounds, and all the above stable isomers are encompassed in the present invention. Cis- and trans-(or E- and Z—) geometric isomers of the compounds of the present invention are described herein and may be isolated as mixtures of isomers or as separated isomeric forms. The compounds of the present invention may be isolated in optically active or racemic forms. All methods for preparing the compounds of the present invention and intermediates prepared therein are considered part of the present invention. In preparing enantiomeric or diastereomeric products, they can be isolated by conventional methods, for example, by chromatography or fractional crystallization. Depending on the process conditions, the final products of the present invention are obtained in free (neutral) or salt form. Both the free forms and salts of these end products are within the scope of the present invention. If desired, one form of the compound may be converted to another form. The free base or acid may be converted to a salt; the salt may be converted to the free compound or another salt; mixtures of isomeric compounds of the present invention may be isolated into the individual isomers. The compounds, free forms and salts thereof of the present invention, may exist in a variety of tautomeric forms in which hydrogen atoms are transposed onto other parts of the molecule and the chemical bonds between the atoms of the molecule are thus rearranged. It is to be understood that all tautomeric forms which may exist are included in the present invention.

Unless otherwise defined, the definitions of substituents of the present invention are each independent and not interrelated, e.g., for $R^a$ (or $R^{a'}$) in substituents, they are each independent in the definition of different substituents. Specifically, when a definition of $R^a$ (or $R^{a'}$) is selected in a substituent, it does not mean that $R^a$ (or $R^{a'}$) has the same definition in other substituents. More specifically, for example (a non-exhaustive list) for $NR^aR^{a'}$, when the definition of $R^a$ (or $R^{a'}$) is selected from hydrogen, it does not mean that in —C(O)—$NR^aR^{a'}$, $R^a$ (or $R^{a'}$) must be hydrogen.

Unless otherwise defined, when a substituent is labeled "optionally substituted", the substituent is selected from, for example, the following substituents consisting of alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine group (in which two amino substituents are selected from alkyl, aryl or arylalkyl), alkanoylamino, aroylamino, aralkanoylamino, substituted alkanoylamino, substituted arylamino, substituted aralkanoylamino, thio, alkylthio, arylthio, arylalkylthio, arylthiocarbonyl, arylalkylthiocarbonyl, alkylsulfonyl, arylsulfonyl, arylalkylsulfonyl, sulfonamido such as —$SO_2NH_2$, substituted sulfonamido, nitro, cyano, carboxy, carbamoyl such as —$CONH_2$, substituted carbamoyl such as —CONH alkyl, —CONH aryl, —CONH arylalkyl or the case where there are two substituents selected from alkyl, aryl or arylalkyl on the nitrogen, alkoxycarbonyl, aryl, substituted aryl, guanidino, heterocyclyl such as indolyl, imidazolyl, furanyl, thienyl, thiazolyl, pyrrolidinyl, pyridyl, pyrimidinyl, pyrrolidinyl, piperidinyl, morpholinyl, piperazinyl, and homopiperazinyl, and substituted heterocyclyl.

As used herein, the term "alkyl" or "alkylene" is intended to include both branched and straight chain saturated aliphatic hydrocarbon groups having the specified number of carbon atoms. For example, "C1-C6 alkyl" denotes an alkyl group having 1 to 6 carbon atoms. Examples of alkyl groups include, but are not limited to, methyl (Me), ethyl (Et), propyl (e.g., n-propyl and isopropyl), butyl (e.g., n-butyl, isobutyl, tert-butyl), and pentyl (e.g., n-pentyl, isopentyl, neopentyl).

The term "alkenyl" denotes a straight or branched chain hydrocarbon group containing one or more double bonds and typically 2 to 20 carbon atoms in length. For example, "C2-C6 alkenyl" contains 2 to 6 carbon atoms. Alkenyl groups include, but are not limited to, for example, ethenyl, propenyl, butenyl, and 1-methyl-2-buten-1-yl.

The term "alkynyl" denotes a straight or branched chain hydrocarbon group containing one or more triple bonds and typically 2 to 20 carbon atoms in length. For example, "C2-C6 alkynyl" contains 2 to 6 carbon atoms. Representative alkynyl groups include, but are not limited to, for example, ethynyl, 1-propynyl, and 1-butynyl.

The term "alkoxy" or "alkyloxy" refers to —O-alkyl. "C1-C6 alkoxy" (or alkyloxy) is intended to include C1, C2, C3, C4, C5, and C6 alkoxy. Examples of alkoxy groups include, but are not limited to, methoxy, ethoxy, propoxy (e.g., n-propoxy and isopropoxy), and t-butoxy. Similarly, "alkylthio" or "thioalkoxy" means an alkyl group, as defined above, with the specified number of carbon atoms linked via a sulfur bridge; for example, methyl-S- and ethyl-S—.

The term "carbonyl" refers to an organic functional group (C=O) composed of two carbon and oxygen atoms linked by a double bond.

The term "aryl", alone or as part of a larger moiety such as "aralkyl", "aralkoxy", or "aryloxyalkyl", refers to a monocyclic, bicyclic, or tricyclic ring system having a total of 5 to 12 ring members, where at least one ring in the system is aromatic and where each ring in the system contains 3 to 7 ring members. In certain embodiments of the present invention, "aryl" refers to an aromatic ring system including, but not limited to, phenyl, biphenyl, indanyl, 1-naphthyl, 2-naphthyl, and tetrahydronaphthyl. The term "aralkyl" or "arylalkyl" refers to an alkyl residue attached to an aryl ring. Non-limiting examples include benzyl, and phenethyl. The fused aryl group may be attached to another group at a suitable position on the cycloalkyl ring or the aromatic ring. For example, a dashed line drawn from a ring system indicates that the bond may be attached to any suitable ring atom.

The term "cycloalkyl" refers to a monocyclic or bicyclic alkyl group. Monocyclic alkyl refers to C3-C8 cyclic alkyl including, but not limited to, cyclopropyl, cyclobutyl, cyclopentyl, cyclohexyl, and norbornyl. Branched cycloalkyl such as 1-methylcyclopropyl and 2-methylcyclopropyl are included in the definition of "cycloalkyl". Bicyclic alkyl includes bridged, spiro, or fused cycloalkyl.

The term "cycloalkenyl" refers to a monocyclic or bicyclic alkenyl group. Monocyclic alkenyl refers to C3-C8 cyclic alkenyl including, but not limited to, cyclopropenyl, cyclobutenyl, cyclopentenyl, cyclohexenyl, and norbornenyl. Branched cycloalkenyl such as 1-methylcyclopropenyl and 2-methylcyclopropenyl are included in the definition of "cycloalkenyl". Bicyclic alkenyl includes bridged, spiro or fused cyclic alkenyl.

"Halo" or "halogen" includes fluoro, chloro, bromo and iodo. "Haloalkyl" is intended to include both branched and straight-chain saturated aliphatic hydrocarbon groups having the specified number of carbon atoms and substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" groups intended to include branched and straight chain saturated aliphatic hydrocarbon groups having the specified number of carbon atoms and substituted with one or more fluorine atoms.

"Haloalkoxy" or "haloalkyloxy" denotes a haloalkyl group, as defined above, having the indicated number of carbon atoms linked via an oxygen bridge. For example, "C1-C6 haloalkoxy" is intended to include C1, C2, C3, C4, C5, and C6 haloalkoxy. Examples of haloalkoxy include, but are not limited to, trifluoromethoxy, 2,2,2-trifluoroethoxy, and pentafluoroethoxy. Similarly, "haloalkylthio" or "thiohaloalkoxy" denotes a haloalkyl group, as defined above, having the indicated number of carbon atoms linked via a sulfur bridge; for example, trifluoromethyl-S— and pentafluoroethyl-S—.

In the present disclosure, the expression Cx1-Cx2 is used when referring to some substituent groups, which means that the number of carbon atoms in the substituent group may be x1 to x2. For example, C0-C8 means that the group contains 0, 1, 2, 3, 4, 5, 6, 7 or 8 carbon atoms, C1-C8 means that the group contains 1, 2, 3, 4, 5, 6, 7 or 8 carbon atoms, C2-C8 means that the group contains 2, 3, 4, 5, 6, 7 or 8 carbon atoms, C3-C8 means that the group contains 3, 4, 5, 6, 7 or 8 carbon atoms, C4-C8 means that the group contains 4, 5, 6, 7 or 8 carbon atoms, C0-C6 means that the group contains 0, 1, 2, 3, 4, 5 or 6 carbon atoms, C1-C6 means that the group contains 1, 2, 3, 4, 5 or 6 carbon atoms, C2-C6 means that the group contains 2, 3, 4, 5 or 6 carbon atoms, and C3-C6 means that the group contains 3, 4, 5 or 6 carbon atoms.

In the present disclosure, the expression "x1-x2 membered ring" is used when referring to cyclic groups such as aryl, heteroaryl, cycloalkyl and heterocycloalkyl, which means that the number of ring atoms of the group may be x1 to x2. For example, the 3- to 12-membered cyclic group (e.g., cycloalkyl or heterocycloalkyl) may be a 3, 4, 5, 6, 7, 8, 9, 10, 11, or 12 membered ring, the number of ring atoms of which may be 3, 4, 5, 6, 7, 8, 9, 10, 11, or 12; the 3- to 6-membered ring means that the cyclic group may be a 3, 4, 5 or 6 membered ring, the number of ring atoms of which may be 3, 4, 5 or 6; the 3- to 8-membered ring means that the cyclic group may be a 3, 4, 5, 6, 7 or 8 membered ring, the number of ring atoms of which may be 3, 4, 5, 6, 7 or 8; the 3- to 9-membered ring means that the cyclic group may be a 3, 4, 5, 6, 7, 8 or 9 membered ring, the number of ring atoms of which may be 3, 4, 5, 6, 7, 8 or 9; the 4- to 7-membered ring means that the cyclic group may be a 4, 5, 6 or 7 membered ring, the number of ring atoms of which may be 4, 5, 6 or 7; the 5- to 8-membered ring means that the cyclic group may be a 5, 6, 7 or 8 membered ring, the number of ring atoms of which may be 5, 6, 7 or 8; the 5- to 12-membered ring means that the cyclic group may be a 5, 6, 7, 8, 9, 10, 11 or 12 membered ring, the number of ring atoms of which may be 5, 6, 7, 8, 9, 10, 11 or 12; and the 6- to 12-membered ring means that the cyclic group may be a 6, 7, 8, 9, 10, 11 or 12 membered ring, the number of ring atoms of which may be 6, 7, 8, 9, 10, 11 or 12. The ring atom may be a carbon atom or a heteroatom, for example, a heteroatom selected from N, O and S. When the ring is a heterocycle, the heterocycle may contain 1, 2, 3, 4, 5, 6, 7, 8, 9, 10 or more ring heteroatoms, for example, a heteroatom selected from N, O and S.

In the present disclosure, one or more halogens may each independently be selected from fluorine, chlorine, bromine, and iodine.

The term "heteroaryl" means a stable 3-, 4-, 5-, 6-, or 7-membered aromatic monocyclic or aromatic bicyclic or 7-, 8-, 9-, 10-, 11-, 12-membered aromatic polycyclic heterocycle, which is fully unsaturated, partially unsaturated, and contains carbon atoms and 1, 2, 3 or 4 heteroatoms independently selected from N, O and S; and includes any polycyclic group in which any heterocycle defined above is fused to a benzene ring. The nitrogen and sulfur heteroatoms may optionally be oxidized. The nitrogen atom is substituted or unsubstituted (i.e., N or NR, where R is H or another substituent if defined). The heterocycle may be attached to its pendant group at any heteroatom or carbon atom that results in a stable structure. If the resulting compound is stable, the heterocyclyl groups described herein may be substituted on a carbon or nitrogen atom. The nitrogen in the heterocycle may be optionally quaternized. Preferably, when the total number of S and O atoms in the heterocycle exceeds 1, then these heteroatoms are not adjacent to each other. Preferably, the total number of S and O atoms in the heterocycle is not greater than 1. When the term "heterocycle" is used, it is intended to include heteroaryl. Examples of heteroaryls include, but are not limited to, acridinyl, azetidinyl, azocinyl, benzimidazolyl, benzofuranyl, benzothiofuranyl, benzothienyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, imidazopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinyl, perimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4- thiadiazolyl, thianthrenyl, thiazolyl, thienyl, thiazolopyridyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl and xanthenyl, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl and 1,2,3,4-tetrahydro-quinazolinyl. The term "heteroaryl" may also include biaryl structures formed from "aryl" and monocyclic "heteroaryl" as defined above, for example, but not limited to "-phenylbipyridyl-", "-phenylbipyrimidinyl", "-pyridylbiphenyl", "-pyridylbipyrimidinyl-", "-pyrimidinylbiphenyl-"; where the present invention also includes fused and spiro compounds containing, for example, the above heterocycles.

As used herein, the term "heterocycloalkyl" refers to a monocyclic heterocycloalkyl system, or a bicyclic heterocycloalkyl system, and also includes spiroheterocycles or bridged heterocycloalkyl groups. The monocyclic heterocycloalkyl refers to a saturated or unsaturated but not aromatic 3- to 8-membered cyclic alkyl system containing at least one atom selected from O, N, S, and P. The bicyclic heterocycloalkyl system refers to a heterocycloalkyl fused with a phenyl, or a cycloalkyl, or a cycloalkenyl, or a heterocycloalkyl, or a heteroaryl.

As used herein, the term "bridged cycloalkyl" refers to polycyclic compounds that share two or more carbon atoms, including bicyclic bridged cyclic hydrocarbons and polycyclic bridged cyclic hydrocarbons. The former are composed of two alicyclic rings sharing more than two carbon atoms; the latter are a bridged cyclic hydrocarbons consisting of more than three rings.

As used herein, the term "spirocycloalkyl" refers to polycyclic hydrocarbons that share one carbon atom (referred to as a spiro atom) between single rings.

As used herein, the term "bridged cycloheteryl" refers to polycyclic compounds that share two or more carbon atoms, and contain at least one atom selected from O, N, S, including bicyclic bridged heterocycles and polycyclic bridged heterocycles.

As used herein, the term "heterospirocyclyl" refers to polycyclic hydrocarbons that share one carbon atom (referred to as a spiro atom) between single rings, and contain at least one atom selected from O, N, S.

As used herein, the term "substituted" means that at least one hydrogen atom is substituted with a non-hydrogen group, provided that normal valency is maintained and that the substitution results in a stable compound. As used herein, the ring double bond is a double bond (e.g., C=C, C=N, or N=N) formed between two adjacent ring atoms.

In the case where nitrogen atoms (e.g., amines) are present on the compounds of the present invention, these nitrogen atoms may be converted to N-oxides by treatment with an oxidizing agent (e.g., mCPBA and/or hydrogen peroxide) to obtain other compounds of the present invention. Thus, the nitrogen atoms shown and claimed are considered to encompass both the nitrogen shown and its N-oxides to obtain the derivatives of the present invention.

When any variable occurs more than once in any composition or formula of a compound, its definition at each occurrence is independent of its definition at every other occurrence. Thus, for example, if a group is shown to be substituted with 0-3R, the group may be optionally substituted with up to three R groups, and at each occurrence R is independently selected from the definition of R. Furthermore, combinations of substituents and/or variables are permissible only if such combinations result in stable compounds.

As used herein, the term "patient" refers to an organism treated by the methods of the present invention. Such organisms preferably include, but are not limited to, mammals (e.g., murine, ape/monkey, equine, bovine, swine, canine, feline, etc.) and most preferably refer to humans.

As used herein, the term "effective amount" means an amount of a drug or pharmaceutical agent (i.e., a compound of the present invention) that will elicit the biological or medical response of a tissue, system, animal or human that is being sought, for example, by a researcher or clinician. Furthermore, the term "therapeutically effective amount" means an amount results in an improved treatment, cure, prevention or alleviation of a disease, disorder or side effect, or a reduction in the rate of progression of a disease or disorder, as compared to a corresponding subject not receiving such an amount. An effective amount can be administered in one or more dosing, administrations, or dosages and is not intended to be limited by the particular formulation or route of administration. The term also includes an amount effective that enhances normal physiological function within its scope.

As used herein, the term "treating" includes any effect that results in amelioration of a condition, disease, or disorder, for example, alleviation, reduction, modulation, amelioration or elimination, or amelioration of a symptom thereof.

The term "pharmaceutically acceptable" is used herein to refer to those compounds, materials, compositions, and/or dosage forms as follows: within the scope of sound medical judgment, suitable for use in contact with the tissues of humans and animals without undue toxicity, irritation, allergic response, and/or other problems or complications, commensurate with a reasonable benefit/risk ratio.

As used herein, the phrase "pharmaceutically acceptable carrier" means a pharmaceutical material, composition or vehicle, such as a liquid or solid filler, diluent, excipient, manufacturing adjuvant (e.g., lubricant, talc, magnesium stearate, calcium stearate or zinc stearate or stearic acid), or solvent encapsulating material, which refers to carrying or transporting the subject compound from one organ or portion of the body to another organ or portion of the body. Each carrier must be "acceptable" in the sense of being compatible with the other ingredients of the formulation and not deleterious to the patient.

The term "pharmaceutical composition" means a composition including a compound of the present invention and at least one other pharmaceutically acceptable carrier. "Pharmaceutically acceptable carrier" means a medium generally accepted in the art for the delivery of a biologically active agent to an animal, particularly a mammal, and includes, i.e., adjuvants, excipients, or vehicles such as diluents, preservatives, fillers, flow regulating agents, disintegrating agents, wetting agents, emulsifying agents, suspending agents, sweetening agents, flavoring agents, perfuming agents, antibacterial agents, antifungal agents, lubricating agents, and dispersing agents, depending on the mode of administration and the nature of the dosage form.

Specific Pharmaceutical and Medical Terms

The term "acceptable", as used herein, refers to a prescription component or active ingredient that does not unduly adversely affect the health of the general therapeutic target.

The term "cancer", as used herein, refers to an uncontrolled abnormal growth of cells and is capable of metastasis (transmission) under certain conditions. This type of cancer includes, but is not limited to, solid tumors (e.g., bladder, bowel, brain, chest, uterus, heart, kidney, lung, lymphoid tissue (lymphoma), ovary, pancreas, or other endocrine organs (e.g., thyroid), prostate, skin (melanoma), or hematological tumors (e.g., aleukemic leukemia).

The term "administered in combination" or similar terms, as used herein, refers to the administration of several selected therapeutic agents to a patient in the same or different modes of administration at the same or different times.

The term "enhance" or "can enhance", as used herein, means that the desired result can be increased or prolonged in potency or duration. Thus, in enhancing the therapeutic effect of a drug, the term "enhance" refers to the ability of the drug to increase or prolong potency or duration in the system. "Synergistic value", as used herein, refers to the ability to maximize the ability of another therapeutic agent in an ideal system.

The term "immunological disease" refers to a disease or condition that responds adversely or deleteriously to endogenous or exogenous antigens. The result is often a dysfunction of the cells, or thus destruction and dysfunction, or destruction of organs or tissues that may produce immune symptoms.

The term "kit" is synonymous with "product package".

The term "subject" or "patient" includes mammals and non-mammals. Mammals include, but are not limited to, mammals: human, non-human primates such as chimpanzees, apes and monkeys; agricultural animals such as bovines, equines, goats, sheep, and swines; domestic animals such as rabbits, and canines; experimental animals include rodents, such as rats, mice, and guinea pigs. Non-mammalian animals include, but are not limited to, birds, and fish. In a preferred embodiment, the selected mammal is a human.

The terms "treatment", "treatment process", or "therapy", as used herein, include alleviating, inhibiting, or ameliorating the symptoms or conditions of a disease; inhibiting the generation of complications; ameliorating or preventing potential metabolic syndrome; inhibiting the development of a disease or condition, such as controlling the development of a disease or condition; alleviating a disease or condition; reducing the disease or symptoms; alleviating complications resulting from the disease or condition, or preventing and/or treating symptoms resulting from the disease or condition.

As used herein, a compound or pharmaceutical composition, upon administration, may result in amelioration of a disease, symptom, or condition, particularly amelioration of the severity, delay of the onset, alleviation of the progression, or reduction of the duration of the condition. Regardless of fixed administration or temporary administration, continuous administration or intermittent administration, it may be attributed to or related to the administration.

Route of Administration

Suitable routes of administration include, but are not limited to, oral, intravenous, rectal, aerosol, parenteral, ophthalmic, pulmonary, transdermal, vaginal, aural, nasal, and topical administration.

In addition, by way of example only, parenteral administration includes intramuscular, subcutaneous, intravenous, intramedullary, ventricular, intraperitoneal, intralymphatic, and intranasal injections.

In one aspect, the compounds described herein are administered locally rather than systemically. In particular embodiments, the prolonged action preparation is administered by implantation (e.g., subcutaneously or intramuscularly) or by intramuscular injection. Further, in another embodiment, the drug is administered by a targeted drug delivery system, for example, liposomes encapsulated by organ-specific antibodies. In this particular embodiment, the liposomes are selectively targeted to specific organs and absorbed.

Pharmaceutical Compositions and Dosages

The present invention also provides pharmaceutical compositions including a therapeutically effective amount of one or more compounds of the present invention formulated together with one or more pharmaceutically acceptable carriers (additives) and/or diluents, and optionally one or more of the other therapeutic agents described above. The compounds of the present invention may be administered for any of the above uses by any suitable means, for example by orally, such as in the form of tablets, pills, powders, granules, elixirs, tinctures, suspensions (including nanosuspensions, microsuspensions, spray-dried dispersions), syrups and emulsions; by sublingually; by buccally; by parenterally, such as by subcutaneous, intravenous, intramuscular or intrasternal injection or infusion techniques (e.g., in the form of sterile injectable aqueous or nonaqueous solutions or suspensions); by nasally, including administration to the nasal mask, such as by inhalation spray; by topically, such as in the form of a cream or ointment; or by rectally, such as in the form of suppositories. They may be administered alone, but are generally administered using pharmaceutical acceptable carriers selected based on the chosen route of administration and standard pharmaceutical practice.

The pharmaceutical acceptable carriers are formulated according to a number of factors within the knowledge of those skilled in the art. These factors include, but are not limited to: types and properties of the formulated active agents; a subject to be administered the composition containing the active agent; the intended route of administration of the composition; and targeted therapeutic indications. The pharmaceutically acceptable carriers include aqueous and non-aqueous liquid media and various solid and semi-solid dosage forms.

The above-mentioned carrier may include many different ingredients and additives in addition to the active agent, and the above-mentioned other ingredients, for example, stabilizing active agent and binder, are included in the formulation for various reasons known to those skilled in the art. For a description of suitable pharmaceutical acceptable carriers and factors involved in the selection of carrier, see a number of readily available sources, such as Allen L. VJr. et al. Remington: The Science and Practice of Pharmacy (2 Volumes), 22nd Edition (2012), Pharmaceutical Press.

The dosage regimen for the compounds of the present invention will, of course, vary depending upon known factors such as the pharmacodynamic characteristics of the particular agent and its mode and route of administration; species, age, sex, health, medical condition and weight of the recipient; the nature and extent of symptoms; kind of concurrent treatment; treatment frequency; routes of administration, renal and hepatic function and desired effects in patients. According to general guidelines, when used for a given effect, the daily oral dosage of each active ingredient should be from about 0.001 mg/day to about 10-5000 mg/day, preferably from about 0.01 mg/day to about 1000 mg/day, and most preferably from about 0.1 mg/day to about 250 mg/day. During constant infusion, the most preferred intravenous dose should be from about 0.01 mg/kg/min to about 10 mg/kg/min. The compounds of the present invention may be administered in a single daily dose, or the total daily dose may be administered in divided doses of two, three or four times daily.

The compounds are generally administered in the form of a mixture of suitable pharmaceutical diluents, excipients, or carriers (collectively referred to herein as pharmaceutical acceptable carriers) suitably selected with respect to the intended form of administration (e.g., oral tablets, capsules, elixirs, and syrups) and consistent with conventional pharmaceutical practice.

Dosage forms (pharmaceutical compositions) suitable for administration may contain from about 1 mg to about 2000 mg of active ingredient per dosage unit. In these pharmaceutical compositions, the active ingredient will generally be present in an amount of about 0.1-95% by weight, based on a total weight of the composition.

Typical capsules for oral administration contain at least one compound of the present invention (250 mg), lactose (75 mg) and magnesium stearate (15 mg). The mixture was processed through a 60 meshes screen and packaged into No. 1 gelatin capsules.

A typical injectable formulation may be prepared as follows: at least one compound of the present invention (250 mg) was placed in a vial in a sterile manner, and lyophilized and sealed in a sterile manner. For use, the contents in the vial were mixed with 2 mL of normal saline to produce an injectable formulation.

The scope of the present invention includes (alone or in combination with a pharmaceutical acceptable carrier) pharmaceutical compositions containing a therapeutically effective amount of at least one compound of the present invention as an active ingredient. Optionally, the compounds of the present invention may be used alone, in combination with other compounds of the present invention, or in combination with one or more other therapeutic agents (e.g., anticancer agents or other pharmaceutically active agents).

Regardless of the selected route of administration, the compounds of the present invention (which may be used in suitable hydrated forms) and/or the pharmaceutical compositions of the present invention are formulated into pharmaceutically acceptable dosage forms by conventional methods known to those skilled in the art.

The actual dosage level of the active ingredient in the pharmaceutical compositions of the present invention may be varied so as to obtain an amount of the active ingredient that is effective to achieve the desired therapeutic response, composition, and mode of administration for a particular patient without being toxic to the patient.

The selected dosage level will depend upon a variety of factors, including the factors well known in the medical field such as the activity of the employed specific compound of the present invention, or an ester, salt or amide thereof; routes of administration; administration time; the discharge rate of the employed specific compound; the absorption rate and extent; duration of treatment; other drugs, compounds and/or substances used in combination with the employed specific compounds; the age, sex, weight, condition, general health and prior medical history of the patient being treated.

A physician or veterinarian having ordinary skill in the art can readily determine and prescribe an effective amount of the desired pharmaceutical composition. For example, to achieve the desired therapeutic effect, the physician or veterinarian may start a relatively small amount of the compound of the present invention used in the pharmaceutical composition below the desired level and gradually increase the dosage until the desired effect is achieved. In general, a suitable daily dose of a compound of the present invention will be that amount of the compound that is the lowest dose effective to produce a therapeutic effect. Such an effective dose will generally depend on such factors. In general, oral, intravenous, intracerebroventricular, and subcutaneous doses of a compound of the present invention for a patient range from about 0.01 to about 50 mg/kg body weight/day. If desired, an effective daily dose of the active compound may be administered in two, three, four, five, six or more sub-doses respectively at appropriate intervals throughout the day, optionally in unit dosage form. In certain aspects of the present invention, the medication is administered once a day.

Although the compound of the present invention may be administered alone, it is preferably administered in the form of a pharmaceutical preparation (composition).

Kit/Product Package

Kits/product packages are also described herein for the treatment of the above indications. These kits may be composed of a conveyor, a medicine pack or a container box. The container box can be divided into multiple compartments to accommodate one or more containers, such as vials, and test tubes, where each container contains all a single component in the method. Suitable containers consist of bottles, vials, syringes, and test tubes. The container is made of an acceptable glass or plastic material.

For example, the container may contain one or more of the compounds described herein; the compound may exist either in the form of a pharmaceutical composition or may exist as a mixture with other ingredients described herein. The container may have a sterile outlet (e.g., the container may be an intravenous infusion bag or bottle and the stopper may be pierced by a hypodermic needle). Such kits may contain a compound and descriptions, labels or instructions for the method of use described herein.

A typical kit may include one or more containers, each containing one or more materials (e.g., reagents, concentrated stock solutions, and/or equipment) to accommodate commercial promotions and the needs of the user for the use of compounds. Such materials include, but are not limited to, buffers, diluents, filters, needles, syringes, conveyors, bags, containers, bottles, and/or tubes, with a list of contents and/or instructions for use, and with a build-in package. The entire set of instructions must be included.

The label may be displayed on or closely related to the container. The appearance of the label on the container means that the label letters, numbers or other features are pasted, molded, or engraved on the container; the label can also appear in the container box or shipping box containing a variety of containers, such as in the product insert. A label may be used to indicate a particular therapeutic use of the contents. The label may also indicate directions for the use of contents, such as described in the methods described above.

All of the features described in this specification (including any accompanying claims, abstract and drawings), and/or all of the steps involved in any method or process, may be present in any combination unless some features or steps are mutually exclusive in the same combination.

The features mentioned above, or the features mentioned in the embodiments mentioned herein, may be combined in any combination. All of the features disclosed in this specification may be combined in any combination, and each feature disclosed in this specification may be replaced by any alternative feature serving the same, equivalent or similar purpose. Thus, unless otherwise specified, the features disclosed are only general examples of equivalent or similar features.

The present invention will be described in detail below in connection with specific examples. It should be understood that these examples are only used to describe the present invention and are not intended to limit the scope of the present invention. The experimental methods in the following examples which are not specified with specific conditions are generally carried out according to conventional conditions or according to the conditions recommended by the manufacturer. All percentages, ratios, ratios, or parts are calculated by weight, unless otherwise stated.

The units in weight-volume percent in the present invention are well known to those skilled in the art and refer, for example, to the weight of solute in a 100 milliliters solution. Unless otherwise defined, all professional and scientific terms used in the text have the same meaning as those familiar to those skilled in the art. In addition, any methods and materials similar or equivalent to those described can be used in the methods of the present invention. The preferred embodiments and materials described herein are exemplary only.

In preferred embodiments of the present invention, the following compounds are provided, but are not limited to:

| No. | Compound structure |
|-----|--------------------|
| 1 | 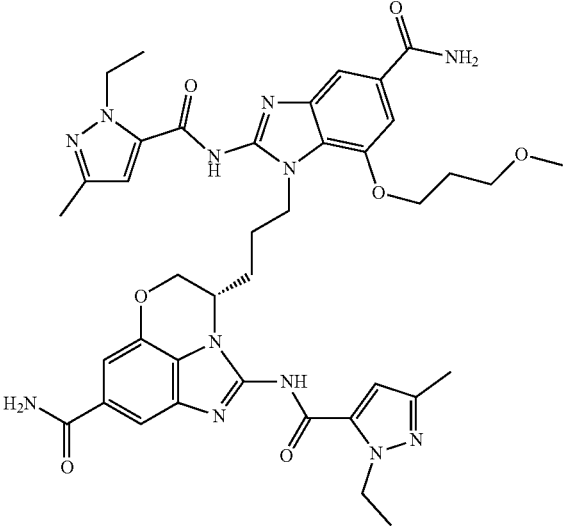 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4cc(C)nn4CC)n1c23] |
| 2 | 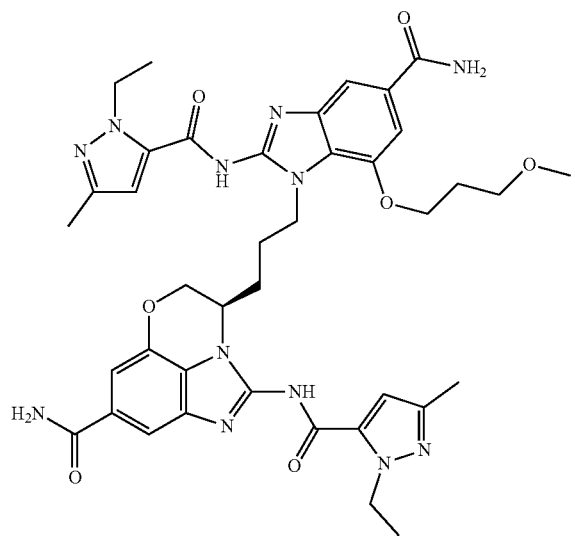 [SMILES: CCn1nc(C)cc1C(=O)Nc1nc2cc(C(N)=O)cc(OCCCOC)c2n1CCC[C@@H]1COc2cc(C(N)=O)cc3nc(NC(=O)c4cc(C)nn4CC)n1c23] |

-continued
| No. | Compound structure |
|---|---|
| 3 | 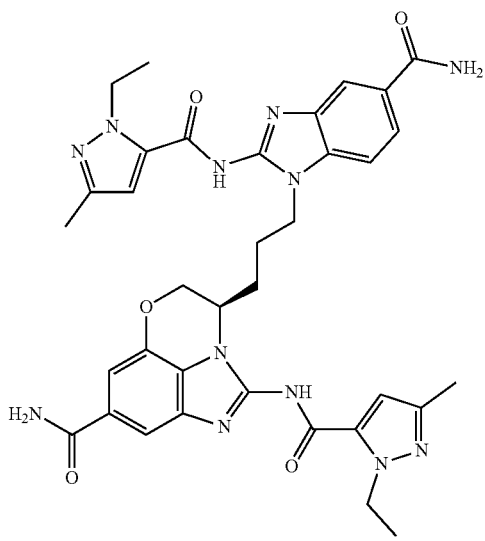 [SMILES: CCn1nc(C)cc1C(=O)Nc1nc2cc(C(N)=O)ccc2n1CCC[C@@H]1COc2cc(C(N)=O)cc3nc(NC(=O)c4cc(C)nn4CC)n1c23] |
| 4 | 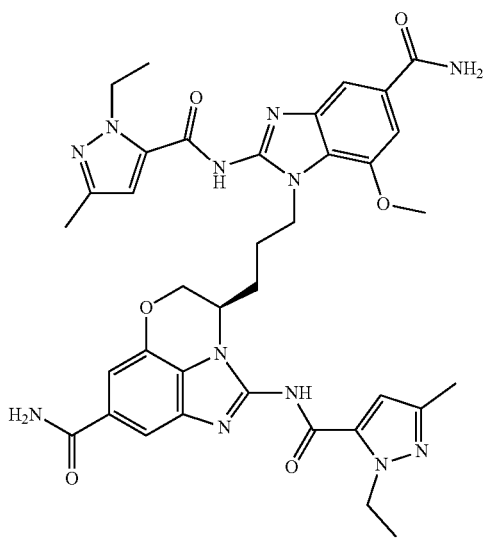 [SMILES: CCn1nc(C)cc1C(=O)Nc1nc2cc(C(N)=O)cc(OC)c2n1CCC[C@@H]1COc2cc(C(N)=O)cc3nc(NC(=O)c4cc(C)nn4CC)n1c23] |
| 5 | 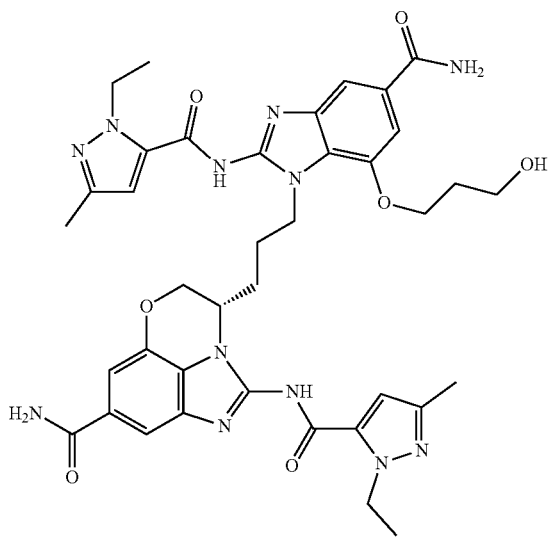 [SMILES: CCn1nc(C)cc1C(=O)Nc1nc2cc(C(N)=O)cc(OCCCO)c2n1CCC[C@H]1COc2cc(C(N)=O)cc3nc(NC(=O)c4cc(C)nn4CC)n1c23] |

-continued
| No. | Compound structure |
|---|---|
| 6 | 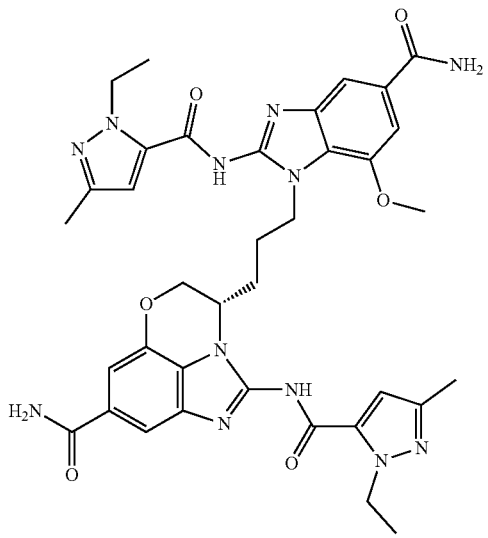 [SMILES: CCn1nc(C)cc1C(=O)Nc1nc2cc(C(N)=O)cc(OC)c2n1CCC[C@H]1COc2cc(C(N)=O)cc3nc(NC(=O)c4cc(C)nn4CC)n1c23] |
| 7 | 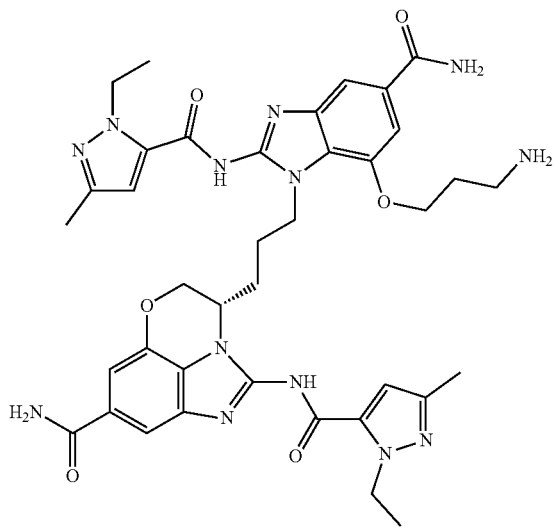 [SMILES: CCn1nc(C)cc1C(=O)Nc1nc2cc(C(N)=O)cc(OCCCN)c2n1CCC[C@H]1COc2cc(C(N)=O)cc3nc(NC(=O)c4cc(C)nn4CC)n1c23] |
| 8 | 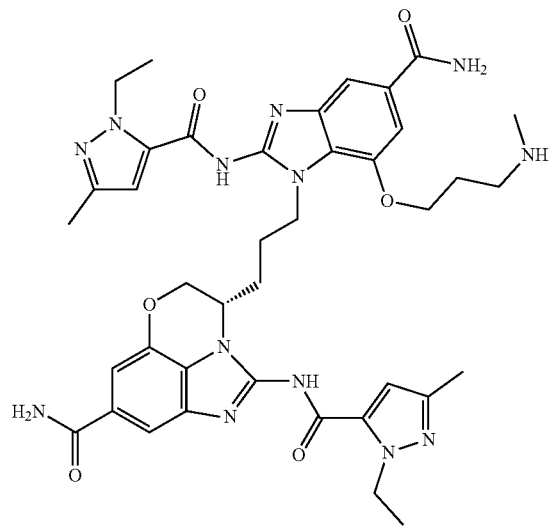 [SMILES: CCn1nc(C)cc1C(=O)Nc1nc2cc(C(N)=O)cc(OCCCNC)c2n1CCC[C@H]1COc2cc(C(N)=O)cc3nc(NC(=O)c4cc(C)nn4CC)n1c23] |

| No. | Compound structure |
|---|---|
| 9 | 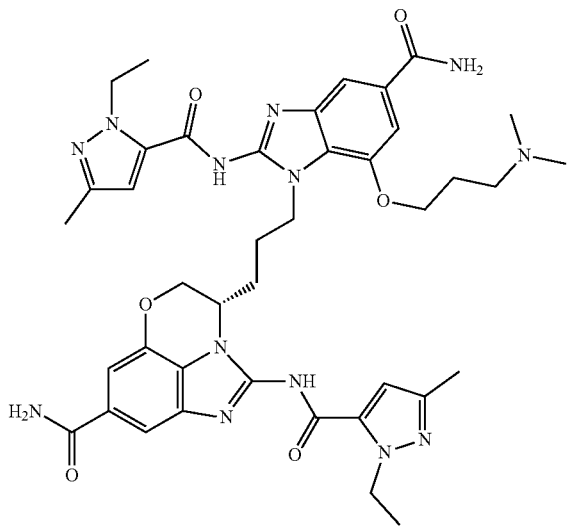 [SMILES: CCn1nc(C)cc1C(=O)Nc1nc2cc(C(N)=O)cc(OCCCN(C)C)c2n1CCC[C@H]1COc2cc(C(N)=O)cc3nc(NC(=O)c4cc(C)nn4CC)n1c23] |
| 10 | 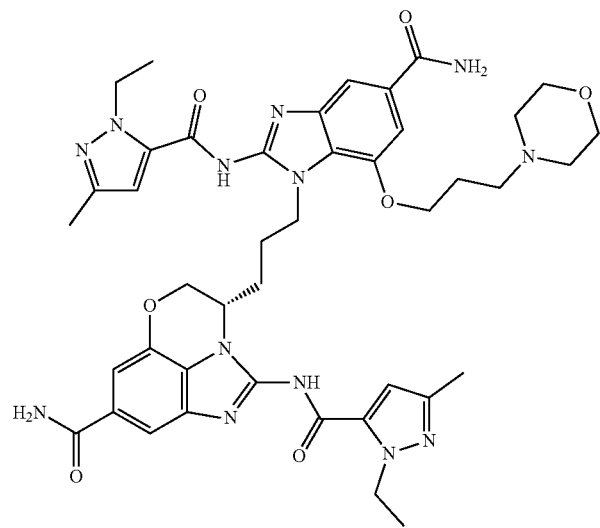 [SMILES: CCn1nc(C)cc1C(=O)Nc1nc2cc(C(N)=O)cc(OCCCN3CCOCC3)c2n1CCC[C@H]1COc2cc(C(N)=O)cc3nc(NC(=O)c4cc(C)nn4CC)n1c23] |

| No. | Compound structure |
|---|---|
| 11 | 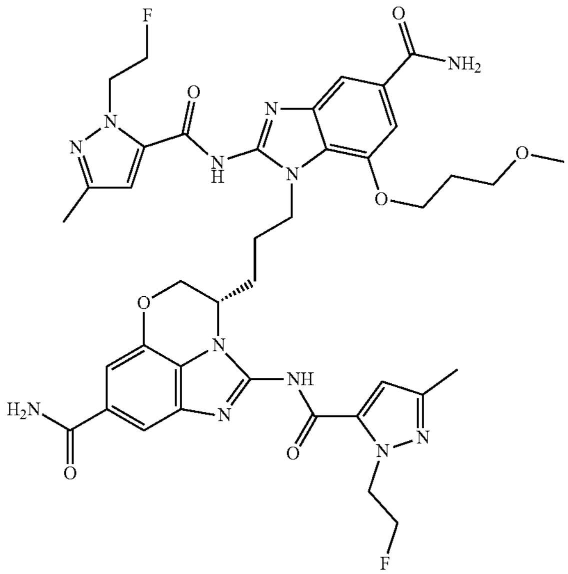 [SMILES: COCCCOc1cc(C(N)=O)cc2nc(NC(=O)c3cc(C)nn3CCF)n(CCC[C@H]3COc4cc(C(N)=O)cc5nc(NC(=O)c6cc(C)nn6CCF)n3c45)c12] |
| 12 | 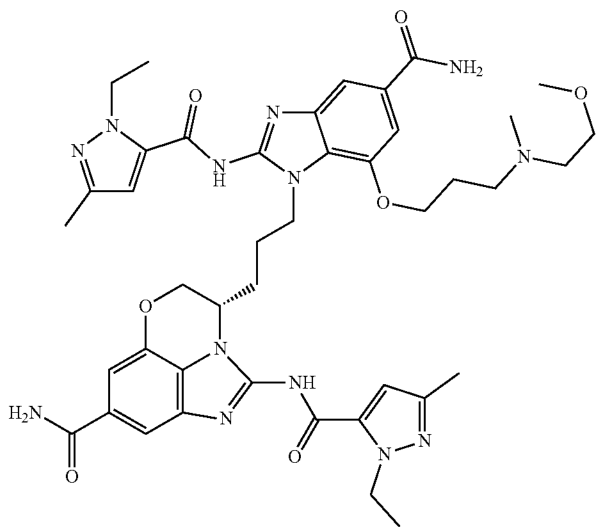 [SMILES: CCn1nc(C)cc1C(=O)Nc1nc2cc(C(N)=O)cc(OCCCN(C)CCOC)c2n1CCC[C@H]1COc2cc(C(N)=O)cc3nc(NC(=O)c4cc(C)nn4CC)n1c23] |
| 13 | 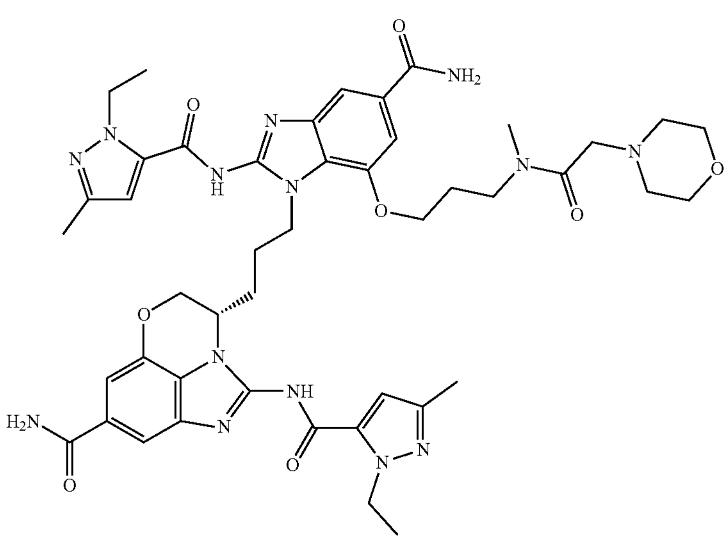 [SMILES: CCn1nc(C)cc1C(=O)Nc1nc2cc(C(N)=O)cc(OCCCN(C)C(=O)CN3CCNCC3)c2n1CCC[C@H]1COc2cc(C(N)=O)cc3nc(NC(=O)c4cc(C)nn4CC)n1c23] |

| No. | Compound structure |
|---|---|
| 14 | 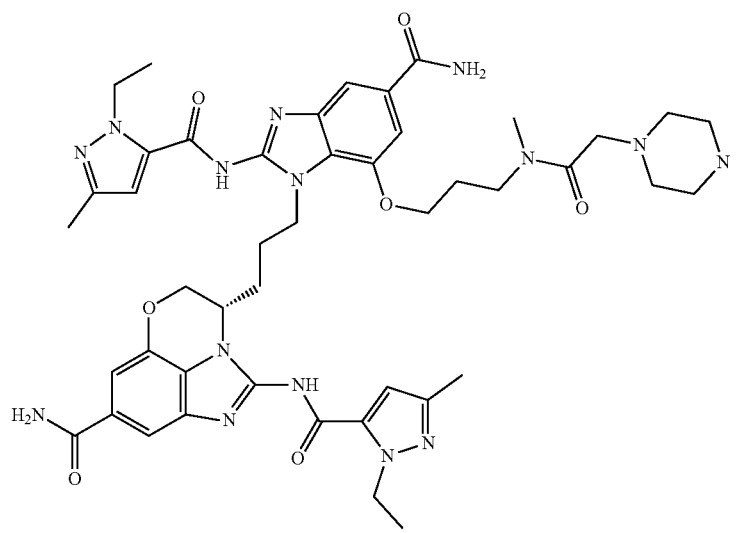 |
| 15 | 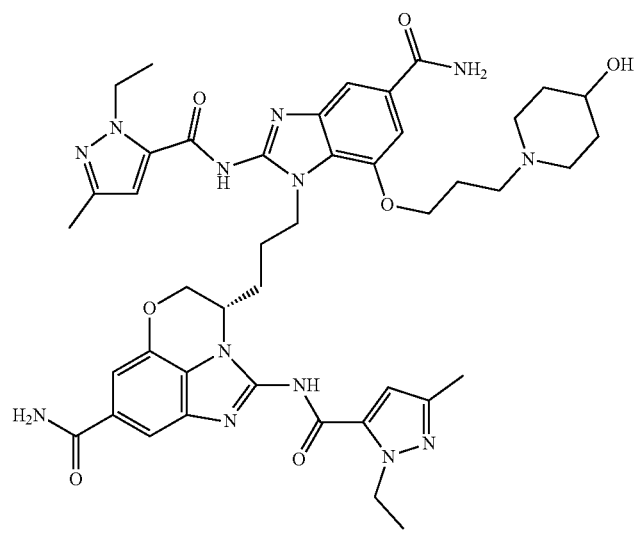 [SMILES: CCn1nc(C)cc1C(=O)Nc1nc2cc(C(N)=O)cc(OCCCN3CCC(O)CC3)c2n1CCC[C@H]1COc2cc(C(N)=O)cc3nc(NC(=O)c4cc(C)nn4CC)n1c23] |
| 16 | 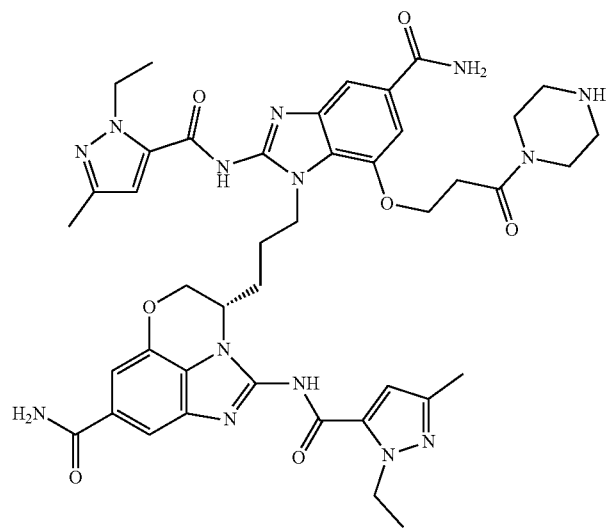 [SMILES: CCn1nc(C)cc1C(=O)Nc1nc2cc(C(N)=O)cc(OCCC(=O)N3CCNCC3)c2n1CCC[C@H]1COc2cc(C(N)=O)cc3nc(NC(=O)c4cc(C)nn4CC)n1c23] |

-continued
| No. | Compound structure |
|-----|-------------------|
| 17 | 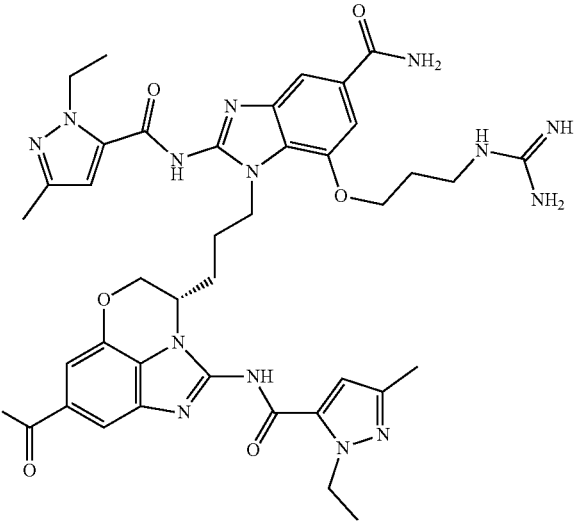 |
| 18 | 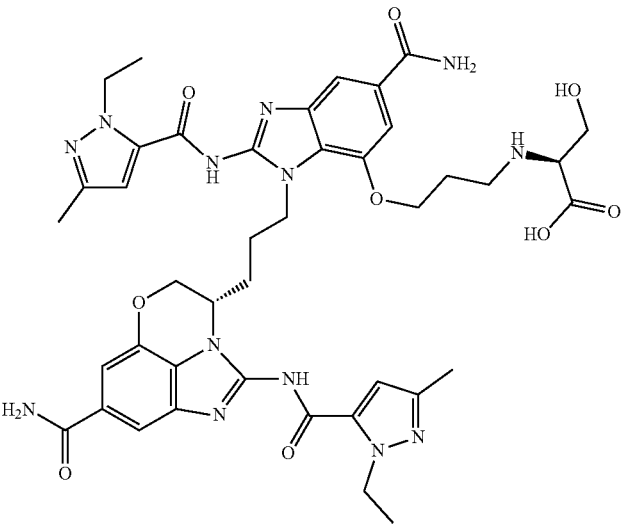 [SMILES: CCn1nc(C)cc1C(=O)Nc1nc2cc(C(N)=O)cc(OCCCN[C@@H](CO)C(=O)O)c2n1CCC[C@H]1COc2cc(C(N)=O)cc3nc(NC(=O)c4cc(C)nn4CC)n1c23] |
| 19 | 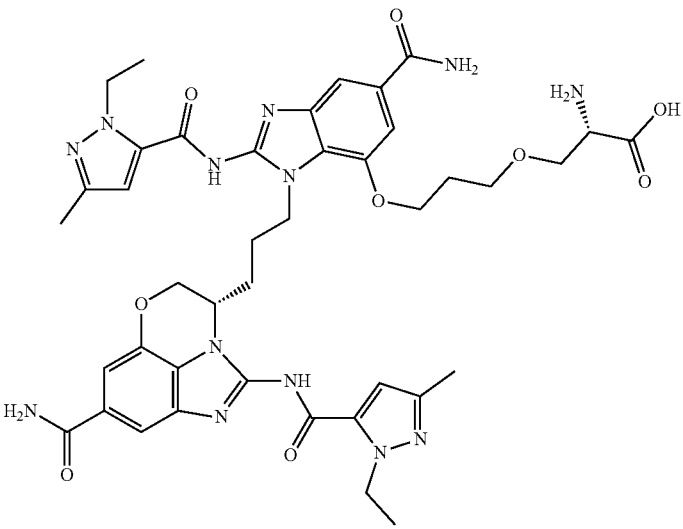 [SMILES: CCn1nc(C)cc1C(=O)Nc1nc2cc(C(N)=O)cc(OCCCOC[C@H](N)C(=O)O)c2n1CCC[C@H]1COc2cc(C(N)=O)cc3nc(NC(=O)c4cc(C)nn4CC)n1c23] |

-continued
| No. | Compound structure |
|---|---|
| 20 | 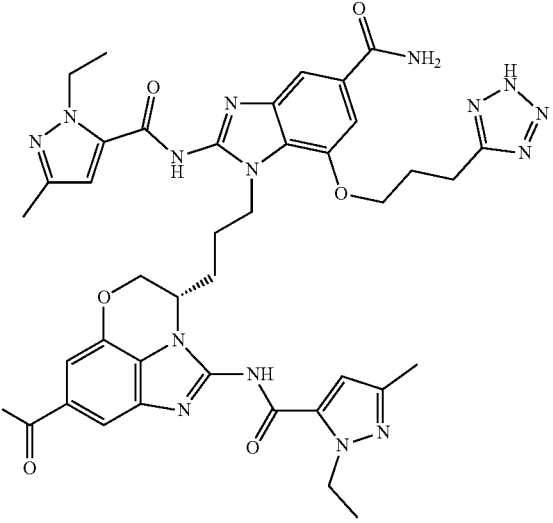 |
| 21 | 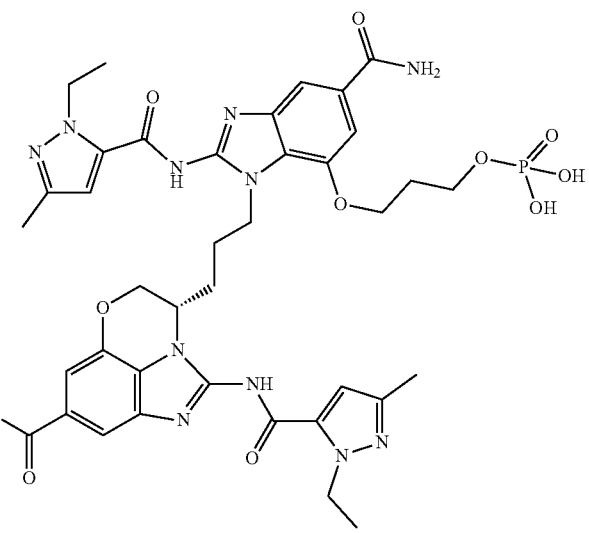 |
| 22 | 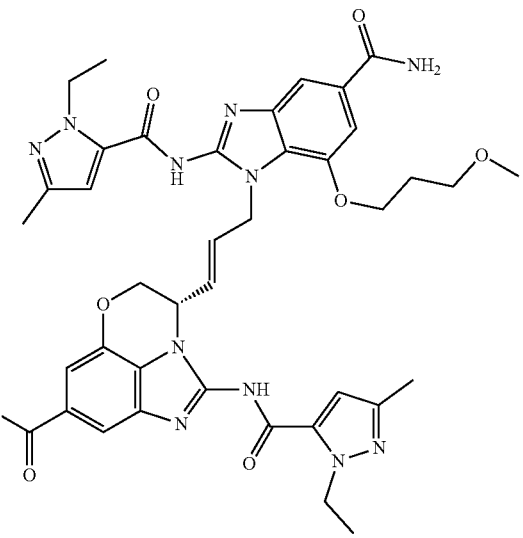 |

| No. | Compound structure |
|---|---|
| 23 | 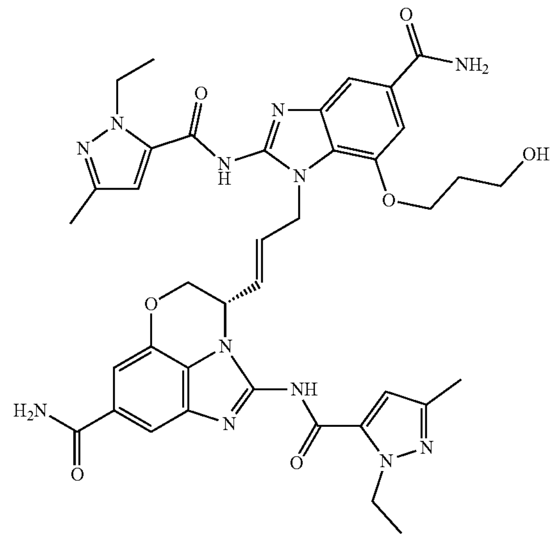 [SMILES: CCn1nc(C)cc1C(=O)Nc1nc2cc(C(N)=O)cc(OCCCO)c2n1C/C=C/[C@H]1COc2cc(C(N)=O)cc3nc(NC(=O)c4cc(C)nn4CC)n1c23] |
| 24 | 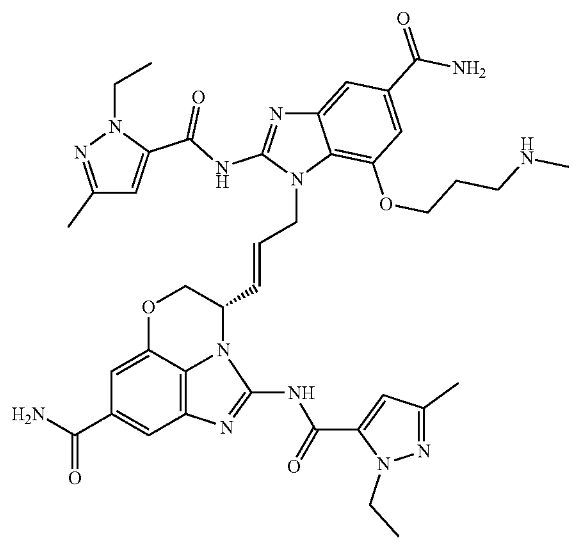 [SMILES: CCn1nc(C)cc1C(=O)Nc1nc2cc(C(N)=O)cc(OCCCNC)c2n1C/C=C/[C@H]1COc2cc(C(N)=O)cc3nc(NC(=O)c4cc(C)nn4CC)n1c23] |
| 25 | 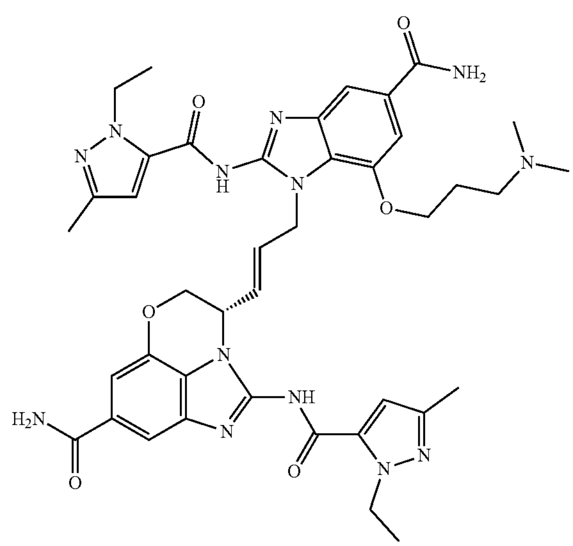 [SMILES: CCn1nc(C)cc1C(=O)Nc1nc2cc(C(N)=O)cc(OCCCN(C)C)c2n1C/C=C/[C@H]1COc2cc(C(N)=O)cc3nc(NC(=O)c4cc(C)nn4CC)n1c23] |

| No. | Compound structure |
|---|---|
| 26 | 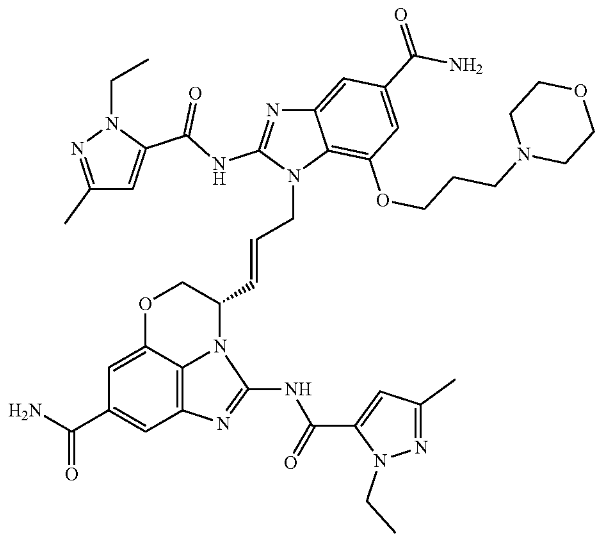 [SMILES: CCn1nc(C)cc1C(=O)Nc1nc2cc(C(N)=O)cc(OCCCN3CCOCC3)c2n1C/C=C/[C@H]1COc2cc(C(N)=O)cc3nc(NC(=O)c4cc(C)nn4CC)n1c23] |
| 27 | 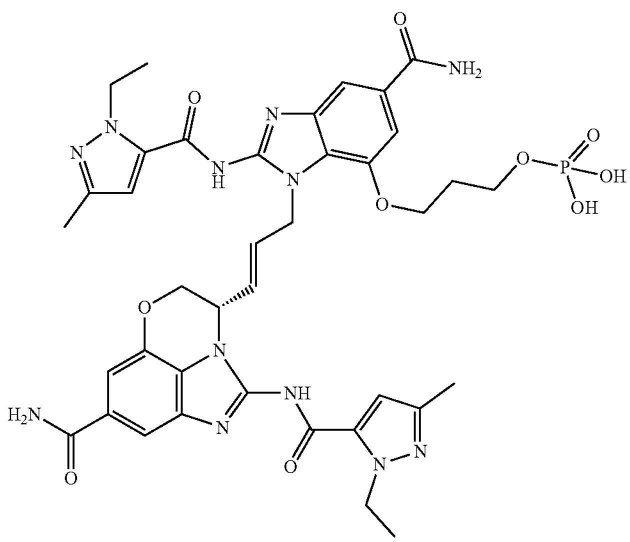 [SMILES: CCn1nc(C)cc1C(=O)Nc1nc2cc(C(N)=O)cc(OCCCOP(=O)(O)O)c2n1C/C=C/[C@H]1COc2cc(C(N)=O)cc3nc(NC(=O)c4cc(C)nn4CC)n1c23] |
| 28 | 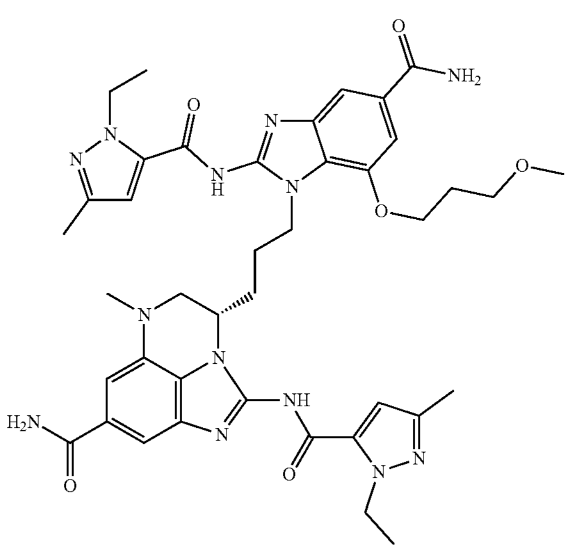 [SMILES: CCn1nc(C)cc1C(=O)Nc1nc2cc(C(N)=O)cc(OCCCOC)c2n1CCC[C@H]1CN(C)c2cc(C(N)=O)cc3nc(NC(=O)c4cc(C)nn4CC)n1c23] |

-continued
| No. | Compound structure |
|---|---|
| 29 | 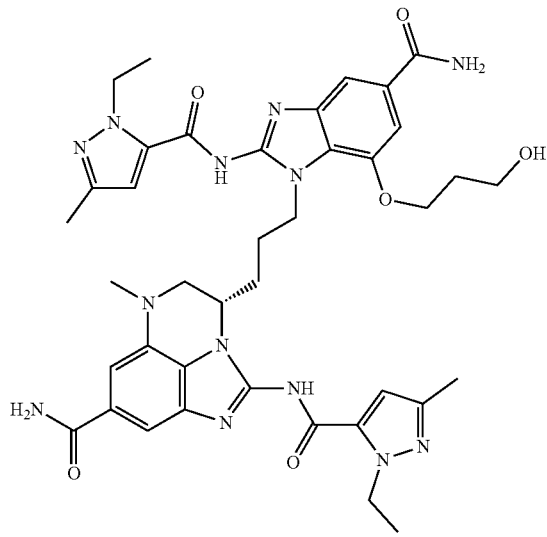 [SMILES: CCn1nc(C)cc1C(=O)Nc1nc2cc(C(N)=O)cc(OCCCO)c2n1CCC[C@H]1CN(C)c2cc(C(N)=O)cc3nc(NC(=O)c4cc(C)nn4CC)n1c23] |
| 30 | 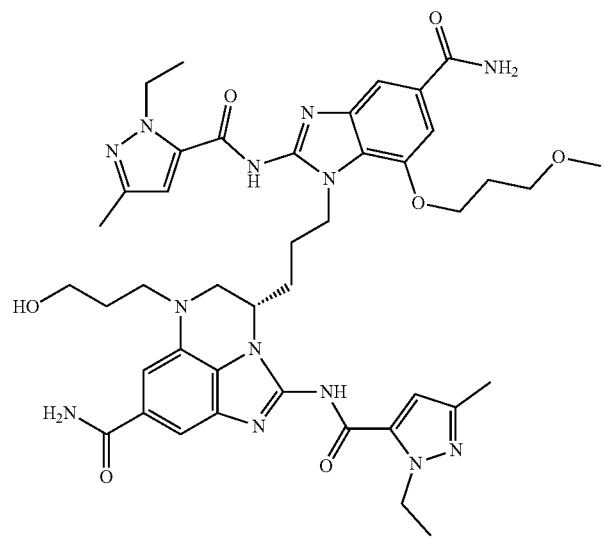 [SMILES: CCn1nc(C)cc1C(=O)Nc1nc2cc(C(N)=O)cc(OCCCOC)c2n1CCC[C@H]1CN(CCCO)c2cc(C(N)=O)cc3nc(NC(=O)c4cc(C)nn4CC)n1c23] |

| No. | Compound structure |
|---|---|
| 31 | 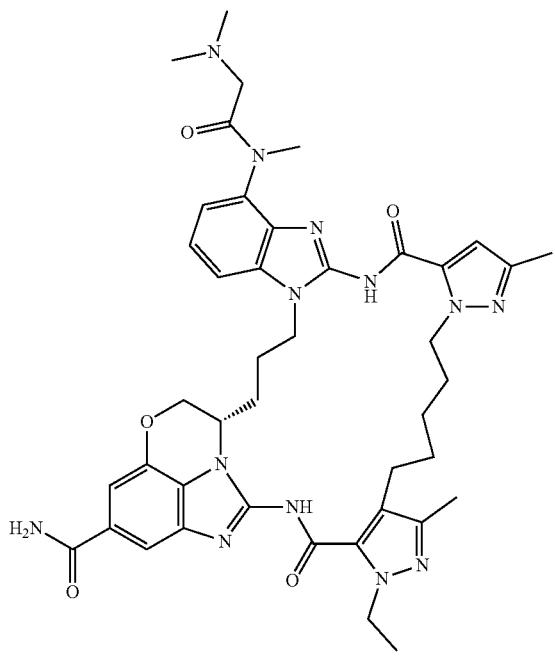 [SMILES: CCn1nc(C)c2c1C(=O)Nc1nc3cc(C(N)=O)cc4c3n1[C@@H](CCCn1c(nc3c(N(C)C(=O)CN(C)C)cccc31)NC(=O)c1cc(C)nn1CCCCC2)CO4] |
| 32 | 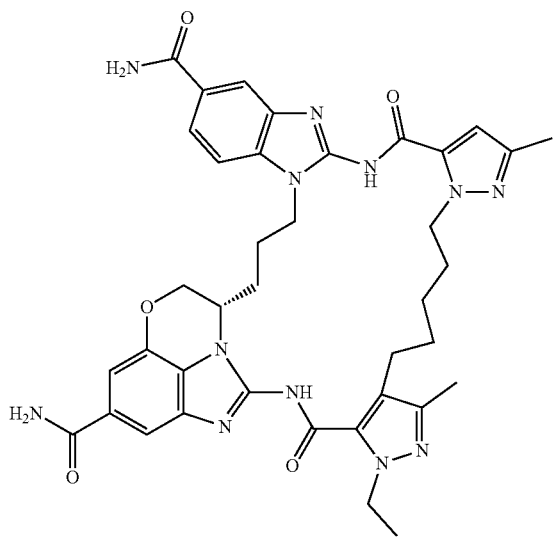 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCCCC2)CO4] |

-continued
| No. | Compound structure |
|---|---|
| 33 | 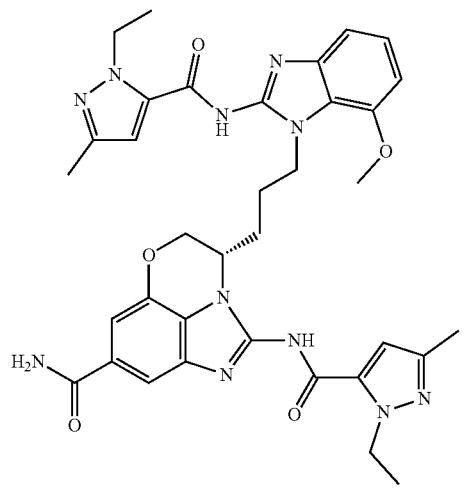 [SMILES: CCn1nc(C)cc1C(=O)Nc1nc2cccc(OC)c2n1CCC[C@H]1COc2cc(C(N)=O)cc3nc(NC(=O)c4cc(C)nn4CC)n1c23] |
| 34 | 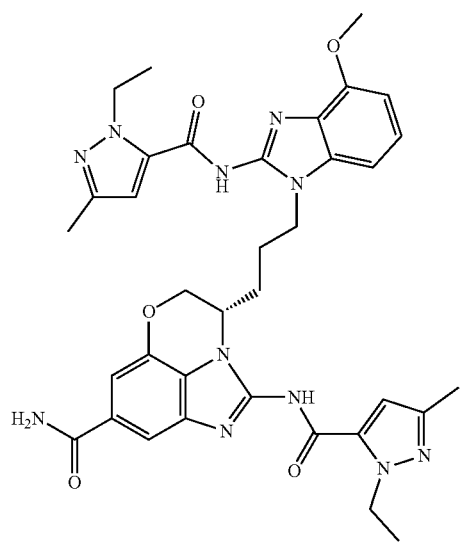 [SMILES: CCn1nc(C)cc1C(=O)Nc1nc2c(OC)cccc2n1CCC[C@H]1COc2cc(C(N)=O)cc3nc(NC(=O)c4cc(C)nn4CC)n1c23] |

|     |                   |
| --- | ----------------- |
| No. | Compound structure |
| 35  | 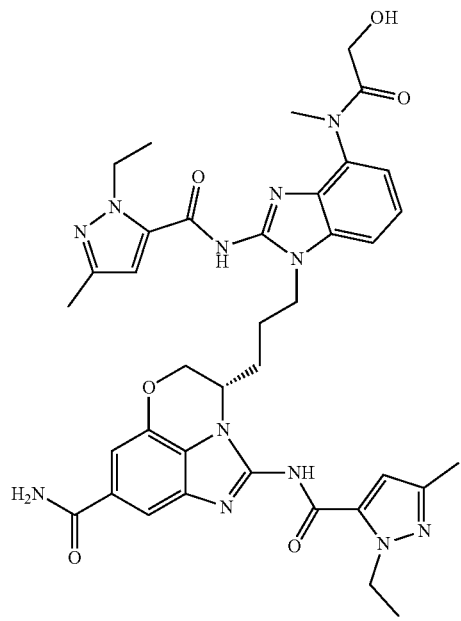 [SMILES: CCn1nc(C)cc1C(=O)Nc1nc2c(N(C)C(=O)CO)cccc2n1CCC[C@H]1COc2cc(C(N)=O)cc3nc(NC(=O)c4cc(C)nn4CC)n1c23] |
| 36  | 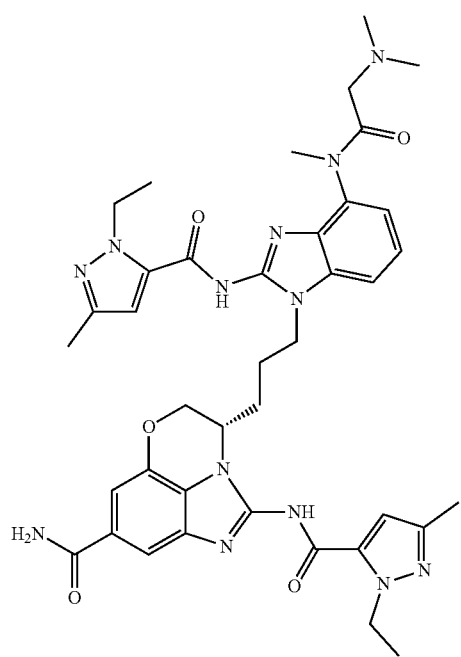 [SMILES: CCn1nc(C)cc1C(=O)Nc1nc2c(N(C)C(=O)CN(C)C)cccc2n1CCC[C@H]1COc2cc(C(N)=O)cc3nc(NC(=O)c4cc(C)nn4CC)n1c23] |

-continued
| No. | Compound structure |
|---|---|
| 37 | 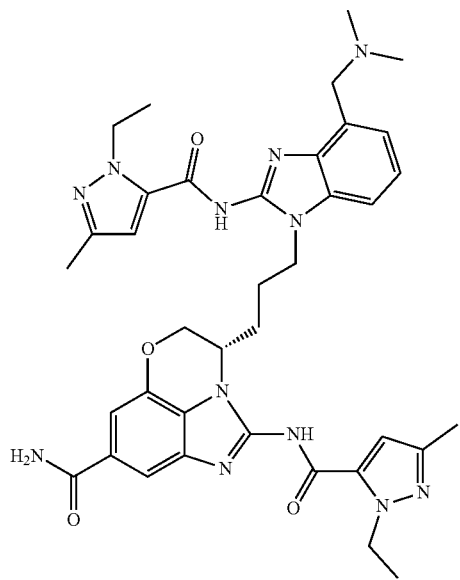 [SMILES: CCn1nc(C)cc1C(=O)Nc1nc2c(CN(C)C)cccc2n1CCC[C@H]1COc2cc(C(N)=O)cc3nc(NC(=O)c4cc(C)nn4CC)n1c23] |
| 38 | 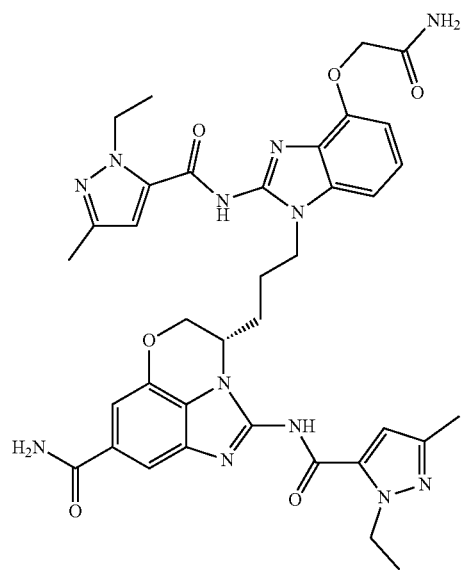 [SMILES: CCn1nc(C)cc1C(=O)Nc1nc2c(OCC(N)=O)cccc2n1CCC[C@H]1COc2cc(C(N)=O)cc3nc(NC(=O)c4cc(C)nn4CC)n1c23] |

| No. | Compound structure |
|---|---|
| 39 | 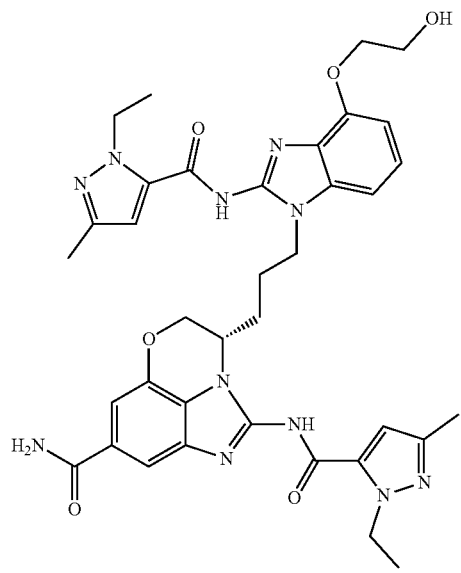 [SMILES: CCn1nc(C)cc1C(=O)Nc1nc2c(OCCO)cccc2n1CCC[C@H]1COc2cc(C(N)=O)cc3nc(NC(=O)c4cc(C)nn4CC)n1c23] |
| 40 | 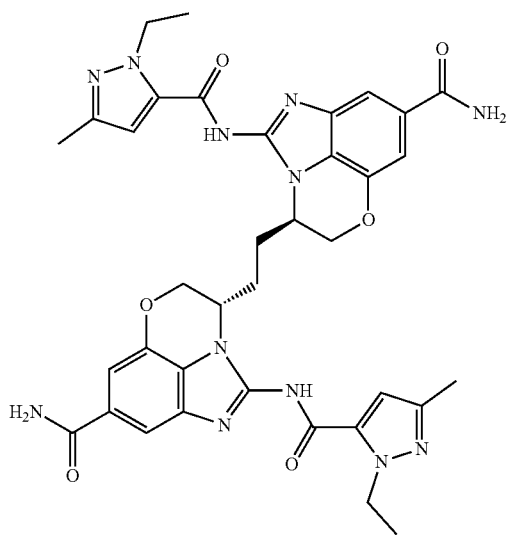 [SMILES: CCn1nc(C)cc1C(=O)Nc1nc2cc(C(N)=O)cc3c2n1[C@H](CC[C@H]1COc2cc(C(N)=O)cc4nc(NC(=O)c5cc(C)nn5CC)n1c24)CO3] |

| No. | Compound structure |
|---|---|
| 41 | 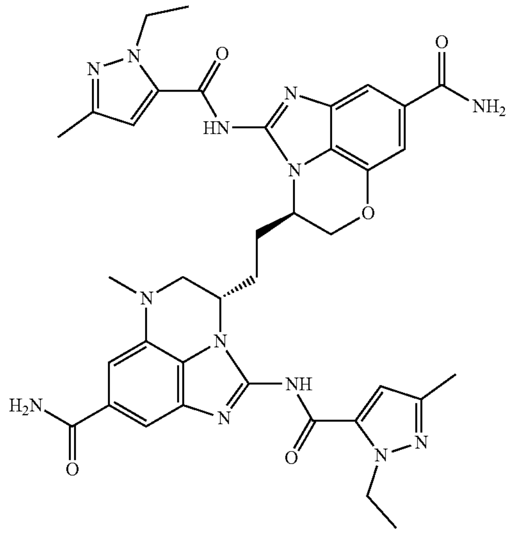 [SMILES: CCn1nc(C)cc1C(=O)Nc1nc2cc(C(N)=O)cc3c2n1[C@H](CC[C@H]1CN(C)c2cc(C(N)=O)cc4nc(NC(=O)c5cc(C)nn5CC)n1c24)CO3] |
| 42 | 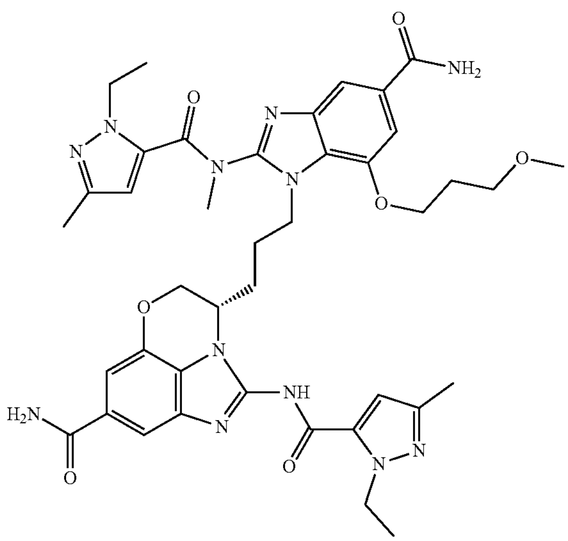 [SMILES: CCn1nc(C)cc1C(=O)Nc1nc2cc(C(N)=O)cc3c2n1[C@@H](CCCn1c(N(C)C(=O)c2cc(C)nn2CC)nc2cc(C(N)=O)cc(OCCCOC)c21)CO3] |
| 43 | 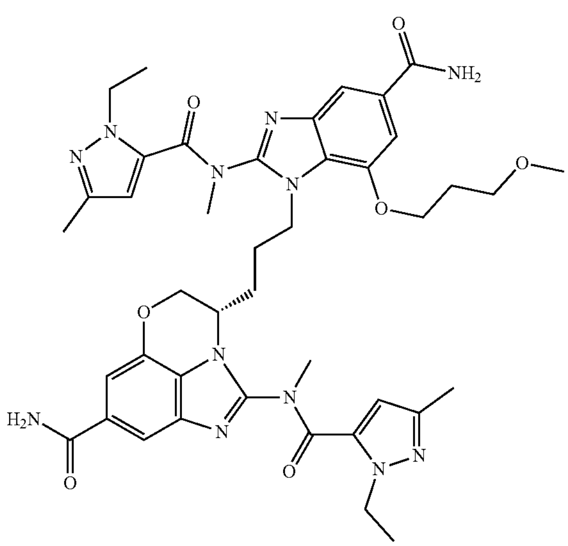 [SMILES: CCn1nc(C)cc1C(=O)N(C)c1nc2cc(C(N)=O)cc(OCCCOC)c2n1CCC[C@H]1COc2cc(C(N)=O)cc3nc(N(C)C(=O)c4cc(C)nn4CC)n1c23] |

| No. | Compound structure |
|---|---|
| 44 | 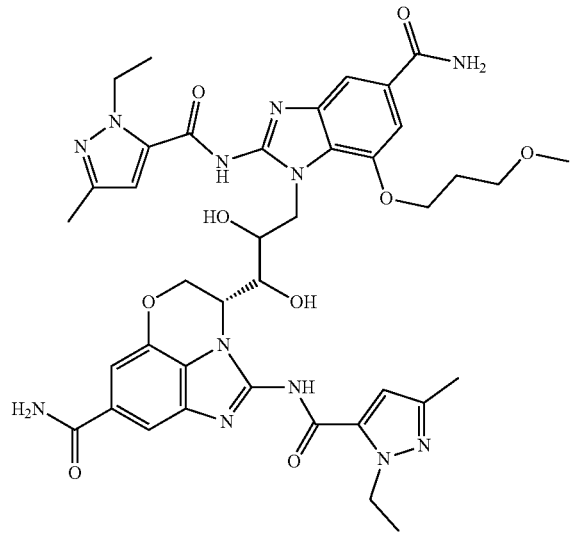 [SMILES: CCn1nc(C)cc1C(=O)Nc1nc2cc(C(N)=O)cc(OCCCOC)c2n1CC(O)C(O)[C@H]1COc2cc(C(N)=O)cc3nc(NC(=O)c4cc(C)nn4CC)n1c23] |
| 45 | 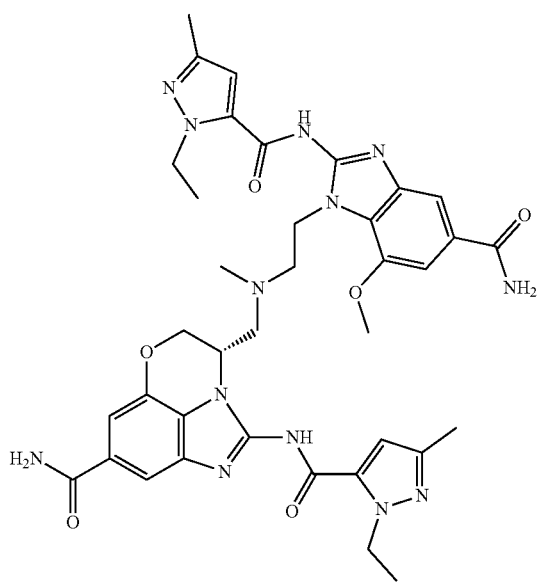 [SMILES: CCn1nc(C)cc1C(=O)Nc1nc2cc(C(N)=O)cc(OC)c2n1CCN(C)C[C@H]1COc2cc(C(N)=O)cc3nc(NC(=O)c4cc(C)nn4CC)n1c23] |

-continued
| No. | Compound structure |
|-----|-------------------|
| 46  | 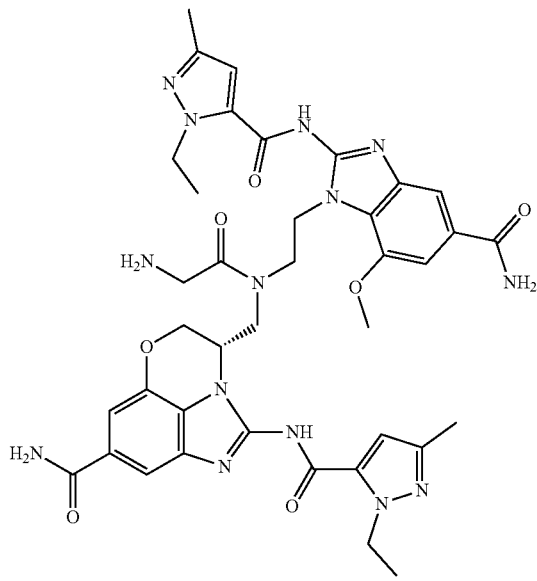 [SMILES: CCn1nc(C)cc1C(=O)Nc1nc2cc(C(N)=O)cc(OC)c2n1CCN(C[C@H]1COc2cc(C(N)=O)cc3nc(NC(=O)c4cc(C)nn4CC)n1c23)C(=O)CN] |
| 47  | 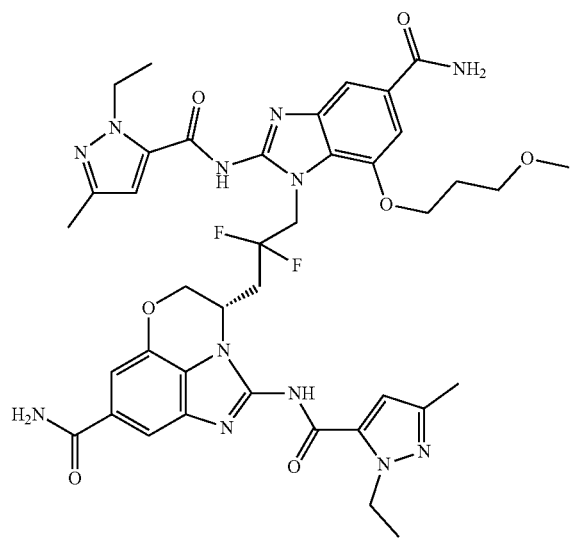 [SMILES: CCn1nc(C)cc1C(=O)Nc1nc2cc(C(N)=O)cc(OCCCOC)c2n1CC(F)(F)C[C@H]1COc2cc(C(N)=O)cc3nc(NC(=O)c4cc(C)nn4CC)n1c23] |

| No. | Compound structure |
|---|---|
| 48 | 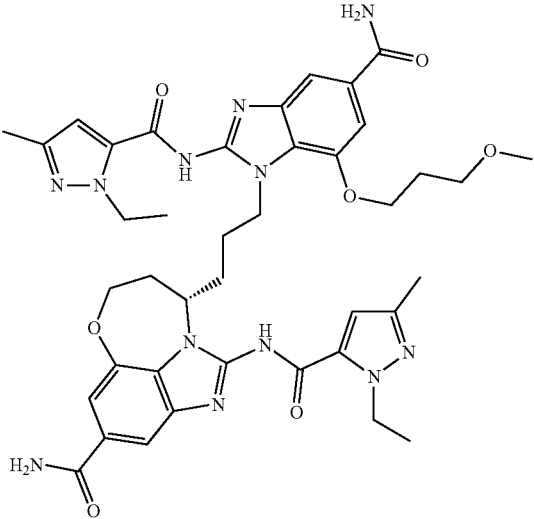 |
| 49 | 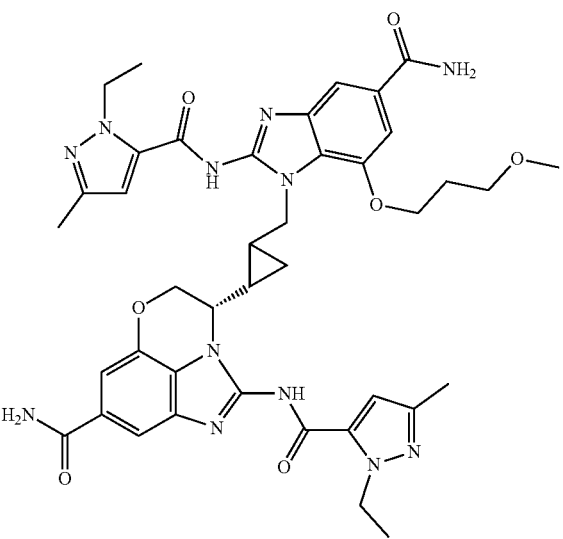 [SMILES: CCn1nc(C)cc1C(=O)Nc1nc2cc(C(N)=O)cc(OCCCOC)c2n1CC1CC1[C@H]1COc2cc(C(N)=O)cc3nc(NC(=O)c4cc(C)nn4CC)n1c23] |
| 50 | 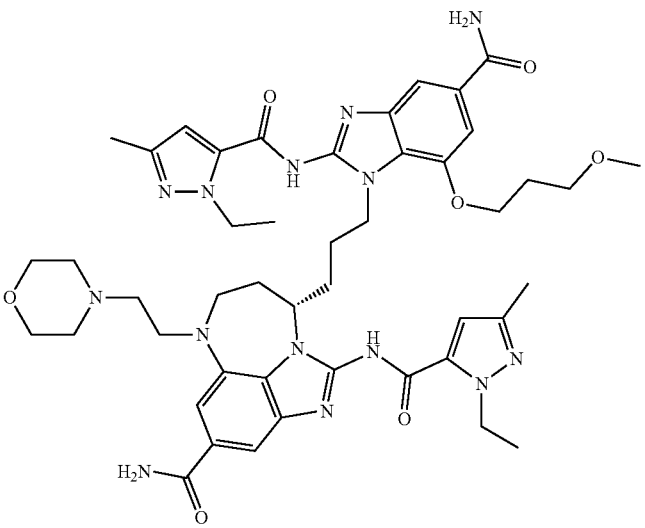 [SMILES: CCn1nc(C)cc1C(=O)Nc1nc2cc(C(N)=O)cc(OCCCOC)c2n1CCC[C@H]1CCN(CCN2CCOCC2)c2cc(C(N)=O)cc3nc(NC(=O)c4cc(C)nn4CC)n1c23] |

| No. | Compound structure |
|---|---|
| 51 | 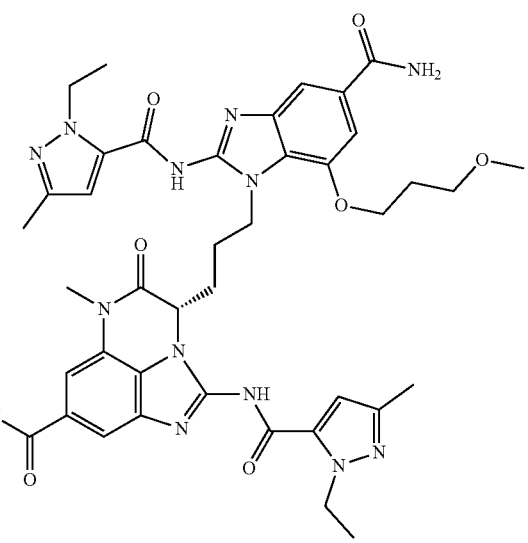 |
| 52 | 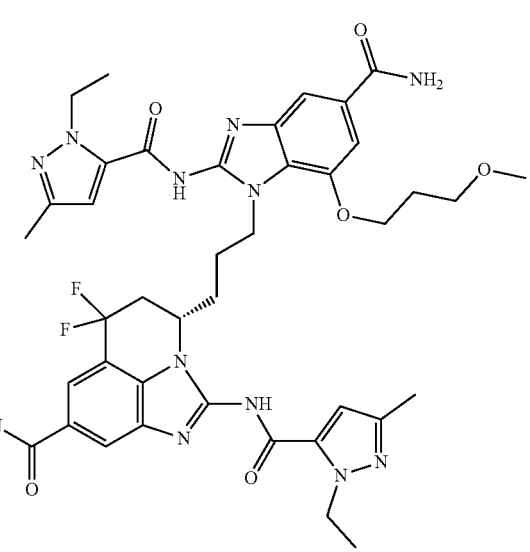 |
| 53 | 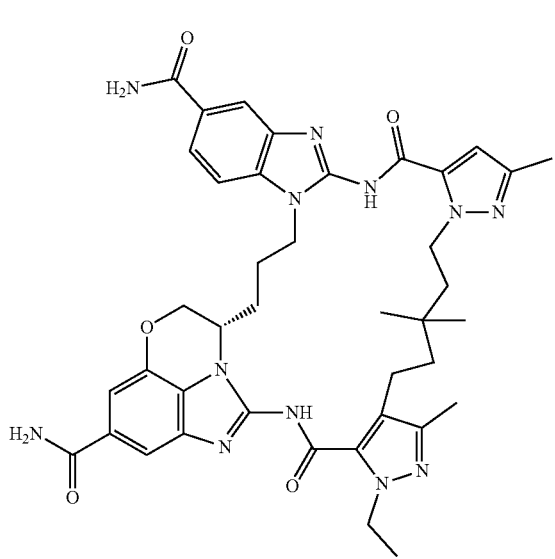 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC(C)(C)CC2)CO4] |

| No. | Compound structure |
|---|---|
| 54 | 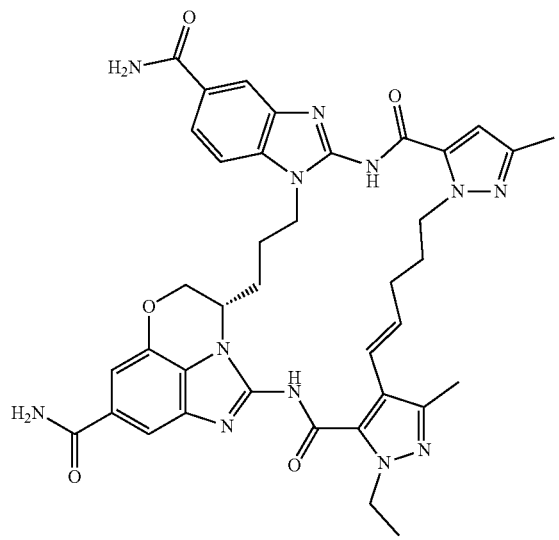 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC/C=C/2)CO4] |
| 55 | 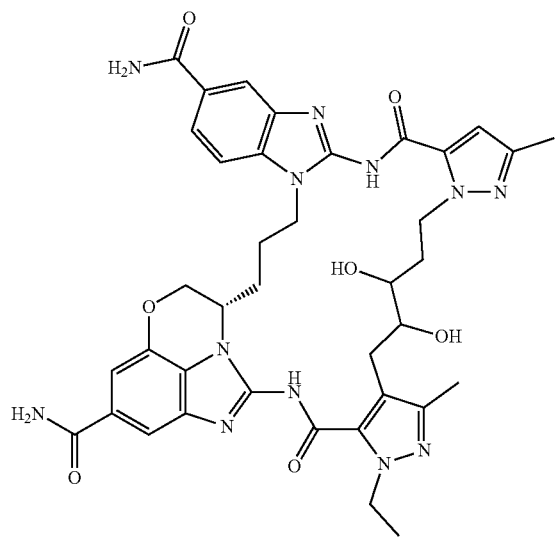 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC(O)C(O)C2)CO4] |

| No. | Compound structure |
|---|---|
| 56 | 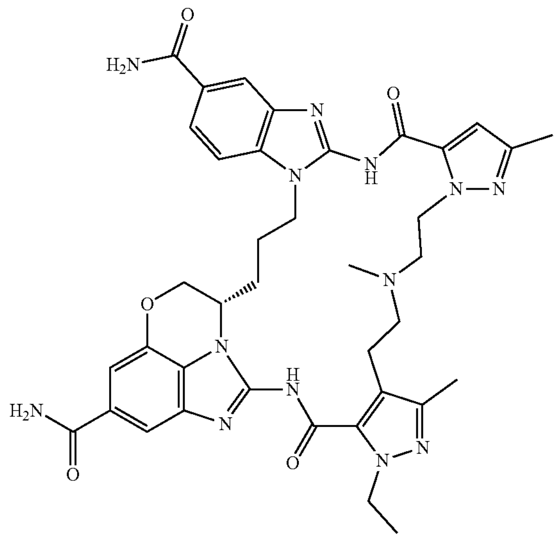 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCN(C)CC2)CO4] |
| 57 | 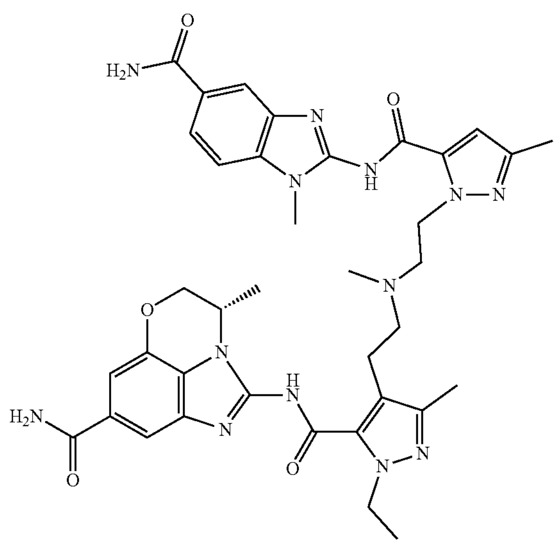 [SMILES: CCn1nc(C)c(CCN(C)CCn2nc(C)cc2C(=O)Nc2nc3cc(C(N)=O)ccc3n2C)c1C(=O)Nc1nc2cc(C(N)=O)cc3c2n1[C@@H](C)CO3] |
| 58 | 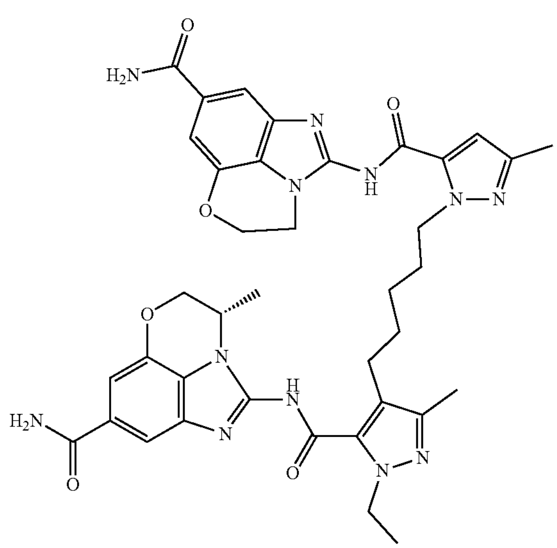 [SMILES: CCn1nc(C)c(CCCCCn2nc(C)cc2C(=O)Nc2nc3cc(C(N)=O)cc4c3n2CCO4)c1C(=O)Nc1nc2cc(C(N)=O)cc3c2n1[C@@H](C)CO3] |

| No. | Compound structure |
|---|---|
| 59 | 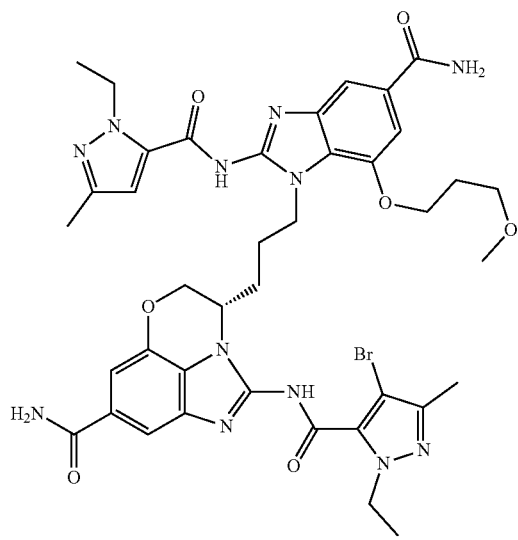 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(Br)c(C)nn4CC)n1c23] |
| 60 | 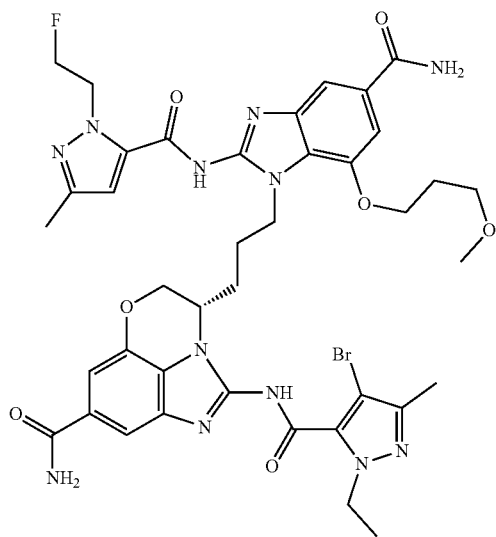 [SMILES: CCn1nc(C)c(Br)c1C(=O)Nc1nc2cc(C(N)=O)cc3c2n1[C@@H](CCCn1c(NC(=O)c2cc(C)nn2CCF)nc2cc(C(N)=O)cc(OCCCOC)c21)CO3] |

-continued
| No. | Compound structure |
|---|---|
| 61 | 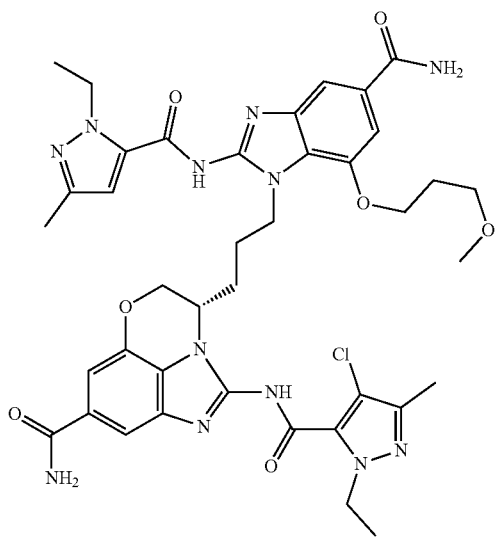 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(Cl)c(C)nn4CC)n1c23] |
| 62 | 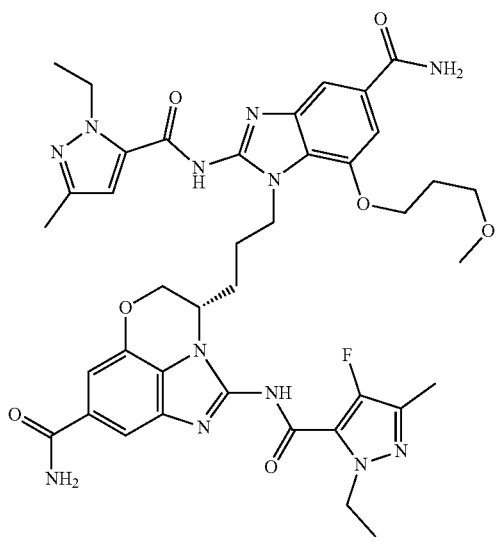 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(F)c(C)nn4CC)n1c23] |
| 63 | 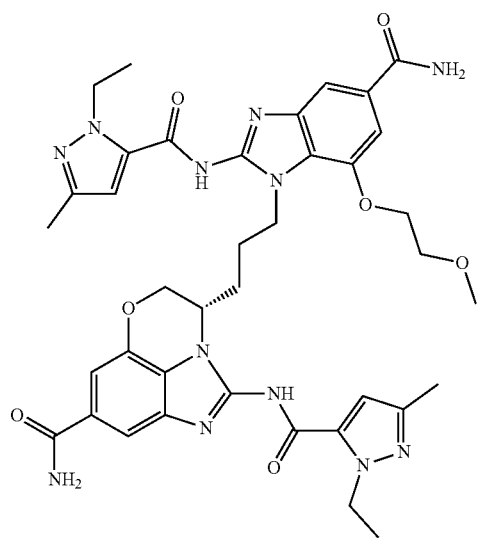 [SMILES: CCn1nc(C)cc1C(=O)Nc1nc2cc(C(N)=O)cc(OCCOC)c2n1CCC[C@H]1COc2cc(C(N)=O)cc3nc(NC(=O)c4cc(C)nn4CC)n1c23] |

-continued
| No. | Compound structure |
|---|---|
| 64 | 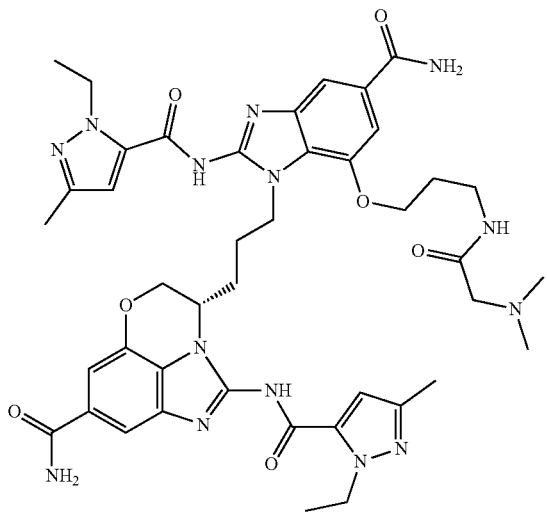 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4cc(C)nn4CC)n1c23] |
| 65 | 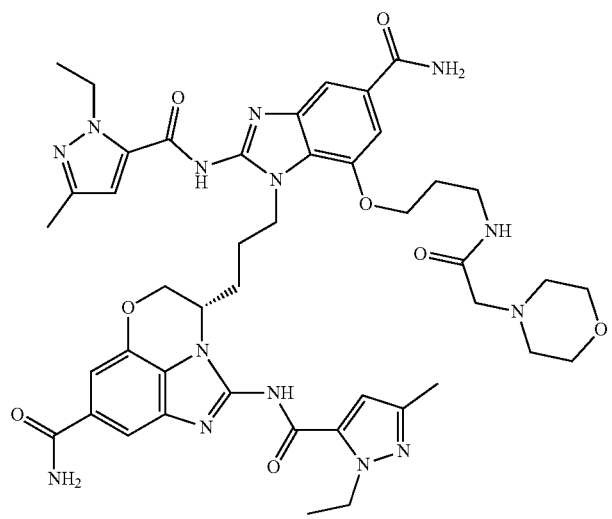 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4cc(C)nn4CC)n1c23] |
| 66 | 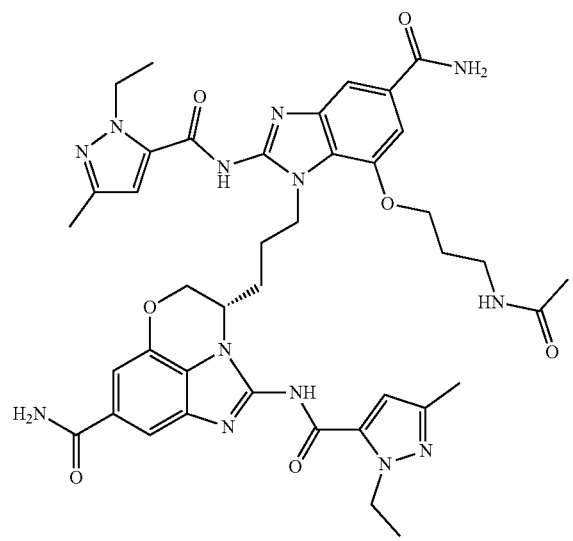 [SMILES: CCn1nc(C)cc1C(=O)Nc1nc2cc(C(N)=O)cc(OCCCNC(C)=O)c2n1CCC[C@H]1COc2cc(C(N)=O)cc3nc(NC(=O)c4cc(C)nn4CC)n1c23] |

| No. | Compound structure |
|---|---|
| 67 | 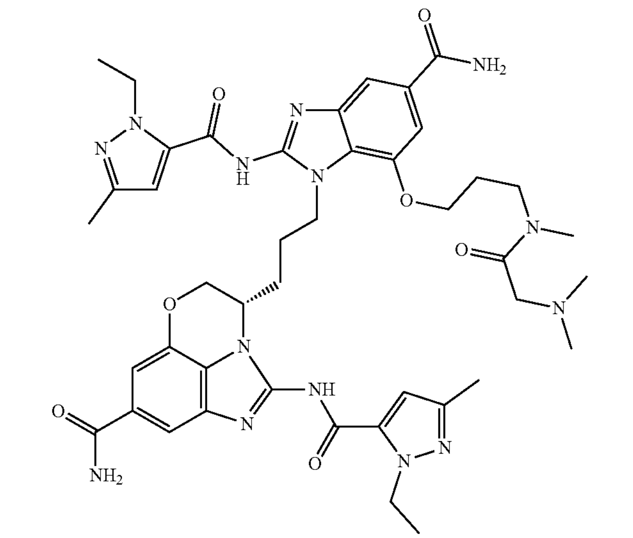 [SMILES: CCn1nc(C)cc1C(=O)Nc1nc2cc(C(N)=O)cc(OCCCN(C)C(=O)CN(C)C)c2n1CCC[C@H]1COc2cc(C(N)=O)cc3nc(NC(=O)c4cc(C)nn4CC)n1c23] |
| 68 | 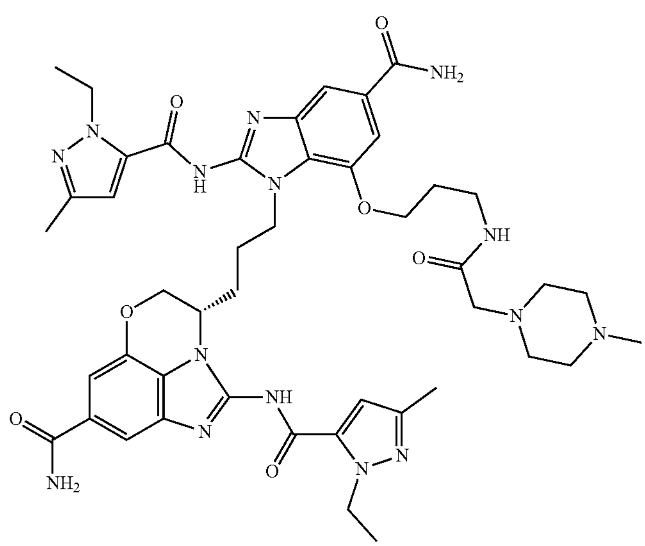 [SMILES: CCn1nc(C)cc1C(=O)Nc1nc2cc(C(N)=O)cc(OCCCNC(=O)CN3CCN(C)CC3)c2n1CCC[C@H]1COc2cc(C(N)=O)cc3nc(NC(=O)c4cc(C)nn4CC)n1c23] |
| 69 | 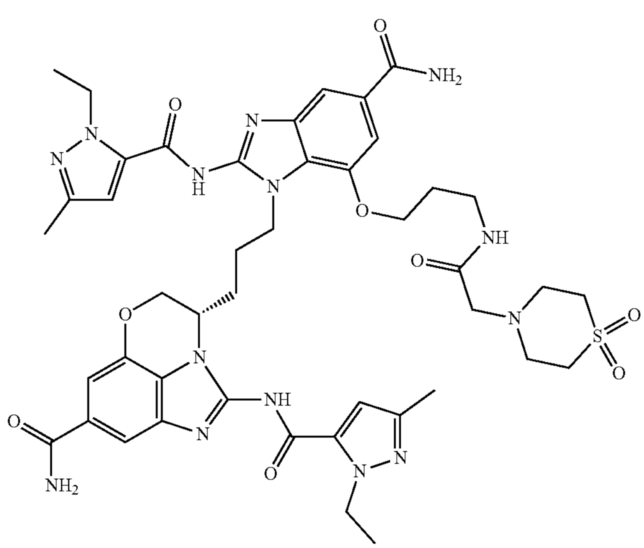 [SMILES: CCn1nc(C)cc1C(=O)Nc1nc2cc(C(N)=O)cc(OCCCNC(=O)CN3CCS(=O)(=O)CC3)c2n1CCC[C@H]1COc2cc(C(N)=O)cc3nc(NC(=O)c4cc(C)nn4CC)n1c23] |

| No. | Compound structure |
|---|---|
| 70 | 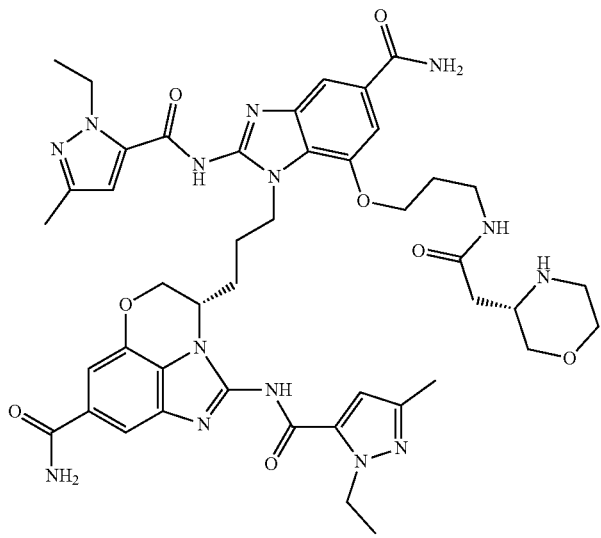 [SMILES: CCn1nc(C)cc1C(=O)Nc1nc2cc(C(N)=O)cc(OCCCNC(=O)C[C@H]3COCCN3)c2n1CCC[C@H]1COc2cc(C(N)=O)cc3nc(NC(=O)c4cc(C)nn4CC)n1c23] |
| 71 | 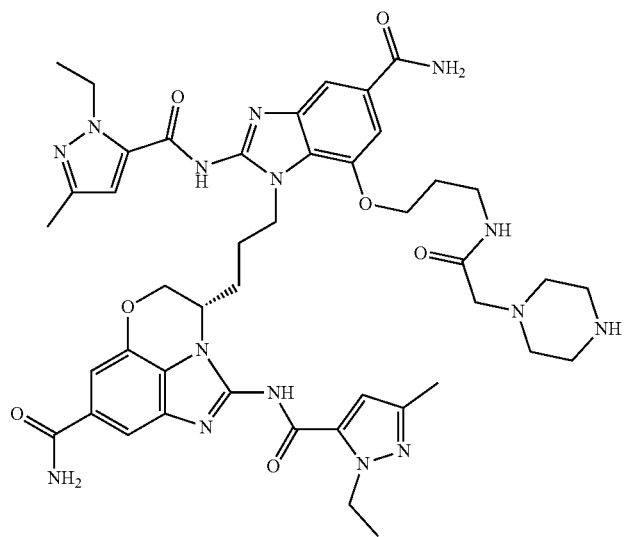 [SMILES: CCn1nc(C)cc1C(=O)Nc1nc2cc(C(N)=O)cc(OCCCNC(=O)CN3CCNCC3)c2n1CCC[C@H]1COc2cc(C(N)=O)cc3nc(NC(=O)c4cc(C)nn4CC)n1c23] |

-continued
| No. | Compound structure |
|---|---|
| 72 | 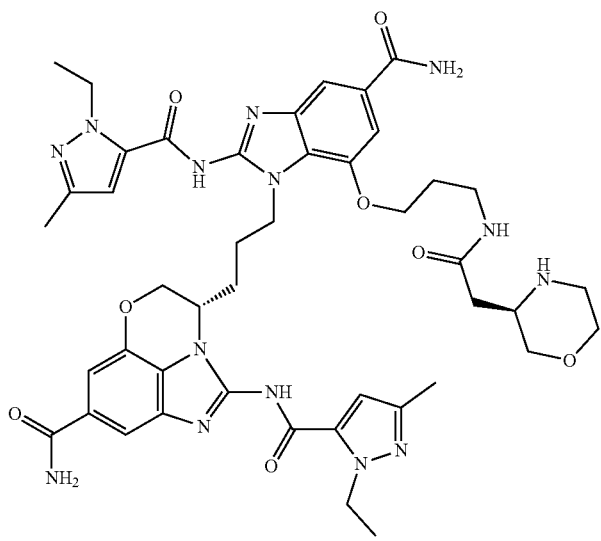 [SMILES: CCn1nc(C)cc1C(=O)Nc1nc2cc(C(N)=O)cc(OCCCNC(=O)C[C@@H]3COCCN3)c2n1CCC[C@H]1COc2cc(C(N)=O)cc3nc(NC(=O)c4cc(C)nn4CC)n1c23] |
| 73 | 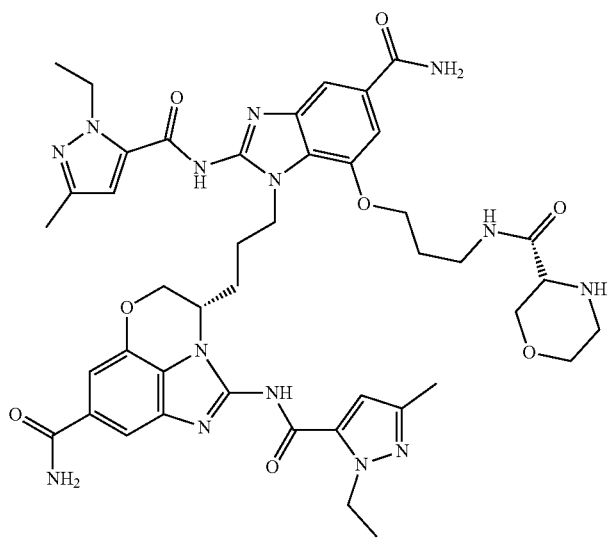 |
| 74 | 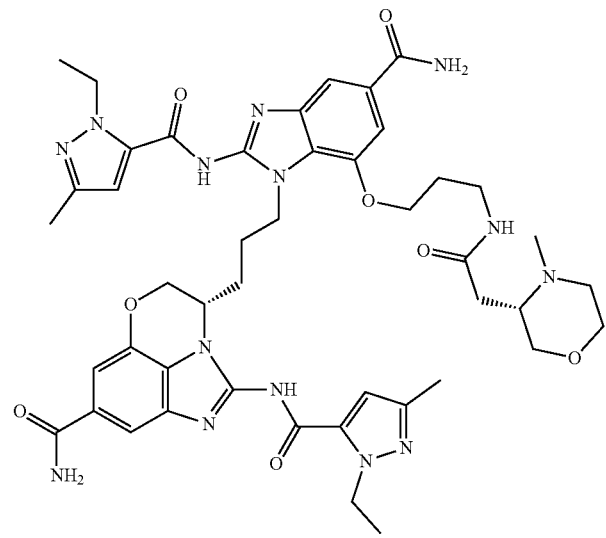 [SMILES: CCn1nc(C)cc1C(=O)Nc1nc2cc(C(N)=O)cc(OCCCNC(=O)C[C@H]3COCCN3C)c2n1CCC[C@H]1COc2cc(C(N)=O)cc3nc(NC(=O)c4cc(C)nn4CC)n1c23] |

| No. | Compound structure |
|---|---|
| 75 | 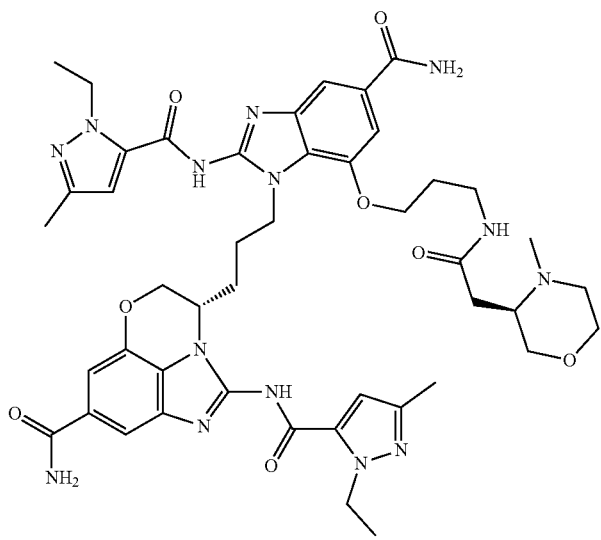 [SMILES: CCn1nc(C)cc1C(=O)Nc1nc2cc(C(N)=O)cc(OCCCNC(=O)C[C@@H]3COCCN3C)c2n1CCC[C@H]1COc2cc(C(N)=O)cc3nc(NC(=O)c4cc(C)nn4CC)n1c23] |
| 76 | 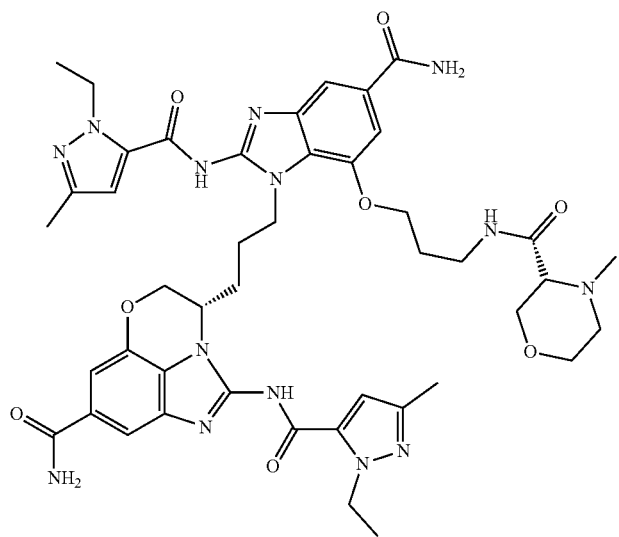 |

| No. | Compound structure |
|---|---|
| 77 | 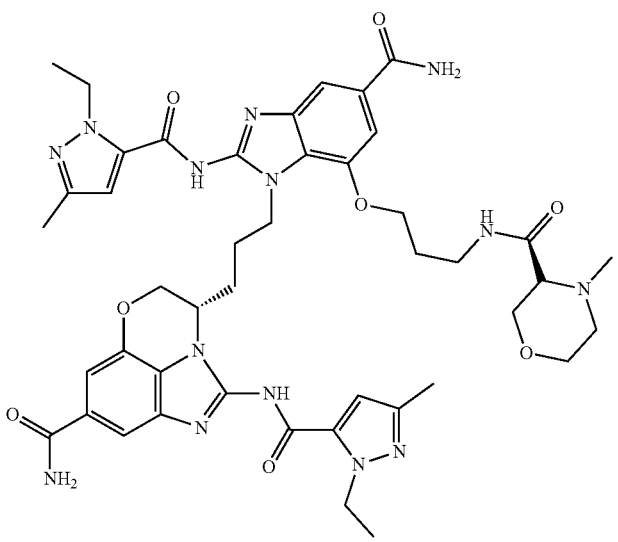 |
| 78 | 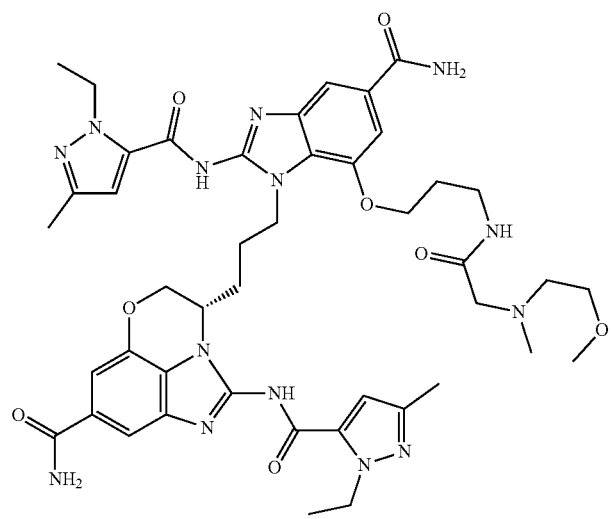 [SMILES: CCn1nc(C)cc1C(=O)Nc1nc2cc(C(N)=O)cc(OCCCNC(=O)CN(C)CCOC)c2n1CCC[C@H]1COc2cc(C(N)=O)cc3nc(NC(=O)c4cc(C)nn4CC)n1c23] |
| 79 | 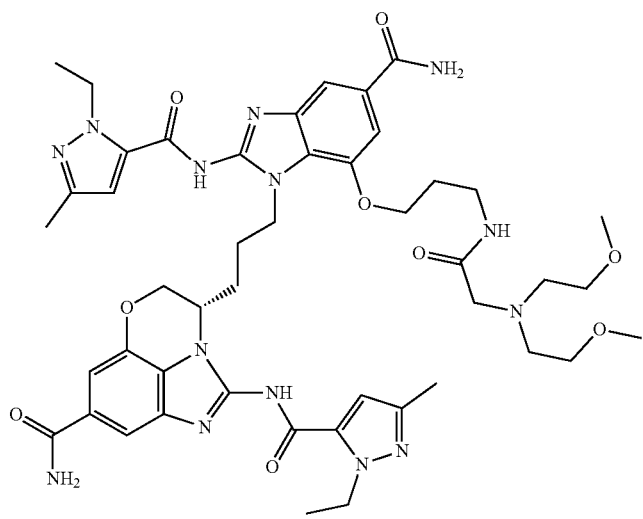 [SMILES: CCn1nc(C)cc1C(=O)Nc1nc2cc(C(N)=O)cc(OCCCNC(=O)CN(CCOC)CCOC)c2n1CCC[C@H]1COc2cc(C(N)=O)cc3nc(NC(=O)c4cc(C)nn4CC)n1c23] |

| No. | Compound structure |
|---|---|
| 80 | 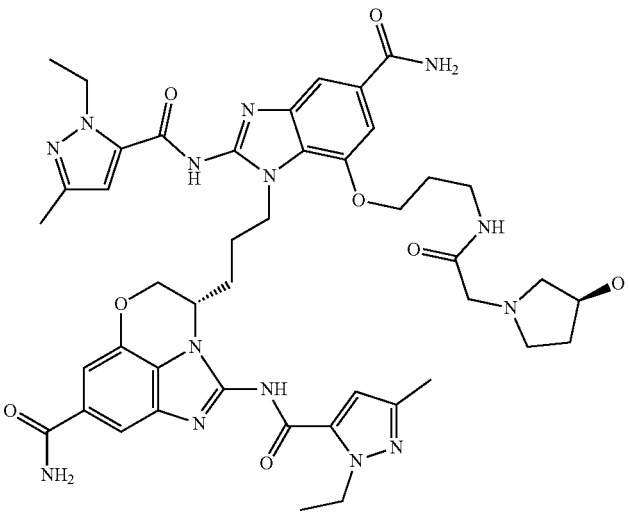 [SMILES: CCn1nc(C)cc1C(=O)Nc1nc2cc(C(N)=O)cc(OCCCNC(=O)CN3CC[C@H](O)C3)c2n1CCC[C@H]1COc2cc(C(N)=O)cc3nc(NC(=O)c4cc(C)nn4CC)n1c23] |
| 81 | 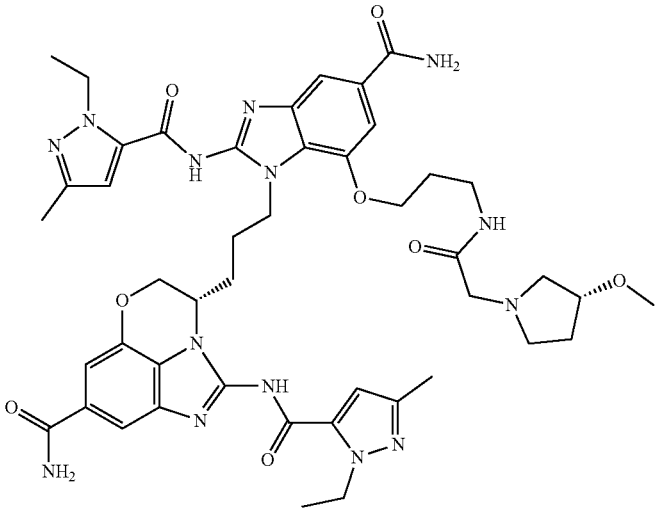 [SMILES: CCn1nc(C)cc1C(=O)Nc1nc2cc(C(N)=O)cc(OCCCNC(=O)CN3CC[C@@H](OC)C3)c2n1CCC[C@H]1COc2cc(C(N)=O)cc3nc(NC(=O)c4cc(C)nn4CC)n1c23] |
| 82 | 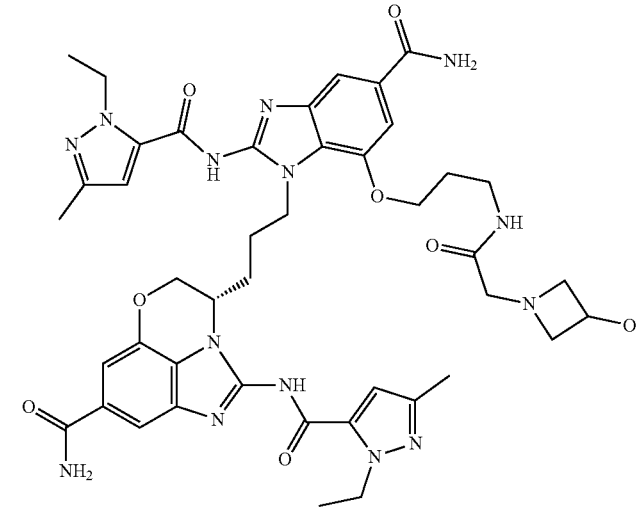 [SMILES: CCn1nc(C)cc1C(=O)Nc1nc2cc(C(N)=O)cc(OCCCNC(=O)CN3CC(O)C3)c2n1CCC[C@H]1COc2cc(C(N)=O)cc3nc(NC(=O)c4cc(C)nn4CC)n1c23] |

-continued

| No. | Compound structure |
|-----|-------------------|
| 83  | 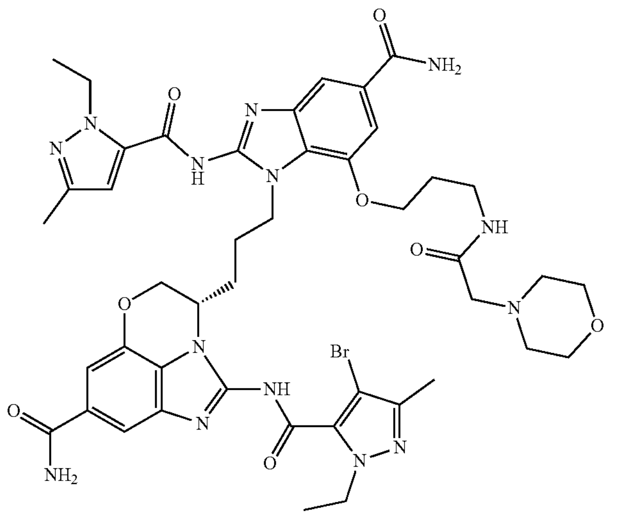 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(Br)c(C)nn4CC)n1c23]                  |
| 84  | 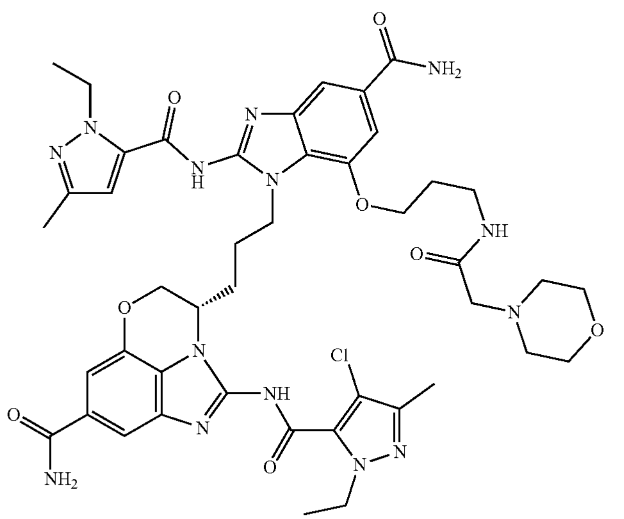 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(Cl)c(C)nn4CC)n1c23]                  |
| 85  | 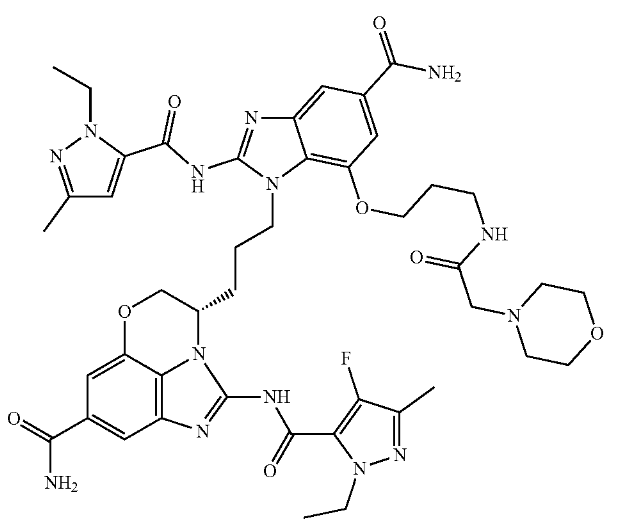 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(F)c(C)nn4CC)n1c23]                  |

| No. | Compound structure |
|---|---|
| 86 | 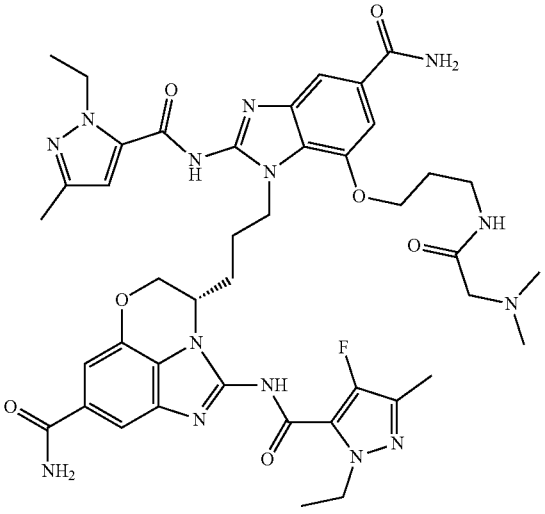 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(F)c(C)nn4CC)n1c23] |
| 87 | 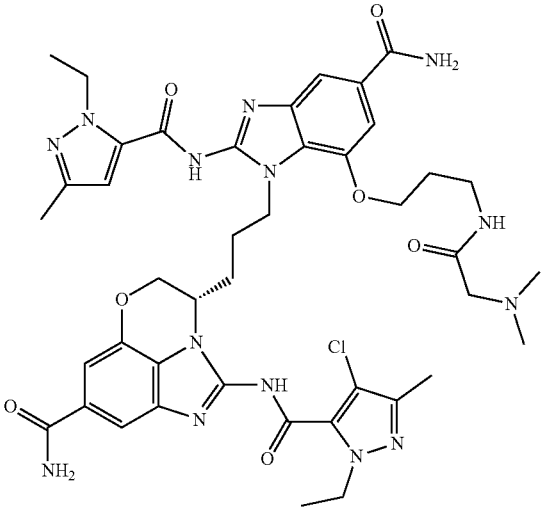 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(Cl)c(C)nn4CC)n1c23] |
| 88 | 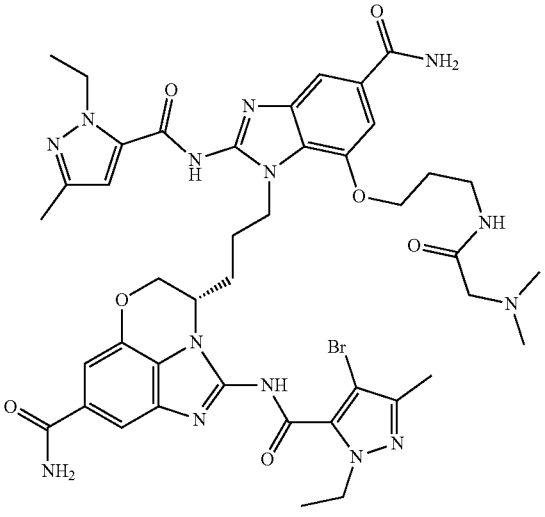 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(Br)c(C)nn4CC)n1c23] |

| No. | Compound structure |
|---|---|
| 89 | 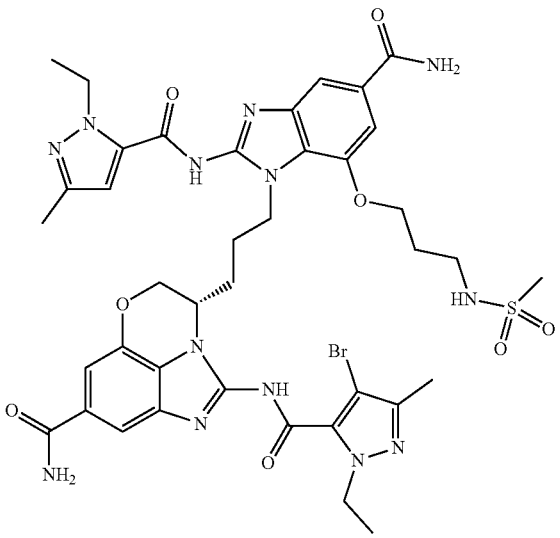 [SMILES: CCn1nc(C)cc1C(=O)Nc1nc2cc(C(N)=O)cc(OCCCNS(C)(=O)=O)c2n1CCC[C@H]1COc2cc(C(N)=O)cc3nc(NC(=O)c4c(Br)c(C)nn4CC)n1c23] |
| 90 | 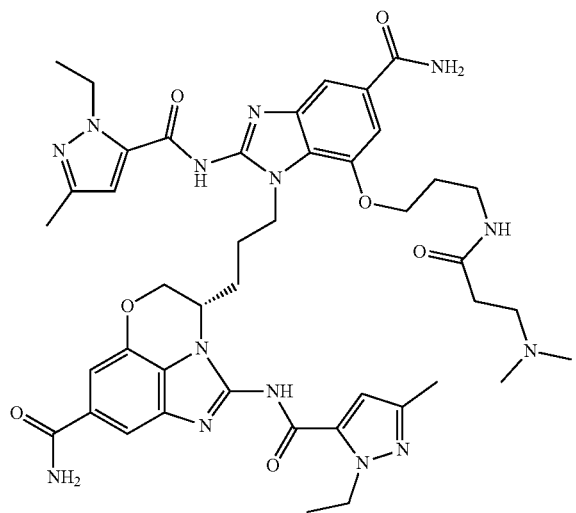 [SMILES: CCn1nc(C)cc1C(=O)Nc1nc2cc(C(N)=O)cc(OCCCNC(=O)CCN(C)C)c2n1CCC[C@H]1COc2cc(C(N)=O)cc3nc(NC(=O)c4cc(C)nn4CC)n1c23] |
| 91 | 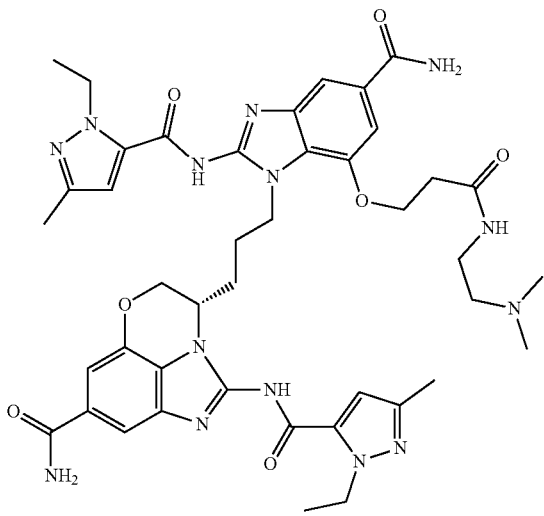 [SMILES: CCn1nc(C)cc1C(=O)Nc1nc2cc(C(N)=O)cc(OCCC(=O)NCCN(C)C)c2n1CCC[C@H]1COc2cc(C(N)=O)cc3nc(NC(=O)c4cc(C)nn4CC)n1c23] |

-continued

| No. | Compound structure |
|---|---|
| 92 | 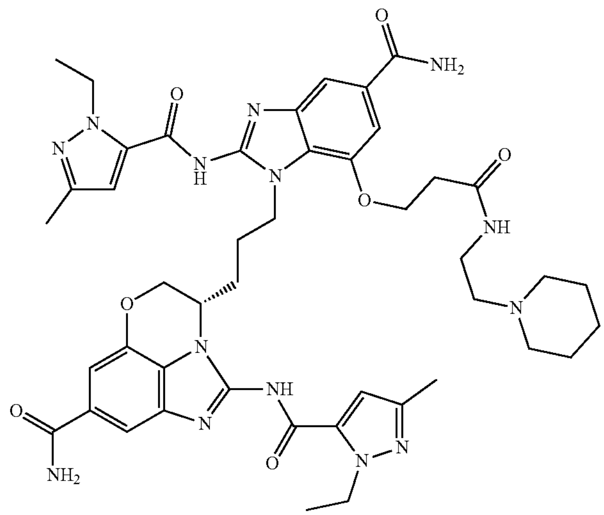 [SMILES: CCn1nc(C)cc1C(=O)Nc1nc2cc(C(N)=O)cc(OCCC(=O)NCCN3CCCCC3)c2n1CCC[C@H]1COc2cc(C(N)=O)cc3nc(NC(=O)c4cc(C)nn4CC)n1c23] |
| 93 | 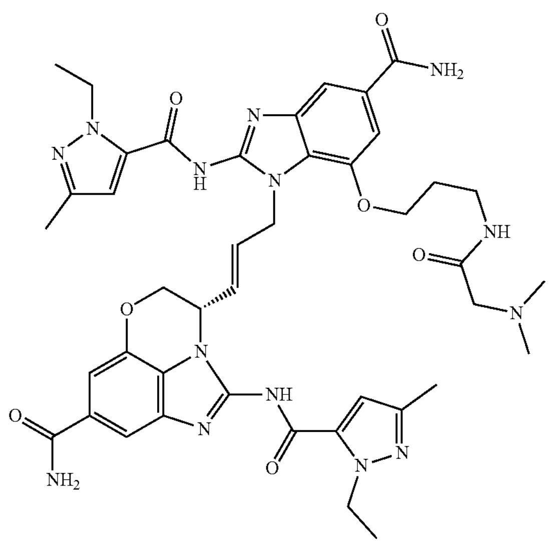 [SMILES: CCn1nc(C)cc1C(=O)Nc1nc2cc(C(N)=O)cc(OCCCNC(=O)CN(C)C)c2n1C/C=C/[C@H]1COc2cc(C(N)=O)cc3nc(NC(=O)c4cc(C)nn4CC)n1c23] |
| 94 | 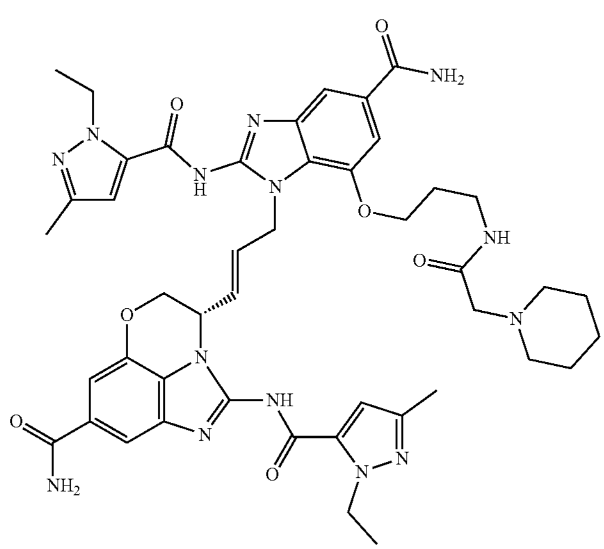 [SMILES: CCn1nc(C)cc1C(=O)Nc1nc2cc(C(N)=O)cc(OCCCNC(=O)CN3CCCCC3)c2n1C/C=C/[C@H]1COc2cc(C(N)=O)cc3nc(NC(=O)c4cc(C)nn4CC)n1c23] |

| No. | Compound structure |
|---|---|
| 95 | 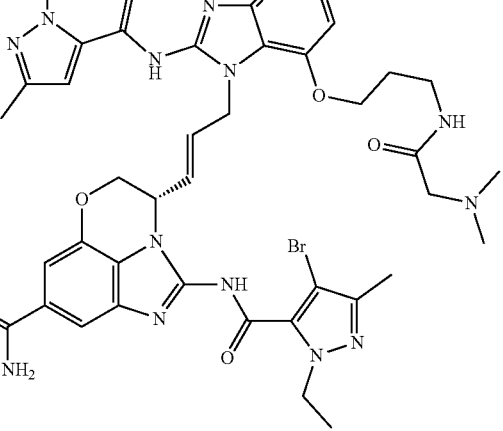 |
| 96 | 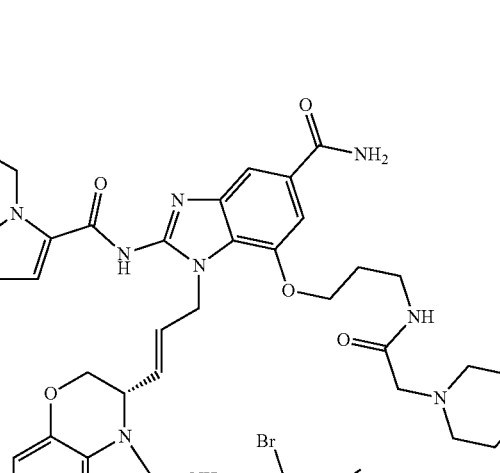 |

SPECIFIC EXAMPLES

When no preparative route is included, related intermediates are commercially available (e.g. from Sigma Aldrich, Alfa).

General Procedure

Commercial reagents were used without further purification. Room temperature refers to 20° C.; to 27° C. 1H-NMR spectra were recorded on a Bruker instrument at 500 MHz. Chemical shift values are expressed in parts per million, i.e. S value. The following abbreviations are used for the multiplicity of NMR signals: s=singlet, brs=broad, d=doublet, t=triplet, m=multiplet. Coupling constants were listed as J values, measured in Hz. NMR and mass spectrum results were corrected for background peaks. Chromatography refers to column chromatography performed using 100 meshes silica gel and completed under nitrogen pressure (flash chromatography). TLC used to monitor the reaction refers to TLC performed using a specific mobile phase and silica gel F254 from Merck as stationary phase.

Example 1
(S)-3-(3-(5-Carbamoyl-2-(1-ethyl-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3, 4-dihydro-5-oxa-1,2a-diazaacenaphthylene-7-carboxamide
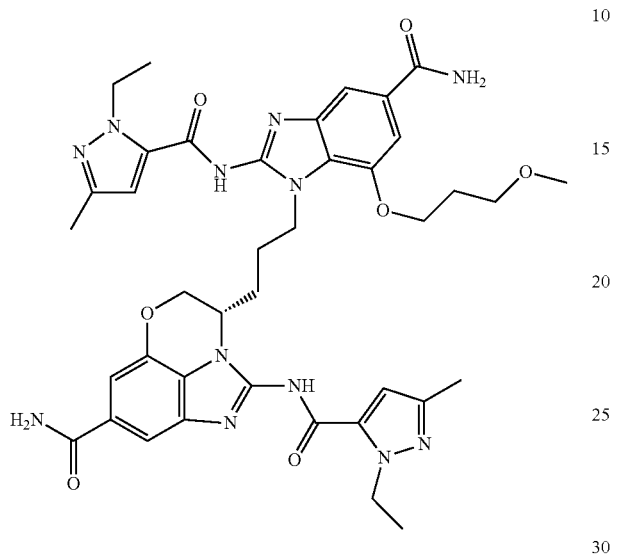
Synthetic scheme:
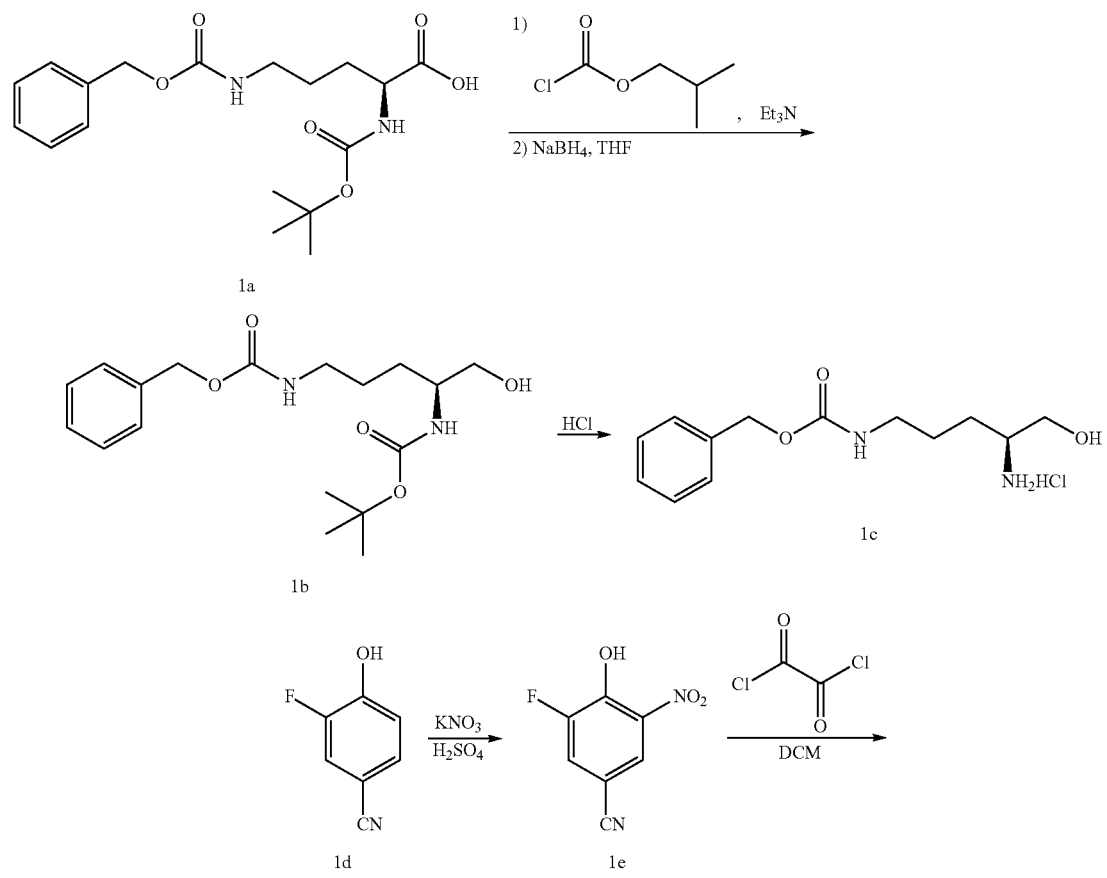

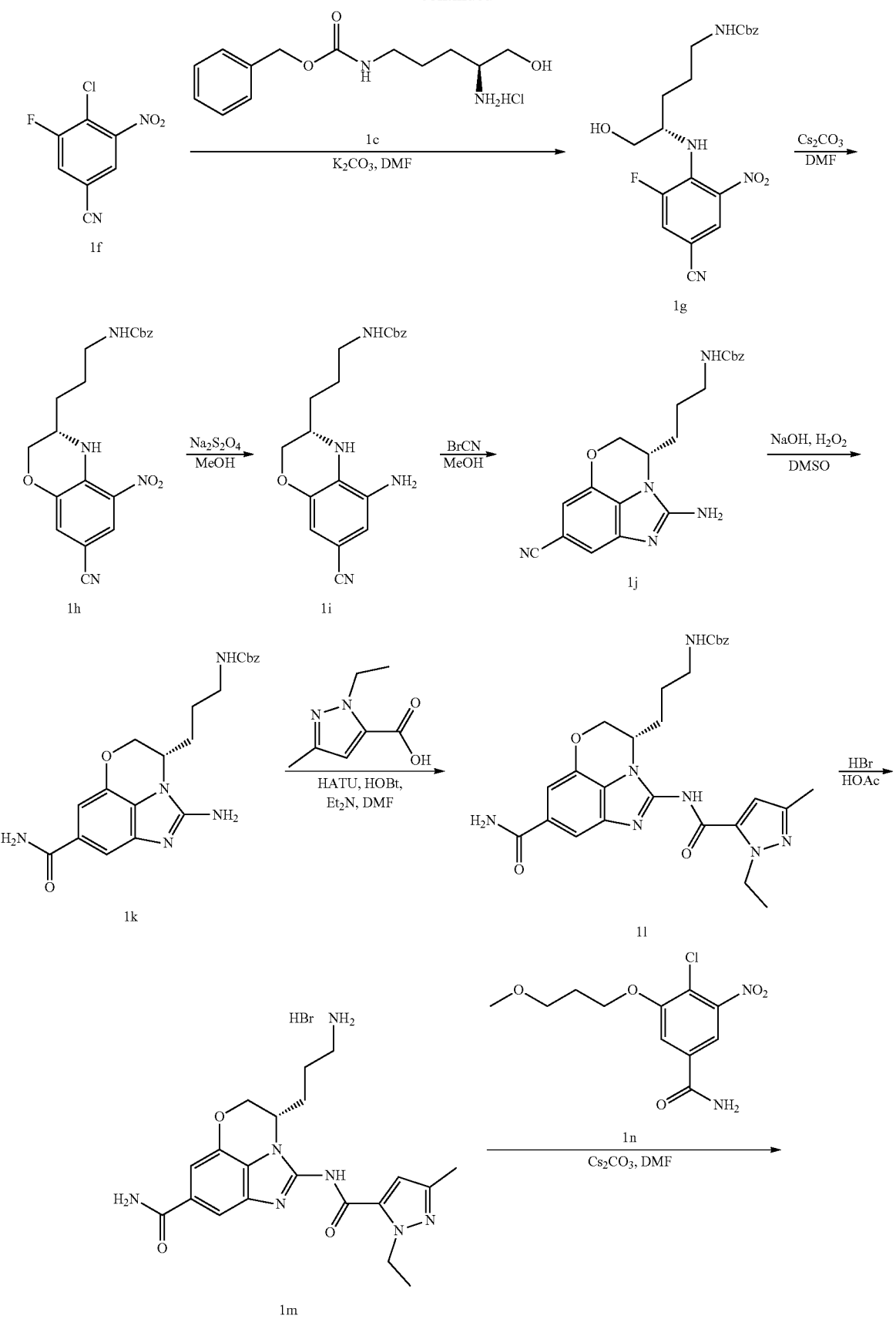

-continued
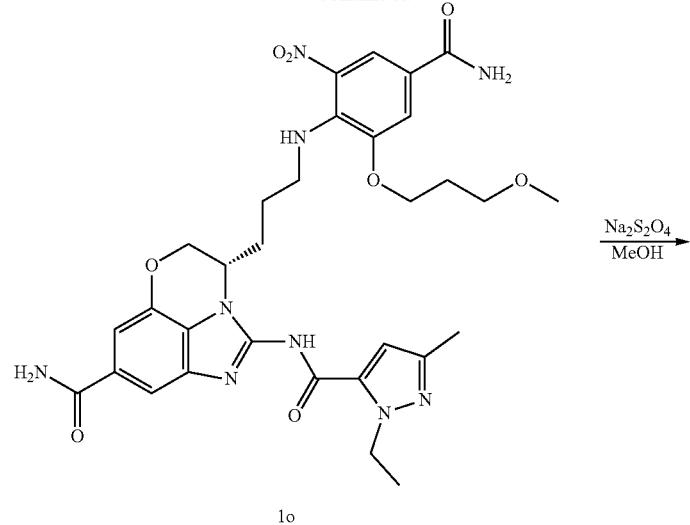
1o
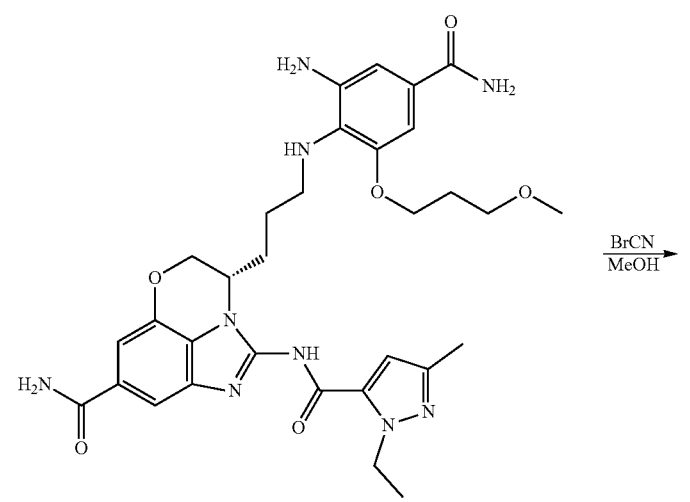
1p
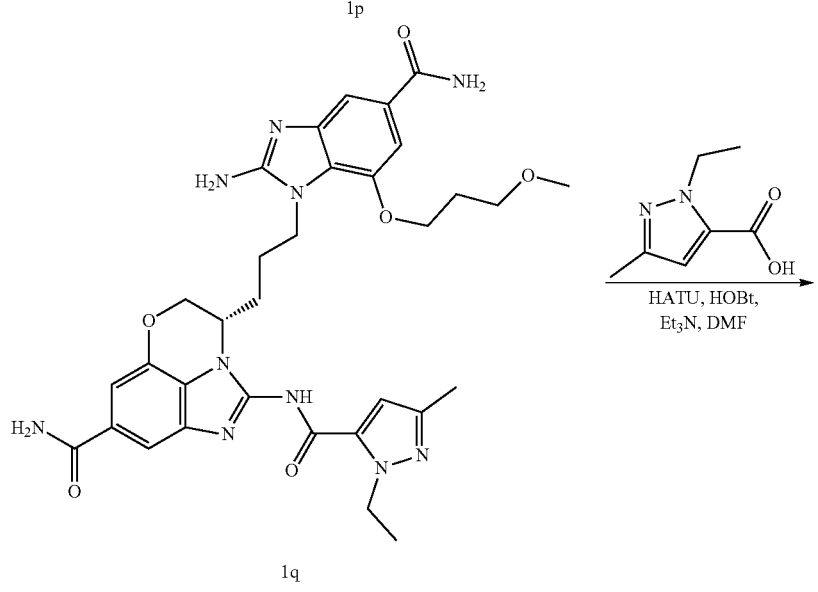
1q

-continued

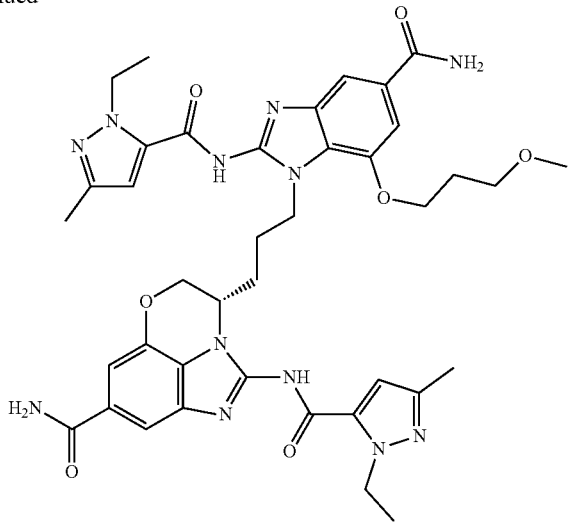

1

Step 1: To a stirring solution of (S)-5-(((benzyloxy)carbonyl)amino)-2-((tert-butoxycarbonyl)amino)pentanoic acid 1a (25 g, 69 mmol) and triethylamne (11.5 mL, 81.9 mmol) in THF (100 mL) was dropwise added isobutyl chloroformate (10 mL, 79 mmol) at 0° C. The mixture was stirred at 0° C.; for 30 minutes, then sodium borohydride (7.8 g, 205 mmol) was added, followed by drop-wise addition of water (3 mL) to the reaction. The mixture was kept stirring at 0° C.; for 2 hours. After the reaction was complete, water (150 mL) was added to the reaction mixture, which was extracted with ethyl acetate (150 mL×3). The combined organic layers were dried over $Na_2SO_4$, filtered and concentrated under reduced pressure to give the compound 1b (20 g, 83% yield) as colorless oil. ESI-MS (m/z): 353.6 [M+H]$^+$; $^1$H NMR (500 MHz, DMSO-d6) δ ppm 7.39-7.25 (m, 5H), 7.19 (t, J=5.2 Hz, 1H), 6.43 (d, J=8.3 Hz, 1H), 4.98 (s, 2H), 4.53 (t, J=5.4 Hz, 1H), 3.30-3.07 (m, 2H), 2.94 (dd, J=12.4, 6.4 Hz, 2H), 1.57-1.39 (m, 2H), 1.35 (s, 9H), 1.23-1.12 (m, 2H).

Step 2: To a stirring solution of compound 1b (20 g, 56 mmol) in dichloromethane (200 mL) was added 4M HCl in dioxane (70 mL, 280 mmol) at room temperature. The mixture was stirred overnight at room temperature and LCMS indicated the product was formed. The mixture was concentrated under reduced pressure to give compound 1c (13 g, 93% yield) as colorless oil. ESI-MS (m/z): 253.6 [M+H]$^+$.

Step 3: Fuming $HNO_3$ (50 mL) was added dropwise to a solution of 3-fluoro-4-hydroxybenzonitrile 1d (13.7 g, 100 mmol) in conc. $H_2SO_4$ (200 mL) at 0° C. The mixture was stirred at 0° C.; for 3 hours. LCMS showed that the starting material was consumed. The reaction mixture was poured into ice slowly and extracted with ethyl acetate (300 mL×3). The combined organic layers were dried over $Na_2SO_4$, filtered and concentrated under reduced pressure to give compound 1e (15 g, 82% yield) as brown solid. $^1$H NMR (500 MHz, DMSO-d6) δ ppm 8.29 (s, 1H), 8.12 (d, J=10.4 Hz, 1H).

Step 4: Oxalyl chloride (13.7 mL, 163 mmol) was added dropwise to a solution of compound 1e (15 g, 82 mmol) in DCM (100 mL) at 0° C. After stirring at 0° C.; for 30 minutes, the reaction was heated to 80° C.; for 2 hours. The reaction mixture was allowed to cool to room temperature, poured into ice water and extracted with ethyl acetate (250 mL×3). The combined organic layers were dried over $Na_2SO_4$, filtered and concentrated under reduced pressure to give compound 1f (11.3 g, 69% yield) as yellow solid. $^1$H NMR (500 MHz, DMSO-d6) δ ppm 8.62 (s, 1H), 8.50 (dd, J=8.8, 1.6 Hz, 1H).

Step 5: To a stirring solution of compound 1f (5 g, 25 mmol) and compound 1c (13 g, 51 mmol) in DMF (20 mL) was added $K_2CO_3$ (6.9 g, 50 mmol), and the resulting mixture was heated at 60° C.; for 24 hours. The reaction mixture was cooled to room temperature, diluted with water (150 mL) and extracted with ethyl acetate (150 mL×3). The combined organic layers were dried over $Na_2SO_4$, filtered and concentrated under reduced pressure, the residue was purified by silica gel chromatography to give compound 1g (6.1 g, 57% yield) as yellow oil. ESI-MS (m/z): 417.6 [M+H]$^+$.

Step 6: To a stirring solution of compound 1g (6 g, 14 mmol) in DMF (15 mL) was added $Cs_2CO_3$ (9.2 g, 28 mmol), and the reaction mixture was heated at 60° C.; for 2 hours. The reaction was cooled to room temperature, diluted with water (100 mL) and extracted with ethyl acetate (150 mL×3). The combined organic layers were dried over $Na_2SO_4$, filtered and concentrated under reduced pressure, the residue was purified by silica gel chromatography to give compound 1h (4.7 g, 82% yield) as yellow solid. ESI-MS (m/z): 397.7 [M+H]$^+$; $^1$H NMR (500 MHz, DMSO-d6) δ ppm 8.88 (s, 1H), 8.12 (s, 1H), 7.38 (s, 1H), 7.36-7.19 (m, 6H), 4.97 (s, 2H), 4.10 (dd, J=23.9, 10.9 Hz, 2H), 3.72 (s, 1H), 3.01 (s, 2H), 1.67-1.52 (m, 4H).

Step 7: Compound 1h (4.7 g, 11.8 mmol) was dissolved in a mixture of MeOH (100 mL) and concentrated ammonium hydroxide (20 mL). And sodium dithionite (10 g, 57 mmol) was dissolved in water (20 mL), the resultant solution was added to the reaction mixture at room temperature. Stirring was continued at room temperature for half an hour. The reaction mixture was diluted with water (200 mL) and extracted with ethyl acetate (200 mL×3). The combined organic layers were dried over $Na_2SO_4$, filtered and concentrated under reduced pressure to give compound 1i (3.8 g, 87% yield) as light yellow solid. ESI-MS (m/z): 367.7

[M+H]⁺; ¹H NMR (500 MHz, DMSO-d6) δ ppm 7.42-7.23 (m, 6H), 6.45 (dd, J=11.9, 1.8 Hz, 2H), 5.45 (d, J=1.6 Hz, 1H), 5.01 (s, 2H), 4.99 (s, 2H), 4.07 (dd, J=10.5, 2.5 Hz, 1H), 3.71 (dd, J=10.5, 6.3 Hz, 1H), 3.34 (dd, J=5.9, 2.8 Hz, 1H), 3.01 (dd, J=12.2, 6.2 Hz, 2H), 1.63-1.29 (m, 4H).

Step 8: To a stirring solution of compound 1i (3.8 g, 10 mmol) in MeOH (60 mL) was added cyanogen bromide (5.4 g, 51 mmol). The resulting mixture was stirred at room temperature overnight. The mixture was concentrated in vacuo to remove the solvent, the residue was suspended in saturated aqueous Na₂CO₃ solution (150 mL) and extracted with ethyl acetate (150 mL×3). The combined organic layers were dried over Na₂SO₄, filtered and concentrated under reduced pressure to yield compound 1j (3.5 g, 86% yield) as light yellow solid. ESI-MS (m/z): 392.6 [M+H]⁺.

Step 9: To a stirring solution of compound 1j (3.5 g, 9 mmol) in DMSO (20 mL) at 0° C.; was added solid NaOH (1 g, 25 mmol), followed by the addition of hydrogen peroxide (30 wt. %, 12 mL). The reaction was warmed to room temperature and stirred for half an hour. The mixture was diluted with water (100 mL) and extracted with EtOAc (150 mL×3). The combined organic layers were dried over Na₂SO₄, filtered and concentrated under reduced pressure to give compound 1k (2.8 g, 76% yield) as yellow solid. ESI-MS (m/z): 410.5 [M+H]⁺.

Step 10: To a stirring solution of 1-ethyl-3-methyl-1H-pyrazole-5-carboxylic acid (1.6 g, 10.3 mmol) in DMF (8 mL) was added HATU (3.9 g, 10.3 mmol), HOBt (700 mg, 5.2 mmol) and triethylamine (2.8 mL, 20 mmol). The mixture was stirred at room temperature for half an hour, then compound 1k (2.8 g, 6.8 mmol) was added. The resulting mixture was heated to 60° C.; for 5 hours. After cooled down to room temperature, the mixture diluted with water (40 mL) and extracted with ethyl acetate (100 mL×3). The combined organic layers were dried over Na₂SO₄, filtered and concentrated under reduced pressure. The residue was purified by silica gel chromatography to give compound 1l (2.6 g, 70% yield) as white solid. ESI-MS (m/z): 546.4 [M+H]⁺; ¹H NMR (500 MHz, DMSO-d6) δ ppm 12.71 (s, 1H), 7.90 (s, 1H), 7.57 (s, 1H), 7.34-7.21 (m, 8H), 6.62 (s, 1H), 4.95 (s, 2H), 4.66-4.53 (m, 4H), 4.23 (d, J=9.5 Hz, 1H), 3.08-2.96 (m, 2H), 2.15 (s, 3H), 1.81-1.72 (m, 2H), 1.62-1.52 (m, 2H), 1.34 (t, J=7.1 Hz, 3H).

Step 11: Compound 1l (2.5 g, 4.6 mmol) was dissolved in Hydrobromic acid in acetic acid solution (33 wt. %, 50 mL), the resulting mixture was stirred at room temperature for half an hour. Diethyl ether (50 mL) was added to the reaction mixture, the formed solid was collected by filtration. The solid was washed by diethyl ether (30 mL×3) and dried in vacuo to give compound 1m (1.8 g, 96% yield) as white solid. ESI-MS (m/z): 412.6 [M+H]⁺.

Step 12: To a stirring solution of compound 1m (100 mg, 0.24 mmol) and compound 1n (144 mg, 0.5 mmol) in DMF (2 mL) was added Cs₂CO₃ (160 mg, 0.5 mmol). The reaction mixture was heated at 70° C.; overnight. The reaction mixture was allowed to cool to room temperature, diluted with water (20 mL) and extracted with ethyl acetate (30 mL×3). The combined organic layers were dried over Na₂SO₄, filtered and concentrated under reduced pressure. The residue was purified by silica gel chromatography to give compound 1o (80 mg, 50% yield) as white solid. ESI-MS (m/z): 664.6 [M+H]⁺.

Step 13: Compound 1o (80 mg, 0.12 mmol) was dissolved in a mixture of MeOH (10 mL) and concentrated ammonium hydroxide (4 mL). Sodium dithionite (105 mg, 50.6 mmol) was dissolved in water (1.5 mL) and added to the reaction mixture at room temperature. Stirring was continued at room temperature for half an hour. The reaction mixture was diluted with water (25 mL) and extracted with ethyl acetate (25 mL×3). The combined organic layers were dried over Na₂SO₄, filtered and concentrated under reduced pressure to give compound 1p (41 mg, 54% yield) as white solid. ESI-MS (m/z): 634.6 [M+H]⁺.

Step 14: To a stirring solution of compound 1p (41 mg, 0.06 mmol) in MeOH (5 mL) was added cyanogen bromide (35 mg, 0.33 mmol). The resulting mixture was stirred at room temperature overnight. The mixture was concentrated in vacuo to remove the solvent. The residue was suspended in ethyl acetate (30 mL), stirred at room temperature for half an hour and filtered to give a yellow powder. The powder was washed with ethyl acetate (30 mL×3) and dried in vacuo to give compound 1q (26 mg, 62% yield) as light yellow solid. ESI-MS (m/z): 659.5 [M+H]⁺.

Step 15: To a stirring solution of 1-ethyl-3-methyl-1H-pyrazole-5-carboxylic acid (10 mg, 0.06 mmol) in DMF (0.5 mL) was added HATU (23 mg, 0.06 mmol), HOBt (4 mg, 0.03 mmol) and triethylamine (20 mg, 0.2 mmol). After stirred at room temperature for half an hour, compound 1q (26 mg, 0.04 mmol) was added to the reaction. The resulting mixture was heated to 60° C.; for 3 hours, LCMS indicated the product was formed. The mixture was purified directly by reversed phase preparative HPLC to give compound 1 (10 mg, 32% yield) as white solid. ESI-MS (m/z): 795.6 [M+H]⁺; ¹H NMR (500 MHz, DMSO-d6) δ ppm 12.80 (s, 2H), 7.95 (d, J=30.3 Hz, 2H), 7.61 (d, J=28.0 Hz, 2H), 7.32 (d, J=14.5 Hz, 4H), 6.52 (d, J=42.9 Hz, 2H), 4.85-4.04 (m, 12H), 3.15 (s, 3H), 2.11 (s, 3H), 2.07 (s, 3H), 2.04-1.80 (m, 7H), 1.33-1.26 (m, 6H).

Example 2: (R)-3-(3-(5-Carbamoyl-2-(1-ethyl-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

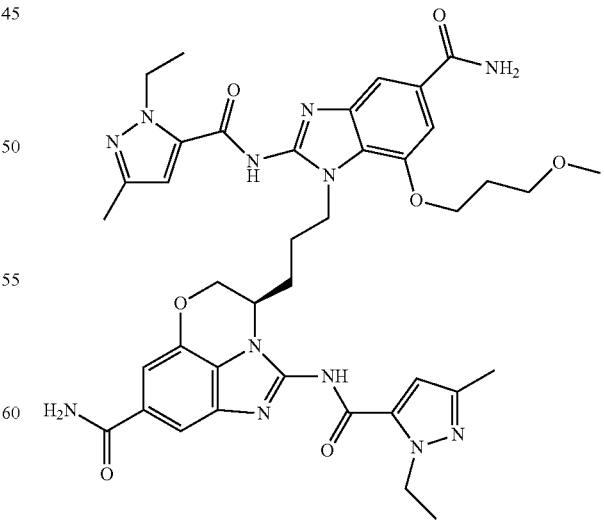

Synthetic Scheme
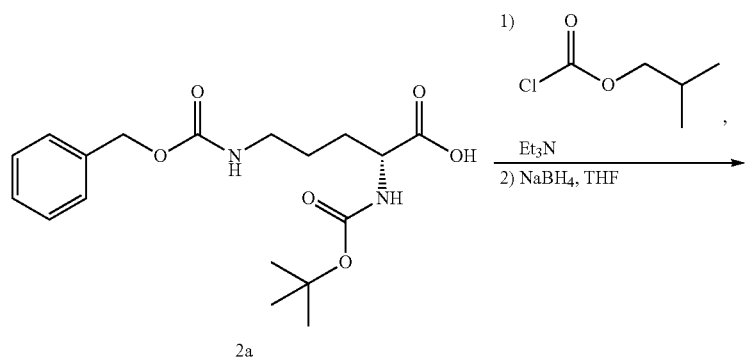
2a
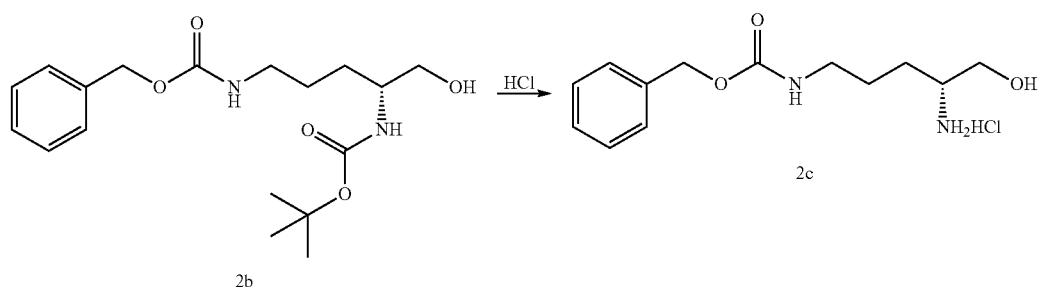
2b, 2c
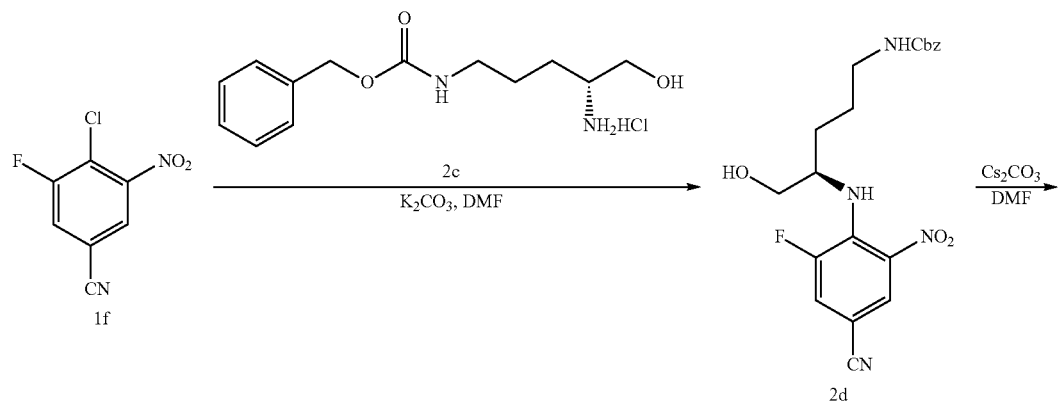
1f, 2c, 2d
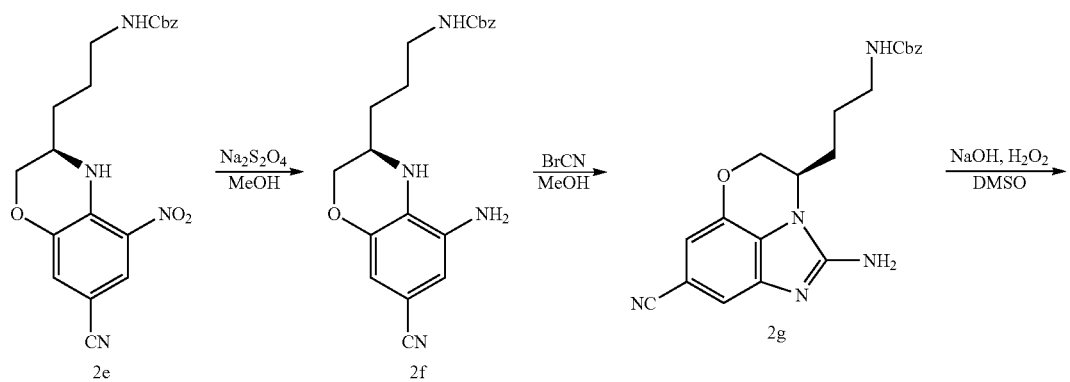
2e, 2f, 2g 119 120
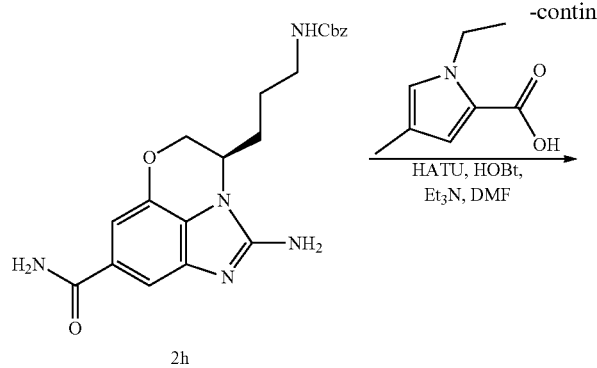
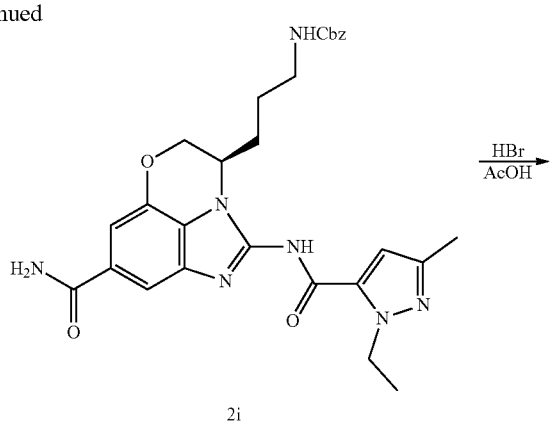
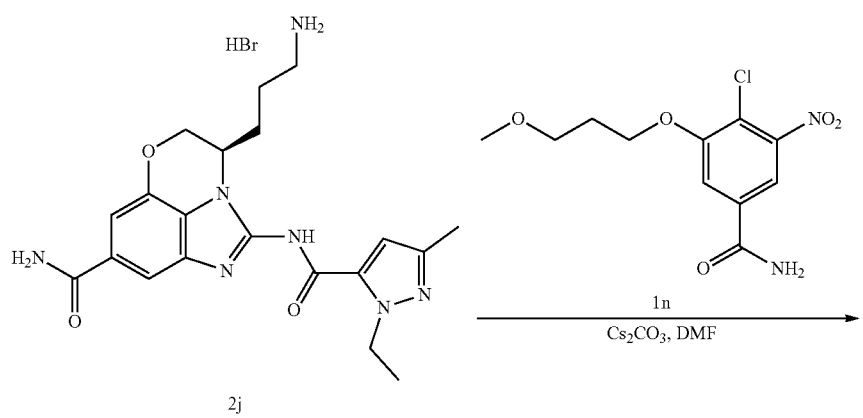
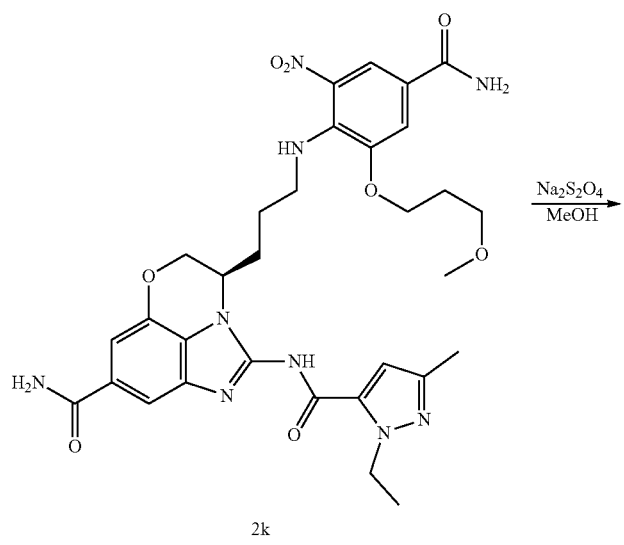

-continued
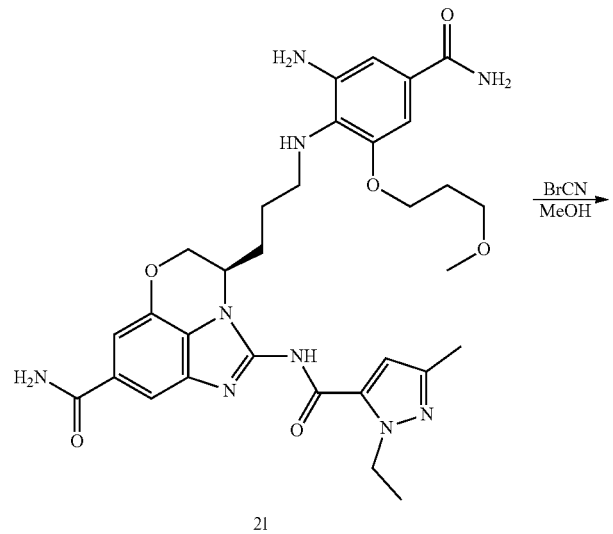
2l
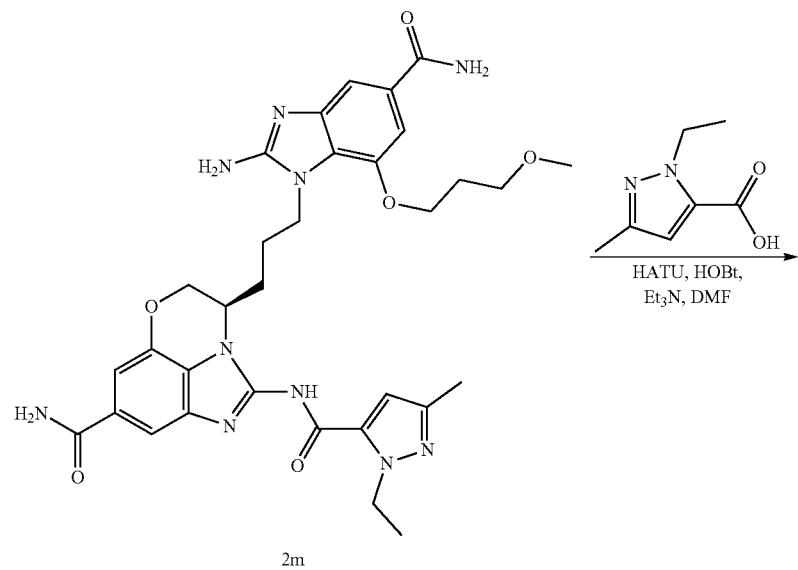
2m
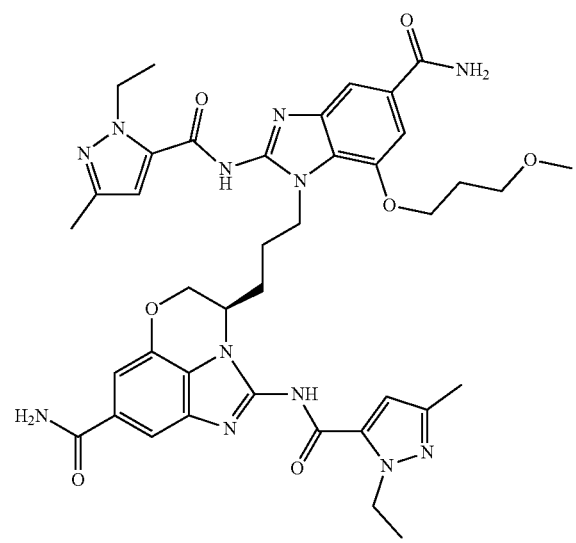
2

Step 1: To a stirring solution of k, (R)-5-(((benzyloxy)carbonyl)amino)-2-((tert-butoxycarbonyl)amino)pentanoic acid 2a (25 g, 68 mmol) and triethylamne (11.5 mL, 81.9 mmol) in THE (100 mL) was dropwise added isobutyl carbonochloridate (10 mL, 79 mmol) at 0° C. The mixture was stirred at 0° C.; for 30 minutes, then sodium borohydride (7.8 g, 205 mmol) was added, followed by drop-wise addition of water (3 mL) to the reaction. The mixture was kept stirring at 0° C.; for 2 hours. After the reaction was complete, water (150 mL) was added to the reaction mixture, which was extracted with ethyl acetate (150 mL×3). The combined organic layers were dried over $Na_2SO_4$, filtered and concentrated under reduced pressure to give the compound 2b (22 g, 91% yield) as colorless oil. ESI-MS (m/z): 353.6 $[M+H]^+$.

Step 2: To a stirring solution of compound 1b (22 g, 56 mmol) in dichloromethane (200 mL) was added 4M HCl in dioxane (75 mL, 300 mmol) at room temperature. The mixture was stirred overnight at rom temperature and LCMS indicated the product was formed. The mixture was concentrated under reduced pressure to give compound 2c (13.5 g, 86% yield) as colorless oil. ESI-MS (m/z): 253.6 $[M+H]^+$.

Step 3: To a stirring solution of compound 1f (5.3 g, 26.5 mmol) and compound 2c (13.4 g, 53 mmol) in DMF (20 mL) was added $K_2CO_3$ (7.4 g, 54 mmol), and the resulting mixture was heated at 60° C.; overnight. The reaction mixture was cooled to room temperature, diluted with water (150 mL) and extracted with ethyl acetate (150 mL×3). The combined organic layers were dried over $Na_2SO_4$, filtered and concentrated under reduced pressure, the residue was purified by silica gel chromatography to give compound 2d (6.9 g, 63% yield) as yellow oil. ESI-MS (m/z): 417.6 $[M+H]^+$.

Step 4: To a stirring solution of compound 2d (6.9 g, 16.5 mmol) in DMF (15 mL) was added $Cs_2CO_3$ (10.8 g, 33 mmol), and the reaction mixture was heated at 60° C.; for 2 hours. The reaction was cooled to room temperature, diluted with water (150 mL) and extracted with ethyl acetate (150 mL×3). The combined organic layers were dried over $Na_2SO_4$, filtered and concentrated under reduced pressure, the residue was purified by silica gel chromatography to give compound 2e (4.4 g, 67% yield) as yellow solid. ESI-MS (m/z): 397.7 $[M+H]^+$.

Step 5: Compound 2e (4.4 g, 11.1 mmol) was dissolved in a mixture of MeOH (100 mL) and concentrated ammonium hydroxide (20 mL). And sodium dithionite (9.6 g, 55 mmol) was dissolved in water (20 mL), the resultant solution was added to the reaction mixture at room temperature. Stirring was continued at room temperature for half an hour. The reaction mixture was diluted with water (200 mL) and extracted with ethyl acetate (200 mL×3). The combined organic layers were dried over $Na_2SO_4$, filtered and concentrated under reduced pressure to give compound 2f (3.5 g, 86% yield) as light yellow solid. ESI-MS (m/z): 367.7 $[M+H]^+$.

Step 6: To a stirring solution of compound 2f (3.5 g, 9.5 mmol) in MeOH (60 mL) was added cyanogen bromide (5.05 g, 47.6 mmol). The resulting mixture was stirred at 60° C.; overnight. The mixture was concentrated in vacuo to remove the solvent, the residue was suspended in saturated aqueous $Na_2CO_3$ solution (150 mL) and extracted with ethyl acetate (150 mL×3). The combined organic layers were dried over $Na_2SO_4$, filtered and concentrated under reduced pressure to yield compound 2g (3.4 g, 91% yield) as light yellow solid. ESI-MS (m/z): 392.6 $[M+H]^+$.

Step 7: To a stirring solution of compound 2g (3.4 g, 8.7 mmol) in DMSO (20 mL) at 0° C.; was added solid NaOH (1 g, 25 mmol), followed by the addition of hydrogen peroxide (30 wt. %, 12 mL). The reaction was warmed to room temperature and stirred for half an hour. The mixture was diluted with water (100 mL) and extracted with EA (150 mL×3). The combined organic layers were dried over $Na_2SO_4$, filtered and concentrated under reduced pressure to give compound 2h (2.7 g, 76% yield) as yellow solid. ESI-MS (m/z): 410.5 $[M+H]^+$.

Step 8: To a stirring solution of 1-ethyl-3-methyl-1H-pyrazole-5-carboxylic acid (1.5 g, 9.7 mmol) in DMF (8 mL) was added HATU (3.8 g, 10 mmol), HOBt (670 mg, 5 mmol) and triethylamine (2.8 mL, 20 mmol). The mixture was stirred at room temperature for half an hour, then compound 2h (2.7 g, 6.6 mmol) was added. The resulting mixture was heated to 60° C.; for 5 hours. After cooled down to room temperature, the mixture diluted with water (35 mL) and extracted with ethyl acetate (100 mL×3). The combined organic layers were dried over $Na_2SO_4$, filtered and concentrated under reduced pressure. The residue was purified by silica gel chromatography to give compound 2i (2.8 g, 77% yield) as white solid. ESI-MS (m/z): 546.4 $[M+H]^+$; $^1$H NMR (500 MHz, DMSO-d6) δ 12.66 (s, 1H), 7.92 (s, 1H), 7.60 (s, 1H), 7.38-7.21 (m, 8H), 6.63 (s, 1H), 4.96 (s, 2H), 4.62 (dd, J=17.3, 8.8 Hz, 4H), 4.30-4.19 (m, 1H), 3.11-2.96 (m, 2H), 2.17 (s, 3H), 1.83-1.74 (m, 2H), 1.59-1.52 (m, 2H), 1.35 (t, J=7.0 Hz, 3H).

Step 9: Compound 2i (2.7 g, 4.9 mmol) was dissolved in Hydrobromic acid in acetic acid solution (33 wt. %, 50 mL), the resulting mixture was stirred at room temperature for half an hour. Diethyl ether (50 mL) was added to the reaction mixture, the formed solid was collected by filtration. The solid was washed by diethyl ether (30 mL×3) and dried in vacuo to give compound 2j (1.9 g, 94% yield) as white solid. ESI-MS (m/z): 412.6 $[M+H]^+$.

Step 10: To a stirring solution of compound 2j (200 mg, 0.48 mmol) and compound 1n (288 mg, 1 mmol) in DMF (4 mL) was added $Cs_2CO_3$ (326 mg, 1 mmol). The reaction mixture was heated at 70° C.; overnight. The reaction mixture was allowed to cool to room temperature, diluted with water (20 mL) and extracted with ethyl acetate (50 mL×3). The combined organic layers were dried over $Na_2SO_4$, filtered and concentrated under reduced pressure. The residue was purified by silica gel chromatography to give compound 2k (170 mg, 53% yield) as white solid. ESI-MS (m/z): 664.6 $[M+H]^+$.

Step 11: Compound 2k (170 mg, 0.25 mmol) was dissolved in a mixture of MeOH (15 mL) and concentrated ammonium hydroxide (6 mL). Sodium dithionite (220 mg, 1.2 mmol) was dissolved in water (4 mL) and added to the reaction mixture at room temperature. Stirring was continued at room temperature for half an hour. The reaction mixture was diluted with water (40 mL) and extracted with ethyl acetate (25 mL×3). The combined organic layers were dried over $Na_2SO_4$, filtered and concentrated under reduced pressure to give compound 2l (100 mg, 61% yield) as white solid. ESI-MS (m/z): 634.6 $[M+H]^+$.

Step 12: To a stirring solution of compound 2l (100 mg, 0.16 mmol) in MeOH (10 mL) was added cyanogen bromide (83 mg, 0.78 mmol). The resulting mixture was stirred at 60° C. overnight. The mixture was concentrated in vacuo to remove the solvent. The residue was suspended in ethyl acetate (50 mL), stirred at room temperature for half an hour and filtered to give a yellow powder. The powder was washed with ethyl acetate (30 mL×3) and dried in vacuo to give compound 2m (34 mg, 33% yield) as light yellow solid. ESI-MS (m/z): 659.5 $[M+H]^+$.

Step 13: To a stirring solution of 1-ethyl-3-methyl-1H-pyrazole-5-carboxylic acid (12 mg, 0.08 mmol) in DMF (0.5 mL) was added HATU (30 mg, 0.08 mmol), HOBt (5 mg, 0.04 mmol) and triethylamine (20 mg, 0.2 mmol). After stirred at room temperature for half an hour, compound 2m (34 mg, 0.05 mmol) was added to the reaction. The resulting mixture was heated to 60° C.; for 3 hours, LCMS indicated the product was formed. The mixture was purified directly by reversed phase preparative HPLC to give compound 2 (4.5 mg, 11% yield) as white solid. ESI-MS (m/z): 795.9 [M+H]$^+$; $^1$H NMR (500 MHz, DMSO-d6) δ ppm 12.81 (s, 1H), 12.70 (s, 1H), 7.97 (s, 1H), 7.91 (s, 1H), 7.63 (s, 1H), 7.57 (s, 1H), 7.39-7.24 (s, 4H), 6.56 (s, 1H), 6.47 (s, 1H), 4.73 (s, 1H), 4.67-3.99 (m, 10H), 3.14 (s, 3H), 2.10 (s, 3H), 2.07 (s, 3H), 2.04-1.78 (m, 6H), 1.29 (s, 6H).

Example 3: (R)-3-(3-(5-Carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

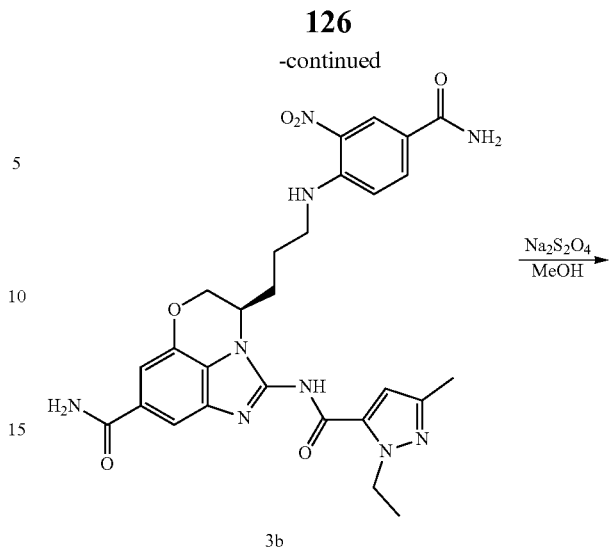

Synthetic Scheme

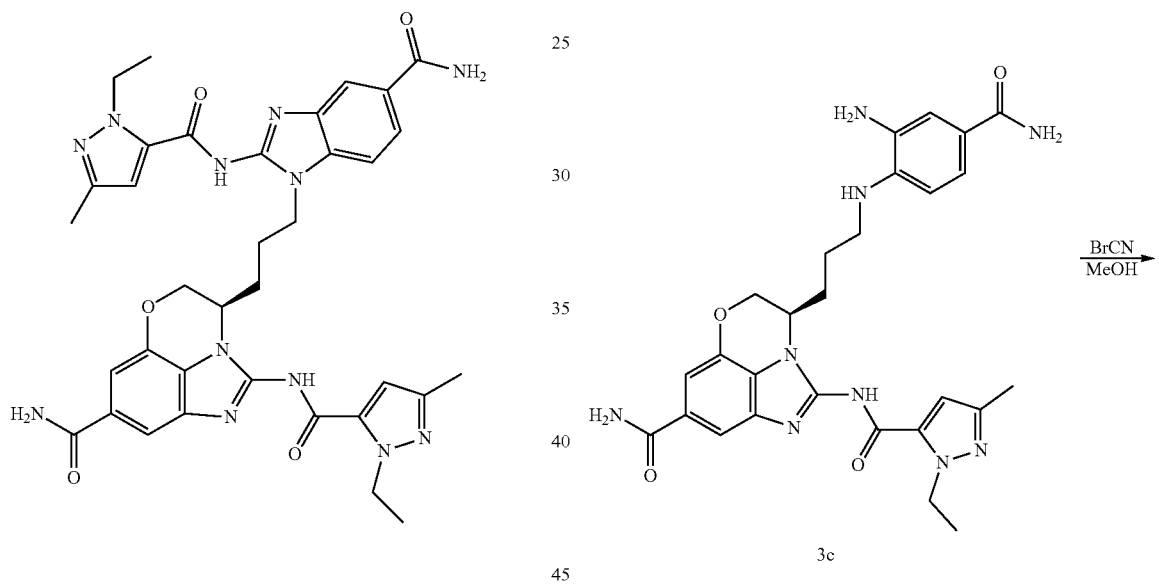

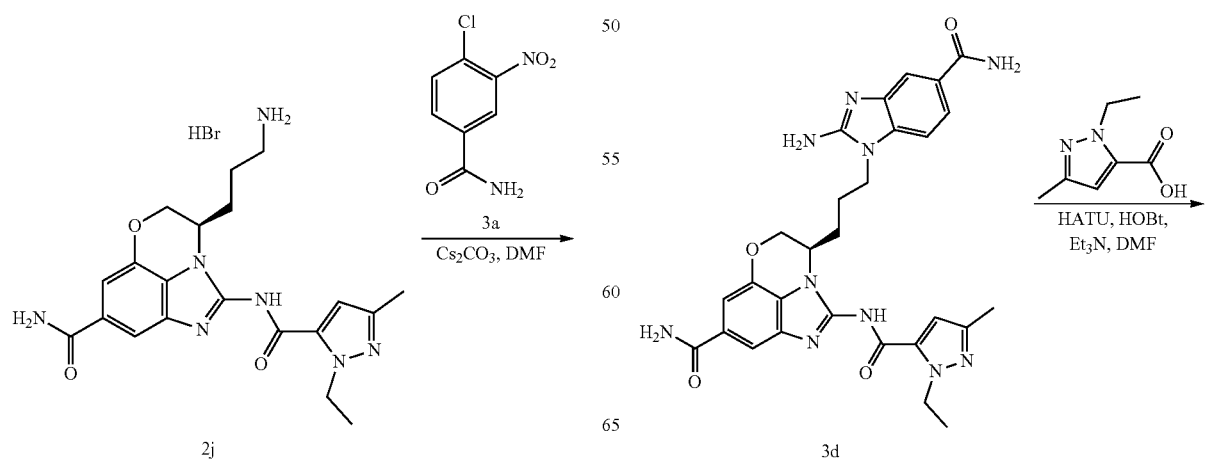

-continued

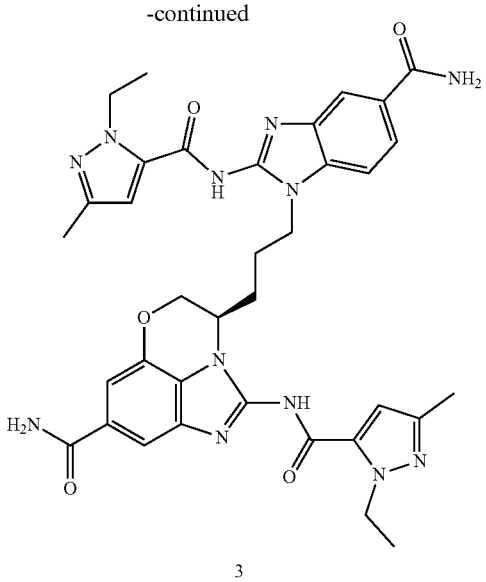

3

Step 1: To a stirring solution of compound 2j (200 mg, 0.48 mmol) and compound 3a (200 mg, 1 mmol) in DMF (4 mL) was added Cs$_2$CO$_3$ (326 mg, 1 mmol). The reaction mixture was heated at 70° C.; overnight. The reaction mixture was allowed to cool to room temperature, diluted with water (20 mL) and extracted with ethyl acetate (50 mL×3). The combined organic layers were dried over Na$_2$SO$_4$, filtered and concentrated under reduced pressure. The residue was purified by silica gel chromatography to give compound 3b (235 mg, 84% yield) as white solid. ESI-MS (m/z): 576.6 [M+H]$^+$.

Step 2: Compound 3b (235 mg, 0.4 mmol) was dissolved in a mixture of MeOH (20 mL) and concentrated ammonium hydroxide (8 mL). Sodium dithionite (350 mg, 2 mmol) was dissolved in water (6 mL) and added to the reaction mixture at room temperature. Stirring was continued at room temperature for half an hour. The reaction mixture was diluted with water (50 mL) and extracted with ethyl acetate (50 mL×3). The combined organic layers were dried over Na$_2$SO$_4$, filtered and concentrated under reduced pressure to give compound 3c (147 mg, 66% yield) as white solid. ESI-MS (m/z): 546.6 [M+H]$^+$.

Step 3: To a stirring solution of compound 3c (147 mg, 0.27 mmol) in MeOH (20 mL) was added cyanogen bromide (140 mg, 1.3 mmol). The resulting mixture was stirred at 60° C.; overnight. The mixture was concentrated in vacuo to remove the solvent. The residue was suspended in ethyl acetate (60 mL), stirred at room temperature for half an hour and filtered to give a yellow powder. The powder was washed with ethyl acetate (30 mL×3) and dried in vacuo to give compound 3d (78 mg, 51% yield) as light yellow solid. ESI-MS (m/z): 571.5 [M+H]$^+$.

Step 4: To a stirring solution of 1-ethyl-3-methyl-1H-pyrazole-5-carboxylic acid (32 mg, 0.2 mmol) in DMF (2 mL) was added HATU (78 mg, 0.2 mmol), HOBt (14 mg, 0.1 mmol) and triethylamine (40 mg, 0.4 mmol). After stirred at room temperature for half an hour, compound 3d (78 mg, 0.14 mmol) was added to the reaction. The resulting mixture was heated to 60° C.; for 3 hours, LCMS indicated the product was formed. The mixture was purified directly by reversed phase preparative HPLC to give compound 3 (28 mg, 29% yield) as white solid. ESI-MS (m/z): 707.4 [M+H]$^+$; $^1$H NMR (500 MHz, DMSO-d6) δ ppm 12.74 (s, 2H), 7.99 (s, 1H), 7.93 (d, J=18.6 Hz, 2H), 7.76 (d, J=8.4 Hz, 2H), 7.59 (s, 1H), 7.54 (d, J=8.4 Hz, 1H), 7.33 (s, 3H), 6.57 (s, 1H), 6.49 (s, 1H), 4.74 (s, 1H), 4.65-4.48 (m, 5H), 4.35-4.15 (m, 3H), 2.10 (s, 3H), 2.07 (s, 3H), 2.04-1.85 (s, 4H), 1.29 (t, J=7.1 Hz, 6H).

Example 4: (R)-3-(3-(5-Carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

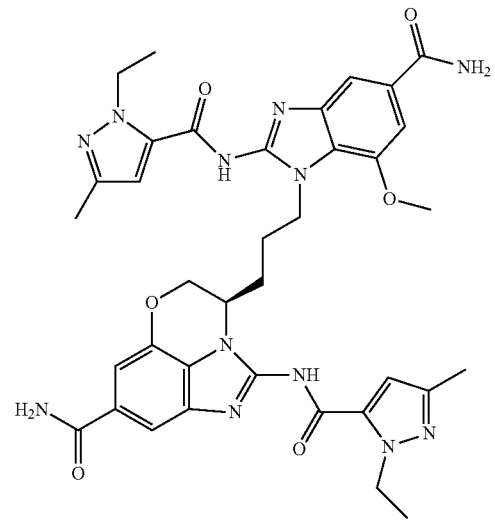 [SMILES: CCn1nc(C)cc1C(=O)Nc1nc2cc(C(N)=O)cc(OC)c2n1CCC[C@@H]1COc2cc(C(N)=O)cc3nc(NC(=O)c4cc(C)nn4CC)n1c23]

Synthetic Scheme

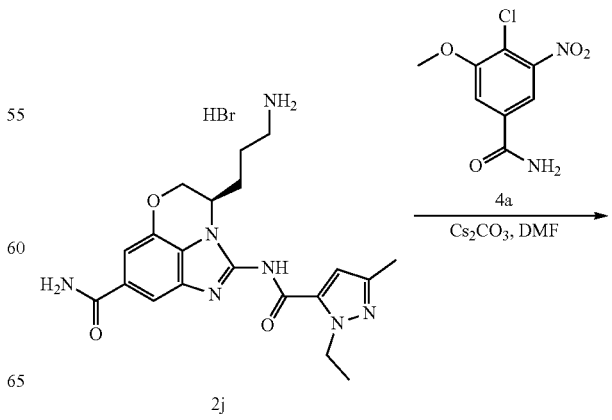

2j

-continued

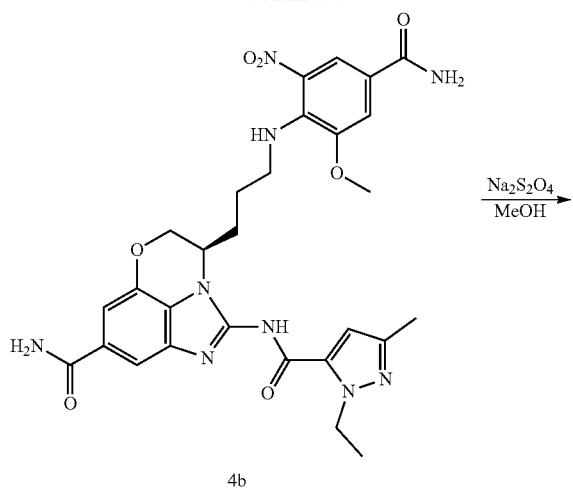

4b

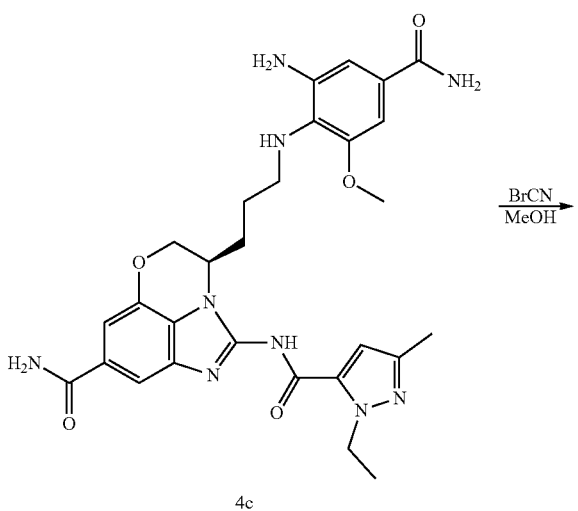

4c

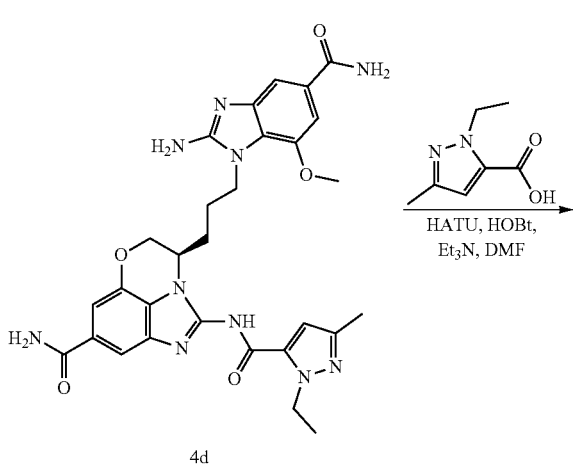

4d

-continued

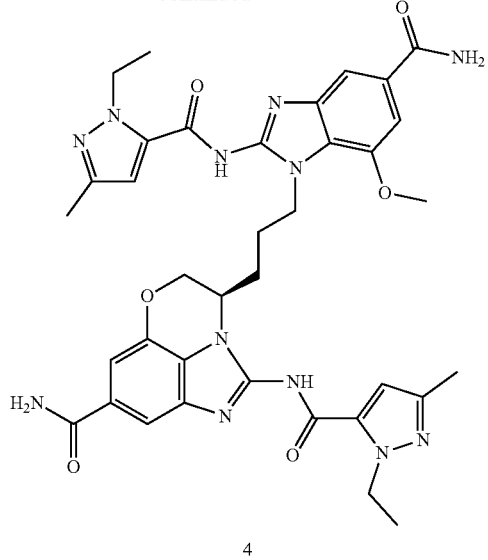

4

Step 1: To a stirring solution of compound 2j (200 mg, 0.48 mmol) and compound 4a (230 mg, 1 mmol) in DMF (4 mL) was added $Cs_2CO_3$ (326 mg, 1 mmol). The reaction mixture was heated at 70° C.; overnight. The reaction mixture was allowed to cool to room temperature, diluted with water (20 mL) and extracted with ethyl acetate (60 mL×3). The combined organic layers were dried over $Na_2SO_4$, filtered and concentrated under reduced pressure. The residue was purified by silica gel chromatography to give compound 4b (210 mg, 71% yield) as white solid. ESI-MS (m/z): 606.5 $[M+H]^+$.

Step 2: Compound 4b (210 mg, 0.35 mmol) was dissolved in a mixture of MeOH (20 mL) and concentrated ammonium hydroxide (8 mL). Sodium dithionite (300 mg, 1.7 mmol) was dissolved in water (5 mL) and added to the reaction mixture at room temperature. Stirring was continued at room temperature for half an hour. The reaction mixture was diluted with water (50 mL) and extracted with ethyl acetate (100 mL×3). The combined organic layers were dried over $Na_2SO_4$, filtered and concentrated under reduced pressure to give compound 4c (110 mg, 55% yield) as white solid. ESI-MS (m/z): 576.6 $[M+H]^+$.

Step 3: To a stirring solution of compound 4c (110 mg, 0.19 mmol) in MeOH (10 mL) was added cyanogen bromide (100 mg, 0.94 mmol). The resulting mixture was stirred at 60° C.; overnight. The mixture was concentrated in vacuo to remove the solvent. The residue was suspended in ethyl acetate (50 mL), stirred at room temperature for half an hour and filtered to give a yellow powder. The powder was washed with ethyl acetate (25 mL×3) and dried in vacuo to give compound 4d (66 mg, 58% yield) as light yellow solid. ESI-MS (m/z): 601.5 $[M+H]^+$.

Step 4: To a stirring solution of 1-ethyl-3-methyl-1H-pyrazole-5-carboxylic acid (25 mg, 0.16 mmol) in DMF (0.5 mL) was added HATU (60 mg, 0.16 mmol), HOBt (11 mg, 0.08 mmol) and triethylamine (40 mg, 0.4 mmol). After stirred at room temperature for half an hour, compound 4d (66 mg, 0.11 mmol) was added to the reaction. The resulting mixture was heated to 60° C.; for 3 hours, LCMS indicated the product was formed. The mixture was purified directly by reversed phase preparative HPLC to give compound 4 (26 mg, 32% yield) as white solid. ESI-MS (m/z): 737.5 [M+H]$^+$; $^1$H NMR (500 MHz, DMSO-d6) δ ppm 12.81 (s, 1H), 12.71 (s, 1H), 7.99 (s, 1H), 7.92 (s, 1H), 7.66 (s, 1H), 7.59 (s, 1H), 7.42-7.28 (m, 4H), 6.55 (s, 1H), 6.52 (s, 1H), 4.79-4.19 (m, 9H), 3.88 (s, 3H), 2.10 (s, 3H), 2.09 (s, 3H), 2.04-1.86 (m, 4H), 1.29 (dt, J=11.2, 7.1 Hz, 6H).

Example 5: (S)-3-(3-(5-carbamoyl-2-(1-ethyl-3-methyl-1H-pyrazole-5-carboxamido)-7-methoxy-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

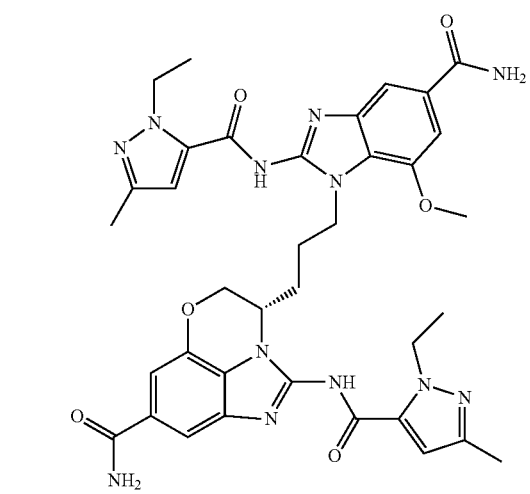 [SMILES: CCn1nc(C)cc1C(=O)Nc1nc2cc(C(N)=O)cc(OC)c2n1CCC[C@H]1COc2cc(C(N)=O)cc3nc(NC(=O)c4cc(C)nn4CC)n1c23]

Synthetic Scheme

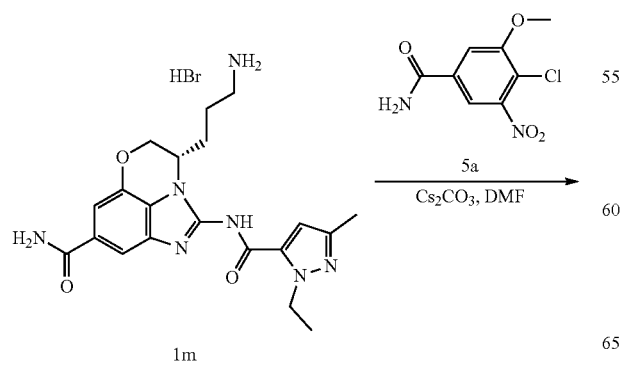

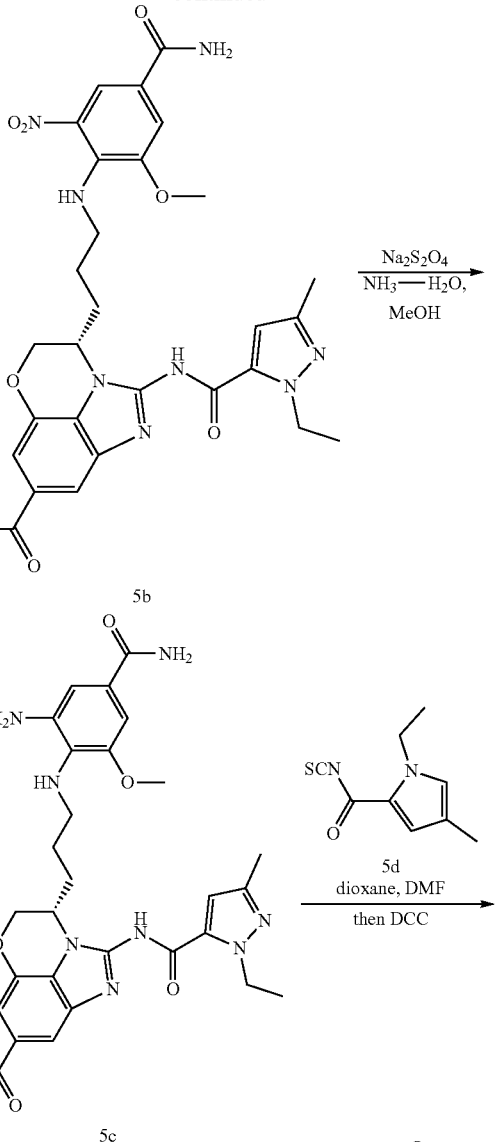

Step 1: To a stirring solution of compound 1m (200 mg, 0.45 mmol) and compound 5a (155 mg, 0.67 mmol) in DMF (4 mL) was added $Cs_2CO_3$ (326 mg, 1 mmol). The reaction mixture was heated at 70° C.; overnight. The reaction mixture was allowed to cool to room temperature, diluted with water (100 mL) and extracted with ethyl acetate (100 mL×3). The combined organic layers were washed with brine, dried over $Na_2SO_4$, filtered and concentrated under reduced pressure. The residue was purified by silica gel chromatography to give compound 5b (130 mg, 48% yield) as white solid. ESI-MS (m/z): 606.7 $[M+H]^+$.

Step 2: Compound 5b (130 mg, 0.21 mmol) was dissolved in a mixture of MeOH (8 mL) and concentrated ammonium hydroxide (2 mL). Sodium dithionite (190 mg, 1.10 mmol) was dissolved in water (2 mL) and added to the reaction mixture at room temperature. Stirring was continued at room temperature for half an hour. The reaction mixture was diluted with water (50 mL) and extracted with ethyl acetate (100 mL×3). The combined organic layers were washed with brine, dried over $Na_2SO_4$, filtered and concentrated under reduced pressure to give compound 5c (70 mg, 57% yield) as white solid. ESI-MS (m/z): 576.6 $[M+H]^+$.

Step 3: Compound 5c (70 mg, 0.12 mmol) was dissolved in DMF (2 mL), and then compound 5d (0.4M in dioxane, 0.3 mL, 0.12 mmol) was added. The reaction mixture was stirred at room temperature for half an hour, then DCC (40 mg, 0.19 mmol) was added to the reaction mixture. The reaction mixture was heated at 80° C.; overnight, LCMS indicated the product was formed. The reaction mixture was purified directly by reversed phase preparative HPLC to give compound 5 (22 mg, 25% yield) as white solid. ESI-MS (m/z): 736.4 $[M+H]^+$; $^1$H NMR (500 MHz, DMSO-d6) δ 12.69 (brs, 1H), 7.97 (s, 1H), 7.90 (s, 1H), 7.66 (s, 1H), 7.59 (s, 1H), 7.37 (s, 1H), 7.33 (s, 2H), 7.28 (s, 1H), 6.54 (s, 1H), 6.52 (s, 1H), 4.73 (br s, 1H), 4.66-4.52 (m, 5H), 4.46-4.36 (m, 1H), 4.36-4.22 (m, 2H), 3.88 (s, 3H), 2.13-2.07 (m, 6H), 2.03-1.96 (m, 2H), 1.95-1.87 (m, 2H), 1.34-1.26 (m, 6H).

Example 6: (S)-3-(3-(5-carbamoyl-2-(1-ethyl-3-methyl-1H-pyrazole-5-carboxamido)-7-(3-hydroxy-propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

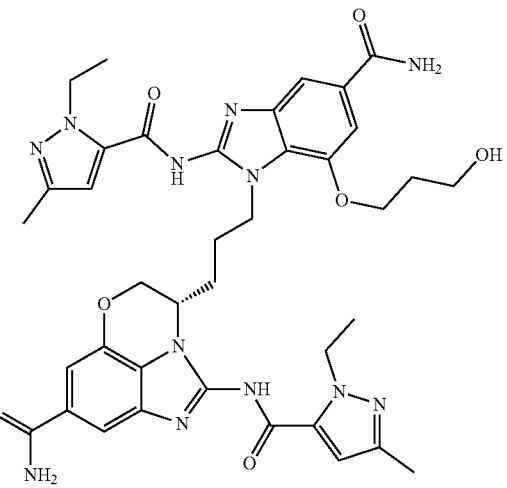

Synthetic Scheme

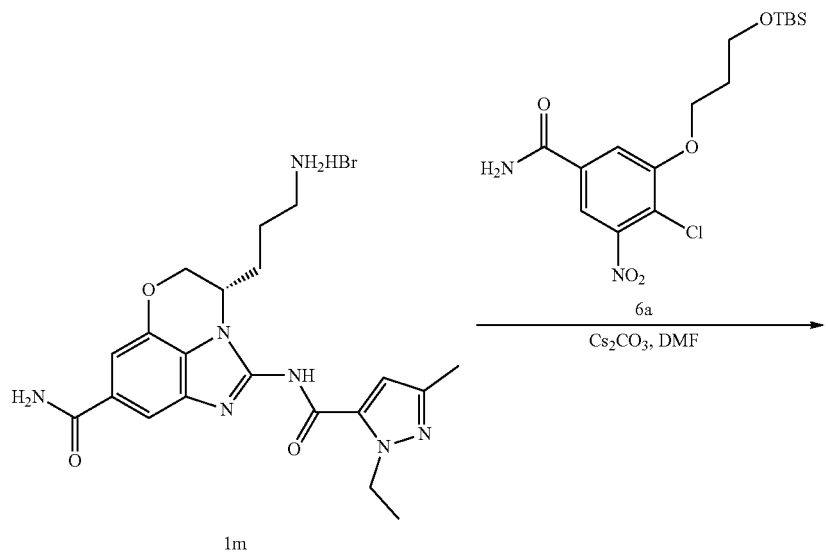

-continued

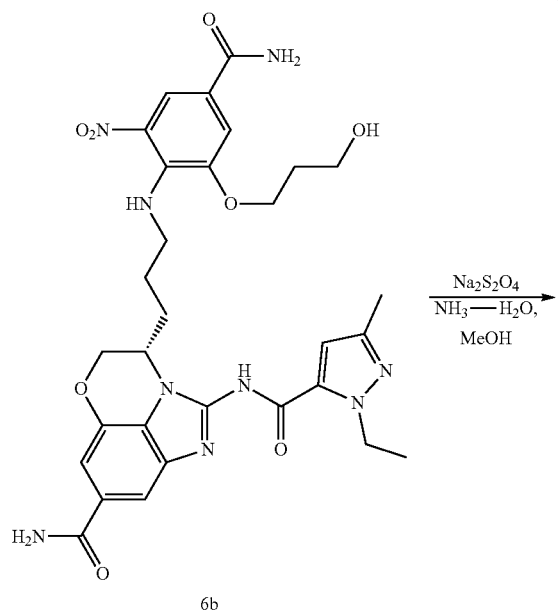

6b

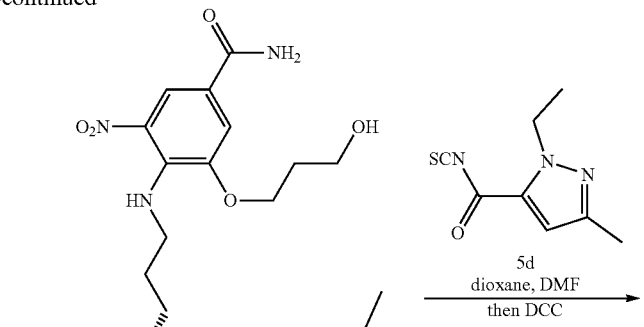

6c

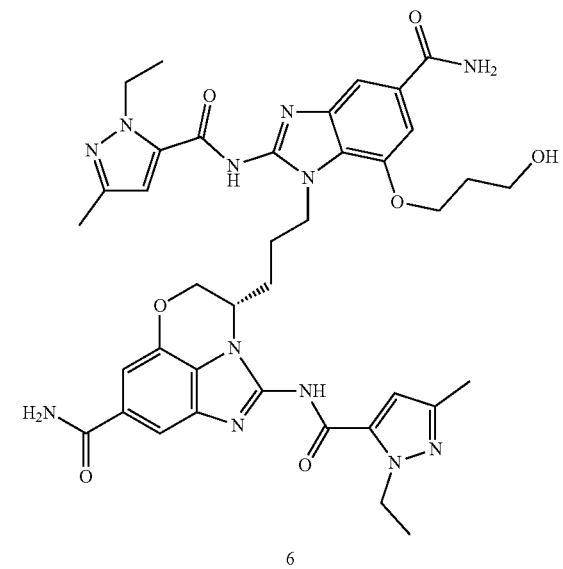

6

Step 1: To a stirring solution of compound 1m (200 mg, 0.45 mmol) and compound 6a (260 mg, 0.67 mmol) in DMF (4 mL) was added $Cs_2CO_3$ (326 mg, 1 mmol). The reaction mixture was heated at 70° C.; overnight. The reaction mixture was allowed to cool to room temperature, diluted with water (100 mL) and extracted with ethyl acetate (100 mL×3). The combined organic layers were washed with brine, dried over $Na_2SO_4$, filtered and concentrated under reduced pressure. The residue was purified by silica gel chromatography to give compound 6b (150 mg, 52% yield) as white solid. ESI-MS (m/z): 650.6 $[M+H]^+$.

Step 2: Compound 6b (150 mg, 0.23 mmol) was dissolved in a mixture of MeOH (10 mL) and concentrated ammonium hydroxide (3 mL). Sodium dithionite (200 mg, 1.15 mmol) was dissolved in water (2 mL) and added to the reaction mixture at room temperature. Stirring was continued at room temperature for half an hour. The reaction mixture was diluted with water (30 mL) and extracted with ethyl acetate (50 mL×3). The combined organic layers were washed with brine, dried over $Na_2SO_4$, filtered and concentrated under reduced pressure to give compound 6c (120 mg) as white solid, which was used directly without further purification. ESI-MS (m/z): 620.6 $[M+H]^+$.

Step 3: Compound 6c (60 mg) was dissolved in DMF (2 mL), and then compound 5d (0.4M in dioxane, 0.25 mL, 0.1 mmol) was added. The reaction mixture was stirred at room temperature for half an hour, then DCC (40 mg, 0.19 mmol) was added to the reaction mixture. The reaction mixture was heated at 80° C.; overnight, LCMS indicated the product was formed. The reaction mixture was purified directly by reversed phase preparative HPLC to give compound 6 (20 mg, 27% yield) as white solid. ESI-MS (m/z): 781.6 $[M+H]^+$; $^1H$ NMR (500 MHz, DMSO-d6) δ 12.71 (br s, 2H), 7.96 (s, 1H), 7.89 (s, 1H), 7.65 (s, 1H), 7.59 (s, 1H), 7.37 (s, 1H), 7.33 (s, 1H), 7.30-7.25 (m, 2H), 6.55 (s, 1H), 6.49 (s, 1H), 4.75 (br s, 1H), 4.65-4.48 (m, 5H), 4.45-4.36 (m, 1H), 4.35-4.28 (m, 1H), 4.28-4.12 (m, 3H), 3.49 (t, J=6.2 Hz, 2H), 2.10 (s, 3H), 2.08 (s, 3H), 2.04-1.97 (m, 2H), 1.96-1.88 (m, 2H), 1.82-1.74 (m, 2H), 1.33-1.26 (m, 6H).
Example 7: (S)-3-(2-(5-carbamoyl-2-(1-ethyl-3-methyl-1H-pyrazole-5-carboxamido)-7-(3-methoxypropoxy)-1H-benzo[d]imidazol-1-yl)ethyl)-2-(1-ethyl-3-methyl-1H-pyrazole-5-carboxamido)-3,4-dihydro-5-oxa-1,2a-diazaacenaphthylene-7-carboxamide
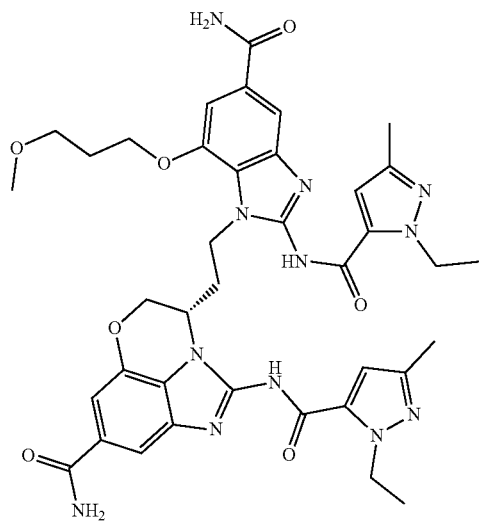 [SMILES: CCn1nc(C)cc1C(=O)Nc1nc2cc(C(N)=O)cc(OCCCOC)c2n1CC[C@H]1COc2cc(C(N)=O)cc3nc(NC(=O)c4cc(C)nn4CC)n1c23]
Synthetic Scheme
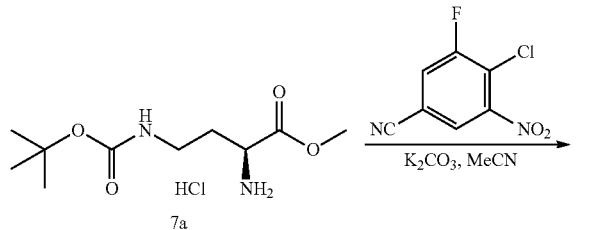
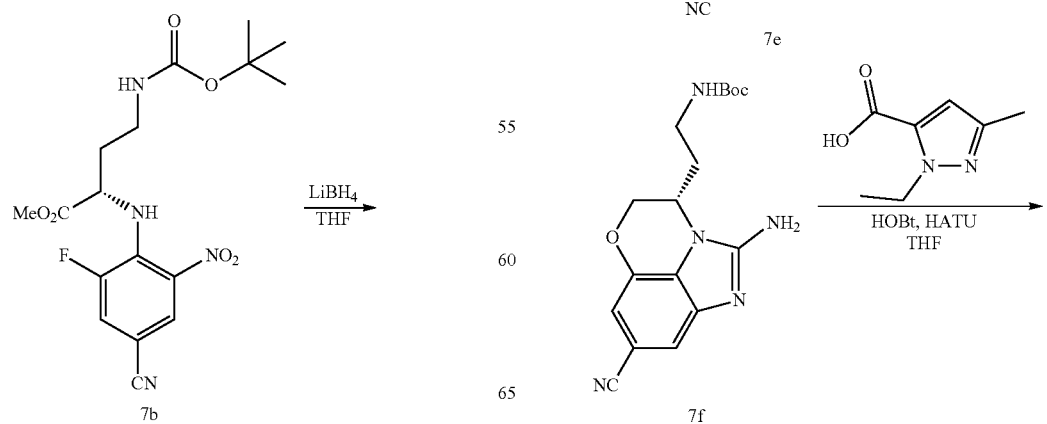
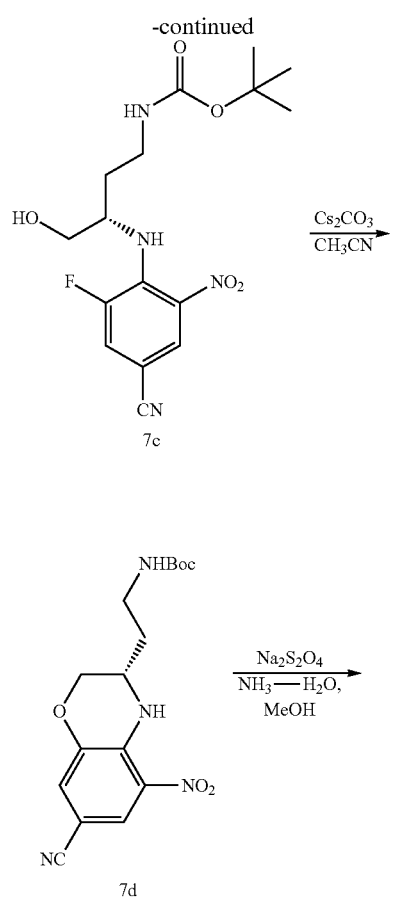

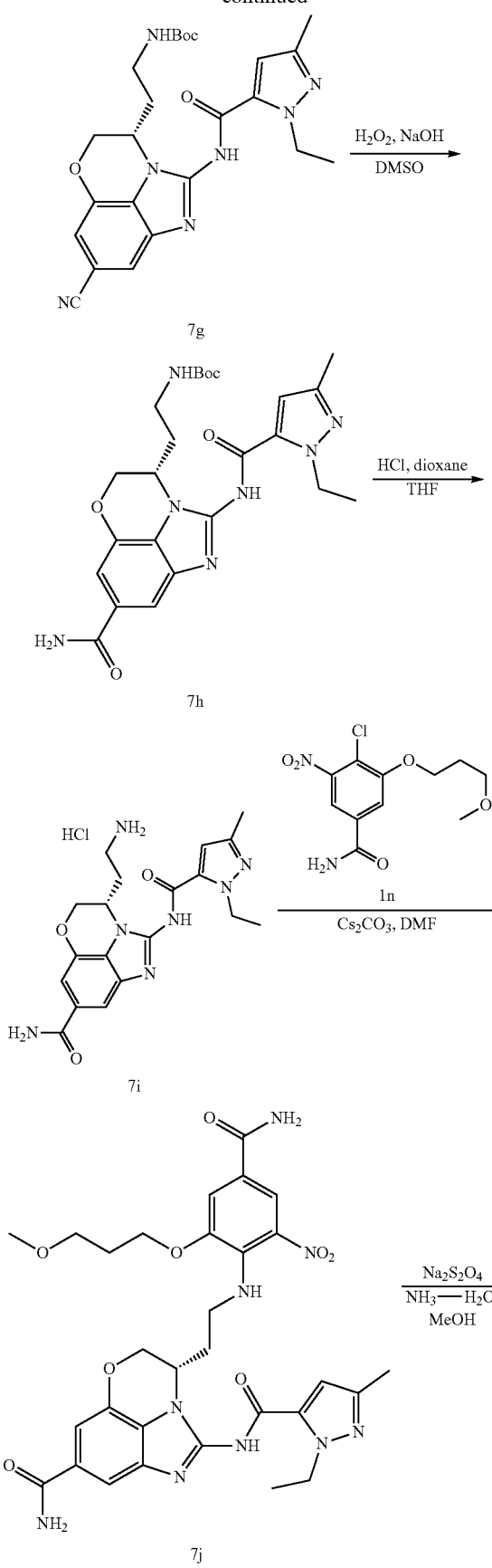

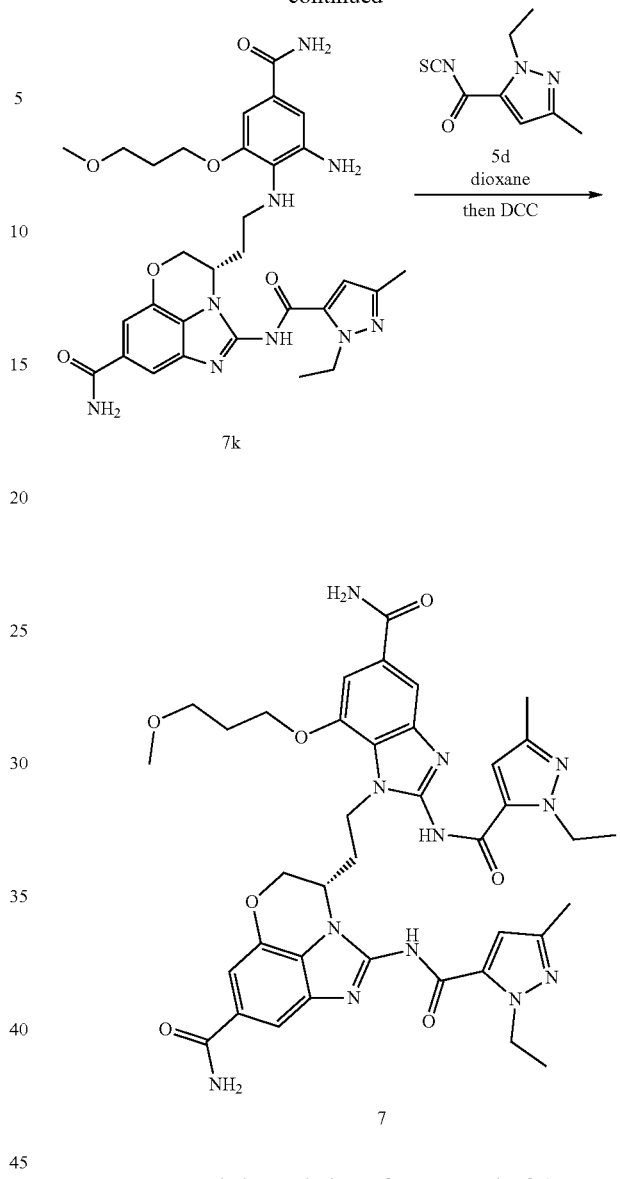

Step 1: To a stirring solution of compound 1f (4.00 g, 20.00 mmol) and compound 7a (10.00 g, 37.21 mmol) in acetonitrile (150 mL) was added K$_2$CO$_3$ (8.30 g, 60.05 mmol), and the resulting mixture was heated at 70° C.; for 24 hours. The reaction mixture was cooled to room temperature, filtered and washed with dichloromethane (100 mL), then concentrated under reduced pressure. The residue was purified by silica gel chromatography to give compound 7b (4.30 g, 54% yield) as yellow oil. ESI-MS (m/z): 397.5 [M+H]$^+$.

Step 2: To a solution of compound 7b (4.30 g, 10.85 mmol) in anhydrous THF (40 mL) at 0° C. was added by portion lithium borohydride (354 mg, 16.27 mmol), and the resulting solution was stirred at room temperature for half an hour. TLC indicated the starting material was consumed. The reaction was slowly quenched with aqueous NH$_4$Cl (10 mL), diluted with water (100 mL), and extracted with ethyl acetate (50 mL×3). The combined organic layers were washed with brine, dried over Na$_2$SO$_4$, filtered and concentrated. The residue was purified by silica gel chromatography to give the compound 7c (2.30 g, 57% yield) as white solid. ESI-MS (m/z): 369.5 [M+H]$^+$.

Step 3: To a stirring solution of compound 7c (2.30 g, 6.24 mmol) in acetonitrile (20 mL) was added $Cs_2CO_3$ (4.00 g, 12.31 mmol), and the reaction mixture was heated at 70° C. overnight. The reaction mixture was cooled to room temperature, filtered and washed with dichloromethane, then concentrated under reduced pressure to give compound 7d (2.00 g) as brown oil. The sample was used directly without further purification. ESI-MS (m/z): 349.4 $[M+H]^+$.

Step 4: Compound 7d (2.00 g) from step 3 was dissolved in a mixture of MeOH (20 mL) and concentrated ammonium hydroxide (5 mL). Sodium dithionite (5.7 g, 32.74 mmol) was dissolved in water (2 mL) and added to the reaction mixture at room temperature. Stirring was continued at room temperature for half an hour, LCMS indicated the product was formed. The reaction mixture was diluted with water (50 mL) and extracted with ethyl acetate (50 mL×3). The combined organic layers were washed with brine, dried over $Na_2SO_4$, filtered and concentrated under reduced pressure to give compound 7e (530 mg) as brown oil, which was used directly without further purification. ESI-MS (m/z): 319.6 $[M+H]^+$.

Step 5: Compound 7e (530 mg) from step 4 was dissolved in MeOH (10 mL), and cyanogen bromide (550 mg, 5 mmol) was added. The resulting mixture was stirred at room temperature overnight. The mixture was concentrated in vacuo to remove the solvent. The residue was suspended in saturated Na2CO3 aqueous solution (20 mL), and extracted with ethyl acetate (20 mL×3). The combined organic layers were washed with brine, dried over $Na_2SO_4$, filtered and concentrated. The residue was purified by silica gel chromatography to give the compound 7f (550 mg, 26% yield, 3 steps) as brown solid. ESI-MS (m/z): 344.5 $[M+H]^+$; $^1H$ NMR (500 MHz, DMSO-d6) δ 7.18 (d, J=1.2 Hz, 1H), 7.01 (s, 2H), 6.88 (t, J=5.7 Hz, 1H), 6.86 (d, J=1.2 Hz, 1H), 4.65-4.55 (m, 2H), 4.18-4.12 (m, 1H), 3.10-3.00 (m, 2H), 1.79-1.68 (m, 2H), 1.37 (s, 9H).

Step 6: To a stirring solution of 1-ethyl-3-methyl-1H-pyrazole-5-carboxylic acid (250 mg, 1.60 mmol) in THE (10 mL) was added HATU (617 mg, 1.60 mmol), HOBt (219 mg, 1.60 mmol) and triethylamine (0.67 mL, 4.86 mmol). After stirred at room temperature for half an hour, compound 7f (550 mg, 1.60 mmol) was added to the reaction. The resulting mixture was stirred at room temperature overnight, LCMS indicated the product was formed. The mixture was diluted with water (20 mL) and extracted with ethyl acetate (15 mL×3). The combined organic layers were washed with brine, dried over $Na_2SO_4$ and concentrated to give compound 7g (700 mg) as brown oil, which was used directly without further purification. ESI-MS (m/z): 480.6$[M+H]^+$.

Step 7: To a stirring solution of compound 7g (20 mg) in DMSO (2 mL) at 0° C.; was added solid NaOH (5 mg, 0.13 mmol), followed by the addition of hydrogen peroxide (30 wt. %, 0.2 mL).

The reaction was warmed to room temperature and stirred for half an hour, LCMS indicated the product was formed. The reaction mixture was purified directly by reversed phase preparative HPLC to give compound 7h (6.8 mg, 32% yield) as white solid. ESI-MS (m/z): 498.6 $[M+H]^+$; $^1HNMR$ (500 MHz, DMSO-d6) δ 12.69 (s, 1H), 7.93 (s, 1H), 7.60 (s, 1H), 7.35 (s, 1H), 7.31 (s, 1H), 6.99-6.91 (m, 1H), 6.69 (s, 1H), 4.72-4.58 (m, 4H), 4.30425 (m, 1H), 3.22-3.12 (m, 1H), 3.11-3.01 (m, 1H), 2.19 (s, 3H), 1.98-1.84 (m, 2H), 1.43-1.30 (m, 12H).

Step 8: To a stirring solution of compound 7h (530 mg, 1.07 mmol) in THE (10 mL) was added 4N HCl in dioxane (10 mL, 40 mmol) at room temperature. The mixture was stirred overnight at rom temperature and LCMS indicated the product was formed. The mixture was concentrated under reduced pressure to give compound 7i (430 mg) as yellow solid, which was used directly withour further purification. ESI-MS (m/z): 396.6 $[M+H]^+$.

Step 9: To a stirring solution of compound 7i (430 mg) and compound 1n (500 mg, 1.73 mmol) in DMF (10 mL) was added $Cs_2CO_3$ (938 mg, 2.88 mmol). The reaction mixture was heated at 80° C. for 24 hours, and LCMS indicated the product was formed. The reaction mixture was allowed to cool to room temperature, diluted with brine (20 mL) and extracted with ethyl acetate (15 mL×4). The combined organic layers were washed with brine, dried over $Na_2SO_4$, filtered and concentrated under reduced pressure. The residue was purified by silica gel chromatography to give compound 7j (250 mg, 33% yield) as red solid. ESI-MS (m/z): 650.4 $[M+H]^+$.

Step 10: Compound 7j (170 mg, 0.26 mmol) was dissolved in a mixture of MeOH (10 mL) and concentrated ammonium hydroxide (3 mL). Sodium dithionite (227 mg, 1.30 mmol) was dissolved in water (2 mL) and added to the reaction mixture at room temperature. Stirring was continued at room temperature for half an hour, and LCMS indicated the product was formed. The reaction mixture was diluted with water (20 mL) and extracted with ethyl acetate (10 mL×3). The combined organic layers were washed with brine, dried over $Na_2SO_4$, filtered and concentrated under reduced pressure to give compound 7k (130 mg) as yellow solid, which was used directly without further purification. ESI-MS (m/z): 620.4 $[M+H]^+$.

Step 11: Compound 7k (130 mg) was dissolved in dioxane (5 mL), and then compound 5d (0.4M in dioxane, 0.58 mL, 0.23 mmol) was added. The reaction mixture was stirred at room temperature for half an hour, LCMS indicated the starting materials were consumed. DCC (47 mg, 0.23 mmol) was added to the reaction mixture, and the mixture was heated at 80° C.; for 2 hours, LCMS indicated the product was formed. The reaction mixture was purified directly by reversed phase preparative HPLC to give compound 7 (22 mg, 11% yield for 2 steps) as white solid. ESI-MS (m/z): 781.5 $[M+H]^+$; $^1H$ NMR (500 MHz, DMSO-d6) δ 12.86 (s, 1H), 12.80 (s, 1H), 8.00 (s, 1H), 7.94 (s, 1H), 7.69 (s, 1H), 7.66 (s, 1H), 7.40 (s, 1H), 7.37 (s, 1H), 7.33 (s, 2H), 6.48 (s, 1H), 6.40 (s, 1H), 4.90-4.84 (m, 1H), 4.83-4.76 (m, 1H), 4.74-4.65 (m, 1H), 4.59-4.48 (m, 5H), 4.36-4.32 (m, 1H), 4.14 (t, J=7.8 Hz, 2H), 3.17 (s, 3H), 2.17 (s, 3H), 2.03 (s, 3H), 1.83-1.76 (m, 2H), 1.32-1.26 (m, 6H).

Example 8: (S)-3-(4-(5-carbamoyl-2-(1-ethyl-3-methyl-1H-pyrazole-5-carboxamido)-7-(3-methoxypropoxy)-1H-benzo[d]imidazol-1-yl)butyl)-2-(1-ethyl-3-methyl-1H-pyrazole-5-carboxamido)-3,4-dihydro-5-oxa-1,2a-diazaacenaphthylene-7-carboxamide
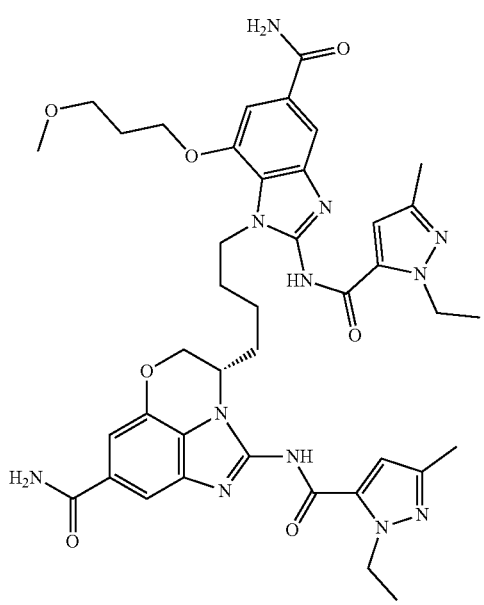 [SMILES: CCn1nc(C)cc1C(=O)Nc1nc2cc(C(N)=O)cc(OCCCOC)c2n1CCCC[C@H]1COc2cc(C(N)=O)cc3nc(NC(=O)c4cc(C)nn4CC)n1c23]
Synthetic Scheme
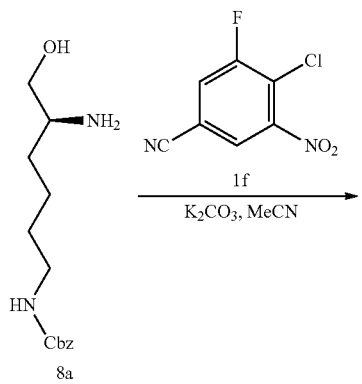
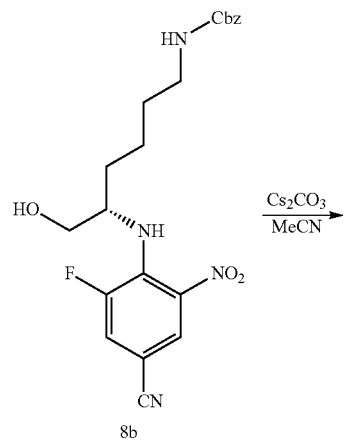
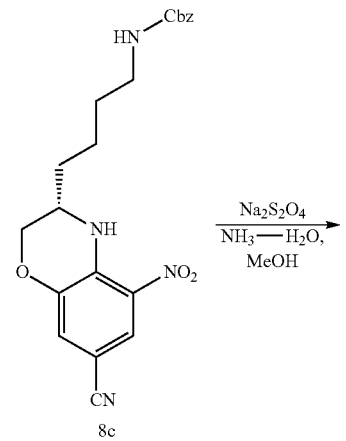
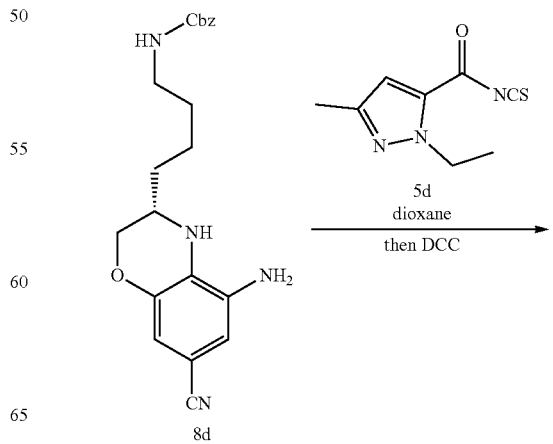

145
-continued
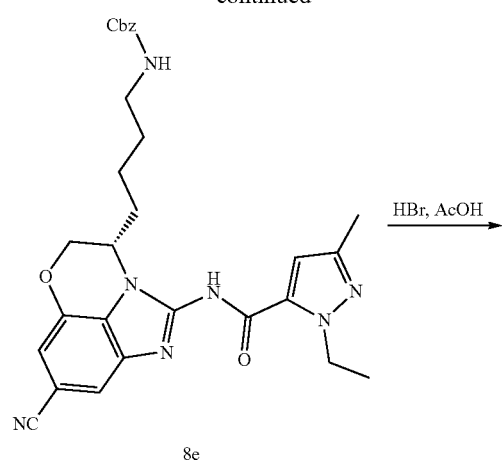
8e
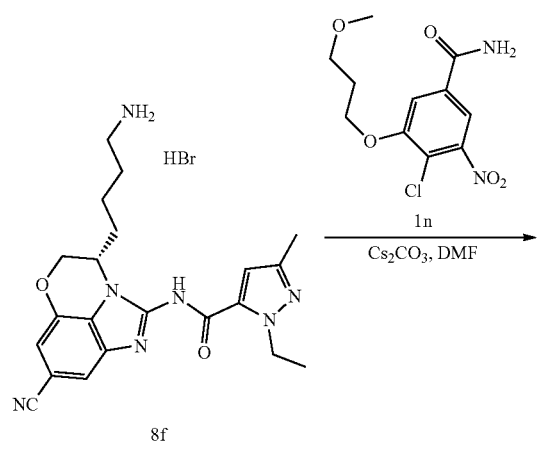
8f
146
-continued
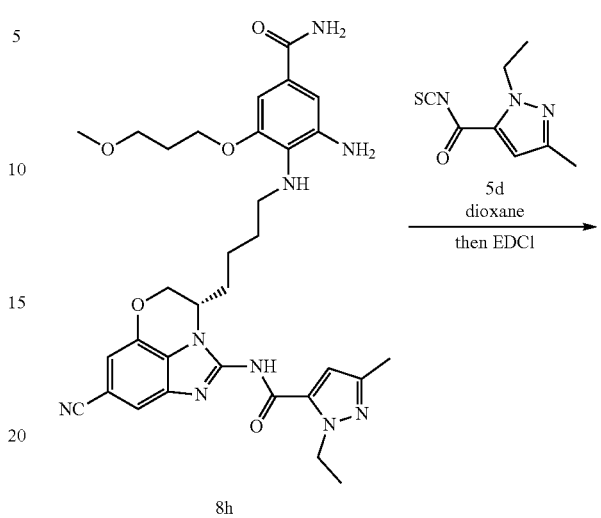
8h
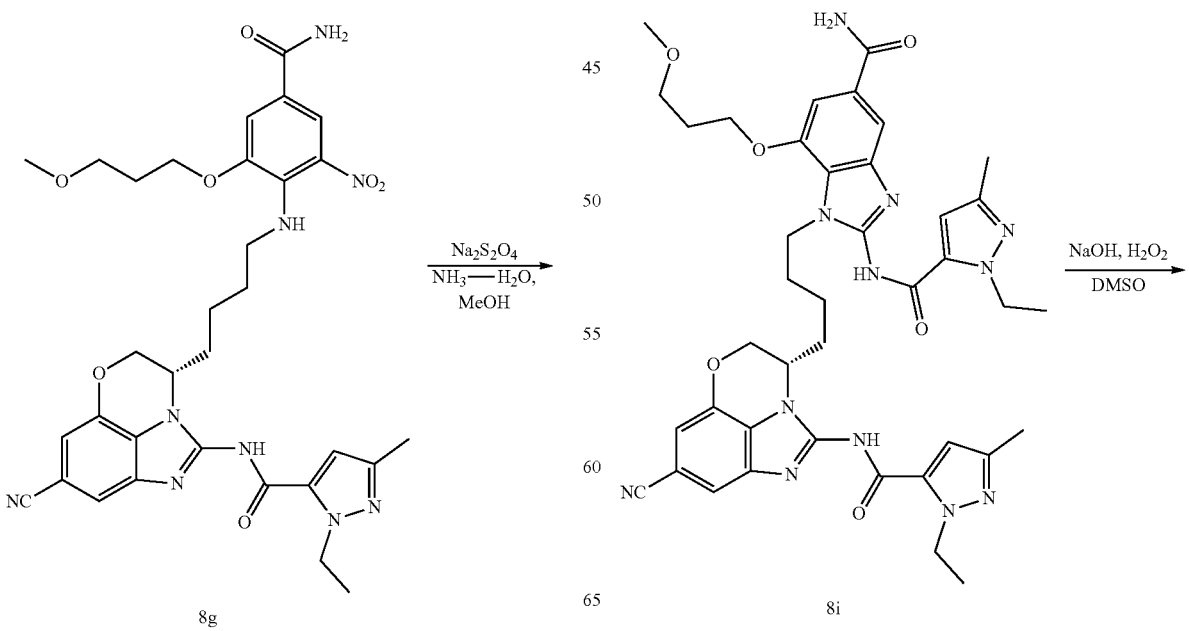
8g
8i -continued

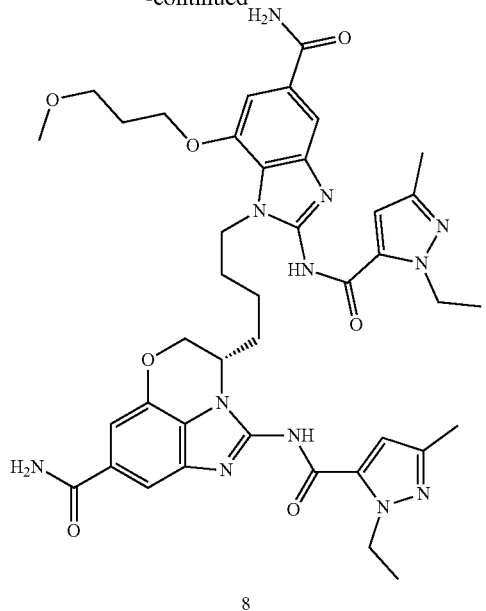

8

Step 1: To a stirring solution of compound 1f (6.0 g, 29.92 mmol) and compound 8a (16 g, 60.07 mmol) in acetonitrile (150 mL) was added K$_2$CO$_3$ (12.4 g, 90.11 mmol), and the resulting mixture was heated at 70° C. for 24 hours, TLC indicated the product was formed. The reaction mixture was cooled to room temperature, the solid was removed by filtration and washed with DCM (100 mL), the filtrate was concentrated. The residue was purified by silica gel chromatography to give compound 8b (8.20 g, 63% yield) as a yellow oil. ESI-MS (m/): 431.2 [M+H]$^+$.

Step 2: To a stirring solution of compound 8b (8.2 g, 9.29 mmol) in acetonitrile (150 mL) was added Cs$_2$CO$_3$ (9.08 g, 27.88 mmol), and the reaction mixture was heated at 70° C.; for 6 hours, TLC indicated the conversion was complete. The reaction mixture was cooled to room temperature, filtered through a pad of silica gel. The filtrate was concentrated under reduced pressure to give compound 8c (3.90 g, 68% purity). The sample was used directly without further purification. ESI-MS (m/): 411.6 [M+H]$^+$.

Step 3: Compound 8c (3.90 g, from step 2) was dissolved in a mixture of MeOH (30 mL) and concentrated ammonium hydroxide (5 mL). Sodium dithionite (5.5 g, 31.59 mmol) was dissolved in water (2 mL) and added to the reaction mixture at room temperature. Stirring was continued at room temperature for half an hour, and LCMS indicated the product was formed. The reaction mixture was diluted with water (50 mL) and extracted with ethyl acetate (50 mL×3). The combined organic layers were washed with brine, dried over Na$_2$SO$_4$, filtered and concentrated under reduced pressure. The residue was purified by silica gel chromatography to give compound 8d (1.2 g, yield 34% for two steps) as yellow solid. ESI-MS (m/): 381.6 [M+H]$^+$.

Step 4: Compound 8d (700 mg, 1.84 mmol) was dissolved in dioxane (10 mL), and then compound 5d (0.4M in dioxane, 4.6 mL, 1.84 mmol) was added. The reaction mixture was stirred at room temperature for half an hour, then DCC (47 mg, 0.23 mmol) was added. The mixture was heated at 80° C. for 6 hours, LCMS indicated the product was formed. The reaction mixture was cooled to room temperature, filtered through a pad of silica gel and washed with ethyl acetate (10 mL×3). The filtrate was concentrated to give compound 8e (970 mg, 61% purity), which was used directly without further purification.

Step 5: Compound 8e (970 mg, from step 4) was dissolved in acetic acid (10 mL), and hydrobromic acid in acetic acid solution (33 wt. %, 5 mL) was added. The resulting mixture was stirred at room temperature for half an hour, LCMS indicated the eproduct was formed. MTBE (100 mL) was added to the reaction mixture, the formed red solid was collected by filtration. The solid was washed by diethyl ether and dried in vacuo to give compound 8f (500 mg), which was used directly without further purification. ESI-MS (m/): 408.2 [M+H]$^+$.

Step 6: To a stirring solution of compound 8f (500 mg, from step 5) and compound 1n (460 mg, 1.6 mmol) in DMF (10 mL) was added Cs$_2$CO$_3$ (1.2 g, 3.69 mmol). The reaction mixture was heated at 80° C. for 16 hours, and LCMS indicated the product was formed. The reaction mixture was allowed to cool to room temperature, filtered through a pad of silica gel. The filtrate was diluted with water (20 mL) and extracted with ethyl acetate (50 mL). The aqueous phase was extracted with ethyl acetate (30 mL×2). The combined organic layers were washed with brine, dried over Na$_2$SO$_4$, filtered and concentrated under reduced pressure. The residue was purified by silica gel chromatography to give compound 8g (490 mg, yield 40% for three steps) as red oil. ESI-MS (m/): 660.3 [M+H]$^+$.

Step 7: Compound 8g (490 mg, 0.74 mmol) was dissolved in a mixture of MeOH (20 mL) and concentrated ammonium hydroxide (7 mL). Sodium dithionite (1.5 g, 8.62 mmol) was dissolved in water (2 mL) and added to the reaction mixture at room temperature. Stirring was continued at room temperature for half an hour, and LCMS indicated the product was formed. The reaction mixture was filtered through a pad of silica gel, and the filtrate was concentrated. The residue was purified by silica gel chromatography to give compound 8h (230 mg, yield 49%). ESI-MS (m/z): 630.3 [M+H]$^+$.

Step 8: Compound 8h (230 mg, 0.37 mmol) was dissolved in dioxane (4 mL), and then compound 5d (0.4M in dioxane, 1 mL, 0.40 mmol) was added. The reaction mixture was stirred at room temperature for 1 hour, then EDCI (76 mg, 0.41 mmol) was added. The mixture was heated at 80° C. for 6 hours, LCMS indicated the product was formed. The reaction mixture was concentrated, and the residue was purified by silica gel chromatography to give compound 8i (140 mg, 48% yield). ESI-MS (m/z): 791.4 [M+H]$^+$.

Step 9: To a stirring solution of compound 8i (140 mg, 0.18 mmol) in DMSO (2 mL) at 0° C. was added solid NaOH (10 mg, 0.26 mmol), followed by the addition of hydrogen peroxide (30 wt. %, 2 mL). The reaction was warmed to room temperature and monitored by LCMS. After the reaction was complete, the reaction mixture was purified directly by reversed phase preparative HPLC to give compound 8 (16 mg, 23% yield) as white solid. ESI-MS (m/z): 809.6 [M+H]$^+$; $^1$H NMR (500 MHz, DMSO-d6) δ12.69 (br s, 2H), 8.36 (s, 1H), 7.98 (s, 1H), 7.93 (s, 1H), 7.66 (s, 1H), 7.61 (s, 1H), 7.44-7.27 (m, 4H), 6.61-6.58 (m, 2H), 4.70-4.49 (m, 6H), 4.33 (t, J=7.6 Hz, 2H), 4.28-4.24 (m, 1H), 4.17 (t, J=6.3 Hz, 2H), 3.17 (s, 3H), 2.15 (s, 3H), 2.11 (s, 3H), 1.99-1.89 (m, 4H), 1.87-1.81 (m, 2H), 1.60-1.51 (m, 2H), 1.35-1.29 (m, 6H).

Example 9: (S)-2-(4-bromo-1-ethyl-3-methyl-1H-pyrazole-5-carboxamido)-3-(3-(5-carbamoyl-2-(1-ethyl-3-methyl-1H-pyrazole-5-carboxamido)-7-(3-methoxypropoxy)-1H-benzo[d]imidazol-1-yl)propyl)-3,4-dihydro-5-oxa-1,2a-diazaacenaphthylene-7-carboxamide
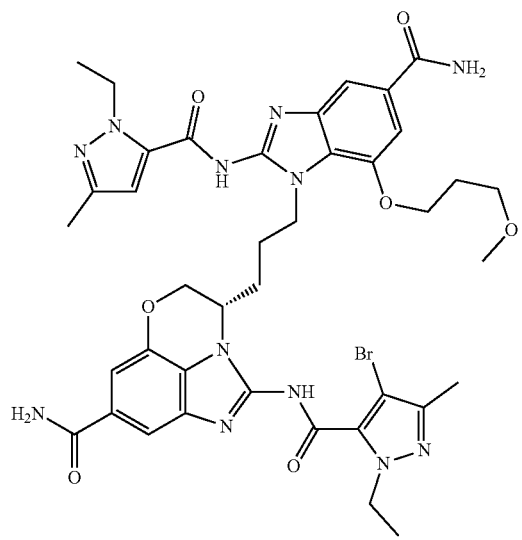
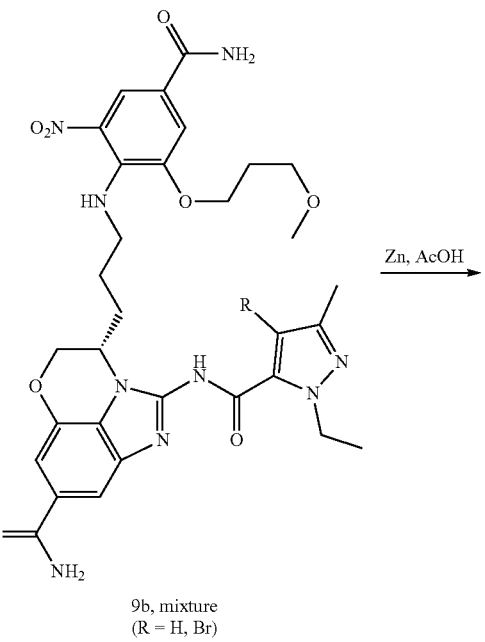
Synthetic Scheme
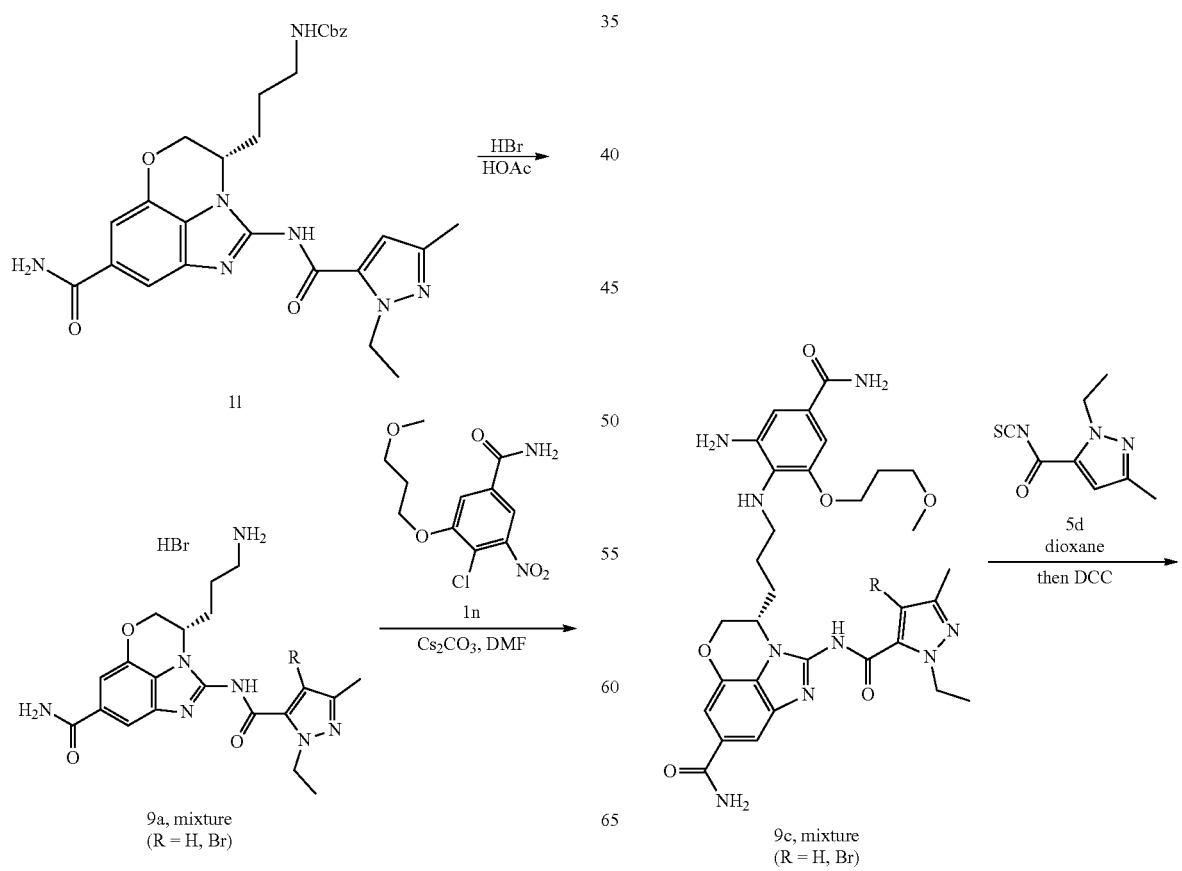

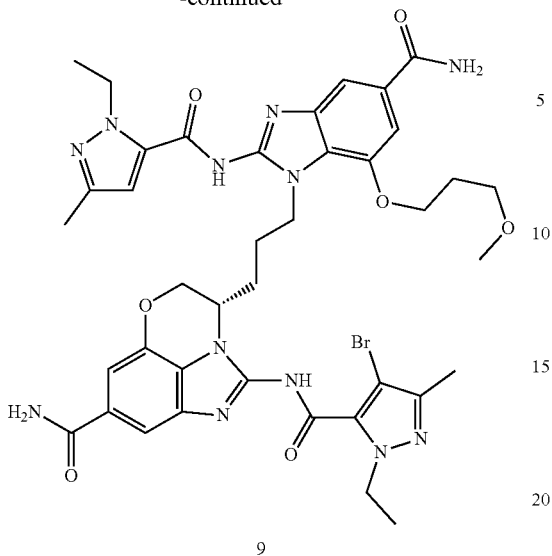

9

Step 1: Compound 11 (1.10 g, 2.02 mmol) was dissolved in acetic acid (10 mL), and hydrobromic acid in acetic acid solution (33 wt. %, 5.44 g, 20.16 mmol) was added. The resulting mixture was stirred at room temperature for 1 hour, LCMS indicated the starting material was consumed. MTBE (40 mL) was added to the reaction mixture, the formed solid was collected by filtration. The solid was washed with MTBE (10 mL×2), dried in vacuo to give compound 9a (900 mg) as a mixture of two products, which was used directly without further purification. ESI-MS (m/z): 412.4 [M+H]$^+$; ESI-MS (m/z): 492.3 [M+H]$^+$.

Step 2: To a stirring solution of compound 9a (900 mg, from step 1) and compound 1n (792 mg, 2.74 mmol) in DMF (8 mL) was added $Cs_2CO_3$ (1.78 g, 5.48 mmol). The reaction mixture was heated at 80° C.; overnight, and LCMS indicated the product was formed. The reaction mixture was allowed to cool to room temperature, diluted with water (15 mL) and extracted with ethyl acetate (20 mL). The aqueous phase was extracted with ethyl acetate (15 mL×3). The combined organic layers were dried over $Na_2SO_4$, filtered and concentrated under reduced pressure. The residue was purified by silica gel chromatography to give compound 9b (350 mg) as a mixture of two products. The sample was used directly without further purification. ESI-MS (m/z): 664.5 [M+H]$^+$; ESI-MS (m/z): 742.4 [M+H]$^+$.

Step 3: Compound 9b (350 mg, from step 2) was dissolved in acetic acid (10 mL), and Zn powder (206 mg, 3.17 mmol) was added by two portions at room temperature. The reaction mixture was stirred at room temperature for 1 hour, LCMS indicated the product was formed. The mixture was filtered, and the cake was rinsed with MeOH (10 mL×2). The filtrate was concentrated and the residue was purified by silica gel chromatography to give the compound 9c (250 mg) as a mixture of two products. The sample was used directly without further purification. ESI-MS (m/z): 634.4 [M+H]$^+$; ESI-MS (m/z): 712.2 [M+H]$^+$.

Step 4: Compound 9c (100 mg) was dissolved in dioxane (3 mL), and then compound 5d (0.4M in dioxane, 0.5 mL, 0.2 mmol) was added. The reaction mixture was stirred at room temperature for 1 hour, then DCC (36 mg, 0.17 mmol) was added. The mixture was heated at 80° C.; for 2 hours, LCMS indicated the product was formed. The reaction mixture was cooled to room temperature, and directly purified by reversed phase preparative HPLC to give compound 9 (15 mg) as white solid. ESI-MS (m/z): 875.5 [M+H]$^+$; $^1$HNMR (500 MHz, DMSO-d6) δ 12.77 (br s, 2H), 7.99 (s, 1H), 7.93 (s, 1H), 7.64 (s, 1H), 7.61 (s, 1H), 7.42-7.25 (m, 4H), 6.55 (s, 1H), 4.76-4.63 (m, 2H), 4.60-4.44 (m, 4H), 4.42-4.29 (m, 2H), 4.27-4.23 (m, 1H), 4.20-4.07 (m, 2H), 3.17 (s, 3H), 2.10 (s, 6H), 2.00-1.81 (m, 6H), 1.31-1.15 (m, 6H).

Example 10: (S)-3-(3-(5-carbamoyl-2-(1-(2-fluoroethyl)-3-methyl-1H-pyrazole-5-carboxamido)-7-(3-methoxypropoxy)-1H-benzo[d]imidazol-1-yl)propyl)-2-(1-(2-fluoroethyl)-3-methyl-1H-pyrazole-5-carboxamido)-3,4-dihydro-5-oxa-1,2a-diazaacenaphthylene-7-carboxamide Synthetic Scheme 153
-continued
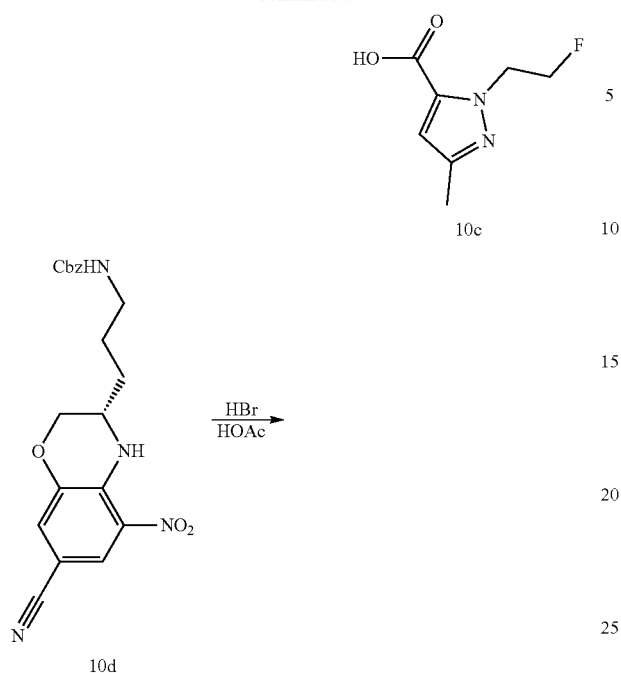
10d
154
-continued
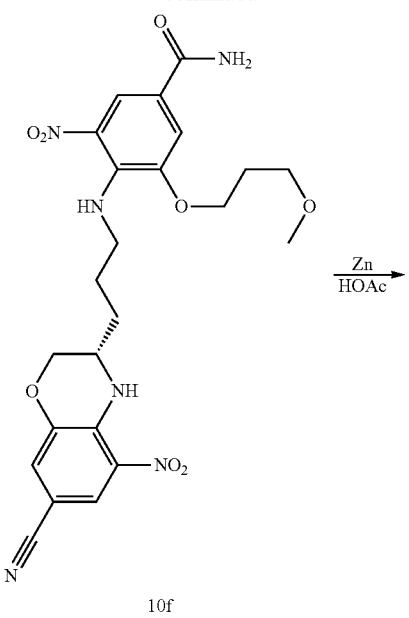
10f
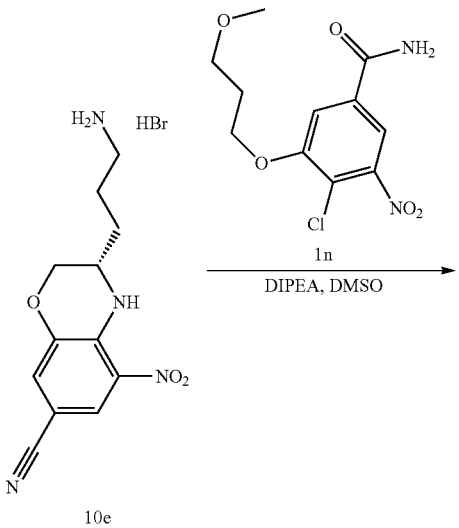
10e
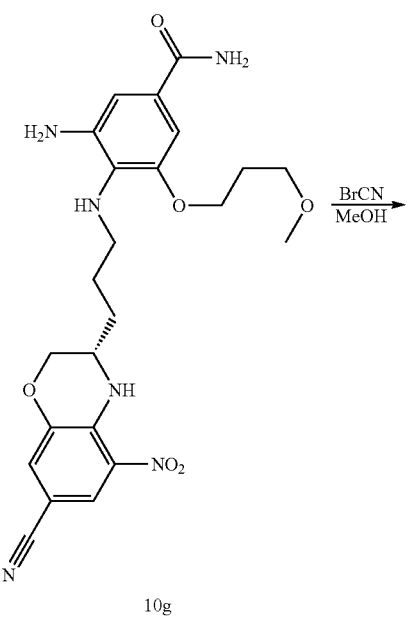
10g -continued

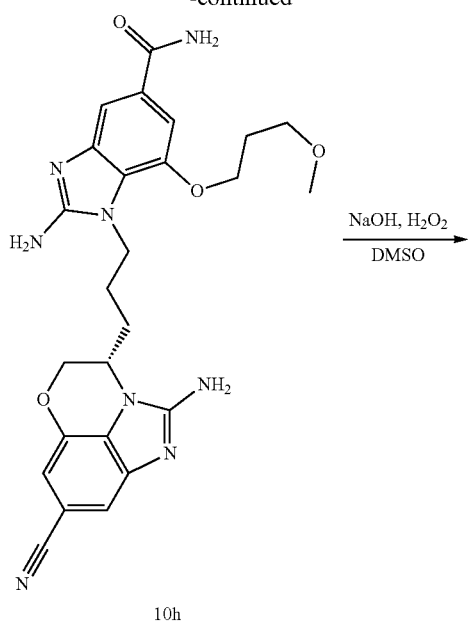

10h

NaOH, H₂O₂
DMSO
→

-continued

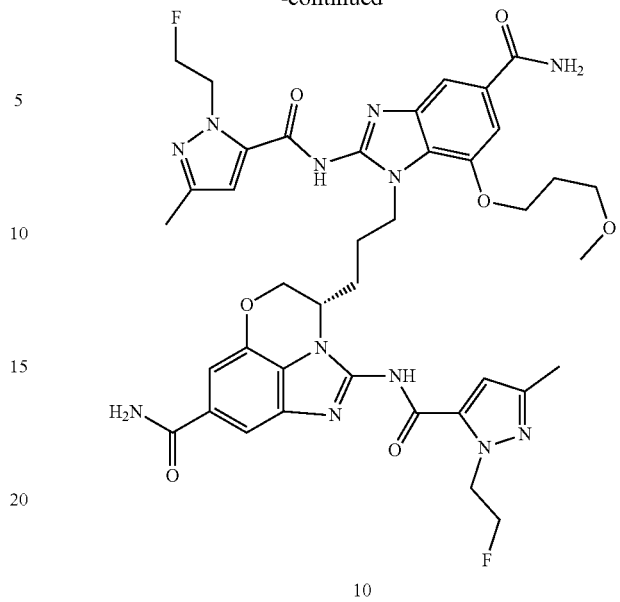

10

Step 1: To the solution of compound 10a (200 mg, 1.43 mmol) and 1-fluoro-2-iodoethane (373 mg, 2.14 mmol) in DMF (3 mL) was added Cs₂CO₃ (699 mg, 2.14 mmol), and the mixture was stirred at room temperature overnight. LCMS indicated the product was formed. The reaction mixture was diluted with water (10 mL) and extracted with ethyl acetate (10 mL), the aqueous phase was extracted with ethyl acetate (10 mL×2). The combined organic layers were washed with brine (10 mL), dried over Na₂SO₄, filtered and concentrated. The residue was purified by silica gel chromatography to give compound 10b (166 mg, 62% yield) as a colorless oil. ESI-MS (m/z): 187.7[M+H]⁺; ¹H NMR (500 MHz, DMSO-d6) δ 6.71 (s, 1H), 4.85-4.75 (m, 2H), 4.75-4.65 (m, 2H), 3.82 (s, 3H), 2.21 (s, 3H).

Step 2: To the solution of compound 10b (166 mg, 0.90 mmol) in MeOH (4 mL) was added NaOH aqueous solution (4 N, 0.7 mL), and the mixture was stirred at room temperature for 2 hours. LCMS indicated the product was formed. The solvent was removed in vacuo; the residue was suspended in water (10 mL). The mixture was acidified to pH 6~7 with 2M HCl aqueous solution, then extracted with ethyl acetate (10 mL×3). The combined organic layers were washed with brine, dried over Na₂SO₄, filtered and concentrated under reduced pressure to give compound 10c (101 mg) as white solid. ESI-MS (m/z): 173.0 [M+H]⁺.

Step 3: Compound 10d (1.00 g, 2.52 mmol) was dissolved in acetic acid (10 mL), and hydrobromic acid in acetic acid solution (33 wt. %, 3.65 g, 15.14 mmol) was added. The resulting mixture was stirred at room temperature for 1.5 hour, LCMS indicated the starting material was consumed. MTBE (25 mL) was added to the reaction mixture, and the mixture was stirred for 15 minutes, then the formed red solid was collected by filtration. The solid was washed with MTBE (10 mL×2), dried in vacuo to give compound 10e (840 mg), which was used directly without further purification. ESI-MS (m/z): 263.3 [M+H]⁺.

Step 4: To a stirring solution of compound 10e (840 mg, from step 3) and compound 1n (564 mg, 1.96 mmol) in DMSO (10 mL) was added DIPEA (1.52 g, 11.75 mmol).

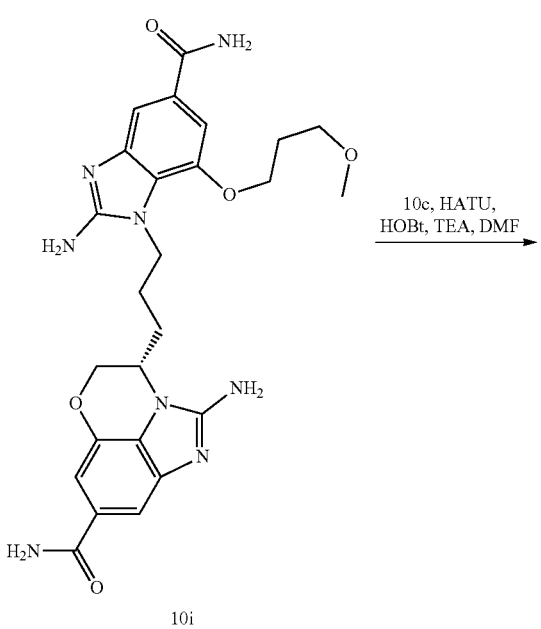

10c, HATU,
HOBt, TEA, DMF
→

10i

The reaction mixture was heated at 120° C. overnight, and LCMS indicated the product was formed. The reaction mixture was allowed to cool to room temperature, diluted with water (20 mL) and extracted with ethyl acetate (20 mL). The aqueous phase was extracted with ethyl acetate (15 mL×3). The combined organic layers were washed with brine (15 mL×3), dried over $Na_2SO_4$, filtered and concentrated under reduced pressure. The residue was purified by silica gel chromatography to give compound 10f (620 mg, 60% yield) as a yellow solid. ESI-MS (m/z): 515.4 $[M+H]^+$.

Step 5: Compound 10f (620 mg, 1.21 mmol) was dissolved in acetic acid (10 mL), and Zn powder (470 mg, 7.23 mmol) was added by portions at room temperature. The reaction mixture was stirred at room temperature for 1 hour, LCMS indicated the product was formed. The mixture was filtered, and the cake was rinsed with EtOAc (10 mL×3). The filtrate was concentrated and the residue was purified by silica gel chromatography to give the compound 10g (438 mg, 80% yield) as a off-white solid. ESI-MS (m/z): 455.3 $[M+H]^+$.

Step 6: Compound 10g (100 mg, 0.22 mmol) was dissolved in MeOH (10 mL), and cyanogen bromide (93 mg, 0.88 mmol) was added. The resulting mixture was stirred at 60° C.; overnight. The mixture was concentrated in vacuo to remove the solvent. The residue was suspended in EtOAc (10 mL and stirred for 15 minutes. The formed solid was collected by filtration, washed with EtOAc (5 mL×2) and dried in vacuo to give compound 10h (105 mg) as an off-white solid. The sample was used directly in next reaction without further purification. ESI-MS (m/z): 505.3 $[M+H]^+$.

Step 7: To a stirring solution of compound 10h (105 mg, from step 6) in DMSO (10 mL) was added solid NaOH (50 mg, 1.24 mmol), followed by the addition of hydrogen peroxide (30 wt. %, 0.2 mL). The reaction was monitored by LCMS. After the reaction was complete, the reaction mixture was diluted with water (10 mL) and extracted with EtOAc (10 mL×2). The combined organic layers were washed with brine, dried over $Na_2SO_4$ and concentrated. The residue was purified by silica gel chromatography to give compound 10i (80 mg, 70% yield) as off-white solid. ESI-MS (m/z): 523.3 $[M+H]^+$.

Step 8: To a stirring solution of 10c (53 mg, 0.31 mmol) in DMF (3 mL) was added HATU (233 mg, 0.61 mmol) and HOBt (41 mg, 0.31 mmol). The mixture was stirred at room temperature for 30 minutes, triethylamine (64 mg, 0.37 mmol) was added, and after another 10 minutes, compound 10i (80 mg, 0.15 mmol) was added. The resulting mixture was stirred at room temperature for 30 minutes, then heated at 60° C.; overnight. LCMS indicated the product was formed. The mixture was purified directly by reversed phase preparative HPLC to give compound 10 (30 mg, 35% yield) as white solid. ESI-MS (m/z): 831.6 $[M+H]^+$; $^1H$ NMR (500 MHz, DMSO-d6) δ 12.68 (br s, 2H), 7.98 (s, 1H), 7.92 (s, 1H), 7.65 (s, 1H), 7.59 (s, 1H), 7.42-7.24 (m, 4H), 6.64 (s, 1H), 6.54 (s, 1H), 5.00-4.78 (m, 6H), 4.77-4.74 (m, 1H), 4.73-4.68 (m, 2H), 4.65-4.58 (m, 1H), 4.47-4.37 (m, 1H), 4.36-4.29 (m, 1H), 4.27-4.20 (m, 1H), 4.19-4.06 (m, 2H), 3.14 (s, 3H), 2.13 (s, 3H), 2.09 (s, 3H), 2.03-1.98 (m, 2H), 1.95-1.88 (m, 2H), 1.88-1.77 (m, 2H).

Example 11: (S)-1-(3-(7-cyano-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-7-(3-methoxypropoxy)-1H-benzo[d]imidazole-5-carboxamide

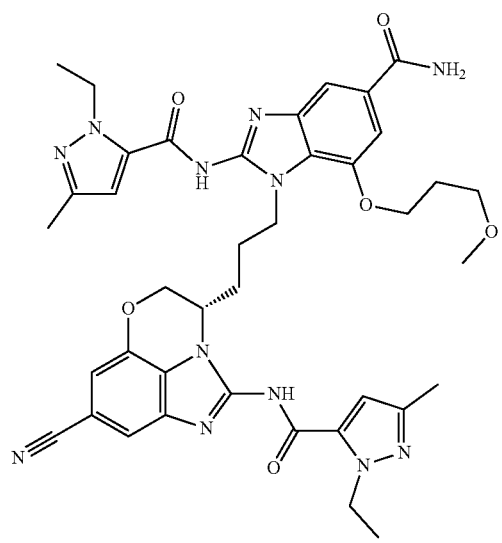 [SMILES: CCn1nc(C)cc1C(=O)Nc1nc2cc(C(N)=O)cc(OCCCOC)c2n1CCC[C@H]1COc2cc(C#N)cc3nc(NC(=O)c4cc(C)nn4CC)n1c23]

Synthetic Scheme

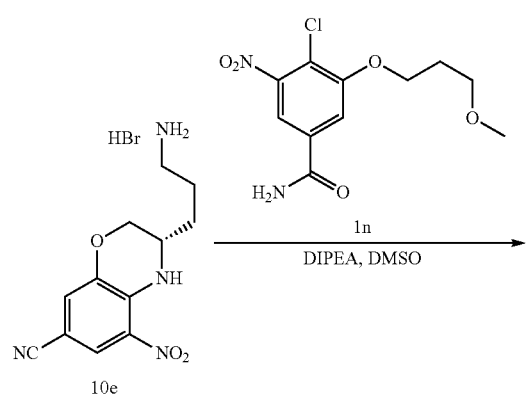

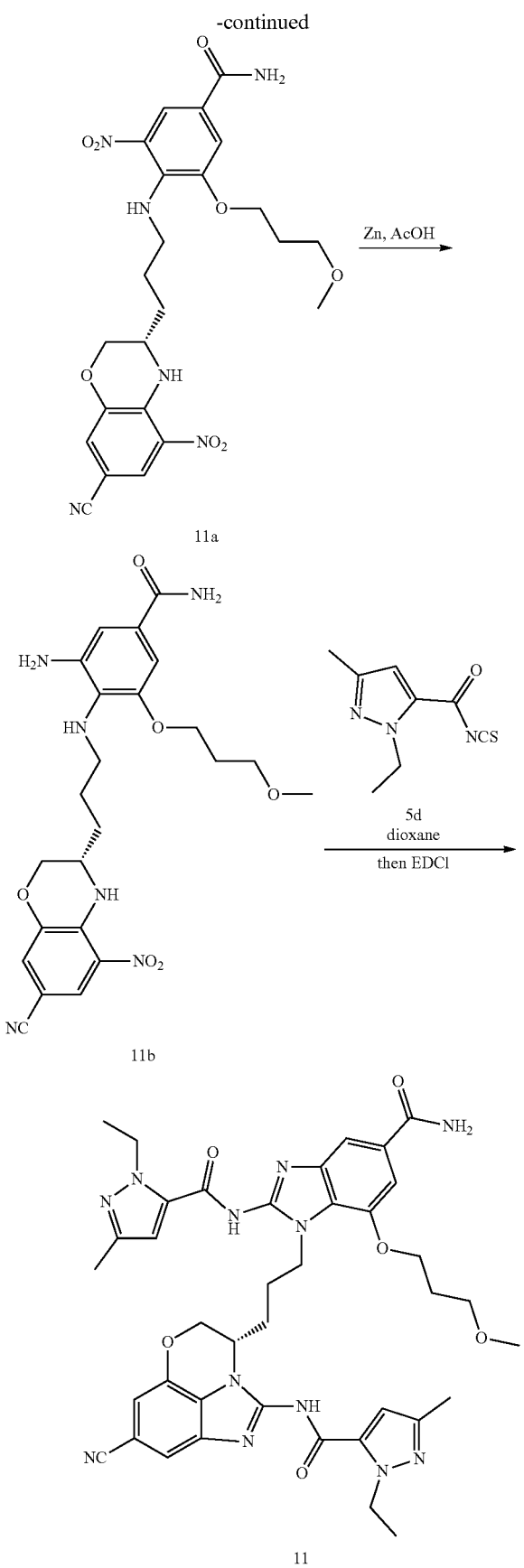

Step 1: To a stirring solution of compound 10e (357 mg, 1.04 mmol) and compound to (250 mg, 0.87 mmol) in DMSO (5 mL) was added DIPEA (560 mg, 4.33 mmol). The reaction mixture was heated at 120° C.; overnight, and LCMS indicated the product was formed. The reaction mixture was allowed to cool to room temperature, diluted with water (15 mL) and extracted with ethyl acetate (20 mL). The aqueous phase was extracted with ethyl acetate (20 mL×3). The combined organic layers were dried over $Na_2SO_4$, filtered and concentrated under reduced pressure. The residue was purified by silica gel chromatography to give compound 11a (440 mg, purity 61%) as a red oil. The sample was used directly without further purification. ESI-MS (m/z): 515.4 $[M+H]^+$.

Step 2: Compound ha (440 mg, from step 1) was dissolved in acetic acid (5 mL), and Zn powder (171 mg, 2.61 mmol) was added by portions at room temperature. The reaction mixture was stirred at room temperature for 1 hour, LCMS indicated the product was formed. The mixture was filtered, and the cake was rinsed with DCM. The filtrate was concentrated and the residue was purified by silica gel chromatography to give the compound 11b (150 mg, 30% yield for 2 steps) as light yellow solid. ESI-MS (m/z): 455.4 $[M+H]^+$.

Step 3: Compound 11b (150 mg, 0.33 mmol) was dissolved in dioxane (10 mL), and then compound 5d (0.4M in dioxane, 1.8 mL, 0.72 mmol) was added. The reaction mixture was stirred at room temperature for 30 minutes, LCMS indicated the starting material was consumed. EDCl (158 mg, 0.83 mmol) was added, and the mixture was heated at 80° C.; for 2 hours, LCMS indicated the product was formed. The reaction mixture was cooled to room temperature, and directly purified by reversed phase preparative HPLC to give compound 11 (115 mg, 45% yield) as white solid. ESI-MS (m/z): 777.5 $[M+H]^+$; $^1H$ NMR (500 MHz, DMSO-d6) δ12.80 (s, 2H), 7.97 (s, 1H), 7.64 (s, 1H), 7.43-7.23 (m, 4H), 6.55 (s, 1H), 6.49 (s, 1H), 4.76 (br s, 1H), 4.67-4.46 (m, 5H), 4.41-4.24 (m, 3H), 4.19-4.06 (m, 2H), 3.17 (s, 3H), 2.11 (s, 3H), 2.07 (s, 3H), 2.04-1.81 (m, 6H), 1.3-91.21 (m, 6H).

Example 12: (S)-3-(3-(5-carbamoyl-2-(1-(2-fluoroethyl)-3-methyl-1H-pyrazole-5-carboxamido)-7-(3-methoxypropoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

161

Example 13: (S)-2-(4-bromo-1-ethyl-3-methyl-1H-pyrazole-5-carboxamido)-3-(3-(5-carbamoyl-2-(1-(2-fluoroethyl)-3-methyl-1H-pyrazole-5-carboxamido)-7-(3-methoxypropoxy)-1H-benzo[d]imidazol-1-yl)propyl)-3,4-dihydro-5-oxa-1,2a-diazaacenaphthylene-7-carboxamide

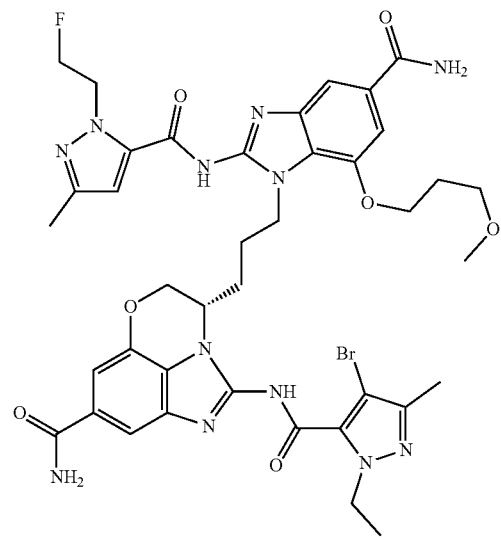 [SMILES: CCn1nc(C)c(Br)c1C(=O)Nc1nc2cc(C(N)=O)cc3c2n1[C@@H](CCCn1c(NC(=O)c2cc(C)nn2CCF)nc2cc(C(N)=O)cc(OCCCOC)c21)CO3]

Synthetic Scheme

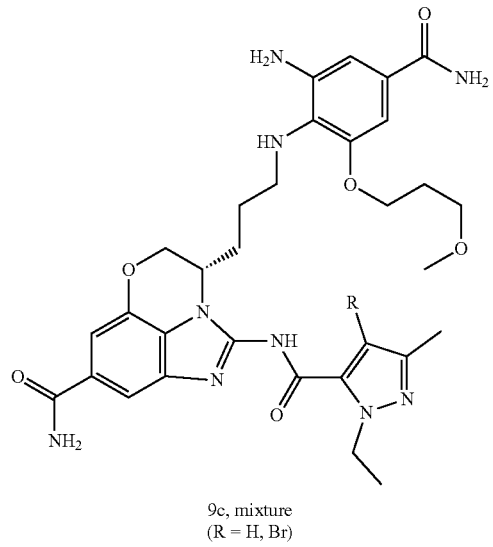

9c, mixture
(R = H, Br)

162

-continued

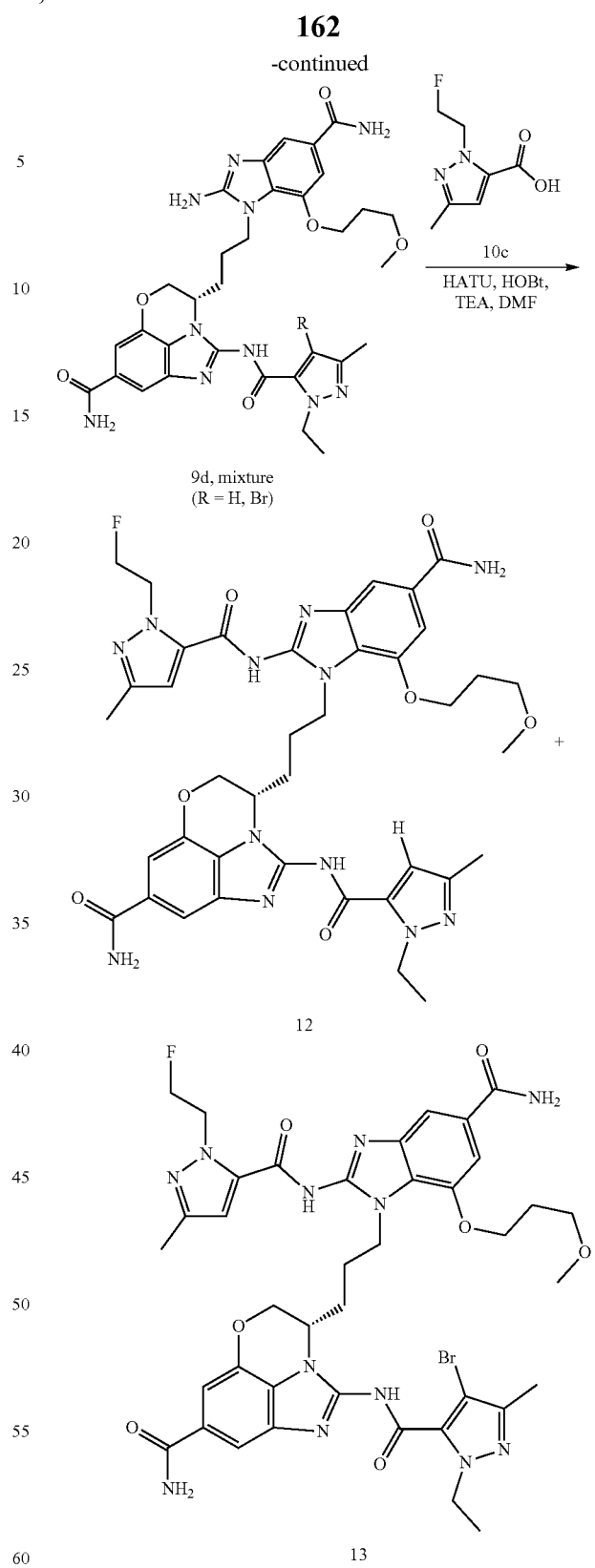

Step 1: Mixture sample 9c (150 mg) was dissolved in MeOH (6 mL), and cyanogen bromide (100 mg, 0.95 mmol) was added. The resulting mixture was stirred at 60° C.; overnight. The mixture was concentrated in vacuo to remove the solvent. The residue was suspended in EtOAc (5 mL)

and stirred for 10 minutes. The formed solid was collected by filtration, washed with EtOAc (5 mL×2) and dried in vacuo to give mixture sample 9d (116 mg) as an off-white solid. The sample was used directly in next reaction without further purification. ESI-MS (m/z): 659.1 [M+H]⁺; ESI-MS (m/z): 737.4 [M+H]⁺.

Step 2: To a stirring solution of 10c (37 mg, 0.21 mmol) in DMF (3 mL) was added HATU (134 mg, 0.35 mmol) and HOBt (24 mg, 0.18 mmol). The mixture was stirred at room temperature for 30 minutes, triethylamine (53 mg, 0.53 mmol) was added, and after another 10 minutes, compound 9d (116 mg, from step 1) was added. The resulting mixture was stirred at room temperature for 30 minutes, then heated at 60° C.; overnight. LCMS indicated the product was formed. The mixture was purified directly by reversed phase preparative HPLC to give compound 12 (15 mg, 16% yield for 2 steps) as white solid and compound 13 (13 mg, 14% yield for 2 steps) as white solid.

Compound 12, ESI-MS (m/z): 813.4 [M+H]⁺; ¹H NMR (500 MHz, DMSO-d6) δ12.55 (s, 1H), 7.91 (s, 1H), 7.84 (s, 1H), 7.57 (s, 1H), 7.51 (s, 1H), 7.31-7.18 (m, 4H), 6.55 (s, 1H), 6.40 (s, 1H), 4.90-4.84 (m, 1H), 4.83-4.79 (m, 1H), 4.75-4.70 (m, 1H), 4.69-4.60 (m, 2H), 4.55-4.51 (m, 1H), 4.50-4.41 (m, 2H), 4.36-4.29 (m, 1H), 4.28-4.21 (m, 1H), 4.18-4.12 (m, 1H), 4.10-3.% (m, 2H), 3.06 (s, 3H), 2.05 (s, 3H), 2.00 (s, 3H), 1.96-1.88 (m, 2H), 1.87-1.80 (m, 2H), 1.79-1.70 (m, 2H), 1.22 (t, J=7.0 Hz, 3H).

Compound 13, ESI-MS (m/z): 891.5 [M+H]⁺; ¹H NMR (500 MHz, DMSO-d6) δ 12.68 (br s, 2H), 7.91 (s, 1H), 7.86 (s, 1H), 7.56 (s, 1H), 7.52 (s, 1H), 7.28-7.22 (m, 4H), 6.53 (s, 1H), 4.88-4.84 (m, 1H), 4.82-4.78 (m, 1H), 4.75-4.70 (m, 1H), 4.66-4.55 (m, 3H), 4.49-4.36 (m, 2H), 4.34-4.22 (m, 2H), 4.20-4.15 (m, 1H), 4.10-3.98 (m, 2H), 3.08 (s, 3H), 2.06 (s, 3H), 2.04 (s, 3H), 1.946-1.82 (m, 4H), 1.79-1.71 (m, 2H), 1.21 (t, J=7.0 Hz, 3H).

Example 14: (S)-3-(3-(7-(3-aminopropoxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide Synthetic Scheme

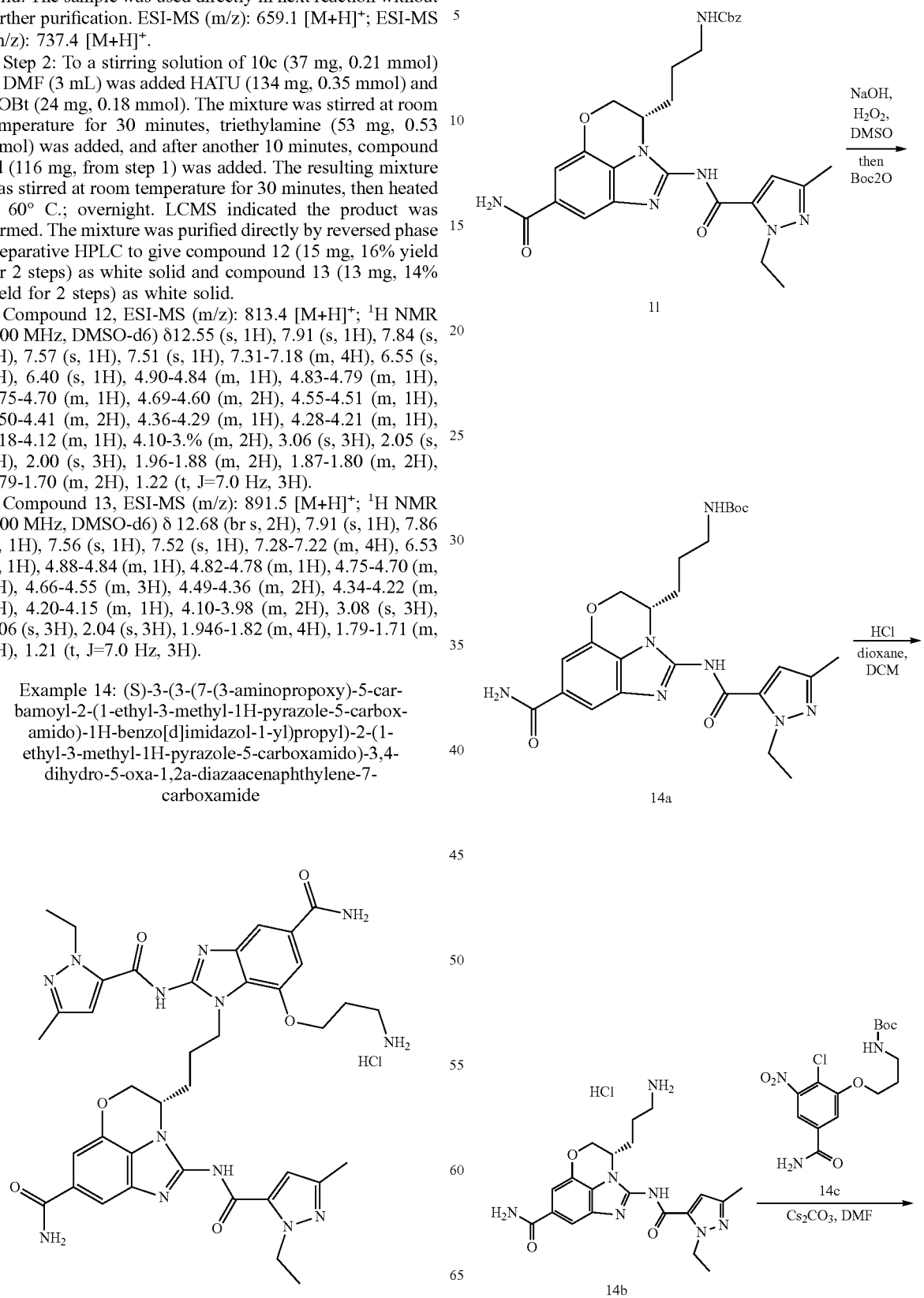

-continued

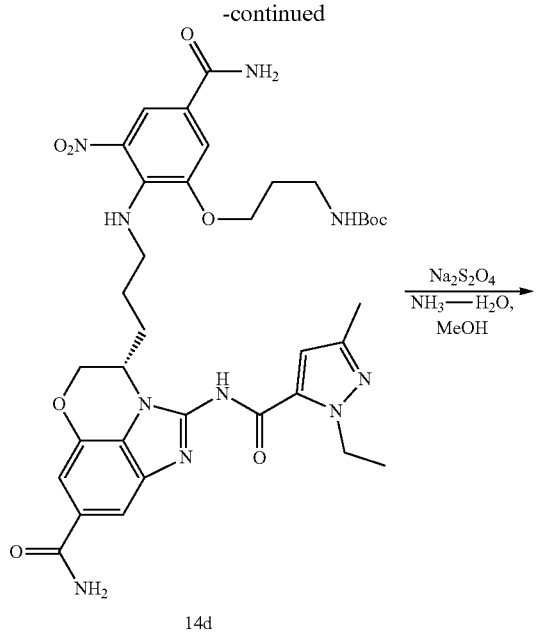

14d

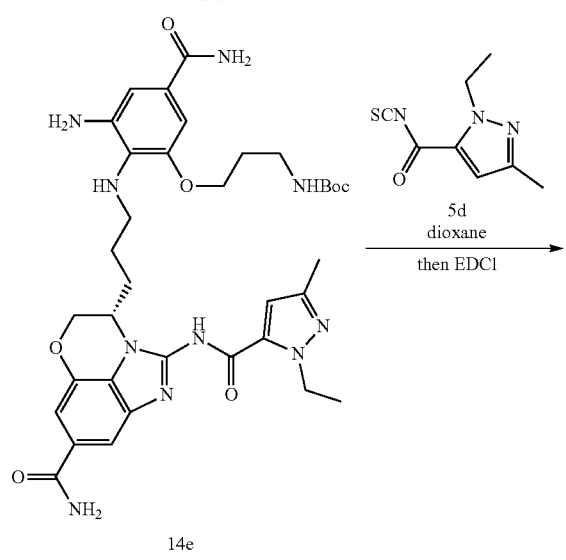

14e

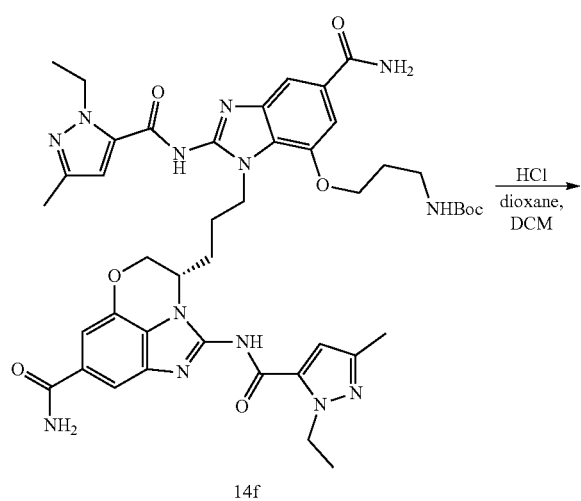

14f

-continued

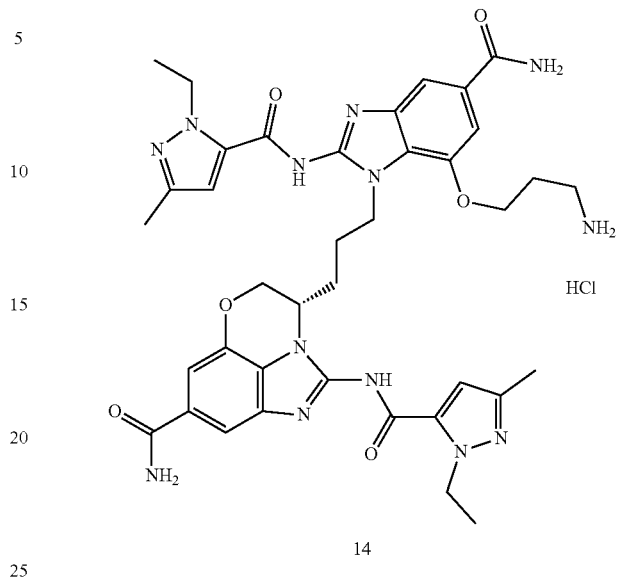

14

Step 1: To a stirring solution of compound 11 (10.0 g, 18.33 mmol) in DMSO (100 mL) was added solid NaOH (2.20 g, 55.00 mmol). The reaction mixture was heated at 60° C., and hydrogen peroxide (30 wt. %, 10 mL) was added dropwise into the reaction mixture. The reaction was stirred at 60° C.; for 30 minutes, then cooled to room temperature. $Boc_2O$ (4.40 g, 20.15 mmol) was added to the reaction mixture, and the reaction was stirred at room temperature for half an hour. LCMS indicated the product was formed. The reaction mixture was diluted with water (200 mL) and extracted with EtOAc (150 mL×3). The combined organic layers were dried over $Na_2SO_4$, filtered and concentrated to give compound 14a (9.30 g) as white solid. The sample was used directly in next reaction without further purification. ESI-MS (m/z): 512.3 $[M+H]^+$.

Step 2: To a stirring solution of compound 14a (9.3 g, from step 1) in DCM (150 mL) was added 4M HCl in dioxane (22.5 mL, 90.0 mmol) at room temperature. The mixture was stirred at rom temperature for 1 hour and LCMS indicated the product was formed. The mixture was concentrated under reduced pressure to give compound 14b (7.10 g) as yellow solid, which was used directly without further purification. ESI-MS (m/z): 412.4 $[M+H]^+$.

Step 3: To a stirring solution of compound 14b (1.00 g, 2.43 mmol) and compound 14c (1.36 g, 3.65 mmol) in DMF (10 mL) was added $Cs_2CO_3$ (3.17 g, 9.72 mmol). The reaction mixture was heated at 80° C. overnight, and TLC indicated the starting material was consumed. The reaction mixture was allowed to cool to room temperature, filtered through a pad of celite. The filtrated was diluted with water (20 mL), extracted with EtOAc (50 mL). The aqueous layer was extracted with EtOAc (30 mL×2). The combined organic layers were washed with brine, dried over $Na_2SO_4$, filtered and concentrated. The residue was purified by silica gel chromatography to give compound 14d (640 mg, 35% yield) as a red oil. ESI-MS (m/z): 749.7 $[M+H]^+$.

Step 4: Compound 14d (640 mg, 0.85 mmol) was dissolved in a mixture of MeOH (20 mL) and concentrated ammonium hydroxide (7 mL). Sodium dithionite (1.49 g, 8.55 mmol) was dissolved in water (2 mL) and added to the reaction mixture at room temperature. Stirring was continued at room temperature for half an hour, and LCMS indicated the product was formed. The reaction mixture was filtered through a pad of celite, and the filtrate was concentrated. The residue was purified by silica gel chromatography to give compound 14e (380 mg, 61% yield). ESI-MS (m/z): 719.8 [M+H]$^+$.

Step 5: Compound 14e (500 mg, 0.70 mmol) was dissolved in dioxane (4 mL), and then compound 5d (0.4M in dioxane, 1.7 mL, 0.69 mmol) was added. The reaction mixture was stirred at room temperature for 1 hour, EDCI (400 mg, 2.09 mmol) was added, and the mixture was heated at 80° C. for 6 hours, LCMS indicated the product was formed. The reaction mixture was concentrated, and the residue was purified by silica gel chromatography to give compound 14f (540 mg, 88% yield). ESI-MS (m/z): 880.2 [M+H]$^+$.

Step 6: To a stirring solution of compound 14f (540 mg, 0.61 mmol) in DCM (10 mL) at 0° C. was added 4M HCl in dioxane (2 mL, 8 mmol). The mixture was stirred at 0° C.; for 1 hour, then concentrated to give compound 14 (400 mg). ESI-MS (m/z): 780.7 [M+H]$^+$; $^1$HNMR (500 MHz, DMSO-d6) δ 8.37 (s, 2H), 8.02 (s, 1H), 7.94 (s, 1H), 7.64 (s, 1H), 7.58 (s, 1H), 7.40-7.25 (m, 3H), 6.54 (s, 1H), 6.45 (s, 1H), 4.73 (br s, 1H), 4.66-4.45 (m, 5H), 4.44-4.25 (m, 2H), 4.24-4.10 (m, 4H), 2.82-2.75 (m, 2H), 2.07 (s, 3H), 2.05 (s, 3H), 2.00-1.80 (m, 6H), 1.36-1.20 (m, 6H).

Example 15: (S)-1-(3-(7-cyano-2-(1-ethyl-3-methyl-1H-pyrazole-5-carboxamido)-3,4-dihydro-5-oxa-1, 2a-diazaacenaphthylen-3-yl)propyl)-7-(3-(2-(dimethylamino)acetamido)propoxy)-2-(1-ethyl-3-methyl-1H-pyrazole-5-carboxamido)-1H-benzo[d]imidazole-5-carboxamide Synthetic Scheme

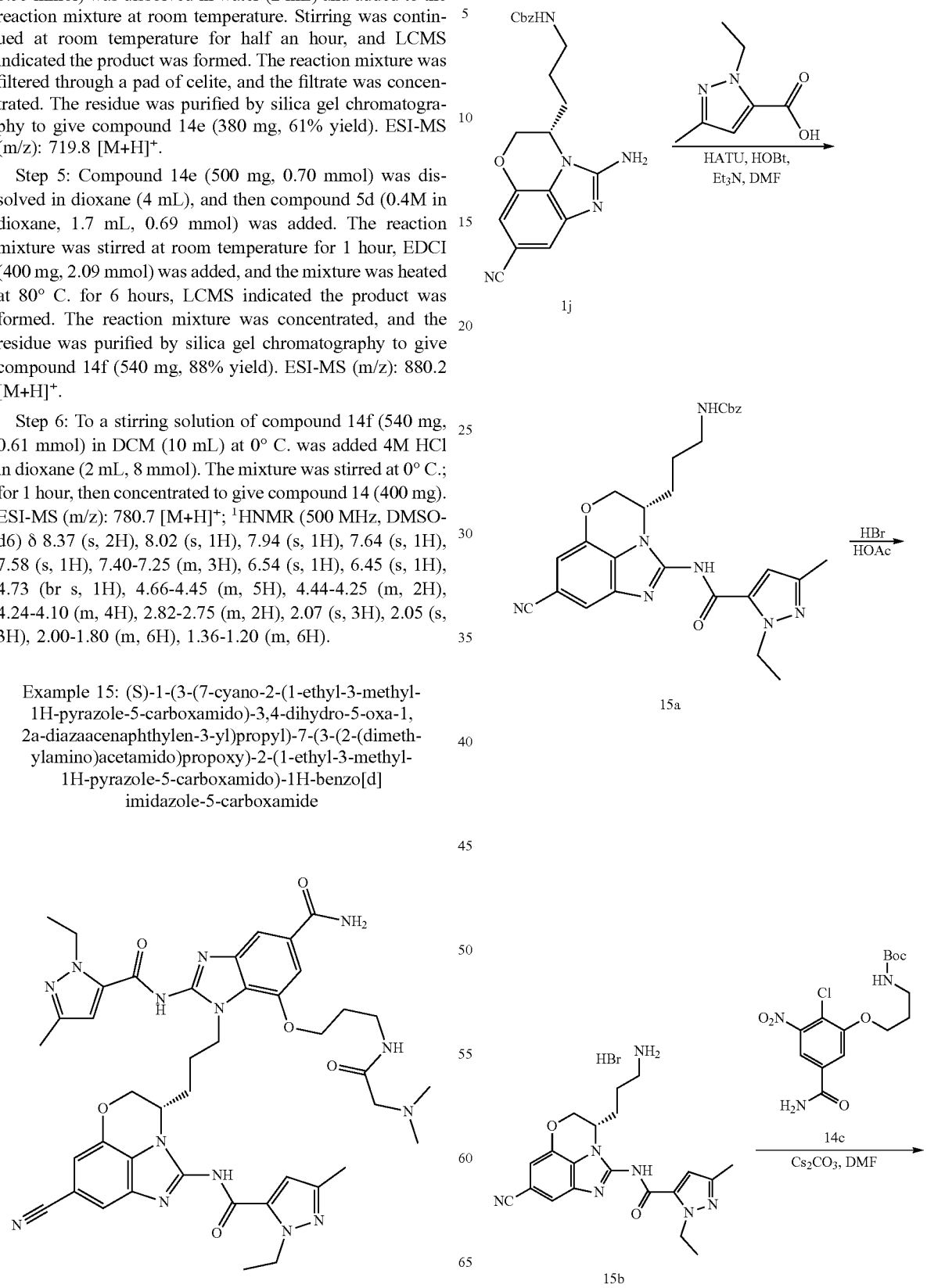

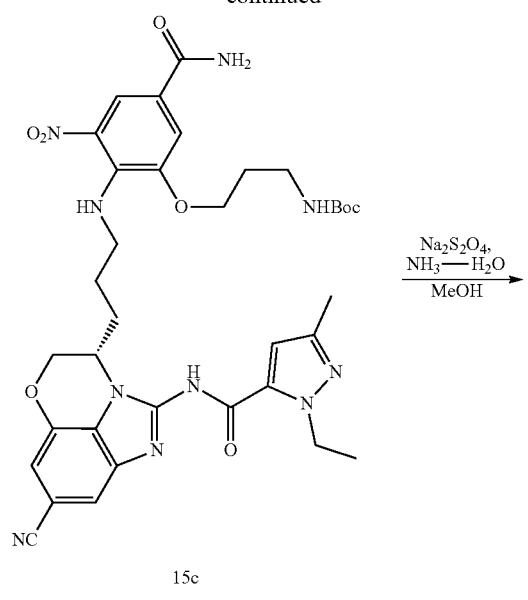

15c

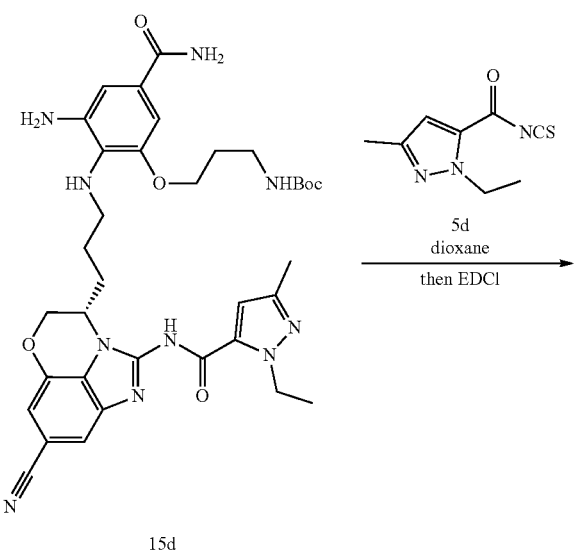

15d

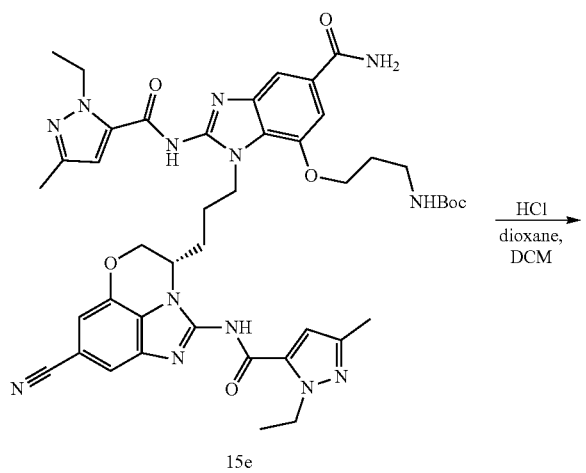

15e

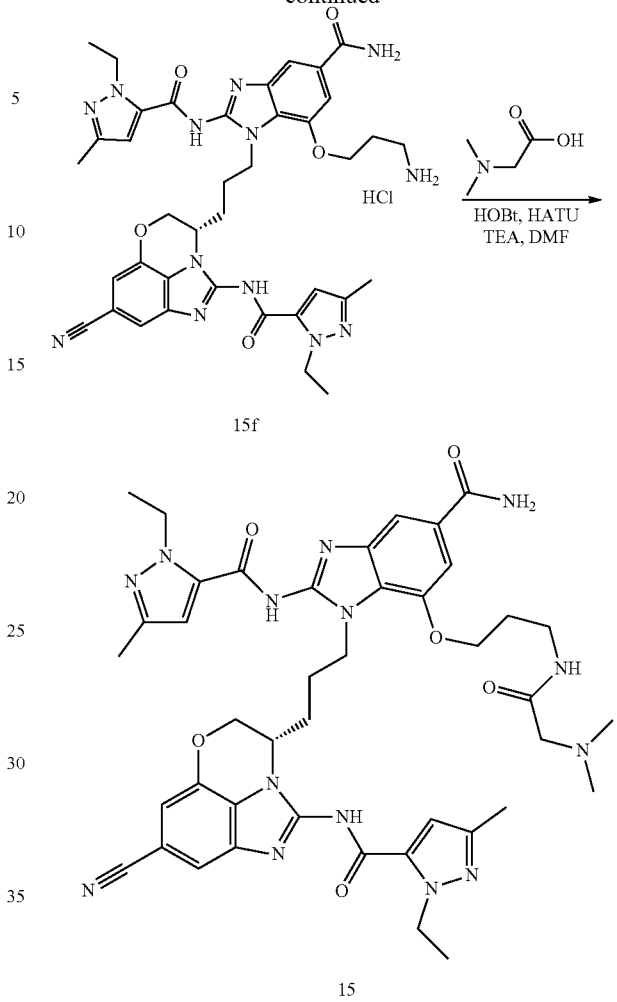

15f

15

Step 1: To a stirring solution of 1-ethyl-3-methyl-1H-pyrazole-5-carboxylic acid (8.0 g, 51.9 mmol) in DMF (60 mL) was added HATU (20.0 g, 52.6 mmol), HOBt (3.5 g, 25.9 mmol) and triethylamine (13.7 mL, 100 mmol). The mixture was stirred at room temperature for 30 minutes, then compound 1j (12.6 g, 32.2 mmol) was added. The resulting mixture was heated at 60° C.; for 3 hours, LCMS indicated the product was formed. The reaction was cooled to room temperature, diluted with water (120 mL) and extracted with EtOAc (150 mL×3). The combined organic layers were dried over $Na_2SO_4$, filtered and concentrated. The residue was purified by silica gel chromatography to give compound 15a (15.1 g, 88% yield) as white solid. ESI-MS (m/z): 528.4 $[M+H]^+$.

Step 2: Compound 15a (1.40 g, 2.65 mmol) was dissolved in acetic acid (10 mL), and hydrobromic acid in acetic acid solution (33 wt. %, 5 mL) was added. The resulting mixture was stirred at room temperature for 1 hour, LCMS indicated the starting material was consumed. MTBE (100 mL) was added to the reaction mixture, the formed red solid was collected by filtration. The solid was dried in vacuo to give compound 15b (1.20 g), which was used directly without further purification. ESI-MS (m/z): 394.1 $[M+H]^+$.

Step 3: To a stirring solution of compound 15b (1.20 g, from step 2) and compound 14c (1.23 g, 3.30 mmol) in DMF (10 mL) was added $Cs_2CO_3$ (2.47 g, 7.62 mmol). The reaction mixture was heated at 80° C. overnight, and TLC indicated the starting material was consumed. The reaction mixture was allowed to cool to room temperature, filtered through a pad of celite. The filtrated was diluted with water (20 mL), extracted with EtOAc (50 mL). The aqueous layer was extracted with EtOAc (30 mL×2). The combined organic layers were washed with brine, dried over $Na_2SO_4$, filtered and concentrated. The residue was purified by silica gel chromatography to give compound 15c (580 mg, 30% yield for 2 steps) as a red oil. ESI-MS (m/z): 731.2 $[M+H]^+$.

Step 4: Compound 15c (580 mg, 0.79 mmol) was dissolved in a mixture of MeOH (20 mL) and concentrated ammonium hydroxide (7 mL). Sodium dithionite (1.50 g, 8.55 mmol) was dissolved in water (2 mL) and added to the reaction mixture at room temperature. Stirring was continued at room temperature for half an hour, and LCMS indicated the product was formed. The reaction mixture was filtered through a pad of celite, and the filtrate was concentrated. The residue was purified by silica gel chromatography to give compound 15d (340 mg, 61% yield). ESI-MS (m/z): 701.3 $[M+H]^+$.

Step 5: Compound 15d (340 mg, 0.49 mmol) was dissolved in dioxane (4 mL), and then compound 5d (0.4M in dioxane, 1.32 mL, 0.53 mmol) was added. The reaction mixture was stirred at room temperature for 1 hour, EDCI (102 mg, 0.53 mmol) was added, and the mixture was heated at 80° C. for 6 hours, LCMS indicated the product was formed. The reaction mixture was concentrated, and the residue was purified by silica gel chromatography to give compound 15e (220 mg, 52% yield). ESI-MS (m/z): 862.4 $[M+H]^+$.

Step 6: To a stirring solution of compound 15e (220 mg, 0.26 mmol) in DCM (10 mL) at 0° C. was added 4M HCl in dioxane (2 mL, 8 mmol). The mixture was stirred at 0° C.; for 1 hour then concentrated. The residue was purified by reversed phase preparative HPLC to give compound 15f (190 mg). ESI-MS (m/z): 762.4 $[M+H]^+$.

Step 7: To a stirring solution of 15f (30 mg, 0.04 mmol) and 2-(dimethylamino)acetic acid (4 mg, 0.04 mmol) in DMF (2 mL) was added HATU (5.32 mg, 0.04 mmol), HOBt (14.97 mg, 0.04 mmol) and triethylamine (12 mg, 0.12 mmol). The mixture was stirred at room temperature overnight, and purified directly by revered phase preparative HPLC to give compound 15 (10 mg, 29% yield). ESI-MS (m/z): 847.6 $[M+H]^+$; $^1$H NMR (500 MHz, DMSO-d6) δ12.81 (br s, 1H), 8.33 (s, 3H), 7.96 (s, 1H), 7.82 (s, 1H), 7.64 (s, 1H), 7.40-7.25 (m, 2H), 6.53 (s, 1H), 6.45 (s, 1H), 4.76-4.70 (m, 1H), 4.66-4.62 (m, 1H), 4.58448 (m, 4H), 4.42430 (m, 2H), 4.14-4.05 (m, 3H), 2.79 (s, 2H), 2.16 (s, 6H), 2.10 (s, 3H), 2.05 (s, 3H), 2.03-1.75 (m, 6H), 1.32-1.20 (m, 6H).

Example 16: (S)-3-(3-(5-carbamoyl-2-(1-ethyl-3-methyl-1H-pyrazole-5-carboxamido)-7-(2-(methylamino) ethoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

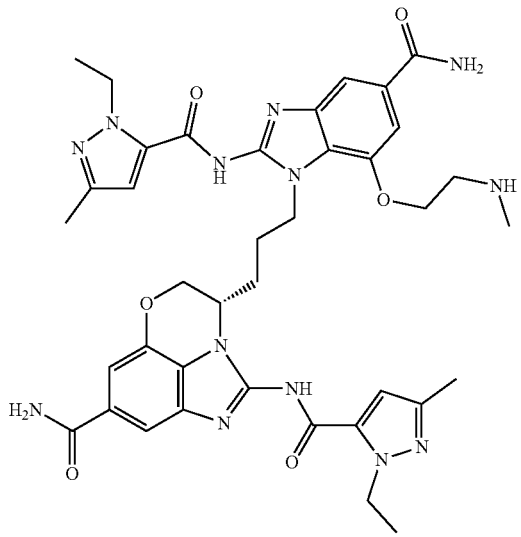 [SMILES: CCn1nc(C)cc1C(=O)Nc1nc2cc(C(N)=O)cc(OCCNC)c2n1CCC[C@H]1COc2cc(C(N)=O)cc3nc(NC(=O)c4cc(C)nn4CC)n1c23]

Synthetic Scheme

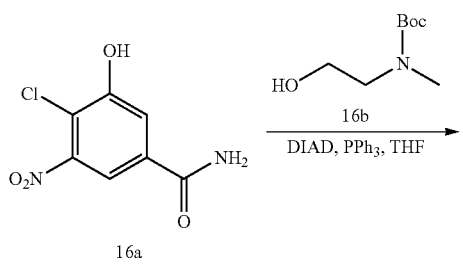

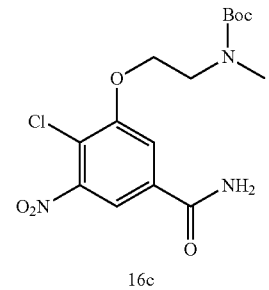

-continued
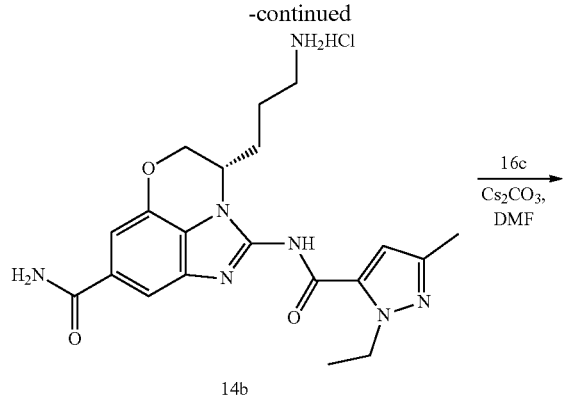
14b
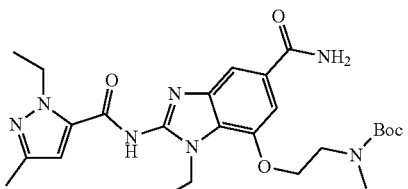
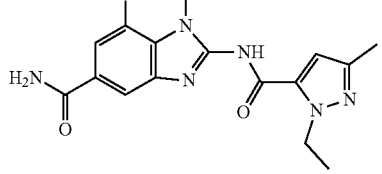
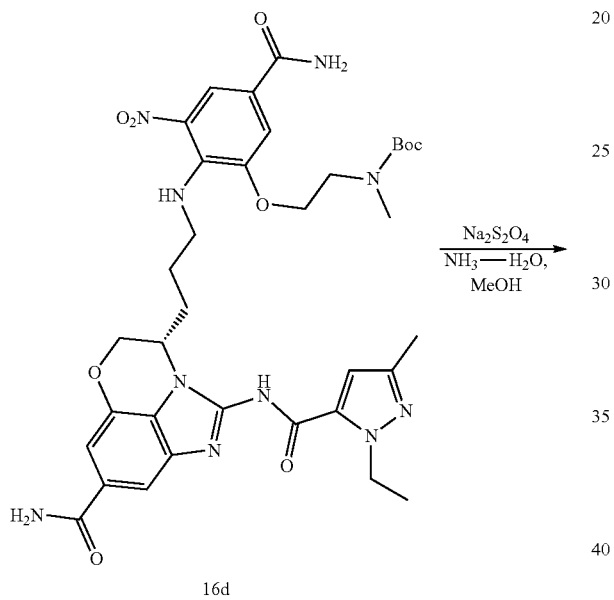
16d
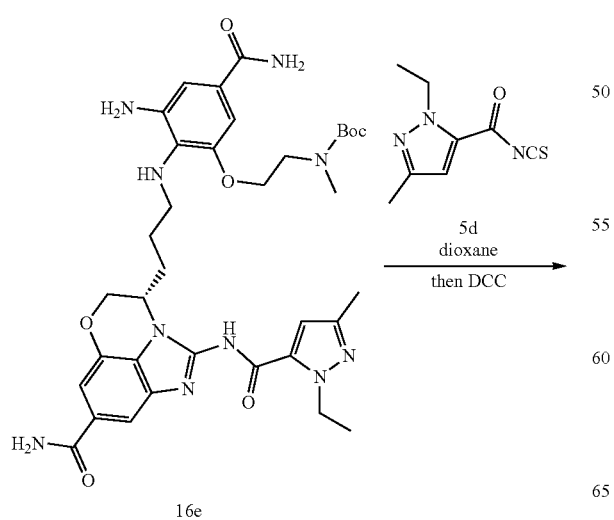
16e
-continued
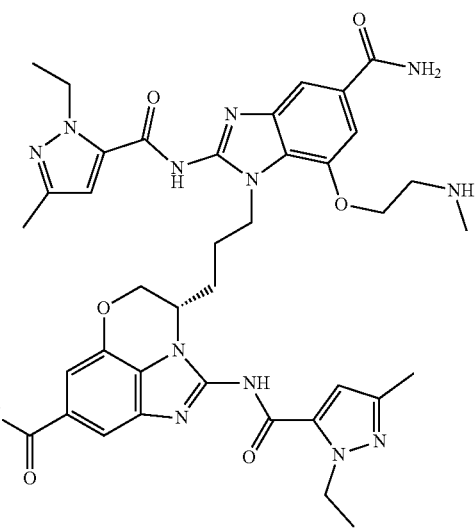
16f
16

Step 1: To a stirred solution of Compound 16a (900 mg, 4.16 mmol), 16b (990 mg, 5.62 mmol) and triphenylphosphine (1.47 g, 5.62 mmol) in THF (15 mL) at 0-10° C. under $N_2$ atmosphere was added DIAD (1.14 g, 5.62 mmol) dropwise. After stirring the solution for 20 minutes at 0-10° C. the reaction mixture was warmed to room temperature and stirred for 40 minutes. LCMS indicated the product was formed. The reaction mixture was concentrated in vacuo and the residue was purified by silica gel chromatography to give compound 16c (1.40 g, 90% yield) as a light-yellow solid. ESI-MS (m/z): 374.4 $[M+H]^+$.

Step 2: To a stirring solution of compound 14b (500 mg, 1.12 mmol) and compound 16c (626 mg, 1.67 mmol) in DMF (5 mL) was added $Cs_2CO_3$ (1.09 g, 3.36 mmol). The reaction mixture was heated at 100° C. overnight, and LCMS indicated the product was formed. The reaction mixture was allowed to cool to room temperature, diluted with water (15 mL), extracted with EtOAc (15 mL). The aqueous layer was extracted with EtOAc (10 mL×4). The combined organic layers were dried over $Na_2SO_4$, filtered and concentrated. The residue was purified by silica gel chromatography to give compound 16d (379 mg, 45% yield) as a red solid. ESI-MS (m/z): 749.4 $[M+H]^+$.

Step 3: Compound 16d (379 mg, 0.51 mmol) was dissolved in a mixture of MeOH (15 mL) and concentrated ammonium hydroxide (1 mL). Sodium dithionite (431 mg, 3.04 mmol) was dissolved in water (0.5 mL) and added to the reaction mixture at room temperature. Stirring was continued at room temperature for 40 minutes, and LCMS indicated the product was formed. The reaction mixture was concentrated, the residue was diluted with water (5 mL), and extracted with EtOAc (15 mL). The aqueous layer was extracted with EtOAc (10 mL×4). The combined organic layers were dried over $Na_2SO_4$, filtered and concentrated. filtered through a pad of celite, and the filtrate was concentrated. The residue was purified by silica gel chromatography to give compound 16e (260 mg, 71% yield) as a yellow oil. ESI-MS (m/z): 719.4 $[M+H]^+$.

Step 4: Compound 16e (260 mg, 0.36 mmol) was dissolved in dioxane (3 mL), and then compound 5d (0.4M in dioxane, 1 mL, 0.40 mmol) was added. The reaction mixture was stirred at room temperature for half an hour, DCC (78 mg, 0.38 mmol) was added, and the mixture was heated at 80° C.; for 1 hour, LCMS indicated the product was formed. The reaction mixture was concentrated to give crude compound 16f, which was used directly without further purification. ESI-MS (m/z): 880.5 $[M+H]^+$.

Step 5: To a stirring solution of crude 16f (half amount from step 4) in 1, 4-dioxane (10 mL) at was added 4M HCl in dioxane (0.3 mL, 1.2 mmol). The mixture was stirred at room temperature overnight. LCMS indicated the starting material was consumed. The reaction mixture concentrated, and the residue was purified by reversed phase preparative HPLC to give compound 16 (30 mg) as a white solid. ESI-MS (m/z): 780.4 $[M+H]^+$; $^1$H NMR (500 MHz, DMSO-d6) δ 8.33 (s, 2H), 7.99 (s, 1H), 7.93 (s, 1H), 7.65 (s, 1H), 7.59 (s, 1H), 7.48-7.50 (m, 4H), 6.56 (s, 1H), 6.47 (s, 1H), 4.72 (br s, 1H), 4.70-4.50 (m, 5H), 4.48-4.30 (m, 2H), 4.28-4.10 (m, 3H), 2.79 (br s, 2H), 2.21 (s, 3H), 2.10 (s, 3H), 2.06 (s, 3H), 2.05-1.96 (m, 2H), 1.95-1.87 (m, 2H), 1.33-1.21 (m, 6H).

Example 17: (S)-3-(3-(5-carbamoyl-2-(1-ethyl-3-methyl-1H-pyrazole-5-carboxamido)-7-(3-(methylamino) propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide Hydrochloride

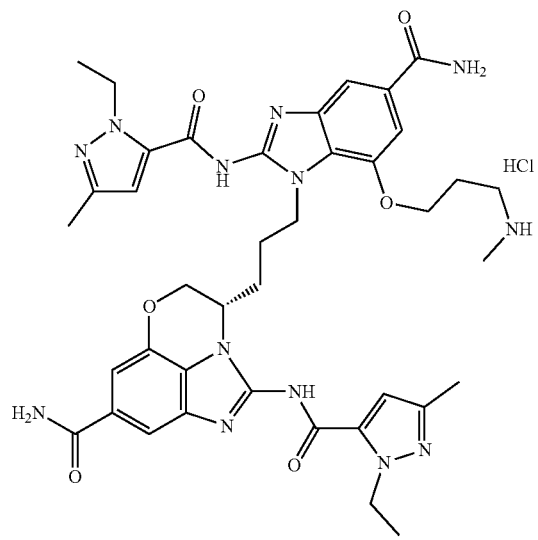 [SMILES: CCn1nc(C)cc1C(=O)Nc1nc2cc(C(N)=O)cc(OCCCNC)c2n1CCC[C@H]1COc2cc(C(N)=O)cc3nc(NC(=O)c4cc(C)nn4CC)n1c23 ; Cl]

Example 18: (S)-3-(3-(5-carbamoyl-7-(3-(dimethylamino)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

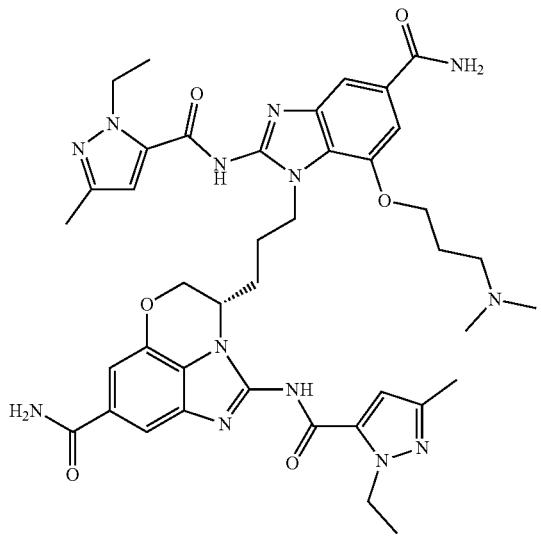 [SMILES: CCn1nc(C)cc1C(=O)Nc1nc2cc(C(N)=O)cc(OCCCN(C)C)c2n1CCC[C@H]1COc2cc(C(N)=O)cc3nc(NC(=O)c4cc(C)nn4CC)n1c23]

Synthetic Scheme
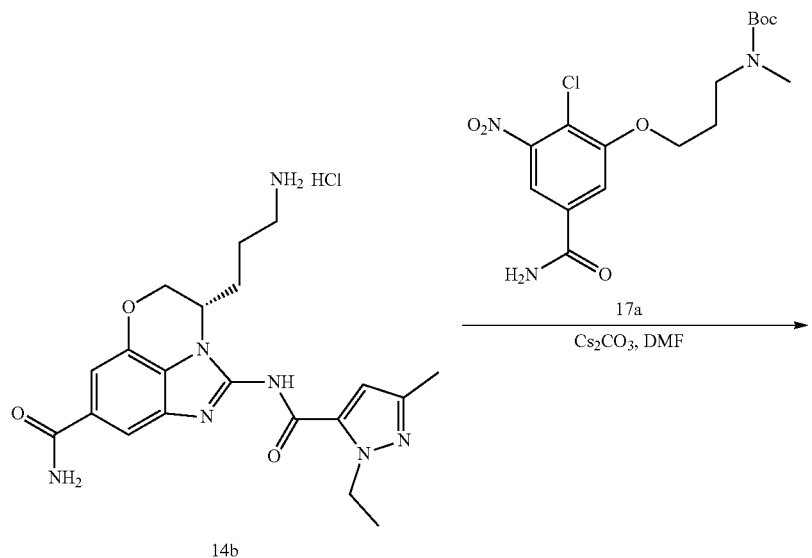
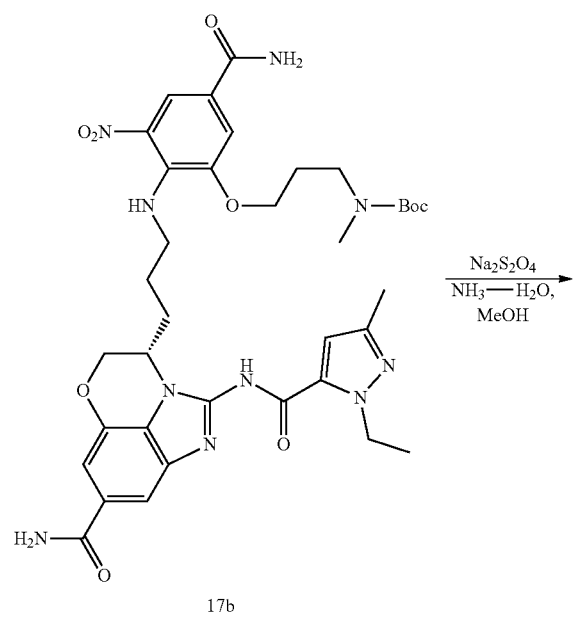

-continued
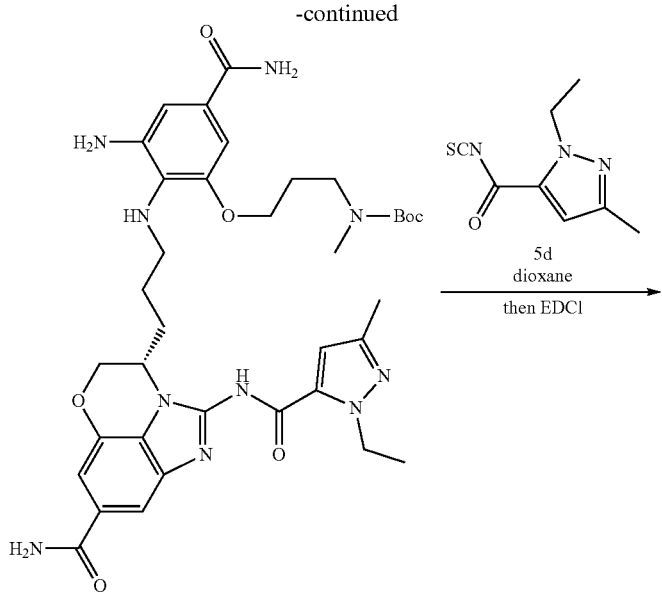
17c
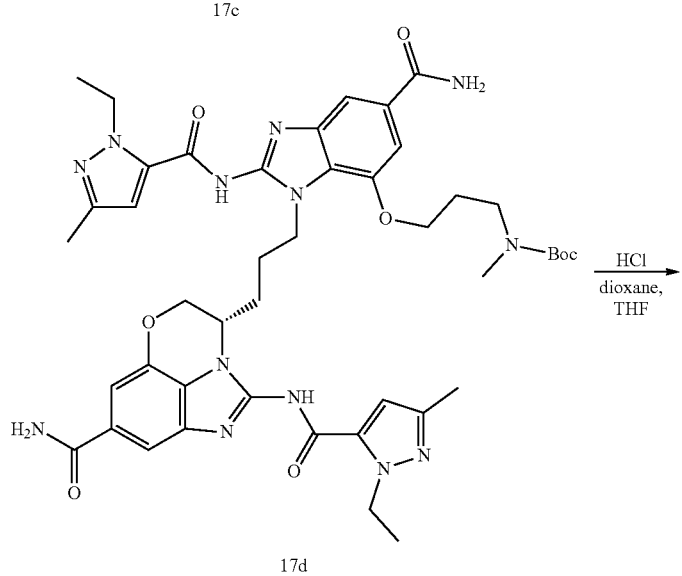
17d
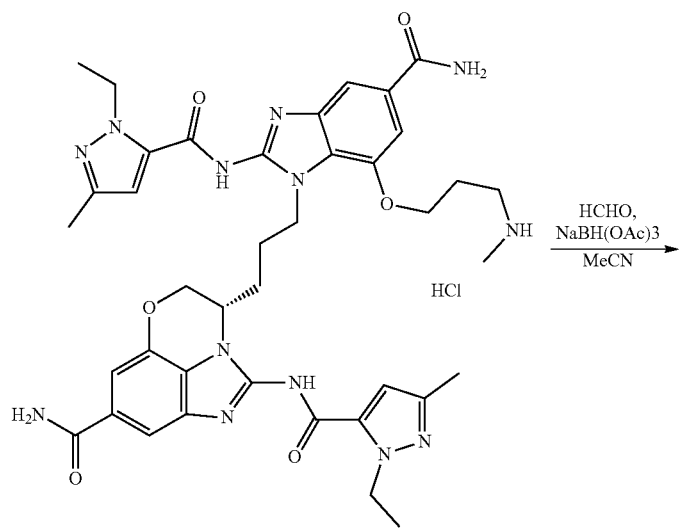
17

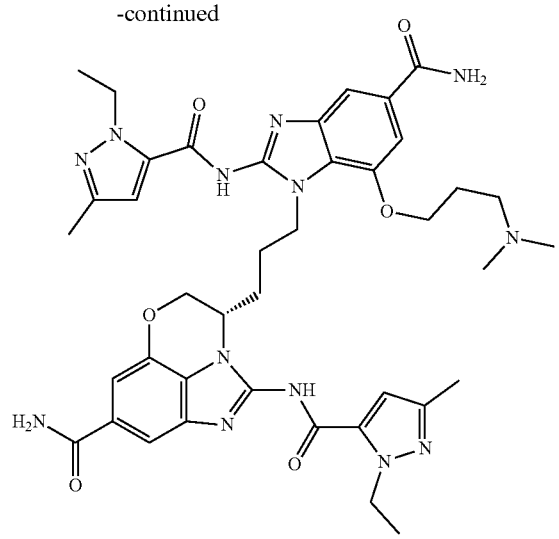

18

Step 1: To a stirring solution of compound 14b (1 g, 2.23 mmol) and compound 17a (1.04 g, 2.68 mmol) in DMF (10 mL) was added $Cs_2CO_3$ (2.18 g, 6.70 mmol). The reaction mixture was heated at 80° C.; overnight, and LCMS indicated the product was formed. The reaction mixture was allowed to cool to room temperature, diluted with water (20 mL), extracted with EtOAc (15 mL×4). The combined organic layers were washed with brine, dried over $Na_2SO_4$, filtered and concentrated. The residue was purified by silica gel chromatography to give compound 17b (500 mg, 29% yield) as yellow solid. ESI-MS (m/z): 763.5 $[M+H]^+$.

Step 2: Compound 17b (500 mg, 0.66 mmol) was dissolved in a mixture of MeOH (10 mL) and concentrated ammonium hydroxide (3 mL). Sodium dithionite (571 mg, 3.28 mmol) was dissolved in water (3 mL) and added to the reaction mixture at room temperature. Stirring was continued at room temperature for 10 minutes, and LCMS indicated the product was formed. The reaction mixture was filtered and the filtrate was concentrated. The residue was purified by silica gel chromatography to give compound 17c (285 mg, 59% yield) as white solid. ESI-MS (m/z): 733.5 $[M+H]^+$.

Step 3: Compound 17c (285 mg, 0.39 mmol) was dissolved in dioxane (10 mL), and then compound 5d (0.4M in dioxane, 1.2 mL, 0.48 mmol) was added. The reaction mixture was stirred at room temperature for half an hour, EDCI (97 mg, 0.51 mmol) was added, and the mixture was heated at 80° C. for 2 hours, LCMS indicated the product was formed. The reaction mixture was concentrated, and the residue was purified by silica gel chromatography to give crude compound 17d (220 mg, 63% yield) as white solid. ESI-MS (m/z): 894.7 $[M+H]^+$.

Step 4: To a stirring solution of 17d (220 mg, 0.25 mmol) in THF (10 mL) at was added 4M HCl in dioxane (5 mL, 20 mmol). The mixture was stirred at room temperature for 2 hours. LCMS indicated the starting material was consumed. The reaction mixture concentrated to give compound 17 (170 mg, 83% yield) as white solid. ESI-MS (m/z): 795.3 $[M+H]^+$; $^1H$ NMR (500 MHz, DMSO-d6) δ 8.32 (s, 1H), 7.98 (s, 1H), 7.92 (s, 1H), 7.63 (s, 1H), 7.58 (s, 1H), 7.37-7.25 (m, 4H), 6.56 (s, 1H), 6.46 (s, 1H), 4.77-4.70 (m, 1H), 4.64-4.45 (m, 6H), 4.43-4.35 (m, 1H), 4.34-4.27 (m, 1H), 4.26-4.20 (m, 1H), 4.19-4.07 (m, 2H), 2.67-2.62 (m, 2H), 2.09 (s, 3H), 2.06 (s, 3H), 2.03-1.95 (m, 2H), 1.94-1.86 (m, 2H), 1.85-1.76 (m, 2H), 1.32-1.24 (m, 6H).

Step 5: To a stirring solution of compound 17 (20 mg, 0.24 mmol) in acetonitrile (5 mL) was added sodium triacetoxyborohydride (20 mg, 0.96 mmol) and formaldehyde (30 wt. %, 7 mg, 0.72 mmol). The reaction mixture was stirred at room temperature for 2 hours. LCMS indicated the product was formed. The reaction mixture was purified directly by reversed phase preparative HPLC to give compound 18 (10 mg, 51% yield) as white solid. ESI-MS (m/z): 808.4 $[M+H]^+$; $^1H$ NMR (500 MHz, DMSO-d6) δ 12.90-12.60 (m, 2H), 8.19 (s, 1H), 7.97 (s, 1H), 7.91 (s, 1H), 7.63 (s, 1H), 7.58 (s, 1H), 7.36-7.27 (m, 4H), 6.57 (s, 1H), 6.46 (s, 1H), 4.75-4.70 (m, 1H), 4.62-4.48 (m, 5H), 4.43-4.37 (m, 1H), 4.36-4.29 (m, 1H), 4.25-4.20 (m, 1H), 4.15-4.03 (m, 2H), 2.23 (t, J=6.9 Hz, 2H), 2.11 (s, 3H), 2.06 (s, 3H), 2.04-1.97 (m, 8H), 1.94-1.87 (m, 2H), 1.77-1.68 (m, 2H), 1.33-1.26 (m, 6H).

Example 19: (S)-3-(3-(5-carbamoyl-2-(1-ethyl-3-methyl-1H-pyrazole-5-carboxamido)-7-(2-methoxyethoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

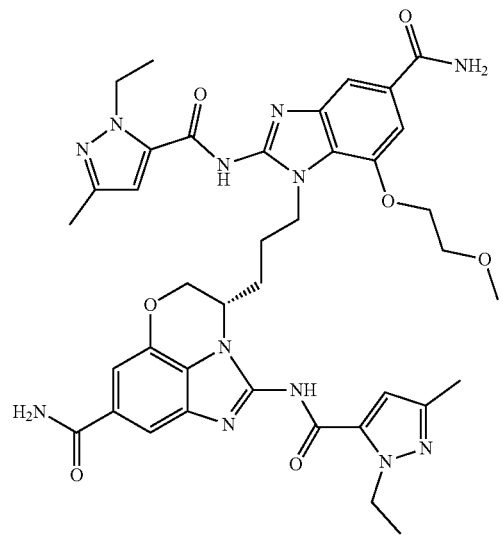 [SMILES: CCn1nc(C)cc1C(=O)Nc1nc2cc(C(N)=O)cc(OCCOC)c2n1CCC[C@H]1COc2cc(C(N)=O)cc3nc(NC(=O)c4cc(C)nn4CC)n1c23]

Synthetic Scheme

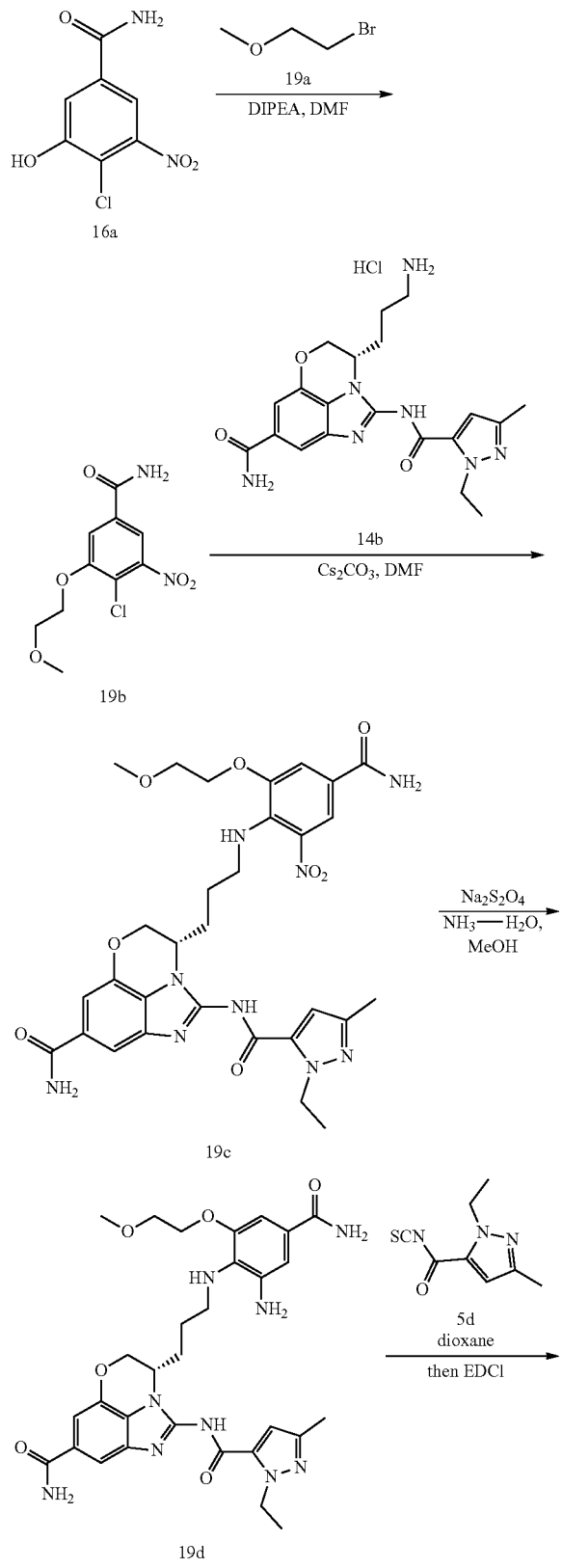

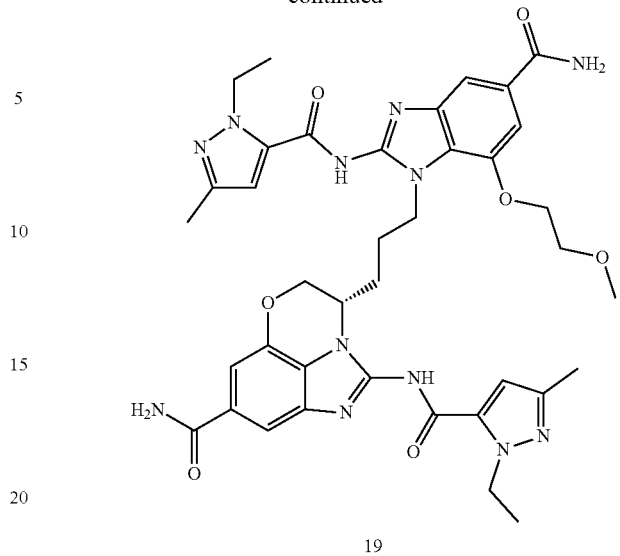

Step 1: To a stirring solution of compound 16a (250 mg, 1.15 mmol) and compound 19a (320 mg, 2.30 mmol) in DMF (5 mL) was added DIPEA (746 mg, 5.77 mmol). The reaction mixture was heated at 80° C.; overnight, and TLC indicated the starting material was consumed. The reaction mixture was allowed to cool to room temperature, diluted with water (10 mL), extracted with EtOAc (20 mL). The aqueous layer was extracted with EtOAc (20 mL×2). The combined organic layers were washed with brine, dried over $Na_2SO_4$, filtered and concentrated. The residue was purified by silica gel chromatography to give compound 19b (200 mg, 63% yield). ESI-MS (m/z): 275.6 $[M+H]^+$.

Step 2: To a stirring solution of compound 19b (200 mg, 0.73 mmol) and compound 14b (500 mg, 1.22 mmol) in DMF (10 mL) was added $Cs_2CO_3$ (1.58 g, 4.86 mmol). The reaction mixture was heated at 80° C.; overnight, and TLC indicated the starting material was consumed. The reaction mixture was filtered through a pad of celite, the filtrate was diluted with water (10 mL), extracted with EtOAc (20 mL). The aqueous layer was extracted with EtOAc (20 mL×2). The combined organic layers were washed with brine, dried over $Na_2SO_4$, filtered and concentrated. The residue was purified by silica gel chromatography to give compound 19c (203 mg, 26% yield) as yellow solid. ESI-MS (m/z): 650.2 $[M+H]^+$.

Step 3: Compound 19c (203 mg, 0.31 mmol) was dissolved in a mixture of MeOH (20 mL) and concentrated ammonium hydroxide (5 mL). Sodium dithionite (500 mg, 31.67 mmol) was dissolved in water (2 mL) and added to the reaction mixture at room temperature. Stirring was continued at room temperature for 30 minutes, and LCMS indicated the product was formed. The reaction mixture was filtered through a pad of celite, and the filtrate was concentrated. The residue was purified by silica gel chromatography to give compound 19d (110 mg, 57% yield). ESI-MS (m/z): 620.2 $[M+H]^+$.

Step 4: Compound 19d (110 mg, 0.18 mmol) was dissolved in dioxane (2 mL), and then compound 5d (0.4M in dioxane, 0.45 mL, 0.18 mmol) was added. The reaction mixture was stirred at room temperature for 1 hour, EDCI (102 mg, 0.53 mmol) was added, and the mixture was heated at 80° C. for 6 hours, LCMS indicated the product was formed. The reaction mixture was concentrated, and the residue was purified by reversed phase preparative HPLC to give compound 19 (25 mg, 18% yield). ESI-MS (m/z): 781.4 [M+H]+; 1H NMR (500 MHz, DMSO-d6) δ 12.71 (br s, 2H), 8.29 (s, 1H), 7.95 (s, 1H), 7.92 (s, 1H), 7.65 (s, 1H), 7.59 (s, 1H), 7.40-7.27 (m, 4H), 6.56 (s, 1H), 6.48 (s, 1H), 4.78-4.71 (m, 1H), 4.65-4.59 (m, 1H), 4.58-4.48 (m, 4H), 4.45-4.36 (m, 1H), 4.36-4.29 (m, 1H), 4.28-4.18 (m, 3H), 3.60-3.53 (m, 3H), 3.12 (s, 3H), 2.10 (s, 3H), 2.06 (s, 3H), 2.04-1.96 (m, 2H), 1.95-1.86 (m, 2H), 1.28 (t, J=7.1 Hz, 6H).

Example 20: (S)-3-(3-(5-carbamoyl-7-(3-(2-(dimethylamino)acetamido)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

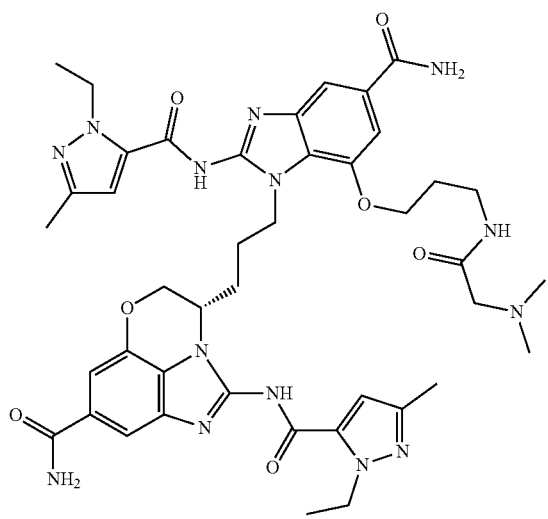 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4cc(C)nn4CC)n1c23]

Synthetic Scheme

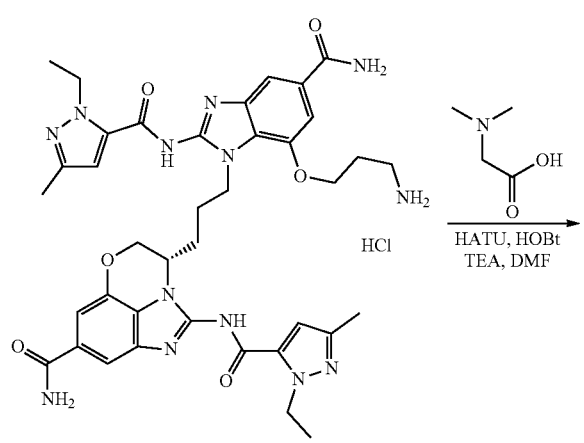

14

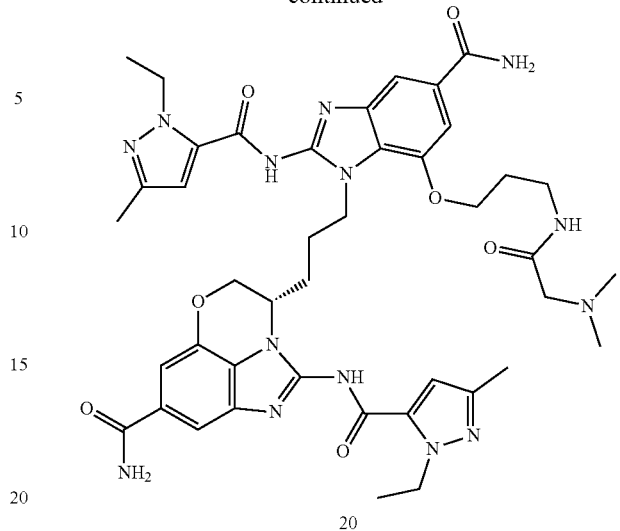

20

Step 1: To a solution of 14 (100 mg, 0.13 mmol) and N,N-dimethyl glycine (13 mg, 0.13 mmol) in DMF (2 mL) was added HATU (49 mg, 0.13 mmol), HOBt (17 mg, 0.13 mmol) and trimethylamine (13 mg, 0.13 mmol). The reaction mixture was stirred at room temperature for 6 hours. LCMS indicated the product was formed. The reaction mixture was purified directly by reversed phase preparative HPLC to give compound 20 (42 mg, 38% yield). ESI-MS (m/z): 865.4 [M+H]+; 1H NMR (500 MHz, DMSO-d6) δ13.00-12.56 (m, 2H), 8.15 (s, 1H), 7.99-7.90 (m, 3H), 7.64 (s, 1H), 7.58 (s, 1H), 7.36-7.29 (m, 4H), 6.54 (s, 1H), 6.46 (s, 1H), 4.76-4.70 (m, 1H), 4.64-4.58 (m, 1H), 4.58-4.49 (m, 4H), 4.45-4.33 (m, 2H), 4.25-4.20 (m, 1H), 4.14-4.06 (m, 2H), 3.22-3.19 (m, 2H), 2.99 (s, 2H), 2.26 (s, 6H), 2.09 (s, 3H), 2.06 (s, 3H), 2.05-2.00 (m, 2H), 1.98-1.91 (m, 2H), 1.84-1.79 (m, 2H), 1.30-1.25 (m, 6H).

Example 21: (S)-3-(3-(5-carbamoyl-2-(1-ethyl-3-methyl-1H-pyrazole-5-carboxamido)-7-(3-(2-morpholino acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

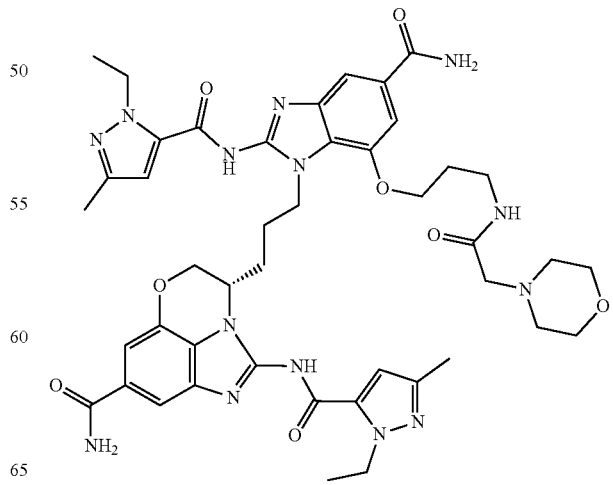

Synthetic Scheme

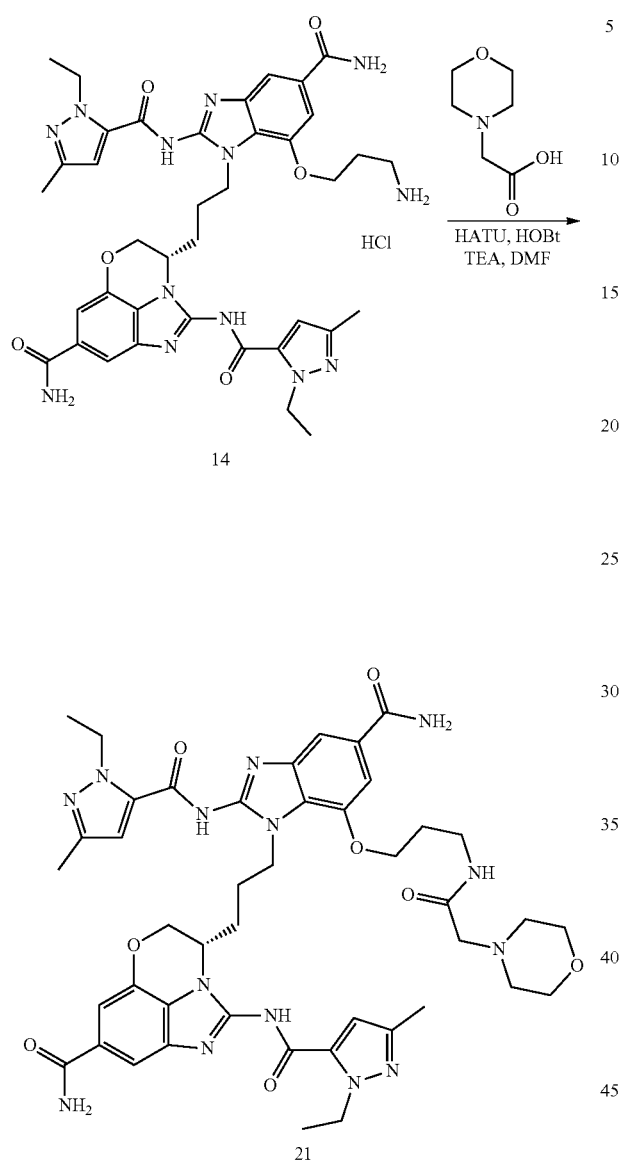

Step 1: To a solution of 14 (100 mg, 0.13 mmol) and 2-morpholinoacetic acid (19 mg, 0.13 mmol) in DMF (2 mL) was added HATU (49 mg, 0.13 mmol), HOBt (17 mg, 0.13 mmol) and trimethylamine (13 mg, 0.13 mmol). The reaction mixture was stirred at room temperature for 6 hours. LCMS indicated the product was formed. The reaction mixture was purified directly by reversed phase preparative HPLC to give compound 21 (32 mg, 28% yield). ESI-MS (m/z): 907.6 [M+H]$^+$; $^1$H NMR (500 MHz, DMSO-d6) δ 12.81 (s, 1H), 12.67 (br s, 1H), 8.14 (s, 1H), 7.96 (s, 1H), 7.91 (s, 1H), 7.81 (s, 1H), 7.63 (s, 1H), 7.58 (s, 1H), 7.37-7.28 (m, 4H), 6.54 (s, 1H), 6.45 (s, 1H), 4.76-4.70 (m, 1H), 4.65-4.60 (m, 1H), 4.59-4.49 (m, 4H), 4.45-4.33 (m, 2H), 4.25-4.20 (m, 1H), 4.14-4.04 (m, 2H), 3.54 (t, J=4.6 Hz, 4H), 3.23-3.18 (m, 2H), 2.90-2.80 (m, 2H), 2.45-2.32 (m, 4H), 2.09 (s, 3H), 2.05 (s, 3H), 2.04-1.99 (m, 2H), 1.98-1.91 (m, 2H), 1.85-1.78 (m, 2H), 1.31-1.25 (m, 6H).

Example 22: (S)-3-(3-(7-(3-acetamidopropoxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-k, 3,4-dihydro-5-oxa-1,2a-diazaacenaphthylene-7-carboxamide

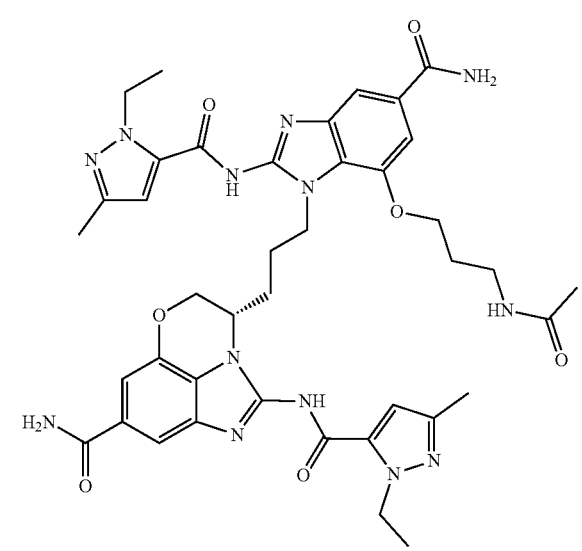 [SMILES: CCn1nc(C)cc1C(=O)Nc1nc2cc(C(N)=O)cc(OCCCNC(C)=O)c2n1CCC[C@H]1COc2cc(C(N)=O)cc3nc(NC(=O)c4cc(C)nn4CC)n1c23]

Synthetic Scheme

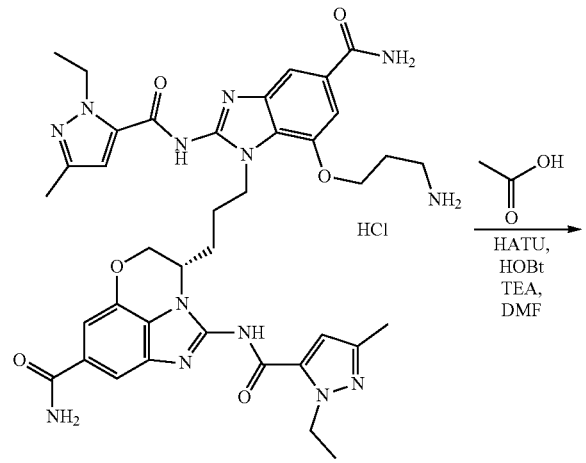

-continued

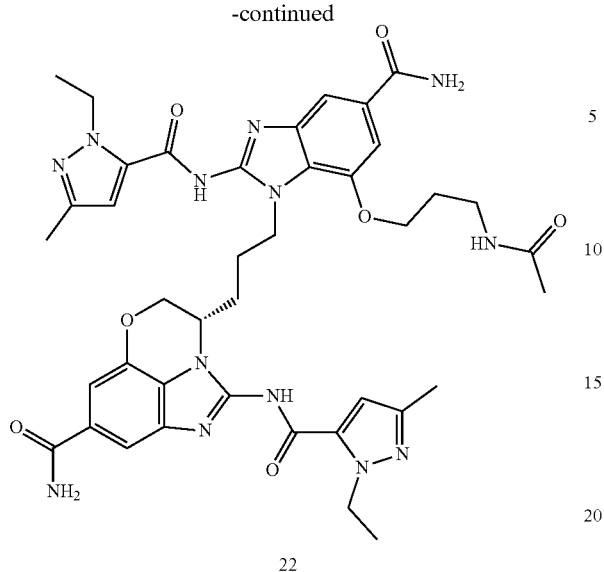

22

Step 1: To a solution of 14 (100 mg, 0.13 mmol) and HOAc (8 mg, 0.13 mg) in DMF (2 mL) was added HATU (49 mg, 0.13 mmol), HOBt (17 mg, 0.13 mmol) and trimethylamine (13 mg, 0.13 mmol). The reaction mixture was stirred at room temperature for 6 hours. LCMS indicated the product was formed. The reaction mixture was purified directly by reversed phase preparative HPLC to give compound 22 (36 mg, 34% yield). ESI-MS (m/z): 822.3 [M+H]$^+$; $^1$H NMR (500 MHz, DMSO-d6) δ 12.90-12.60 (m, 2H), 8.25 (s, 1H), 7.98 (s, 1H), 7.92 (s, 1H), 7.85 (s, 1H), 7.64 (s, 1H), 7.58 (s, 1H), 7.38-7.28 (m, 4H), 6.54 (s, 1H), 6.46 (s, 1H), 4.76-4.72 (m, 1H), 4.65-4.60 (m, 1H), 4.59-4.48 (m, 4H), 4.45-4.31 (m, 2H), 4.26-4.20 (m, 1H), 4.16-4.05 (m, 2H), 3.18-3.10 (m, 2H), 2.09 (s, 3H), 2.06 (s, 3H), 2.05-1.98 (m, 2H), 1.98-1.89 (m, 2H), 1.82-1.75 (m, 2H), 1.75 (s, 3H), 1.32-1.24 (m, 6H).

Example 23: (S)-3-(3-(5-carbamoyl-2-(1-ethyl-3-methyl-1H-pyrazole-5-carboxamido)-7-(4-(methylamino) butoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide Synthetic Scheme

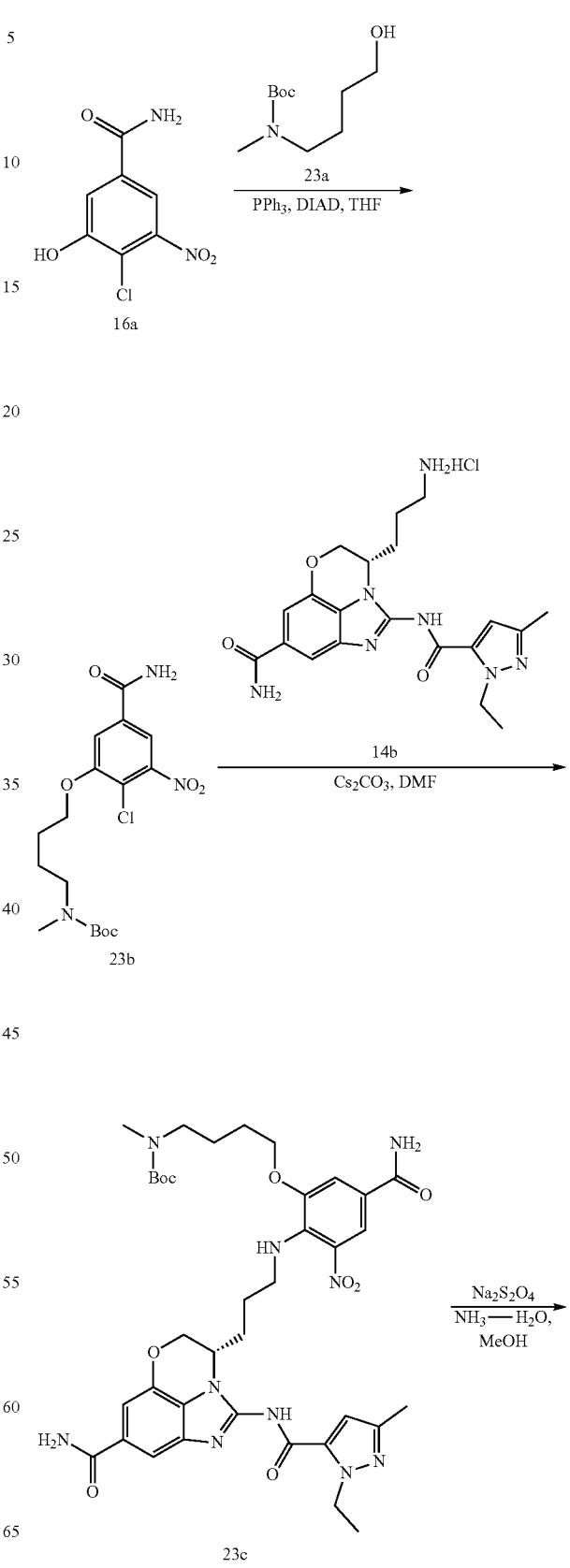

-continued

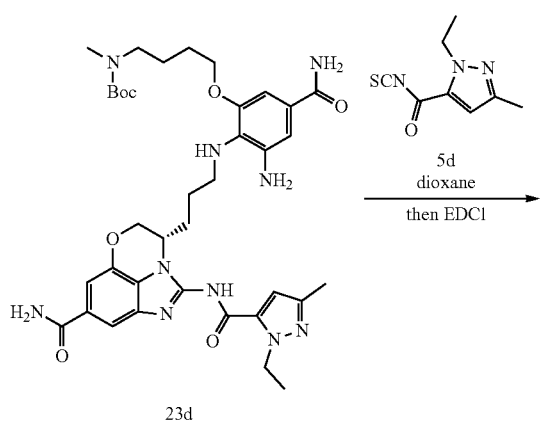

23d

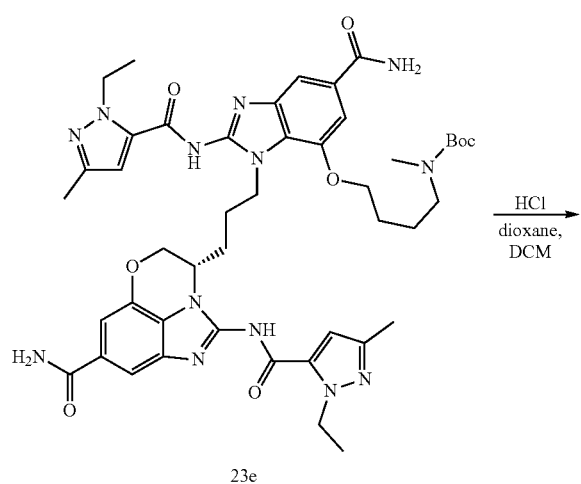

23e

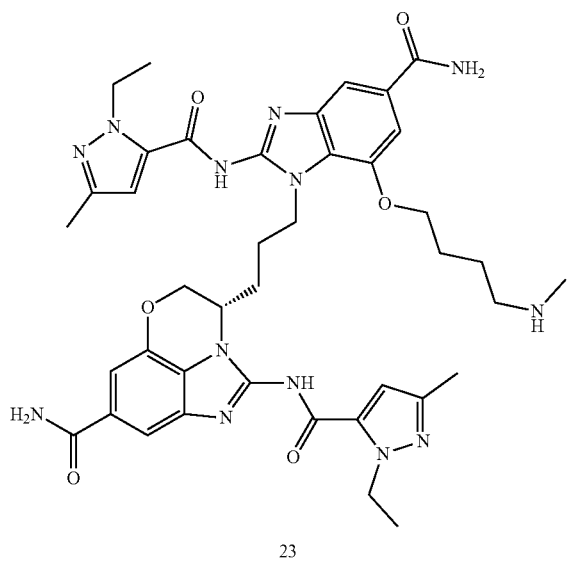

23

Step 1: To a stirred solution of Compound 16a (1.00 g, 4.62 mmol) and triphenylphosphine (1.82 g, 6.93 mmol) in THF (4 mL) at 0-10° C. under $N_2$ atmosphere was added DIAD (1.40 g, 6.93 mmol) dropwise. After stirring the solution for 10 minutes at 0-10° C., compound 23a (1.41 g, 6.93 mmol, dissolved in 2 mL THF) was added dropwise. The reaction mixture was warmed room temperature and stirred for 2 hours. TLC indicated the starting material was consumed. The reaction mixture was diluted with water (20 mL), and extracted with EtOAc (20 mL). The aqueous layer was extracted with EtOAc (20 mL×2). The combined organic layers were washed with brine, dried over $Na_2SO_4$, filtered and concentrated in vacuo. The residue was purified by silica gel chromatography to give compound 23b (1.40 g, 75% yield). ESI-MS (m/z): 402.3 $[M+H]^+$.

Step 2: To a stirring solution of compound 23b (600 mg, 1.49 mmol) and compound 14b (410 mg, 0.99 mmol) in DMF (10 mL) was added $Cs_2CO_3$ (1.30 g, 3.98 mmol). The reaction mixture was heated at 80° C.; overnight, and TLC indicated the starting material was consumed. The reaction mixture was filtered through a pad of celite, the filtrate was diluted with water (20 mL), extracted with EtOAc (20 mL). The aqueous layer was extracted with EtOAc (20 mL×2). The combined organic layers were washed with brine, dried over $Na_2SO_4$, filtered and concentrated. The residue was purified by silica gel chromatography to give compound 23c (420 mg, 54% yield). ESI-MS (m/z): 777.2 $[M+H]^+$.

Step 3: Compound 23c (420 mg, 0.54 mmol) was dissolved in a mixture of MeOH (20 mL) and concentrated ammonium hydroxide (7 mL). Sodium dithionite (940 mg, 5.41 mmol) was dissolved in water (2 mL) and added to the reaction mixture at room temperature. Stirring was continued at room temperature for 30 minutes, and LCMS indicated the product was formed. The reaction mixture was filtered through a pad of celite, and the filtrate was concentrated. The residue was purified by silica gel chromatography to give compound 23d (200 mg, 50% yield). ESI-MS (m/z): 748.2 $[M+H]^+$.

Step 4: Compound 23d (200 mg, 0.27 mmol) was dissolved in dioxane (4 mL), and then compound 5d (0.4M in dioxane, 0.68 mL, 0.27 mmol) was added. The reaction mixture was stirred at room temperature for 1 hour, EDCI (51 mg, 0.27 mmol) was added, and the mixture was heated at 80° C. for 6 hours, LCMS indicated the product was formed. The reaction mixture was concentrated, and the residue was purified by silica gel chromatography to give compound 23e (200 mg, 82% yield). ESI-MS (m/z): 908.4 $[M+H]^+$.

Step 5: To a stirring solution of 23e (200 mg, 0.22 mmol) in DCM (10 mL) at 0° C.; was added 4M HCl in dioxane (2 mL, 8.00 mmol). The mixture was stirred at 0° C.; for 1 hour, then concentrated. The residue was purified by reversed phase preparative HPLC to give compound 23 (40 mg, 22% yield). ESI-MS (m/z): 808.4 $[M+H]^+$; $^1H$ NMR (500 MHz, DMSO-d6) δ 8.39 (s, 2H), 8.00 (br s, 2H), 7.64 (s, 1H), 7.60 (s, 1H), 7.39-7.28 (m, 4H), 6.57 (s, 1H), 6.45 (s, 1H), 4.76-4.71 (m, 1H), 4.64-4.50 (m, 4H), 4.40-4.29 (m, 2H), 4.24-4.20 (m, 1H), 4.14-4.03 (m, 2H), 2.68-2.60 (m, 2H), 2.41 (s, 3H), 2.11 (s, 3H), 2.06 (s, 3H), 2.02-1.96 (m, 2H), 1.94-1.87 (m, 2H), 1.68-1.57 (m, 4H), 1.33-1.24 (m, 6H).

Example 24: (S)-3-(3-(5-carbamoyl-2-(1-ethyl-3-methyl-1H-pyrazole-5-carboxamido)-7-(3-morpholinopr opoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide
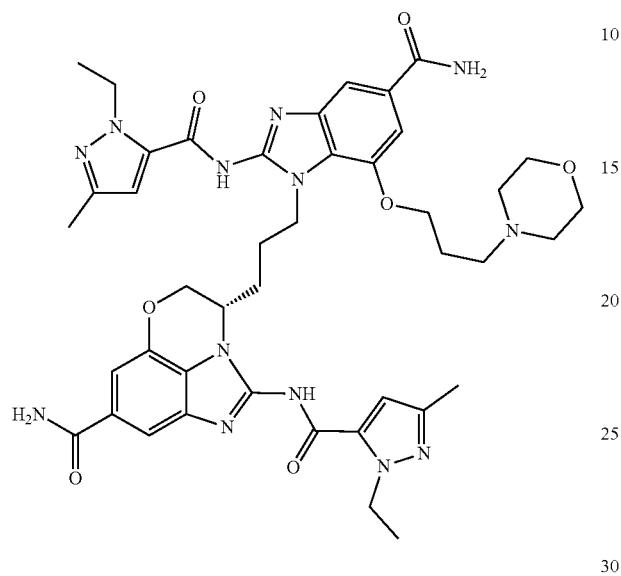
Synthetic Scheme
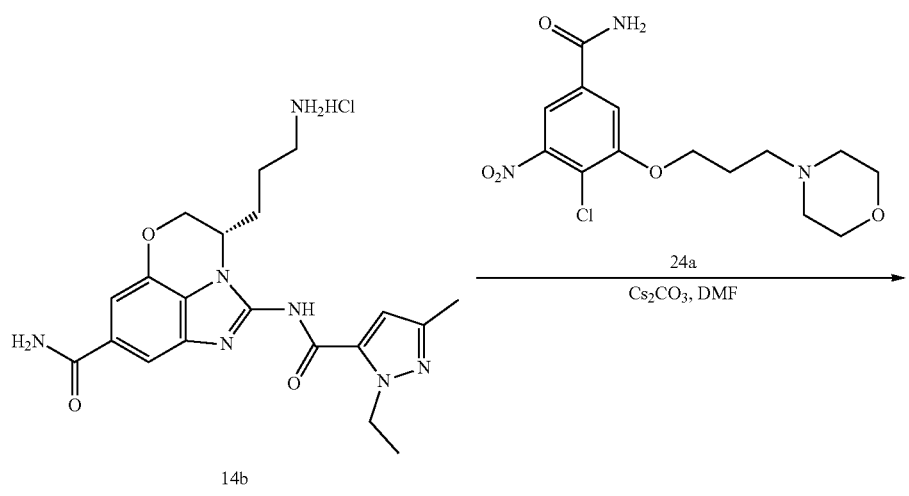

-continued
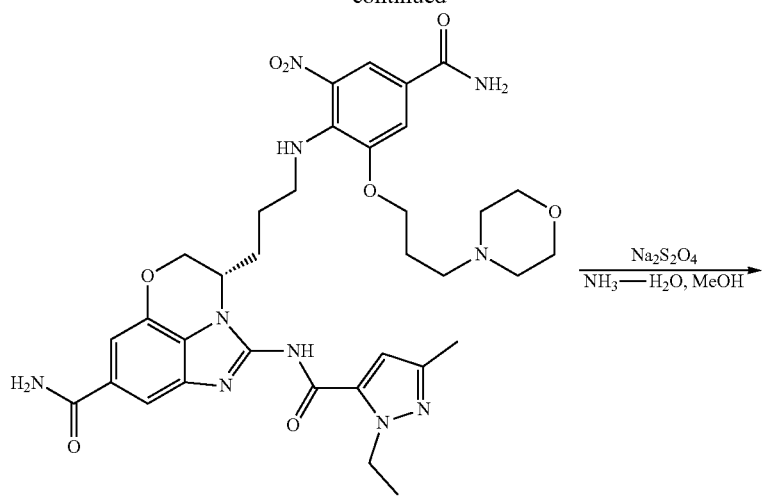
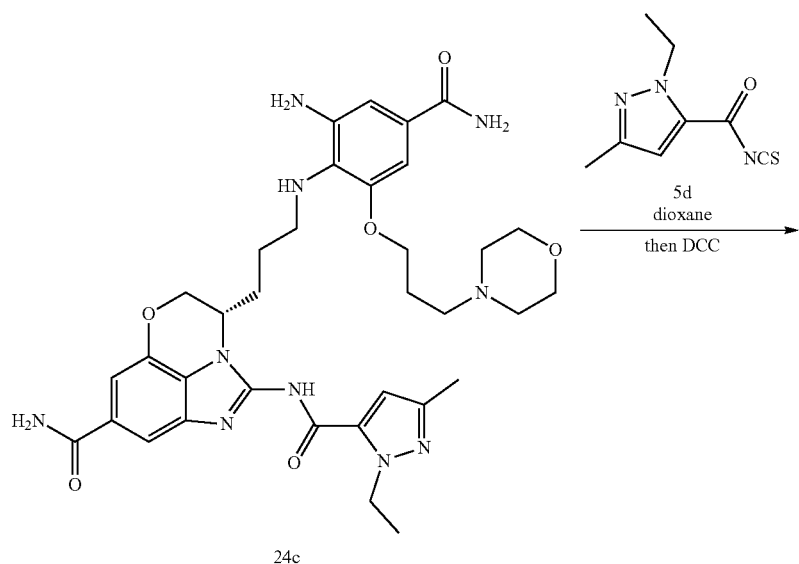
24c
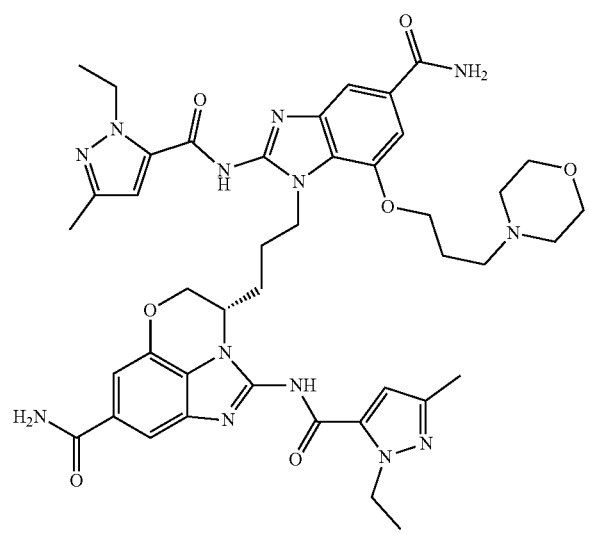
24

Step 1: To a stirring solution of compound 14b (450 mg, 1.00 mmol) and compound 24a (514 mg, 1.5 mmol) in DMF (5 mL) was added Cs₂CO₃ (650 mg, 2 mmol). The reaction mixture was heated at 70° C.; overnight, and LCMS indicated the product was formed. The reaction mixture was diluted with water (100 mL), extracted with EtOAc (100 mL×3). The combined organic layers were dried over Na₂SO₄, filtered and concentrated. The residue was purified by silica gel chromatography to give compound 24b (270 mg, 38% yield) as a white solid. ESI-MS (m/z): 719.7 [M+H]⁺.

Step 2: Compound 24b (230 mg, 0.30 mmol) was dissolved in a mixture of MeOH (20 mL) and concentrated ammonium hydroxide (3 mL). Sodium dithionite (260 mg, 1.50 mmol) was dissolved in water (4 mL) and added dropwise to the reaction mixture at room temperature. Stirring was continued at room temperature for 30 minutes, and LCMS indicated the product was formed. The reaction mixture was diluted with water (80 mL), and extracted with EtOAc (100 mL×3). The combined organic layers were dried over Na₂SO₄, filtered and concentrated to give compound 24c (160 mg, 73% yield) as a white solid. ESI-MS (m/z): 689.6 [M+H]⁺.

Step 3: Compound 24c (160 mg, 0.23 mmol) was dissolved in DMF (3 mL), and then compound 5d (0.4 M in dioxane, 0.6 mL, 0.24 mmol) was added. The reaction mixture was stirred at room temperature for 30 minutes, DCC (100 mg, 0.5 mmol) was added, and the mixture was heated at 80° C.; overnight, LCMS indicated the product was formed. The reaction mixture was purified directly by reversed phase preparative HPLC to give compound 24 (51 mg, 26% yield) as a white solid. ESI-MS (m/z): 850.3 [M+H]⁺; ¹HNMR (500 MHz, DMSO-d6) δ12.82 (br s, 1H), 12.70 (br s, 1H), 8.20 (s, 1H), 7.97 (s, 1H), 7.92 (s, 1H), 7.64 (s, 1H), 7.60 (s, 1H), 7.36-7.25 (m, 4H), 6.59 (s, 1H), 6.46 (s, 1H), 4.77-4.70 (m, 1H), 4.63-4.50 (m, 5H), 4.44-4.31 (m, 2H), 4.26-4.20 (m, 1H), 4.16-4.10 (m, 1H), 4.09-4.03 (m, 1H), 3.47 (t, J=4.6 Hz, 4H), 2.29 (t, J=7.1 Hz, 2H), 2.23-2.15 (m, 4H), 2.12 (s, 3H), 2.07 (s, 3H), 2.04-1.98 (m, 2H), 1.95-1.89 (m, 2H), 1.79-1.71 (m, 2H), 1.35-1.25 (m, 6H).

Example 25: (S)-3-(3-(5-carbamoyl-2-(1-ethyl-3-methyl-1H-pyrazole-5-carboxamido)-7-(2-(2-methoxyethoxy)ethoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

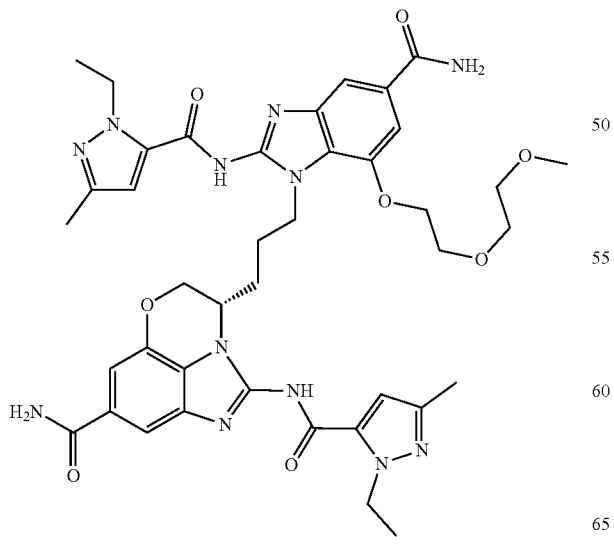

Synthetic Scheme

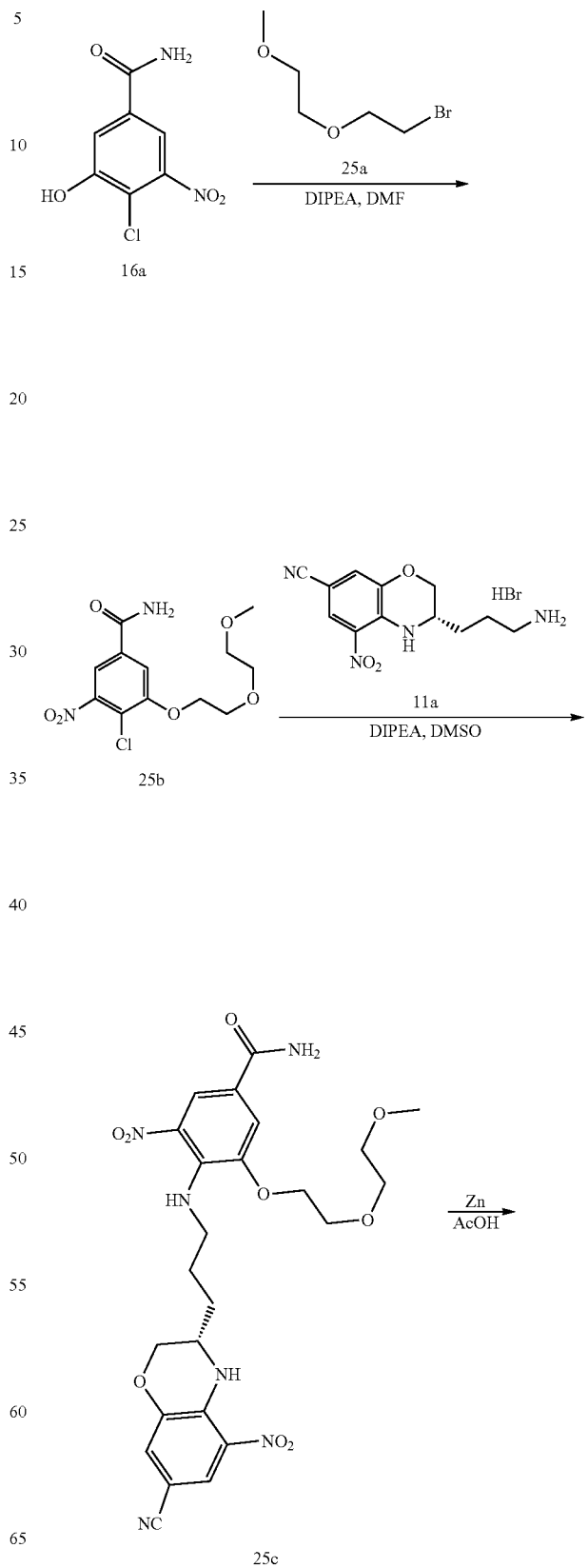

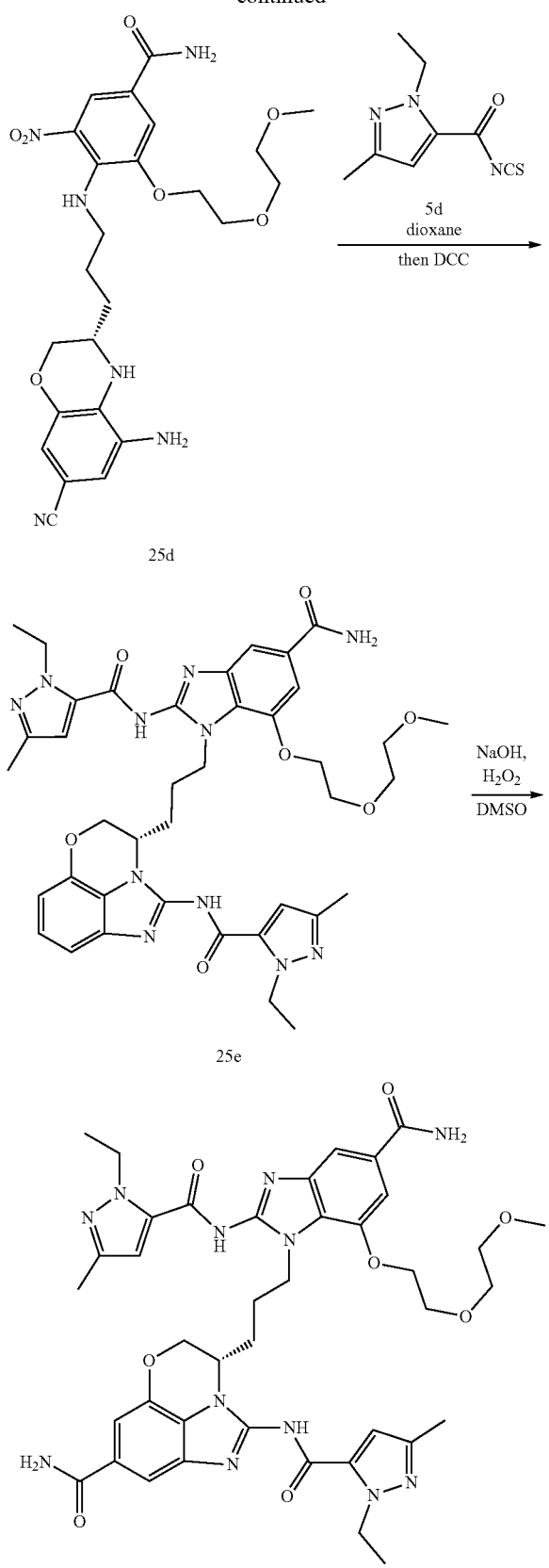

Step 1: To a stirring solution of compound 16a (500 mg, 2.31 mmol) and compound 25a (845 mg, 4.62 mmol) in DMF (10 mL) was added DIPEA (1.49 g, 11.54 mmol). The reaction mixture was heated at 100° C.; overnight, and LCMS indicated the starting material 16a was consumed. The reaction mixture was cooled to room temperature, diluted with water (20 mL), extracted with EtOAc (20 mL×3). The combined organic layers were washed with brine, dried over $Na_2SO_4$, filtered and concentrated. The residue was purified by silica gel chromatography to give compound 25b (700 mg, 95% yield) as yellow solid. ESI-MS (m/z): 319.4 [M+H]$^+$.

Step 2: To a stirring solution of compound ha (830 mg, 2.42 mmol) and compound 25b (700 mg, 2.20 mmol) in DMSO (10 mL) was added DIPEA (1.42 g, 10.98 mmol). The reaction mixture was heated at 120° C.; overnight, and LCMS indicated the starting materials were consumed. The reaction mixture was cooled to room temperature, diluted with water (20 mL), extracted with EtOAc (20 mL). The aqueous layer was extracted with EtOAc (20 mL×3). The combined organic layers were washed with brine, dried over $Na_2SO_4$, filtered and concentrated. The residue was purified by silica gel chromatography to give compound 25c (730 mg, 61% yield) as red solid. ESI-MS (m/z): 545.2[M+H]$^+$.

Step 3: Compound 25c (730 mg, 1.34 mmol) was dissolved in acetic acid (10 mL), and Zn powder (483 mg, 6.70 mmol) was added by portions at room temperature. The reaction mixture was stirred at room temperature for 30 minutes, LCMS indicated the product was formed. The mixture was filtered through a pad of celite, the filtrate was concentrated and the residue was purified by silica gel chromatography to give the compound 25d (270 mg, 42% yield) as white solid. ESI-MS (m/z): 485.4 [M+H]$^+$.

Step 4: Compound 25d (270 mg, 0.56 mmol) was dissolved in dioxane (5 mL), and then compound 5d (0.4 M in dioxane, 3 mL, 1.20 mmol) was added. The reaction mixture was stirred at room temperature for 30 minutes, EDCI (267 mg, 1.39 mmol) was added, and the mixture was heated at 80° C. for 2 hours, LCMS indicated the product was formed. The reaction mixture was concentrated to give the crude compound 25e (450 mg) as brown oil, which was used directly without further purification. ESI-MS (m/z): 807.5 [M+H]$^+$.

Step 5: To a stirring solution of crude compound 25e (450 mg, from step 4) in DMSO (6 mL) at room temperature was added solid NaOH (67 mg, 1.67 mmol), followed by the addition of hydrogen peroxide (30 wt. %, 1.5 mL). The reaction was stirred at room temperature for 30 minutes, LCMS indicated the reaction was complete. The mixture was purified directly by reversed phase preparative HPLC to give compound 25 (149 mg, 32% yield for 2 steps) as white solid. ESI-MS (m/z): 825.6 [M+H]$^+$; $^1$H NMR (500 MHz, DMSO-d6) δ 12.76 (br s, 2H), 7.95 (s, 1H), 7.92 (s, 1H), 7.65 (s, 1H), 7.59 (s, 1H), 7.40-7.28 (m, 4H), 6.57 (s, 1H), 6.50 (s, 1H), 4.78-4.72 (m, 1H), 4.64-4.51 (m, 5H), 4.48-4.39 (m, 1H), 4.38-4.30 (m, 1H), 4.27-4.18 (m, 3H), 3.67-3.60 (m, 2H), 3.41-3.37 (m, 2H), 3.31-3.28 (m, 2H), 3.12 (s, 3H), 2.10 (s, 3H), 2.07 (s, 3H), 2.05-1.99 (m, 2H), 1.96-1.86 (m, 2H), 1.34-1.26 (m, 6H).

Example 26: (S)-2-(1-ethyl-3-methyl-1H-pyrazole-5-carboxamido)-1-(3-(2-(1-ethyl-3-methyl-1H-pyrazole-5-carboxamido)-7-(2H-tetrazol-5-yl)-3,4-dihydro-5-oxa-1,2a-diazaacenaphthylen-3-yl)propyl)-7-(3-methoxypropoxy)-1H-benzo[d]imidazole-5-carboxamide

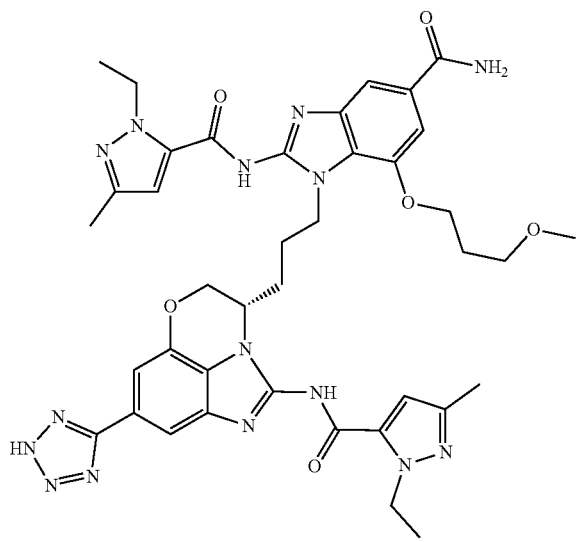 [SMILES: CCn1nc(C)cc1C(=O)Nc1nc2cc(C(N)=O)cc(OCCCOC)c2n1CCC[C@H]1COc2cc(-c3nn[nH]n3)cc3nc(NC(=O)c4cc(C)nn4CC)n1c23]

Synthetic Scheme

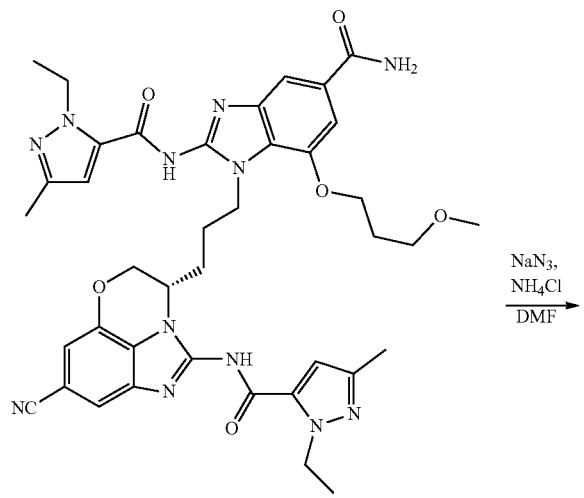

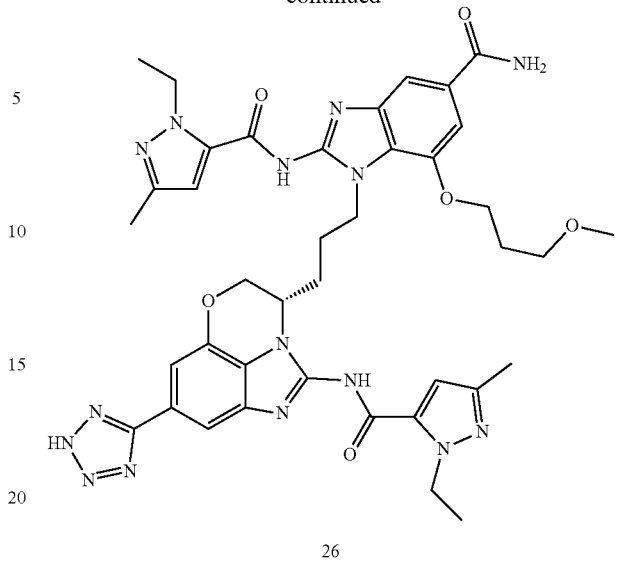

26

Step 1: To a solution of compound 11 (30 mg, 0.039 mmol) in DMF (5 mL) was added sodium azide (24 mg, 0.37 mmol) and ammonium chloride (20 mg, 0.37 mmol). The mixture was heated at 100° C. overnight. LCMS indicated the product was formed. The reaction mixture was cooled to room temperature, and purified directly by reversed phase preparative HPLC to give compound 26 (9 mg, 30% yield) as a white solid. ESI-MS (m/z): 819.2 [M+H]$^+$; $^1$H NMR (500 Hz, DMSO-d6) δ 12.82 (s, 1H), 12.78 (s, 1H), 7.99 (s, 1H), 7.75 (s, 1H), 7.64 (s, 1H), 7.44 (s, 1H), 7.34 (br s, 2H), 6.57 (s, 1H), 6.49 (s, 1H), 4.80-4.73 (m, 1H), 4.67-6.63 (m, 1H), 4.61-4.52 (m, 4H), 4.47-4.27 (m, 3H), 4.19-4.08 (m, 2H), 3.12 (s, 3H), 2.10 (s, 3H), 2.08 (s, 3H), 2.06-1.99 (m, 2H), 1.98-1.92 (m, 2H), 1.89-1.81 (m, 2H), 1.33-1.26 (m, 6H).

Example 27: (S)-3-(3-(5-carbamoyl-2-(1-ethyl-3-methyl-1H-pyrazole-5-carboxamido)-7-(3-(N-methylacetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

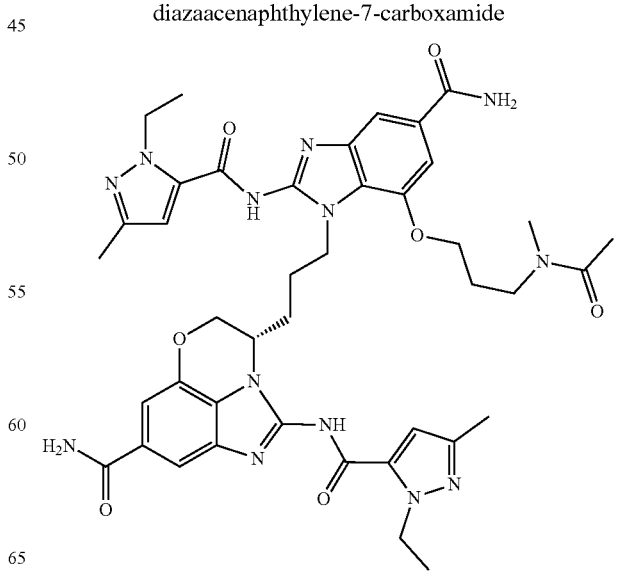

Synthetic Scheme

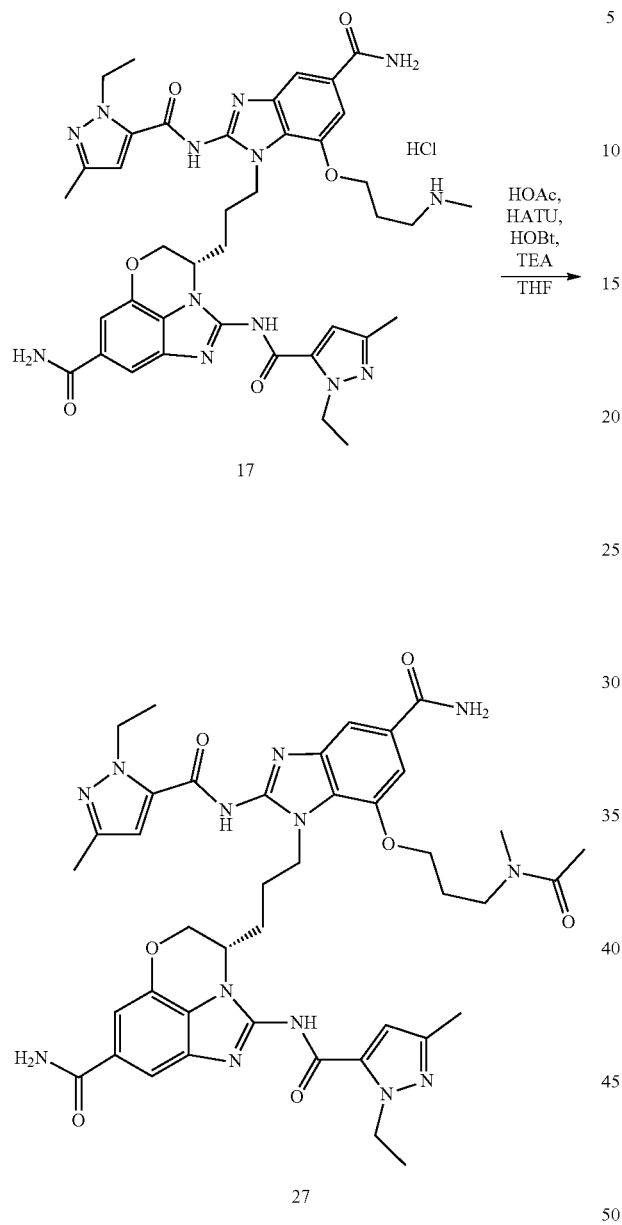

Example 28: (S)-3-(3-(5-carbamoyl-7-(3-(2-(dimethylamino)-N-methylacetamido)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

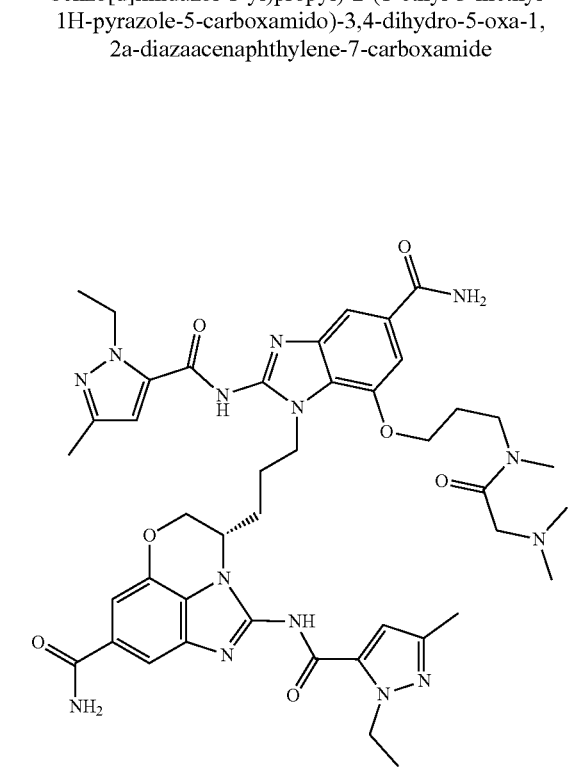

Synthetic Scheme

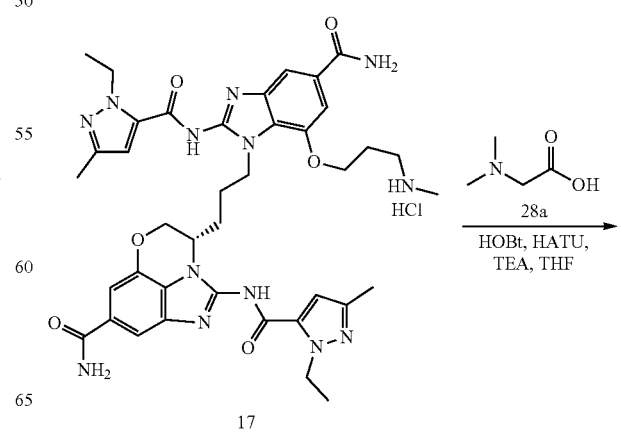

Step 1: To a solution of 17 (40 mg, 0.05 mmol) and HOAc (3 mg, 0.05 mmol) in THF (5 mL) was added HATU (24 mg, 0.06 mmol), HOBt (8 mg, 0.06 mmol) and trimethylamine (15 mg, 0.14 mmol). The reaction mixture was stirred at room temperature overnight. LCMS indicated the reaction was complete. The reaction mixture was purified directly by reversed phase preparative HPLC to give compound 27 (16 mg, 40% yield) as white solid. ESI-MS (m/z): 836.6 [M+H]$^+$; $^1$H NMR (500 MHz, DMSO-d6) δ12.82 (br s, 1H), 12.69 (br s, 1H), 8.00-7.86 (m, 2H), 7.68-7.54 (m, 2H), 7.37-7.26 (m, 4H), 6.58-6.54 (m, 1H), 6.47 (s, 0.3H), 6.43 (s, 0.7H), 4.78-4.67 (m, 1H), 4.63-4.49 (m, 5H), 4.45-4.30 (m, 2H), 4.24-4.18 (m, 1H), 4.14-3.97 (m, 2H), 3.28-3.22 (m, 2H), 2.77 (s, 1.9H), 2.66 (s, 1.1H), 2.11 (s, 3H), 2.08-1.88 (m, 7H), 1.86-1.70 (m, 5H), 1.32-1.25 (m, 6H).

-continued

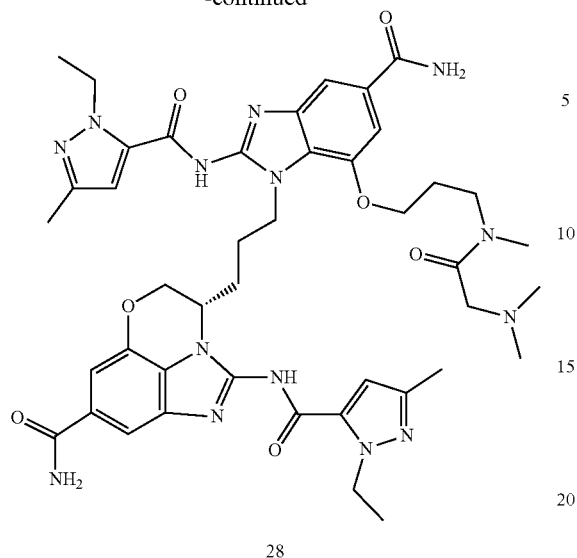

28

Step 1: To a solution of 17 (40 mg, 0.05 mmol) and 28a (6 mg, 0.06 mmol) in THF (5 mL) was added HATU (24 mg, 0.06 mmol), HOBt (8 mg, 0.06 mmol) and trimethylamine (15 mg, 0.14 mmol). The reaction mixture was stirred at room temperature overnight. LCMS indicated the reaction was complete. The reaction mixture was purified directly by reversed phase preparative HPLC to give compound 28 (16 mg, 38% yield) as a white solid. ESI-MS (m/z): 880.6 [M+H]$^+$; $^1$H NMR (500 MHz, DMSO-d6) δ 12.83 (br s, 1H), 12.68 (br s, 1H), 8.15 (s, 1H), 7.99-7.89 (m, 2H), 7.65-7.52 (m, 2H), 7.36-7.27 (m, 4H), 6.57 (br s, 1H), 6.48 (s, 0.3H), 6.44 (s, 0.7H), 4.76-4.67 (m, 1H), 4.64-4.49 (m, 5H), 4.46-4.31 (m, 2H), 4.25-4.18 (m, 1H), 4.14-3.99 (m, 2H), 2.82 (s, 2H), 2.68 (s, 1H), 2.30 (s, 4H), 2.17 (s, 2H), 2.14 (s, 2H), 2.11 (s, 3H), 2.06 (s, 1H), 2.04 (s, 2H), 2.03-1.97 (m, 1H), 1.96-1.85 (m, 3H), 1.82-1.75 (m, 1H), 1.32-1.25 (m, 6H).

Example 29: (S)-3-(3-(5-carbamoyl-2-(1-ethyl-3-methyl-1H-pyrazole-5-carboxamido)-7-(3-(N-methyl-2-morpholinoacetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

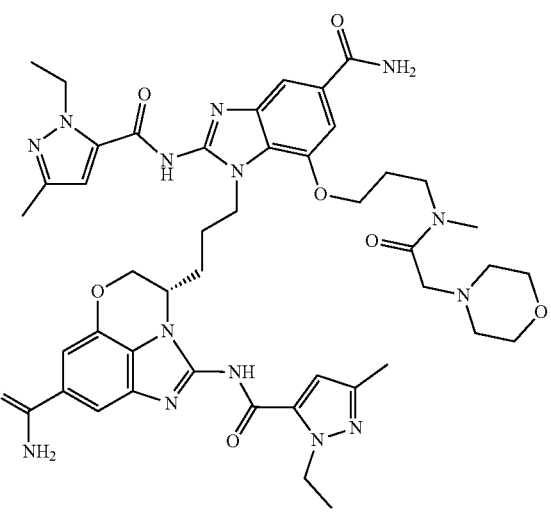

Synthetic Scheme

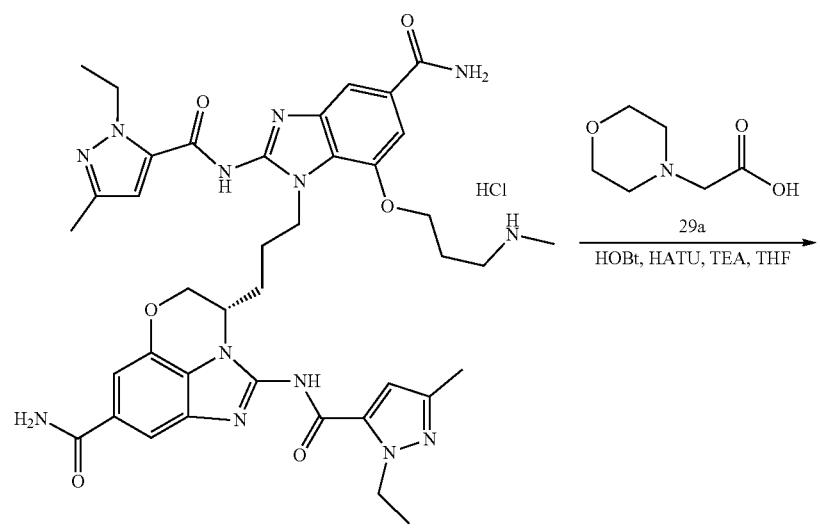

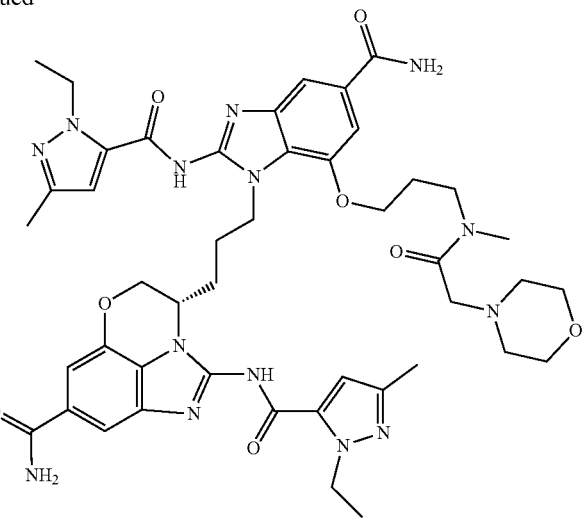

29

Step 1: To a solution of 17 (40 mg, 0.05 mmol) and 2-morpholinoacetic acid (8 mg, 0.06 mmol) in THF (5 mL) was added HATU (24 mg, 0.06 mmol), HOBt (8 mg, 0.06 mmol) and trimethylamine (15 mg, 0.14 mmol). The reaction mixture was stirred at room temperature overnight. LCMS indicated the reaction was complete. The reaction mixture was purified directly by reversed phase preparative HPLC to give compound 29 (17 mg, 39% yield) as white solid. ESI-MS (m/z): 921.6 [M+H]$^+$; $^1$H NMR (500 MHz, DMSO-d6) δ 12.82 (br s, 1H), 12.66 (br s, 1H), 8.15 (s, 1H), 7.98-7.89 (m, 2H), 7.65-7.61 (m, 1H), 7.59-7.56 (m, 1H), 7.40-7.26 (m, 4H), 6.56 (br s, 1H), 6.47 (s, 0.3H), 6.44 (s, 0.7H), 4.76-4.70 (m, 1H), 4.63-4.50 (m, 5H), 4.46-4.35 (m, 2H), 4.24-4.17 (m, 1H), 4.12-3.97 (m, 2H), 3.52-3.43 (m, 4H), 3.04-2.96 (m, 2H), 2.85 (s, 2H), 2.65 (s, 1H), 2.34 (br s, 3H), 2.27 (br s, 1H), 2.11 (s, 3H), 2.08-1.98 (m, 4H), 1.97-1.86 (m, 3H), 1.82-1.75 (m, 1H), 1.33-1.25 (m, 6H).

Example 30: (S)-3-(3-(5-carbamoyl-2-(1-ethyl-3-methyl-1H-pyrazole-5-carboxamido)-7-(3-(methylsulfonamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide Synthetic Scheme

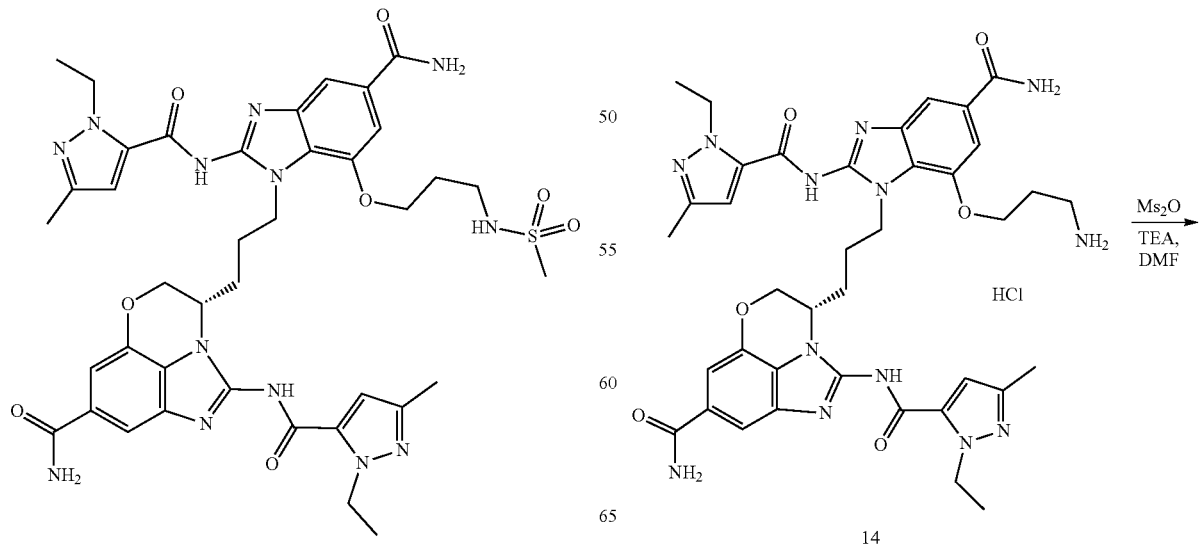

14

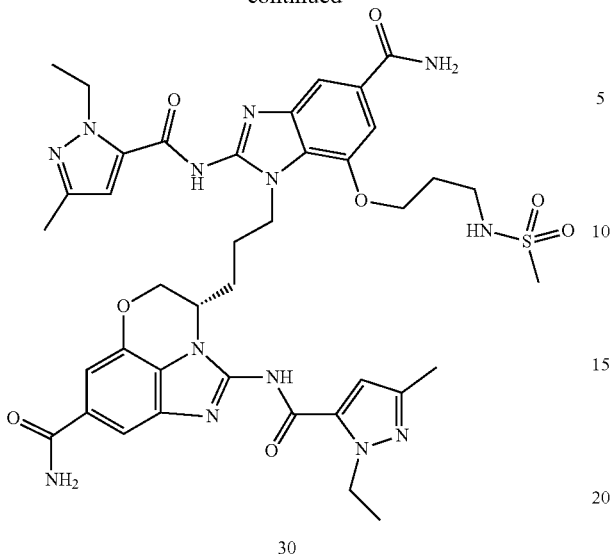

30

Step 1: To a solution of compound 14 (58 mg, 0.07 mmol) in DMF (2 mL) was added methanesulfonic anhydride (13 mg, 0.07 mmol), followed by triethylamine (23 mg, 0.23 mmol). The mixture was stirred at room temperature for 6 hours, LCMS indicated the reaction was complete. The reaction mixture was purified directly by reversed phase preparative HPLC to give compound 30 (17 mg, 27% yield). ESI-MS (m/z): 858.4 [M+H]$^+$; $^1$H NMR (500 MHz, DMSO-d6) δ 12.85-12.55 (m, 2H), 7.96 (s, 1H), 7.88 (s, 1H), 7.62 (s, 1H), 7.55 (s, 1H), 7.40-7.25 (m, 4H), 7.07 (t, J=5.9 Hz, 1H), 6.50 (s, 1H), 6.44 (s, 1H), 4.73-4.68 (m, 1H), 4.62-4.57 (m, 1H), 4.56-4.47 (m, 4H), 4.42-4.34 (m, 1H), 4.34-4.26 (m, 1H), 4.23-4.10 (m, 3H), 3.05-2.99 (m, 2H), 2.82 (s, 3H), 2.05 (s, 3H), 2.04 (s, 3H), 2.01-1.95 (m, 2H), 1.93-1.87 (m, 2H), 1.86-1.80 (m, 2H), 1.28-1.21 (m, 6H).

Example 31: (S)-3-(3-(6-carbamoyl-2-(1-ethyl-3-methyl-1H-pyrazole-5-carboxamido)-4-(3-(2-(piperazin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

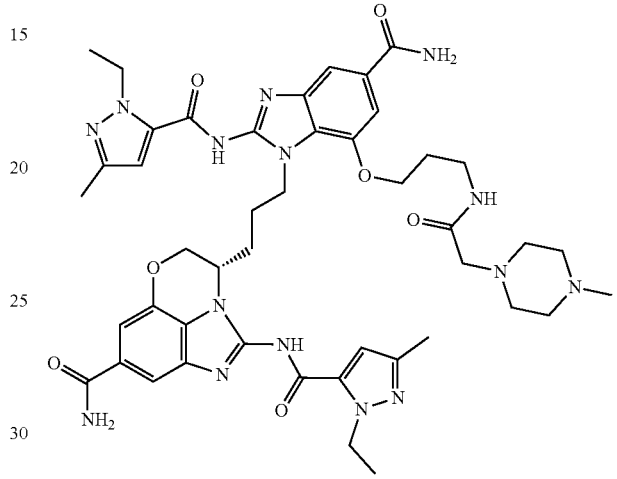

Synthetic Scheme

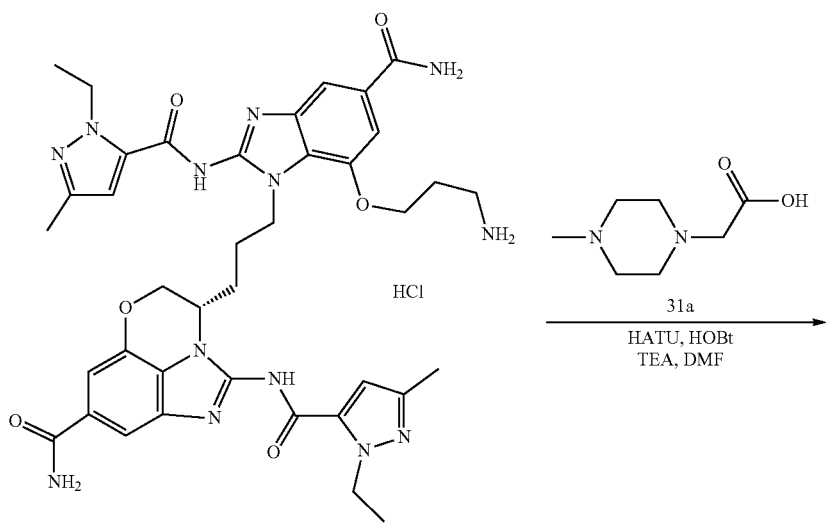

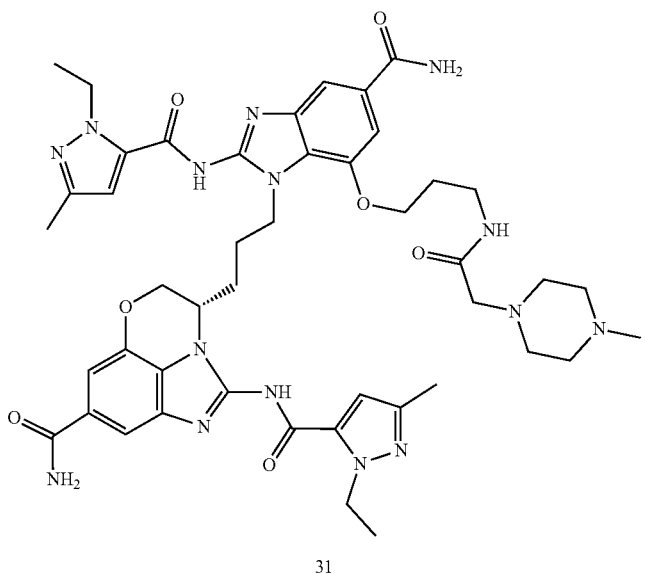

31

Step 1: To a solution of compound 14 (80 mg, 0.10 mmol) and compound 31a (17 mg, 0.11 mmol) in DMF (2 mL) was added HATU (41 mg, 0.11 mmol), HOBt (15 mg, 0.11 mmol) and trimethylamine (30 mg, 0.29 mmol). The reaction mixture was stirred at room temperature for 3 hours. LCMS indicated the reaction was complete. The reaction mixture was purified directly by reversed phase preparative HPLC to give compound 31 (13 mg, 14% yield) as white solid. ESI-MS (m/z): 920.3 [M+H]$^+$; $^1$H NMR (500 MHz, DMSO-d$_6$) δ 12.77 (br s, 1H), 12.64 (br s, 1H), 8.22 (s, 1H), 7.93 (s, 1H), 7.88 (s, 1H), 7.68 (t, J=6.0 Hz, 1H), 7.61 (s, 1H), 7.55 (s, 1H), 7.37-7.25 (m, 4H), 6.52 (s, 1H), 6.43 (s, 1H), 4.73-4.68 (m, 1H), 4.63-4.47 (m, 5H), 4.44-4.27 (m, 2H), 4.23-4.17 (m, 1H), 4.14-4.02 (m, 2H), 3.22-3.14 (m, 2H), 2.78 (s, 2H), 2.41-2.18 (m, 8H), 2.10-1.85 (m, 13H), 1.82-1.76 (m, 2H), 1.30-1.20 (m, 6H).

Example 32: (S)-3-(3-(6-carbamoyl-4-(3-(2-(1,1-dioxidothiomorpholino)acetamido)propoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

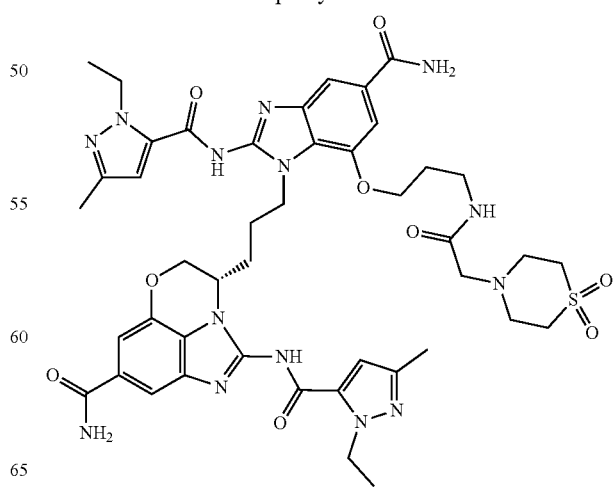

Synthetic Scheme
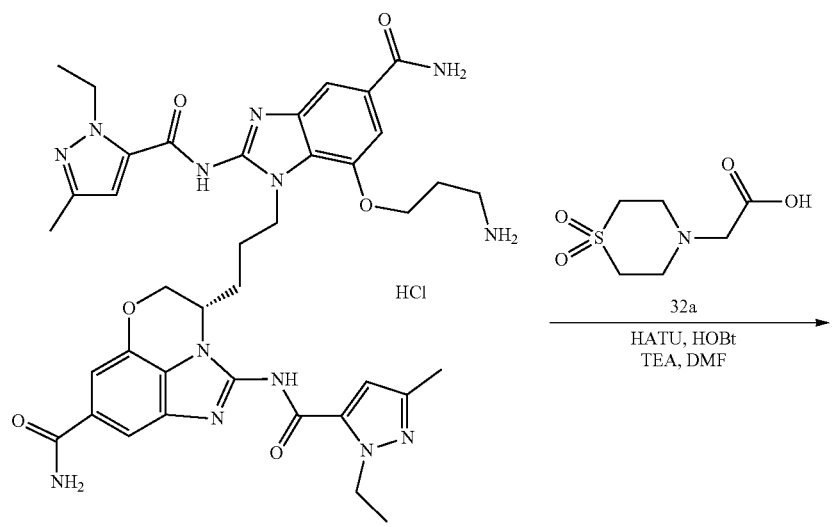
14
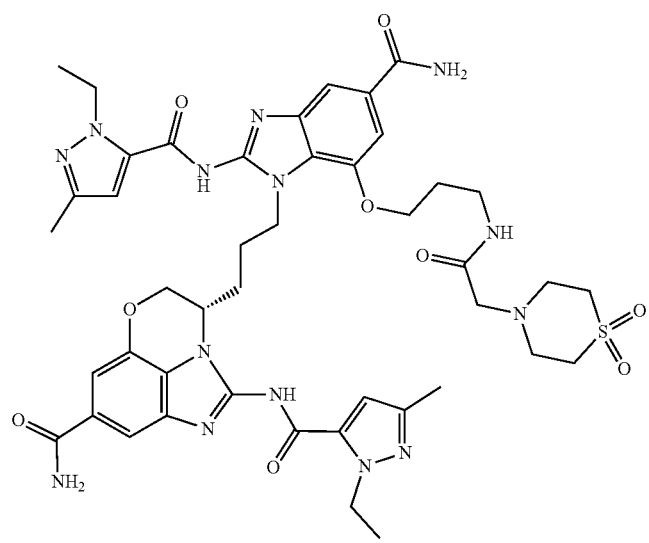 [SMILES: CCn1nc(C)cc1C(=O)Nc1nc2cc(C(N)=O)cc(OCCCNC(=O)CN3CCS(=O)(=O)CC3)c2n1CCC[C@H]1COc2cc(C(N)=O)cc3nc(NC(=O)c4cc(C)nn4CC)n1c23]
32

Step 1: To a solution of compound 14 (80 mg, 0.10 mmol) and compound 32a (21 mg, 0.11 mmol) in DMF (2 mL) was added HATU (41 mg, 0.11 mmol), HOBt (15 mg, 0.11 mmol) and trimethylamine (30 mg, 0.30 mmol). The reaction mixture was stirred at room temperature for 2 hours. LCMS indicated the reaction was complete. The reaction mixture was purified directly by reversed phase preparative HPLC to give compound 32 (16 mg, 16% yield). ESI-MS (m/z): 955.3 [M+H]$^+$; $^1$H NMR (500 MHz, DMSO-$d_6$) δ 12.80 (br s, 1H), 12.67 (br s, 1H), 7.99-7.91 (m, 2H), 7.89 (s, 1H), 7.61 (s, 1H), 7.55 (s, 1H), 7.39-7.26 (m, 4H), 6.52 (s, 1H), 6.42 (s, 1H), 4.74-4.68 (m, 1H), 4.63-4.47 (m, 5H), 4.44-4.30 (m, 2H), 4.24-4.17 (m, 1H), 4.12-4.00 (m, 2H), 3.28 (s, 1H), 3.20-3.14 (m, 2H), 3.12-3.07 (m, 4H), 3.02 (s, 2H), 2.93-2.85 (m, 4H), 2.07 (s, 3H), 2.05-1.97 (m, 5H), 1.97-1.86 (m, 2H), 1.83-1.74 (m, 2H), 1.31-1.22 (m, 6H).

Example 33: (S)-3-(3-(6-carbamoyl-2-(1-ethyl-3-methyl-1H-pyrazole-5-carboxamido)-4-(3-(2-((S)-morpholin-3-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

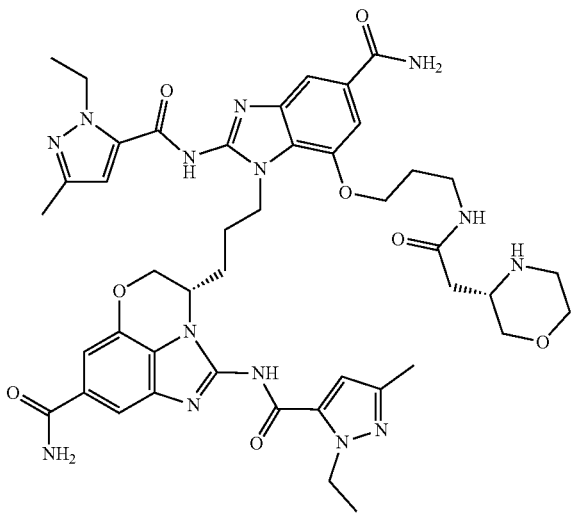 [SMILES: CCn1nc(C)cc1C(=O)Nc1nc2cc(C(N)=O)cc(OCCCNC(=O)C[C@H]3COCCN3)c2n1CCC[C@H]1COc2cc(C(N)=O)cc3nc(NC(=O)c4cc(C)nn4CC)n1c23]

Synthetic Scheme

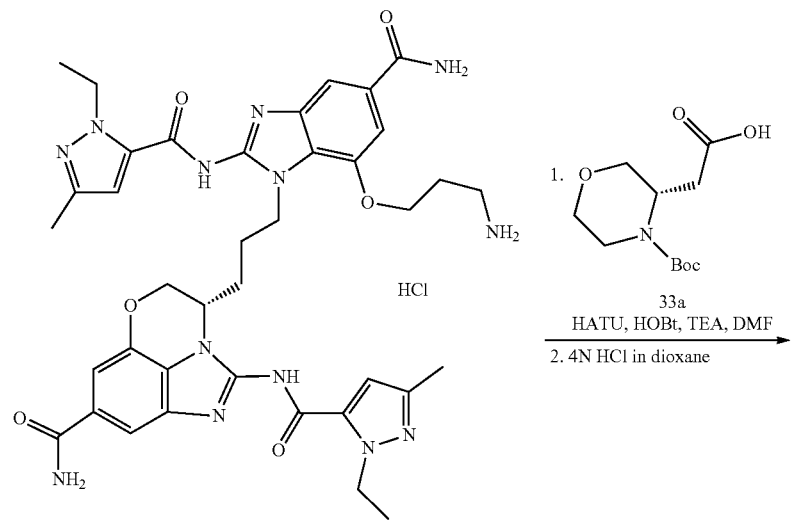

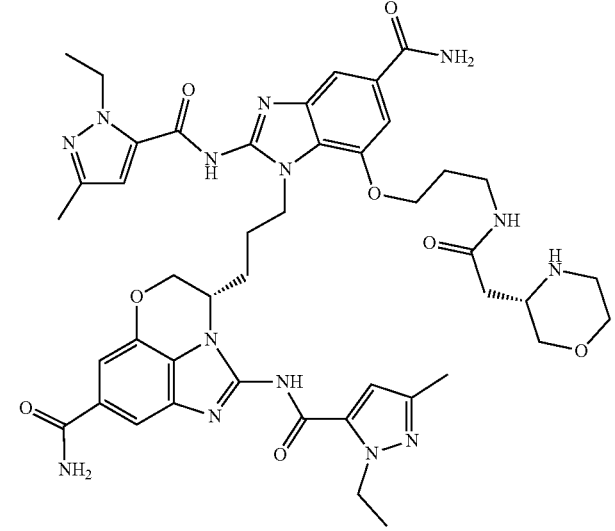

33

Step 1: To a solution of compound 14 (80 mg, 0.10 mmol) and compound 33a (25 mg, 0.11 mmol) in DMF (2 mL) was added HATU (41 mg, 0.11 mmol), HOBt (15 mg, 0.11 mmol) and trimethylamine (30 mg, 0.29 mmol). The reaction mixture was stirred at room temperature for 3 hours. LCMS indicated the reaction was complete. 4M HCl in dioxane (0.50 mL, 2.00 mmol) was added to the reaction, and the reaction mixture was heated at 70° C.; for 2 hours. LCMS indicated the second conversion was complete. The reaction mixture was cooled to room temperature, and purified directly by reversed phase preparative HPLC to give compound 33 (9 mg, 10% yield) as white solid. ESI-MS (m/z): 907.3 [M+H]$^+$; $^1$H NMR (500 MHz, DMSO-d6) δ 8.14 (s, 1H), 7.99-7.92 (m, 2H), 7.89 (s, 1H), 7.61 (s, 1H), 7.55 (s, 1H), 7.33-7.25 (m, 4H), 6.51 (s, 1H), 6.43 (s, 1H), 4.75-4.69 (m, 1H), 4.62-4.46 (m, 5H), 4.43-4.28 (m, 2H), 4.23-4.17 (m, 1H), 4.14-4.02 (m, 2H), 3.65-3.58 (m, 2H), 3.17-3.08 (m, 2H), 3.07-2.95 (m, 2H), 2.79-2.68 (m, 2H), 2.06 (s, 3H), 2.05-1.96 (m, 5H), 1.95-1.87 (m, 2H), 1.80-1.72 (m, 2H), 1.30-1.20 (m, 6H).

Example 34: (S)-3-(3-(6-carbamoyl-2-(1-ethyl-3-methyl-1H-pyrazole-5-carboxamido)-4-(3-(2-(piperazin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

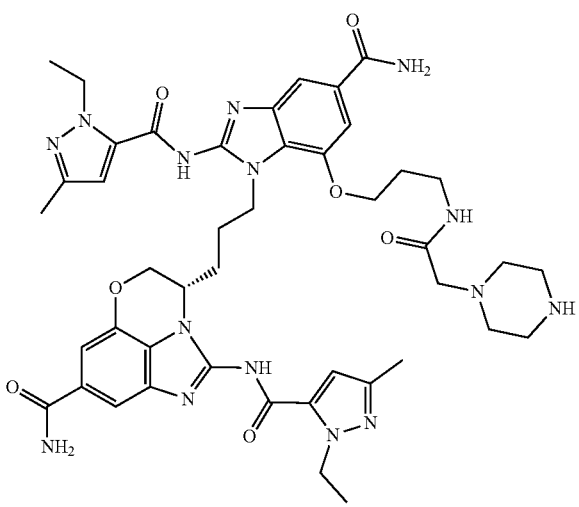 [SMILES: CCn1nc(C)cc1C(=O)Nc1nc2cc(C(N)=O)cc(OCCCNC(=O)CN3CCNCC3)c2n1CCC[C@H]1COc2cc(C(N)=O)cc3nc(NC(=O)c4cc(C)nn4CC)n1c23]

Synthetic Scheme

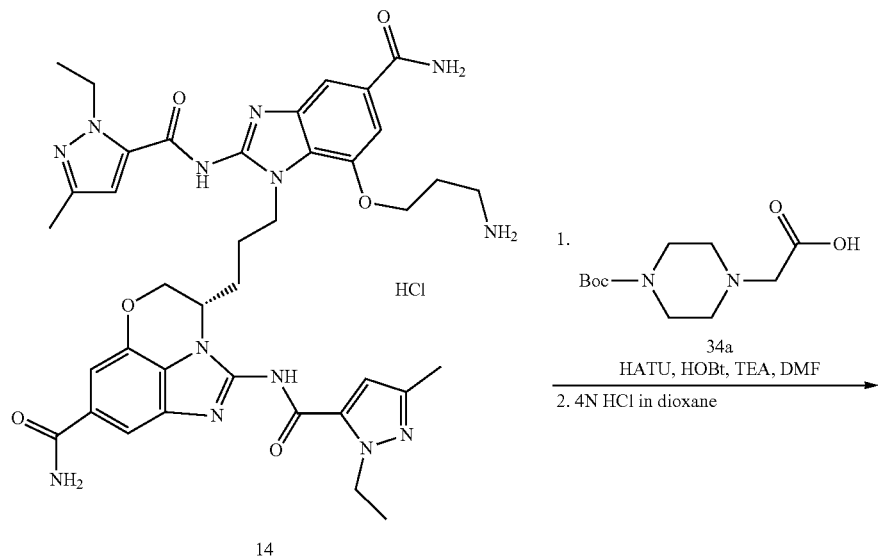

14

34

Step 1: To a solution of compound 14 (80 mg, 0.10 mmol) and compound 34a (27 mg, 0.11 mg) in DMF (2 mL) was added HATU (41 mg, 0.11 mmol), HOBt (15 mg, 0.11 mmol) and trimethylamine (30 mg, 0.29 mmol). The reaction mixture was stirred at room temperature for 3 hours. LCMS indicated the reaction was complete. 4M HCl in dioxane (0.50 mL, 2.00 mmol) was added to the reaction, and the reaction mixture was heated at 70° C.; for 2 hours. LCMS indicated the second conversion was complete. The reaction mixture was cooled to room temperature, and purified directly by reversed phase preparative HPLC to give compound 34 (4 mg, 5% yield) as white solid. ESI-MS (m/z): 906.4 [M+H]$^+$; $^1$H NMR (500 MHz, DMSO-d6) δ 8.30 (s, 3H), 7.94 (s, 1H), 7.89 (s, 1H), 7.77 (s, 1H), 7.61 (s, 1H), 7.55 (s, 1H), 7.34-7.27 (m, 4H), 6.52 (s, 1H), 6.43 (s, 1H), 4.72-4.68 (m, 1H), 4.62-4.58 (m, 1H), 4.54-4.48 (m, 4H), 4.43-4.31 (m, 2H), 4.22-4.18 (m, 1H), 4.12-4.01 (m, 2H), 3.20-3.15 (m, 3H), 2.85-2.75 (m, 6H), 2.40-2.32 (m, 4H), 2.07 (s, 3H), 2.03 (s, 3H), 2.02-1.98 (m, 2H), 1.94-1.89 (m, 2H), 1.81-1.76 (m, 2H), 1.28-1.19 (m, 6H).

Example 35: (S)-3-(3-(6-carbamoyl-2-(1-ethyl-3-methyl-1H-pyrazole-5-carboxamido)-4-(3-(2-((R)-morpholin-3-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide
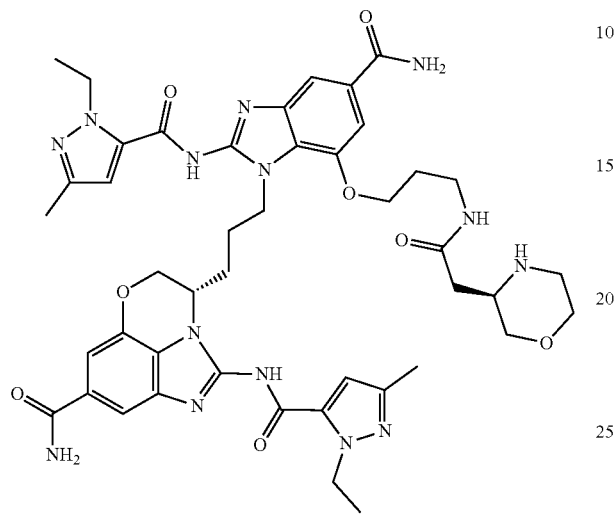
Synthetic Scheme
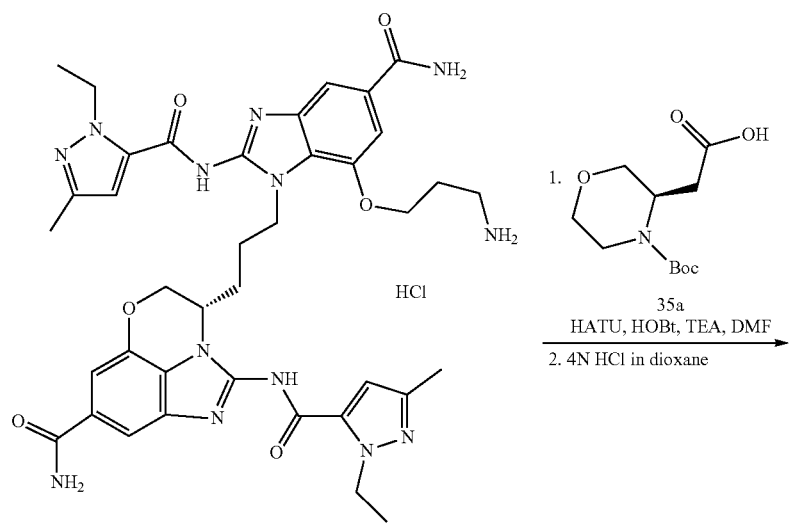

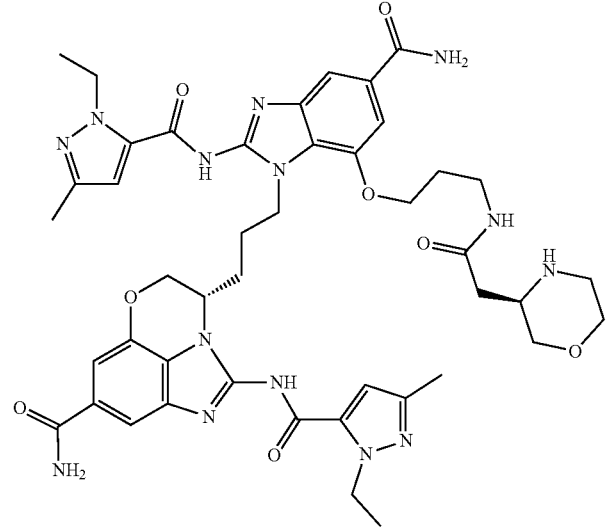

35

Step 1: To a solution of compound 14 (80 mg, 0.10 mmol) and compound 35a (27 mg, 0.11 mg) in DMF (2 mL) was added HATU (41 mg, 0.11 mmol), HOBt (15 mg, 0.11 mmol) and trimethylamine (30 mg, 0.29 mmol). The reaction mixture was stirred at room temperature for 3 hours. LCMS indicated the reaction was complete. 4M HCl in dioxane (0.50 mL, 2.00 mmol) was added to the reaction, and the reaction mixture was heated at 70° C.; for 2 hours. LCMS indicated the second conversion was complete. The reaction mixture was cooled to room temperature, and purified directly by reversed phase preparative HPLC to give compound 35 (3 mg, 3% yield) as white solid. ESI-MS (m/z): 907.2 [M+H]$^+$; $^1$H NMR (500 MHz, DMSO-d6) δ 8.20-8.15 (m, 1H), 8.03-7.90 (m, 3H), 7.63 (s, 1H), 7.57 (s, 1H), 7.38-7.29 (m, 4H), 6.53 (s, 1H), 6.45 (s, 1H), 4.74-4.70 (m, 1H), 4.64-4.48 (m, 5H), 4.44-4.32 (m, 2H), 4.23-4.18 (m, 1H), 4.14-4.05 (m, 2H), 3.65-3.60 (m, 2H), 3.16-3.11 (m, 2H), 3.09-2.97 (m, 2H), 2.80-2.70 (m, 2H), 2.10-1.96 (m, 8H), 1.95-1.87 (m, 2H), 1.80-1.73 (m, 2H), 1.30-1.20 (m, 6H).

Example 36: (S)-3-(3-(6-carbamoyl-2-(1-ethyl-3-methyl-1H-pyrazole-5-carboxamido)-4-(3-((R)-morpholine-3-carboxamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

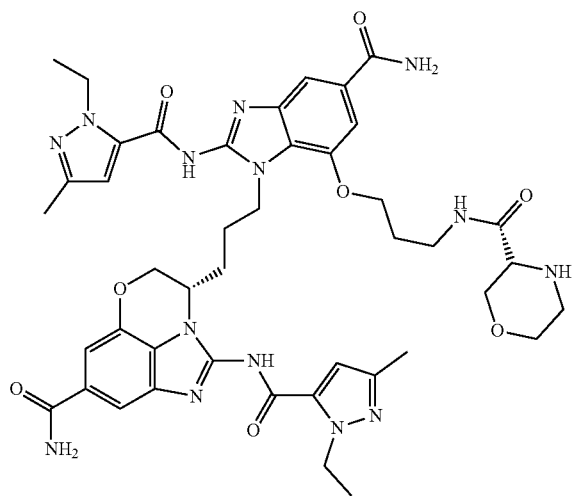

Synthetic Scheme

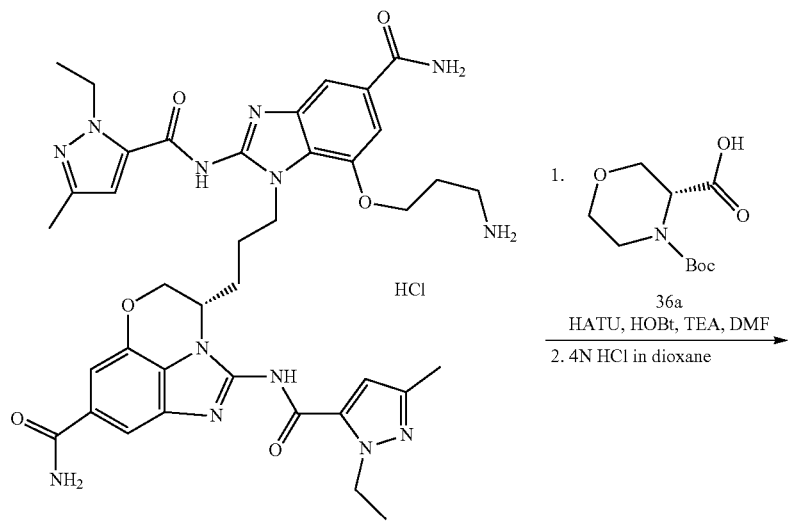

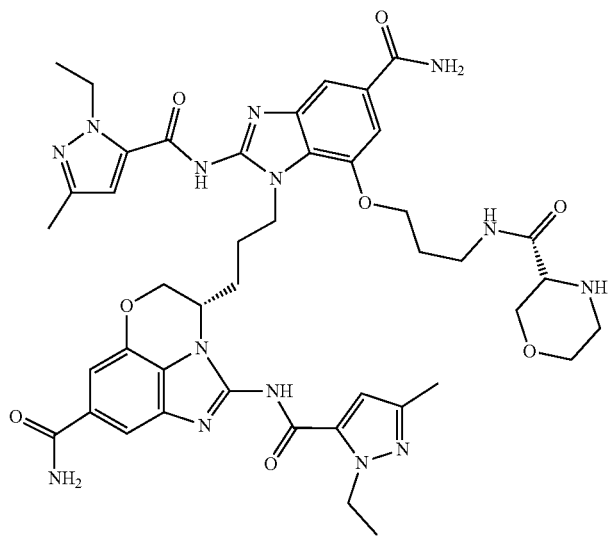

Step 1: To a solution of compound 14 (80 mg, 0.10 mmol) and compound 36a (25 mg, 0.11 mg) in DMF (2 mL) was added HATU (41 mg, 0.11 mmol), HOBt (15 mg, 0.11 mmol) and trimethylamine (30 mg, 0.29 mmol). The reaction mixture was stirred at room temperature for 3 hours. LCMS indicated the reaction was complete. 4M HCl in dioxane (0.50 mL, 2.00 mmol) was added to the reaction, and the reaction mixture was heated at room temperature for 2 hours. LCMS indicated the second conversion was complete. The reaction mixture was purified directly by reversed phase preparative HPLC to give compound 36 (6 mg, 7% yield) as a white solid. ESI-MS (m/z): 893.3 [M+H]$^+$; $^1$H NMR (500 MHz, DMSO-d6) δ 8.20-8.10 (m, 2H), 7.95-7.85 (m, 2H), 7.61 (s, 1H), 7.55 (s, 1H), 7.35-7.25 (m, 4H), 6.52 (s, 1H), 6.42 (s, 1H), 4.76-4.65 (m, 2H), 4.64-4.27 (m, 7H), 4.22-4.18 (m, 1H), 4.15-4.00 (s, 2H), 3.70-3.50 (m, 5H), 3.20-3.10 (m, 2H), 2.10-1.88 (m, 10H), 1.82-1.75 (m, 2H), 1.32-1.20 (m, 6H).

Example 37: (S)-3-(3-(5-carbamoyl-2-(1-ethyl-3-methyl-1H-pyrazole-5-carboxamido)-7-(3-(methylsulfonyl)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide
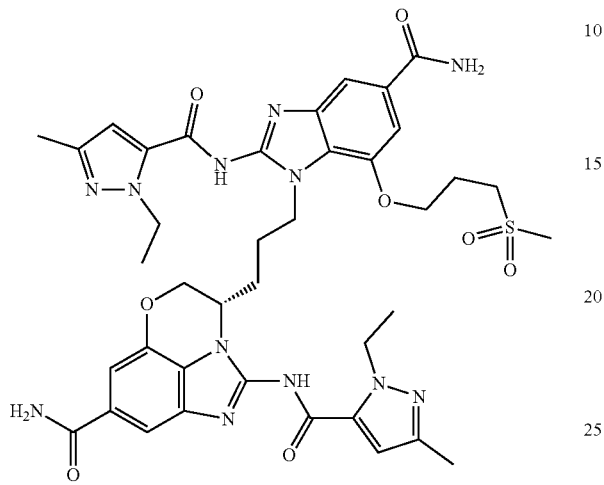
Synthetic Scheme
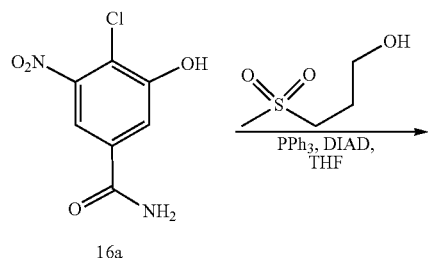
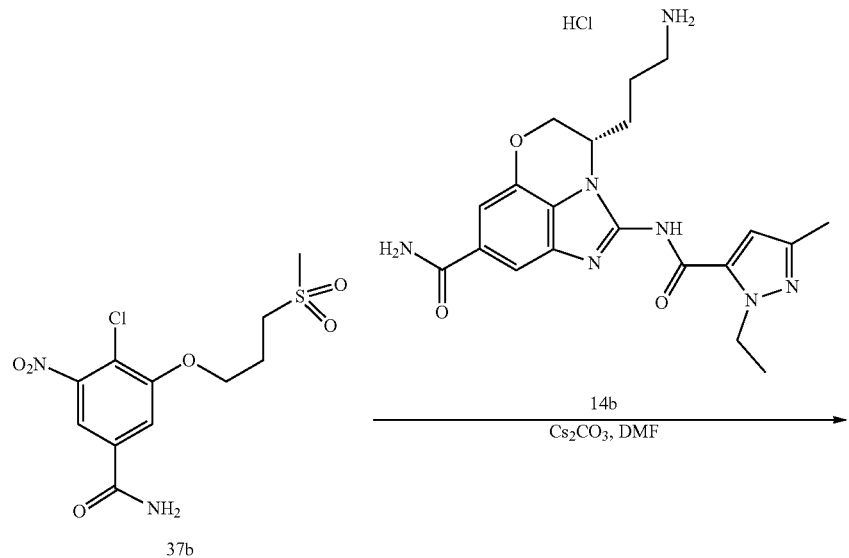

-continued
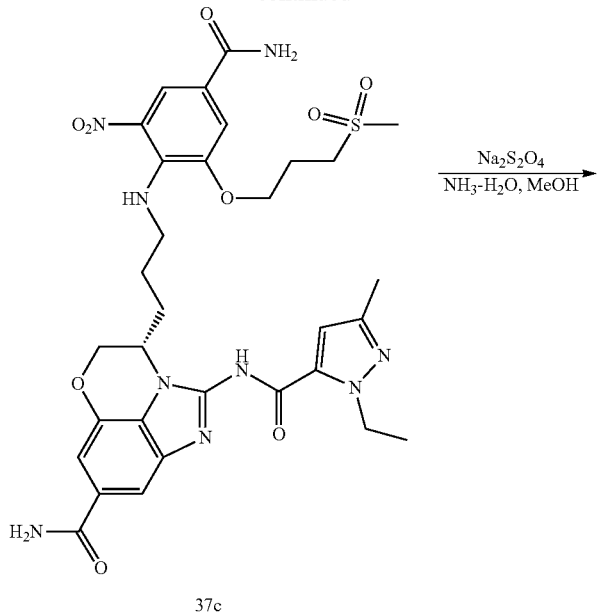
37c
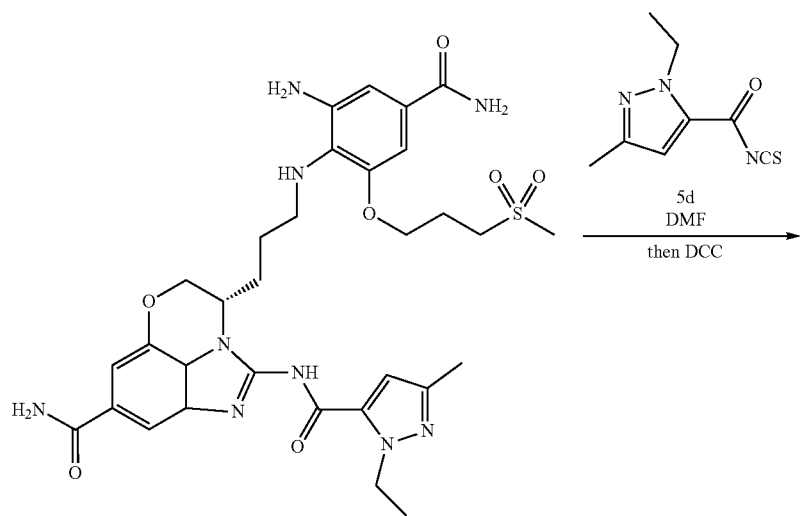
37d
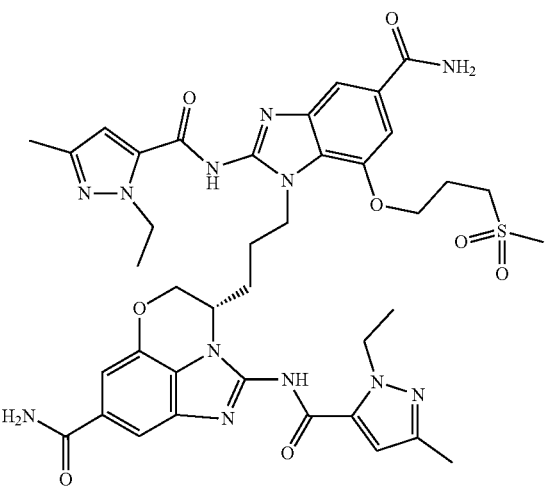
37

Step 1: To a stirred solution of Compound 37a (288 mg, 2.08 mmol) and triphenylphosphine (545 mg, 2.08 mmol) in THF (4 mL) at 0° C. under $N_2$ atmosphere was added DIAD (420 mg, 2.08 mmol) dropwise. After stirring the solution for 30 minutes at 0° C., compound 16a (300 mg, 1.39 mmol) was added. The reaction mixture was warmed room temperature and stirred for 3 hours. LCMS indicated the starting material was consumed. The reaction mixture was concentrated in vacuo. The residue was purified by silica gel chromatography to give compound 37b (338 mg, 73% yield) as white solid. ESI-MS (m/z): 337.5 [M+H]$^+$.

Step 2: To a stirring solution of compound 37b (338 mg, 1.01 mmol) and compound 14b (375 mg, 0.84 mmol) in DMF (6 mL) was added $Cs_2CO_3$ (545 mg, 1.67 mmol). The reaction mixture was heated at 70° C.; overnight, and LCMS indicated the starting materials were consumed. The reaction mixture was cooled to room temperature, diluted with water (50 mL), extracted with EtOAc (50 mL×3). The combined organic layers were dried over $Na_2SO_4$, filtered and concentrated. The residue was purified by silica gel chromatography to give compound 37c (328 mg, 55% yield) as brown solid. ESI-MS (m/z): 712.5 [M+H]$^+$.

Step 3: Compound 37c (328 mg, 0.46 mmol) was dissolved in a mixture of MeOH (25 mL) and concentrated ammonium hydroxide (1 mL). Sodium dithionite (400 mg, 2.29 mmol) was dissolved in water (4 mL) and added dropwise to the reaction mixture at room temperature. Stirring was continued at room temperature for 30 minutes, and LCMS indicated the product was formed. The reaction mixture was diluted with water (100 mL), and extracted with EtOAc (100 mL×3). The combined organic layers were washed with brine, dried over $Na_2SO_4$, filtered and concentrated. The residue was purified by silica gel chromatography to give compound 37d (176 mg, 56% yield) as white solid. ESI-MS (m/z): 682.3 [M+H].

Step 4: Compound 37d (60 mg, 0.09 mmol) was dissolved in DMF (5 mL), and then compound 5d (1 M in dioxane, 0.1 mL, 0.1 mmol) was added. The reaction mixture was stirred at room temperature for 30 minutes, DCC (35 mg, 0.18 mmol) was added, and the mixture was heated at 80° C. for 1 hour, LCMS indicated the product was formed. The reaction mixture was cooled to room temperature, and purified directly by reversed phase preparative HPLC to give the compound 37 (31 mg, 42% yield) as white solid. ESI-MS (m/z): 843.2 [M+H]$^+$; $^1$H NMR (500 MHz, DMSO-d6) δ 12.69 (br s, 2H), 7.96 (s, 1H), 7.88 (s, 1H), 7.63 (s, 1H), 7.55 (s, 1H), 7.37-7.25 (m, 4H), 6.49 (s, 1H), 6.41 (s, 1H), 4.74-4.67 (m, 1H), 4.58 (d, J=11.5 Hz, 1H), 4.55-4.44 (m, 4H), 4.41-4.27 (m, 2H), 4.26-4.15 m, 3H), 3.21 (t, J=7.5 Hz, 2H), 2.92 (s, 3H), 2.15-1.85 (m, 12H), 1.28-1.19 (m, 6H).

Example 38: (S)-3-(3-(5-carbamoyl-7-((R)-3,4-dihydroxybutoxy)-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

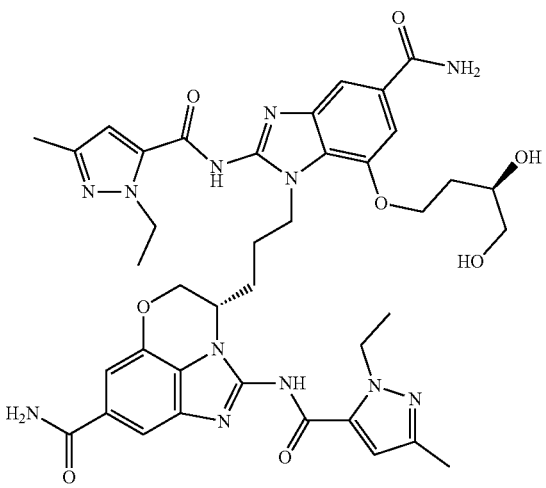 [SMILES: CCn1nc(C)cc1C(=O)Nc1nc2cc(C(N)=O)cc(OCC[C@@H](O)CO)c2n1CCC[C@H]1COc2cc(C(N)=O)cc3nc(NC(=O)c4cc(C)nn4CC)n1c23]

Synthetic Scheme

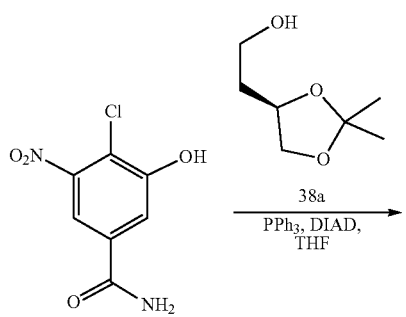

-continued
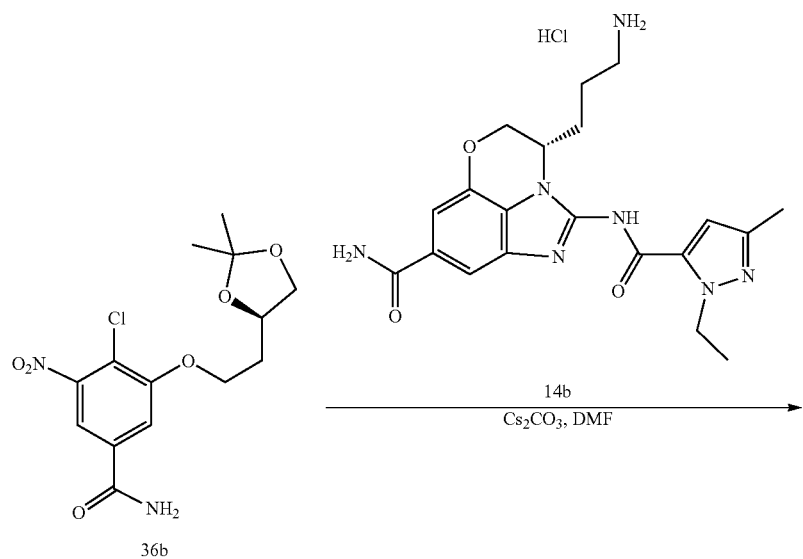
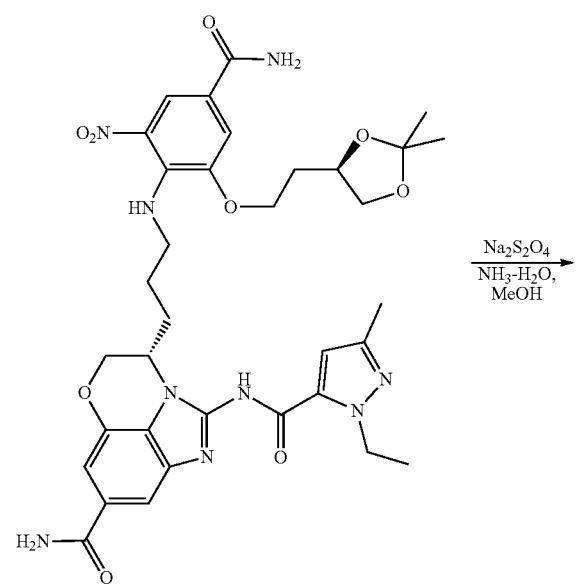

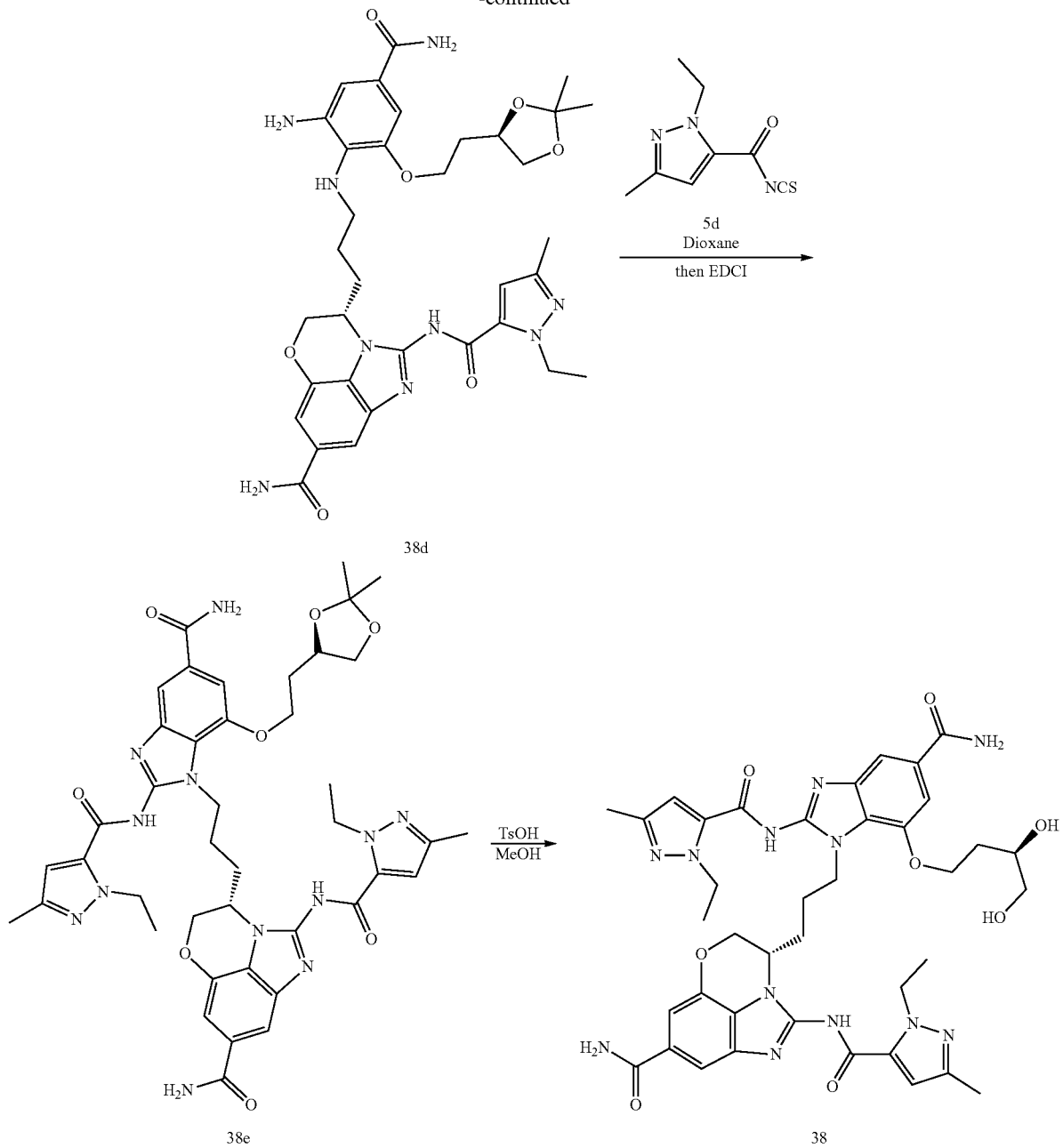

Step 1: To a stirred solution of Compound 16a (700 mg, 3.23 mmol) and triphenylphosphine (1.7 g, 6.46 mmol) in THF (15 mL) at 0° C. under $N_2$ atmosphere was added DIAD (1.27 mL, 6.46 mmol) dropwise. After stirring the solution for 20 minutes at 0° C., 38a (708 mg, 4.85 mmol) in anhydrous THF (2 mL) was added. The reaction mixture was warmed room temperature and stirred for 2 hours. TLC indicated the starting material was consumed. The reaction mixture was concentrated in vacuo. The residue was purified by silica gel chromatography to give compound 38b (2.0 g, 50% purity, 38b/PPh$_3$O: around 1/1). ESI-MS (m/z): 337.5 [M+H]$^+$.

Step 2: To a stirring solution of compound 38b (804 mg, from step 1) and compound 14b (400 mg, 0.97 mmol) in DMF (10 mL) was added Cs$_2$CO$_3$ (792 mg, 2.43 mmol). The reaction mixture was heated at 80° C.; overnight, and LCMS indicated the starting materials were consumed. The reaction mixture was cooled to room temperature, diluted with water (20 mL), extracted with EtOAc (20 mL). The aqueous layer was extracted with EtOAc (20 mL×3). The combined organic layers were washed with brine, dried over Na$_2$SO$_4$, filtered and concentrated. The residue was purified by silica gel chromatography to give compound 38c (360 mg, yield 38% for 2 steps) as a red oil. ESI-MS (m/z): 720.2 [M+H]$^+$.

Step 3: Compound 38c (360 mg, 0.50 mmol) was dissolved in a mixture of MeOH (10 mL) and concentrated ammonium hydroxide (3 mL). Sodium dithionite (435 mg, 2.5 mmol) was dissolved in water (3 mL) and added dropwise to the reaction mixture at room temperature. Stirring was continued at room temperature for 1 hour, and LCMS indicated the product was formed. The reaction mixture was filtered, and the filtrate was concentrated. The residue was purified by silica gel chromatography to give compound 38d (270 mg, 78% yield) as a yellow solid. ESI-MS (m/z): 690.3 [M+H]$^+$.

Step 4: Compound 38d (270 mg, 0.39 mmol) was dissolved in 1,4-dioxane (5 mL), and then compound 5d (0.4 M dioxane, 1 mL, 0.40 mmol) was added. The reaction mixture was stirred at room temperature for 30 minutes, LCMS indicated the starting material was consumed. EDCI (97 mg, 0.50 mmol) was added, and the mixture was heated at 80° C.; for 2 hours, LCMS indicated the product was formed. The reaction mixture was concentrated, and the residue was purified by silica gel chromatography to give the compound 38e (170 mg, 51% yield) as a yellow solid. ESI-MS (m/z): 851.1 [M+H]$^+$.

Step 5: To a solution of compound 38e (170 mg, 0.2 mmol) in MeOH (4 mL) was added TsOH (10 mg, 0.059 mmol), the reaction mixture was stirred at room temperature for 2 hours. LCMS indicated the reaction was complete. The reaction mixture was purified directly by reversed phase preparative HPLC to give compound 38 (18 mg, 11% yield) as a white solid. ESI-MS (m/z): 811.3 [M+H]$^+$; $^1$H NMR (500 MHz, DMSO-d6) δ 12.49 (s, 2H), 7.99 (s, 1H), 7.90 (s, 1H), 7.64 (s, 1H), 7.57 (s, 1H), 7.33 (t, J=18.0 Hz, 4H), 6.51 (s, 1H), 6.43 (s, 1H), 4.73 (s, 1H), 4.61 (d, J=11.5 Hz, 1H), 4.58-4.44 (m, 5H), 4.35 (s, 2H), 4.29-4.21 (m, 2H), 4.17 (s, 1H), 3.62 (s, 2H), 3.25-3.19 (m, 2H), 2.07 (s, 3H), 2.04 (s, 3H), 2.00 (s, 2H), 1.93 (s, 2H), 1.83 (s, 2H), 1.59 (s, 1H), 1.28-1.22 (m, 6H).

Example 39: (S)-3-(3-(5-carbamoyl-2-(1-ethyl-3-methyl-1H-pyrazole-5-carboxamido)-7-(3-(2-((R)-3-methoxypyrrolidin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

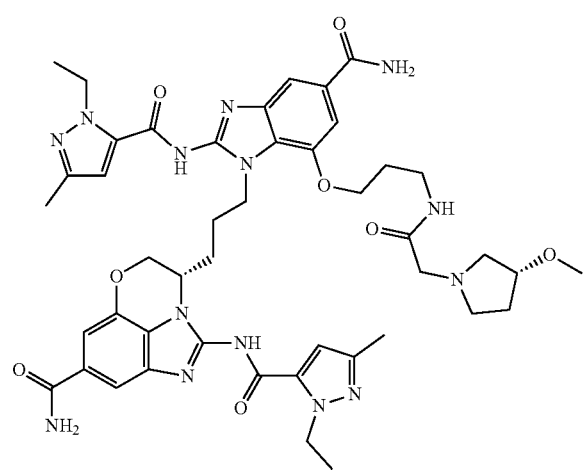 [SMILES: CCn1nc(C)cc1C(=O)Nc1nc2cc(C(N)=O)cc(OCCCNC(=O)CN3CC[C@@H](OC)C3)c2n1CCC[C@H]1COc2cc(C(N)=O)cc3nc(NC(=O)c4cc(C)nn4CC)n1c23]

Synthetic Scheme

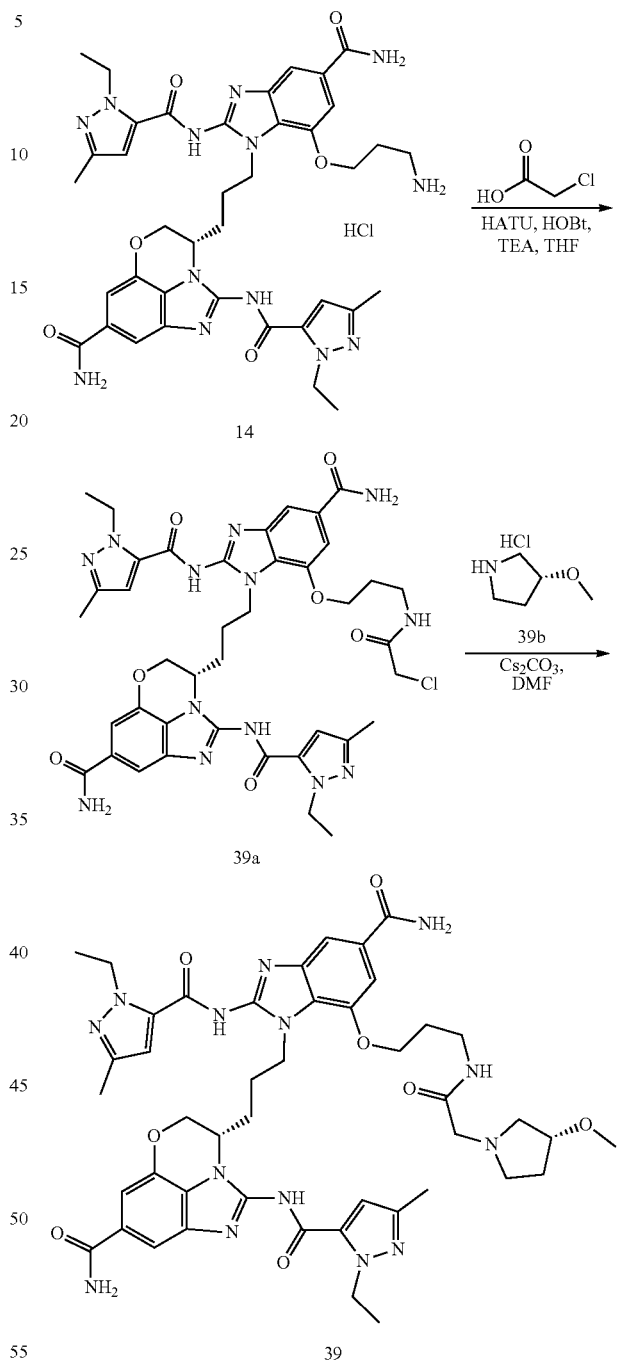

Step 1: To a solution of compound 14 (500 mg, 0.61 mmol) and 2-chloroacetic acid (60 mg, 0.64 mmol) in THF (20 mL) was added HATU (230 mg, 0.61 mmol), HOBt (42 mg, 0.31 mmol) and trimethylamine (0.25 mL, 1.83 mmol). The reaction mixture was stirred at room temperature overnight. LCMS indicated the reaction was complete. The reaction mixture was concentrated, and the residue was purified by silica gel chromatography to give compound 39a (410 mg, 78% yield) as white solid. ESI-MS (m/z): 855.7 [M+H]$^+$.

Step 2: To a stirring solution of compound 39a (100 mg, 0.12 mmol) and compound 39b (25 mg, 0.18 mmol) in DMF (3 mL) was added $Cs_2CO_3$ (78 mg, 0.24 mmol). The reaction mixture was heated at 70° C.; overnight, and LCMS indicated the reaction was complete. The reaction mixture was purified directly by reversed phase preparative HPLC to give compound 39 (61 mg, 57% yield) as white solid. ESI-MS (m/z): 921.9 [M+H]$^+$; $^1$H NMR (500 MHz, DMSO-d$_6$) δ 12.79 (s, 1H), 12.64 (s, 1H), 7.94 (s, 1H), 7.89 (s, 1H), 7.71 (t, J=6.0 Hz, 1H), 7.61 (s, 1H), 7.55 (s, 1H), 7.36-7.25 (m, 4H), 6.51 (s, 1H), 6.43 (s, 1H), 4.73-4.66 (m, 1H), 4.63-4.29 (m, 7H), 4.25-4.15 (m, 1H), 4.11-4.01 (m, 2H), 3.83-3.75 (m, 1H), 3.17 (q, J=6.7 Hz, 2H), 3.09 (s, 3H), 2.92 (s, 2H), 2.72-2.67 (m, 1H), 2.56-2.49 (m, 2H), 2.45-2.37 (m, 2H), 2.08-1.75 (m, 13H), 1.65-1.52 (m, 1H), 1.29-1.20 (m, 6H).

Example 40: (S)-3-(3-(5-carbamoyl-2-(1-ethyl-3-methyl-1H-pyrazole-5-carboxamido)-7-(3-(2-(4-hydroxy piperidin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

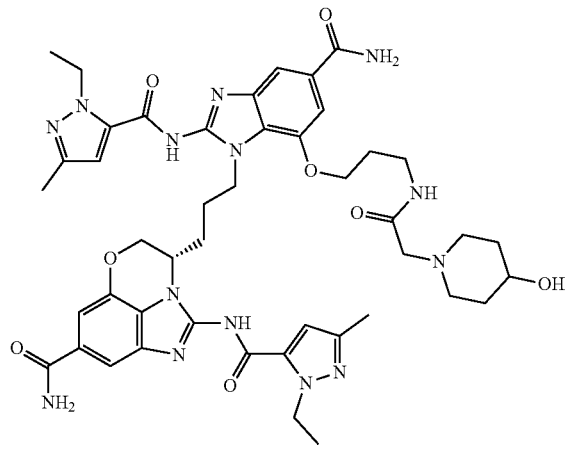 [SMILES: CCn1nc(C)cc1C(=O)Nc1nc2cc(C(N)=O)cc(OCCCNC(=O)CN3CCC(O)CC3)c2n1CCC[C@H]1COc2cc(C(N)=O)cc3nc(NC(=O)c4cc(C)nn4CC)n1c23]

Synthetic Scheme

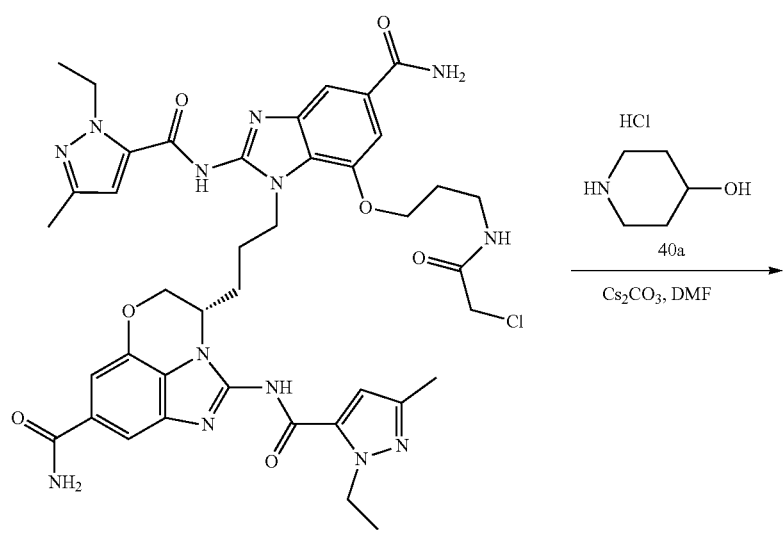

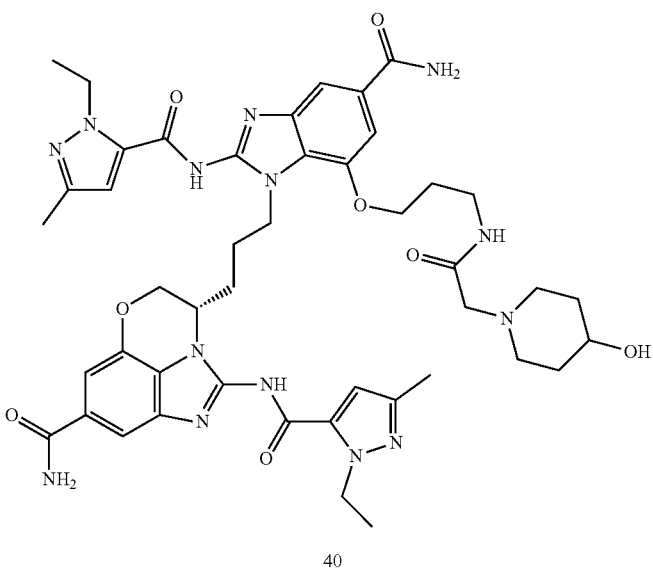

40

Step 1: To a stirring solution of compound 39a (80 mg, 0.09 mmol) and compound 40a (19 mg, 0.14 mmol) in DMF (3 mL) was added Cs$_2$CO$_3$ (59 mg, 0.18 mmol). The reaction mixture was heated at 70° C.; overnight, and LCMS indicated the reaction was complete. The reaction mixture was purified directly by reversed phase preparative HPLC to give compound 40 (45 mg, 52% yield) as a white solid. ESI-MS (m/z): 921.9 [M+H]$^+$; $^1$H NMR (500 MHz, DMSO-d$_6$) δ 12.81 (br s, 1H), 12.66 (br s, 1H), 7.96 (s, 1H), 7.91 (s, 1H), 7.75 (t, J=6.0 Hz, 1H), 7.63 (s, 1H), 7.57 (s, 1H), 7.39-7.24 (m, 4H), 6.53 (s, 1H), 6.45 (s, 1H), 4.75-4.68 (m, 1H), 4.66-4.46 (m, 5H), 4.45-4.29 (m, 2H), 4.25-4.20 (m, 1H), 4.15-4.00 (m, 2H), 3.47-3.35 (m, 2H), 3.20 (q, J=6.7 Hz, 2H), 2.80 (s, 2H), 2.67-2.55 (m, 2H), 2.18-1.89 (m, 10H), 1.85-1.76 (m, 2H), 1.71-1.59 (m, 2H), 1.49-1.33 (m, 2H), 1.31-1.22 (m, 6H).

Example 41: (S)-3-(3-(5-Carbamoyl-2-(1-ethyl-3-methyl-1H-pyrazole-5-carboxamido)-7-(3-(2-(3-(methoxymethyl)azetidin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

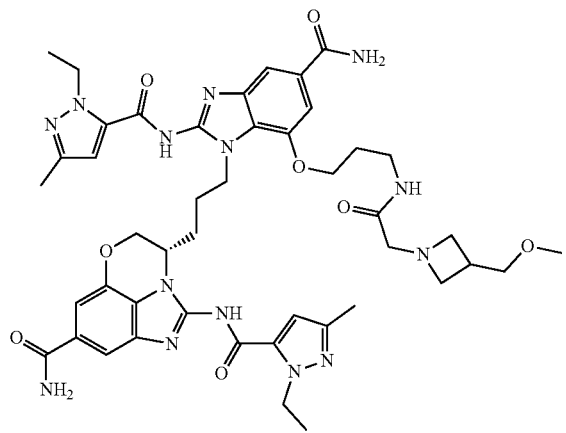 [SMILES: CCn1nc(C)cc1C(=O)Nc1nc2cc(C(N)=O)cc(OCCCNC(=O)CN3CC(COC)C3)c2n1CCC[C@H]1COc2cc(C(N)=O)cc3nc(NC(=O)c4cc(C)nn4CC)n1c23]

Synthetic Scheme

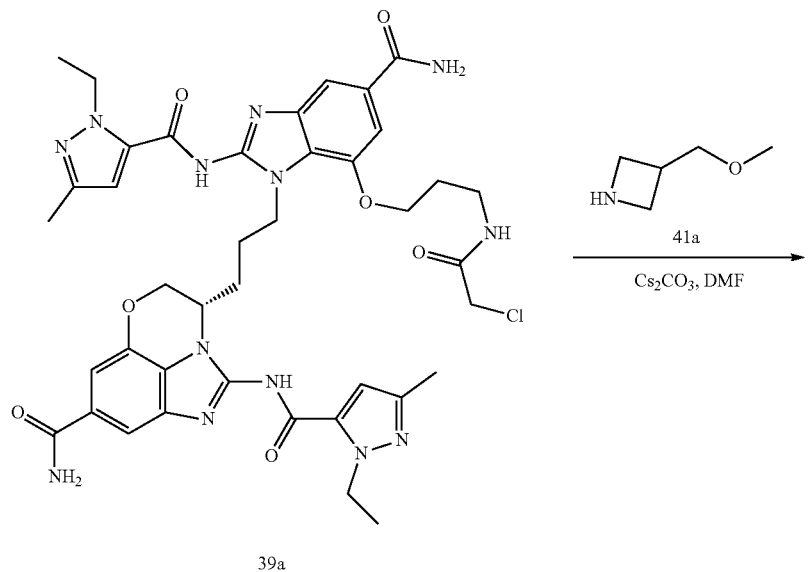

39a

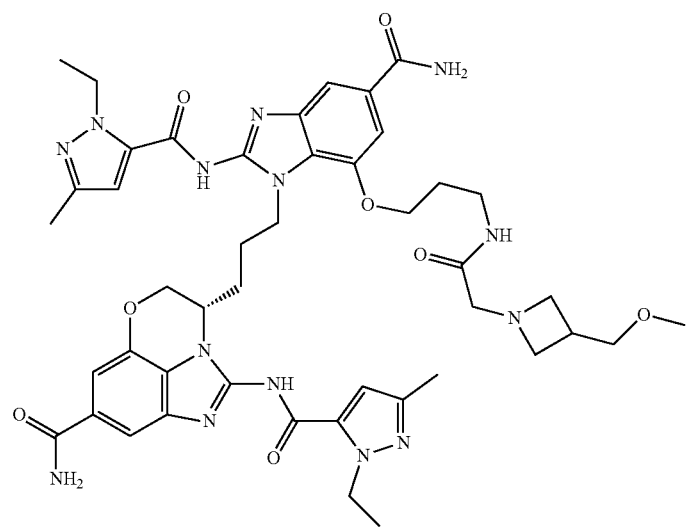

41

Step 1: To a stirring solution of compound 39a (80 mg, 0.09 mmol) and compound 41a (19 mg, 0.14 mmol) in DMF (3 mL) was added Cs$_2$CO$_3$ (59 mg, 0.18 mmol). The reaction mixture was heated at 70° C.; overnight, and LCMS indicated the reaction was complete. The reaction mixture was purified directly by reversed phase preparative HPLC to give compound 41 (33 mg, 38% yield) as a white solid. ESI-MS (m/z): 921.8 [M+H]$^+$; $^1$H NMR (500 MHz, DMSO-d$_6$) δ 12.79 (br s, 1H), 12.64 (br s, 1H), 7.94 (s, 1H), 7.89 (s, 1H), 7.69-7.64 (m, 1H), 7.61 (s, 1H), 7.55 (s, 1H), 7.36-7.22 (m, 4H), 6.51 (s, 1H), 6.42 (s, 1H), 4.72-4.66 (m, 1H), 4.58 (d, J=11.5 Hz, 1H), 4.55-4.28 (m, 6H), 4.19 (d, J=11.5 Hz, 1H), 4.11-3.98 (m, 2H), 3.36 (d, J=6.8 Hz, 2H), 3.26 (t, J=7.4 Hz, 2H), 3.17 (s, 3H), 3.16-3.11 (m, 2H), 2.90 (s, 2H), 2.86 (t, J=6.7 Hz, 2H), 2.55-2.47 (m, 1H), 2.10-1.87 (m, 10H), 1.81-1.72 (m, 2H), 1.28-1.20 (m, 6H).

Example 42: (S)-3-(3-(5-carbamoyl-2-(1-ethyl-3-methyl-1H-pyrazole-5-carboxamido)-7-(3-(2-(4-methoxy piperidin-1-yl)acetamido)propoxy)-1H-benzo[d]imidazol-1-yl) propyl)-2-(1-ethyl-3-methyl-1H-pyrazole-5-carboxamido)-3,4-dihydro-5-oxa-1,2a-diazaacenaphthylene-7-carboxamide

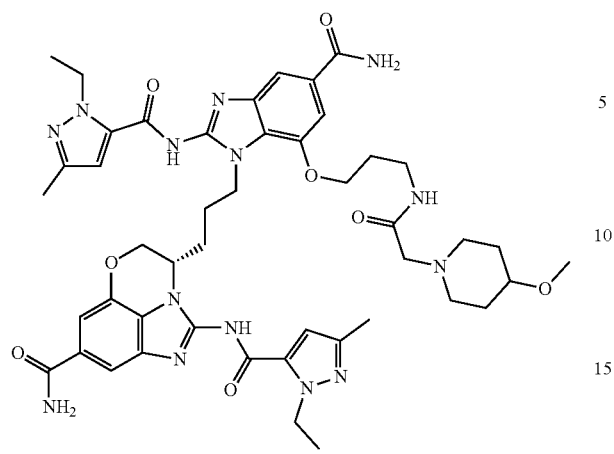
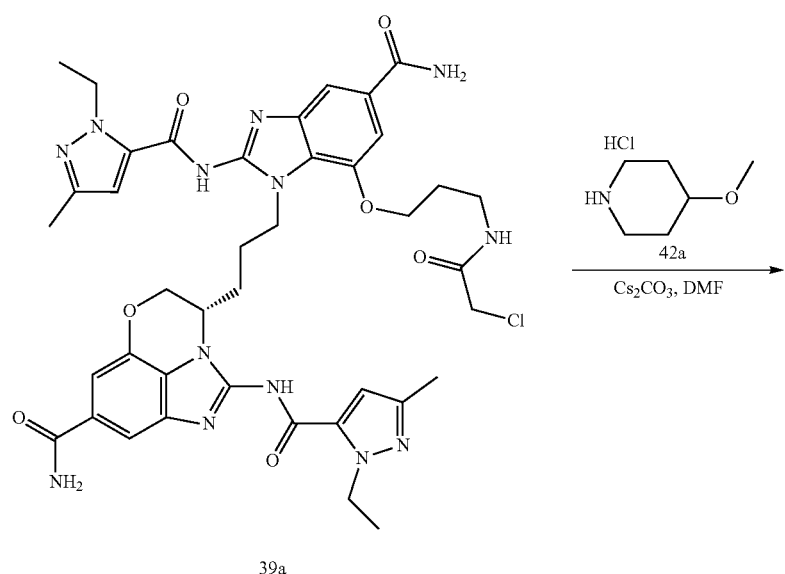
Synthetic Scheme
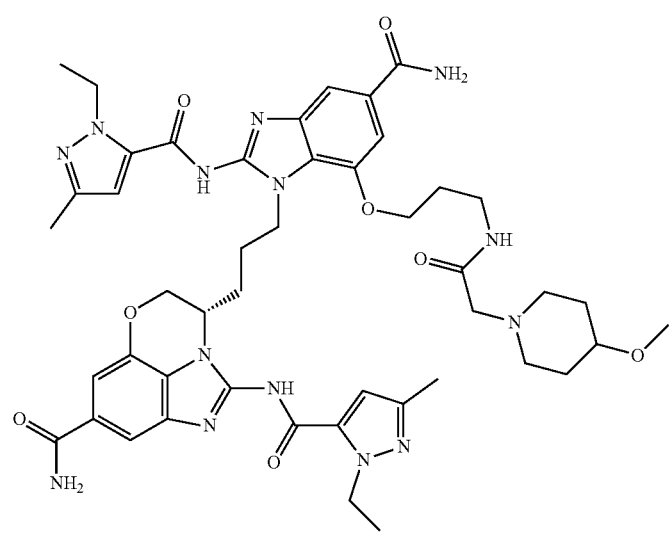

Step 1: To a stirring solution of compound 39a (80 mg, 0.09 mmol) and compound 42a (19 mg, 0.14 mmol) in DMF (3 mL) was added Cs$_2$CO$_3$ (59 mg, 0.18 mmol). The reaction mixture was heated at 70° C.; overnight, and LCMS indicated the reaction was complete. The reaction mixture was purified directly by reversed phase preparative HPLC to give compound 42 (45 mg, 68% yield) as a white solid. ESI-MS (m/z): 936.4 [M+H]$^+$; $^1$H NMR (500 MHz, DMSO-d$_6$) δ 12.79 (br s, 1H), 12.64 (br s, 1H), 7.94 (s, 1H), 7.89 (s, 1H), 7.73 (t, J=6.0 Hz, 1H), 7.61 (s, 1H), 7.55 (s, 1H), 7.36-7.26 (m, 4H), 6.52 (s, 1H), 6.43 (s, 1H), 4.73-4.66 (m, 1H), 4.59 (d, J=11.5 Hz, 1H), 4.56-4.27 (m, 6H), 4.25-4.16 (m, 1H), 4.12-3.99 (m, 2H), 3.21-3.17 (m, 2H), 3.16 (s, 3H), 3.11-3.04 (m, 1H), 2.78 (s, 2H), 2.60-2.51 (m, 2H), 2.13-1.87 (m, 10H), 1.84-1.63 (m, 4H), 1.44-1.33 (m, 2H), 1.29-1.20 (m, 6H).

Example 43: (S)-3-(3-(5-carbamoyl-2-(1-ethyl-3-methyl-1H-pyrazole-5-carboxamido)-7-(3-(2-(3-methoxy azetidin-1-yl)acetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

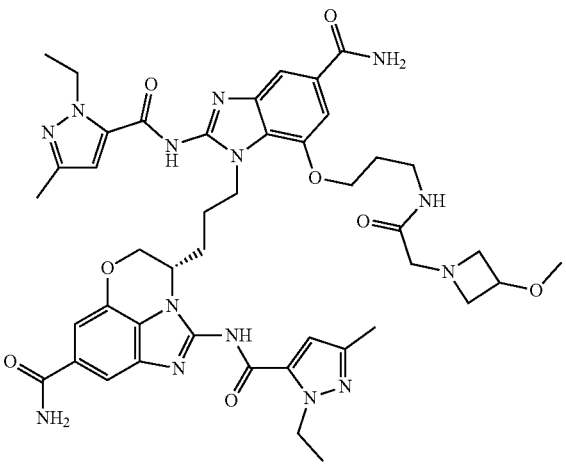 [SMILES: CCn1nc(C)cc1C(=O)Nc1nc2cc(C(N)=O)cc(OCCCNC(=O)CN3CC(OC)C3)c2n1CCC[C@H]1COc2cc(C(N)=O)cc3nc(NC(=O)c4cc(C)nn4CC)n1c23]

Synthetic Scheme

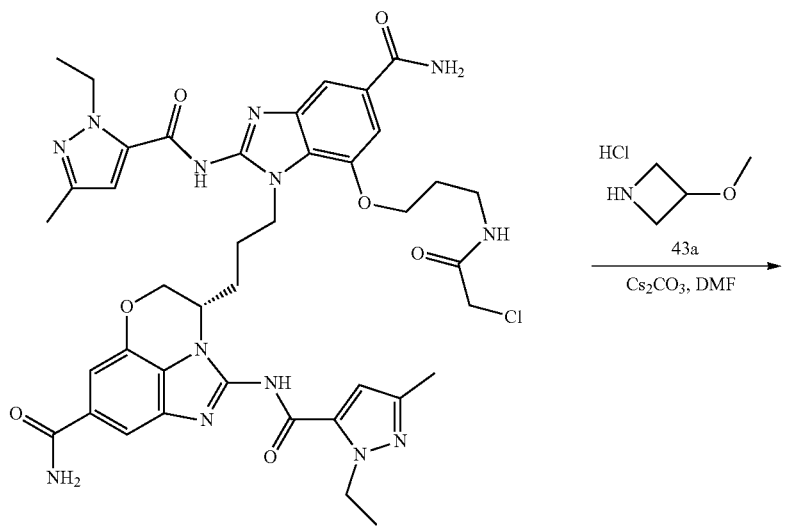

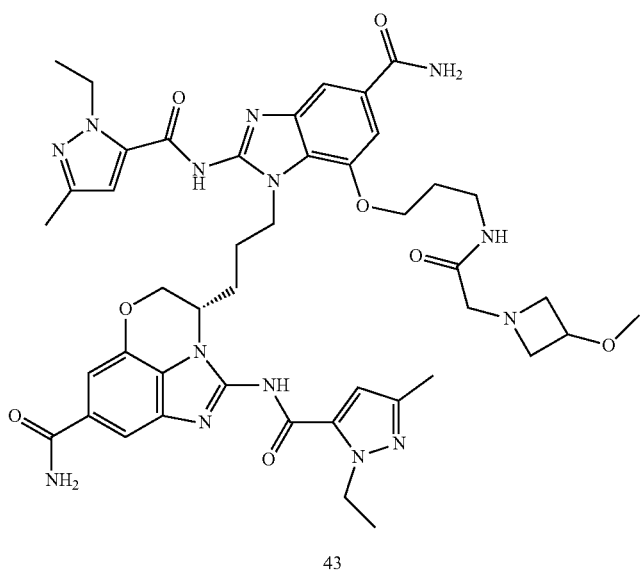

43

Step 1: To a stirring solution of compound 39a (80 mg, 0.09 mmol) and compound 43a (17 mg, 0.14 mmol) in DMF (3 mL) was added Cs$_2$CO$_3$ (59 mg, 0.18 mmol). The reaction mixture was heated at 70° C.; overnight, and LCMS indicated the reaction was complete. The reaction mixture was purified directly by reversed phase preparative HPLC to give compound 43 (47 mg, 56% yield) as a white solid. ESI-MS (m/z): 908.0 [M+H]$^+$; $^1$H NMR (500 MHz, DMSO-d$_6$) δ 12.79 (br s, 1H), 12.64 (br s, 1H), 7.94 (s, 1H), 7.89 (s, 1H), 7.69 (t, J=6.0 Hz, 1H), 7.61 (s, 1H), 7.55 (s, 1H), 7.37-7.21 (m, 4H), 6.51 (s, 1H), 6.43 (s, 1H), 4.73-4.66 (m, 1H), 4.62-4.44 (m, 5H), 4.43-4.28 (m, 2H), 4.24-4.17 (m, 1H), 4.12-3.98 (m, 2H), 3.92-3.84 (m, 1H), 3.52-3.45 (m, 2H), 3.14 (q, J=6.5 Hz, 2H), 3.08 (s, 3H), 2.94 (s, 2H), 2.89-2.83 (m, 2H), 2.06-1.88 (m, 10H), 1.82-1.71 (m, 2H), 1.31-1.18 (m, 6H).

Example 44: (S)-3-(3-(7-(3-(2-aminoethylsulfonamido)propoxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

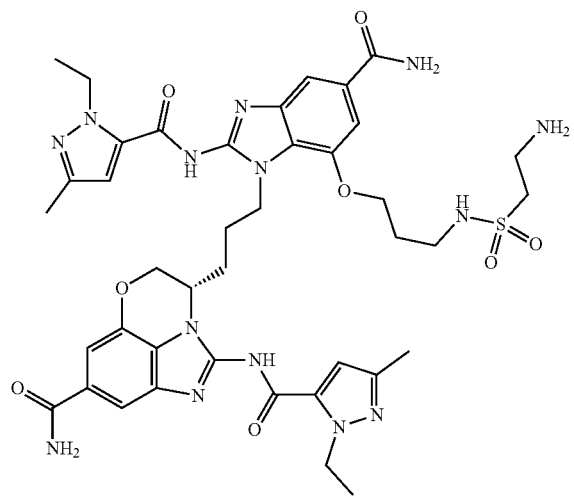 [SMILES: CCn1nc(C)cc1C(=O)Nc1nc2cc(C(N)=O)cc(OCCCNS(=O)(=O)CCN)c2n1CCC[C@H]1COc2cc(C(N)=O)cc3nc(NC(=O)c4cc(C)nn4CC)n1c23]

Synthetic Scheme
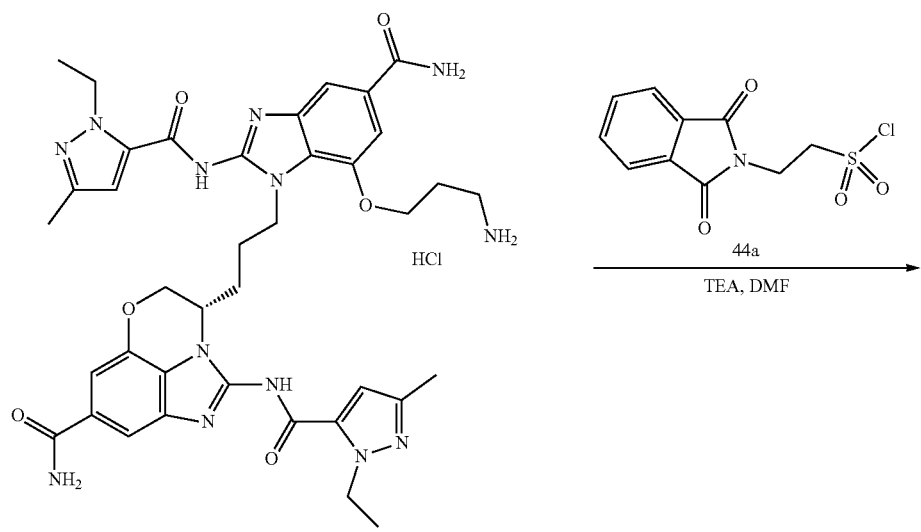
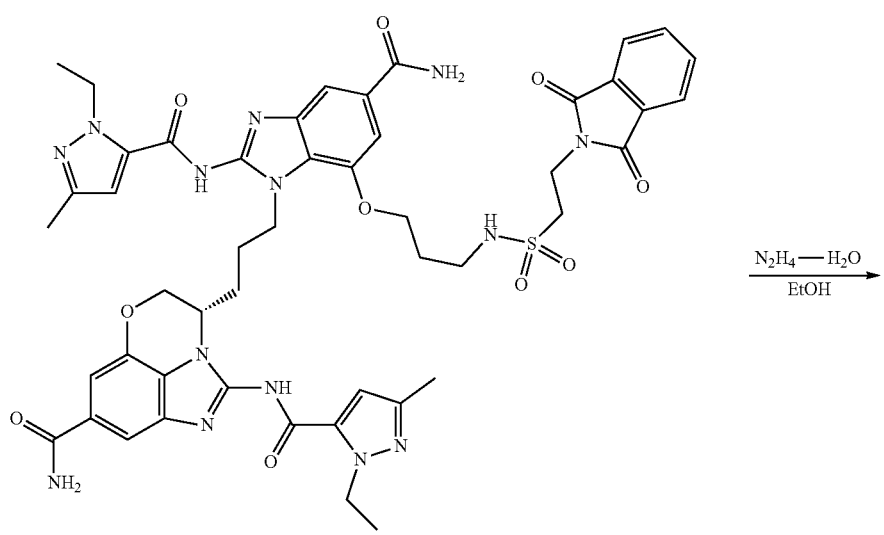

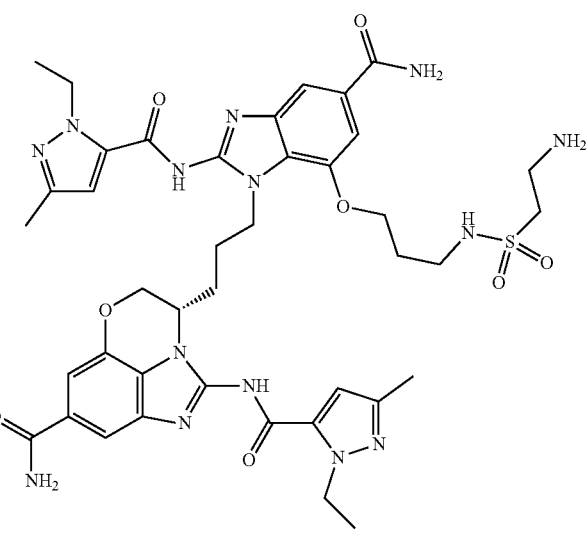

44

Step 1: To a solution of compound 14 (50 mg, 0.06 mmol) in DMF (2 mL) was added compound 44a (83 mg, 0.30 mmol) and triethylamine (50 mg, 0.50 mmol). The reaction mixture was stirred at room temperature for 16 hours. The reaction mixture was diluted with water (30 mL), and extracted with EtOAc (40 mL×3). The combined organic layers were washed with brine, dried over Na$_2$SO$_4$, filtered and concentrated under reduced pressure. The crude material was purified by silica gel chromatography to give compound 44b (15 mg, 25% yield) as a white solid. ESI-MS (m/z): 1017.5 [M+H]$^+$.

Step 2: To a solution of compound 44b (15 mg, 0.01 mmol) in EtOH (5 mL) was added hydrazine hydrate (5 mg, 0.12 mmol). The reaction mixture was stirred at 80° C.; for 2 hours, LCMS indicated the starting material was consumed. The mixture was concentrated, and the residue was purified by prep-HPLC to give compound 44 (8 mg, 62% yield) as a white solid. ESI-MS (m/z): 887.8 [M+H]$^+$; $^1$H NMR (500 MHz, DMSO-d$_6$) δ 7.94 (s, 1H), 7.87 (s, 1H), 7.62 (s, 1H), 7.55 (s, 1H), 7.41-7.22 (m, 4H), 6.50 (s, 1H), 6.44 (s, 1H), 4.74-4.67 (m, 1H), 4.62-4.44 (m, 5H), 4.41-4.26 (m, 2H), 4.24-4.08 (m, 3H), 3.06-2.95 (m, 4H), 2.83 (t, J=6.7 Hz, 2H), 2.06 (s, 3H), 2.04 (s, 3H), 2.02-1.94 (m, 2H), 1.94-1.87 (m, 2H), 1.85-1.77 (m, 2H), 1.30-1.17 (m, 6H).

Example 45: (S)-3-(3-(5-carbamoyl-2-(1-ethyl-3-methyl-1H-pyrazole-5-carboxamido)-7-(3-(piperidine-4-sulfonamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

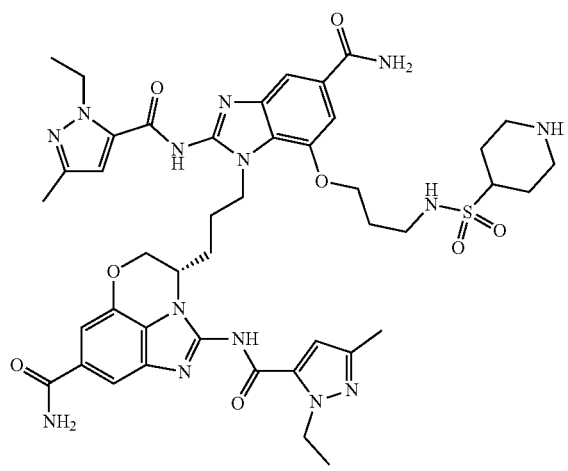 [SMILES: CCn1nc(C)cc1C(=O)Nc1nc2cc(C(N)=O)cc(OCCCNS(=O)(=O)C3CCNCC3)c2n1CCC[C@H]1COc2cc(C(N)=O)cc3nc(NC(=O)c4cc(C)nn4CC)n1c23]

Synthetic Scheme
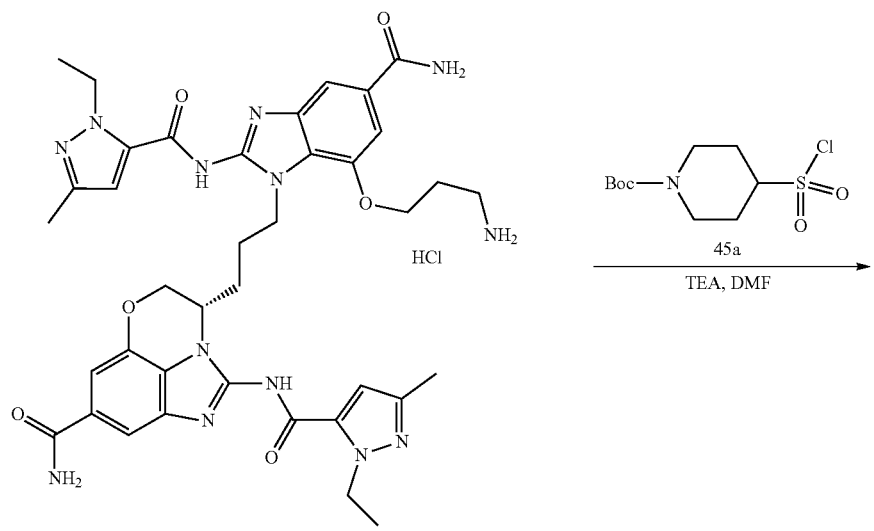
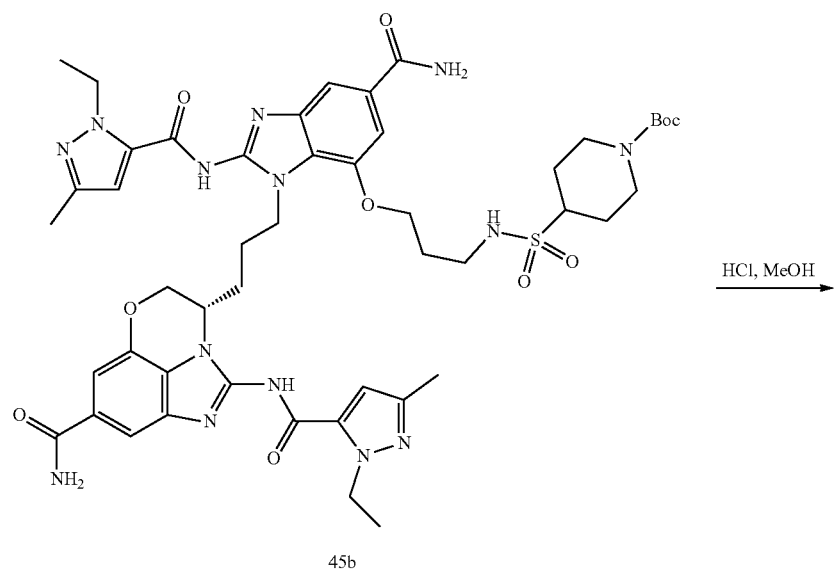

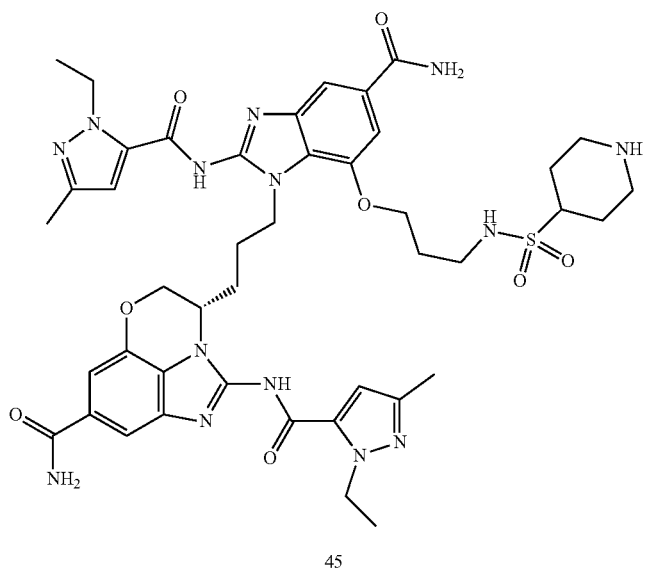

45

Step 1: To a solution of compound 14 (50 mg, 0.06 mmol) in DMF (2 mL) was added compound 45a (83 mg, 0.30 mmol) and triethylamine (50 mg, 0.50 mmol). The reaction mixture was stirred at room temperature for 16 hours. The reaction mixture was diluted with water (30 mL), and extracted with EtOAc (40 mL×3). The combined organic layers were washed with brine, dried over $Na_2SO_4$, filtered and concentrated under reduced pressure. The crude material was purified by silica gel chromatography to give compound 45b (18 mg, 28% yield) as a white solid. ESI-MS (m/z): 1027.3 $[M+H]^+$.

Step 2: To a stirring solution of 45b (18 mg, 0.02 mmol) in MeOH (5 mL) at 0° C.; was added 4M HCl in dioxane (0.05 mL, 0.20 mmol). The mixture was stirred at room temperature for 2 hours, LCMS indicated the product was formed. The mixture was concentrated, and the residue was purified by reversed phase preparative HPLC to give compound 45 (9 mg, 59% yield) as white solid. ESI-MS (m/z): 927.8 $[M+H]^+$; $^1H$ NMR (500 MHz, DMSO-$d_6$) δ 7.96 (s, 1H), 7.88 (s, 1H), 7.62 (s, 1H), 7.56 (s, 1H), 7.42-7.24 (m, 4H), 7.21-7.15 (m, 1H), 6.50 (s, 1H), 6.44 (s, 1H), 4.75-4.67 (m, 1H), 4.62-4.43 (m, 5H), 4.42-4.26 (m, 2H), 4.24-4.07 (m, 3H), 3.11-2.91 (m, 6H), 2.12-1.70 (m, 14H), 1.53-1.42 (m, 2H), 1.33-1.19 (m, 6H).

Example 46: (S)-3-(3-(5-cyano-2-(1-ethyl-3-methyl-1H-pyrazole-5-carboxamido)-7-(3-(2-morpholinoacetamido)propoxy)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

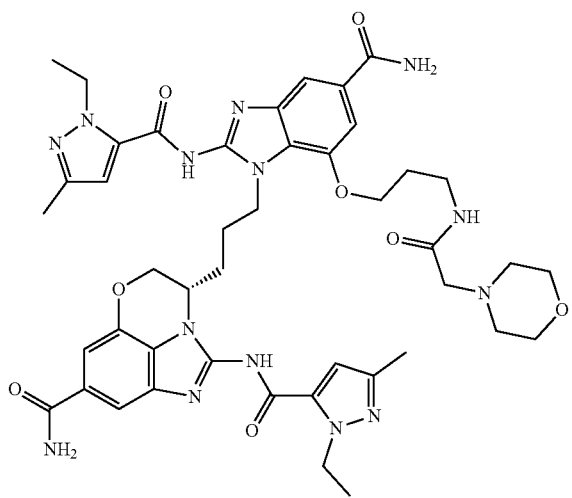 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4cc(C)nn4CC)n1c23]

259

Example 47: (S)-1-(3-(7-cyano-2-(1-ethyl-3-methyl-1H-pyrazole-5-carboxamido)-3,4-dihydro-5-oxa-1,2a-diazaacenaphthylen-3-yl)propyl)-2-(1-ethyl-3-methyl-1H-pyrazole-5-carboxamido)-7-(3-(2-morpholinoacetamido)propoxy)-1H-benzo[d]imidazole-5-carboxamide

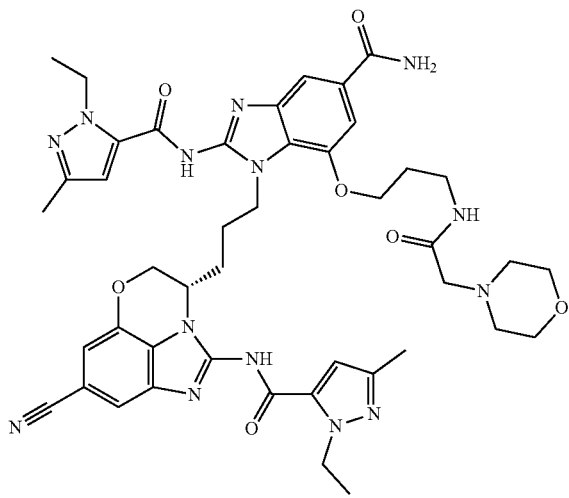 [SMILES: CCn1nc(C)cc1C(=O)Nc1nc2cc(C(N)=O)cc(OCCCNC(=O)CN3CCOCC3)c2n1CCC[C@H]1COc2cc(C#N)cc3nc(NC(=O)c4cc(C)nn4CC)n1c23]

Example 48: (S)—N-(5-cyano-1-(3-(7-cyano-2-(1-ethyl-3-methyl-1H-pyrazole-5-carboxamido)-3,4-dihydro-5-oxa-1,2a-diazaacenaphthylen-3-yl)propyl)-7-(3-(2-morpholinoacetamido)propoxy)-1H-benzo[d]imidazol-2-yl)-1-ethyl-3-methyl-1H-pyrazole-5-carboxamide

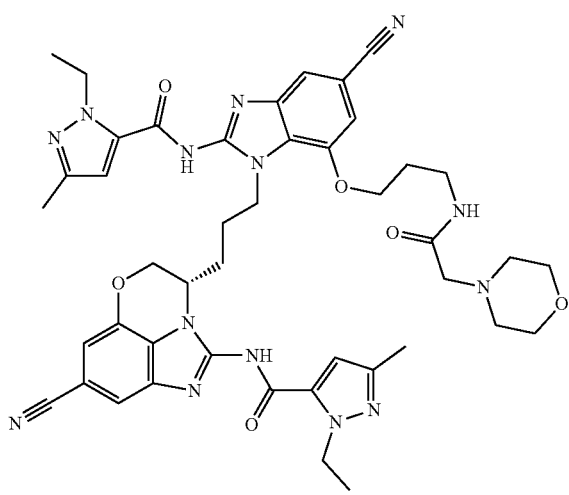 [SMILES: CCn1nc(C)cc1C(=O)Nc1nc2cc(C#N)cc(OCCCNC(=O)CN3CCOCC3)c2n1CCC[C@H]1COc2cc(C#N)cc3nc(NC(=O)c4cc(C)nn4CC)n1c23]

260

Synthetic Scheme

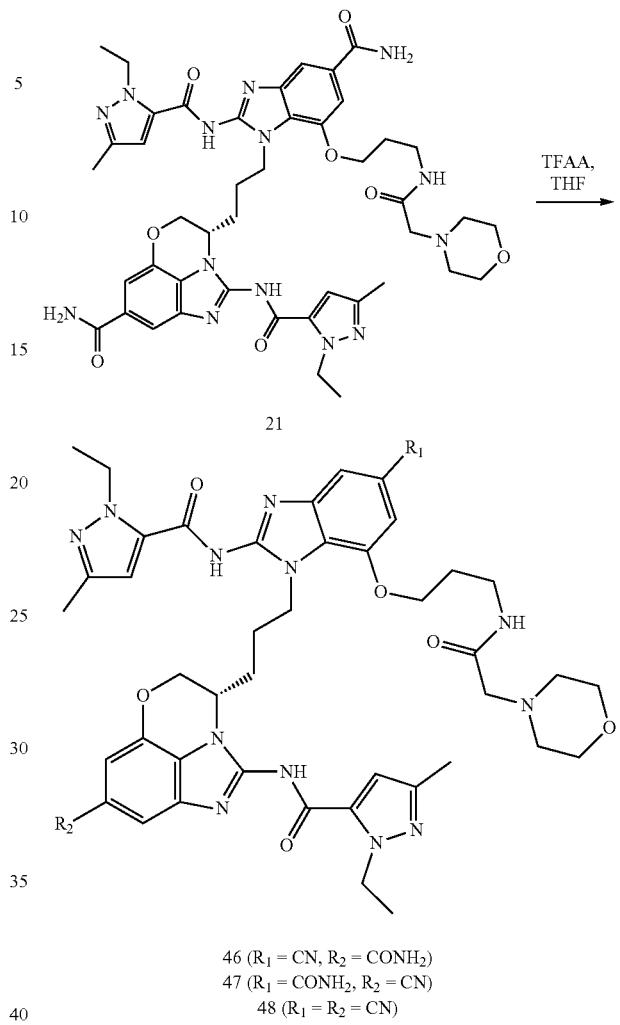

46 ($R_1$ = CN, $R_2$ = $CONH_2$)
47 ($R_1$ = $CONH_2$, $R_2$ = CN)
48 ($R_1$ = $R_2$ = CN)

Step 1: To a solution of compound 21 (100 mg, 0.11 mmol) in THF (10 mL) was added trifluoroacetic anhydride (0.31 mL, 2.2 mmol). The reaction was stirred at room temperature for 6 hours, then directly purified by reversed phase preparative HPLC to give compound 46 (5 mg, 6% yield, white solid), compound 47 (26.0 mg, 27% yield, white solid), and compound 48 (47.0 mg, 49% yield, white solid).

Compound 46: ESI-MS (m/z): 889.2 [M+H]$^+$; $^1$H NMR (500 MHz, DMSO-$d_6$) δ 12.92 (s, 1H), 12.67 (s, 1H), 7.92 (s, 1H), 7.82-7.71 (m, 1H), 7.57 (s, 1H), 7.44 (s, 1H), 7.37-7.30 (m, 2H), 7.20 (s, 1H), 6.57 (s, 1H), 6.36 (s, 1H), 4.73-4.66 (m, 1H), 4.65-4.46 (m, 5H), 4.42-4.30 (m, 2H), 4.26-4.15 (m, 1H), 4.08-3.93 (m, 2H), 3.55 (t, J=4.6 Hz, 4H), 3.20-3.08 (m, 2H), 2.81 (s, 2H), 2.34 (s, 4H), 2.10 (s, 3H), 2.05 (s, 3H), 2.01-1.88 (m, 4H), 1.76-1.60 (m, 2H), 1.35-1.21 (m, 6H).

Compound 47: ESI-MS (m/z): 889.2 [M+H]$^+$; $^1$H NMR (500 MHz, DMSO-d6) δ 7.97 (s, 1H), 7.83-7.77 (m, 1H), 7.63 (s, 1H), 7.37 (s, 1H), 7.36 (s, 1H), 7.31 (s, 1H), 7.26 (s, 1H), 6.54 (s, 1H), 6.45 (s, 1H), 4.79-4.71 (m, 1H), 4.64 (d, J=11.6 Hz, 1H), 4.60-4.45 (m, 4H), 4.43-4.32 (m, 2H), 4.29-4.22 (m, 1H), 4.13-4.01 (m, 2H), 3.54 (t, J=4.6 Hz, 4H), 3.17 (q, J=6.9 Hz, 2H), 2.82 (s, 2H), 2.38-2.32 (m, 4H), 2.09 (s, 3H), 2.05 (s, 3H), 2.03-1.90 (m, 4H), 1.83-1.73 (m, 2H), 1.32-1.24 (m, 6H).

Compound 48: ESI-MS (m/z): 871.2 [M+H]+; 1H NMR (500 MHz, DMSO-d6) δ 7.77 (t, J=6.1 Hz, 1H), 7.44 (s, 1H), 7.36 (s, 1H), 7.25 (s, 1H), 7.18 (s, 1H), 6.57 (s, 1H), 6.37 (s, 1H), 4.74-4.68 (m, 1H), 4.63 (d, J=11.6 Hz, 1H), 4.58-4.45 (m, 4H), 4.39-4.30 (m, 2H), 4.27-4.21 (m, 1H), 4.09-3.91 (m, 2H), 3.56 (t, J=4.6 Hz, 4H), 3.18-3.06 (m, 2H), 2.81 (s, 2H), 2.40-2.30 (m, 4H), 2.11 (s, 3H), 2.05 (s, 3H), 2.01-1.90 (m, 4H), 1.80-1.61 (m, 2H), 1.33-1.24 (m, 6H).
Example 49: (S)-3-(3-(5-carbamoyl-2-(1-ethyl-4-fluoro-3-methyl-1H-pyrazole-5-carboxamido)-7-(3-methoxypropoxy)-1H-benzo[d]imidazol-1-yl)propyl)-2-(1-ethyl-4-fluoro-3-methyl-1H-pyrazole-5-carboxamido)-3,4-dihydro-5-oxa-1,2a-diazaacenaphthylene-7-carboxamide
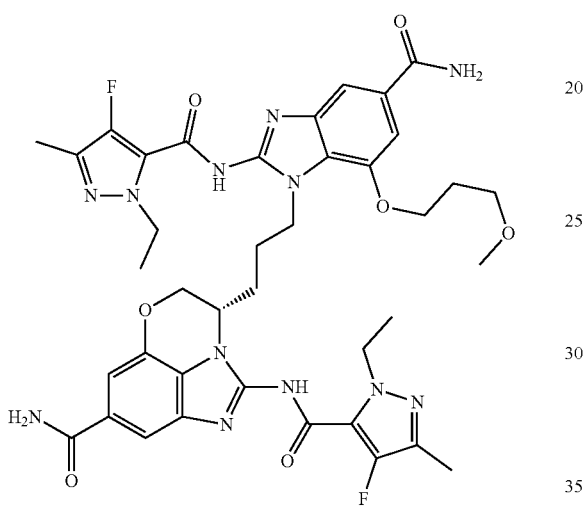
Synthetic Scheme
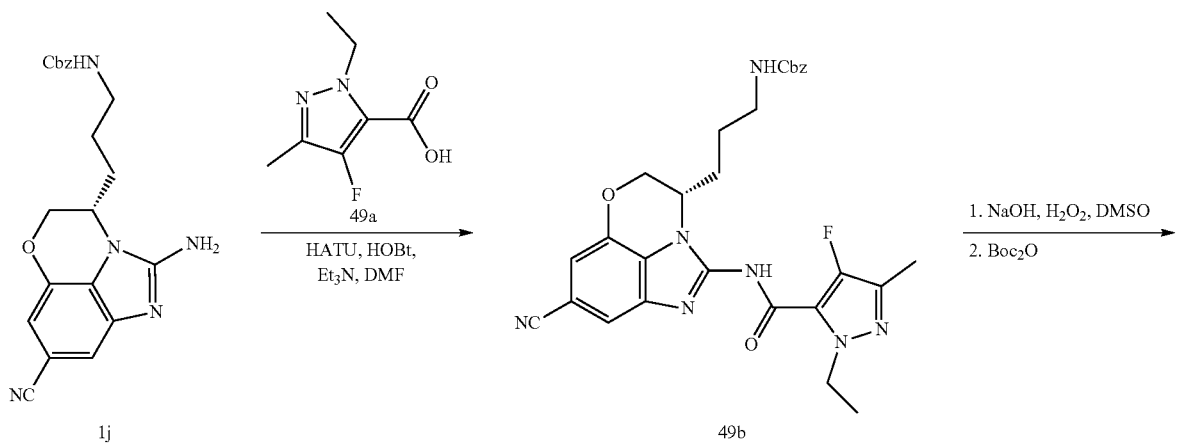

-continued
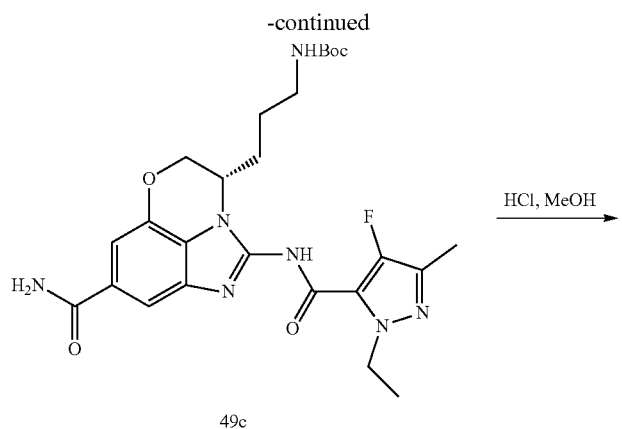
49c
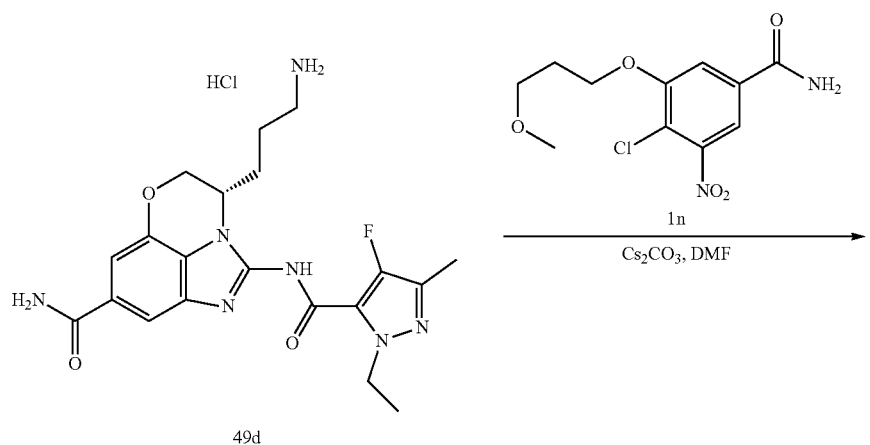
49d
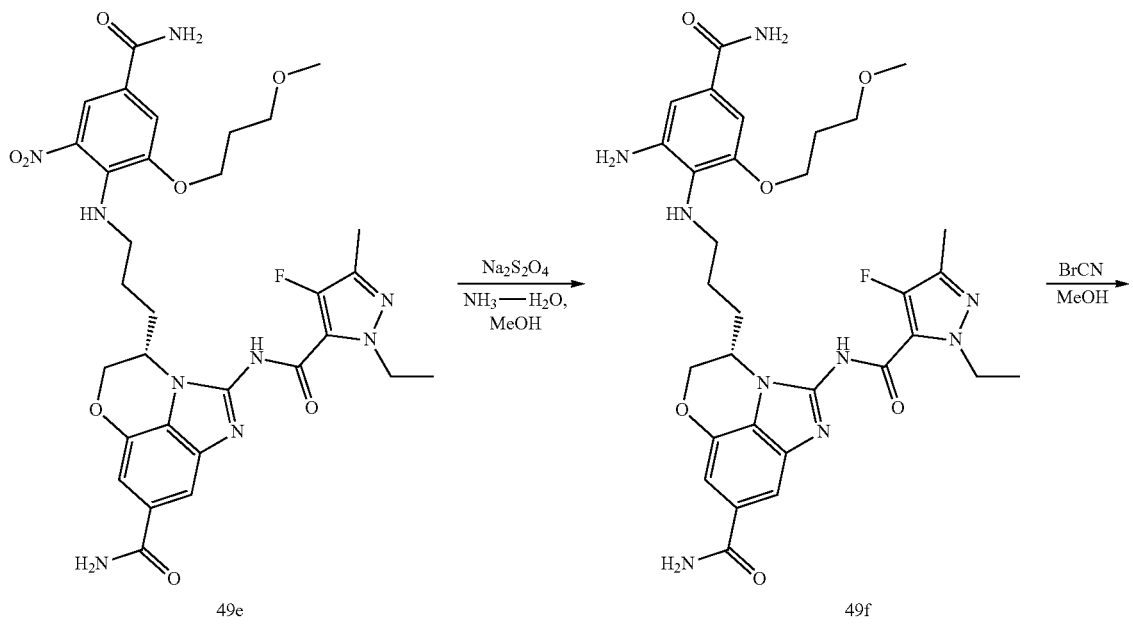
49e → 49f

-continued

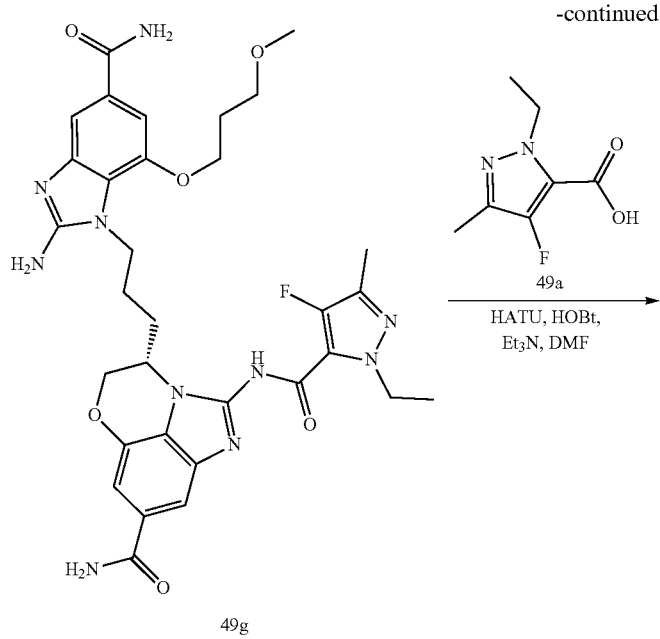

49g

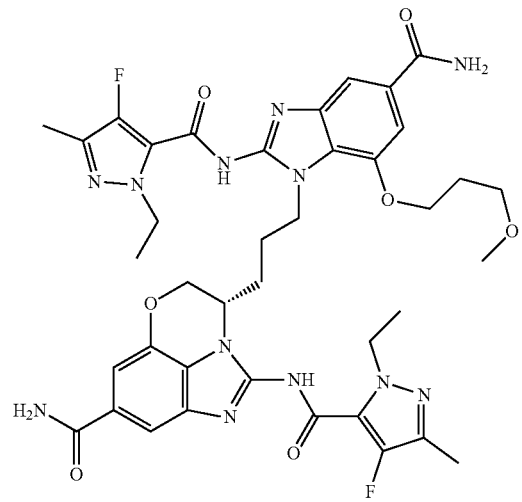 [SMILES: CCn1nc(C)c(F)c1C(=O)Nc1nc2cc(C(N)=O)cc(OCCCOC)c2n1CCC[C@H]1COc2cc(C(N)=O)cc3nc(NC(=O)c4c(F)c(C)nn4CC)n1c23]

49

Step 1: To a solution of compound 1j (200 mg, 0.51 mmol) and compound 49a (85 mg, 0.49 mmol) in DMF (4 mL) was added HATU (186 mg, 0.49 mmol), HOBt (34 mg, 0.25 mmol) and triethylamine (0.2 mL, 1.48 mmol). The mixture was stirred at room temperature overnight, LCMS indicated the product was formed. The mixture was diluted with water (50 mL) and extracted with ethyl acetate (50 mL×3). The combined organic layers were washed with brine, dried over $Na_2SO_4$, filtered and concentrated under reduced pressure. The residue was purified by silica gel chromatography to give compound 49b (253 mg, 90% yield) as yellow solid. ESI-MS (m/z): 546.4 $[M+H]^+$.

Step 2: To a stirring solution of 49b (250 mg, 0.46 mmol) in DMSO (5 mL) was added solid NaOH (55 mg, 1.37 mmol). The reaction mixture was heated at 60° C., and hydrogen peroxide (30 wt. %, 3 mL) was added dropwise into the reaction mixture. The reaction was stirred at 60° C.; for 30 minutes, then cooled to room temperature. $Boc_2O$ (100 mg, 0.46 mmol) was added to the reaction mixture, and the reaction was stirred at room temperature for half an hour. LCMS indicated the product was formed. The reaction mixture was diluted with water (50 mL) and extracted with EtOAc (50 mL×3). The combined organic layers were dried over $Na_2SO_4$, filtered and concentrated. The residue was purified by silica gel chromatography to give compound 49c (210 mg, 86% yield) as white solid. ESI-MS (m/z): 530.1 $[M+H]^+$.

Step 3: To a stirring solution of 49c (210 mg, 0.39 mmol) in MeOH (10 mL) was added 4M HCl in dioxane (0.5 mL, 2 mmol). The mixture was stirred at room temperature for 1 hour, LCMS indicated the product was formed. The reaction mixture was concentrated to give compound 49d (175 mg) as white solid. ESI-MS (m/z): 430.3$[M+H]^+$.

Step 4: To a stirring solution of 49d (175 mg, from step 3) and compound 1n (162 mg, 0.56 mmol) in DMF (4 mL) was added $Cs_2CO_3$ (240 mg, 0.74 mmol). The reaction mixture was heated at 70° C.; overnight, and LCMS indicated the reaction was complete. The reaction mixture was diluted with water (50 mL), and extracted with EtOAc (50 mL×3). The combined organic layers were dried over $Na_2SO_4$, filtered and concentrated. The residue was purified directly by silica gel chromatography to give compound 49e (188 mg, 71% yield for 2 steps) as white solid. ESI-MS (m/z): 682.1 $[M+H]^+$.

Step 5: Compound 49e (188 mg, 0.28 mmol) was dissolved in a mixture of MeOH (15 mL) and concentrated ammonium hydroxide (1 mL). Sodium dithionite (245 mg, 1.41 mmol) was dissolved in water (3 mL) and added dropwise to the reaction mixture at room temperature. Stirring was continued at room temperature for 30 minutes, and LCMS indicated the product was formed. The reaction mixture was diluted with water (70 mL), and extracted with EtOAc (80 mL×3). The combined organic layers were washed with brine, dried over $Na_2SO_4$, filtered, and concentrated to give compound 49f (142 mg) as white solid, which was used directly without further purification. ESI-MS (m/z): 652.5 $[M+H]^+$.

Step 6: Compound 49f (47 mg) was dissolved in MeOH (10 mL), and cyanogen bromide (40 mg, 0.38 mmol) was added. The resulting mixture was stirred at room temperature overnight, LCMS indicated the product was formed. The mixture was concentrated in vacuo to remove the solvent. The residue was suspended in EtOAc (45 mL), and washed with saturated $Na_2CO_3$ solution. The aqueous layer was extracted with EtOAc (30 mL×2), the combined organic layers were washed with brine, dried over $Na_2SO_4$, filtered and concentrated. The residue was purified by silica gel chromatography to give compound 49g (41 mg, 67% yield for 2 steps) as white solid. ESI-MS (m/z): 677.1 $[M+H]^+$.

Step 7: To a solution of compound 49g (41 mg, 0.06 mmol) and compound 49a (11 mg, 0.06 mmol) in DMF (1.5 mL) was added HATU (22 mg, 0.06 mmol), HOBt (4 mg, 0.03 mmol) and trimethylamine (20 mg, 0.19 mmol). The reaction mixture was stirred at room temperature overnight. LCMS indicated the reaction was complete. The reaction mixture was purified directly by reversed phase preparative HPLC to give compound 49 (26 mg, 52% yield) as white solid.

ESI-MS (m/z): 831.3 $[M+H]^+$; $^1$H NMR (500 MHz, DMSO-d6) δ 12.77 (br s, 2H), 7.98 (s, 1H), 7.92 (s, 1H), 7.64 (s, 1H), 7.59 (s, 1H), 7.35-7.30 (m, 4H), 4.70-4.63 (m, 1H), 4.59 (d, J=11.5 Hz, 1H), 4.53-4.44 (m, 4H), 4.38-4.30 (m, 2H), 4.25 (d, J=9.5 Hz, 1H), 4.20-4.07 (m, 2H), 3.37-3.34 (m, 2H), 3.16 (s, 3H), 2.09 (s, 3H), 2.07 (s, 3H), 2.02-1.79 (m, 6H), 1.30-1.23 (m, 6H).

Example 50: (S)-3-(3-(5-carbamoyl-2-(1-ethyl-3-methyl-1H-pyrazole-5-carboxamido)-7-(3-methoxy-propoxy)-1H-benzo[d]imidazol-1-yl)propyl)-2-(1-ethyl-4-fluoro-3-methyl-1H-pyrazole-5-carboxamido)-3,4-dihydro-5-oxa-1,2a-diazaacenaphthylene-7-carboxamide

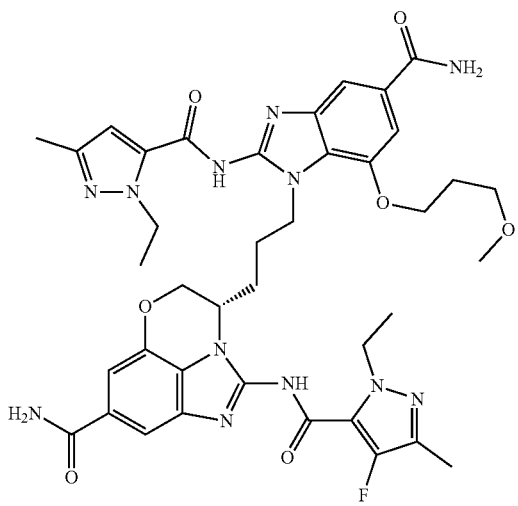 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(F)c(C)nn4CC)n1c23]

Synthetic Scheme

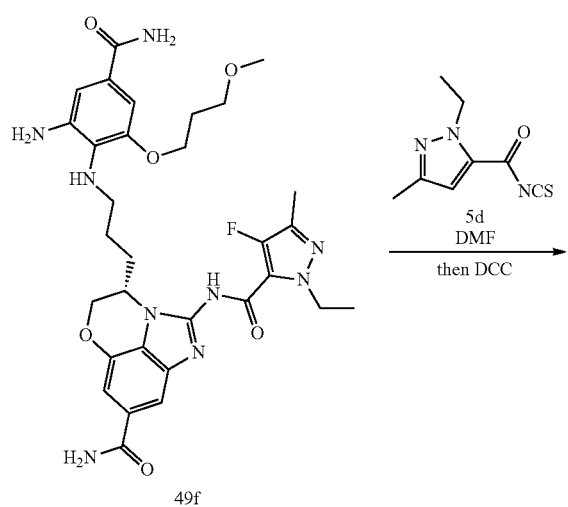

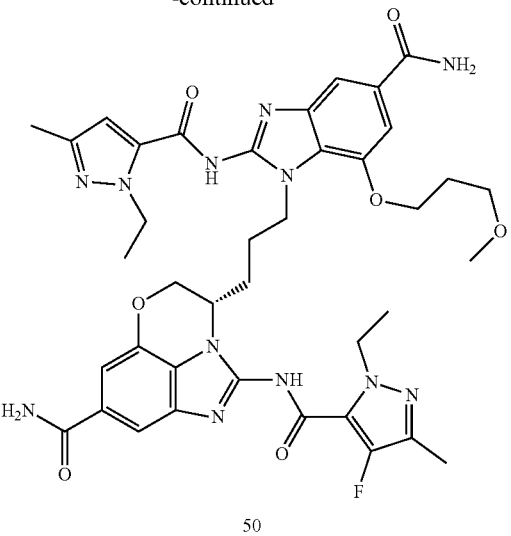

50

Step 1: Compound 49f (45 mg, 0.07 mmol) was dissolved in DMF (1.5 mL), and then compound 5d (1 M in dioxane, 0.1 mL, 0.10 mmol) was added. The reaction mixture was stirred at room temperature for 30 minutes, DCC (26 mg, 0.14 mmol) was added, and the mixture was heated at k, 80° C. for 1 hour, LCMS indicated the product was formed. The reaction mixture was purified directly by reversed phase preparative HPLC to give compound 50 (28 mg, 50% yield) as a white solid. ESI-MS (m/z): 813.2 [M+H]$^+$; $^1$H NMR (500 MHz, DMSO-d6) δ 12.77 (br s, 1H), 7.97 (s, 1H), 7.92 (s, 1H), 7.64 (s, 1H), 7.59 (s, 1H), 7.36-7.28 (m, 4H), 6.55 (s, 1H), 4.70-4.65 (m, 1H), 4.63-4.43 (m, 5H), 4.41-4.30 (m, 2H), 4.28-4.23 (m, 1H), 4.20-4.08 (m, 2H), 3.38-3.33 (m, 2H), 3.16 (s, 3H), 2.11 (s, 3H), 2.08 (s, 3H), 2.02-1.82 (m, 6H), 1.33-1.25 (m, 6H).

Example 51: (S)-3-(3-(7-(3-aminopropoxy)-5-carbamoyl-2-(1-ethyl-3-methyl-1H-pyrazole-5-carboxamido)-1H-benzo[d]imidazol-1-yl)propyl)-2-(1-ethyl-4-fluoro-3-methyl-1H-pyrazole-5-carboxamido)-3,4-dihydro-5-oxa-1,2a-diazaacenaphthylene-7-carboxamide hydrochloride

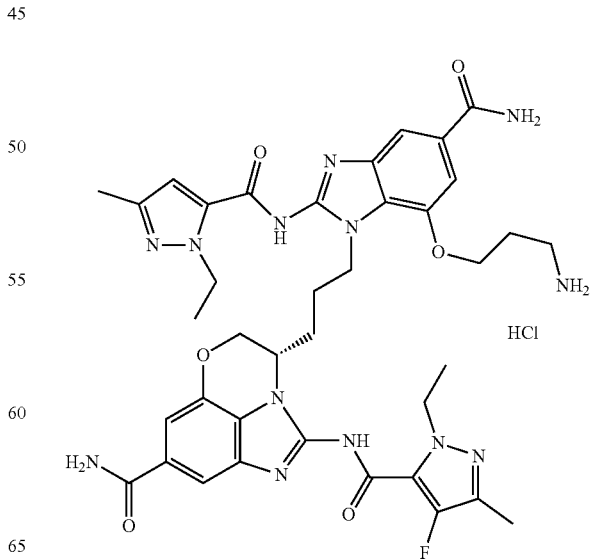

Synthetic Scheme

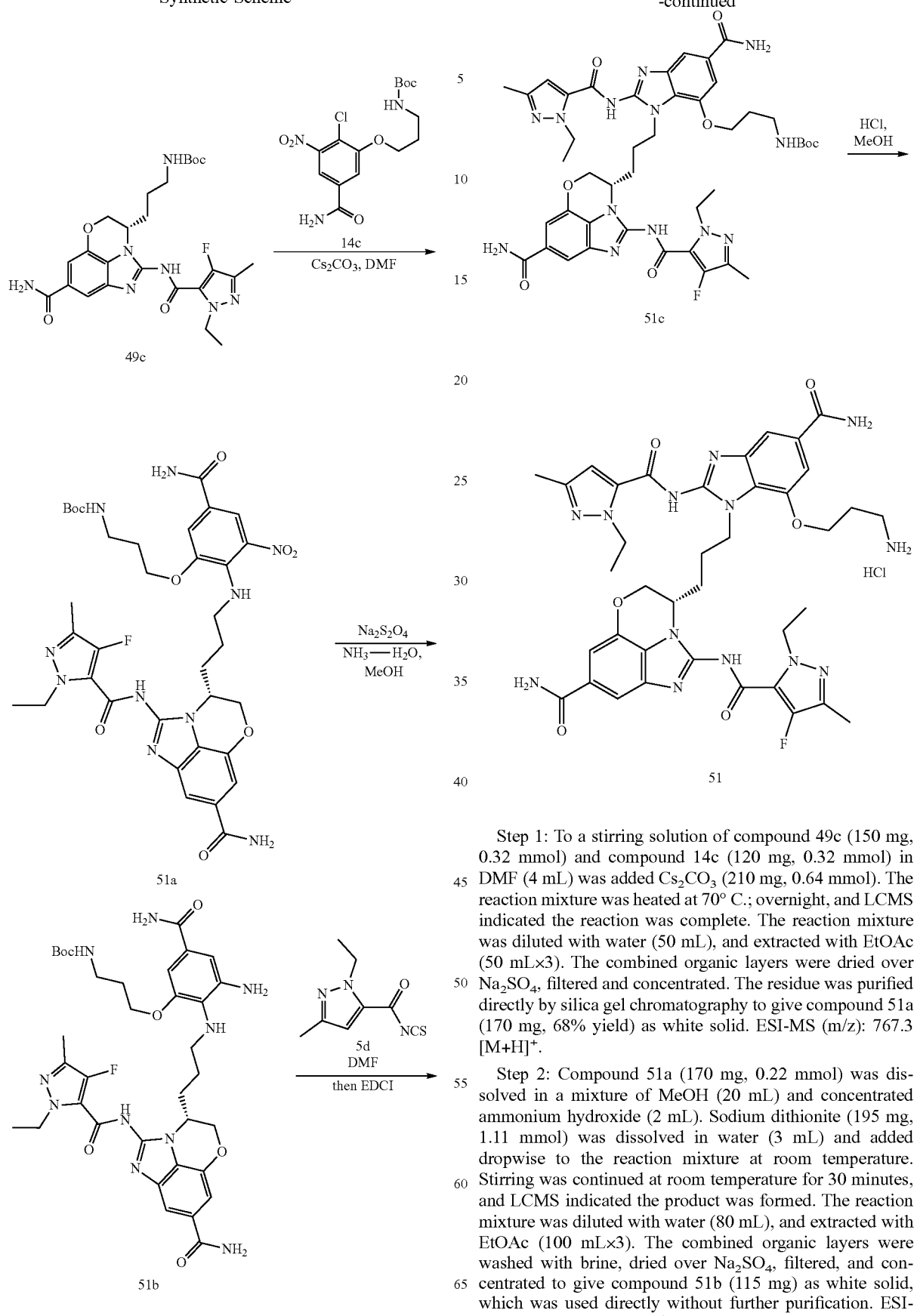

Step 1: To a stirring solution of compound 49c (150 mg, 0.32 mmol) and compound 14c (120 mg, 0.32 mmol) in DMF (4 mL) was added $Cs_2CO_3$ (210 mg, 0.64 mmol). The reaction mixture was heated at 70° C.; overnight, and LCMS indicated the reaction was complete. The reaction mixture was diluted with water (50 mL), and extracted with EtOAc (50 mL×3). The combined organic layers were dried over $Na_2SO_4$, filtered and concentrated. The residue was purified directly by silica gel chromatography to give compound 51a (170 mg, 68% yield) as white solid. ESI-MS (m/z): 767.3 $[M+H]^+$.

Step 2: Compound 51a (170 mg, 0.22 mmol) was dissolved in a mixture of MeOH (20 mL) and concentrated ammonium hydroxide (2 mL). Sodium dithionite (195 mg, 1.11 mmol) was dissolved in water (3 mL) and added dropwise to the reaction mixture at room temperature. Stirring was continued at room temperature for 30 minutes, and LCMS indicated the product was formed. The reaction mixture was diluted with water (80 mL), and extracted with EtOAc (100 mL×3). The combined organic layers were washed with brine, dried over $Na_2SO_4$, filtered, and concentrated to give compound 51b (115 mg) as white solid, which was used directly without further purification. ESI-MS (m/z): 737.5 $[M+H]^+$.

Step 3: Compound 51b (115 mg, from step 2) was dissolved in 1, 4-dioxane (6 mL), and then compound 5d (1 M in dioxane, 0.2 mL, 0.2 mmol) was added. The reaction mixture was stirred at room temperature for 30 minutes, DCC (57 mg, 0.30 mmol) was added, and the mixture was heated at 80° C. for 1 hour, LCMS indicated the product was formed. The reaction mixture was concentrated, and the residue was purified by silica gel chromatography to give compound 51c (91 mg, 46% yield for 2 steps) as white solid. ESI-MS (m/z): 898.1 [M+H]+.

Step 4: To a stirring solution of 51c (91 mg, 0.10 mmol) in MeOH (6 mL) was added 4M HCl in dioxane (0.13 mL, 0.52 mmol). The mixture was stirred at room temperature for 1 hour, LCMS indicated the product was formed. The reaction mixture was concentrated to give compound 49d (72 mg, 86% yield) as white solid. ESI-MS (m/z): 798.7 [M+H]+; $^1$H NMR (500 MHz, DMSO-d6) δ 8.33 (s, 2H), 8.01 (s, 1H), 7.94 (s, 1H), 7.64 (s, 1H), 7.58 (s, 1H), 7.41-7.28 (m, 4H), 6.52 (s, 1H), 4.71-4.64 (m, 1H), 4.61 (d, J=11.5 Hz, 1H), 4.56-4.14 (m, 9H), 2.84 (t, J=6.9 Hz, 2H), 2.08 (s, 3H), 2.07 (s, 3H), 2.01-1.87 (m, 6H), 1.29-1.23 (m, 6H).

Example 52: (S)-3-(3-(5-carbamoyl-7-(3-(2-(dimethylamino)acetamido)propoxy)-2-(1-ethyl-3-methyl-1H-pyrazole-5-carboxamido)-1H-benzo[d]imidazol-1-yl)propyl)-2-(1-ethyl-4-fluoro-3-methyl-1H-pyrazole-5-carboxamido)-3,4-dihydro-5-oxa-1,2a-diazaacenaphthylene-7-carboxamide Synthetic Scheme

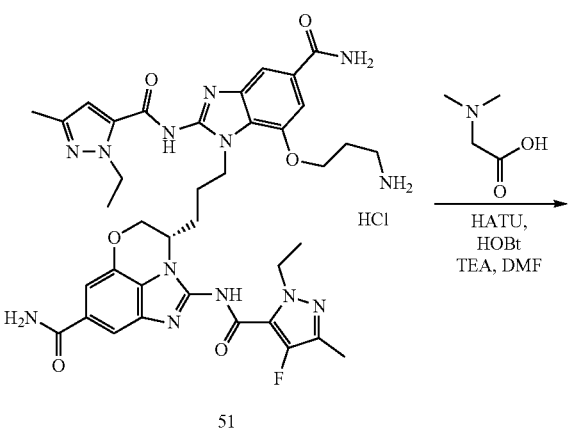

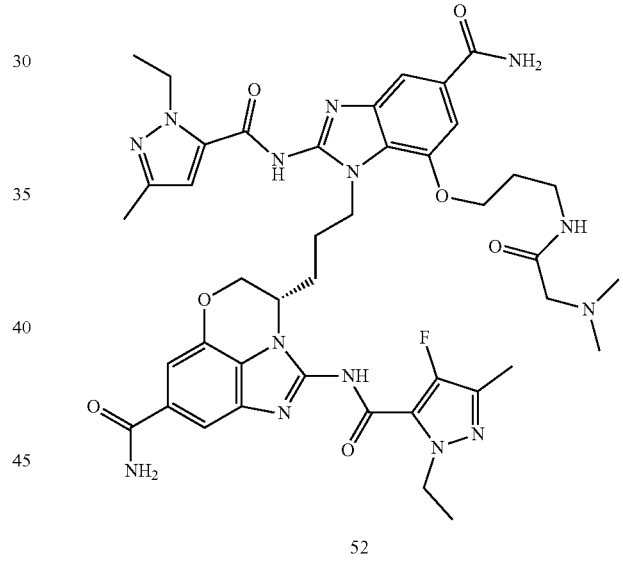

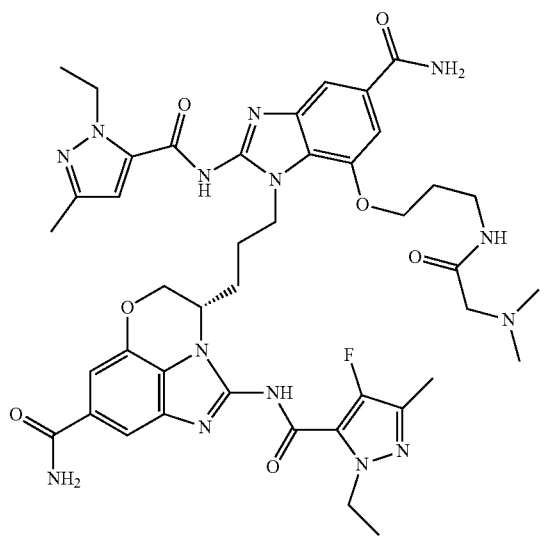 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(F)c(C)nn4CC)n1c23]

Step 1: To a solution of compound 51 (35 mg, 0.04 mmol) and N, N-dimethylglycine (5 mg, 0.05 mmol) in DMF (1.5 mL) was added HATU (15 mg, 0.04 mmol), HOBt (3 mg, 0.02 mmol) and trimethylamine (12 mg, 0.12 mmol). The reaction mixture was stirred at room temperature overnight. LCMS indicated the reaction was complete. The reaction mixture was purified directly by reversed phase preparative HPLC to give compound 52 (29 mg, 78% yield) as a white solid. ESI-MS (m/z): 883.8 [M+H]+; $^1$H NMR (500 MHz, DMSO-d6) δ 12.81 (br s, 1H), 12.76 (br s, 1H), 8.14 (s, 1H), 8.05 (s, 1H), 7.95 (s, 1H), 7.92 (s, 1H), 7.63 (s, 1H), 7.58 (s, 1H), 7.36-7.30 (m, 4H), 6.52 (s, 1H), 4.70-4.65 (m, 1H), 4.61 (d, J=11.0 Hz, 1H), 4.58-4.30 (m, 6H), 4.25 (d, J=9.5 Hz, 1H), 4.17-4.05 (m, 2H), 3.25-3.20 (m, 2H), 3.13 (br s, 2H), 2.34 (s, 6H), 2.09 (s, 3H), 2.07 (s, 3H), 2.05-1.90 (m, 4H), 1.86-1.76 (m, 2H), 1.31-1.23 (m, 6H).

Example 53: (S)-3-(3-(5-carbamoyl-2-(1-ethyl-3-methyl-1H-pyrazole-5-carboxamido)-7-(3-(2-morpholino acetamido)propoxy)-1H-benzo[d]imidazol-1-yl)propyl)-2-(1-ethyl-4-fluoro-3-methyl-1H-pyrazole-5-carboxamido)-3,4-dihydro-5-oxa-1,2a-diazaacenaphthylene-7-carboxamide

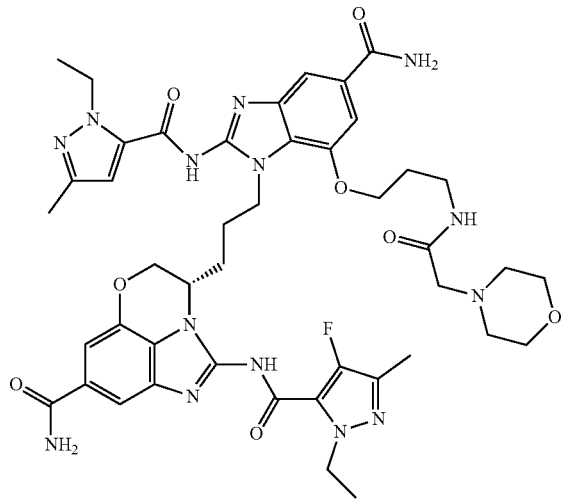 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(F)c(C)nn4CC)n1c23]

Synthetic Scheme

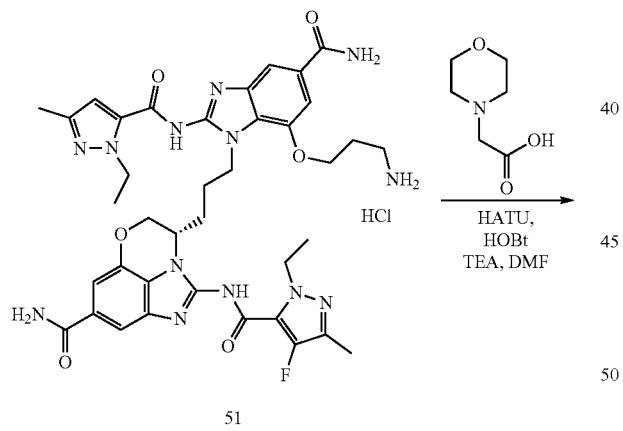

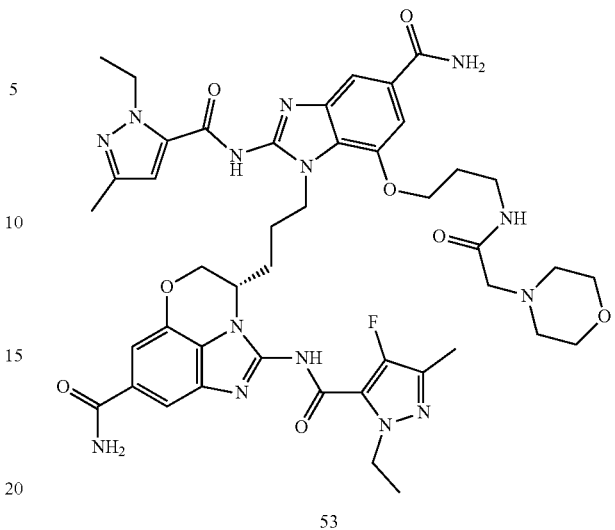

53

Step 1: To a solution of compound 51 (35 mg, 0.04 mmol) and 2-morpholinoacetic acid (6 mg, 0.04 mmol) in DMF (1.5 mL) was added HATU (15 mg, 0.04 mmol), HOBt (3 mg, 0.02 mmol) and trimethylamine (12 mg, 0.12 mmol). The reaction mixture was stirred at room temperature overnight. LCMS indicated the reaction was complete. The reaction mixture was purified directly by reversed phase preparative HPLC to give compound 53 (31 mg, 81% yield) as a white solid. ESI-MS (m/z): 925.8 [M+H]$^+$; $^1$H NMR (500 MHz, DMSO-d6) δ 12.81 (s, 1H), 12.75 (s, 1H), 8.14 (s, 1H), 7.95 (s, 1H), 7.93 (s, 1H), 7.63 (s, 1H), 7.58 (s, 1H), 7.38-7.29 (m, 4H), 6.53 (s, 1H), 4.70-4.30 (m, 8H), 4.25 (d, J=9.5 Hz, 1H), 4.15-4.04 (m, 2H), 3.58 (br s, 4H), 3.22 (q, J=6.0 Hz, 2H), 2.85 (br s, 2H), 2.37 (br s, 2H), 2.09 (s, 3H), 2.07 (s, 3H), 2.05-1.90 (m, 4H), 1.86-1.76 (m, 2H), 1.31-1.21 (m, 6H).

Example 54: (S)-3-(3-(5-carbamoyl-7-(3-(2-(dimethylamino)acetamido)propoxy)-2-(1-ethyl-3-methyl-1H-pyrazole-5-carboxamido)-1H-benzo[d]imidazol-1-yl)propyl)-2-(4-chloro-1-ethyl-3-methyl-1H-pyrazole-5-carboxamido)-3,4-dihydro-5-oxa-1,2a-diazaacenaphthylene-7-carboxamide
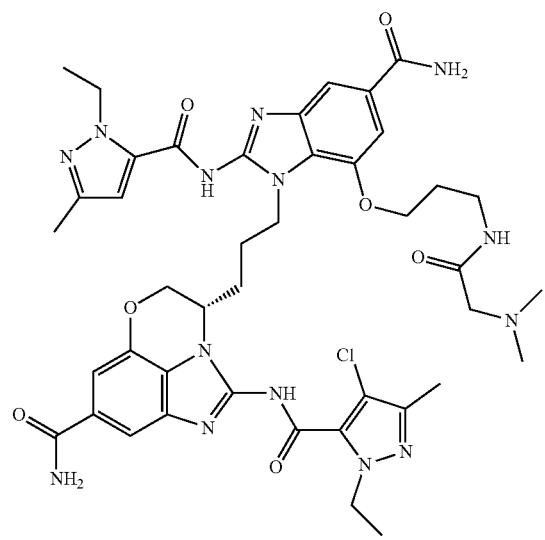 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(Cl)c(C)nn4CC)n1c23]
Synthetic Scheme
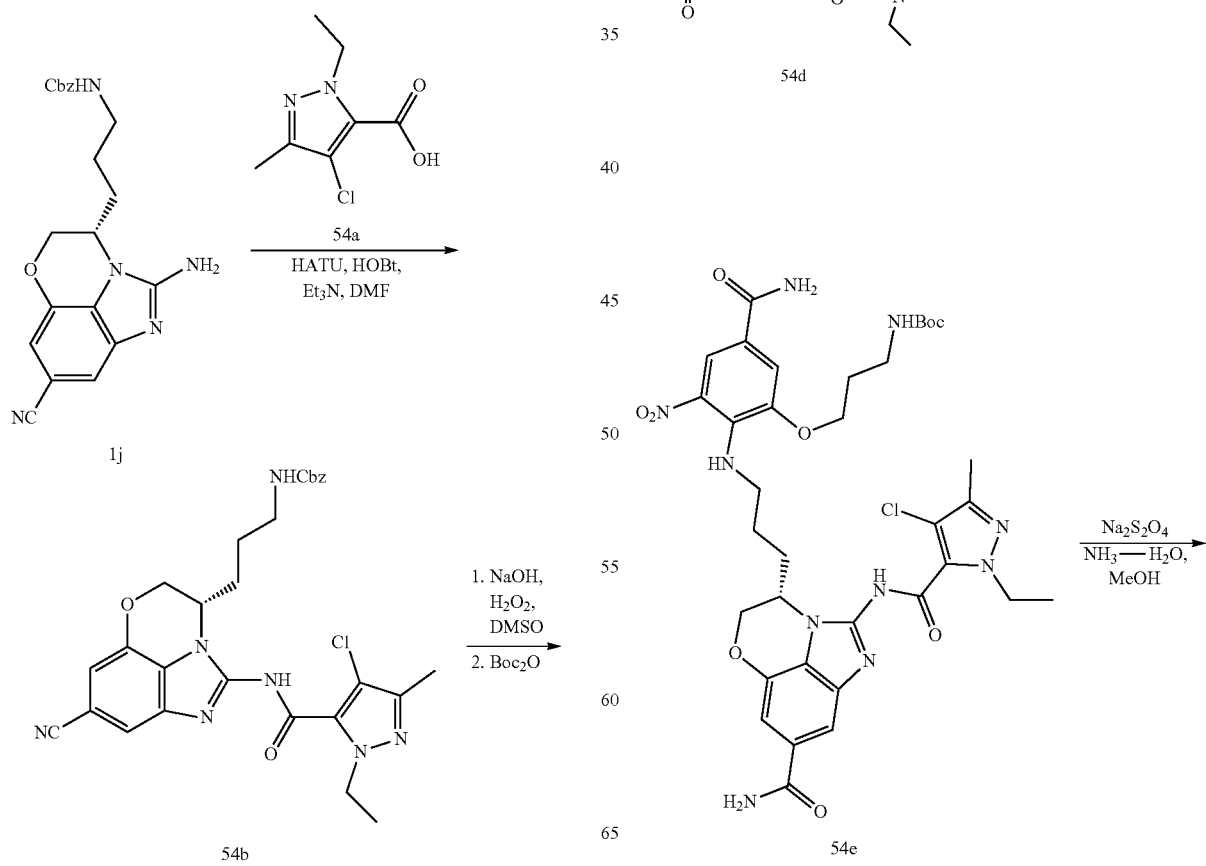

277
-continued

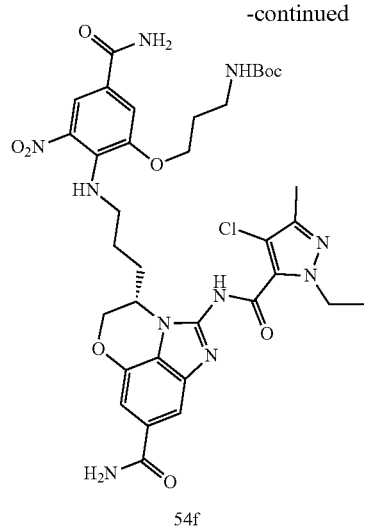

54f

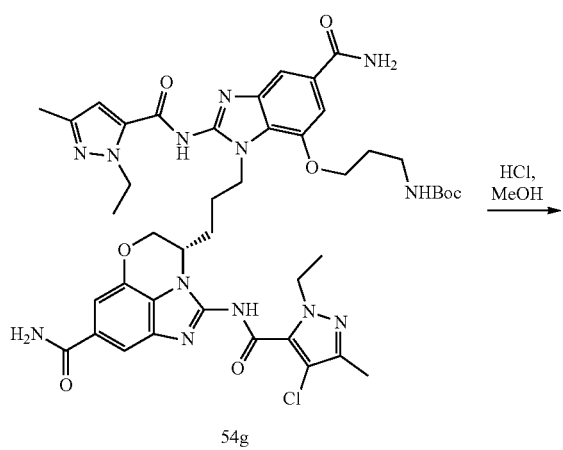

54g

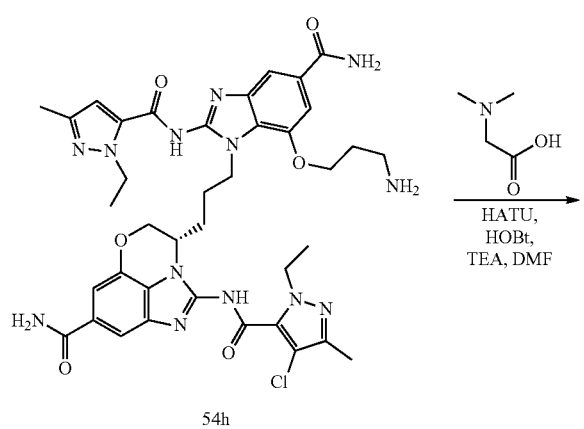

54h

278
-continued

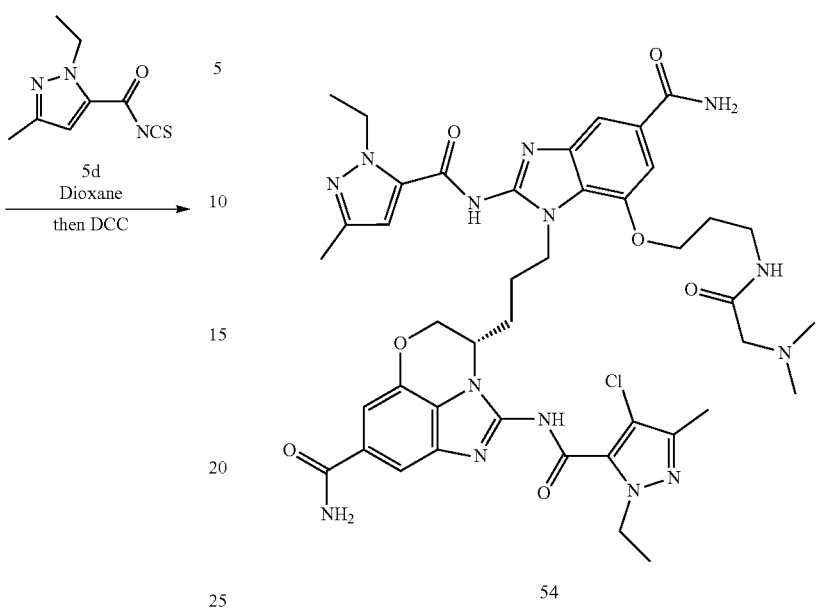

54

Step 1: To a solution of compound 1j (500 mg, 1.28 mmol) and compound 54a (240 mg, 1.28 mmol) in DMF (4 mL) was added HATU (486 mg, 1.28 mmol), HOBt (86 mg, 0.64 mmol) and triethylamine (0.50 mL). The mixture was stirred at room temperature overnight, LCMS indicated the product was formed. The mixture was diluted with water (50 mL) and extracted with ethyl acetate (70 mL×3). The combined organic layers were washed with brine, dried over $Na_2SO_4$, filtered and concentrated under reduced pressure. The residue was purified by silica gel chromatography to give compound 54b (552 mg, 77% yield) as a yellow solid. ESI-MS (m/z): 562.3 $[M+H]^+$.

Step 2: To a stirring solution of 54b (552 mg, 0.98 mmol) in DMSO (8 mL) was added solid NaOH (118 mg, 2.95 mmol). The reaction mixture was heated at 60° C., and hydrogen peroxide (30 wt. %, 5 mL) was added dropwise into the reaction mixture. The reaction was stirred at 60° C. for 30 minutes, then cooled to room temperature. $Boc_2O$ (215 mg, 0.99 mmol) was added to the reaction mixture, and the reaction was stirred at room temperature for half an hour. LCMS indicated the product was formed. The reaction mixture was diluted with water (60 mL) and extracted with EtOAc (80 mL×3). The combined organic layers were dried over $Na_2SO_4$, filtered and concentrated. The residue was purified by silica gel chromatography to give compound 54c (439 mg, 82% yield) as white solid. ESI-MS (m/z): 546.7 $[M+H]^+$.

Step 3: To a stirring solution of 54c (439 mg, 0.81 mmol) in MeOH (10 mL) was added 4M HCl in dioxane (1.0 mL, 4.0 mmol). The mixture was stirred at room temperature for 1 hour, LCMS indicated the product was formed. The reaction mixture was concentrated to give compound 54d (360 mg) as a yellow solid, which was used directly without further purification. ESI-MS (m/z): 446.5 $[M+H]^+$.

Step 4: To a stirring solution of compound 54d (360 mg, from step 3) and compound 1n (335 mg, 0.89 mmol) in DMF (4 mL) was added Cs$_2$CO$_3$ (485 mg, 1.49 mmol). The reaction mixture was heated at 70° C.; overnight, and LCMS indicated the reaction was complete. The reaction mixture was diluted with water (70 mL), and extracted with EtOAc (90 mL×3). The combined organic layers were dried over Na$_2$SO$_4$, filtered and concentrated. The residue was purified directly by silica gel chromatography to give compound 54e (351 mg, 56% yield for 2 steps) as a red solid. ESI-MS (m/z): 783.5 [M+H]$^+$.

Step 5: Compound 54e (351 mg, 0.45 mmol) was dissolved in a mixture of MeOH (25 mL) and concentrated ammonium hydroxide (2 mL). Sodium dithionite (390 mg, 2.24 mmol) was dissolved in water (4 mL) and added dropwise to the reaction mixture at room temperature. Stirring was continued at room temperature for 30 minutes, and LCMS indicated the product was formed. The reaction mixture was diluted with water (90 mL), and extracted with EtOAc (100 mL×3). The combined organic layers were washed with brine, dried over Na$_2$SO$_4$, filtered, and concentrated to give compound 54f (253 mg) as yellow solid, which was used directly without further purification. ESI-MS (m/z): 753.6[M+H]$^+$.

Step 6: Compound 54f (253 mg, from step 5) was dissolved in 1, 4-dioxane (15 mL), and then compound 5d (1 M in dioxane, 0.4 mL, 0.40 mmol) was added. The reaction mixture was stirred at room temperature for 30 minutes, DCC (125 mg, 0.66 mmol) was added, and the mixture was heated at 80° C.; for 1 hour, LCMS indicated the product was formed. The reaction mixture was concentrated, and the residue was purified by silica gel chromatography to give compound 54g (245 mg, 60% yield for two steps) as white solid. ESI-MS (m/z): 914.3 [M+H]$^+$.

Step 7: To a stirring solution of 54 g (245 mg, 0.27 mmol) in MeOH (15 mL) was added 4M HCl in dioxane (0.33 mL, 1.33 mmol). The mixture was stirred at room temperature for 1 hour, LCMS indicated the product was formed. The reaction mixture was concentrated to give compound 54h (209 mg) as a white solid as white solid, which was used directly without further purification. ESI-MS (m/z): 814.7 [M+H]$^+$.

Step 8: To a solution of compound 54h (105 mg, from step 7) and N, N-dimethylglycine (13 mg, 0.12 mmol) in DMF (1.5 mL) was added HATU (46 mg, 0.12 mmol), HOBt (8 mg, 0.06 mmol) and trimethylamine (36 mg, 0.36 mmol). The reaction mixture was stirred at room temperature overnight. LCMS indicated the reaction was complete. The reaction mixture was purified directly by reversed phase preparative HPLC to give compound 54 (50 mg, 42% yield for 2 steps) as a white solid. ESI-MS (m/z): 899.8 [M+H]$^+$; $^1$H NMR (500 MHz, DMSO) δ 12.79 (br s, 2H), 8.14 (s, 1H), 7.95 (s, 1H), 7.91 (s, 1H), 7.82 (t, J=5.7 Hz, 1H), 7.62 (s, 1H), 7.58 (s, 1H), 7.37-7.27 (m, 4H), 6.51 (s, 1H), 4.70-4.63 (m, 2H), 4.58-4.29 (m, 6H), 4.23 (d, J=9.5 Hz, 1H), 4.17-4.03 (m, 2H), 3.20 (q, J=6.5 Hz, 2H), 2.81 (s, 2H), 2.16 (s, 6H), 2.09 (s, 6H), 2.04-1.88 (m, 4H), 1.85-1.77 (m, 2H), 1.31-1.22 (m, 6H).

Example 55: (S)-3-(3-(5-carbamoyl-2-(1-ethyl-3-methyl-1H-pyrazole-5-carboxamido)-7-(3-(2-morpholino acetamido)propoxy)-1H-benzo[d]imidazol-1-yl)propyl)-2-(4-chloro-1-ethyl-3-methyl-1H-pyrazole-5-carboxamido)-3,4-dihydro-5-oxa-1,2a-diazaacenaphthylene-7-carboxamide

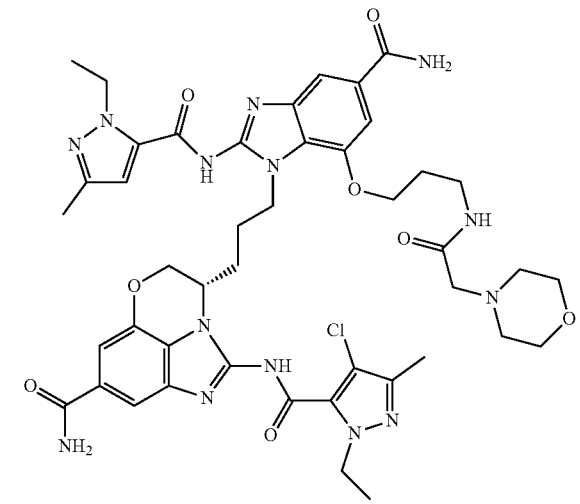 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(Cl)c(C)nn4CC)n1c23]

Synthetic Scheme

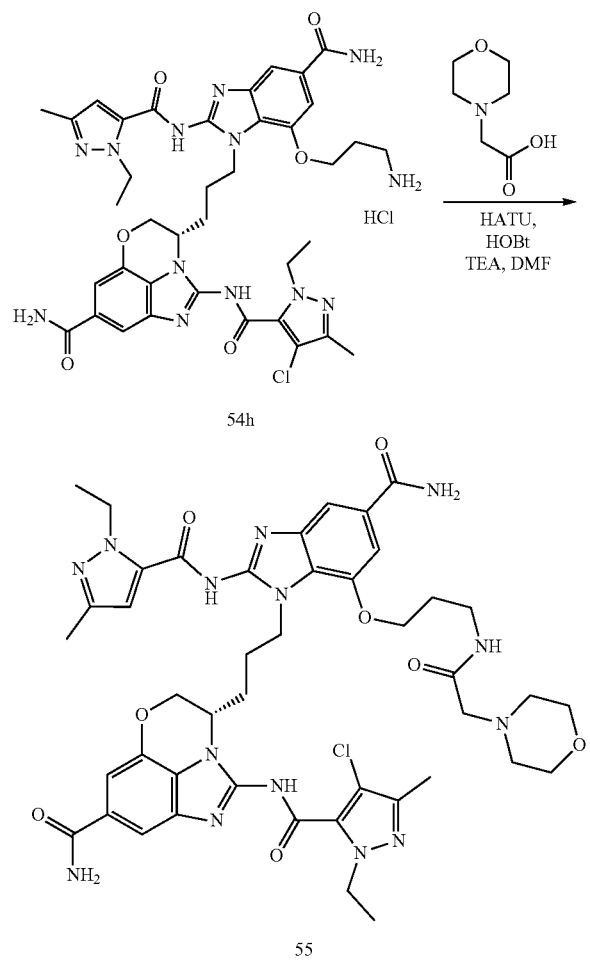

54h

55

Step 1: To a solution of compound 54h (105 mg, from step 7 of example 54) and 2-morpholinoacetic acid (18 mg, 0.12 mmol) in DMF (3 mL) was added HATU (46 mg, 0.12 mmol), HOBt (8 mg, 0.06 mmol) and trimethylamine (36 mg, 0.36 mmol). The reaction mixture was stirred at room temperature overnight. LCMS indicated the reaction was complete. The reaction mixture was purified directly by reversed phase preparative HPLC to give compound 55 (47 mg, 41% yield for 2 steps) as white solid. ESI-MS (m/z): 941.8 [M+H]$^+$; $^1$H NMR (500 MHz, DMSO-d6) δ 12.79 (s, 2H), 8.13 (s, 1H), 7.95 (s, 1H), 7.91 (s, 1H), 7.78 (s, 1H), 7.62 (s, 1H), 7.58 (s, 1H), 7.37-7.28 (m, 4H), 6.51 (s, 1H), 4.69-4.62 (m, 2H), 4.59-4.30 (m, 6H), 4.23 (d, J=9.8 Hz, 1H), 4.15-4.01 (m, 2H), 3.57-3.49 (m, 4H), 3.20 (q, J=6.3 Hz, 2H), 2.84 (br s, 2H), 2.36 (br s, 4H), 2.09 (s, 6H), 2.04-1.89 (m, 4H), 1.86-1.76 (m, 2H), 1.31-1.23 (m, 6H).

Example 56: (S)-3-(3-(7-(3-((bis(dimethylamino)methylene)amino)propoxy)-5-carbamoyl-2-(1-ethyl-3-methyl-1H-pyrazole-5-carboxamido)-1H-benzo[d]imidazol-1-yl)propyl)-2-(1-ethyl-3-methyl-1H-pyrazole-5-carboxamido)-3,4-dihydro-5-oxa-1,2a-diazaacenaphthylene-7-carboxamide

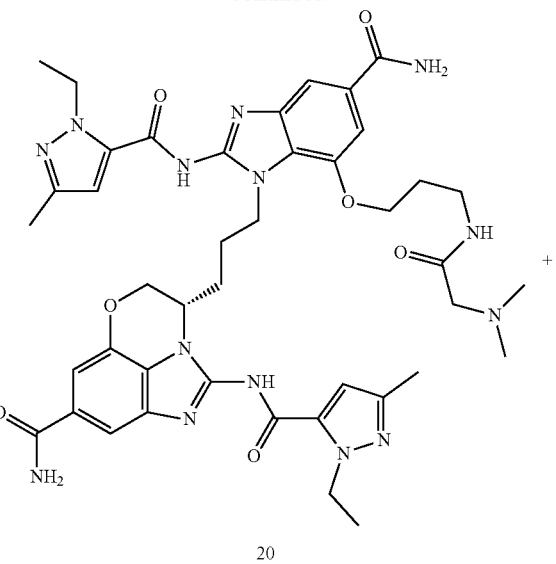

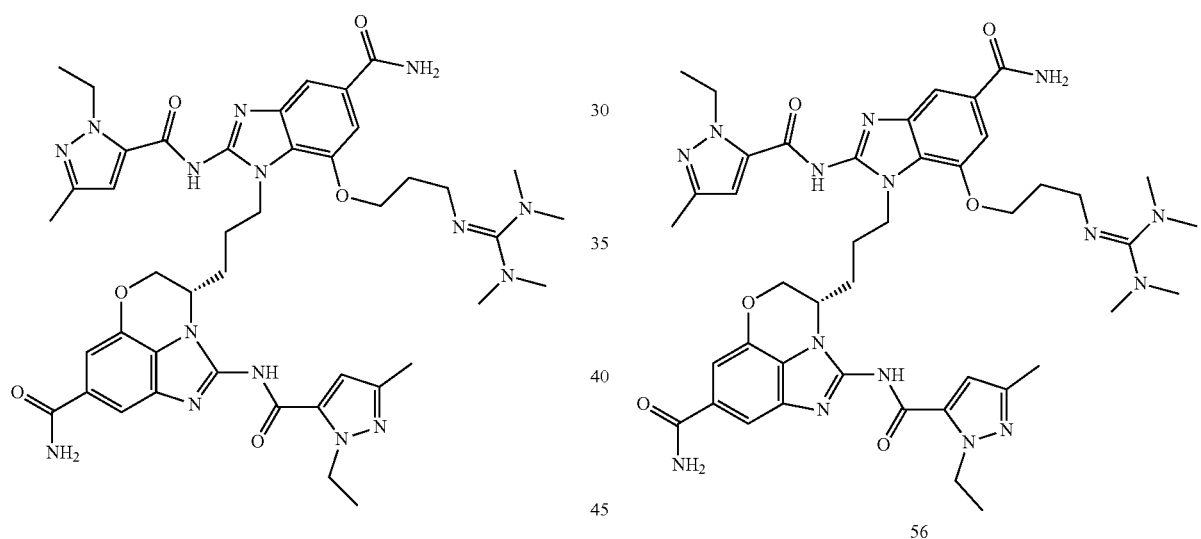

56

Synthetic Scheme

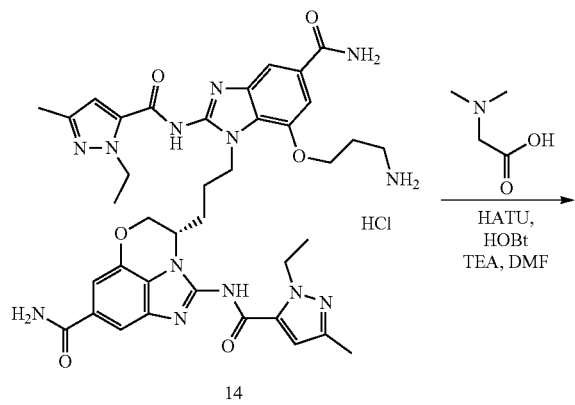

Step 1: To a solution of compound 14 (700 mg, 0.86 mmol) and N, N-dimethylglycine (101 mg, 0.98 mmol) in DMF (4 mL) was added HATU (445 mg, 1.17 mmol), HOBt (157 mg, 1.16 mmol) and trimethylamine (0.58 mL, 4.49 mmol). The reaction mixture was stirred at room temperature overnight. LCMS indicated the reaction was complete. The reaction mixture was purified directly by reversed phase preparative HPLC to give compound 20 (120 mg, 13% yield, white solid) and byproduct 56 (9 mg, 1% yield, white solid).

Compound 56: ESI-MS (m/z): 878.4 [M+H]$^+$; $^1$H NMR (500 MHz, DMSO-d6) δ 7.87 (s, 1H), 7.77 (s, 1H), 7.62 (s, 1H), 7.52 (s, 1H), 7.22 (s, 2H), 7.09 (s, 2H), 6.54 (s, 1H), 6.22 (s, 1H), 4.76 (br s, 1H), 4.60 (q, J=7.0 Hz, 2H), 4.55-4.42 (m, 3H), 4.34-4.23 (m, 1H), 4.22-4.07 (m, 3H), 4.05-3.98 (m, 1H), 3.12 (t, J=6.8 Hz, 2H), 2.92 (br s, 6H), 2.78 (br s, 6H), 2.14 (s, 3H), 2.04 (s, 3H), 1.86-1.70 (m, 4H), 1.31 (t, J=7.1 Hz, 3H), 1.21 (t, J=7.0 Hz, 3H).

Example 57: (S)-4-(3-(5-carbamoyl-2-(1-ethyl-3-methyl-1H-pyrazole-5-carboxamido)-7-(3-hydroxypropoxy)-1H-benzo[d]imidazol-1-yl)propyl)-2-(1-ethyl-3-methyl-1H-pyrazole-5-carboxamido)-6-methyl-5,6-dihydro-4H-imidazo[1,5,4-de]quinoxaline-8-carboxamide
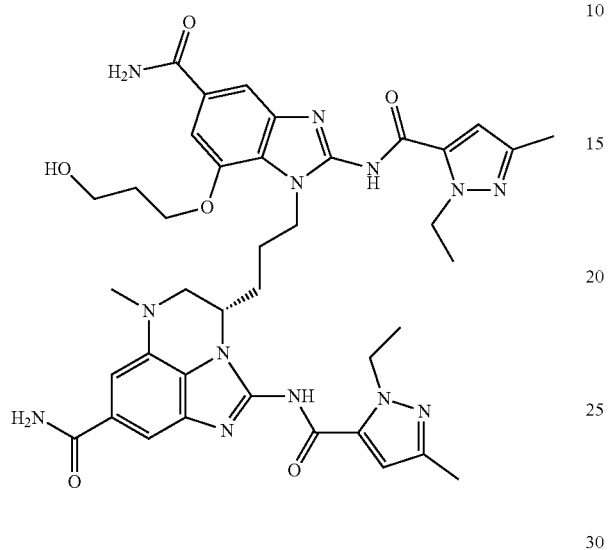
Synthetic Scheme
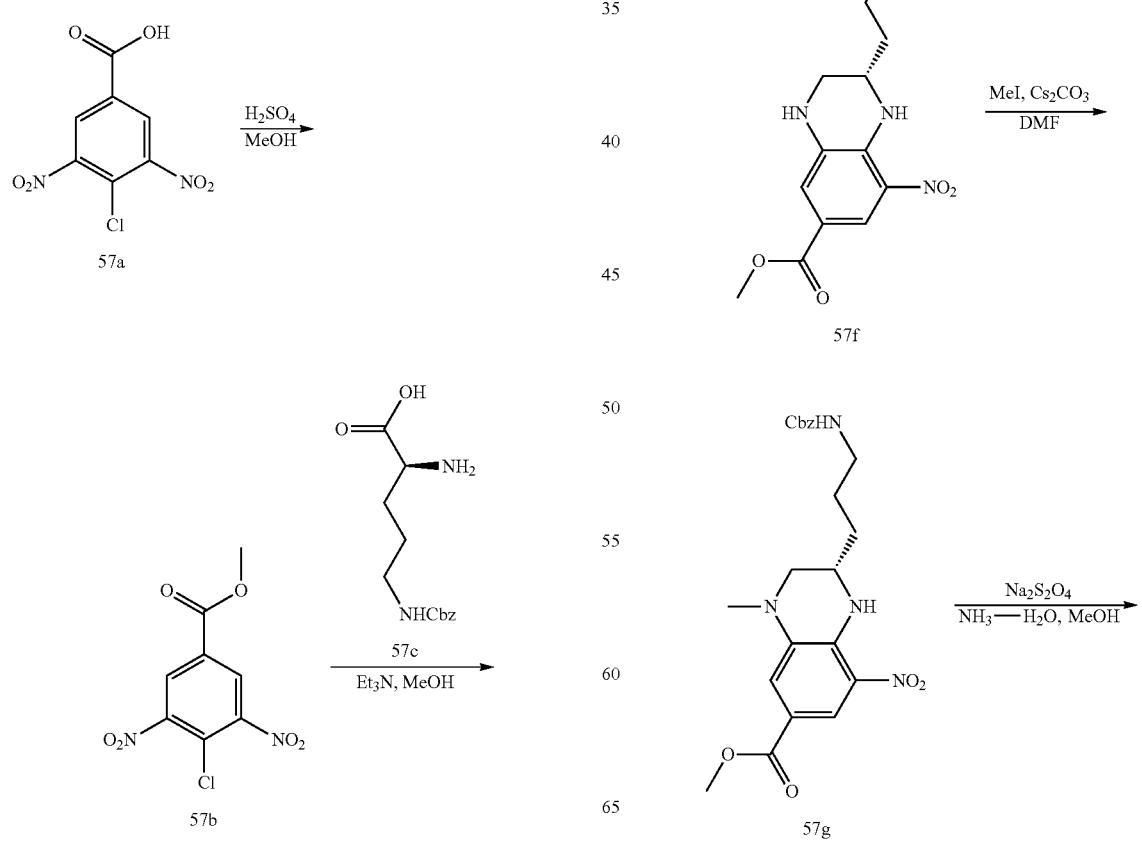

285
-continued
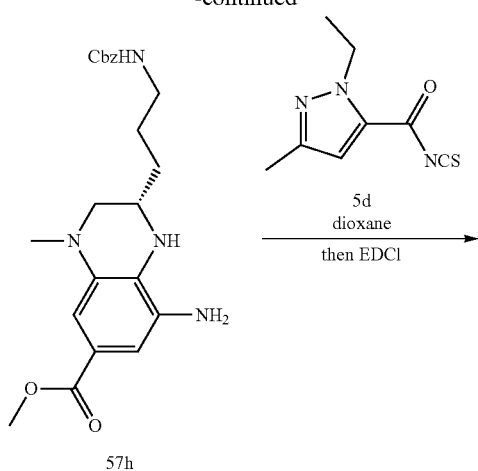
57h
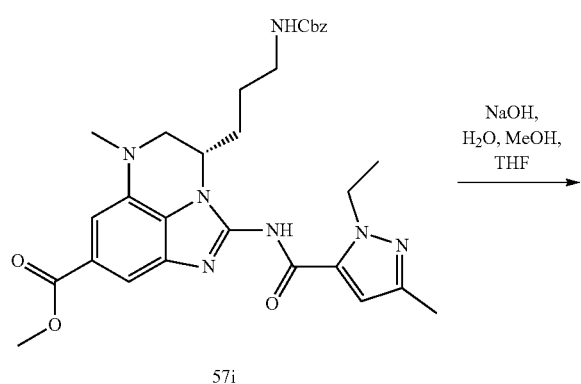
57i
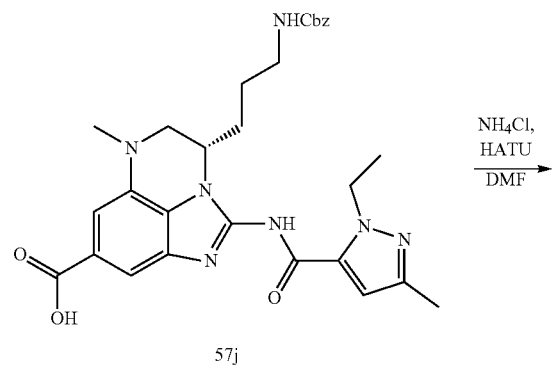
57j
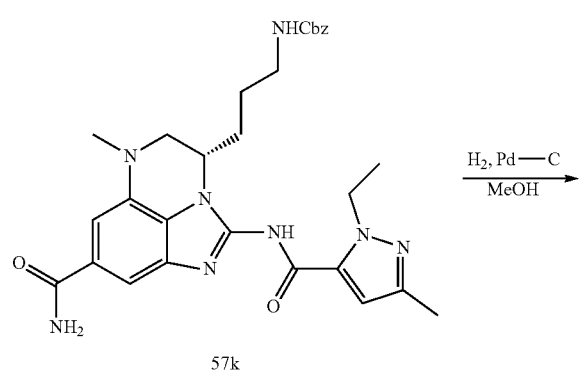
57k
286
-continued
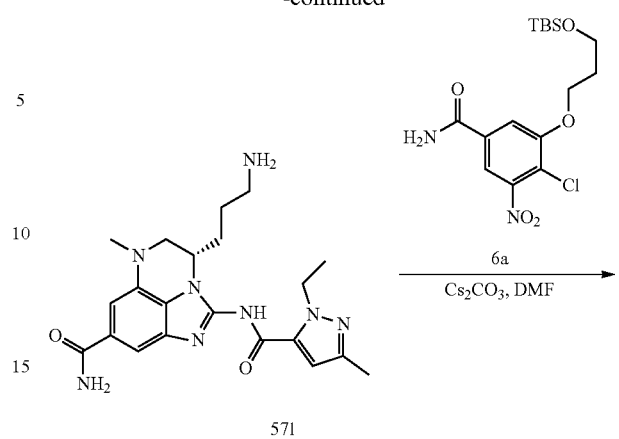
57l
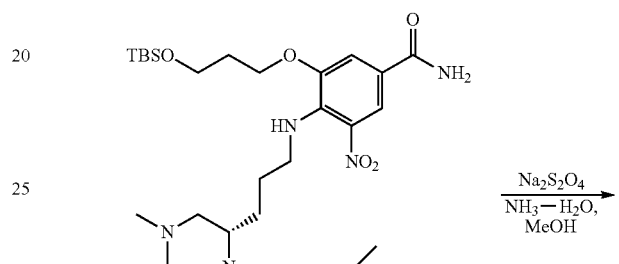
57m
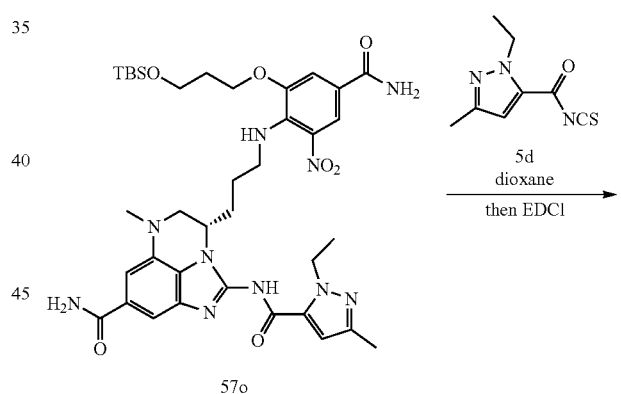
57o
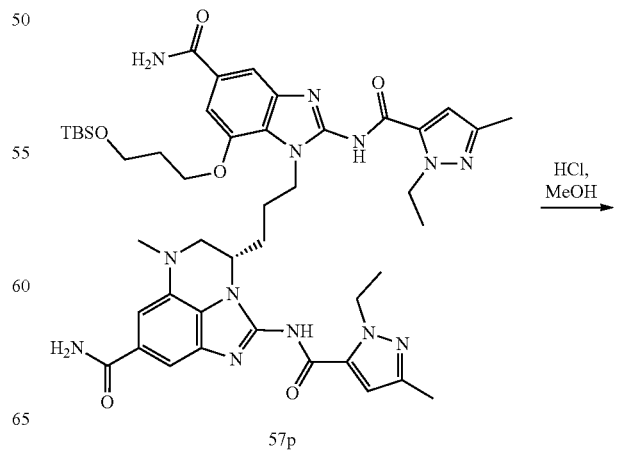
57p -continued

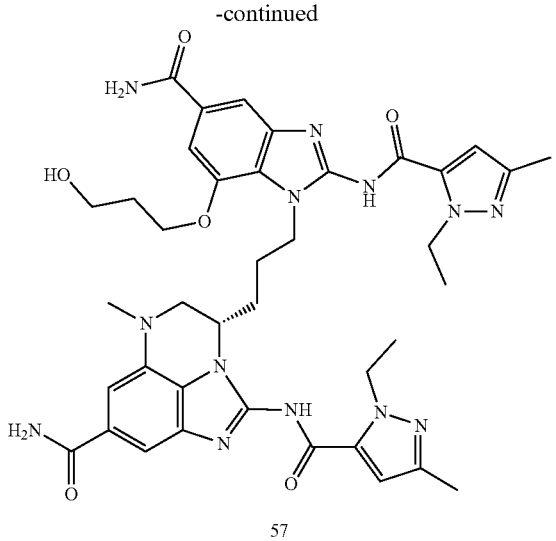

57

Step 1: Compound 57a (10.0 g, 40.6 mmol) was dissolved in MeOH (200 mL), followed by addition of concentrated $H_2SO_4$ (2 mL) at room temperature. The mixture was refluxed overnight, TLC indicated the starting material was consumed. The reaction mixture was concentrated, the residue was mixed with water (20 mL), extracted with EtOAc (15 mL×3). The combined organic layers were washed with saturated $NaHCO_3$ solution (10 mL) and brine (10 mL), dried over $Na_2SO_4$, filtered and concentrated. The residue was purified by silica chromatography to give the compound 57b (8.2 g, 78% yield) as yellow solid.

Step 2: To a stirring solution of compound 57b (4.0 g, 15.4 mmol) and compound 57c (4.9 g, 18.5 mmol) in MeOH (100 mL) was added trimethylamine (3.1 g, 30.8 mmol). The reaction mixture was heated at 80° C.; for 3 hours, and LCMS indicated the reaction was complete. The reaction mixture was concentrated to give compound 57d (4.3 g) as red oil, which was used directly without further purification. ESI-MS (m/z): 490.9 $[M+H]^+$.

Step 3: compound 57d (4.3 g, from step 2) was dissolved in acetic acid (30 mL), and Fe powder (0.94 g, 16.7 mmol)) was added by portions at room temperature. The reaction mixture was heated at 80° C.; for 3 hours, LCMS indicated the product was formed. The mixture was diluted with water (20 mL), and extracted with EtOAc (15 mL×3). The combined organic layers were washed with saturated $NaHCO_3$ solution (10 mL) and brine (10 mL), dried over $Na_2SO_4$, filtered and concentrated. The residue was purified by silica chromatography to give the compound 57e (3.9 g, 57% yield for 2 steps) as red oil. ESI-MS (m/z): 443.0 $[M+H]^+$.

Step 4: A solution of 57e (3.9 g, 8.85 mmol) in THF (50 mL) was treated with borane-methyl sulfide complex in THF (2 M, 8.8 mL, 17.6 mmol), and the solution was heated at 70° C.; for 2 hours. LCMS indicated the reaction was complete. The mixture was concentrated, the residue was purified by silica gel chromatography (petroleum ether/EtOAc=1/1) to give compound 57f (1.3 g, 34% yield) as red oil. ESI-MS (m/z): 429.0 $[M+H]^+$.

Step 5: To a solution of compound 57f (1.6 g, 3.73 mmol) in DMF (30 mL) at room temperature was added $Cs_2CO_3$ (2.4 g, 7.48 mmol), followed by the addition of MeI (0.8 g, 5.6 mmol). The reaction mixture was heated at 90° C. for 8 hours, LCMS indicated the reaction was complete. The reaction was cooled to room temperature, diluted with water (15 mL) and extracted with EtOAc (15 mL×4). The combined organic layers were washed with brine, dried over $Na_2SO_4$, filtered and concentrated. The residue was purified by silica gel chromatography (petroleum ether/EtOAc=1/1) to give compound 57g (1.3 g, 76% yield) as red oil. ESI-MS (m/z): 443.0 $[M+H]^+$.

Step 6: To a solution of compound 57g (2.6 g, 5.88 mmol) in a mixture of MeOH (50 mL) and concentrated ammonium hydroxide (18 mL) at 0° C.; was added dropwise the solution of sodium dithionite (10.2 g, 58.8 mmol) in water (20 mL). Stirring was continued at room temperature for 1 hour, and LCMS indicated the product was formed. The reaction mixture was diluted with water (200 mL), and extracted with EtOAc (80 mL×4). The combined organic layers were washed with brine (40 mL), dried over $Na_2SO_4$, filtered, and concentrated. The residue was purified by silica gel chromatography to give compound 57h (1.7 g, 70% yield) as red oil. ESI-MS (m/z): 413.0 $[M+H]^+$.

Step 7: Compound 57h (250 mg, 0.61 mmol) was dissolved in 1, 4-dioxane (10 mL), and then compound 5d (0.4 M in dioxane, 1.7 mL, 0.67 mmol) was added. The reaction mixture was stirred at room temperature for 1 hour, LCMS indicated the starting material was consumed. EDCI (140 mg, 0.15 mmol) was added, and the mixture was heated at 80° C.; for 4 hours, LCMS indicated the product was formed. The reaction mixture was cooled to room temperature, diluted with water (50 mL), and extracted with EtOAc (30 mL×4). The combined organic layers were washed with brine, dried over $Na_2SO_4$, filtered and concentrated. The residue was purified by silica gel chromatography (pure EtOAc) to give compound 57i (190 mg, 55% yield) as brown solid. ESI-MS (m/z): 574.0 $[M+H]^+$.

Step 8: To a solution of compound 57i (260 mg, 0.45 mmol) in MeOH (10 mL) and THF (10 mL) was added 1M NaOH in water (1.82 mL, 1.82 mmol). The mixture was stirred at room temperature for 48 hours, LCMS indicated the reaction was complete. The mixture was concentrated, the residue was suspended in water and carefully adjusted to pH 3-4 with 2M HCl aqueous solution. The formed solid was collected by filtration and dried in vacuo to give the compound 57j (165 mg, 65% yield) as white solid.

Step 9: To a solution of compound 57j (150 mg, 0.27 mmol) and $NH_4Cl$ (143 mg, 2.68 mmol) in DMF (10 mL) was added EDCI (77 mg, 0.40 mmol), HOBt (54 mg, 0.40 mmol) and DIPEA (104 mg, 0.81 mmol). The mixture was stirred at room temperature for 16 hours, LCMS indicated the reaction was complete. The reaction mixture was poured into water (30 mL) and extracted with EtOAc (20 mL×3). The combined organic layers were washed with brine, dried over $Na_2SO_4$, filtered and concentrated. The residue was purified by Preparative TLC to give compound 57k (22 mg, 15% yield) as white solid. ESI-MS (m/z): 559.4 $[M+H]^+$; $^1H$ NMR (400 MHz, DMSO-$d_6$) δ 12.61 (s, 1H), 7.87 (s, 1H), 7.38 (s, 1H), 7.33-7.21 (m, 6H), 7.07 (s, 1H), 6.61 (s, 1H), 5.04-4.92 (m, 2H), 4.69-4.54 (m, 3H), 3.43 (d, J=12.0 Hz, 1H), 3.25 (d, J=11.6 Hz, 1H), 3.10-3.00 (m, 2H), 2.98 (s, 3H), 2.16 (s, 3H), 1.84-1.69 (m, 2H), 1.66-1.50 (m, 2H), 1.35 (t, J=7.0 Hz, 3H).

Step 10: A suspension of compound 57k (1.70 g, 3.05 mmol) and 10% palladium on carbon (300 mg) in MeOH (50 mL) was flushed with $H_2$ and stirred at room temperature ($H_2$ balloon) overnight. LCMS indicated the reaction was complete. The reaction mixture was filtered through Celite, and the filtrate was concentrated to give compound 57l (750 mg, 58% yield) as white solid.

Step 11: To a stirring solution of compound 57l (820 mg, 1.93 mmol) and compound 6a (826 mg, 2.13 mmol) in DMF (30 mL) was added $Cs_2CO_3$ (1.12 g, 3.48 mmol). The reaction mixture was heated at 100° C.; for 24 hours, and LCMS indicated the reaction was complete. The reaction mixture was concentrated, and the residue was purified directly by silica gel chromatography to give compound 57m (630 mg, 42% yield) as yellow solid. ESI-MS (m/z): 777.0 $[M+H]^+$.

Step 12: Compound 57m (450 mg, 0.58 mmol) was dissolved in a mixture of MeOH (50 mL) and concentrated ammonium hydroxide (2 mL), and the resulting solution was cooled to 0° C. Sodium dithionite (1.0 g, 5.80 mmol) was dissolved in water (4 mL) and added dropwise to the reaction mixture. Stirring was continued at room temperature for 1 hour, and LCMS indicated the product was formed. The reaction mixture was diluted with water (200 mL), and extracted with EtOAc (100 mL×3). The combined organic layers were washed with brine, dried over $Na_2SO_4$, filtered, and concentrated. The residue was purified by silica gel chromatography to give compound 57o (280 mg, 65% yield) as yellow solid. ESI-MS (m/z): 747.0 $[M+H]^+$.

Step 13: Compound 57o (250 mg, 0.34 mmol) was dissolved in 1, 4-dioxane (20 mL), and then compound 5d (1 M in dioxane, 0.4 mL, 0.40 mmol) was added. The reaction mixture was stirred at room temperature for 30 minutes, DCC (76 mg, 0.40 mmol) was added. The mixture was heated at 80° C.; for 4 hours, LCMS indicated the product was formed. The reaction mixture was cooled to room temperature, diluted with water (30 mL), and extracted with EtOAc (40 mL×3). The combined organic layers were washed with brine, dried over $Na_2SO_4$, filtered and concentrated. The residue was purified by silica gel chromatography to give compound 57p (180 mg, 59% yield) as yellow solid. ESI-MS (m/z): 907.9 $[M+H]^+$.

Step 14: To a stirring solution of 57p (200 mg, 0.22 mmol) in MeOH (50 mL) was added 4M HCl in dioxane (0.55 mL, 2.20 mmol). The mixture was stirred at room temperature for 2 hours, LCMS indicated the product was formed. The reaction mixture was concentrated, and the residue was purified by reversed phase preparative HPLC to give compound 57 (72 mg, 41% yield) as white solid. ESI-MS (m/z): 793.8 $[M+H]^+$; $^1$H NMR (400 MHz, DMSO-$d_6$) δ 12.82 (s, 1H), 12.60 (s, 1H), 8.00 (s, 1H), 7.87 (s, 1H), 7.63 (s, 1H), 7.38-7.20 (m, 4H), 7.07 (s, 1H), 6.55 (s, 1H), 6.47 (s, 1H), 4.75-4.10 (m, 10H), 3.60-3.40 (m, 3H), 3.26-3.18 (m, 1H), 2.93 (s, 3H), 2.10-1.75 (m, 12H), 1.35-1.20 (m, 6H).

Example 58: (S)-7-Ethyl-24-(3-methoxypropoxy)-9, 16-dimethyl-6,18-dioxo-5,6,7,10,11,12,13,14,18,19, 26,27,27a,28-tetradecahydro-25H-29-oxa-4,4a1,5,7, 8,14a,15,19,20,24b-decaaza-dicyclopenta[11, 12:18, 19]indeno[1',2':7,8]cyclohenicosa[1,2,3-bc] acenaphthylene-2,22-dicarboxamide

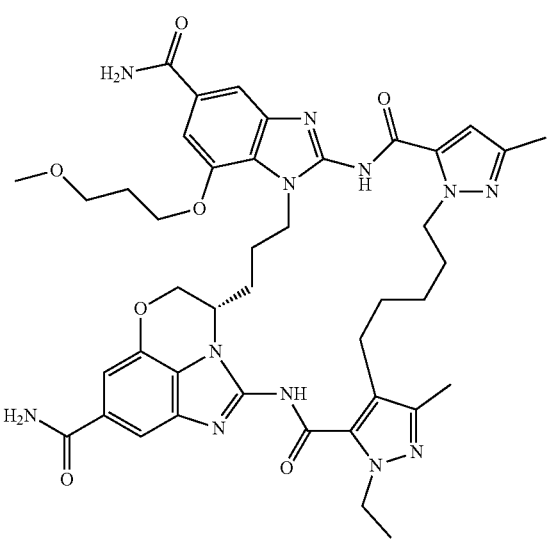

Example 59: (S)-17-ethyl-24-(3-methoxypropoxy)- 8,15-dimethyl-6,18-dioxo-5,6,10,11,12,13,14,17, 18, 19, 26, 27, 27a,28-tetradecahydro-25H-29-oxa-4, 4a1,5,9,9a,16, 17, 19, 20, 24b-decaazadicyclopenta [11, 12:18,19]indeno[1',2':7,8]cyclohenicosa[1,2,3-bc]acenaphthylene-2,22-dicarboxamide

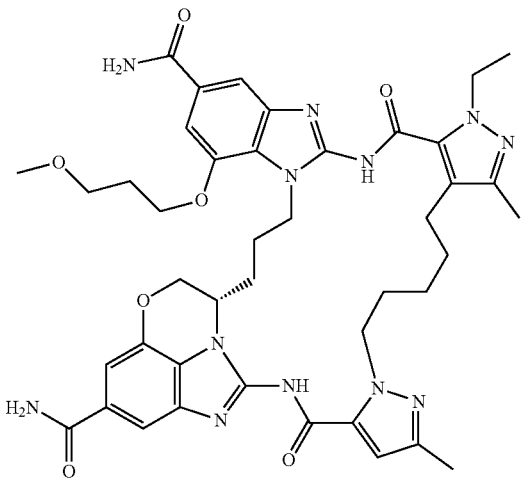

Synthetic Scheme
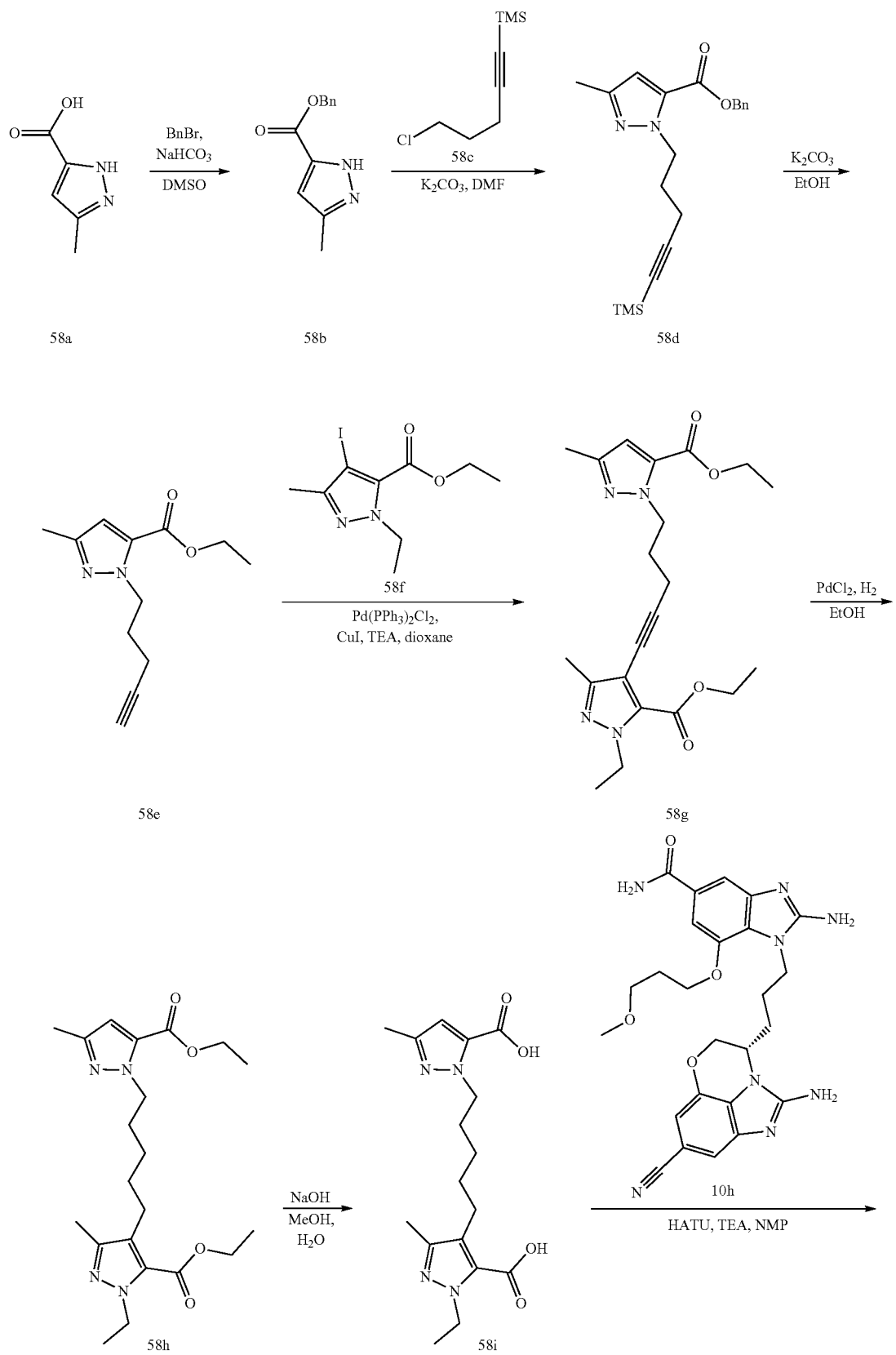

-continued

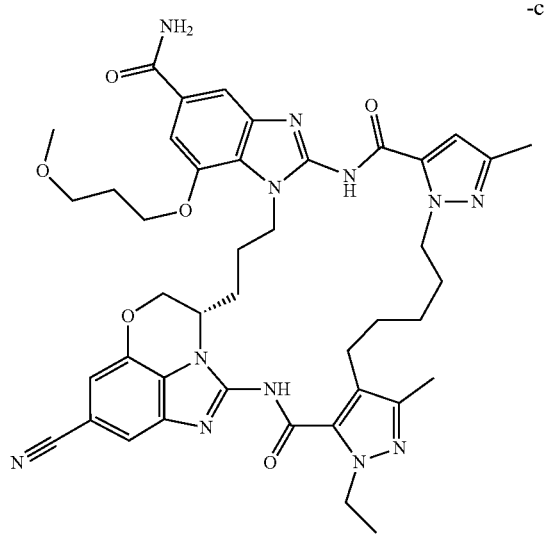

58j-P1

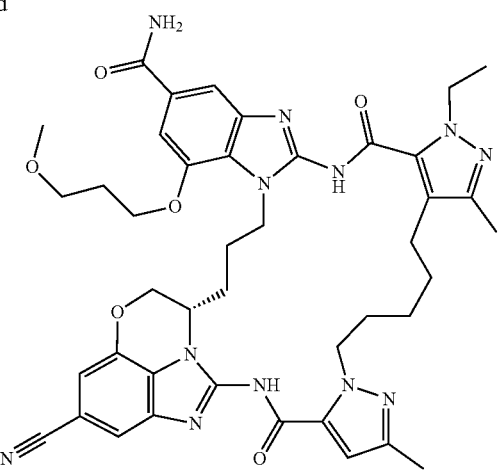

58j-P2

↓ NaOH, H₂O₂, DMSO

↓ NaOH, H₂O₂, DMSO

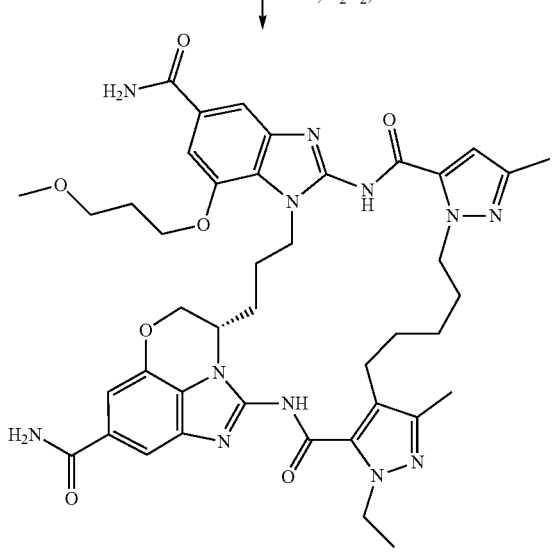

58

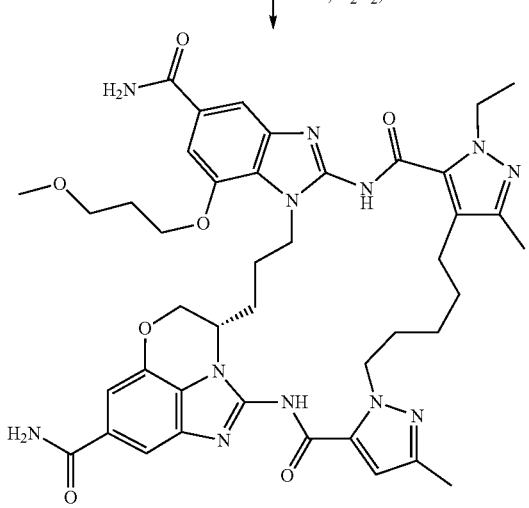

59

Step 1: To a solution of compound 58a (10 g, 79.29 mmol) was dissolved in DMSO (100 mL) was added NaHCO₃ (109, 118.94 mmol). The mixture was stirred at room temperature for 30 minutes, then benzyl bromide (8.95 mL, 75.33 mmol) was added to the reaction. The reaction was stirred at room temperature overnight. LCMS indicated the starting material was consumed. The reaction mixture was poured into water (300 mL) and extracted with EtOAc (100 mL×3). The combined organic layers were washed with brine, dried over Na₂SO₄, filtered and concentrated. The residue was purified by silica gel chromatography to give compound 58b (4.5 g, 26% yield) as white solid. ESI-MS (m/z): 217.2 [M+H]⁺.

Step 2: To a stirring solution of compound 58b (4.5 g, 20.81 mmol 1) and compound 58c (3.82 g, 21.85 mmol) in DMF (50 mL) was added K₂CO₃ (5.75 g, 41.62 mmol). The reaction mixture was heated at 60° C.; overnight, and LCMS indicated the starting material was consumed. The reaction mixture was cooled to room temperature, diluted with water (200 mL), and extracted with EtOAc (50 mL×3). The combined organic layers were washed with brine, dried over Na₂SO₄, filtered and concentrated to give crude compound 58d (7.0 g) as yellow oil, which was used directly without further purification. ESI-MS (m/z): 355.3 [M+H]⁺.

Step 3: To a solution of crude compound 58d (7.0 g, from step 2) in EtOH (100 mL) was added K₂CO₃ (4.09 g, 29.62 mmol). The mixture was stirred at room temperature overnight. LCMS indicated the reaction was complete. The reaction mixture was filtered, and the filtrate was concentrated. The residue was purified by silica gel chromatography to gibe compound 58e (1.2 g, 27% yield for 2 steps) as yellow solid. ESI-MS (m/z): 221.2[M+H]⁺.

Step 4: To a solution of compound 58e (1.2 g, 5.45 mmol) and 58f (2.0 g, 6.54 mmol) in dioxane (20 mL) were added copper (I) iodide (103 mg, 0.54 mmol), Pd(PPh₃)₂C₁₋₂ (382 mg, 0.54 mmol) and triethylamine (2.27 mL, 16.34 mmol) at room temperature under nitrogen atmosphere. After addition, the reaction mixture was heated at 50° C.; overnight. LCMS indicated the reaction was complete. The reaction mixture was concentrated, and the residue was purified by silica gel chromatography to give compound 58g (1.8 g, 82% yield) as a white solid. ESI-MS (m/z): 401.1 [M+H]$^+$.

Step 5: A solution of compound 58g (1.8 g, 4.49 mmol) and Palladium chloride (80 mg, 0.45 mmol) in EtOH (20 mL) was stirred under a hydrogen atmosphere at room temperature overnight. LCMS indicated the starting material was consumed. The reaction mixture was filtered through celite and concentrated, and the obtained residue was purified by silica gel chromatography to give compound 58h (1.2 g, 66% yield) as light yellow solid. ESI-MS (m/z): 405.3 [M+H]$^+$.

Step 6: A solution of compound 58h (1.2 g, 2.97 mmol) in MeOH (20 mL) was treated with NaOH (154 mg, 3.86 mmol) in water (5 mL). The reaction mixture was stirred at room temperature overnight, LCMS indicated the starting material was consumed. The mixture was concentrated; the residue was suspended in water (30 mL), and washed with DCM (20 mL×2). The aqueous layer was adjusted to pH 3-4 with concentrated HCl solution, then extracted with EtOAc (30 mL×3). The combined EtOAc layers were washed with brine, dried over Na$_2$SO$_4$, filtered and concentrated to give compound 58i (650 mg, 62% yield) as yellow solid. ESI-MS (m/z): 349.4 [M+H]$^+$.

Step 7: To a solution of compound 10h (100 mg, 0.19 mmol) and compound 58i (69 mg, 0.19 mmol) in NMP (6 mL) was added HATU (165 mg, 0.43 mmol) and TEA (60 mg, 0.59 mmol). The mixture was heated at 140° C.; with microwave for 1 hour, LCMS indicated the reaction was complete. The reaction mixture was purified directly by reversed phase preparative HPLC to provide two regioisomers as brown solids.

Compound 58j-P1 (20 mg), high polar and eluted first. ESI-MS (m/z): 817.3 [M+H]$^+$. Compound 58j-P2 (20 mg), low polar. ESI-MS (m/z): 817.3 [M+H]$^+$. Total isolated yield: 24%.

The structure of each isomer was tentatively assigned as drawn.

Step 8: To a stirring solution of 58j-P1 (20 mg, 0.024 mmol) in DMSO (3 mL) was added solid NaOH (3 mg, 0.073 mmol). The reaction mixture was heated at 60° C., and hydrogen peroxide (30 wt. %, 0.5 mL) was added dropwise into the reaction mixture. The reaction was stirred at 60° C.; for 5 minutes, then cooled to room temperature. The reaction mixture was purified directly by reversed phase preparative HPLC to give compound 58 (4 mg, 19% yield) as white solid. ESI-MS (m/z): 835.8 [M+H]$^+$; $^1$H NMR (500 MHz, DMSO-d$_6$) δ 8.40 (s, 2H), 7.96 (s, 1H), 7.87 (s, 1H), 7.74 (s, 1H), 7.67 (s, 1H), 7.35-7.25 (m, 3H), 7.21 (s, 1H), 4.88-4.78 (m, 1H), 4.60-4.50 (m, 1H), 4.47-4.38 (m, 2H), 4.23-4.15 (m, 2H), 4.11-4.02 (m, 2H), 4.00-3.90 (m, 3H), 3.05 (s, 3H), 3.02-2.92 (m, 2H), 2.15 (s, 3H), 2.07 (s, 3H), 1.93-1.64 (m, 8H), 1.40-1.31 (m, 4H), 1.24 (t, J=7.1 Hz, 3H).

With similar method to hydrolyze the 58j-P2 (20 mg) gave compound 59 (5 mg, 24% yield) as white solid. ESI-MS (m/z): 836.1 [M+H]$^+$; $^1$H NMR (500 MHz, DMSO-d$_6$) δ 12.71 (s, 2H), 8.40 (s, 2H), 7.96 (s, 1H), 7.88 (s, 1H), 7.59 (s, 1H), 7.40-7.20 (m, 5H), 6.40 (s, 1H), 4.55-4.40 (m, 4H), 4.21-4.10 (m, 6H), 4.05-3.88 (m, 3H), 3.15 (s, 3H), 3.13-3.08 (m, 2H), 2.22 (s, 3H), 2.05 (s, 3H), 2.00-1.70 (m, 8H), 1.40-1.20 (m, 7H).

Example 60: (S)-21-Bromo-7-ethyl-9,16-dimethyl-6,18-dioxo-5,6,7,10,11,12,13,14,18,19,26,27,27a,28-tetra decahydro-25H-29-oxa-4,4a1,5,7,8,14a,15,19,20,24b-decaaza-dicyclopenta[11,12:18,19]indeno[1',2':7,8]cyclohenicosa[1,2,3-bc]acenaphthylene-2-carboxamide

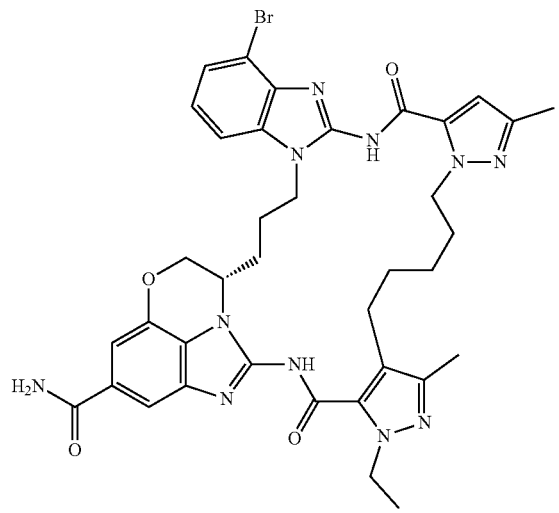 [SMILES: CCn1nc(C)c2c1C(=O)Nc1nc3cc(C(N)=O)cc4c3n1[C@@H](CCCn1c(nc3c(Br)cccc31)NC(=O)c1cc(C)nn1CCCCC2)CO4]

Example 61: (S)-21-bromo-17-ethyl-8,15-dimethyl-6,18-dioxo-5,6,10,11,12,13,14,17,18,19,26,27,27a,28-tetradecahydro-25H-29-oxa-4,4a1,5,9,9a,16,17,19,20,24b-decaaza-dicyclopenta[11,12:18,19]indeno[1',2':7,8]cyclohenicosa[1,2,3-bc]acenaphthylene-2-carboxamide

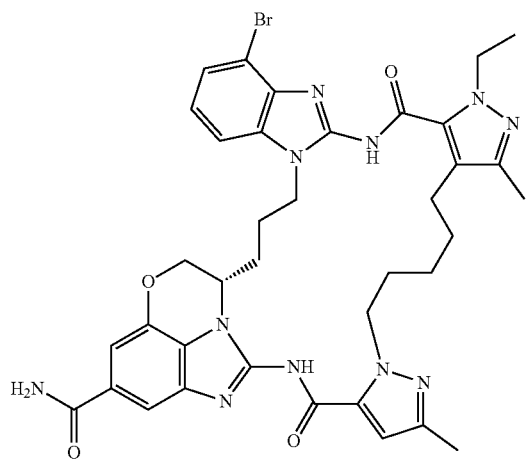 [SMILES: CCn1nc(C)c2c1C(=O)Nc1nc3c(Br)cccc3n1CCC[C@H]1COc3cc(C(N)=O)cc4nc(n1c34)NC(=O)c1cc(C)nn1CCCCC2]

Synthetic Scheme
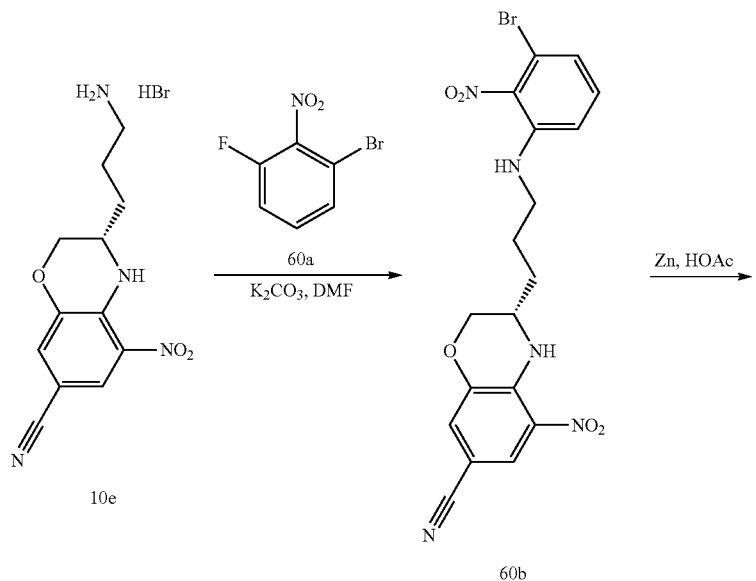
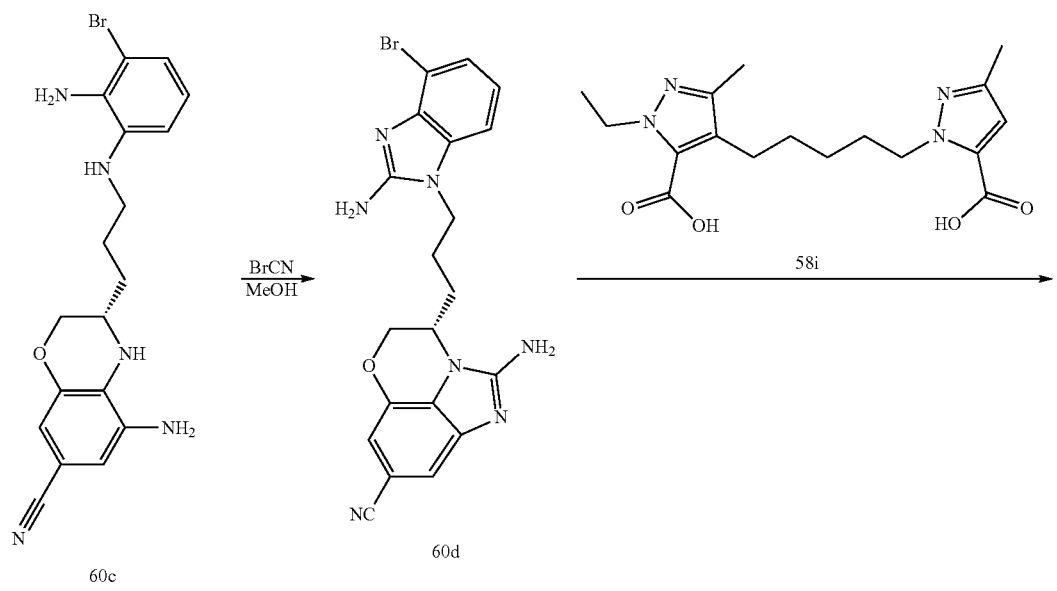

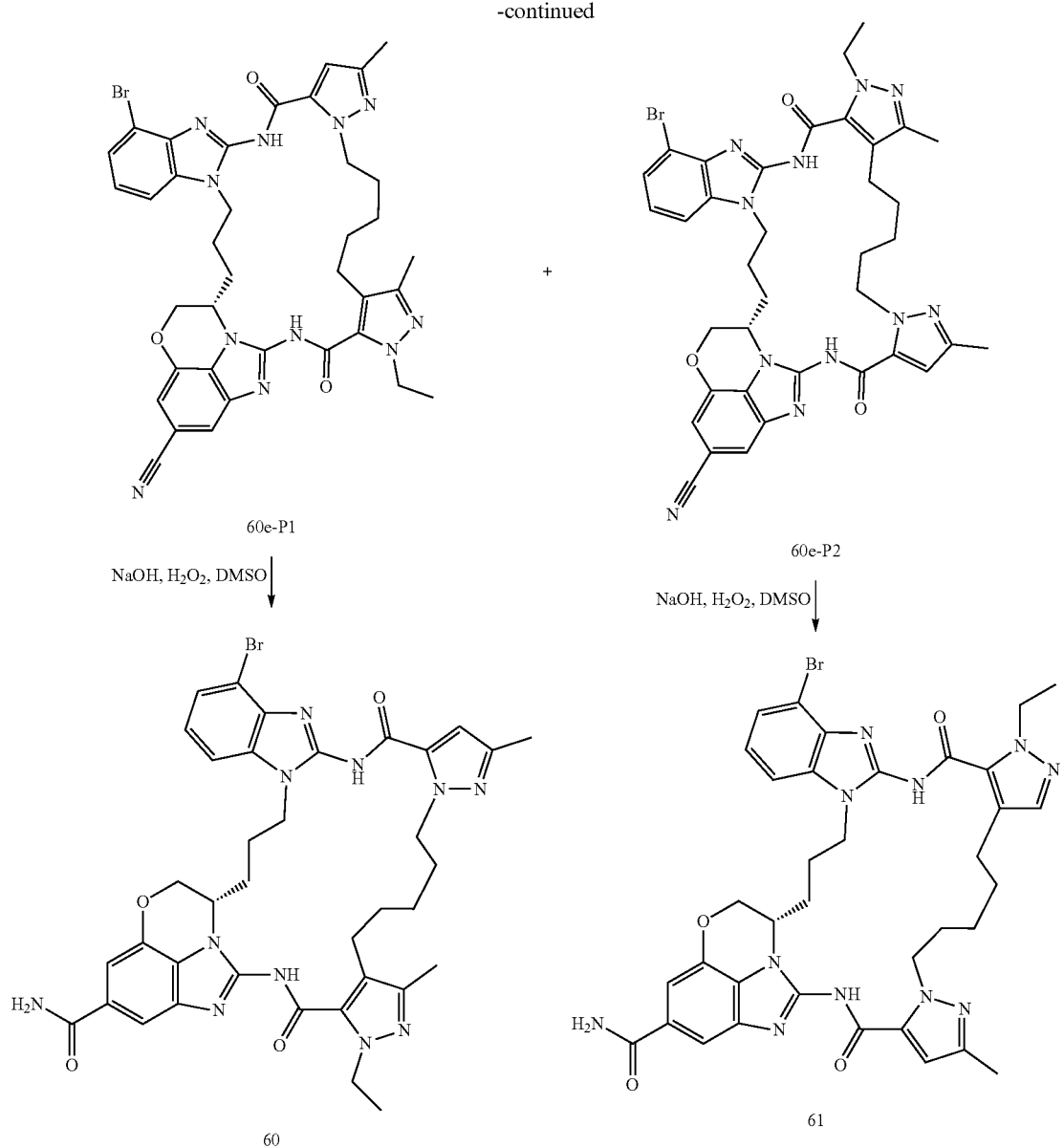

Step 1: To a stirring solution of compound 10e (2.0 g, 5.83 mmol) and compound 60a (1.54 g, 6.99 mmol) in DMF (20 mL) was added $K_2CO_3$ (3.22 g, 23.31 mmol). The reaction mixture was heated to 70° C.; for 4 hours, LCMS indicated the reaction was complete. The reaction mixture was allowed to cool to room temperature, diluted with water (100 mL) and extracted with ethyl acetate (30 mL×3). The combined organic layers were dried over $Na_2SO_4$, filtered and concentrated under reduced pressure. The residue was purified by silica gel chromatography to give compound 60b (1.8 g, 66% yield) as a yellow solid.

Step 2: Compound 60b (1.8 g, 3.89 mmol) was dissolved in acetic acid (20 mL), and Zn powder (1.27 g, 19.47 mol) was added by portions at room temperature. The reaction mixture was stirred at room temperature for 2 hour, LCMS indicated the product was formed. The mixture was filtered, and the filtrate was concentrated. The residue was purified by silica gel chromatography to give the compound 60c (1.4 g, 89% yield) as a red solid. ESI-MS (m/z): 403.3 [M+H]$^+$.

Step 3: Compound 60c (1.4 g, 3.48 mmol) was dissolved in MeOH (40 mL), and cyanogen bromide (1.84 g, 17.4 mmol) was added. The resulting mixture was stirred at room temperature overnight, LCMS indicated the product was formed. The mixture was concentrated in vacuo to remove the solvent. The residue was triturated with EtOAc, and filtered to give compound 60d (1.0 g, 63% yield) as a brown solid. ESI-MS (m/z): 452.1 [M+H]$^+$.

Step 4: To a solution of compound 60d (500 mg, 1.11 mmol) and compound 58i (348 mg, 1.11 mmol) in NMP (10 mL) was added HATU (924 mg, 2.43 mmol) and triethylamine (335 mg, 3.32 mmol). The mixture was heated at 140° C.; with microwave for 1 hour, LCMS indicated the reaction was complete. The reaction mixture was purified directly by reversed phase preparative HPLC to provide two regioisomers as brown solids.

Compound 60e-P1 (70 mg), high polar and eluted first, ESI-MS (m/z): 764.1 [M+H]$^+$.

Compound 60e-P2 (80 mg), low polar, ESI-MS (m/z): 764.1 [M+H]$^+$. Total isolated yield: 17.74%. The structure of each isomer was tentatively assigned as drawn.

Step 5: To a stirring solution of 60e-P1 (70 mg, 0.091 mmol) in DMSO (3 mL) was added solid NaOH (11 mg, 0.27 mmol). The reaction mixture was heated at 60° C., and hydrogen peroxide (30 wt. %, 0.5 mL) was added dropwise into the reaction mixture. The reaction was stirred at 60° C. for 5 minutes, LCMS indicated the product was formed. The reaction mixture was purified directly by reversed phase preparative HPLC to give compound 60 (30 mg, 41% yield) as a white solid. ESI-MS (m/z): 782.2 [M+H]$^+$; $^1$H NMR (500 MHz, DMSO-d$_6$) δ 8.27 (s, 1H), 7.90 (s, 1H), 7.70 (s, 1H), 7.47 (d, J=8.0 Hz, 1H), 7.38 (d, J=8.0 Hz, 1H), 7.28 (s, 1H), 7.24 (s, 1H), 7.15 (t, J=8.0 Hz, 1H), 6.20 (s, 1H), 4.81 (br s, 1H), 4.53-4.35 (m, 4H), 4.21 (dd, J=12.0, 3.0 Hz, 2H), 4.06-4.00 (m, 2H), 2.90-2.80 (m, 1H), 2.72-2.60 (m, 1H), 2.22 (s, 3H), 2.09 (s, 3H), 2.05-1.70 (m, 6H), 1.48-1.30 (m, 2H), 1.24 (d, J=6.5 Hz, 3H), 1.20-1.08 (m, 2H).

With similar method to hydrolyze the 60e-P2 (80 mg) gave compound 61 (25 mg, 34% yield) as white solid. ESI-MS (m/z): 782.1 [M+H]$^+$; $^1$H NMR (500 MHz, DMSO-d$_6$) δ 8.33 (s, 1H), 7.87 (s, 1H), 7.60 (s, 1H), 7.57 (d, J=8.0 Hz, 1H), 7.44 (d, J=8.0 Hz, 1H), 7.26 (s, 2H), 7.19 (t, J=8.0 Hz, 1H), 6.34 (s, 1H), 4.60-4.50 (m, 2H), 4.46-4.37 (m, 1H), 4.30-4.20 (m, 1H), 4.15-4.02 (m, 4H), 2.90-2.65 (m, 2H), 2.25 (s, 3H), 2.10 (s, 3H), 1.90-1.66 (m, 6H), 1.40-1.00 (m, 7H).

Biology Screening Result of STING Agonist Compound

Example I: STING variants (WT & HAQ) activation by compounds in BEK Blue™ ISG KO-STING cells (Method 1)

Activation of STING can be determined using a SEAP reporter assay in HEK-Blue™ ISG KO-STING cells (Invivogen, cat #hkb-kostg) transfected with plasmids expressing STING variants (WT & HAQ) (referred to WO2017/175147A1). STING variants (WT & HAQ) vector were constructed based on STING-232H vector (Origene, RC208418). GFP vector (VT2069) was bought from Youbio. The detailed protocol as follows: HEK-Blue™ ISG KO-STING cells were harvest and seeding into 96 well plate, the final cell number was 0.8×10$^5$ cells/well. Transfections were prepared using Lipofectamine 2000 (Invitrogen, Cat #11668-027) following the manufacturer's instructions (Lipo2000/DNA=1/10), 20 ul of transfection suspension containing 1 ng STING vector was added to cell culture plate and incubated at 37° C., 5% CO2 for 24 hours. After 24 hours' incubation, compounds were added at proper concentration, and the final DMSO concentration was 0.5%. After 24 h incubation, the supernatant was collected to detect SEAP signal using Great EscAPe SEAP chemiluminescence KIT (Clontech, cat #631738) and cells were collected to detect cell viability using CellTiter-Glo Luminescent Cell Viability Assay (Promega, cat #G7573) following the manufacturer's instructions. The data were described by the ratio of the stimulating signal of compounds to 0.5% DMSO.

| | | HEK-Blue ™ ISG-KO-STING/variants reporter assay | |
|---|---|---|---|
| | | Fold change related to DMSO control | |
| Compounds | Concentration (uM) | WT | HAQ |
| 1 | 7.8 | 2.29 | 36.93 |
| 2 | 15.65 | 1.99 | 2.52 |
| 4 | 26.8 | 2.22 | 10.21 |
| 5 | 22.1 | 1.41 | 22.85 |
| 6 | 57.9 | 1.71 | 32.88 |
| 7 | 80.2 | 1.96 | 20.29 |
| 8 | 4.7 | 2.08 | 8.09 |
| 9 | 2.5 | 2.27 | — |
| | 5 | — | 14.14 |
| 10 | 2.5 | 1.98 | — |
| | 5 | — | 16.63 |
| 11 | 2.5 | 1.83 | — |
| | 5 | — | 27.74 |
| 12 | 2.5 | 1.89 | — |
| | 5 | — | 26.28 |
| 13 | 2.5 | 1.79 | — |
| | 5 | — | 26.64 |
| 14 | 2.5 | 2.17 | — |
| | 5 | — | 16.68 |
| 15 | 2.5 | 2.11 | — |
| | 5 | — | 11.61 |
| 16 | 2.5 | 2.07 | — |
| | 5 | — | 20.47 |
| 17 | 2.5 | 2.35 | — |
| | 5 | — | 33.85 |
| 18 | 2.5 | 2.64 | — |
| | 5 | — | 40.66 |
| 19 | 2.5 | 2.33 | — |
| | 5 | — | 60.17 |
| 20 | 2.5 | 2.63 | — |
| | 5 | — | 41.58 |
| 21 | 2.5 | 2.38 | — |
| | 5 | — | 40.44 |
| 22 | 2.5 | 2.40 | — |
| | 5 | — | 47.36 |
| 23 | 2.5 | 2.82 | — |
| | 5 | — | 38.85 |
| 24 | 2.5 | 2.70 | — |
| | 5 | — | 56.42 |
| 25 | 2.5 | 1.95 | — |
| | 5 | — | 46.51 |
| 26 | 2.5 | 1.03 | — |
| | 5 | — | 2.36 |
| 27 | 2.5 | 2.22 | — |
| | 5 | — | 45.86 |
| 28 | 2.5 | 2.05 | — |
| | 5 | — | 22.84 |
| 29 | 2.5 | 1.99 | — |
| | 5 | — | 27.10 |
| 30 | 2.5 | 1.96 | — |
| | 5 | — | 33.34 |
| 31 | 2.5 | 1.65 | — |
| | 5 | — | 12.75 |
| 32 | 2.5 | 1.84 | — |
| | 5 | — | 22.71 |
| 33 | 2.5 | 1.88 | — |
| | 5 | — | 16.31 |
| 34 | 2.5 | 1.51 | — |
| | 5 | — | 6.51 |
| 35 | 2.5 | 2.16 | — |
| | 5 | — | 12.04 |
| 36 | 2.5 | 1.92 | — |
| | 5 | — | 16.18 |
| 37 | 2.5 | 2.14 | — |
| | 5 | — | 23.71 |
| 38 | 2.5 | 2.15 | — |
| | 5 | — | 18.05 |

—Not detected

Example II: STING Variants (WT & HAQ) Activation by Compounds in HEK-Blue™ ISG KO-STING Cells (Method 2)

Activation of STING can be determined using a SEAP reporter assay in HEK-Blue™ ISG KO-STING cells (Invivogen, cat #hkb-kostg) transfected with plasmids expressing STING variants (WT & HAQ) (referred to WO2017/175147A1). STING variants (WT & HAQ) vector were constructed based on STING-232H vector (Origene, RC208418). GFP vector (VT2069) was bought from Youbio. The detailed protocol as follows: HEK-Blue™ ISG KO-STING cells were harvest and seeding into 96 well plate and the final cell number was $0.8 \times 10^5$ cells/well. Transfections were prepared using Lipofectamine 2000 (Invitrogen, Cat #11668-027) following the manufacturer's instructions (Lipo2000/DNA=1/10), 20 ul of transfection suspension containing 1 ng (WT variant) or 0.0625 ng (HAQ variant) STING vector was added to cell culture plate and incubated at 37° C., 5% CO2 for 24 hours. After 24 hours incubation, compounds were added at proper concentration, the final DMSO concentration was 0.5%. After 24 h incubation, the supernatant was collected to detect SEAP signal using Great EscAPe SEAP chemiluminescence KIT (Clontech, cat #631738) and cells were collected to detect cell viability using CellTiter-Glo Luminescent Cell Viability Assay (Promega, cat #G7573) following the manufacturer's instructions. The data were described by the ratio of the stimulating signal of compounds to 0.5% DMSO.

| | HEK-Blue™ ISG-KO-STING/variants reporter assay | | |
|---|---|---|---|
| | Concentration | Fold change related to DMSO control | |
| Compounds | (uM) | WT | HAQ |
| 1 | 2.5 | 13.65 | — |
| | 5 | — | 24.13 |
| 39 | 2.5 | 11.39 | — |
| | 5 | — | 16.45 |
| 40 | 2.5 | 7.82 | — |
| | 5 | — | 13.94 |
| 41 | 2.5 | 7.15 | — |
| | 5 | — | 19.38 |
| 42 | 2.5 | 10.04 | — |
| | 5 | — | 17.42 |
| 43 | 2.5 | 7.12 | — |
| | 5 | — | 19.89 |
| 44 | 2.5 | 6.47 | — |
| | 5 | — | 31.46 |
| 45 | 2.5 | 4.43 | — |
| | 5 | — | 21.63 |
| 46 | 2.5 | 10.68 | — |
| | 5 | — | 12.84 |
| 47 | 2.5 | 9.80 | — |
| | 5 | — | 9.16 |
| 48 | 2.5 | 5.70 | — |
| | 5 | — | 7.94 |
| 49 | 2.5 | 11.17 | — |
| | 5 | — | 27.58 |
| 50 | 2.5 | 8.92 | — |
| | 5 | — | 32.38 |
| 51 | 2.5 | 9.66 | — |
| | 5 | — | 11.97 |
| 52 | 2.5 | 11.79 | — |
| | 5 | — | 18.32 |
| 53 | 2.5 | 10.85 | — |
| | 5 | — | 17.39 |
| 54 | 2.5 | 13.02 | — |
| | 5 | — | 19.74 |
| 55 | 2.5 | 11.71 | — |
| | 5 | — | 26.34 |
| 56 | 2.5 | 6.76 | — |
| | 5 | — | 10.61 |
| 57 | 2.5 | 11.24 | — |
| | 5 | — | 23.35 |

—Not detected

Example III: Compound Stimulate THP1 to Release IFN f by STING Activation

In this assay, activation of STING by compounds was evaluated by detecting their ability to stimulate the secretion of IFN-β (interferon-beta) from THP1. THP1 was purchased from National Collection of Authenticated Cell Cultures (Cat #TCHu 57). The top dose of compounds was setted according to their solubility. First, Compounds were 3 times diluted with medium, 8-dose points in total. The final DMSO concentration was 0.2%. THP1 during the logarithmic phase was resuspended to $2 \times 10^6$ cells/ml in assay medium. The THP1-cell suspension was dispensed into a 96-well U bottom plate containing 50 ul of compound diluted in medium. After 24 h incubation at 37° C., 5% $CO_2$, the supernatant was collected. The concentration of IFN-β in the supernatant was measured using a human IFNβ ELISA KIT (R&D, DY814-05). The data was fitted with GraphPad Prism or XLfit to calculate $EC_{50}$ values.

| Compounds | hIFNβ ELISA (EC50, μM) |
|---|---|
| 1 | 2.1 |
| 2 | inactive |
| 4 | inactive |
| 5 | 3.7 |
| 6 | 4.8 |
| 7 | inactive |
| 8 | inactive |
| 9 | 2.6 |
| 10 | inactive |
| 11 | NT |
| 12 | >9.1 |
| 13 | >3.0 |
| 14 | >13.7 |
| 15 | inactive |
| 16 | >17.9 |
| 17 | 9.8 |
| 18 | 18.2 |
| 19 | 6.2 |
| 20 | 11.4 |
| 21 | 1.4 |
| 22 | 3.9 |
| 23 | 1.1 |
| 24 | 1.1 |
| 25 | 0.7 |
| 26 | inactive |
| 27 | 3.9 |
| 28 | 11.7 |
| 29 | 6.7 |
| 30 | >13.0 |
| 31 | 7.6 |
| 32 | 2.2 |
| 33 | 12.0 |
| 34 | 9.1 |

305
-continued

| Compounds | hIFNβ ELISA (EC50, μM) |
|---|---|
| 35 | 6.2 |
| 36 | 13.7 |
| 37 | inactive |
| 38 | inactive |
| 39 | 2.2 |
| 40 | 4.7 |
| 41 | 8.8 |
| 42 | 2.2 |
| 43 | 4.6 |
| 44 | >39.7 |
| 45 | >50 |
| 46 | >6.9 |
| 47 | inactive |
| 48 | inactive |
| 49 | 0.5 |
| 50 | 1.6 |
| 51 | >50 |
| 52 | >50 |
| 53 | 1.2 |
| 54 | 5.2 |
| 55 | 1.2 |
| 56 | 17.3 |
| 57 | 2.6 |
| 58 | >4.3 |
| 59 | >5.6 | inactive: indicated that IFNβ was not detected at the maximum concentration of compounds;
NT: not tested.

Example 4: Efficacy Study of STING Agonist in Mouse Colon Cancer (CT26) Model by IV (Intravenous) Dosing 0.1 ml (2×105 cells) of CT26 cells were subcutaneously inoculated on the back of right forelimb of BALB/c mice. Tumors were grown to 100 mm³ followed by randomization and three repeat IV dosing. The day of grouping was recorded as the day 0. On days 0, 4 and 8 after grouping, the compound of the invention was given intravenously through tail vein (solvent: DMAC/PEG400/pH5 acetate buffer=0.5/30/69.5, compound concentration: 1 mg/ml), and the dosage of each mouse was 100 μg. The tumor volumes are shown in FIG. 1.

Figure 2:
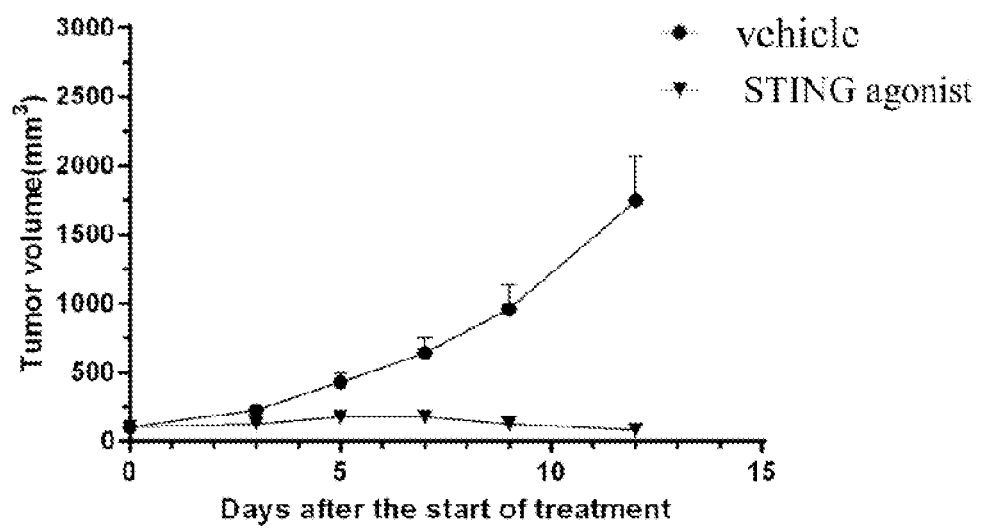

Example 5: Efficacy Study of STING Agonist in Mouse Colon Cancer (CT26) Model by IT (Intratumor) Dosing 0.1 ml (2×105 cells) of CT26 cells were subcutaneously inoculated on the back of right forelimb of BALB/c mice. Tumors were grown to 100 mm³ followed by randomization and three repeat IT dosing. The day of grouping was recorded as the day 0. On days 0, 4 and 8 after grouping, the compound of the invention was given intratumor injection (solvent: DMAC/PEG400/pH 5 acetate buffer=0.5/30/69.5, compound concentration: 2.5 mg/ml), and the dosage of each mouse was 50 μg. The tumor volumes are shown in FIG. 2.

306

The invention claimed is:
1. A compound having a structure of Formula (I) or (II),

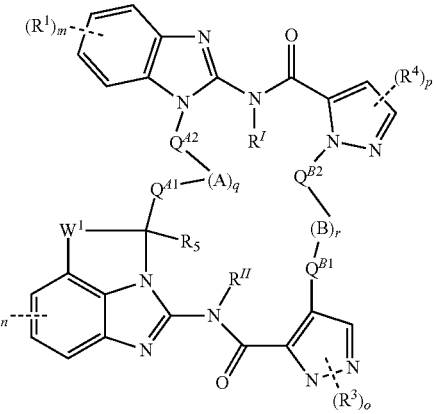

Formula (I)

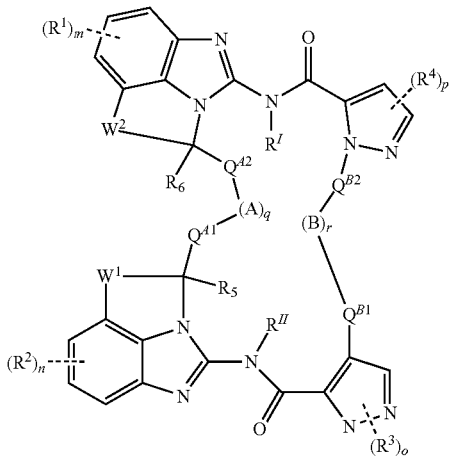

Formula (II)

wherein $W^1$ represents $(CR^aR^{a'})s$, any one $CR^aR^{a'}$ is optionally substituted by 0, 1 or 2 O, S or $NR^b$, or any one $CR^aR^{a'}$ is optionally taken together to form —C=O;

$W^2$ represents $(CR^hR^{h'})_t$, wherein any one $CR^hR^{h'}$ is optionally substituted by 0, 1 or 2 O, S or NR, or any one $CR^hR^{h'}$ is optionally taken together to form —C=O:

s and t each independently consist of an integer selected from 1, 2, and 3;

q is selected from 0 and 1;

r is selected from 0 and 1; and q and r are not 0 at the same time;

wherein $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R$, —$CON(R^c)(R^{c'})$, —$C(=NH)N(R^c)(R^{c'})$, —$NR^cC(O)R^{c'}$, —$SO_2R^c$, —$SO_2NR^cR^{c'}$, —$N(R^c)$—$SO_2$—($C_1$-$C_6$ alkyl)-$NR^cR^{c'}$, —$N(R^c)$—$C(O)$—($C_1$-$C_6$ alkyl)-$NR^cR^{c'}$, —$NR^cS(O)R^{c'}$, —$NR^cSO_2R^{c'}$, —O—P(O)$(OR^c)(OR^{c'})$, 6- to 12-membered aryl or 5- to 12-membered heteroaryl;

$R^5$ and $R^6$ are each independently selected from hydrogen or $C_1$-$C_6$ alkyl;

wherein when q=0, $Q^{41}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $QA^1$ and $R^5$ together with atoms adjacent thereto form a 3- to 6-membered ring optionally containing 0, 1 or 2 heteroatoms selected from O, N and S; $Q^{A2}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or $QA^2$ and $R^6$ together with atoms adjacent thereto, form a 3- to 6-membered ring optionally containing 0, 1, or 2 heteroatoms selected from O, N, and S:

when q=1, -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

wherein when r=0, $Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

when r=1, -$Q^{B1}$-B-$Q^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$R^I$ and $R^{II}$ each independently represent hydrogen or $C_1$-$C_6$ alkyl;

wherein $R^a$, $R^{a'}$, $R^h$ and $R^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^dR^{d'}$, —$NR^dCOR^{d'}$, —$NR^dS(O)R^{d'}$, —$NR^dSO_2R^{d'}$, —OR, or —$OCOR^d$;

$R^b$ and $R^j$ each independently represent hydrogen, $C_1$-$C_6$ alkyl, $C_3$-$C_6$ cycloalkyl, —($C_0$-$C_6$ alkylene)-(6- to 12-membered aryl), —C(O)$R^e$, —$SOR^e$, —$SO_2R^e$, —C(O)$OR^e$, or —C(O)$NR^eR^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

or $R^h$ and $R^{h'}$ together with the atom bound thereto are optionally cyclized to each other into a 3- to 6-membered ring optionally containing 0, 1, or 2 heteroatoms selected from O, N and S:

wherein m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from O, N and S;

or when n=2, the two adjacent $R^2$ and the atom bound thereto are optionally cyclized to each other into a 5- to 8-membered ring optionally containing 0, 1 or 2 heteroatoms selected from O, N and S;

or when p=2, the two adjacent $R^4$ and the atom bound thereto are optionally cyclized to each other into a 5- to 8-membered ring optionally containing 0, 1 or 2 heteroatoms selected from O, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —OC(O)$R^f$, —S(O)$R^f$, —$S(O)_2R^f$, —$S(O)_2NR^fR^{f'}$, —$OCONR^fR^{f'}$, —$NR^fCOR^{f'}$, —$NR^fS(O)R^{f'}$, —$NR^fS(O)_2R^{f'}$, —$NR^fC(O)OR^{f'}$, —$CONR^fR^{f'}$, —$NR^fR^{f'}$, —NHC=$NHNR^fR^{f'}$, $C_1$-$C_6$ haloalkyl, $C_1$-$C_6$ haloalkoxy, and —O—P(O)($OR^f$)($OR^{f'}$);

wherein $R^d$, $R^{d'}$, $R^e$, $R^{e'}$, $R^f$, and $R^{f'}$ each independently represent hydrogen or $C_1$-$C_6$ alkyl, wherein the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —C(O)—$OR^g$, —OC(O)$R^g$, —S(O)$R^g$, —$S(O)_2R^g$, —$S(O)_2NR^gR^{g'}$, —$NR^gCOR^{g'}$, —$NR^gS(O)R^{g'}$, —$NR^gS(O)_2R^{g'}$, —$NR^gC(O)OR^{g'}$, —$CONR^gR^{g'}$, —$NR^gR^{g'}$, $C_1$-$C_6$ haloalkyl, $C_1$-$C_6$ haloalkoxy, or —O—P(O)($OR^g$)($OR^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

wherein $R^g$ and $R^{g'}$ are each independently selected from hydrogen or $C_1$-$C_6$ alkyl.

2. The compound according to claim 1, having the following structure:

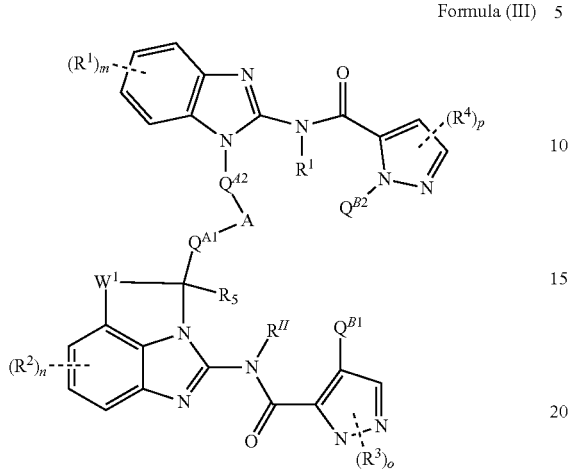

Formula (III)

wherein $W^1$ represents $(CR^aR^{a'})_s$, wherein any one $CR^aR^{a'}$ is optionally substituted by 0, 1 or 2 O, S or $NR^b$, or any one $CR^aR^{a'}$ is optionally taken together to form —C=O;

s is selected from integers of 1, 2 and 3;

wherein $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R^c$, —$CON(R^c)(R^{c'})$, —$C(=NH)N(R^c)(R^{c'})$, —$NR^cC(O)R^{c'}$, —$SO_2R^c$, —$SO_2NR^cR^{c'}$, —$N(R^c)$—$SO_2$—($C_1$-$C_6$ alkyl)-$NR^cR^{c'}$, —$N(R^c)$—$C(O)$—($C_1$-$C_6$ alkyl)-$NR^cR^{c'}$, —$NR^cS(O)R^{c'}$, —$NR^cSO_2R^{c'}$, —O—P(O)$(OR^c)(OR^{c'})$, 6- to 12-membered aryl or 5- to 12-membered heteroaryl;

$R^5$ is selected from hydrogen or $C_1$-$C_6$ alkyl;

wherein -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

$Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);

$R^I$ and $R^{II}$ each independently represent hydrogen or $C_1$-$C_6$ alkyl;

wherein $R^a$ and $R^{a'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^aR^{a'}$, —$NR^dCOR^{d'}$, —$NR^dS(O)R^{d'}$, —$NR^dSO_2R^{d'}$, —OR, or —$OCOR^d$;

$R^b$ each independently represents hydrogen, $C_1$-$C_6$ alkyl, $C_3$-$C_6$ cycloalkyl, —($C_0$-$C_6$ alkylene)-(6- to 12-membered aryl), —$C(O)R^e$, —$SOR^e$, —$SO_2R^e$, —C(O)$OR^e$, or —$C(O)NR^eR^{e'}$;

$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or $R^a$ and $R^{a'}$ together with the atom bound thereto are optionally cyclized to each other into a 3- to 6-membered ring optionally containing 0, 1, or 2 heteroatoms selected from O, N and S;

or $R^c$ and $R^{c'}$ together with the atom bound thereto are optionally cyclized to each other into a 3- to 6-membered ring optionally containing 0, 1, or 2 heteroatoms selected from O, N and S;

wherein m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from O, N and S;

or when n=2, the two adjacent $R^2$ and the atom bound thereto are optionally cyclized to each other into a 5- to 8-membered ring optionally containing 0, 1 or 2 heteroatoms selected from O, N and S;

or when p=2, the two adjacent $R^4$ and the atom bound thereto are optionally cyclized to each other into a 5- to 8-membered ring optionally containing 0, 1 or 2 heteroatoms selected from O, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —$OC(O)R^f$, —$S(O)R^f$, —$S(O)_2R^f$, —$S(O)_2NR^fR^{f'}$, —$OCONR^fR^{f'}$, —$NR^fCOR^{f'}$, —$NR^fS(O)R^{f'}$, —$NR^fS(O)_2R^{f'}$, —$NR^fC(O)OR^{f'}$, —$CONR^fR^{f'}$, —$NR^fR^{f'}$, —NHC=$NHNR^fR^{f'}$, $C_1$-$C_6$ haloalkyl, $C_1$-$C_6$ haloalkoxy, and —O—P(O)$(OR^f)(OR^{f'})$;

wherein $R^d$, $R^{d'}$, $R^e$, $R^{e'}$, $R^f$, and $R^{f'}$ each independently represent hydrogen or $C_1$-$C_6$ alkyl, wherein the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —C(O)—$OR^g$, —$OC(O)R^g$, —$S(O)R^g$, —$S(O)_2R^g$, —$S(O)_2NR^gR^{g'}$, —$NR^gCOR^{g'}$, —$NR^gS(O)R^{g'}$, —$NR^gS(O)_2R^{g'}$, —$NR^gC(O)OR^{g'}$, —$CONR^gR^{g'}$, —$NR^gR^{g'}$, $C_1$-$C_6$ haloalkyl, $C_1$-$C_6$ haloalkoxy, or —O—P(O)$(OR^g)(OR^{g'})$;

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

wherein $R^g$ and $R^{g'}$ are each independently selected from hydrogen or $C_1$-$C_6$ alkyl.

3. The compound according to claim 1, having the following structure:

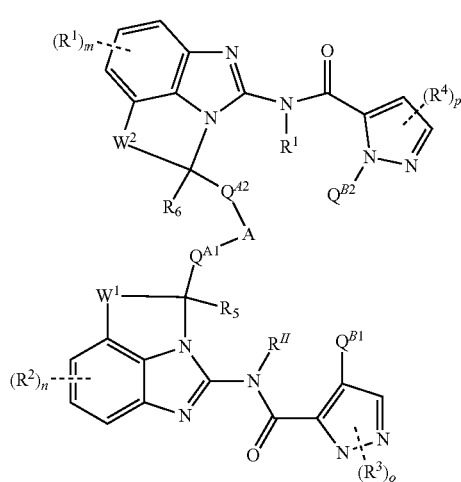

Formula (IV)

wherein $W^1$ represents $(CR^aR^{a'})s$, wherein any one $CR^aR^{a'}$ is optionally substituted by 0, 1 or 2 O, S or $NR^b$, or any one $CR^aR^{a'}$ is optionally taken together to form —C=O;
$W^2$ represents $(CR^hR^{h'})_t$, wherein any one $CR^hR^{h'}$ is optionally substituted by 0, 1 or 2 O, S or $NR^j$, or any one $CR^hR^{h'}$ is optionally taken together to form —C=O;
s and t each independently consist of an integer selected from 1, 2, and 3;
wherein $R^1$, $R^2$, $R^3$, and $R^4$ each independently represent hydrogen, halogen, cyano, $C_1$-$C_6$ alkyl, $C_2$-$C_6$ alkenyl, $C_2$-$C_6$ alkynyl, —$OR^c$, —O—($C_1$-$C_6$ alkylene)-$NR^cR^{c'}$, —$NR^cR^{c'}$, —$OC(O)R^c$, —$C(O)R^c$, —$CO_2R$, —$CON(R^c)(R^{c'})$, —C(=NH)N($R^c$)($R^{c'}$), —$NR^cC(O)R^{c'}$, —$SO_2R^c$, —$SO_2NR^cR^{c'}$, —N($R^c$)—$SO_2$—($C_1$-$C_6$ alkyl)-$NR^cR^{c'}$, —N($R^c$)—C(O)—($C_1$-$C_6$ alkyl)-$NR^cR^{c'}$, —$NR^cS(O)R^{c'}$, —$NR^cSO_2R^{c'}$, —O—P(O)(O$R^c$)(O$R^{c'}$), 6- to 12-membered aryl, or 5- to 12-membered heteroaryl;
$R^5$ and $R^6$ are each independently selected from hydrogen or $C_1$-$C_6$ alkyl;
wherein -$Q^{A1}$-A-$Q^{A2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-$NR^c$—C(O)—($C_0$-$C_6$ alkylene)-, —($C_0$-$C_6$ alkylene)-C(O)—$NR^c$—($C_0$-$C_6$ alkylene)-, —($C_0$-$C_6$ alkylene)-$NR^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;
$Q^{B1}$ and $Q^{B2}$ are each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl);
$R^I$ and $R^{II}$ each independently represent hydrogen or $C_1$-$C_6$ alkyl;
wherein $R^a$, $R^{a'}$, $R^h$, and $R^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —$NR^dR^{d'}$, —$NR^dCOR^{d'}$, —$NR^dS(O)R^{d'}$, —$NR^dSO_2R^{d'}$, —$OR^d$, or —$OCOR^d$;
$R^b$ and $R^j$ each independently represent hydrogen, $C_1$-$C_6$ alkyl, $C_3$-$C_6$ cycloalkyl, —($C_0$-$C_6$ alkylene)-(6- to 12-membered aryl), —$C(O)R^e$, —$SOR^e$, —$SO_2R^e$, —$C(O)OR^e$, or —$C(O)NR^eR^{e'}$;
$R^c$ and $R^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);
or $R^a$ and $R^{a'}$ together with the atom bound thereto are optionally cyclized to each other into a 3- to 6-membered ring optionally containing 0, 1, or 2 heteroatoms selected from O, N and S;
or $R^c$ and $R^{c'}$ together with the atom bound thereto are optionally cyclized to each other into a 3- to 6-membered ring optionally containing 0, 1, or 2 heteroatoms selected from O, N and S;
or $R^h$ and $R^{h'}$ together with the atom bound thereto are optionally cyclized to each other into a 3- to 6-membered ring optionally containing 0, 1, or 2 heteroatoms selected from O, N and S;
wherein m=1, 2, 3 or 4;
n=1, 2 or 3;
o=1 or 2; and
p=1 or 2;
or when m=2, the two adjacent $R^1$ and the atom bound thereto are optionally cyclized to each other into a 5- to 8-membered ring optionally containing 0, 1 or 2 heteroatoms selected from O, N and S;
or when n=2, the two adjacent $R^2$ and the atom bound thereto are optionally cyclized to each other into a 5- to 8-membered ring optionally containing 0, 1 or 2 heteroatoms selected from O, N and S;
or when p=2, the two adjacent $R^4$ and the atom bound thereto are optionally cyclized to each other into a 5- to 8-membered ring optionally containing 0, 1 or 2 heteroatoms selected from O, N and S;
any alkyl, alkoxy, alkenyl, alkynyl, alkylene, aryl, heteroaryl, carbocyclyl, heterocyclyl defined above are optionally substituted by 0, 1, 2, 3, or 4 substituents selected from:
$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —$OC(O)R^f$, —S(O)$R^f$, —S(O)$_2R^f$, —S(O)$_2NR^fR^{f'}$, —$OCONR^fR^{f'}$, —$NR^fCOR^{f'}$, —$NR^fS(O)R^{f'}$, —$NR^fS(O)_2R^{f'}$, —$NR^fC(O)OR^{f'}$, —$CONR^fR^{f'}$, —$NR^fR^{f'}$, $C_1$-$C_8$ haloalkyl, $C_1$-$C_8$ haloalkoxy, and —O—P(O)(O$R^f$)(O$R^e$);
wherein $R^d$, $R^{d'}$, $R^e$, $R^{e'}$, $R^f$, and $R^{f'}$ each independently represent hydrogen or $C_1$-$C_6$ alkyl, wherein the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR$^g$, —C(O)—OR$^g$, —OC(O)R$^g$, —S(O)R$^g$, —S(O)$_2$R$^g$, —S(O)$_2$NR$^g$R$^{g'}$, —NR$^g$COR$^{g'}$, —NR$^g$S(O)R$^{g'}$, —NR$^g$S(O)$_2$R$^{g'}$, —NR$^g$C(O)OR$^{g'}$, —CONR$^g$R$^{g'}$, —NR$^g$R$^{g'}$, C$_1$-C$_6$ haloalkyl, C$_1$-C$_6$ haloalkoxy, or —O—P(O)(OR$^g$)(OR$^{g'}$);

or R$^d$, R$^{d'}$, R$^e$, R$^{e'}$, R$^f$, and R$^{f'}$ together with the nitrogen atom bound thereto form a 5- to 8-membered carbocycle or a 5- to 8-membered heterocycle;

wherein R$^g$ and R$^{g'}$ are each independently selected from hydrogen or C$_1$-C$_6$ alkyl.

4. The compound according to claim 1, having the following structure:

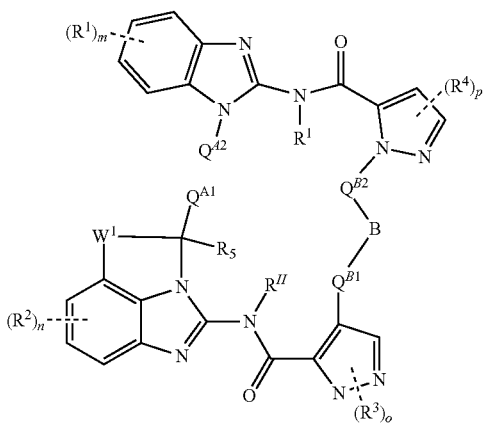

Formula (V)

wherein W$^1$ represents (CR$^a$R$^{a'}$)s, wherein any one CR$^a$R$^{a'}$ is optionally substituted by 0, 1 or 2 O, S or NR$^b$, or any one CR$^a$R$^{a'}$ is optionally taken together to form —C=O;

s is selected from integers of 1, 2 and 3;

wherein R$^1$, R$^2$, R$^3$, and R$^4$ each independently represent hydrogen, halogen, cyano, C$_1$-C$_6$ alkyl, C$_2$-C$_6$ alkenyl, C$_2$-C$_6$ alkynyl, —OR$^c$, —O—(C$_1$-C$_6$ alkylene)-NR$^c$R$^{c'}$, —NR$^c$R$^{c'}$, —OC(O)R$^c$, —C(O)R$^c$, —CO$_2$R, —CON(R$^c$)(R$^{c'}$), —C(=NH)N(R$^c$)(R$^{c'}$), —NR$^c$C(O)R$^{c'}$, —SO$_2$R$^c$, —SO$_2$NR$^c$R$^{c'}$, —N(R$^c$)—SO$_2$—(C$_1$-C$_6$ alkyl)-NR$^c$R$^{c'}$, —N(R$^c$)—C(O)—(C$_1$-C$_6$ alkyl)-NR$^c$R$^{c'}$, —NR$^c$S(O)R$^{c'}$, —NR$^c$SO$_2$R$^{c'}$, —O—P(O)(OR$^c$)(OR$^{c'}$), 6- to 12-membered aryl or 5- to 12-membered heteroaryl;

R$^5$ is selected from hydrogen or C$_1$-C$_6$ alkyl;

wherein Q$^{A1}$ is each independently selected from the group consisting of hydrogen, C$_1$-C$_6$ alkyl, C$_2$-C$_6$ alkenyl, C$_2$-C$_6$ alkynyl, —(C$_0$-C$_6$ alkyl)-(C$_3$-C$_6$ cycloalkyl), —(C$_0$-C$_6$ alkyl)-(4- to 6-membered heterocyclyl), —(C$_0$-C$_6$ alkyl)-(6- to 12-membered aryl), and —(C$_0$-C$_6$ alkyl)-(5- to 12-membered heteroaryl); or QA$^1$ and R$^5$ together with the atoms adjacent thereto, form a 3- to 6-membered ring optionally containing 0, 1, or 2 heteroatoms selected from O, N, and S; Q$^{A2}$ is each independently selected from the group consisting of hydrogen, C$_1$-C$_6$ alkyl, C$_2$-C$_6$ alkenyl, C$_2$-C$_6$ alkynyl, —(C$_0$-C$_6$ alkyl)-(C$_3$-C$_6$ cycloalkyl), —(C$_0$-C$_6$ alkyl)-(4- to 6-membered heterocyclyl), —(C$_0$-C$_6$ alkyl)-(6- to 12-membered aryl), and —(C$_0$-C$_6$ alkyl)-(5- to 12-membered heteroaryl);

wherein -Q$^{B1}$-B-Q$^{B2}$- is taken together to form a linking group selected from: —C$_1$-C$_6$ alkylene-, —C$_2$-C$_6$ alkenylene-, —C$_2$-C$_6$ alkynylene-, —(C$_0$-C$_6$ alkylene)-O—(C$_0$-C$_6$ alkylene)-, —(C$_0$-C$_6$ alkylene)-C(O)—(C$_0$-C$_6$ alkylene)-, —C(O)—(C$_0$-C$_6$ alkylene)-O—(C$_0$-C$_6$ alkylene)-, —(C$_0$-C$_6$ alkylene)-OC(O)—(C$_0$-C$_6$ alkylene)-, —(C$_0$-C$_6$ alkylene)-NR$^c$—C(O)—(C$_0$-C$_6$ alkylene)-, —(C$_0$-C$_6$ alkylene)-C(O)—NR$^c$—(C$_0$-C$_6$ alkylene)-, —(C$_0$-C$_6$ alkylene)-NR$^c$—(C$_0$-C$_6$ alkylene)-, —(C$_0$-C$_6$ alkylene)-C(O)O—(C$_0$-C$_6$ alkylene)-, —(C$_0$-C$_6$ alkylene)-(C$_3$-C$_6$ carbocyclyl)-(C$_0$-C$_6$ alkylene)-, —(C$_0$-C$_6$ alkylene)-(4- to 6-membered heterocyclyl)-(C$_0$-C$_6$ alkylene)-, —(C$_0$-C$_6$ alkylene)-(6- to 12-membered aryl)-(C$_0$-C$_6$ alkylene)-, and —(C$_0$-C$_6$ alkylene)-(5- to 12-membered heteroaryl)-(C$_0$-C$_6$ alkylene)-;

R$^I$ and R$^{II}$ each independently represent hydrogen or C$_1$-C$_6$ alkyl;

wherein R$^a$ and R$^{a'}$ each independently represent hydrogen, halogen, hydroxy, C$_1$-C$_6$ alkyl, C$_1$-C$_6$ alkylthio, —(C$_0$-C$_6$ alkylene)-(C$_3$-C$_6$ cycloalkyl), —(C$_0$-C$_6$ alkylene)-(4- to 6-membered heterocyclyl), —(C$_0$-C$_6$ alkylene)-(6- to 12-membered aryl), —(C$_0$-C$_6$ alkylene)-(5- to 12-membered heteroaryl), —NR$^d$R$^{d'}$, —NR$^d$COR$^{d'}$, —NR$^d$S(O)R$^{d'}$, —NR$^d$SO$_2$R$^{d'}$, —OR, or —OCOR$^d$;

R$^b$ each independently represents hydrogen, C$_1$-C$_6$ alkyl, C$_3$-C$_6$ cycloalkyl, —(C$_0$-C$_6$ alkylene)-(6- to 12-membered aryl), —C(O)R$^e$, —SOR$^e$, —SO$_2$R$^e$, —C(O)OR$^e$, or —C(O)NR$^e$R$^{e'}$;

R$^c$ and R$^{c'}$ each independently represent hydrogen, C$_1$-C$_6$ alkyl, —(C$_0$-C$_6$ alkylene)-(C$_3$-C$_6$ cycloalkyl), or —(C$_0$-C$_6$ alkylene)-(4- to 6-membered heterocyclyl);

or R$^a$ and R$^{a'}$ together with the atom bound thereto are optionally cyclized to each other into a 3- to 6-membered ring optionally containing 0, 1, or 2 heteroatoms selected from O, N and S;

or R$^c$ and R$^{c'}$ together with the atom bound thereto are optionally cyclized to each other into a 3- to 6-membered ring optionally containing 0, 1, or 2 heteroatoms selected from O, N and S;

wherein m=1, 2, 3 or 4;

n=1, 2 or 3;

o=1 or 2; and p=1 or 2;

or when m=2, the two adjacent R$^1$ and the atom bound thereto are optionally cyclized to each other into a 5- to 8-membered ring optionally containing 0, 1 or 2 heteroatoms selected from O, N and S;

or when n=2, the two adjacent R$^2$ and the atom bound thereto are optionally cyclized to each other into a 5- to 8-membered ring optionally containing 0, 1 or 2 heteroatoms selected from O, N and S;

or when p=2, the two adjacent R$^4$ and the atom bound thereto are optionally cyclized to each other into a 5- to 8-membered ring optionally containing 0, 1 or 2 heteroatoms selected from O, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

C$_1$-C$_6$ alkyl, C$_2$-C$_6$ alkenyl, C$_2$-C$_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, C$_1$-C$_6$ mercapto, C$_1$-C$_6$ alkoxy, —OR$^f$, —C(O)—OR$^f$, —OC(O)R$^f$, —S(O)R$^f$, —S(O)$_2$R$^f$, —S(O)$_2$NR$^f$R$^{f'}$, —OCONR$^f$R$^{f'}$, —NR$^f$COR$^f$, —NR$^f$S(O)R$^e$, —NR$^f$S(O)$_2$R$^f$, —NR$^f$C (O)OR$^f$', —CONR$^f$R$^f$', —NR$^f$R$^f$', —NHC=NHNR$^f$R$^f$', $C_1$-$C_6$ haloalkyl, $C_1$-$C_6$ haloalkoxy, and —O—P(O)(OR$^f$)(OR$^f$');

wherein R$^d$, R$^{d'}$, R$^e$, R$^{e'}$, R$^f$, and R$^{f'}$ each independently represent hydrogen or $C_1$-$C_6$ alkyl, wherein the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —OR$^g$, —C(O)—OR$^g$, —OC(O)R$^g$, —S(O)R$^g$, —S(O)$_2$R$^g$, —S(O)$_2$NR$^g$R$^{g'}$, —NR$^g$COR$^{g'}$, —NR$^g$S(O)R$^{g'}$, —NR$^g$S(O)$_2$R$^{g'}$, —NR$^g$C(O)OR$^{g'}$, —CONR$^g$R$^{g'}$, —NR$^g$R$^{g'}$, $C_1$-$C_6$ haloalkyl, $C_1$-$C_6$ haloalkoxy, or —O—P(O)(OR$^g$)(OR$^{g'}$);

or R$^d$, R$^{d'}$, R$^e$, R$^{e'}$, R$^f$, and R$^{f'}$ together with the nitrogen atom bound thereto form a 5- to 8-membered carbocycle or a 5- to 8-membered heterocycle;

wherein R$^g$ and R$^{g'}$ are each independently selected from hydrogen or $C_1$-$C_6$ alkyl.

5. The compound according to claim 1, having the following structure:

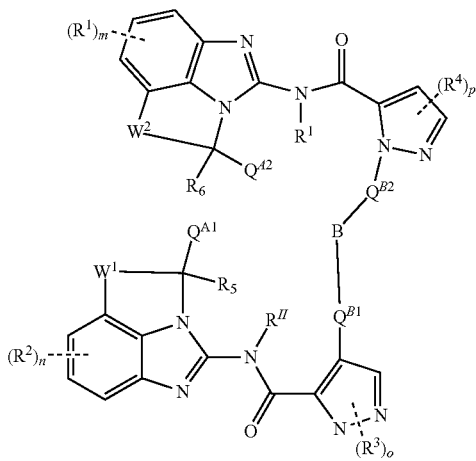

Formula (VI)

wherein W$^1$ represents (CR$^a$R$^{a'}$)s, wherein any one CR$^a$R$^{a'}$ is optionally substituted by 0, 1 or 2 O, S or NR$^b$, or any one CR$^a$R$^{a'}$ is optionally taken together to form —C=O;

W$^2$ represents (CR$^h$R$^{h'}$)$_t$, wherein any one CR$^h$R$^{h'}$ is optionally substituted by 0, 1 or 2 O, S or NR$^j$, or any one CR$^h$R$^{h'}$ is optionally taken together to form —C=O;

s and t each independently consist of an integer selected from 1, 2, and 3;

wherein R$^1$, R$^2$, R$^3$, and R$^4$ each independently represent hydrogen, halogen, cyano, $C_1$-$C_6$ alkyl, $C_2$-$C_6$ alkenyl, $C_2$-$C_6$ alkynyl, —OR$^c$, —O—($C_1$-$C_6$ alkylene)-NR$^c$R$^{c'}$, —NR$^c$R$^{c'}$, —OC(O)R$^c$, —C(O)R$^c$, —CO$_2$R, —CON(R$^c$)(R$^{c'}$), —C(=NH)N(R$^c$)(R$^{c'}$), —NR$^c$C(O)R$^{c'}$, —SO$_2$R$^c$, —SO$_2$NR$^c$R$^{c'}$, —N(R$^c$)—SO$_2$—($C_1$-$C_6$ alkyl)-NR$^c$R$^{c'}$, —N(R$^c$)—C(O)—($C_1$-$C_6$ alkyl)-NR$^c$R$^{c'}$, —NR$^c$S(O)R$^{c'}$, —NR$^c$SO$_2$R$^{c'}$, —O—P(O)(OR$^c$)(OR$^{c'}$), 6- to 12-membered aryl, or 5- to 12-membered heteroaryl;

R$^5$ and R$^6$ are each independently selected from hydrogen or $C_1$-$C_6$ alkyl;

wherein Q$^{41}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or QA$^1$ and R$^5$ together with the atoms adjacent thereto, form a 3- to 6-membered ring optionally containing 0, 1, or 2 heteroatoms selected from O, N, and S; Q$^{42}$ is each independently selected from the group consisting of hydrogen, $C_1$-$C_6$ alkyl, $C_2$-$C_6$ alkenyl, $C_2$-$C_6$ alkynyl, —($C_0$-$C_6$ alkyl)-($C_3$-$C_6$ cycloalkyl), —($C_0$-$C_6$ alkyl)-(4- to 6-membered heterocyclyl), —($C_0$-$C_6$ alkyl)-(6- to 12-membered aryl), and —($C_0$-$C_6$ alkyl)-(5- to 12-membered heteroaryl); or QA$^2$ and R$^6$ together with the atoms adjacent thereto, form a 3- to 6-membered ring optionally containing 0, 1, or 2 heteroatoms selected from O, N, and S;

where -Q$^{B1}$-B-Q$^{B2}$- is taken together to form a linking group selected from: —$C_1$-$C_6$ alkylene-, —$C_2$-$C_6$ alkenylene-, —$C_2$-$C_6$ alkynylene-, —($C_0$-$C_6$ alkylene)-O—($C_0$-$C_6$ alkylene)-, —($C_0$-$C_6$ alkylene)-C(O)—($C_0$-$C_6$ alkylene)-, —C(O)—($C_0$-$C_6$ alkylene)-O—($C_0$-$C_6$ alkylene)-, —($C_0$-$C_6$ alkylene)-OC(O)—($C_0$-$C_6$ alkylene)-, —($C_0$-$C_6$ alkylene)-NR$^c$—C(O)—($C_0$-$C_6$ alkylene)-, —($C_0$-$C_6$ alkylene)-C(O)—NR$^c$—($C_0$-$C_6$ alkylene)-, —($C_0$-$C_6$ alkylene)-NR$^c$—($C_0$-$C_6$ alkylene)-, —($C_0$-$C_6$ alkylene)-C(O)O—($C_0$-$C_6$ alkylene)-, —($C_0$-$C_6$ alkylene)-($C_3$-$C_6$ carbocyclyl)-($C_0$-$C_6$ alkylene)-, —($C_0$-$C_6$ alkylene)-(4- to 6-membered heterocyclyl)-($C_0$-$C_6$ alkylene)-, —($C_0$-$C_6$ alkylene)-(6- to 12-membered aryl)-($C_0$-$C_6$ alkylene)-, and —($C_0$-$C_6$ alkylene)-(5- to 12-membered heteroaryl)-($C_0$-$C_6$ alkylene)-;

R$^I$ and R$^{II}$ each independently represent hydrogen or $C_1$-$C_6$ alkyl;

wherein R$^a$, R$^{a'}$, R$^h$, and R$^{h'}$ each independently represent hydrogen, halogen, hydroxy, $C_1$-$C_6$ alkyl, $C_1$-$C_6$ alkylthio, —($C_0$-$C_6$ alkylene)-($C_3$-$C_6$ cycloalkyl), —($C_0$-$C_6$ alkylene)-(4- to 6-membered heterocyclyl), —($C_0$-$C_6$ alkylene)-(6- to 12-membered aryl), —($C_0$-$C_6$ alkylene)-(5- to 12-membered heteroaryl), —NR$^d$R$^{d'}$, —NR$^d$COR$^{d'}$, —NR$^d$S(O)R$^{d'}$, —NR$^d$SO$_2$R$^{d'}$, —OR$^d$, or —OCOR$^d$;

R$^b$ and R$^j$ each independently represent hydrogen, $C_1$-$C_6$ alkyl, $C_3$-$C_6$ cycloalkyl, —($C_0$-$C_6$ alkylene)-(6- to 12-membered aryl), —C(O)R$^e$, —SOR$^e$, —SO$_2$R$^e$, —C(O)OR$^e$, or —C(O)NR$^e$R$^{e'}$;

R$^c$ and R$^{c'}$ each independently represent hydrogen, $C_1$-$C_6$ alkyl, —($C_0$-$C_6$ alkylene)-($C_3$-$C_6$ cycloalkyl), or —($C_0$-$C_6$ alkylene)-(4- to 6-membered heterocyclyl);

or R$^a$ and R$^{a'}$ together with the atom bound thereto are optionally cyclized to each other into a 3- to 6-membered ring optionally containing 0, 1, or 2 heteroatoms selected from O, N and S;

or R$^c$ and R$^{c'}$ together with the atom bound thereto are optionally cyclized to each other into a 3- to 6-membered ring optionally containing 0, 1, or 2 heteroatoms selected from O, N and S;

or R$^h$ and R$^{h'}$ together with the atom bound thereto are optionally cyclized to each other into a 3- to 6-membered ring optionally containing 0, 1, or 2 heteroatoms selected from O, N and S;

wherein m=1, 2, 3 or 4;

n=1, 2 or 3;

o=1 or 2; and p=1 or 2;

or when m=2, the two adjacent $R^1$ and the atom bound thereto are optionally cyclized to each other into a 5- to 8-membered ring optionally containing 0, 1 or 2 heteroatoms selected from O, N and S;

or when n=2, the two adjacent $R^2$ and the atom bound thereto are optionally cyclized to each other into a 5- to 8-membered ring optionally containing 0, 1 or 2 heteroatoms selected from O, N and S;

or when p=2, the two adjacent $R^4$ and the atom bound thereto are optionally cyclized to each other into a 5- to 8-membered ring optionally containing 0, 1 or 2 heteroatoms selected from O, N and S;

any alkyl, alkoxy, alkenyl, alkynyl, alkylene, aryl, heteroaryl, carbocyclyl, heterocyclyl defined above are optionally substituted by 0, 1, 2, 3, or 4 substituents selected from:

$C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^f$, —C(O)—$OR^f$, —OC(O)$R^f$, —S(O)$R^f$, —S(O)$_2R^f$, —S(O)$_2NR^fR^{f'}$, —OCONR$^fR^{f'}$, —NR$^f$COR$^{f'}$, —NR$^f$S(O)$R^{f'}$, —NR$^f$S(O)$_2R^{f'}$, —NR$^f$C(O)OR$^{f'}$, —CONR$^fR^{f'}$, —NR$^fR^{f'}$, $C_1$-$C_8$ haloalkyl, $C_1$-$C_8$ haloalkoxy, and —O—P(O)(OR$^f$)(OR$^{f'}$);

wherein $R^d$, $R^{d'}$, $R^e$, $R^{e'}$, $R^f$, and $R^{f'}$ each independently represent hydrogen or $C_1$-$C_6$ alkyl, wherein the $C_1$-$C_6$ alkyl is also optionally substituted by $C_1$-$C_6$ alkyl, $C_2$-$C_6$ alkenyl, $C_2$-$C_6$ alkynyl, halogen, sulfo, cyano, 3- to 8-membered carbocyclyl, 3- to 8-membered heterocyclyl, 6- to 12-membered aryl, 5- to 12-membered heteroaryl, nitro, oxo, $C_1$-$C_6$ mercapto, $C_1$-$C_6$ alkoxy, —$OR^g$, —C(O)—$OR^g$, —OC(O)$R^g$, —S(O)$R^g$, —S(O)$_2R^g$, —S(O)$_2NR^gR^{g'}$, —NR$^g$COR$^{g'}$, —NR$^g$S(O)$R^{g'}$, —NR$^g$S(O)$_2R^{g'}$, —NR$^g$C(O)OR$^{g'}$, —CONR$^gR^{g'}$, —NR$^gR^{g'}$, $C_1$-$C_6$ haloalkyl, $C_1$-$C_6$ haloalkoxy, or —O—P(O)(OR$^g$)(OR$^{g'}$);

or $R^d$, $R^{d'}$, $R^e$, $R^{e'}$, $R^f$, and $R^{f'}$ together with the nitrogen atom bound thereto form a 5- to 8-membered carbocycle or a 5- to 8-membered heterocycle;

wherein $R^g$ and $R^{g'}$ are each independently selected from hydrogen or $C_1$-$C_6$ alkyl.

6. The compound according to claim 1, wherein $R^1$ and $R^2$ are each independently selected from the group consisting of hydrogen, halogen, cyano, $C_1$-$C_6$ alkyl, —$OR^c$, —O—($C_1$-$C_6$ alkylene)-NR$^cR^{c'}$, —NR$^cR^{c'}$, —CON(R$^c$)(R$^{c'}$), —C(=NH)N(R$^c$)(R$^{c'}$), and —NR$^c$C(O)R$^{c'}$.

7. The compound according to claim 1, wherein $R^1$ is each independently selected from: $C_1$-$C_6$ alkyl, $C_1$-$C_6$ alkoxy, —CON(R$^c$)(R$^{c'}$), —NR$^cR^{c'}$, —O—($C_1$-$C_6$ alkylene)-NR$^cR^{c'}$.

8. The compound according to claim 1, wherein $R^1$ is each independently selected from: —O—($C_1$-$C_6$ alkylene)-NR$^cR^{c'}$;

wherein $R^2$ is each independently selected from: —CON(R$^c$)(R$^{c'}$);

wherein $R^c$ and $R^{c'}$ consist of hydrogen or $C_1$-$C_6$ alkyl, and are also optionally substituted by 0, 1, 2, 3 or 4 substituents selected from the group consisting of —OR$^d$, —C(O)—OR$^d$, —OC(O)R$^d$, —CONR$^dR^{d'}$, —NR$^dR^{d'}$, and —O—P(O)(OR$^d$)(OR$^{d'}$), wherein $R^d$ and $R^{d'}$ consist of hydrogen or $C_1$-$C_6$ alkyl, or $R^d$ and $R^{d'}$ together with the nitrogen atom adjacent thereto form a 5- to 8-membered carbocycle or a 5- to 8-membered heterocycle;

wherein $R^3$ and $R^4$ are each independently selected from the group consisting of hydrogen, $C_1$-$C_6$ alkyl, $C_3$-$C_6$ cycloalkyl, and $C_1$-$C_6$ haloalkyl;

wherein $R^5$ consists of hydrogen or $C_1$-$C_6$ alkyl;

wherein $R^6$ consists of hydrogen or $C_1$-$C_6$ alkyl;

wherein $W^1$ consists of —(CR$^aR^{a'}$)—O—, —O—(CR$^aR^{a'}$)—, —C(O)—NR$^b$—, or —NR$^b$—C(O)—, wherein $R^a$, $R^{a'}$, and $R^b$ independently represent hydrogen, $C_1$-$C_6$ alkyl, or $C_3$-$C_6$ cycloalkyl;

wherein $W^2$ consists of —(CR$^hR^{h'}$)—O—, —O—(CR$^hR^{h'}$)—, —C(O)—NR$^j$—, or —NR$^j$—C(O)—, wherein $R^h$, $R^{h'}$, and $R^j$ each independently represent hydrogen, $C_1$-$C_6$ alkyl, or $C_3$-$C_6$ cycloalkyl;

wherein when q=1, -$Q^{A1}$-A-$Q^{A2}$- is taken together to form —CH$_2$CH$_2$CH$_2$CH$_2$—, —CH$_2$CH=CHCH$_2$—, —CH(OH)CH(OH)CH$_2$—, —CH$_2$CH$_2$CH$_2$—, —CH$_2$CH=CH—, —CH(OH)CH$_2$CH$_2$—, —CH=CHCH$_2$—, —CH$_2$CH=CH—, —CH$_2$CH(OH)CH$_2$—, —CH$_2$CH$_2$CH(OH)—, —CH$_2$NHCH$_2$CH$_2$—, —CH$_2$CH$_2$NHCH$_2$—, —CH$_2$N(CH$_3$)CH$_2$CH$_2$—, —CH$_2$CH$_2$N(CH$_3$)CH$_2$—, —CH=CH—, —CH$_2$CH$_2$—, —CH(OH)CH$_2$, —CH$_2$CH(OH)—, or —CH$_2$OCH$_2$CH$_2$—;

wherein when q=0, $Q^{A1}$ and $Q^{A2}$ are each independently selected from the group consisting of hydrogen, $C_1$-$C_6$ alkyl, $C_1$-$C_6$ haloalkyl, $C_2$-$C_6$ alkenyl, and $C_3$-$C_6$ cycloalkyl;

wherein when r=0, $Q^{B1}$ and $Q^{B2}$ are each independently selected from the group consisting of hydrogen, $C_1$-$C_6$ alkyl, $C_1$-$C_6$ haloalkyl, $C_2$-$C_6$ alkenyl, and $C_3$-$C_6$ cycloalkyl; or wherein when r=1, -$Q^{B1}$-A-$Q^{B2}$- is taken together to form —CH$_2$CH$_2$CH$_2$CH$_2$—, —CH$_2$CH=CHCH$_2$—, —CH(OH)CH(OH)CH$_2$—, —CH$_2$CH$_2$CH$_2$—, —CH$_2$CH=CH—, —CH(OH)CH$_2$CH$_2$—, —CH=CHCH$_2$—, —CH$_2$CH=CH—, —CH$_2$CH(OH)CH$_2$—, —CH$_2$CH$_2$CH(OH)—, —CH$_2$NHCH$_2$CH$_2$—, —CH$_2$CH$_2$NHCH$_2$—, —CH$_2$N(CH$_3$)CH$_2$CH$_2$—, —CH$_2$CH$_2$N(CH$_3$)CH$_2$—, —CH=CH—, —CH$_2$CH$_2$—, —CH(OH)CH$_2$, —CH$_2$CH(OH)—, or —CH$_2$OCH$_2$CH$_2$—.

9. The compound according to claim 2, wherein -$Q^{A1}$-A-$Q^{A2}$- is taken together to form —CH$_2$CH$_2$CH$_2$CH$_2$—, —CH$_2$CH=CHCH$_2$—, —CH(OH)CH(OH)CH$_2$—, —CH$_2$CH$_2$CH$_2$—, —CH$_2$CH=CH—, —CH(OH)CH$_2$CH$_2$—, —CH=CHCH$_2$—, —CH$_2$CH=CH—, —CH$_2$CH(OH)CH$_2$—, —CH$_2$CH$_2$CH(OH)—, —CH$_2$NHCH$_2$CH$_2$—, —CH$_2$CH$_2$NHCH$_2$—, —CH$_2$N(CH$_3$)CH$_2$CH$_2$—, —CH$_2$CH$_2$N(CH$_3$)CH$_2$—, —CH=CH—, —CH$_2$CH$_2$—, —CH(OH)CH$_2$, —CH$_2$CH(OH)—, or —CH$_2$OCH$_2$CH$_2$—.

10. The compound according to claim 4, wherein -$Q^{B1}$-A-$Q^{B2}$- is taken together to form —CH$_2$CH$_2$CH$_2$CH$_2$—, —CH$_2$CH=CHCH$_2$—, —CH(OH)CH(OH)CH$_2$—, —CH$_2$CH$_2$CH$_2$—, —CH$_2$CH=CH—, —CH(OH)CH$_2$CH$_2$—, —CH=CHCH$_2$—, —CH$_2$CH=CH—, —CH$_2$CH(OH)CH$_2$—, —CH$_2$CH$_2$CH(OH)—, —CH$_2$NHCH$_2$CH$_2$—, —CH$_2$CH$_2$NHCH$_2$—, —CH$_2$N(CH$_3$)CH$_2$CH$_2$—, —CH$_2$CH$_2$N(CH$_3$)CH$_2$—, —CH=CH—, —CH$_2$CH$_2$—, —CH(OH)CH$_2$, —CH$_2$CH(OH)—, or —CH$_2$OCH$_2$CH$_2$—.

11. The compound according to claim 1, having a structure selected from:
| No. | Compound structure |
|---|---|
| 1 | 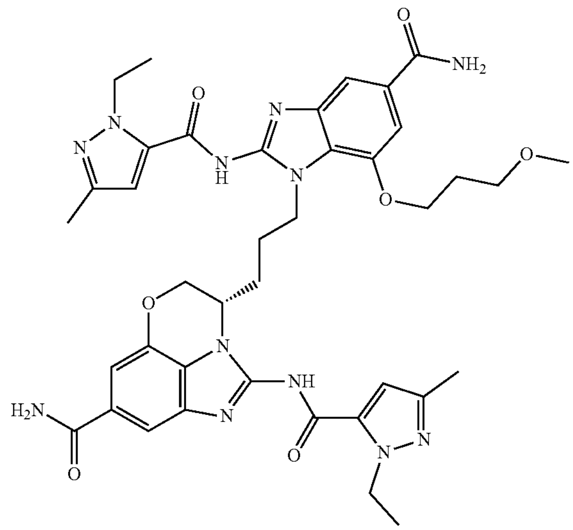 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4cc(C)nn4CC)n1c23] |
| 2 | 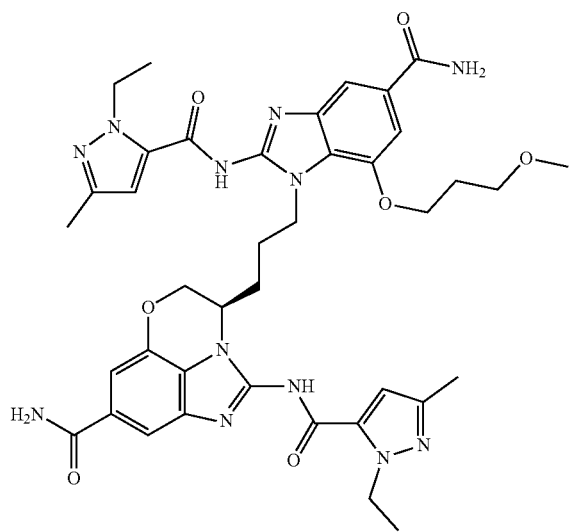 [SMILES: CCn1nc(C)cc1C(=O)Nc1nc2cc(C(N)=O)cc(OCCCOC)c2n1CCC[C@@H]1COc2cc(C(N)=O)cc3nc(NC(=O)c4cc(C)nn4CC)n1c23] |

-continued
| No. | Compound structure |
|---|---|
| 3 | 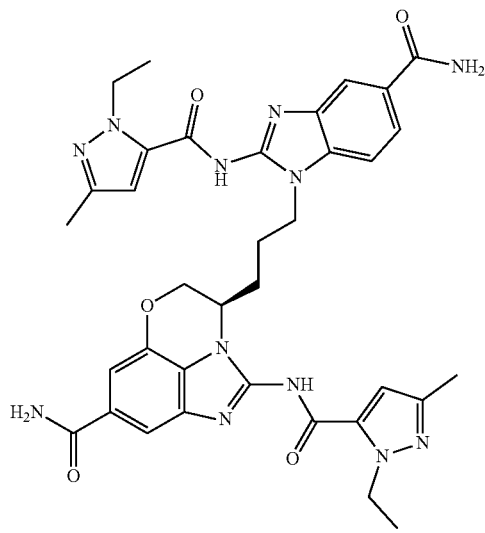 [SMILES: CCn1nc(C)cc1C(=O)Nc1nc2cc(C(N)=O)ccc2n1CCC[C@@H]1COc2cc(C(N)=O)cc3nc(NC(=O)c4cc(C)nn4CC)n1c23] |
| 4 | 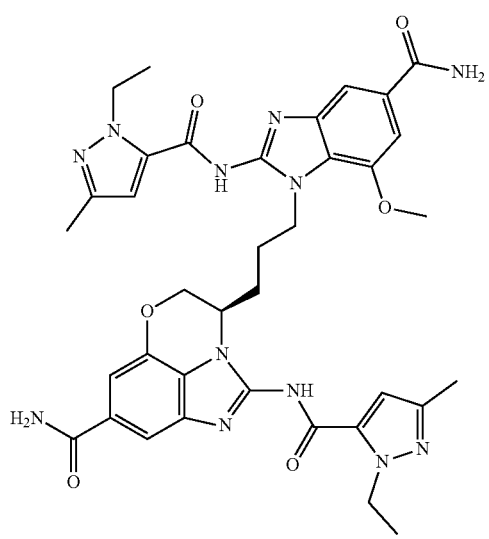 [SMILES: CCn1nc(C)cc1C(=O)Nc1nc2cc(C(N)=O)cc(OC)c2n1CCC[C@@H]1COc2cc(C(N)=O)cc3nc(NC(=O)c4cc(C)nn4CC)n1c23] |
| 5 | 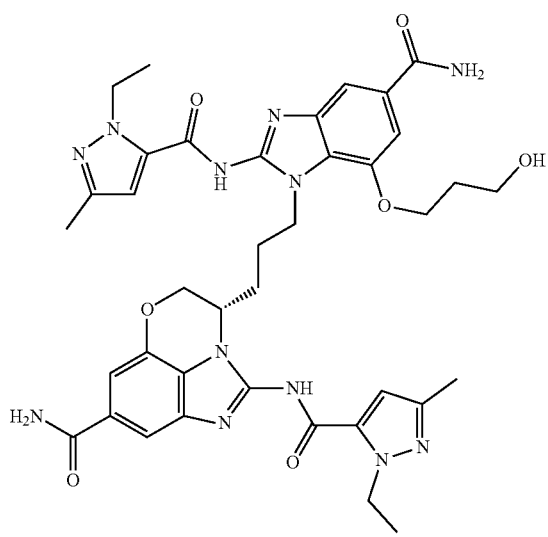 [SMILES: CCn1nc(C)cc1C(=O)Nc1nc2cc(C(N)=O)cc(OCCCO)c2n1CCC[C@H]1COc2cc(C(N)=O)cc3nc(NC(=O)c4cc(C)nn4CC)n1c23] |

-continued
| No. | Compound structure |
|---|---|
| 6 | 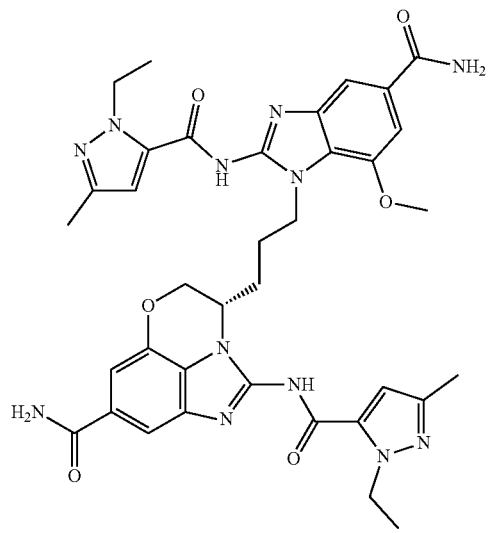 [SMILES: CCn1nc(C)cc1C(=O)Nc1nc2cc(C(N)=O)cc(OC)c2n1CCC[C@H]1COc2cc(C(N)=O)cc3nc(NC(=O)c4cc(C)nn4CC)n1c23] |
| 7 | 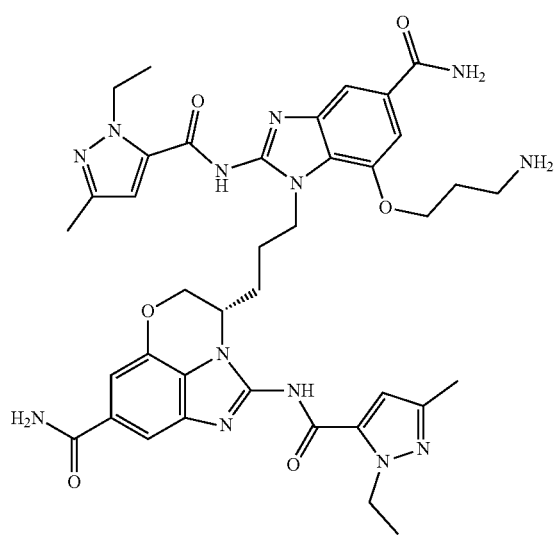 [SMILES: CCn1nc(C)cc1C(=O)Nc1nc2cc(C(N)=O)cc(OCCCN)c2n1CCC[C@H]1COc2cc(C(N)=O)cc3nc(NC(=O)c4cc(C)nn4CC)n1c23] |
| 8 | 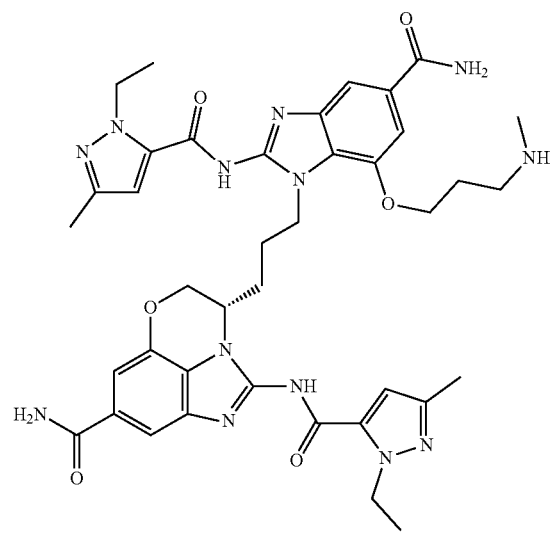 [SMILES: CCn1nc(C)cc1C(=O)Nc1nc2cc(C(N)=O)cc(OCCCNC)c2n1CCC[C@H]1COc2cc(C(N)=O)cc3nc(NC(=O)c4cc(C)nn4CC)n1c23] |

| No. | Compound structure |
|---|---|
| 9 | 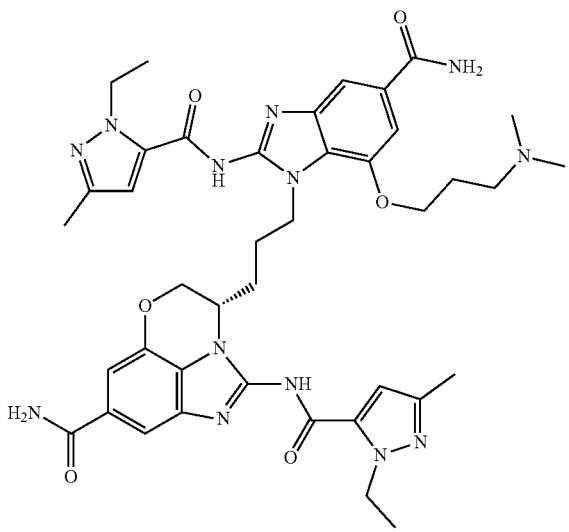 [SMILES: CCn1nc(C)cc1C(=O)Nc1nc2cc(C(N)=O)cc(OCCCN(C)C)c2n1CCC[C@H]1COc2cc(C(N)=O)cc3nc(NC(=O)c4cc(C)nn4CC)n1c23] |
| 10 | 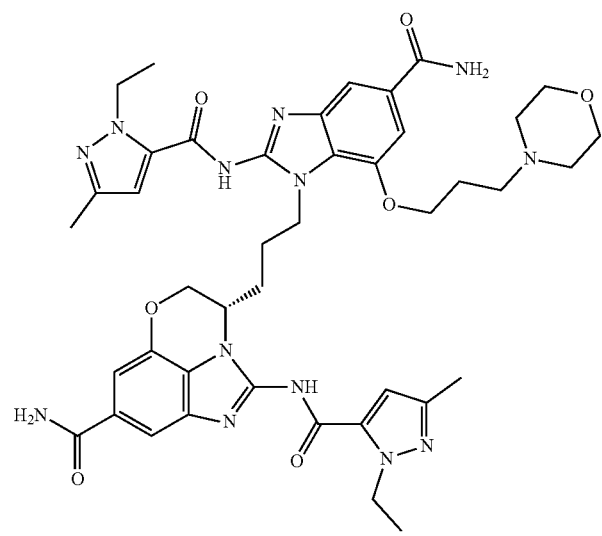 [SMILES: CCn1nc(C)cc1C(=O)Nc1nc2cc(C(N)=O)cc(OCCCN3CCOCC3)c2n1CCC[C@H]1COc2cc(C(N)=O)cc3nc(NC(=O)c4cc(C)nn4CC)n1c23] |

-continued
| No. | Compound structure |
|---|---|
| 11 | 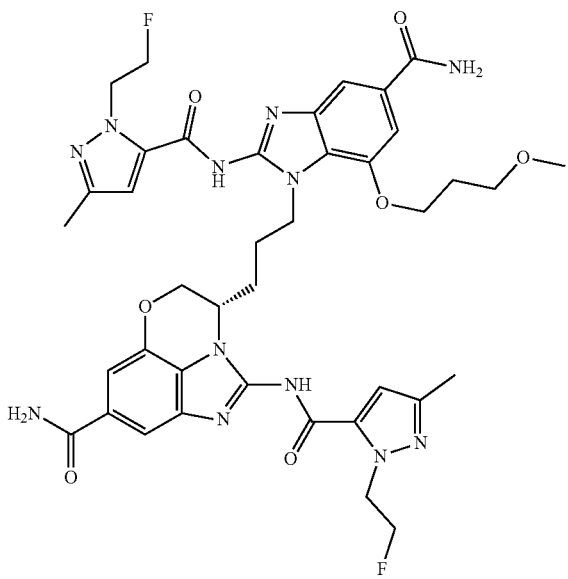 [SMILES: COCCCOc1cc(C(N)=O)cc2nc(NC(=O)c3cc(C)nn3CCF)n(CCC[C@H]3COc4cc(C(N)=O)cc5nc(NC(=O)c6cc(C)nn6CCF)n3c45)c12] |
| 12 | 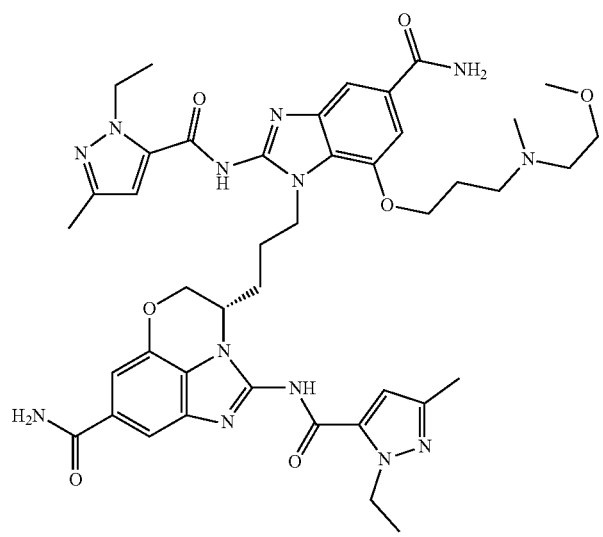 [SMILES: CCn1nc(C)cc1C(=O)Nc1nc2cc(C(N)=O)cc(OCCCN(C)CCOC)c2n1CCC[C@H]1COc2cc(C(N)=O)cc3nc(NC(=O)c4cc(C)nn4CC)n1c23] |

-continued
| No. | Compound structure |
|---|---|
| 13 | 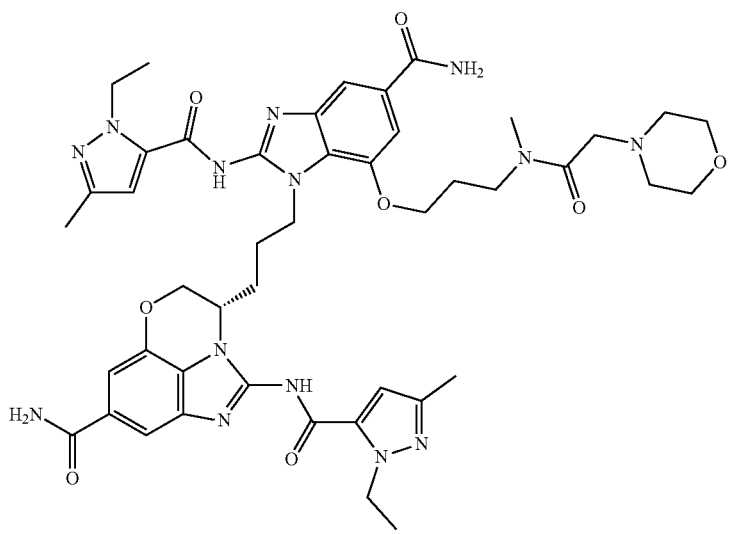 [SMILES: CCn1nc(C)cc1C(=O)Nc1nc2cc(C(N)=O)cc(OCCCN(C)C(=O)CN3CCOCC3)c2n1CCC[C@H]1COc2cc(C(N)=O)cc3nc(NC(=O)c4cc(C)nn4CC)n1c23] |
| 14 | 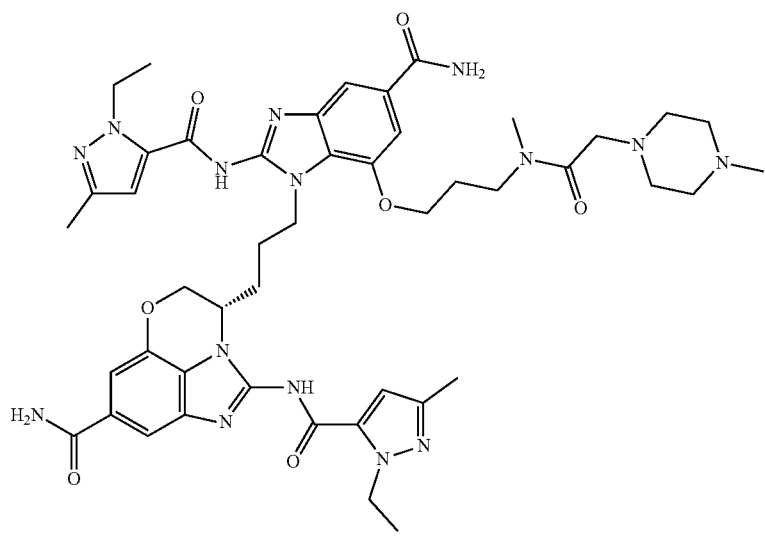 [SMILES: CCn1nc(C)cc1C(=O)Nc1nc2cc(C(N)=O)cc(OCCCN(C)C(=O)CN3CCN(C)CC3)c2n1CCC[C@H]1COc2cc(C(N)=O)cc3nc(NC(=O)c4cc(C)nn4CC)n1c23] |
| 15 | 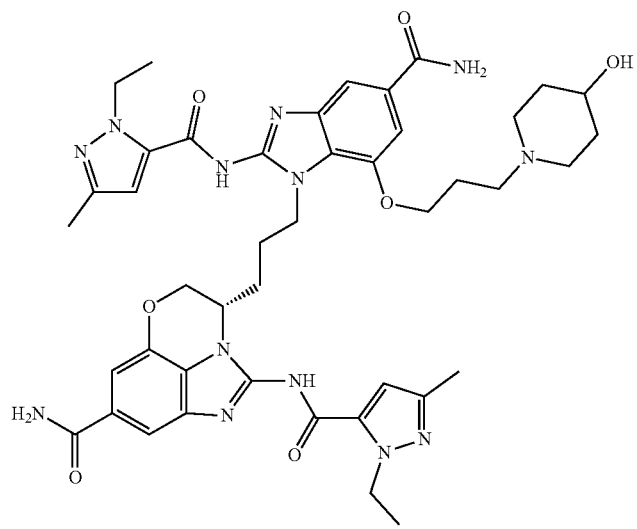 [SMILES: CCn1nc(C)cc1C(=O)Nc1nc2cc(C(N)=O)cc(OCCCN3CCC(O)CC3)c2n1CCC[C@H]1COc2cc(C(N)=O)cc3nc(NC(=O)c4cc(C)nn4CC)n1c23] |

-continued
| No. | Compound structure |
|---|---|
| 16 | 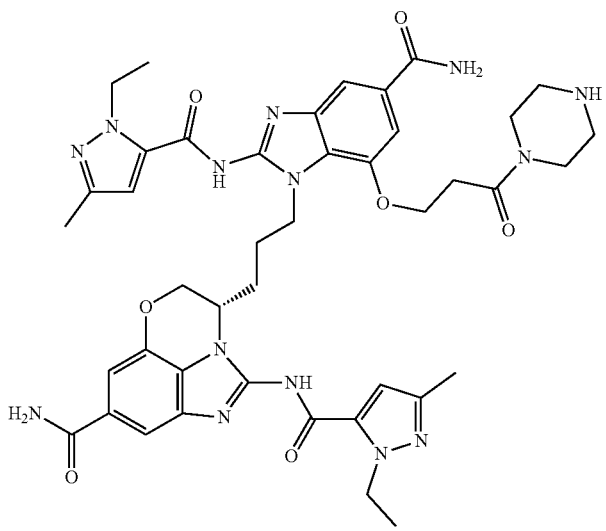 [SMILES: CCn1nc(C)cc1C(=O)Nc1nc2cc(C(N)=O)cc(OCCC(=O)N3CCNCC3)c2n1CCC[C@H]1COc2cc(C(N)=O)cc3nc(NC(=O)c4cc(C)nn4CC)n1c23] |
| 17 | 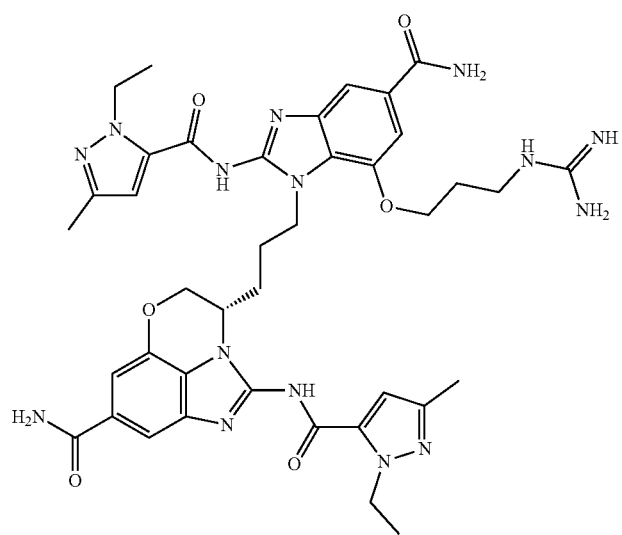 [SMILES: CCn1nc(C)cc1C(=O)Nc1nc2cc(C(N)=O)cc(OCCCNC(=N)N)c2n1CCC[C@H]1COc2cc(C(N)=O)cc3nc(NC(=O)c4cc(C)nn4CC)n1c23] |
| 18 | 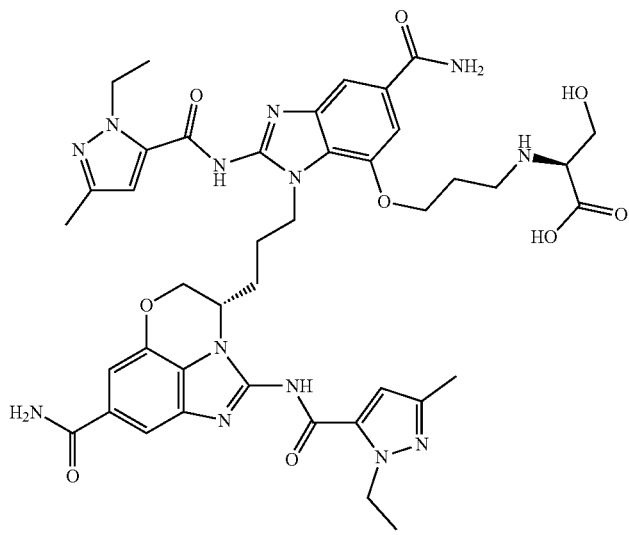 [SMILES: CCn1nc(C)cc1C(=O)Nc1nc2cc(C(N)=O)cc(OCCCN[C@@H](CO)C(=O)O)c2n1CCC[C@H]1COc2cc(C(N)=O)cc3nc(NC(=O)c4cc(C)nn4CC)n1c23] |

-continued
| No. | Compound structure |
|---|---|
| 19 | 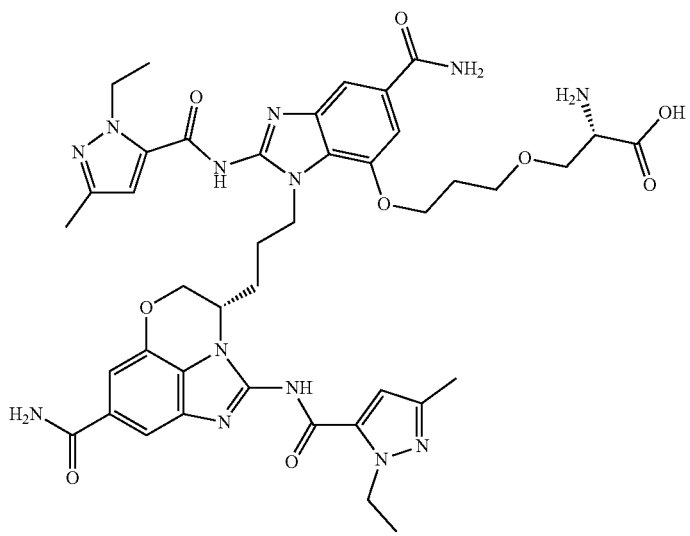 [SMILES: CCn1nc(C)cc1C(=O)Nc1nc2cc(C(N)=O)cc(OCCCOC[C@H](N)C(=O)O)c2n1CCC[C@H]1COc2cc(C(N)=O)cc3nc(NC(=O)c4cc(C)nn4CC)n1c23] |
| 20 | 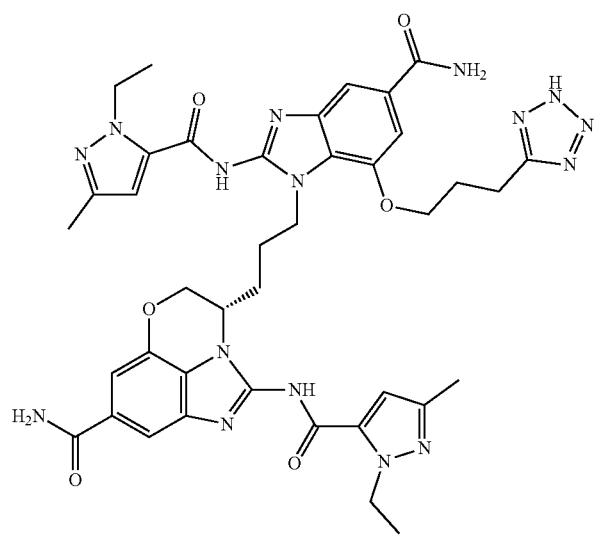 [SMILES: CCn1nc(C)cc1C(=O)Nc1nc2cc(C(N)=O)cc(OCCCc3nn[nH]n3)c2n1CCC[C@H]1COc2cc(C(N)=O)cc3nc(NC(=O)c4cc(C)nn4CC)n1c23] |
| 21 | 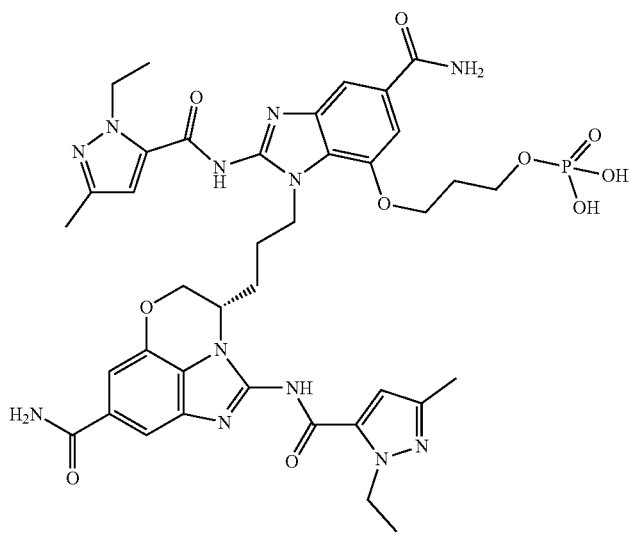 [SMILES: CCn1nc(C)cc1C(=O)Nc1nc2cc(C(N)=O)cc(OCCCOP(=O)(O)O)c2n1CCC[C@H]1COc2cc(C(N)=O)cc3nc(NC(=O)c4cc(C)nn4CC)n1c23] |

-continued
| No. | Compound structure |
|---|---|
| 22 | 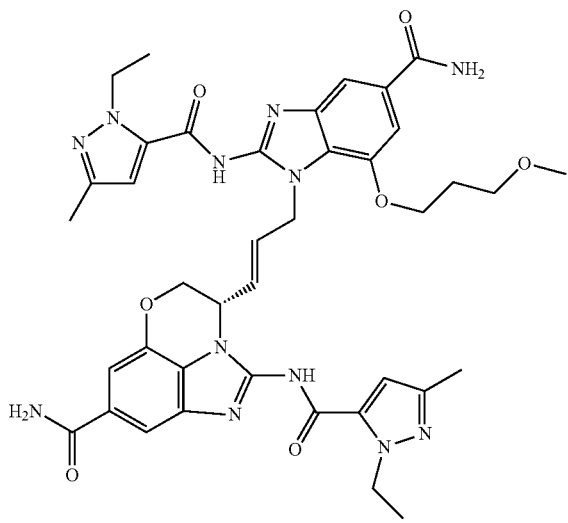 [SMILES: CCn1nc(C)cc1C(=O)Nc1nc2cc(C(N)=O)cc(OCCCOC)c2n1C/C=C/[C@H]1COc2cc(C(N)=O)cc3nc(NC(=O)c4cc(C)nn4CC)n1c23] |
| 23 | 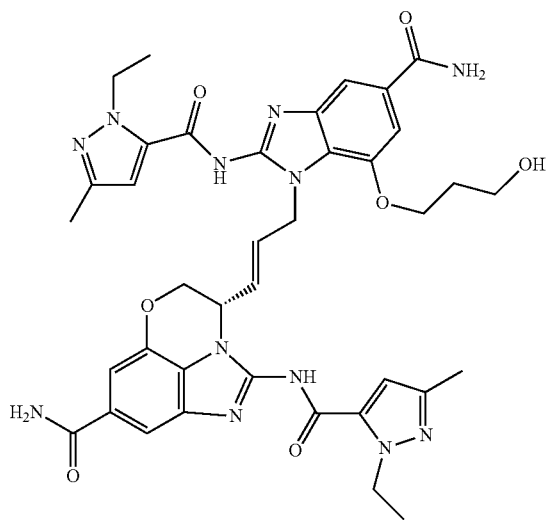 [SMILES: CCn1nc(C)cc1C(=O)Nc1nc2cc(C(N)=O)cc(OCCCO)c2n1C/C=C/[C@H]1COc2cc(C(N)=O)cc3nc(NC(=O)c4cc(C)nn4CC)n1c23] |
| 24 | 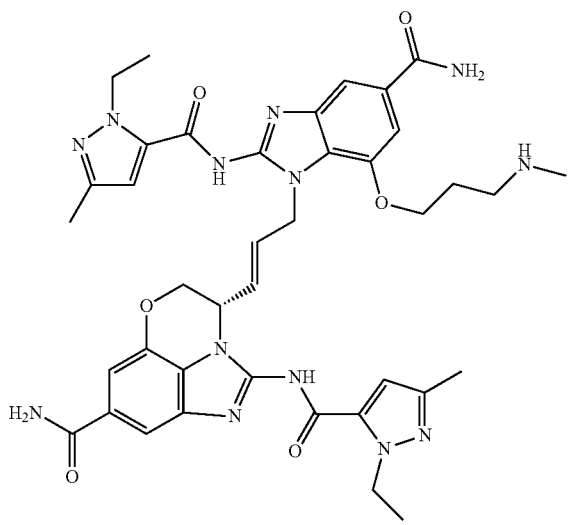 [SMILES: CCn1nc(C)cc1C(=O)Nc1nc2cc(C(N)=O)cc(OCCCNC)c2n1C/C=C/[C@H]1COc2cc(C(N)=O)cc3nc(NC(=O)c4cc(C)nn4CC)n1c23] |

| No. | Compound structure |
|---|---|
| 25 | 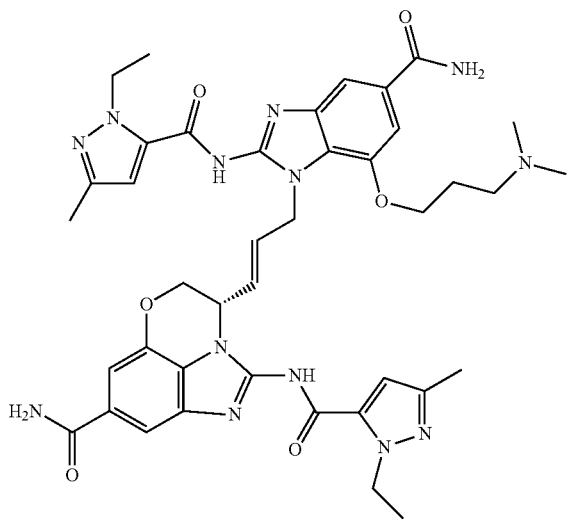 [SMILES: CCn1nc(C)cc1C(=O)Nc1nc2cc(C(N)=O)cc(OCCCN(C)C)c2n1C/C=C/[C@H]1COc2cc(C(N)=O)cc3nc(NC(=O)c4cc(C)nn4CC)n1c23] |
| 26 | 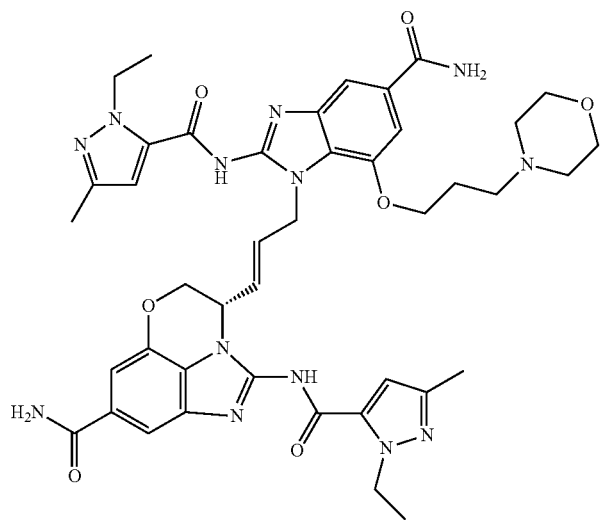 [SMILES: CCn1nc(C)cc1C(=O)Nc1nc2cc(C(N)=O)cc(OCCCN3CCOCC3)c2n1C/C=C/[C@H]1COc2cc(C(N)=O)cc3nc(NC(=O)c4cc(C)nn4CC)n1c23] |
| 27 | 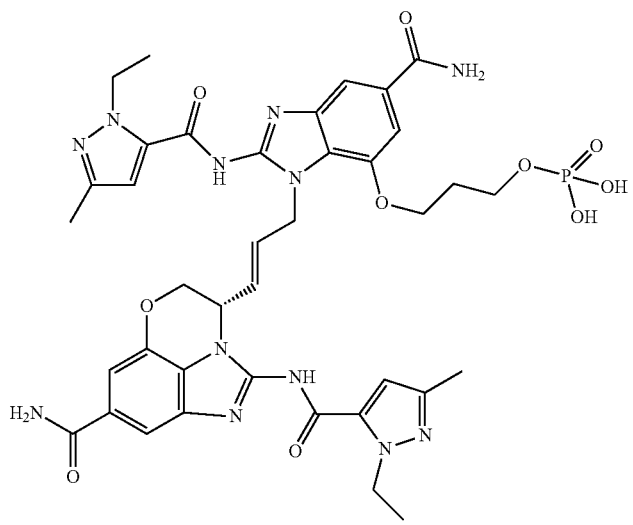 [SMILES: CCn1nc(C)cc1C(=O)Nc1nc2cc(C(N)=O)cc(OCCCOP(=O)(O)O)c2n1C/C=C/[C@H]1COc2cc(C(N)=O)cc3nc(NC(=O)c4cc(C)nn4CC)n1c23] |

| No. | Compound structure |
|---|---|
| 28 | 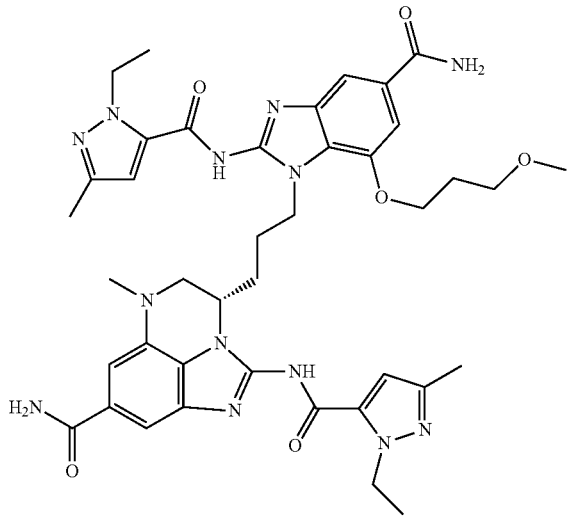 [SMILES: CCn1nc(C)cc1C(=O)Nc1nc2cc(C(N)=O)cc(OCCCOC)c2n1CCC[C@H]1CN(C)c2cc(C(N)=O)cc3nc(NC(=O)c4cc(C)nn4CC)n1c23] |
| 29 | 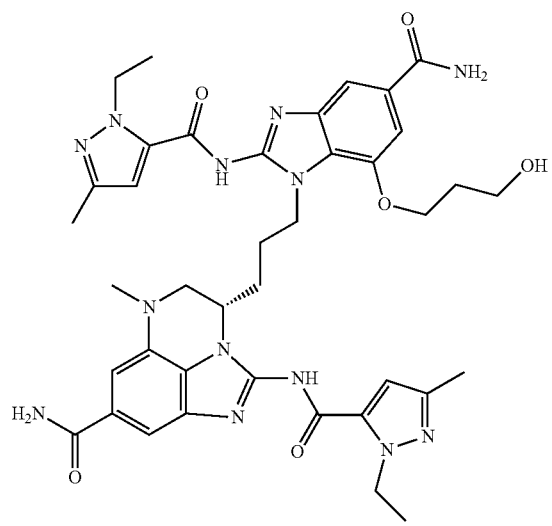 [SMILES: CCn1nc(C)cc1C(=O)Nc1nc2cc(C(N)=O)cc(OCCCO)c2n1CCC[C@H]1CN(C)c2cc(C(N)=O)cc3nc(NC(=O)c4cc(C)nn4CC)n1c23] |
| 30 | 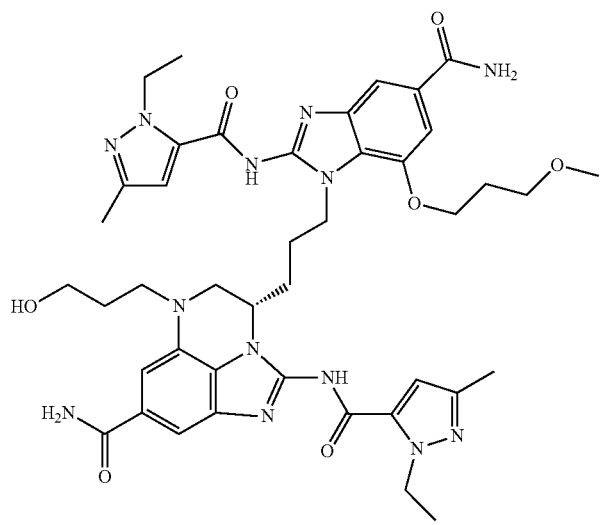 [SMILES: CCn1nc(C)cc1C(=O)Nc1nc2cc(C(N)=O)cc(OCCCOC)c2n1CCC[C@H]1CN(CCCO)c2cc(C(N)=O)cc3nc(NC(=O)c4cc(C)nn4CC)n1c23] |

| No. | Compound structure |
|---|---|
| 31 | 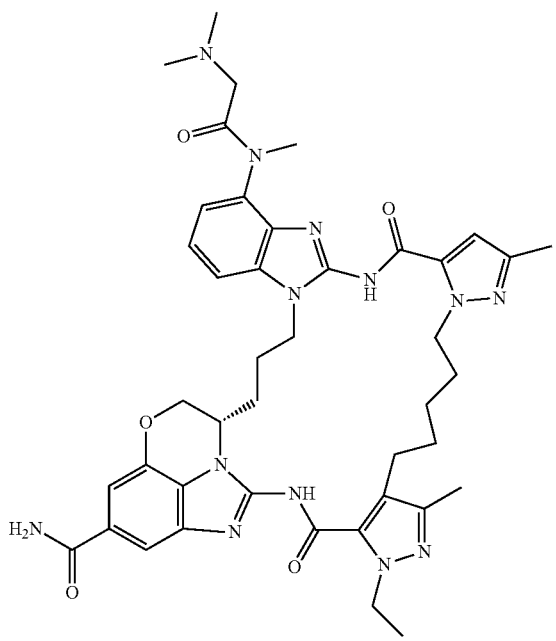 [SMILES: CCn1nc(C)c2c1C(=O)Nc1nc3cc(C(N)=O)cc4c3n1[C@@H](CCCn1c(nc3c(N(C)C(=O)CN(C)C)cccc31)NC(=O)c1cc(C)nn1CCCCC2)CO4] |
| 32 | 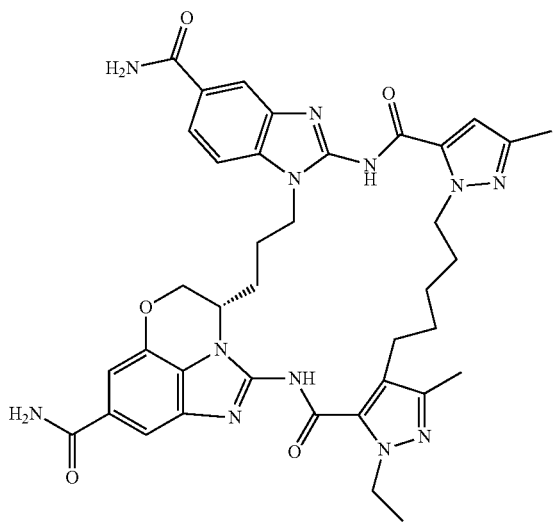 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCCCC2)CO4] |

| No. | Compound structure |
|---|---|
| 33 | 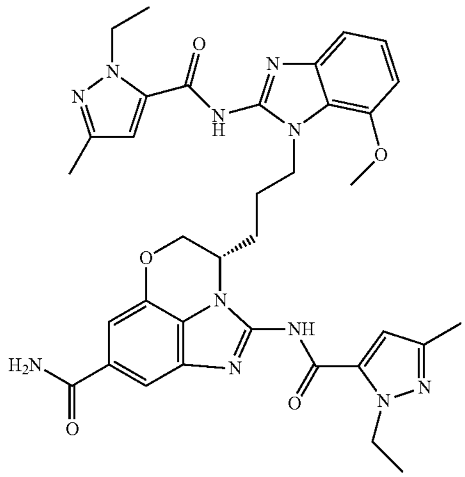 [SMILES: CCn1nc(C)cc1C(=O)Nc1nc2cccc(OC)c2n1CCC[C@H]1COc2cc(C(N)=O)cc3nc(NC(=O)c4cc(C)nn4CC)n1c23] |
| 34 | 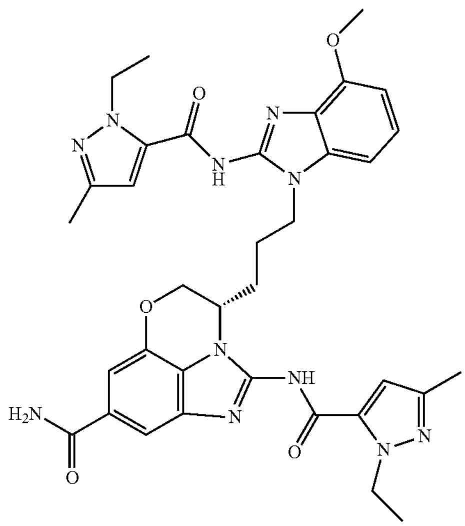 [SMILES: CCn1nc(C)cc1C(=O)Nc1nc2c(OC)cccc2n1CCC[C@H]1COc2cc(C(N)=O)cc3nc(NC(=O)c4cc(C)nn4CC)n1c23] |
| 35 | 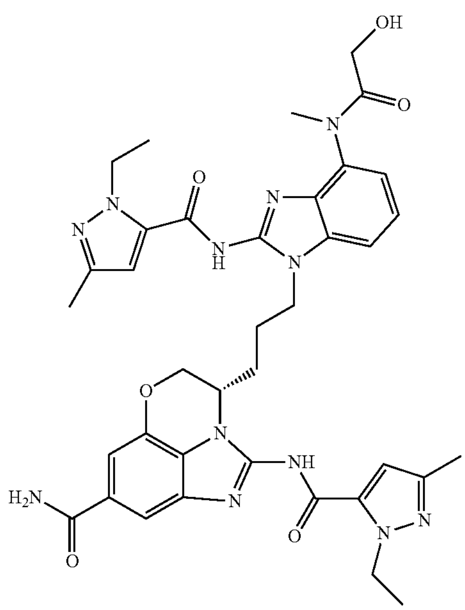 [SMILES: CCn1nc(C)cc1C(=O)Nc1nc2c(N(C)C(=O)CO)cccc2n1CCC[C@H]1COc2cc(C(N)=O)cc3nc(NC(=O)c4cc(C)nn4CC)n1c23] |

-continued
| No. | Compound structure |
|---|---|
| 36 | 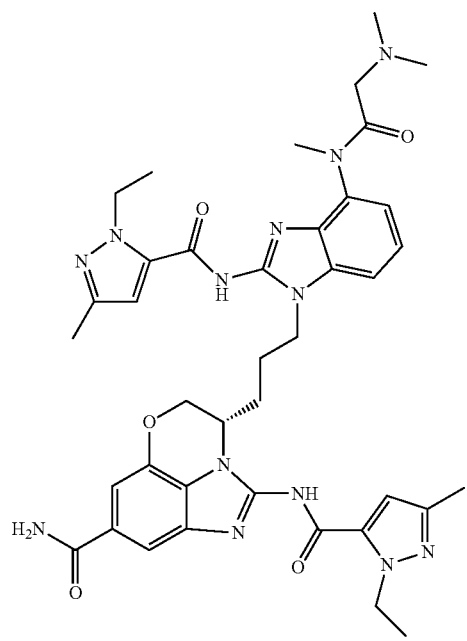 [SMILES: CCn1nc(C)cc1C(=O)Nc1nc2c(N(C)C(=O)CN(C)C)cccc2n1CCC[C@H]1COc2cc(C(N)=O)cc3nc(NC(=O)c4cc(C)nn4CC)n1c23] |
| 37 | 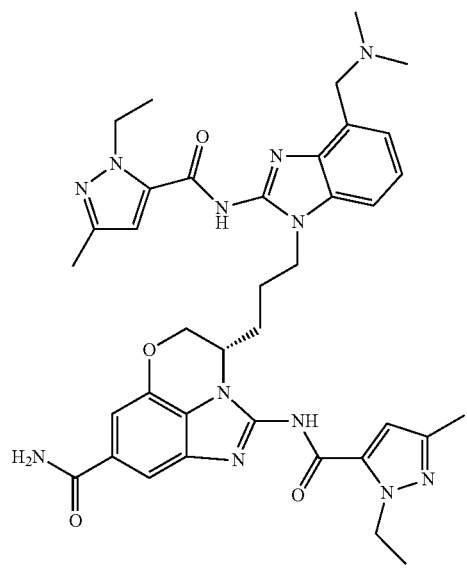 [SMILES: CCn1nc(C)cc1C(=O)Nc1nc2c(CN(C)C)cccc2n1CCC[C@H]1COc2cc(C(N)=O)cc3nc(NC(=O)c4cc(C)nn4CC)n1c23] |

| No. | Compound structure |
|---|---|
| 38 | 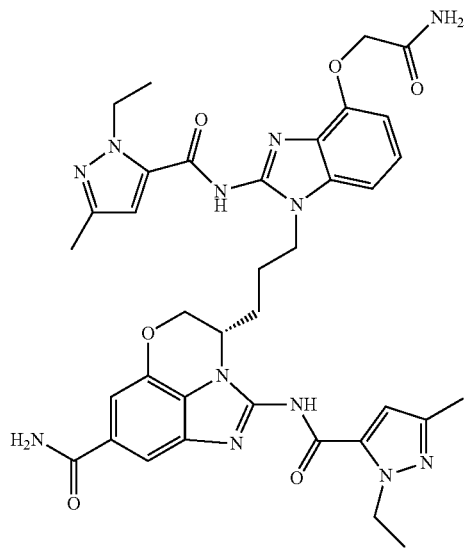 [SMILES: CCn1nc(C)cc1C(=O)Nc1nc2c(OCC(N)=O)cccc2n1CCC[C@H]1COc2cc(C(N)=O)cc3nc(NC(=O)c4cc(C)nn4CC)n1c23] |
| 39 | 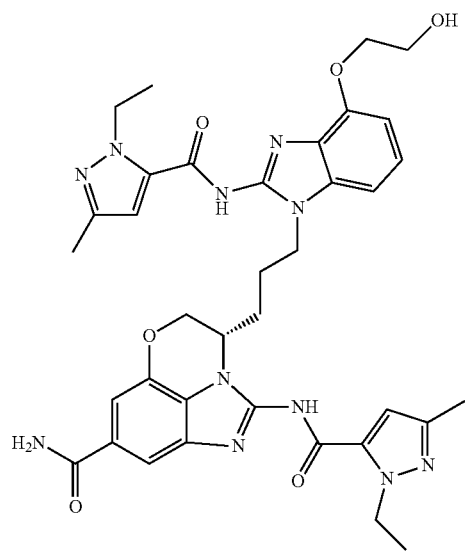 [SMILES: CCn1nc(C)cc1C(=O)Nc1nc2c(OCCO)cccc2n1CCC[C@H]1COc2cc(C(N)=O)cc3nc(NC(=O)c4cc(C)nn4CC)n1c23] |
| 40 | 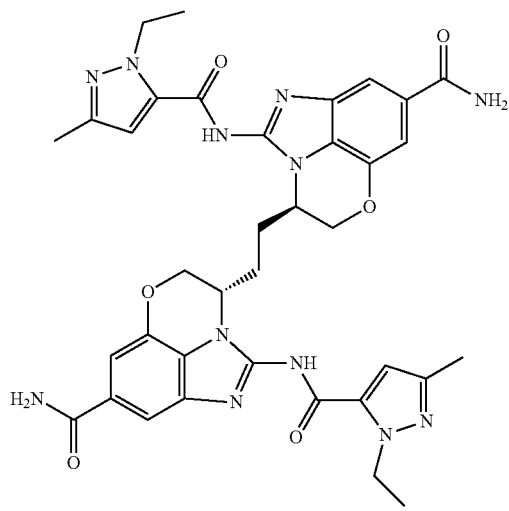 [SMILES: CCn1nc(C)cc1C(=O)Nc1nc2cc(C(N)=O)cc3c2n1[C@H](CC[C@H]1COc2cc(C(N)=O)cc4nc(NC(=O)c5cc(C)nn5CC)n1c24)CO3] |

| No. | Compound structure |
|---|---|
| 41 | 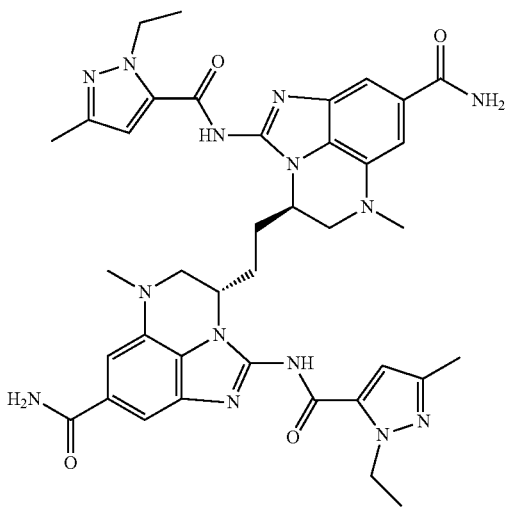 [SMILES: CCn1nc(C)cc1C(=O)Nc1nc2cc(C(N)=O)cc3c2n1[C@H](CC[C@H]1CN(C)c2cc(C(N)=O)cc4nc(NC(=O)c5cc(C)nn5CC)n1c24)CN3C] |
| 42 | 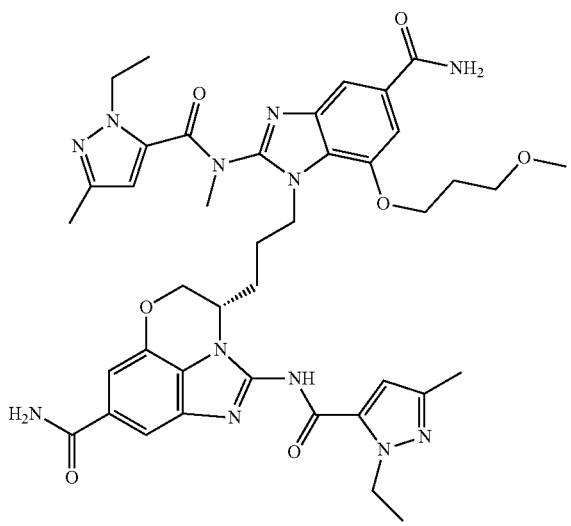 [SMILES: CCn1nc(C)cc1C(=O)Nc1nc2cc(C(N)=O)cc3c2n1[C@@H](CCCn1c(N(C)C(=O)c2cc(C)nn2CC)nc2cc(C(N)=O)cc(OCCCOC)c21)CO3] |
| 43 | 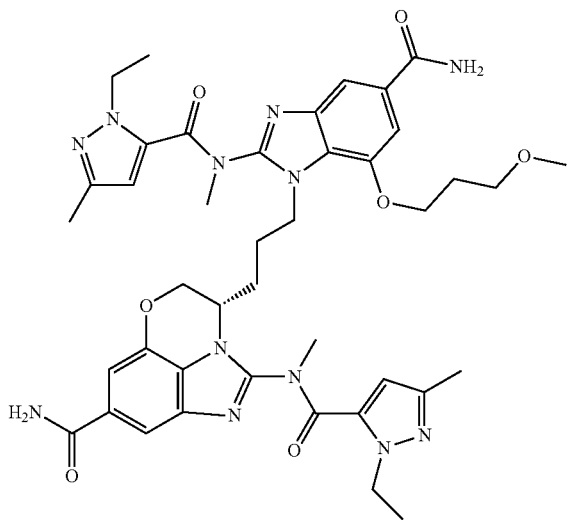 [SMILES: CCn1nc(C)cc1C(=O)N(C)c1nc2cc(C(N)=O)cc(OCCCOC)c2n1CCC[C@H]1COc2cc(C(N)=O)cc3nc(N(C)C(=O)c4cc(C)nn4CC)n1c23] |

-continued
| No. | Compound structure |
|---|---|
| 44 | 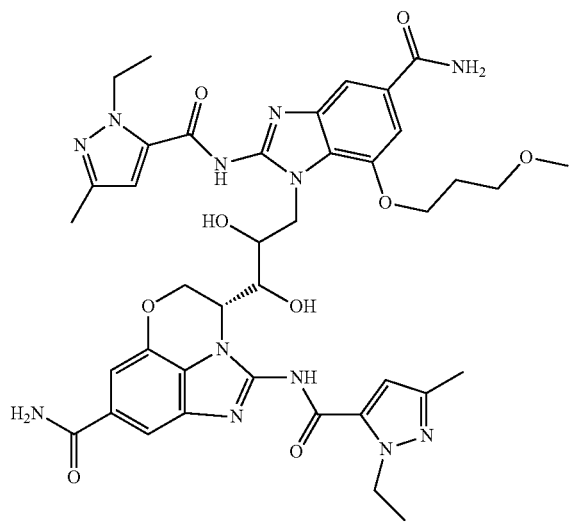 [SMILES: CCn1nc(C)cc1C(=O)Nc1nc2cc(C(N)=O)cc(OCCCOC)c2n1CC(O)C(O)[C@H]1COc2cc(C(N)=O)cc3nc(NC(=O)c4cc(C)nn4CC)n1c23] |
| 45 | 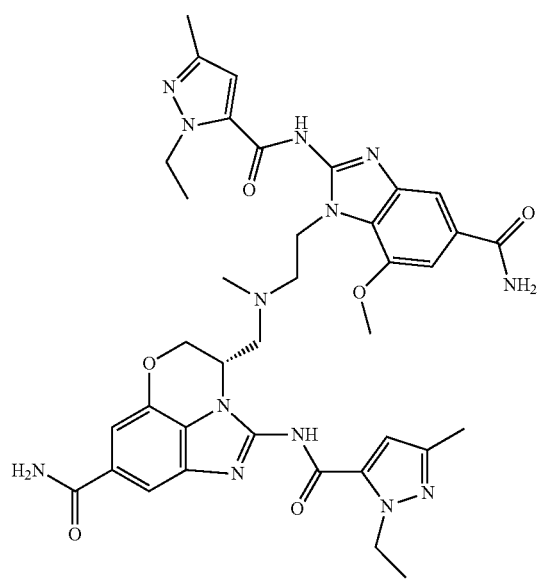 [SMILES: CCn1nc(C)cc1C(=O)Nc1nc2cc(C(N)=O)cc(OC)c2n1CCN(C)C[C@H]1COc2cc(C(N)=O)cc3nc(NC(=O)c4cc(C)nn4CC)n1c23] |

| No. | Compound structure |
|---|---|
| 46 | 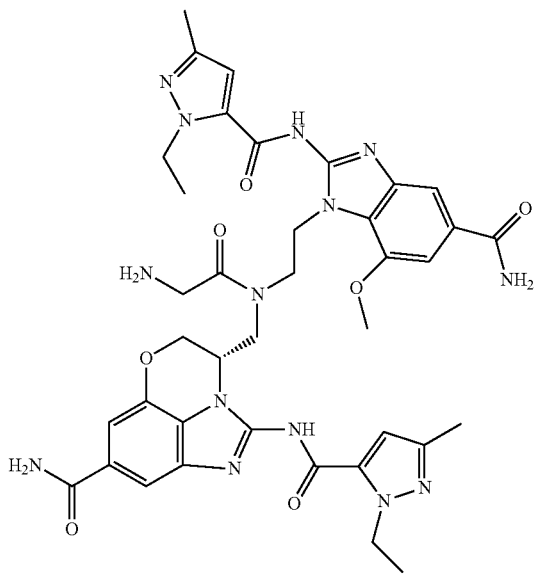 [SMILES: CCn1nc(C)cc1C(=O)Nc1nc2cc(C(N)=O)cc(OC)c2n1CCN(C[C@H]1COc2cc(C(N)=O)cc3nc(NC(=O)c4cc(C)nn4CC)n1c23)C(=O)CN] |
| 47 | 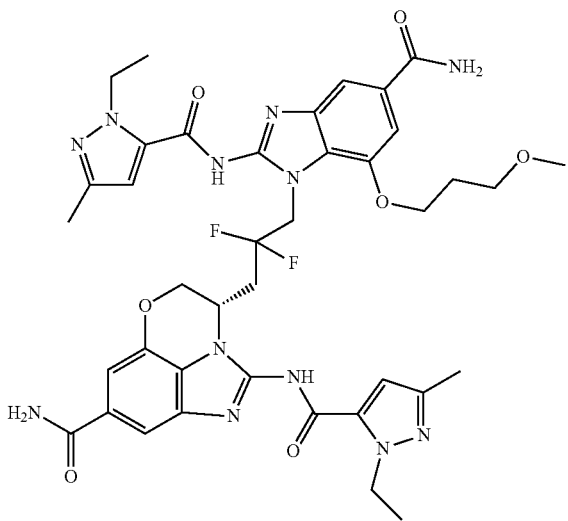 [SMILES: CCn1nc(C)cc1C(=O)Nc1nc2cc(C(N)=O)cc(OCCCOC)c2n1CC(F)(F)C[C@H]1COc2cc(C(N)=O)cc3nc(NC(=O)c4cc(C)nn4CC)n1c23] |
| 48 | 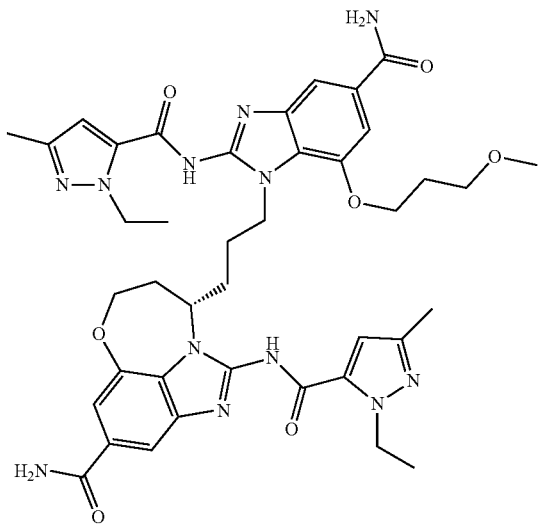 |

| No. | Compound structure |
|---|---|
| 49 | 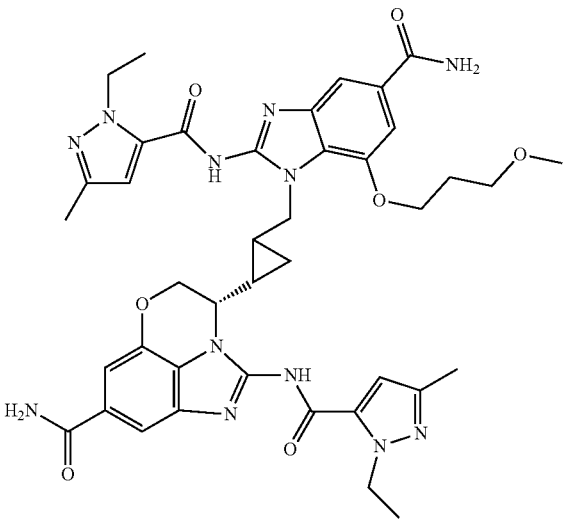 [SMILES: CCn1nc(C)cc1C(=O)Nc1nc2cc(C(N)=O)cc(OCCCOC)c2n1CC1CC1[C@H]1COc2cc(C(N)=O)cc3nc(NC(=O)c4cc(C)nn4CC)n1c23] |
| 50 | 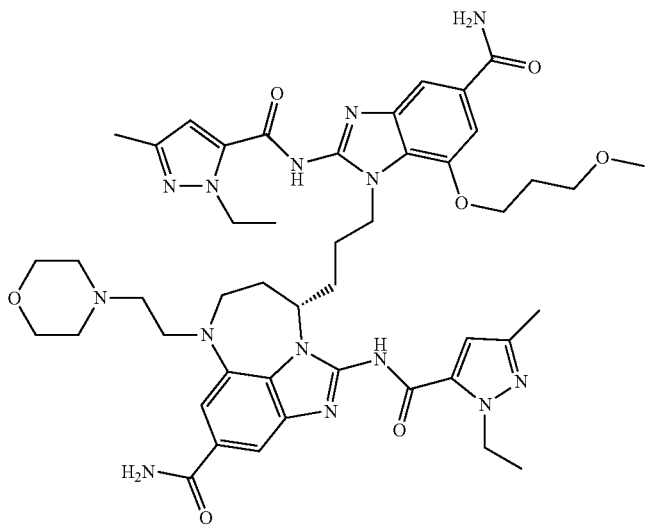 [SMILES: CCn1nc(C)cc1C(=O)Nc1nc2cc(C(N)=O)cc(OCCCOC)c2n1CCC[C@H]1CCN(CCN2CCOCC2)c2cc(C(N)=O)cc3nc(NC(=O)c4cc(C)nn4CC)n1c23] |
| 51 | 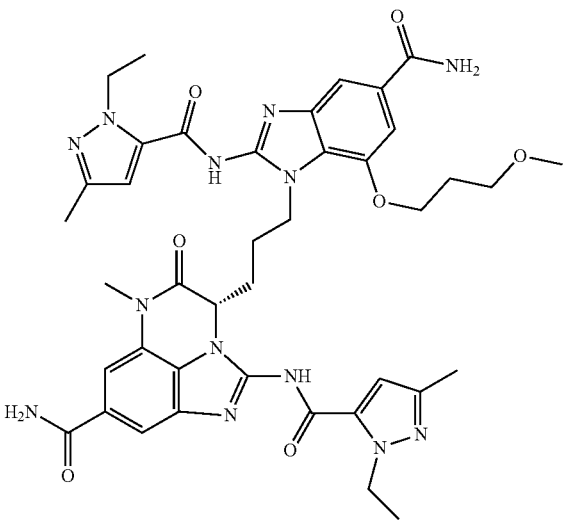 [SMILES: CCn1nc(C)cc1C(=O)Nc1nc2cc(C(N)=O)cc(OCCCOC)c2n1CCC[C@H]1C(=O)N(C)c2cc(C(N)=O)cc3nc(NC(=O)c4cc(C)nn4CC)n1c23] |

-continued
| No. | Compound structure |
|---|---|
| 52 | 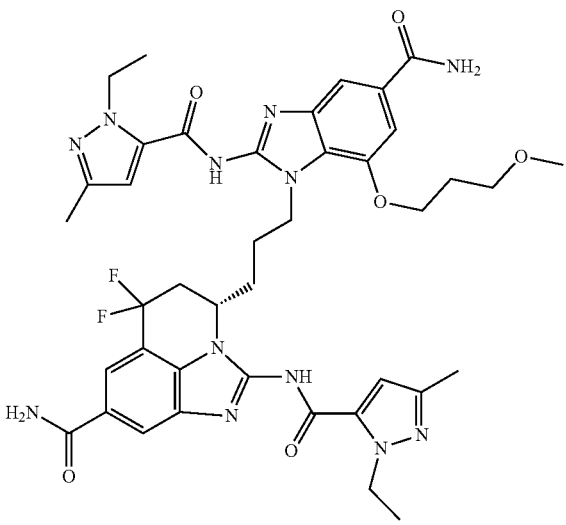 [SMILES: CCn1nc(C)cc1C(=O)Nc1nc2cc(C(N)=O)cc(OCCCOC)c2n1CCC[C@H]1CC(F)(F)c2cc(C(N)=O)cc3nc(NC(=O)c4cc(C)nn4CC)n1c23] |
| 53 | 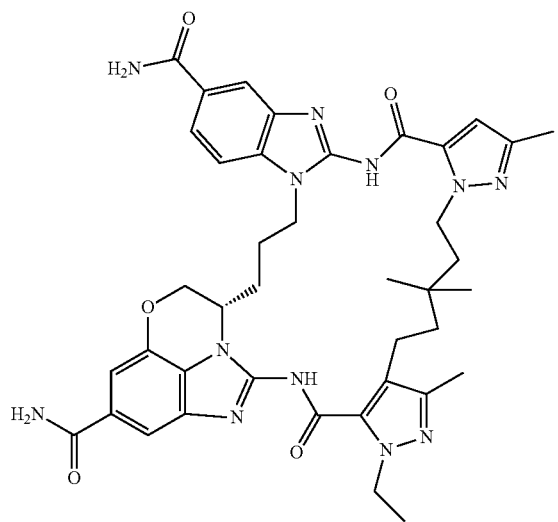 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC(C)(C)CC2)CO4] |
| 54 | 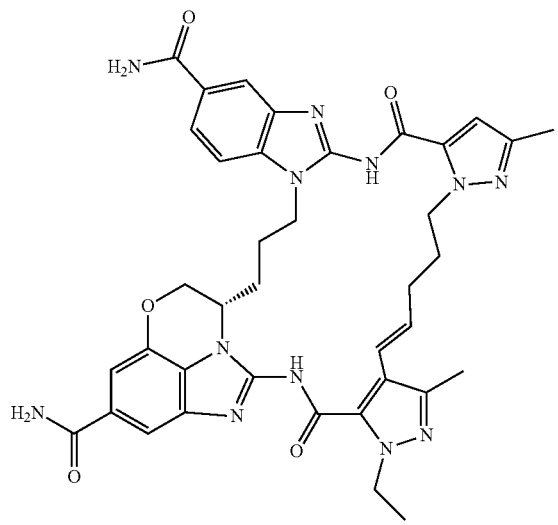 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC/C=C/2)CO4] |

-continued
| No. | Compound structure |
|---|---|
| 55 | 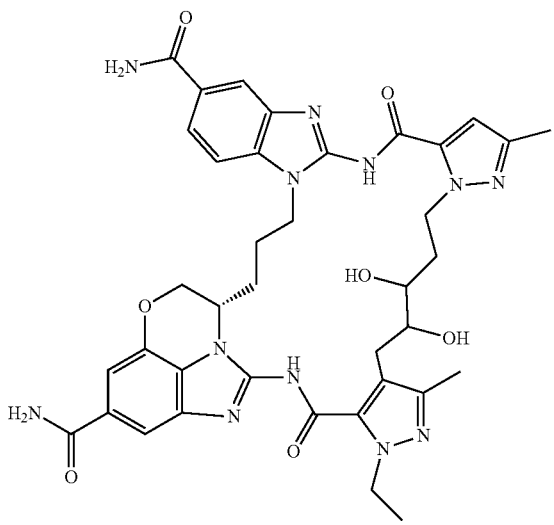 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCC(O)C(O)C2)CO4] |
| 56 | 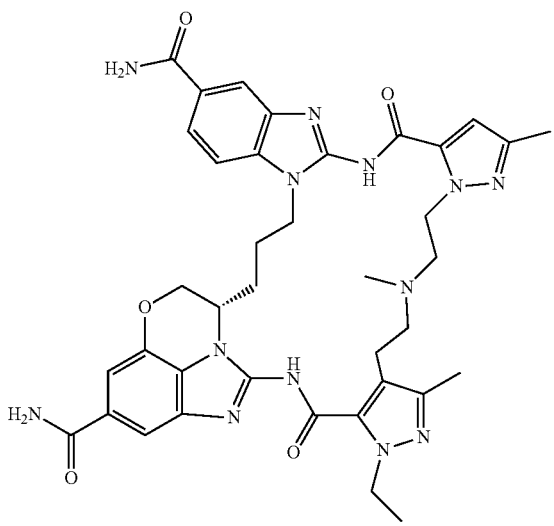 [SMILES: CCn1nc(C)c2c1C(=O)Nc1nc3cc(C(N)=O)cc4c3n1[C@@H](CCCn1c(nc3cc(C(N)=O)ccc31)NC(=O)c1cc(C)nn1CCN(C)CC2)CO4] |
| 57 | 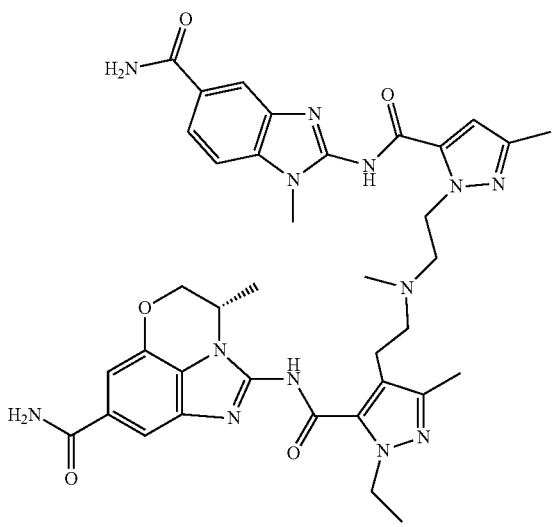 [SMILES: CCn1nc(C)c(CCN(C)CCn2nc(C)cc2C(=O)Nc2nc3cc(C(N)=O)ccc3n2C)c1C(=O)Nc1nc2cc(C(N)=O)cc3c2n1[C@@H](C)CO3] |

-continued
| No. | Compound structure |
|---|---|
| 58 | 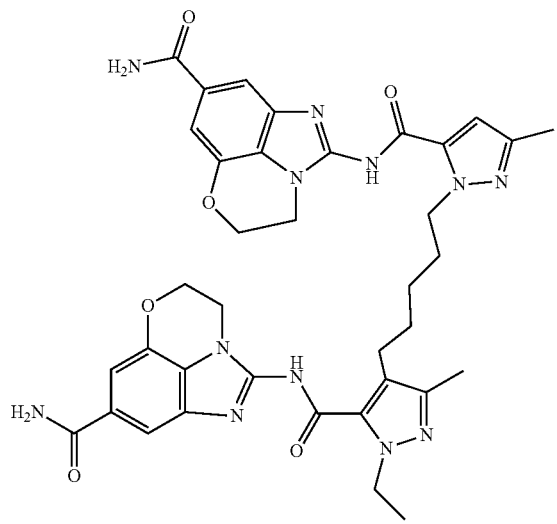 [SMILES: CCn1nc(C)c(CCCCCn2nc(C)cc2C(=O)Nc2nc3cc(C(N)=O)cc4c3n2CCO4)c1C(=O)Nc1nc2cc(C(N)=O)cc3c2n1CCO3] |
| 59 | 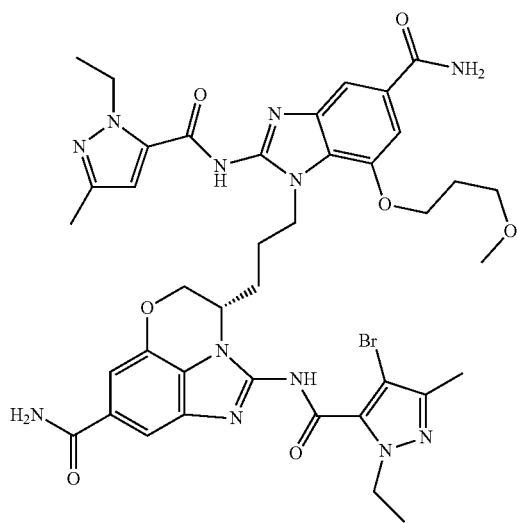 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(Br)c(C)nn4CC)n1c23] |
| 60 | 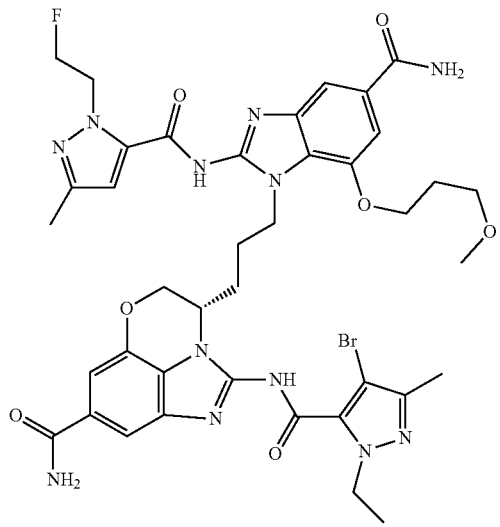 [SMILES: CCn1nc(C)c(Br)c1C(=O)Nc1nc2cc(C(N)=O)cc3c2n1[C@@H](CCCn1c(NC(=O)c2cc(C)nn2CCF)nc2cc(C(N)=O)cc(OCCCOC)c21)CO3] |

| No. | Compound structure |
|---|---|
| 61 | 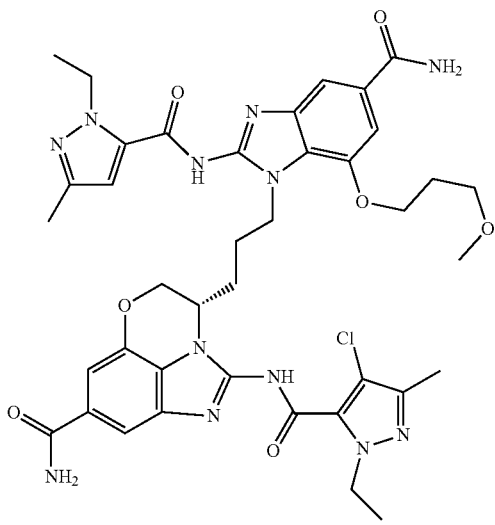 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(Cl)c(C)nn4CC)n1c23] |
| 62 | 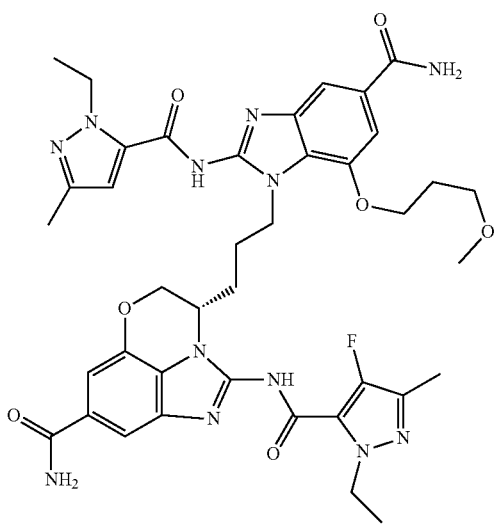 [SMILES: CCn1nc(C)cc1C(=O)Nc1nc2cc(C(N)=O)cc(OCCCOC)c2n1CCC[C@H]1COc2cc(C(N)=O)cc3nc(NC(=O)c4c(F)c(C)nn4CC)n1c23] |
| 63 | 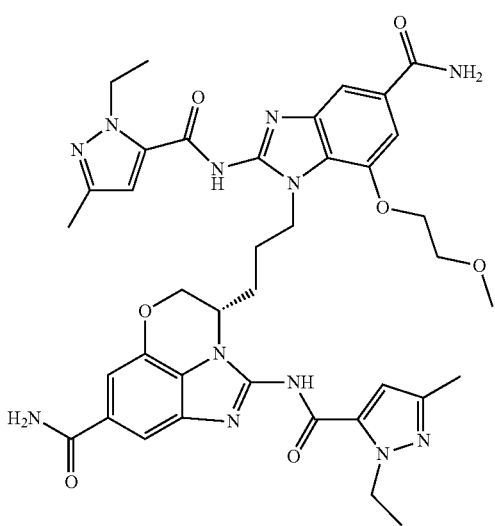 [SMILES: CCn1nc(C)cc1C(=O)Nc1nc2cc(C(N)=O)cc(OCCOC)c2n1CCC[C@H]1COc2cc(C(N)=O)cc3nc(NC(=O)c4cc(C)nn4CC)n1c23] |

| No. | Compound structure |
|---|---|
| 64 | 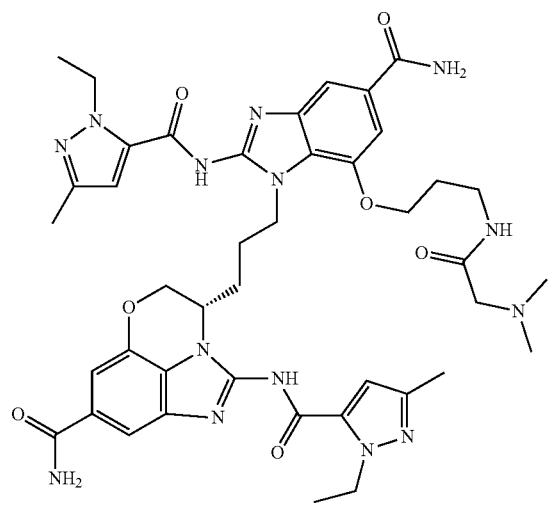 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4cc(C)nn4CC)n1c23] |
| 65 | 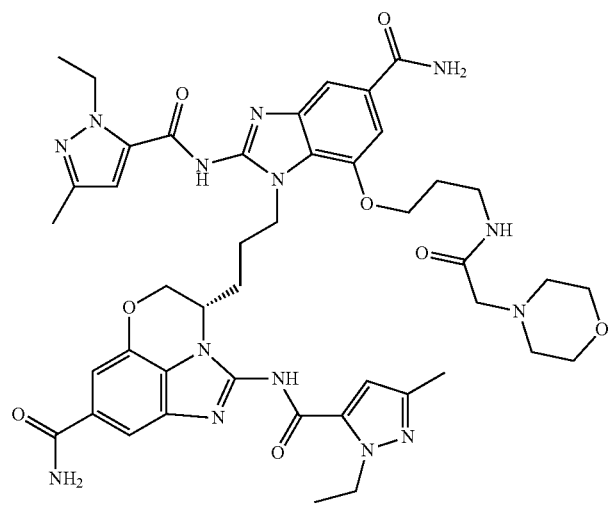 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4cc(C)nn4CC)n1c23] |
| 66 | 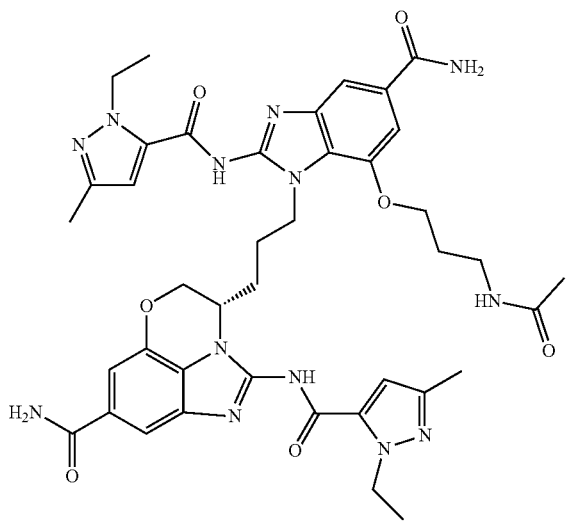 [SMILES: CCn1nc(C)cc1C(=O)Nc1nc2cc(C(N)=O)cc(OCCCNC(C)=O)c2n1CCC[C@H]1COc2cc(C(N)=O)cc3nc(NC(=O)c4cc(C)nn4CC)n1c23] |

| No. | Compound structure |
|---|---|
| 67 | 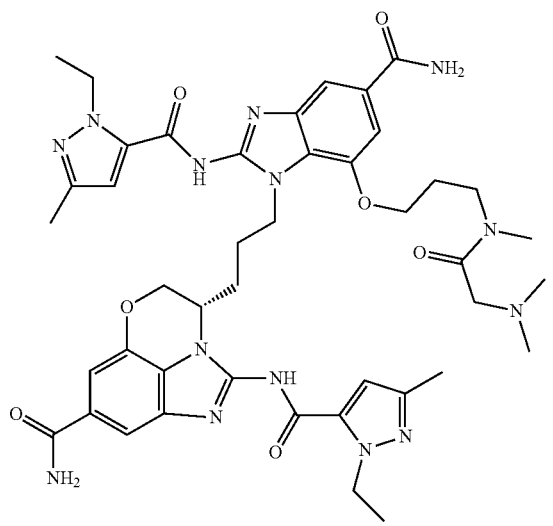 [SMILES: CCn1nc(C)cc1C(=O)Nc1nc2cc(C(N)=O)cc(OCCCN(C)C(=O)CN(C)C)c2n1CCC[C@H]1COc2cc(C(N)=O)cc3nc(NC(=O)c4cc(C)nn4CC)n1c23] |
| 68 | 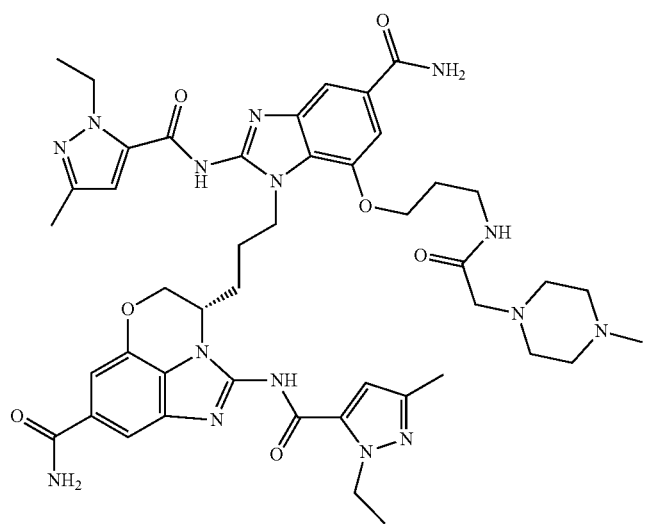 [SMILES: CCn1nc(C)cc1C(=O)Nc1nc2cc(C(N)=O)cc(OCCCNC(=O)CN3CCN(C)CC3)c2n1CCC[C@H]1COc2cc(C(N)=O)cc3nc(NC(=O)c4cc(C)nn4CC)n1c23] |
| 69 | 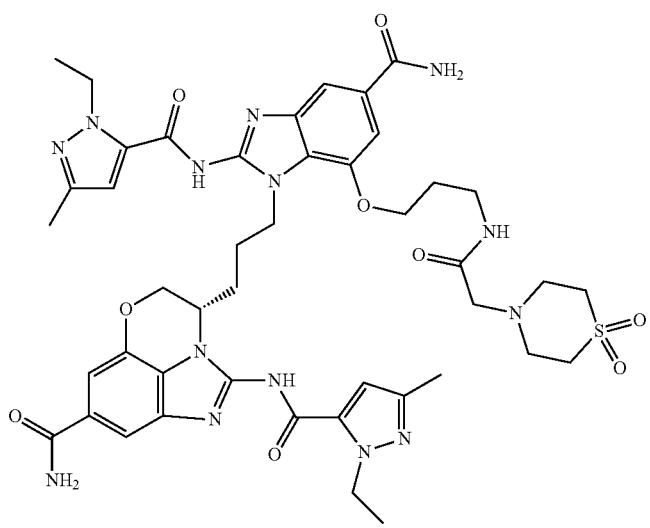 [SMILES: CCn1nc(C)cc1C(=O)Nc1nc2cc(C(N)=O)cc(OCCCNC(=O)CN3CCS(=O)(=O)CC3)c2n1CCC[C@H]1COc2cc(C(N)=O)cc3nc(NC(=O)c4cc(C)nn4CC)n1c23] |

| No. | Compound structure |
|---|---|
| 70 | 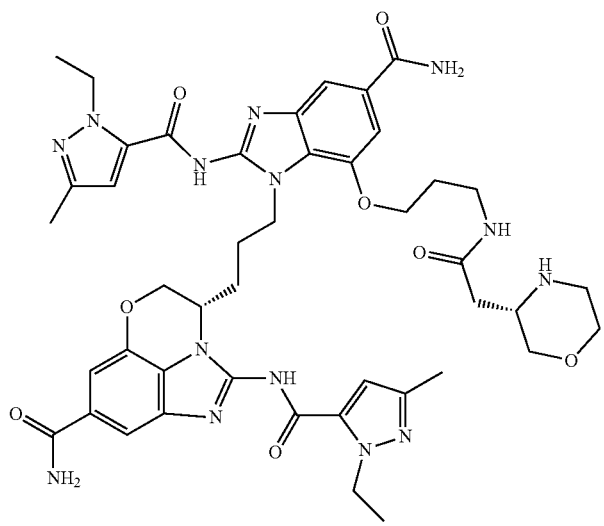 [SMILES: CCn1nc(C)cc1C(=O)Nc1nc2cc(C(N)=O)cc(OCCCNC(=O)C[C@H]3COCCN3)c2n1CCC[C@H]1COc2cc(C(N)=O)cc3nc(NC(=O)c4cc(C)nn4CC)n1c23] |
| 71 | 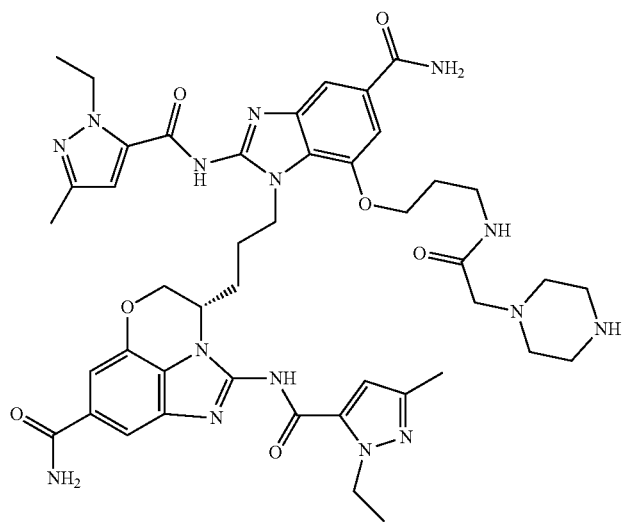 [SMILES: CCn1nc(C)cc1C(=O)Nc1nc2cc(C(N)=O)cc(OCCCNC(=O)CN3CCNCC3)c2n1CCC[C@H]1COc2cc(C(N)=O)cc3nc(NC(=O)c4cc(C)nn4CC)n1c23] |
| 72 | 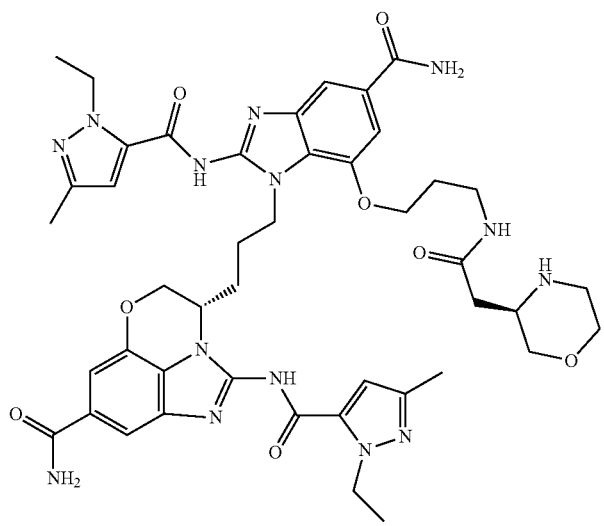 [SMILES: CCn1nc(C)cc1C(=O)Nc1nc2cc(C(N)=O)cc(OCCCNC(=O)C[C@@H]3COCCN3)c2n1CCC[C@H]1COc2cc(C(N)=O)cc3nc(NC(=O)c4cc(C)nn4CC)n1c23] |

| No. | Compound structure |
|---|---|
| 73 | 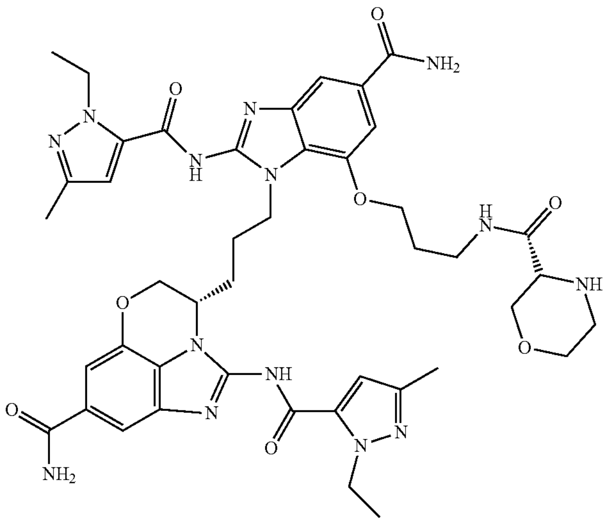 |
| 74 | 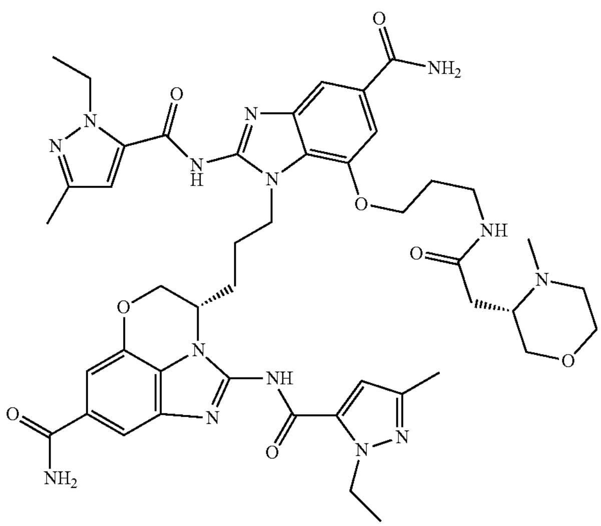 [SMILES: CCn1nc(C)cc1C(=O)Nc1nc2cc(C(N)=O)cc(OCCCNC(=O)C[C@H]3COCCN3C)c2n1CCC[C@H]1COc2cc(C(N)=O)cc3nc(NC(=O)c4cc(C)nn4CC)n1c23] |
| 75 | 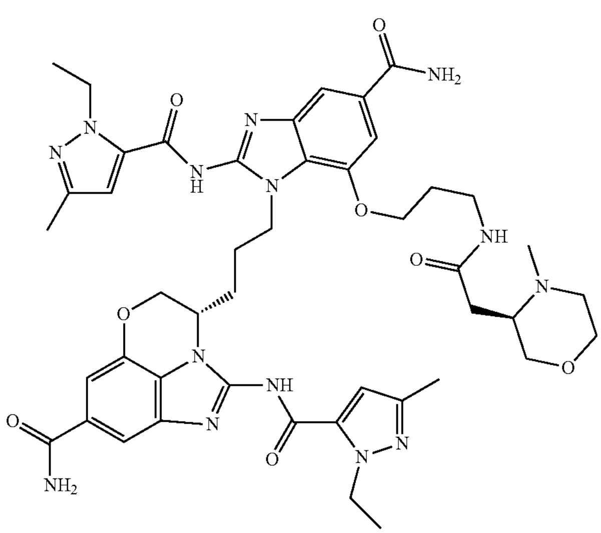 [SMILES: CCn1nc(C)cc1C(=O)Nc1nc2cc(C(N)=O)cc(OCCCNC(=O)C[C@@H]3COCCN3C)c2n1CCC[C@H]1COc2cc(C(N)=O)cc3nc(NC(=O)c4cc(C)nn4CC)n1c23] |

| No. | Compound structure |
|---|---|
| 76 | 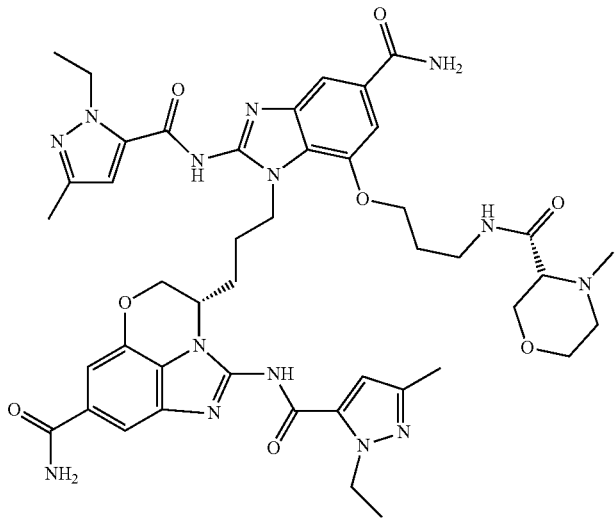 |
| 77 | 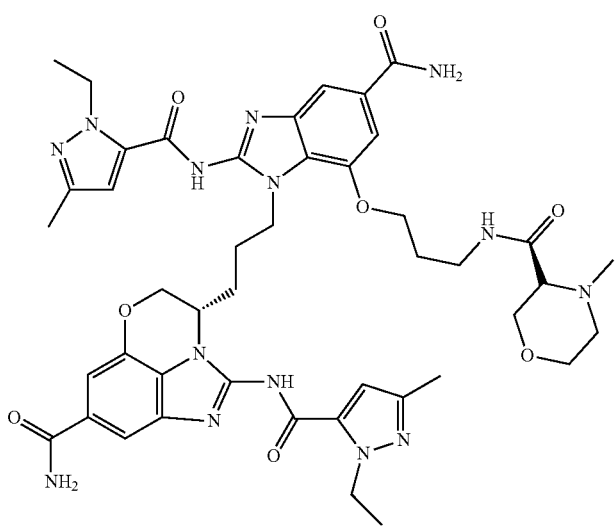 |
| 78 | 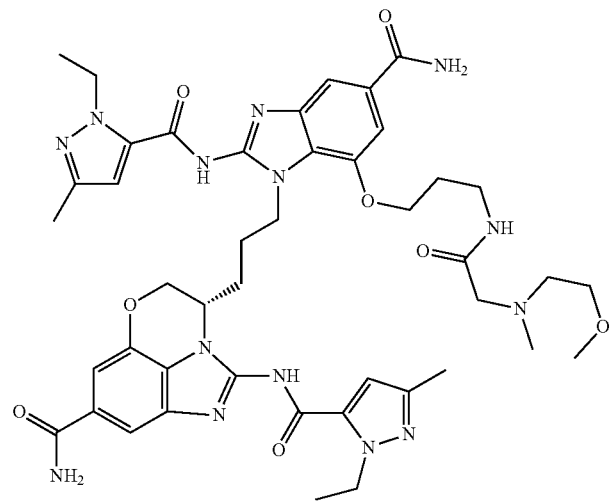 [SMILES: CCn1nc(C)cc1C(=O)Nc1nc2cc(C(N)=O)cc(OCCCNC(=O)CN(C)CCOC)c2n1CCC[C@H]1COc2cc(C(N)=O)cc3nc(NC(=O)c4cc(C)nn4CC)n1c23] |

| No. | Compound structure |
|---|---|
| 79 | 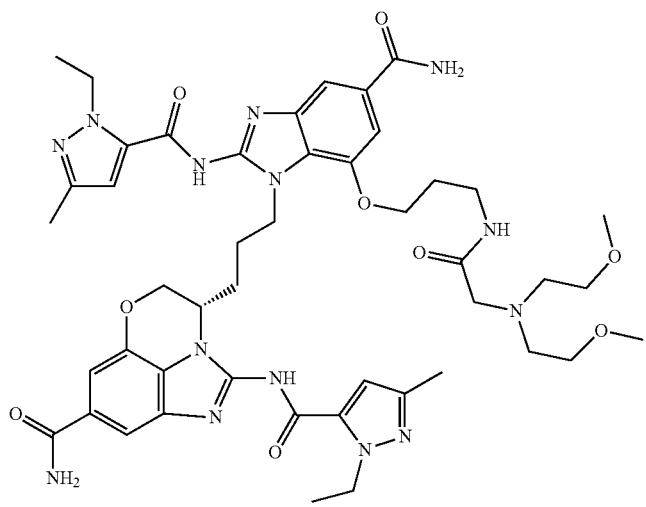 [SMILES: CCn1nc(C)cc1C(=O)Nc1nc2cc(C(N)=O)cc(OCCCNC(=O)CN(CCOC)CCOC)c2n1CCC[C@H]1COc2cc(C(N)=O)cc3nc(NC(=O)c4cc(C)nn4CC)n1c23] |
| 80 | 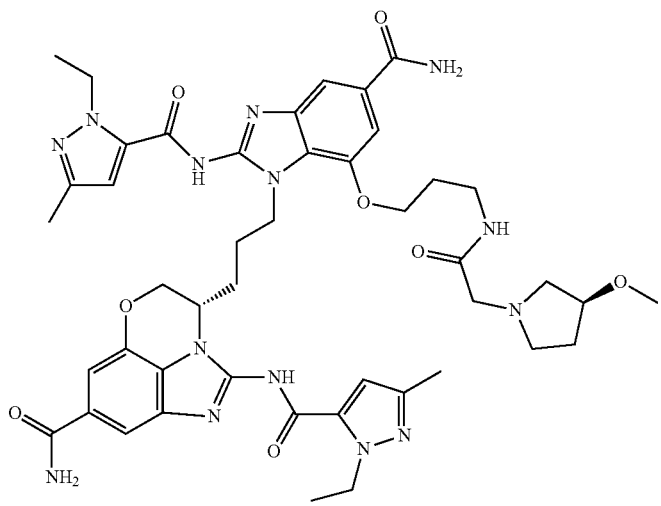 [SMILES: CCn1nc(C)cc1C(=O)Nc1nc2cc(C(N)=O)cc(OCCCNC(=O)CN3CC[C@H](OC)C3)c2n1CCC[C@H]1COc2cc(C(N)=O)cc3nc(NC(=O)c4cc(C)nn4CC)n1c23] |
| 81 | 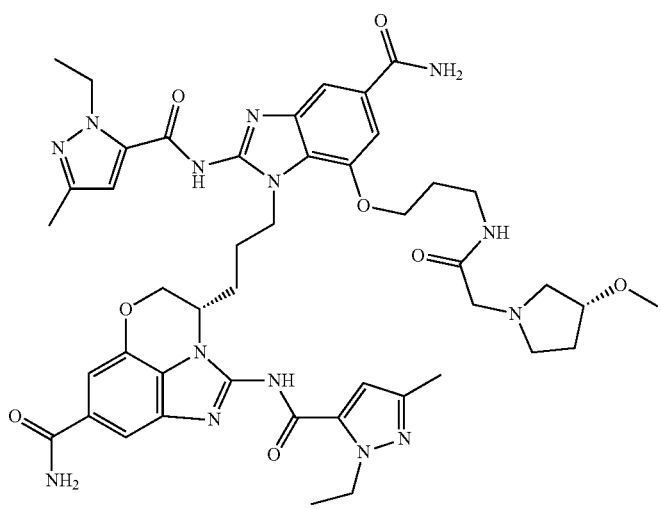 [SMILES: CCn1nc(C)cc1C(=O)Nc1nc2cc(C(N)=O)cc(OCCCNC(=O)CN3CC[C@@H](OC)C3)c2n1CCC[C@H]1COc2cc(C(N)=O)cc3nc(NC(=O)c4cc(C)nn4CC)n1c23] |

| No. | Compound structure |
|---|---|
| 82 | 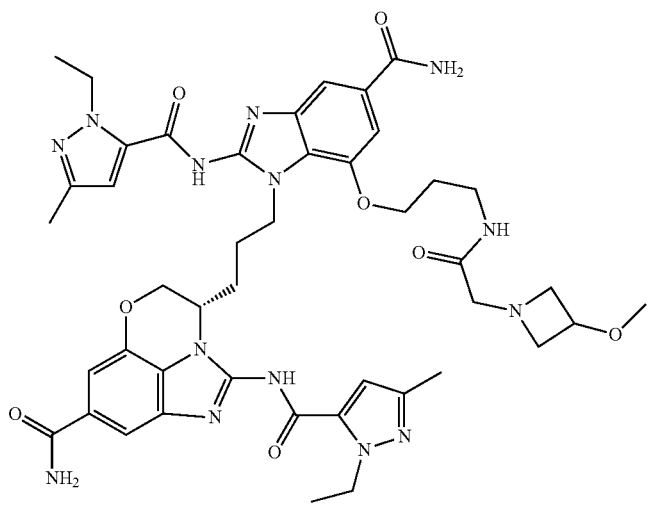 [SMILES: CCn1nc(C)cc1C(=O)Nc1nc2cc(C(N)=O)cc(OCCCNC(=O)CN3CC(OC)C3)c2n1CCC[C@H]1COc2cc(C(N)=O)cc3nc(NC(=O)c4cc(C)nn4CC)n1c23] |
| 83 | 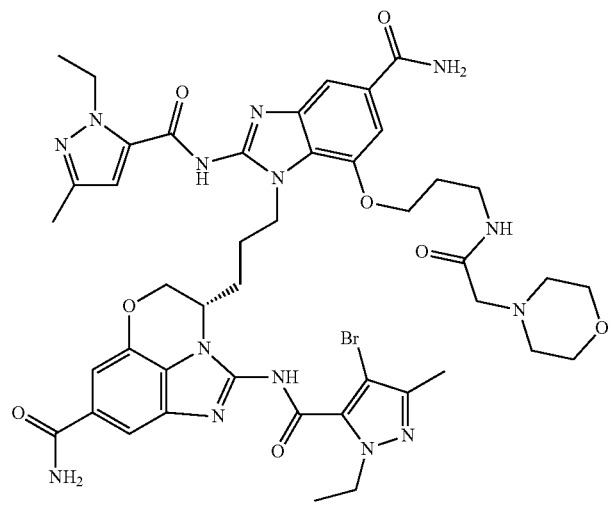 |
| 84 | 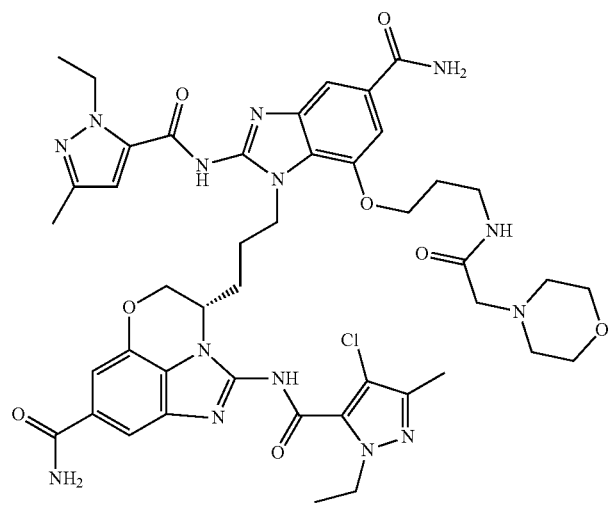 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(Cl)c(C)nn4CC)n1c23] |

| No. | Compound structure |
|---|---|
| 85 | 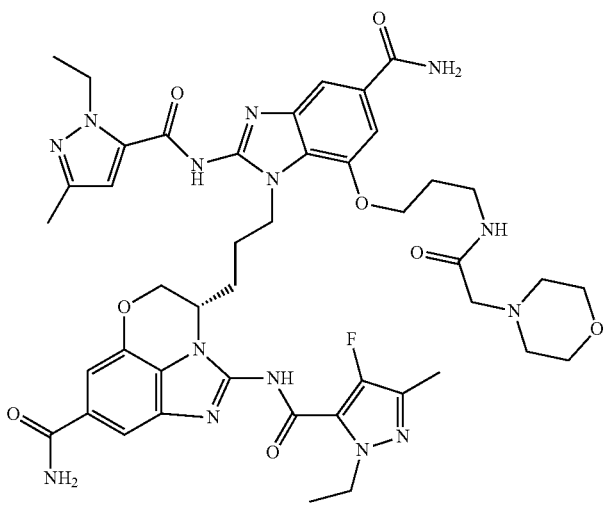 [SMILES: CCn1nc(C)cc1C(=O)Nc1nc2cc(C(N)=O)cc(OCCCNC(=O)CN3CCOCC3)c2n1CCC[C@H]1COc2cc(C(N)=O)cc3nc(NC(=O)c4c(F)c(C)nn4CC)n1c23] |
| 86 | 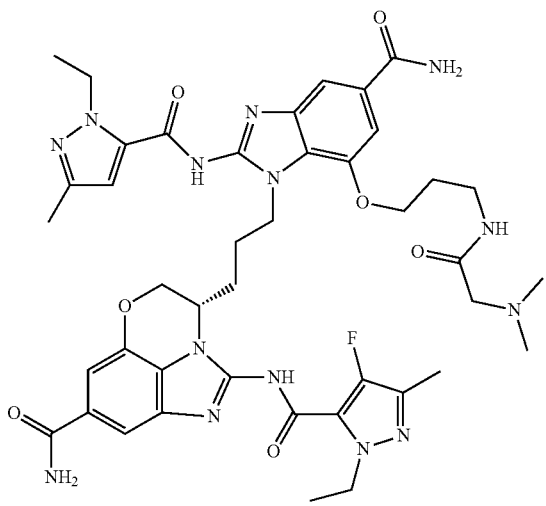 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(F)c(C)nn4CC)n1c23] |
| 87 | 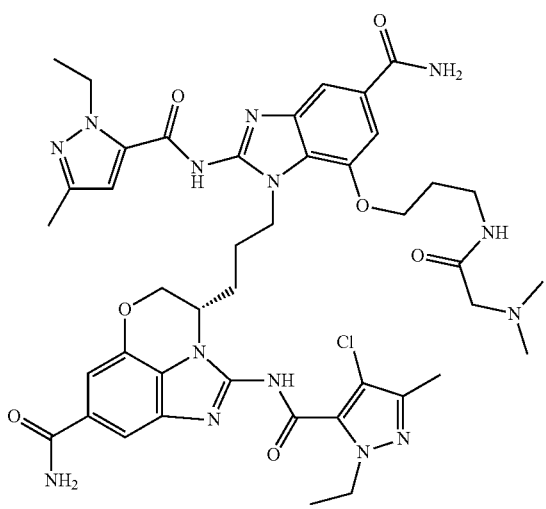 [SMILES: CCn1nc(C)cc1C(=O)Nc1nc2cc(C(N)=O)cc(OCCCNC(=O)CN(C)C)c2n1CCC[C@H]1COc2cc(C(N)=O)cc3nc(NC(=O)c4c(Cl)c(C)nn4CC)n1c23] |

-continued
| No. | Compound structure |
|---|---|
| 88 | 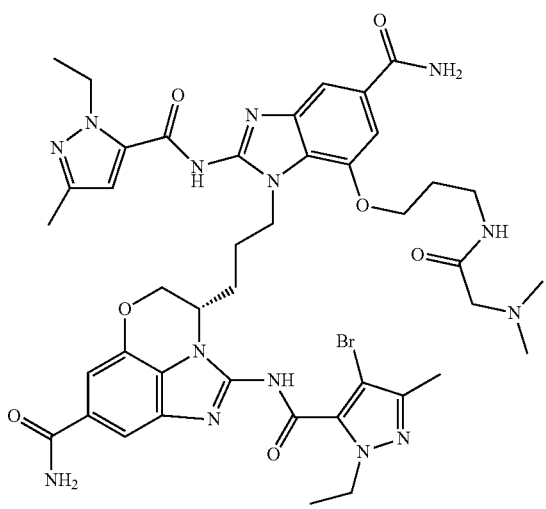 |
| 89 | 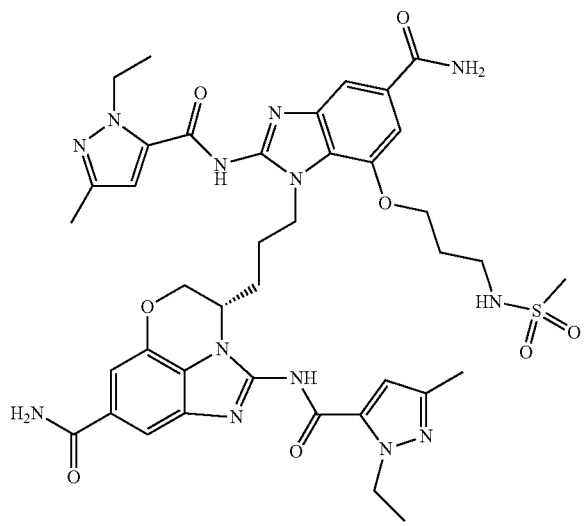 [SMILES: CCn1nc(C)cc1C(=O)Nc1nc2cc(C(N)=O)cc(OCCCNS(C)(=O)=O)c2n1CCC[C@H]1COc2cc(C(N)=O)cc3nc(NC(=O)c4cc(C)nn4CC)n1c23] |
| 90 | 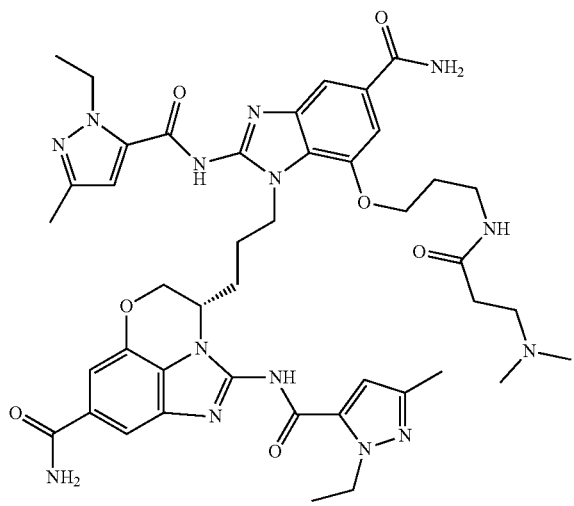 [SMILES: CCn1nc(C)cc1C(=O)Nc1nc2cc(C(N)=O)cc(OCCCNC(=O)CCN(C)C)c2n1CCC[C@H]1COc2cc(C(N)=O)cc3nc(NC(=O)c4cc(C)nn4CC)n1c23] |

-continued
| No. | Compound structure |
|---|---|
| 91 | 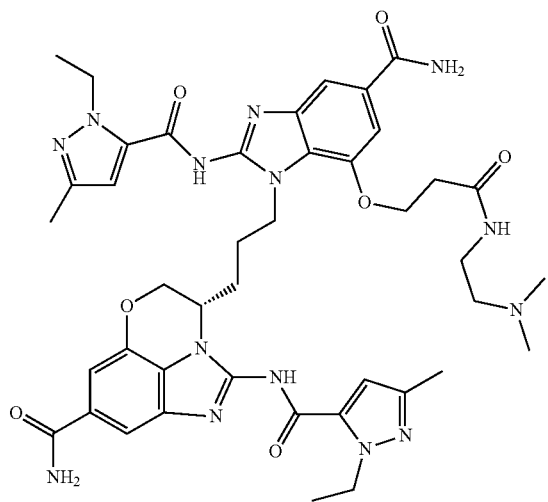 [SMILES: CCn1nc(C)cc1C(=O)Nc1nc2cc(C(N)=O)cc(OCCC(=O)NCCN(C)C)c2n1CCC[C@H]1COc2cc(C(N)=O)cc3nc(NC(=O)c4cc(C)nn4CC)n1c23] |
| 92 | 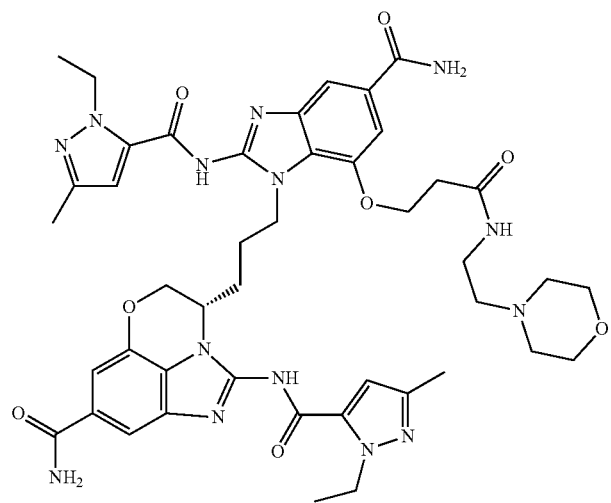 [SMILES: CCn1nc(C)cc1C(=O)Nc1nc2cc(C(N)=O)cc(OCCC(=O)NCCN3CCOCC3)c2n1CCC[C@H]1COc2cc(C(N)=O)cc3nc(NC(=O)c4cc(C)nn4CC)n1c23] |
| 93 | 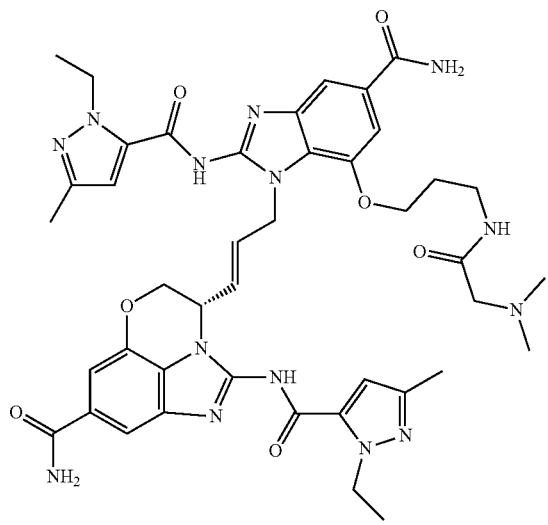 [SMILES: CCn1nc(C)cc1C(=O)Nc1nc2cc(C(N)=O)cc(OCCCNC(=O)CN(C)C)c2n1C/C=C/[C@H]1COc2cc(C(N)=O)cc3nc(NC(=O)c4cc(C)nn4CC)n1c23] |

| No. | Compound structure |
|---|---|
| 94 | 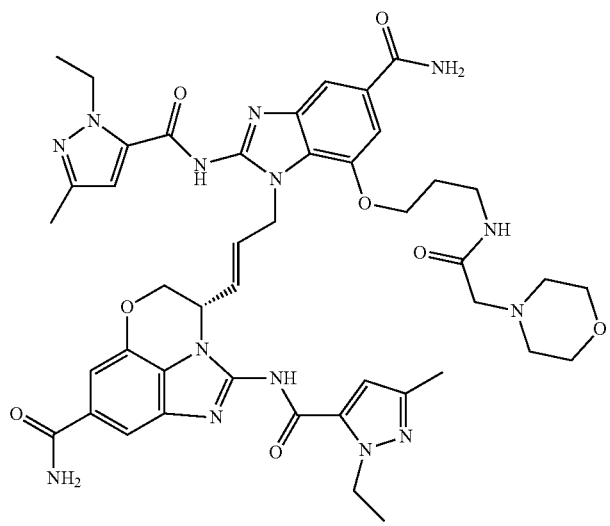 [SMILES: CCn1nc(C)cc1C(=O)Nc1nc2cc(C(N)=O)cc(OCCCNC(=O)CN3CCOCC3)c2n1C/C=C/[C@H]1COc2cc(C(N)=O)cc3nc(NC(=O)c4cc(C)nn4CC)n1c23] |
| 95 | 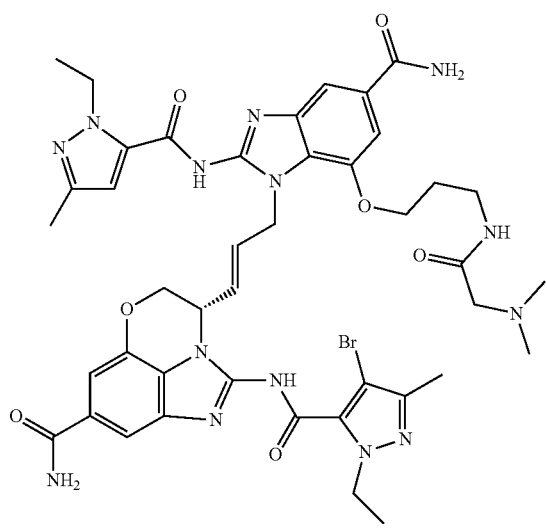 [SMILES: CCn1nc(C)cc1C(=O)Nc1nc2cc(C(N)=O)cc(OCCCNC(=O)CN(C)C)c2n1C/C=C/[C@H]1COc2cc(C(N)=O)cc3nc(NC(=O)c4c(Br)c(C)nn4CC)n1c23] |
| 96 | 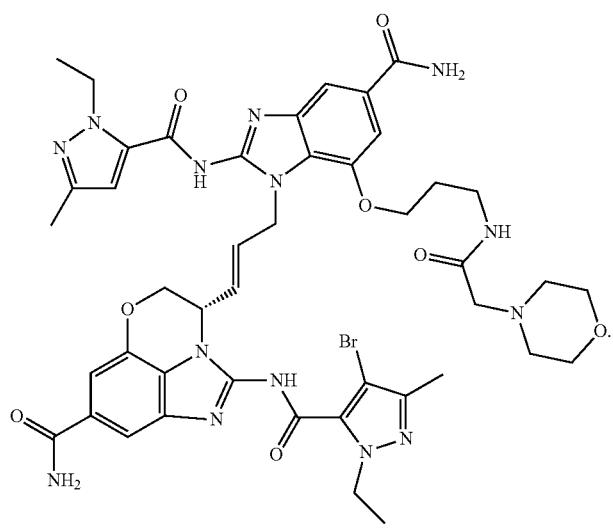 [SMILES: CCn1nc(C)cc1C(=O)Nc1nc2cc(C(N)=O)cc(OCCCNC(=O)CN3CCOCC3)c2n1C/C=C/[C@H]1COc2cc(C(N)=O)cc3nc(NC(=O)c4c(Br)c(C)nn4CC)n1c23] |

12. The compound according to claim 3, wherein -$Q^{A1}$-A-$Q^{A2}$- is taken together to form —$CH_2CH_2CH_2CH_2$—, —$CH_2CH=CHCH_2$—, —$CH(OH)CH(OH)CH_2$—, —$CH_2CH_2CH_2$—, —$CH_2CH=CH$—, —$CH(OH)CH_2CH_2$—, —$CH=CHCH_2$—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —$CH=CH$—, —$CH_2CH_2$—, —$CH(OH)CH_2$, —$CH_2CH(OH)$—, or —$CH_2OCH_2CH_2$—.

13. The compound according to claim 5, wherein -$Q^{B1}$-A-$Q^{B2}$- is taken together to form —$CH_2CH_2CH_2CH_2$—, —$CH_2CH=CHCH_2$—, —$CH(OH)CH(OH)CH_2$—, —$CH_2CH_2CH_2$—, —$CH_2CH=CH$—, —$CH(OH)CH_2CH_2$—, —$CH=CHCH_2$—, —$CH_2CH=CH$—, —$CH_2CH(OH)CH_2$—, —$CH_2CH_2CH(OH)$—, —$CH_2NHCH_2CH_2$—, —$CH_2CH_2NHCH_2$—, —$CH_2N(CH_3)CH_2CH_2$—, —$CH_2CH_2N(CH_3)CH_2$—, —$CH=CH$—, —$CH_2CH_2$—, —$CH(OH)CH_2$, —$CH_2CH(OH)$—, or —$CH_2OCH_2CH_2$—.

\* \* \* \* \*